(12) United States Patent
Brubaker et al.

(10) Patent No.: US 11,236,086 B2
(45) Date of Patent: Feb. 1, 2022

(54) SUBSTITUTED PYRROLOPYRIDINES AS INHIBITORS OF ACTIVIN RECEPTOR-LIKE KINASE

(71) Applicant: BLUEPRINT MEDICINES CORPORATION, Cambridge, MA (US)

(72) Inventors: Jason D. Brubaker, Cambridge, MA (US); Paul E. Fleming, Wellesley, MA (US); Joseph L. Kim, Cambridge, MA (US); Brett Williams, Boston, MA (US); Brian L. Hodous, Arlington, MA (US)

(73) Assignee: Blueprint Medicines Corporation, Cambridge, MA (US)

( * ) Notice: Subject to any disclaimer, the term of this patent is extended or adjusted under 35 U.S.C. 154(b) by 0 days.

(21) Appl. No.: 16/754,184

(22) PCT Filed: Oct. 18, 2018

(86) PCT No.: PCT/US2018/056589
§ 371 (c)(1),
(2) Date: Apr. 7, 2020

(87) PCT Pub. No.: WO2019/079649
PCT Pub. Date: Apr. 25, 2019

(65) Prior Publication Data
US 2020/0331908 A1    Oct. 22, 2020

Related U.S. Application Data

(60) Provisional application No. 62/574,200, filed on Oct. 18, 2017.

(51) Int. Cl.
*C07D 471/04* (2006.01)
*C07D 519/00* (2006.01)

(52) U.S. Cl.
CPC ......... *C07D 471/04* (2013.01); *C07D 519/00* (2013.01)

(58) Field of Classification Search
CPC ............................. C07D 471/04; C07D 519/00
USPC .................................................... 514/210.18
See application file for complete search history.

(56) References Cited

U.S. PATENT DOCUMENTS

| 8,415,336 | B2 | 4/2013 | Steinhagen et al. |
| 8,802,697 | B2 | 8/2014 | Bifulco, Jr. et al. |
| 8,980,878 | B2 | 3/2015 | Siegel et al. |
| 9,126,951 | B2 | 9/2015 | Bifulco, Jr. et al. |
| 9,200,002 | B2 | 12/2015 | Hodous et al. |
| 9,334,263 | B2 | 5/2016 | Hodous et al. |
| 9,340,514 | B2 | 5/2016 | Bifulco, Jr. et al. |
| 9,434,700 | B2 | 9/2016 | Bifulco, Jr. et al. |
| 9,499,522 | B2 | 11/2016 | DiPietro et al. |
| 9,688,680 | B2 | 6/2017 | Hodous |
| 9,695,165 | B2 | 7/2017 | Bifulco, Jr. et al. |
| 9,884,861 | B2 | 2/2018 | Hodous et al. |
| 9,944,651 | B2 | 4/2018 | Hodous et al. |
| 9,994,552 | B2 | 6/2018 | DiPietro et al. |
| 9,994,575 | B2 | 6/2018 | Hodous et al. |
| 10,000,490 | B2 | 6/2018 | Bifulco, Jr. et al. |
| 10,000,496 | B2 | 6/2018 | Hodous et al. |
| 10,017,512 | B2 | 7/2018 | Wenglowsky et al. |
| 10,030,005 | B2 | 7/2018 | Brubaker et al. |
| 10,035,789 | B2 | 7/2018 | Brubaker et al. |
| 10,196,436 | B2 | 2/2019 | Miduturu |
| 10,233,186 | B2 | 3/2019 | Brooijmans |
| 10,669,277 | B2 | 6/2020 | Wilson et al. |
| 2007/0027093 | A1 | 2/2007 | Ogawa et al. |
| 2009/0176778 | A1 | 7/2009 | Schmitz et al. |
| 2009/0181941 | A1 | 7/2009 | Leblanc et al. |
| 2013/0273037 | A1 | 10/2013 | Siegel et al. |

(Continued)

FOREIGN PATENT DOCUMENTS

WO    2006/046024 A1    5/2006
WO    2007/067537 A1    6/2007

(Continued)

OTHER PUBLICATIONS

Bocciardi et al. Mutational analysis of the ACVR1 gene in Italian patients affected with fibrodysplasia ossificans progressiva: confirmations and advancements. Eur J Hum Genet. 2009;17(3):311-318.
Chakkalakal et al., An Acvr1 R206H knock-in mouse has fibrodysplasia ossificans progressiva. J Bone Miner Res 2012;27(8):1746-1756.
Crofford et al., Failure of surgery and isotretinoin to relieve jaw immobilization in fibrodysplasia ossificans progressiva: report of two cases. J Oral Maxillofac Surg. 1990;48(2):204-208.
Eekhoff et al., Flare-Up After Maxillofacial Surgery in a Patient With Fibrodysplasia Ossificans Progressiva: An [18F]-NaF PET/CT Study and a Systematic Review. JBMR Plus. 2017;2(1):55-58.

(Continued)

*Primary Examiner* — Niloofar Rahmani
(74) *Attorney, Agent, or Firm* — McCarter & English, LLP; Steven G. Davis; Wei Song

(57) ABSTRACT

Described herein are compounds that inhibit ALK2 and its mutants, pharmaceutical compositions including such compounds, and methods of using such compounds and compositions.

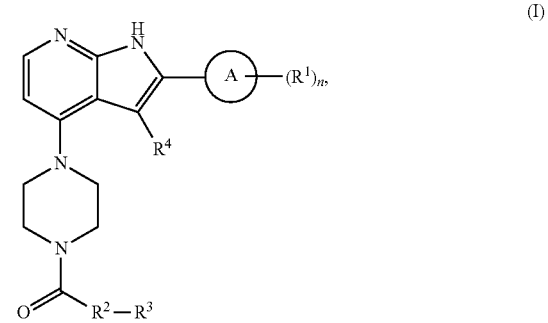

19 Claims, No Drawings

(56) References Cited

U.S. PATENT DOCUMENTS

| | | |
|---|---|---|
| 2014/0187559 A1 | 7/2014 | Miduturu |
| 2014/0275009 A1 | 9/2014 | Brenchley et al. |
| 2015/0064196 A1 | 3/2015 | Thakkar et al. |
| 2016/0045528 A1 | 2/2016 | Blatt et al. |
| 2017/0066812 A1 | 3/2017 | Bifulco, Jr. et al. |
| 2017/0145018 A1 | 5/2017 | Wenglowsky et al. |
| 2017/0174652 A1 | 6/2017 | Bifulco, Jr. et al. |
| 2017/0267661 A1 | 9/2017 | Kim et al. |
| 2017/0298069 A1 | 10/2017 | Brooijmans et al. |
| 2018/0022731 A1 | 1/2018 | Brooijmans et al. |
| 2018/0022732 A1 | 1/2018 | Brubaker et al. |
| 2019/0119280 A1 | 4/2019 | Hodous et al. |
| 2019/0144454 A1 | 5/2019 | Hodous et al. |
| 2019/0169194 A1 | 6/2019 | Wenglowsky et al. |
| 2019/0185454 A1 | 6/2019 | Brubaker et al. |

FOREIGN PATENT DOCUMENTS

| | | | |
|---|---|---|---|
| WO | 2009/087225 A2 | | 7/2009 |
| WO | 2010/003133 A2 | | 1/2010 |
| WO | 2011/002772 A1 | | 1/2011 |
| WO | 2011/003418 A1 | | 1/2011 |
| WO | 2014/138088 A1 | | 9/2014 |
| WO | 2014/151444 A1 | | 9/2014 |
| WO | 2015/187684 A1 | | 12/2015 |
| WO | 2016/165808 | * | 10/2016 |
| WO | 2016/165808 A1 | | 10/2016 |
| WO | 2017/181117 A1 | | 10/2017 |
| WO | 2018/049233 A1 | | 3/2018 |

OTHER PUBLICATIONS

Fukuda et al., Generation of a mouse with conditionally activated signaling through the BMP receptor, ALK2. Genesis. 2006;44(4):159-167.

Garner, Characterization of Highly Selective ALK2 Inhibitors for the Treatment of FOP. Slides presented at the 2016 FOP Drug Development Forum in Boston, MA. 9 pages, Oct. 24, 2016.

Garner, Generation of Highly Selective ALK2 Inhibitors for the Treatment of FOP. Slides presented at the 2016 Annual FOP Italia Meeting, 17 pages, Apr. 16, 2016.

Gregson et al., A novel ACVR1 mutation in the glycine/serine-rich domain found in the most benign case of a fibrodysplasia ossificans progressiva variant reported to date. Bone. 2011;48(3):654-658.

Jones et al., Unique genetic and epigenetic mechanisms driving paediatric diffuse high-grade glioma. Nat Rev Cancer. Sep. 18, 2014;14:651-661.

Kaplan et al., Classic and atypical fibrodysplasia ossificans progressiva (FOP) phenotypes are caused by mutations n the bone morphogenetic protein (BMP) type I receptor ACVR1 Hum Mutat. 2009;30(3):379-390.

Kaplan et al., Eady diagnosis of fibrodysplasia ossificans progressiva. Pediatrics. 2008;121(5):e1295-e1300.

Kaplan et al., Hard targets for a second skeleton: therapeutic horizons for fibrodysplasia ossificans progressiva (FOP) Expert Opin Orphan Drugs 2017;5(4):291-294.

Kaplan et al., Multi-system involvement in a severe variant of fibrodysplasia ossificans progressiva (ACVR1 c.772G>A; R258G): A report of two patients. Am J Med Genet A 2015;167A(10):2265-2271.

Mohedas et al., Development of an ALK2-biased BMP type I receptor kinase inhibitor. ACS Chem Biol. 2013;8(6):1291-1302.

Pacifici et al., Common mutations in ALK2/ACVR1, a multi-faceted receptor, have roles in distinct pediatric musculoskeletal and neural orphan disorders Cytokine Growth Factor Rev 2016;27:93-104.

Petrie et al., Novel mutations in ACVR1 result in atypical features in two fibrodysplasia ossificans progressiva patients. PLoS One. 2009;4(3):e5005, 4 pages.

Shore et al., A recurrent mutation in the BMP type I receptor ACVR1 causes inherited and sporadic fibrodysplasia ossificans progressiva. Nat Genet. 2006;38(5):525-527. [published correction appears in Nat Genet. Feb. 2007;39 (2):276.

Yu et al., BMP type I receptor inhibition reduces heterotopic [corrected] ossification [published correction appears in Nat Med. Jan. 2009;15(1):117]. Nat Med. 2008;14(12):1363-1369, including Erratum (1 page).

U.S. Appl. No. 16/002,587, filed Jun. 7, 2018, by Blueprint Medicines Corp.—Abandoned.

International Search Report and Written Opinion for Application No. PCT/US2017/027775, dated Jul. 21, 2017, 9 pages.

International Search Report and Written Opinion for Application No. PCT/US2018/056589, dated Jan. 2, 2019, 10 pages.

* cited by examiner

SUBSTITUTED PYRROLOPYRIDINES AS INHIBITORS OF ACTIVIN RECEPTOR-LIKE KINASE

This application is a U.S. national stage filing, under 35 U.S.C. § 371(c), of International Application No. PCT/US2018/056589, filed Oct. 18, 2018, which claims priority from U.S. Provisional Application No. 62/574,200, filed Oct. 18, 2017. The entire contents of each of the aforementioned applications are incorporated herein by reference.

This disclosure relates to inhibitors of activin receptor-like kinase-2 (ALK2).

Activin receptor-like kinase-2 (ALK2) is encoded by the activin A receptor, type I gene (ACVR1). ALK2 is a serine/threonine kinase in the bone morphogenetic protein (BMP) pathway (Shore et al., Nature Genetics 2006, 38: 525-27). It binds to complexes comprising bone morphogenetic proteins (BMPs) and is responsible for transducing BMP signals. Certain mutations in ALK2 cause the kinase to be constitutively active and are associated with various diseases. Fibrodysplasia ossificans progressiva (FOP) is a rare, severely debilitating heritable disorder characterized by progressive heterotopic ossification in extraskeletal sites. Individuals with this disease experience significantly reduced mobility and shortened lifespan. Current therapy is limited to ameliorating swellings (flare-ups) that characterize the disease.

All FOP patients carry heterozygous, activating mutations in the ACVR1 gene. Furthermore, the vast majority of FOP patients harbor the same ALK2 mutation, R206H. Transgenic mice that express ALK2-R206H recapitulate the key features of the human disease, including malformation of the first digit in the hind limbs and inflammatory infiltration and muscle cell apoptosis followed by formation of heterotopic bone through an endochondral pathway (Chakkalakal et al, J Bone Miner Res. 2012, 27(8): 1746-1756). A second engineered mouse strain has been developed that expresses the activated ALK2-Q207D variant in muscle and phenocopies key features of human FOP. Treatment of these mice with an inhibitor of BMP receptor type 1 kinases resulted in inhibition of SMAD signaling and reduction in ectopic ossification and associated functional impairment (Fukuda et al., Genesis 2006, 44, 159-167). Other mutations in ALK2 that have been associated with FOP include, but are not limited to, L196P, PF197-8L, R202I, R258S, R258G, G328A, G328W, G328E, G328R, G356D, and R375P (Kaplan et al., Hum Mutat. 2009, 30(3): 379-390; Gregson et al., Bone 2011, 48:654-658; Kaplan et al., Am J Med Genet 2015, 167: 2265-2271; Petrie et al., PLoS One 2009, 4(3): e5005; Bocciardi et al., Eur J Hum Genetics 2009, 17:311-318; Pacifici and Shore, Cytokine & Growth Factor Reviews 2016, 27:93-104).

In certain circumstances, heterotopic ossification (HO) can also be induced in people who are wild-type ALK2. These circumstances can include osteochondromas, major surgical interventions, trauma (such as head or blast injuries), protracted immobilization, or severe burns. Debilitating HO can occur in diseases such as hereditary multiple exostoses. An ALK2 inhibitor could potentially be an effective therapy for the treatment of FOP and other conditions caused by HO.

Diffuse intrinsic pontine glioma (DIPG) is a rare, aggressive, and typically fatal pediatric brain stem cancer with no effective treatment options. Due to its anatomical location and diffuse nature, DIPG cannot be treated by surgery. DIPG arises exclusively in young children and the two year survival rate is approximately less than 10%. Because of their location in the brainstem, DIPGs cause pressure on cranial nerves leading to double vision, difficulty in controlling eye movement, difficulty chewing and/or swallowing, and weakness in the arms and/or legs leading to loss of movement and difficulty speaking. As the tumor progresses, there is increasing pressure inside the skull causing severe headaches, nausea/vomiting, and fatigue. Unlike many other pediatric cancers, there has been virtually no progress in improving treatments for DIPG over the last few decades. Historically, the lack of understanding regarding the drivers of DIPG has hindered the identification of potential new treatment options. Consequently, the medical need for DIPG treatments is exceedingly high. Recent genomic characterization has demonstrated that approximately 25% of DIPG tumors possess somatic, heterozygous ALK2 activating mutations. Mutations in ALK2 associated with DIPG include, but are not limited to, R206H, G328V, G328W, G328E, and G356D (Jones and Baker, Nature Rev Cancer 2014, 14:651-661).

Notably, the ALK2 mutations found in DIPG overlap with those found in FOP, suggesting a potential synergy between inhibitor development efforts for the two diseases (e.g., via overlapping screening funnels and chemistry efforts). The finding that a significant proportion of DIPG contain activating ALK2 mutations suggests that ALK2 inhibitors may be of clinical benefit for DIPG patients.

Anemia of chronic disease, inflammation, or cancer can develop in settings of chronic inflammatory, infectious, or neoplastic disease. In this form of anemia, inflammatory cytokines induce hepatic expression of hepcidin, which negatively regulates iron bioavailability by inactivating ferroportin. Hepcidin is transcriptionally regulated by amongst other things bone morphogenetic protein (BMP) signaling. Inhibition of BMP phosphorylation through inhibition of ALK2 can modulate BMP-mediated signaling, thus reducing hepcidin expression. Reduced hepcidin expression may be an effective strategy for the treatment of anemia of chronic disease, inflammation, or cancer.

The present disclosure provides inhibitors of ALK2 and ALK2 mutants, e.g., ALK2 mutants as defined herein, for example, inhibitors of Formula (I) and pharmaceutically acceptable salts and compositions thereof. The present disclosure further provides methods of using the compounds of the disclosure, and pharmaceutically acceptable salts and compositions thereof, to inhibit the activity of ALK2 or ALK2 mutants in a cell or in a patient. The present disclosure further provides methods for using the compounds of the disclosure and pharmaceutically acceptable salts and compositions thereof, to treat a subject or patient suffering from a condition mediated by aberrant ALK2 activity, e.g., at least one of fibrodysplasia ossificans progressiva (FOP) or heterotopic ossification or diffuse intrinsic pontine glioma (DIPG) or anemia of chronic disease or anemia of inflammation or anemia of cancer.

In one aspect, the disclosure features a compound of Formula (I) or at least one of pharmaceutically acceptable salt thereof:

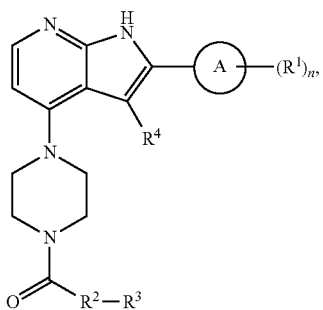

(I)

wherein each of ring A, $R^1$, $R^2$, $R^3$, $R^4$, and n is defined as described herein.

In another aspect, the present disclosure provides pharmaceutical compositions comprising a compound of Formula (I) or a pharmaceutically acceptable salt thereof and a pharmaceutically acceptable carrier.

In another aspect, the present disclosure provides a method for treating or ameliorating fibrodysplasia ossificans progressiva in a subject. In some embodiments, said method comprises administering to said subject a therapeutically effective amount of a compound of Formula (I) or a pharmaceutically acceptable salt or composition thereof. In some embodiments, the subject has a mutation in an ALK2 gene that results in the expression of an ALK2 enzyme having at least one amino acid modification chosen from L196P, PF197-8L, R202, R206H, Q207E, R258S, R258G, G328A, G328W, G328E, G328R, G356D, and R375P.

In another aspect, the present disclosure provides a method of treating or ameliorating diffuse intrinsic pontine glioma in a subject. In some embodiments, said method comprises administering to said subject a therapeutically effective amount of a compound of Formula (I) or a pharmaceutically acceptable salt or composition thereof. In some embodiments, the subject has a mutation in an ALK2 gene that results in the expression of an ALK2 enzyme having at least one amino acid modification chosen from R206H, G328V, G328W, G328E, and G356D.

In another aspect, the present disclosure provides a method of inhibiting aberrant ALK2 activity in a subject. In some embodiments, said method comprises administering to said subject a therapeutically effective amount of a compound of Formula (I) or a pharmaceutically acceptable salt or composition thereof. In some embodiments, the subject has a mutation in an ALK2 gene that results in the expression of an ALK2 enzyme having at least one amino acid modification chosen from L196P, PF197-8L, R202I, R206H, Q207E, R258S, R258G, G328A, G328V, G328W, G328E, G328R, G356D, and R375P.

The methods described herein can additionally comprise various evaluation steps prior to, during, and/or following treatment with a compound of the disclosure. In some embodiments, prior to, during and/or following treatment with a compound of the disclosure, the method further comprises the step of evaluating, e.g., visualizing, heterotopic ossification in the subject. This may be achieved by spectroscopic analysis, e.g., magnetic resonance-based analysis, e.g., MRI, positron emission tomography (PET), micro computed tomography (CT), or by histology.

In some embodiments, the methods comprise evaluating a pre-treatment or baseline level of the heterotopic ossification in a subject, e.g., using spectroscopic analysis, e.g., magnetic resonance-based analysis, e.g., MRI, positron emission tomography (PET), micro computed tomography (CT), or by histology. In some embodiments, the methods further comprise administering to the subject a compound of the disclosure; evaluating the post-treatment level of heterotopic ossification, e.g., using spectroscopic analysis, e.g., magnetic resonance-based analysis, e.g., MRI, positron emission tomography (PET), micro computed tomography (μCT), or by histology; comparing the post-treatment level of heterotopic ossification in the subject with the pre-treatment or baseline level of heterotopic ossification; and determining whether to continue treatment, e.g., using spectroscopic analysis, e.g., magnetic resonance-based analysis, e.g., MRI, positron emission tomography (PET), micro computed tomography (μCT), or by histology.

In some embodiments, the heterotopic ossification is preceded by edema, e.g., sustained edema.

As used herein, the terms a "patient," "subject," "individual," and "host" refer to either a human or a non-human animal suffering from or suspected of suffering from a disease or disorder associated with aberrant ALK2 activity (i.e., aberrant ALK2 activity due to a mutation in an ALK2 gene that results in the expression of an ALK2 enzyme having an amino acid modification) or aberrant ALK2 biological activity.

As used herein, "treat," "treatment," and "treating" such a disease or disorder refers to ameliorating at least one symptom of the disease or disorder described herein. These terms, when used in connection with a condition such as fibrodysplasia ossificans progressiva, refer to one or more of: controlling the rate of heterotropic bone growth; relieving pain and inflammation associated with development of new bone; extending the expected survival time of the patient; reducing the size or the number of heterotopic bone growth lesions; maintaining or improving mobility; preventing or treating new flare ups; inhibiting the development of new heterotopic bone lesions; enabling surgery to remove existing heterotopic ossifications to restore limb function and/or mobility; prolonging survival; prolonging progression-free survival; prolonging time to progression; inhibiting FOP related injury induced edema, and/or enhancing quality of life. When used in connection with a condition such as diffuse intrinsic pontine glioma, these terms refer to one or more of: impeding growth of the glioma, causing the glioma to shrink by weight or volume, extending the expected survival time of the patient, inhibiting glial tissue growth, reducing glial tumor mass, reducing size or number of metastatic lesions, inhibiting the development of new metastatic lesions, prolonging survival, prolonging progression-free survival, prolonging time to progression, and/or enhancing quality of life.

As used herein, the term "therapeutic effect" refers to a beneficial local or systemic effect in animals, particularly mammals, and more particularly humans, caused by administration of a compound or composition of the disclosure. The phrases "therapeutically effective amount" and "pharmaceutically effective amount" are used interchangeably and mean that amount of a compound or composition of the disclosure that is effective to treat a disease or condition associated with aberrant ALK2 activity at a reasonable benefit/risk ratio. The therapeutically effective amount of such substance will vary, for example, depending upon the subject and disease condition being treated, the weight and age of the subject, the severity of the disease condition, the manner of administration, etc., which can readily be determined by one of skill in the art.

"Aliphatic group," as used herein, refers to a straight chain, branched chain, or cyclic hydrocarbon group and includes saturated and unsaturated groups, such as an alkyl group, an alkenyl group, or an alkynyl group.

"Alkenyl," as used herein, refers to an aliphatic group containing at least one double bond.

"Alkylene" refers to a divalent radical of an alkyl group, e.g., —$CH_2$—, —$CH_2CH_2$—, and —$CH_2CH_2CH_2$—.

"Alkynyl," as used herein, refers to a straight or branched hydrocarbon chain containing two to twelve carbon atoms and characterized in having one or more triple bonds. Examples of alkynyl groups include, but are not limited to, ethynyl, propargyl, and 3-hexynyl. One of the triple bond carbons may optionally be the point of attachment of the alkynyl substituent.

"Alkyl" or "alkyl group" refers to a monovalent radical of a saturated straight or branched hydrocarbon, such as a straight or branched group of 1-12, 1-10, or 1-6 carbon atoms, referred to herein as $C_1$-$C_{12}$ alkyl, $C_1$-$C_{10}$ alkyl, and $C_1$-$C_6$ alkyl, respectively. Example alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, and octyl.

"Aromatic" when referring to a ring, refers to a fully conjugated, unsaturated ring that has (4n+27) electrons and is often characterized by structural formulae showing alternating double and single bonds. Aromatic rings include both aryl rings (e.g., benzene) and heteroaryl rings (e.g., rings containing one or more heteroatoms chosen from N, O, and S).

"Aryl" refers to a monocyclic, bicyclic, or polycyclic hydrocarbon ring system wherein at least one ring is aromatic.

"Halo" refers to a radical of any halogen, e.g., —F, —Cl, —Br, or —I.

"Carbocyclic ring system" refers to a monocyclic, bicyclic, or polycyclic hydrocarbon ring system, wherein each ring is either completely saturated or contains one or more units of unsaturation, but where no ring is aromatic.

"Carbocyclyl" refers to a monovalent radical of a carbocyclic ring system. Representative carbocyclyl groups include cycloalkyl groups (e.g., cyclopentyl, cyclobutyl, cyclopentyl, cyclohexyl and the like), and cycloalkenyl groups (e.g., cyclopentenyl, cyclohexenyl, cyclopentadienyl, and the like). As used herein, carbocyclyls are monovalent radicals of partially saturated monocyclic, bicyclic, or polycyclic hydrocarbon ring systems having an sp2 point of attachment to the rest of the molecule.

"Cycloalkyl" refers to a cyclic, bicyclic, tricyclic, or polycyclic non-aromatic hydrocarbon groups having 3 to 12 carbons. Any substitutable ring atom may be substituted (e.g., by one or more substituents). The cycloalkyl groups can contain fused or spiro rings. Fused rings are rings that share at least two common (carbon) atoms. Examples of cycloalkyl moieties include, but are not limited to, cyclopropyl, cyclohexyl, methylcyclohexyl, adamantyl, and norbornyl.

"Heteroalkyl" refers to a monovalent, straight or branched alkyl chain where one methylene unit other than the methylene unit bound to the rest of the molecule is replaced with —O—, —S—, or —N($R^d$), wherein $R^d$ is defined below. For the sake of clarity, the moiety —$CH_2$—NH—$CH_3$ would be a heteroalkyl, but —NH—$CH_2$—$CH_3$ would not because the NH group is bound to the rest of the molecule.

"Heteroalkylene" refers to a divalent radical of a heteroalkyl group. "Heteroaromatic ring system" refers to a monocyclic, bicyclic, or polycyclic ring system wherein at least one ring is both aromatic and comprises at least one heteroatom (e.g., N, O, or S); and wherein no other rings are heterocyclyl (as defined below). In certain instances, a ring which is aromatic and comprises a heteroatom contains 1, 2, 3, or 4 ring heteroatoms in such ring.

"Heteroaryl" refers to a monovalent radical of a heteroaromatic ring system. Representative heteroaryl groups include ring systems where (i) each ring comprises a heteroatom and is aromatic, e.g., imidazolyl, oxazolyl, thiazolyl, triazolyl, pyrrolyl, furanyl, thiophenyl, pyrazolyl, pyridinyl, pyrazinyl, pyridazinyl, pyrimidinyl, indolizinyl, purinyl, naphthyridinyl, and pteridinyl; (ii) each ring is aromatic or carbocyclyl, at least one aromatic ring comprises a heteroatom and at least one other ring is a hydrocarbon ring or e.g., indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, carbazolyl, acridinyl, phenazinyl, phenothiazinyl, phenoxazinyl, pyrido[2,3-b]-1,4-oxazin-3-(4H)-one, 5,6,7,8-tetrahydroquinolinyl and 5,6,7,8-tetrahydroisoquinolinyl; and (iii) each ring is aromatic or carbocyclyl, and at least one aromatic ring shares a bridgehead heteroatom with another aromatic ring, e.g., 4H-quinolizinyl.

"Heterocyclic ring system" refers to a monocyclic, bicyclic, and polycyclic ring system wherein at least one ring is saturated or partially unsaturated (but not aromatic) and that ring comprises at least one heteroatom. A heterocyclic ring system can be attached to its pendant group at any heteroatom or carbon atom that results in a stable structure and any of the ring atoms can be optionally substituted. Heterocyclic ring systems may be fused rings or spiro rings.

"Heterocyclyl" refers to a monovalent radical of a heterocyclic ring system. Representative heterocyclyls include ring systems in which (i) every ring is non-aromatic and at least one ring comprises a heteroatom, e.g., tetrahydrofuranyl, tetrahydropyranyl, tetrahydrothienyl, pyrrolidinyl, pyrrolidonyl, piperidinyl, pyrrolinyl, decahydroquinolinyl, oxazolidinyl, piperazinyl, dioxanyl, dioxolanyl, diazepinyl, oxazepinyl, thiazepinyl, morpholinyl, and quinuclidinyl; (ii) at least one ring is non-aromatic and comprises a heteroatom and at least one other ring is an aromatic carbon ring, e.g., 1,2,3,4-tetrahydroquinolinyl, 1,2,3,4-tetrahydroisoquinolinyl; and (iii) at least one ring is non-aromatic and comprises a heteroatom and at least one other ring is aromatic and comprises a heteroatom, e.g., 3,4-dihydro-1H-pyrano[4,3-c]pyridine, and 1,2,3,4-tetrahydro-2,6-naphthyridine.

"Cyano" refers to a —CN radical.

"Hydroxy" or "hydroxyl" refers to —OH.

Certain compounds of the present disclosure may exist in particular geometric or stereoisomeric forms. The present disclosure contemplates all such compounds, including cis- and trans-isomers, R- and S-enantiomers, diastereomers, (D)-isomers, (L)-isomers, racemic mixtures thereof, and other mixtures thereof, as falling within the scope of the disclosure. Additional asymmetric carbon atoms may be present in a substituent, such as an alkyl group. All such isomers, as well as mixtures thereof, are intended to be included in this disclosure. Thus, when a disclosed compound is named or depicted by a structure without specifying the stereochemistry and has one or more chiral centers, it is understood to represent all possible stereoisomers of the compound, as well as enantiomeric mixtures thereof. When a disclosed compound is named or depicted by a structure specifying stereochemistry at each chiral center, it is understood to represent only the compound having the designated stereochemistry at such chiral centers. However, when a disclosed compound specifies stereochemistry at some, but not all chiral centers, it is understood to represent all possible stereoisomers at the non-specified chiral centers of the compound, as well as enantiomeric mixtures thereof.

If, for instance, a particular enantiomer of compound of the present disclosure is desired, it may be prepared by asymmetric synthesis, or by derivation with a chiral auxiliary, where the resulting diastereomeric mixture is separated and the auxiliary group cleaved to provide the pure desired enantiomers. Alternatively, where the molecule contains a basic functional group, such as amino, or an acidic functional group, such as carboxyl, diastereomeric salts are formed with an appropriate optically-active acid or base, followed by resolution of the diastereomers thus formed by fractional crystallization or chromatographic means well known in the art, and subsequent recovery of the pure enantiomers.

The "enantiomeric excess" or "% enantiomeric excess" of a composition can be calculated using the equation shown below. In the example shown below a composition contains 90% of one enantiomer, e.g., the S enantiomer, and 10% of the other enantiomer, i.e., the R enantiomer.

$$ee=(90-10)/100=80\%.$$

Thus, a composition containing 90% of one enantiomer and 10% of the other enantiomer is said to have an enantiomeric excess of 80%.

The compounds or compositions described herein may contain an enantiomeric excess of at least 50%, 75%, 90%, 95%, or 99% of one form of the compound, e.g., the S-enantiomer. In other words, such compounds or compositions contain an enantiomeric excess of the S enantiomer over the R enantiomer.

The compounds described herein may also contain unnatural proportions of atomic isotopes at one or more of the atoms that constitute such compounds. For example, the compounds may be radiolabeled with radioactive isotopes, such as, for example, deuterium ($^2$H), tritium ($^3$H), carbon-13 ($^{13}$C), or carbon-14 ($^4$C). All isotopic variations of the compounds disclosed herein, whether radioactive or not, are intended to be encompassed within the scope of the present disclosure. In addition, all tautomeric forms of the compounds described herein are intended to be within the scope of the claimed disclosure.

The compound can be useful as the free base or as a salt. Representative salts include the hydrobromide, hydrochloride, sulfate, bisulfate, phosphate, nitrate, acetate, valerate, oleate, palmitate, stearate, laurate, benzoate, lactate, phosphate, tosylate, citrate, maleate, fumarate, succinate, tartrate, naphthalate, mesylate, glucoheptonate, lactobionate, and laurylsulfonate salts and the like. (See, e.g., Berge et al. (1977) "Pharmaceutical Salts", J. Pharm. Sci. 66:1-19.)

As described herein, compounds of the disclosure may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent chosen from a specified group, the substituent may be either the same or different at each position. Combinations of substituents envisioned under this disclosure are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable substituents for an optionally substituted alkyl, alkylene, carbocyclyl, heterocyclyl, aryl group, or heteroaryl group include halogen, =O, —CN, —OR, —NR$^d$R$^e$, —S(O)$_k$R$^c$, —NR$^c$S(O)$_2$R$^c$, —S(O)$_2$NR$^d$R$^e$, —C(=O)OR$^c$, —OC(=O)OR$^c$, —OC(=O)R$^c$, —OC(=S)OR$^c$, —C(=S)OR$^c$, —O(C=S)R$^c$, —C(=O)NR$^d$R$^e$, —NR$^c$C(=O)R$^c$, —C(=S)NR$^d$R$^e$, —NR$^c$C(=S)R$^c$, —NR$^c$(C=O)OR$^c$, —O(C=O)NR$^d$R$^e$, —NR$^c$(C=S)OR$^c$, —O(C=S)NR$^d$R$^e$, —NR$^c$(C=O)NR$^d$R$^e$, —NR$^c$(C=S)NR$^d$R$^e$, —C(=S)R$^c$, —C(=O)R$^c$, C$_1$-C$_6$ alkyl, C$_1$-C$_6$ haloalkyl, C$_1$-C$_6$ heteroalkyl, carbocyclyl, (CC alkylene)-carbocyclyl, (C$_1$-C$_6$ heteroalkylene)-carbocyclyl, heterocyclyl, (C$_1$-C$_6$ alkylene)-heterocyclyl, (C$_1$-C$_6$ heteroalkylene)-heterocyclyl, aryl, (C$_1$-C$_6$ alkylene)-aryl, (C$_1$-C$_6$ heteroalkylene)-aryl, heteroaryl, (C$_1$-C$_6$ alkylene)-heteroaryl, or (C$_1$-C$_6$ heteroalkylene)-heteroaryl, wherein each of said alkyl, alkylene, heteroalkyl, heteroalkylene, carbocyclyl, heterocyclyl, aryl, and heteroaryl are optionally substituted with one or more of halogen, OR$^c$, —NO$_2$, —CN, —NR$^c$C(=O)R$^c$, —NR$^d$R$^e$, —S(O)$_k$R$^c$, —C(=O)OR$^c$, —C(=O)NR$^d$R$^e$, —C(=O)R$^c$, C$_1$-C$_6$ alkyl, C$_1$-C$_6$ haloalkyl, or C$_1$-C$_6$ heteroalkyl, and wherein R$^c$ is hydrogen, hydroxy, C$_1$-C$_6$ alkyl, C$_1$-C$_6$ heteroalkyl, carbocyclyl, (CC alkylene)-carbocyclyl, (C$_1$-C$_6$ heteroalkylene)-carbocyclyl, heterocyclyl, (C$_1$-C$_6$ alkylene)-heterocyclyl, (C$_1$-C$_6$ heteroalkylene)-heterocyclyl, aryl, (C$_1$-C$_6$ alkylene)-aryl, (C$_1$-C$_6$ heteroalkylene)-aryl, heteroaryl, (C$_1$-C$_6$ alkylene)-heteroaryl, or (C$_1$-C$_6$ heteroalkylene)-heteroaryl, each of which is optionally substituted with one or more of halogen, hydroxy, C$_1$-C$_6$ alkyl, C$_1$-C$_6$ haloalkyl, C$_1$-C$_6$ heteroalkyl, carbocyclyl, heterocyclyl, aryl, or heteroaryl; R$^d$ and R$^e$ are each independently chosen from hydrogen, C$_1$-C$_6$ alkyl, and C$_1$-C$_6$ heteroalkyl; and k is 0, 1, or 2. The claimed disclosure is not intended to be limited in any manner by the above example listing of substituents.

In one aspect, the present disclosure features a compound having the Formula (I):

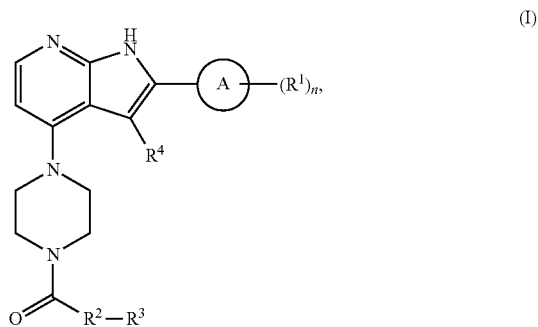

or a pharmaceutically acceptable salt thereof, wherein:
ring A is chosen from monocyclic aryl, monocyclic heteroaryl, quinolinyl, and bicyclic heterocyclyl, wherein only one ring of said bicyclic heterocyclyl is aromatic;
each R$^1$ is independently chosen from halo, cyano, oxo, C$_1$-C$_4$ alkyl, —O—(C$_1$-C$_4$ alkyl), —C(O)—(C$_1$-C$_4$ alkyl), —C(O)—O—(C$_1$-C$_4$ alkyl), —C(O)—N(R$^8$)—(C$_1$-C$_4$ alkyl), —N(R$^8$)$_2$, —N(R$^8$)—C(O)—(C$_1$-C$_4$ alkyl), —S (O)$_p$—(C$_1$-C$_4$ alkyl), —O—(C$_1$-C$_4$ alkylene)-C(O)—O—(C$_1$-C$_4$ alkyl), —O—(C$_1$-C$_4$ alkylene)-N(R$^8$)$_2$, —O—(C$_1$-C$_4$ alkylene)-C(O)—N(R$^8$)$_2$, —Si(R$^9$)(C$_1$-C$_4$ alkyl)$_2$, C$_3$-C$_8$ carbocyclyl, —C(O)—(C$_3$-C$_8$ carbocyclyl), —O—(C$_0$-C$_4$ alkylene)-(C$_3$-C$_8$ carbocyclyl), —O—(C$_0$-C$_4$ alkylene)-C(O)—(C$_3$-C$_8$ carbocyclyl), —(C$_0$-C$_4$ alkylene)-aryl, —O—(C$_0$-C$_4$ alkylene)-aryl, heterocyclyl, —C(O)-heterocyclyl, —O—(C$_0$-C$_4$ alkylene)-heterocyclyl, and —O—(C$_0$-C$_4$ alkylene)-C(O)-heterocyclyl, wherein:

any said alkyl or said alkylene portion of R$^1$ is optionally substituted with one to five substituents independently chosen from halo, cyano, hydroxyl, and —O—(C$_1$-C$_4$ alkyl); and any said carbocyclyl, said aryl, or said heterocyclyl portion of R$^1$ is optionally substituted with one to five substituents independently chosen from halo, C$_1$-C$_4$ alkyl, C$_1$-C$_4$ haloalkyl, cyano, hydroxyl, —O—(C$_1$-C$_4$ alkyl), heterocyclyl, —N(R$^8$)$_2$, and —N(R$^8$)—C(O)—O—(C$_1$-C$_4$ alkyl);

R$^2$ is a bond or —O—;

R$^3$ is chosen from C$_1$-C$_6$ alkyl, —(C$_0$-C$_6$ alkylene)-(C$_3$-C$_8$ carbocyclyl), and —(C$_0$-C$_6$ alkylene)-(monocyclic O- or S-containing heterocyclyl), wherein:

a carbon atom of said monocylic heterocyclyl is the attachment point for said monocylic heterocyclyl;

any said alkyl or said alkylene portion of R$^3$ is optionally substituted with one to five substituents independently chosen from halo, cyano, hydroxyl, C$_1$-C$_4$ alkyl, —O—(C$_1$-C$_4$ alkyl), —O—(C$_3$-C$_8$ cycloalkyl), and —S(O)$_p$—(C$_1$-C$_4$ alkyl); and any said carbocyclyl or said heterocyclyl portion of R$^3$ is optionally substituted with one to five substituents independently chosen from halo, cyano, oxo, hydroxyl, C$_1$-C$_4$ alkyl, C$_1$-C$_4$ haloalkyl, —O—(C$_1$-C$_4$ alkyl), —O—(C$_1$-C$_4$ haloalkyl), —C(O)—(C$_1$-C$_4$ alkyl), —C(O)—O—(C$_1$-C$_4$ alkyl), —S(O)$_p$—(C$_1$-C$_4$ alkyl), —O-phenyl, —(C$_1$-C$_4$ alkyl)-phenyl, and morpholin-4-yl;

R$^4$ is chosen from hydrogen, C$_1$-C$_4$ alkyl, C$_2$-C$_4$ alkenyl, C$_2$-C$_4$ alkynyl, C$_3$-C$_6$ cycloalkyl, —C(O)—(C$_1$-C$_4$ alkyl), halo, and cyano, wherein:

any said alkyl portion of R$^4$ is optionally substituted with hydroxyl;

each R$^8$ is independently chosen from hydrogen and C$_1$-C$_4$ alkyl, or two R$^8$ together with the nitrogen atom to which they are joined form a heterocyclyl;

each R$^9$ is independently chosen from hydrogen, C$_1$-C$_4$ alkyl, and hydroxyl;

n is 0, 1, 2, 3, 4, 5, or 6; and p is 0, 1, or 2.

In some embodiments, p is 0. In some embodiments, p is 1. In some embodiments, p is 2. In some embodiments, p is 1 or 2.

In some embodiments, n is 0. In some embodiments, n is 1. In some embodiments, n is 2. In some embodiments, n is 3. In some embodiments, n is 4. In some embodiments, n is 5. In some embodiments, n is 6. In some embodiments, n is 1, 2, or 3.

In some embodiments, R$^4$ is cyano, methyl, chloro, bromo, fluoro, but-2-ynyl, or butan-2-onyl.

In some embodiments, ring A is chosen from 6-membered monocyclic aryl, 5-membered heteroaryl, 6-membered monocyclic heteroaryl, 9-membered bicyclic heterocyclyl, and 10-membered bicyclic heterocyclyl.

For example, in some embodiments, ring A is chosen from phenyl, pyrrolyl, pyrazolyl, imidazolyl, thiazolyl, isothiazolyl, oxazolyl, isoxazolyl, thiophenyl, 1,2,4-thiadiazolyl, 1,3,4-thiadiazolyl, 1,2,3-triazolyl, pyridinyl, pyrimidinyl, pyrazinyl,

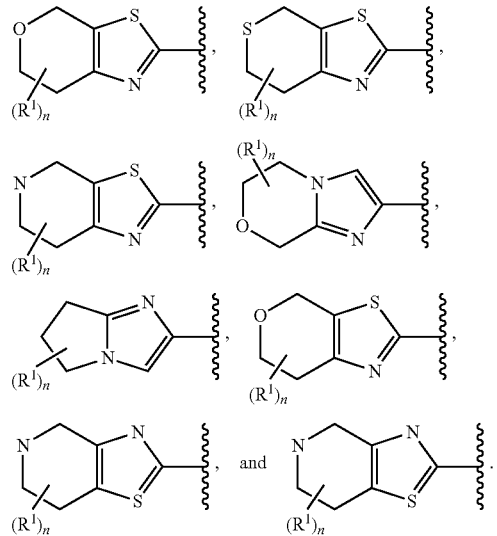

For example, in some embodiments, ring A is chosen from:

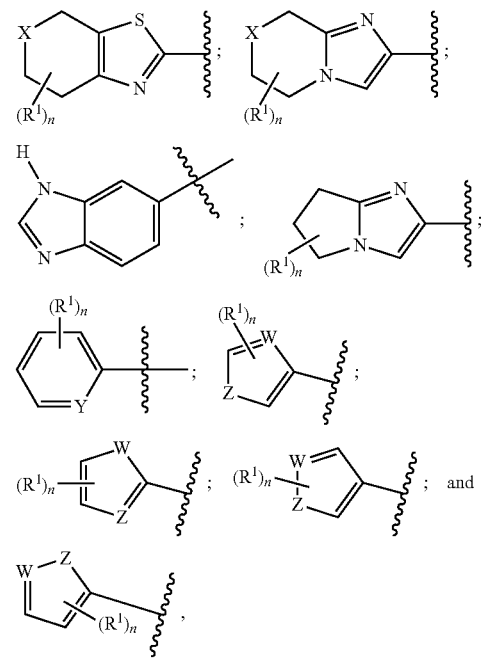

wherein:

X is chosen from O, N, and S(O)$_p$;

Y is CH or N;

W is chosen from CH, N, S, and O;

Z is chosen from CH, NH, S, and O; and p is 0, 1, or 2.

In some embodiments, ring A is chosen from

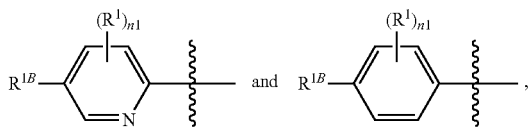 and , wherein:
R$^{1B}$ is chosen from hydrogen, halo, cyano, C$_1$-C$_4$ alkyl, —O—(C$_1$-C$_4$ alkyl), —C(O)—(C$_1$-C$_4$ alkyl), —C(O)—(C$_3$-C$_6$ cycloalkyl), —C(O)—O—(C$_1$-C$_4$ alkyl), —N(R$^8$)—C(O)—(C$_1$-C$_4$ alkyl), —S(O)$_p$—(C$_1$-C$_4$ alkyl), C$_3$-C$_6$ cycloalkyl, and 3- to 6-membered heterocyclyl, wherein:
  any said alkyl portion of R$^{1B}$ is optionally substituted with one to five substituents independently chosen from halo and cyano;
  any said cycloalkyl or said heterocyclyl portion of R$^{1B}$ is optionally substituted with one to five substituents independently chosen from halo, —N(R$^8$)$_2$, C$_1$-C$_4$ alkyl, heterocyclyl, and C$_1$-C$_4$ haloalkyl;
p is 0, 1, or 2; and
when R$^{1B}$ is hydrogen, then n1 is 0, 1, 2, 3, 4, 5, or 6, and, when R$^{1B}$ is not hydrogen, then n1 is 0, 1, 2, 3, 4, or 5.

In some embodiments, ring A is chosen from:

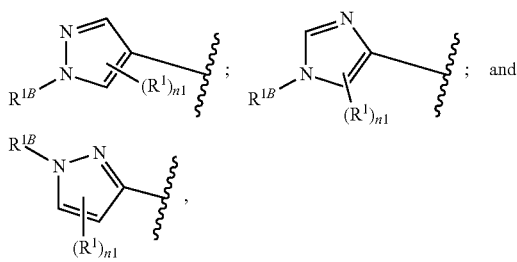

wherein:
R$^{1B}$ is chosen from C$_1$-C$_4$ alkyl, C$_3$-C$_6$ cycloalkyl, —(C$_0$-C$_4$ alkylene)-aryl, heterocyclyl, and —S(O)$_p$—(C$_1$-C$_4$ alkyl), wherein:
  any said alkyl portion of R$^{1B}$ is optionally substituted with one to five substituents independently chosen from halo and cyano;
p is 0, 1, or 2;
each R$^1$ is independently chosen from C$_1$-C$_4$ alkyl, C$_3$-C$_6$ cycloalkyl, halo, cyano, and —N(R$^8$)$_2$, wherein:
  any said alkyl portion of R$^{1B}$ is optionally substituted with one to five substituents independently chosen from halo and cyano;
each R$^8$ is independently chosen from C$_1$-C$_4$ alkyl; and
when R$^{1B}$ is hydrogen, then n1 is 0, 1, 2, 3, 4, 5, or 6, and, when R$^{1B}$ is not hydrogen, then n1 is 0, 1, 2, 3, 4, or 5.

In some embodiments, ring A is chosen from:

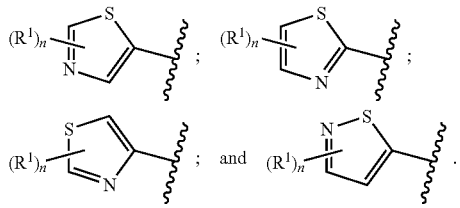

In some non-limiting embodiments, each R$^1$ is independently chosen from C$_1$-C$_4$ alkyl, C$_3$-C$_6$ cycloalkyl, —O—(C$_1$-C$_4$ alkyl), —C(O)-heterocyclyl, and cyano, wherein any said alkyl portion of R$^1$ is optionally substituted with one to five substituents independently chosen from halo, hydroxyl, and cyano.

In some embodiments, ring A is chosen from:

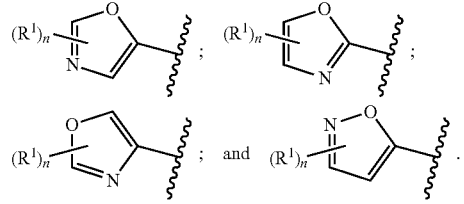

In some non-limiting embodiments, each R$^1$ is independently chosen from C$_1$-C$_4$ alkyl optionally substituted with one to five substituents independently chosen from halo, hydroxyl, and cyano. In some embodiments, ring A is chosen from

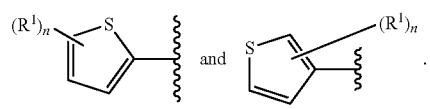

In some non-limiting embodiments, each R$^1$ is independently chosen from C$_1$-C$_4$ alkyl and cyano, wherein any said alkyl portion of R$^1$ is optionally substituted with one to five substituents independently chosen from halo, hydroxyl, and cyano.

In some embodiments, each R$^1$ is independently chosen from tetrahydropyranyl, tetrahydrofuranyl, 3,6-dihydro-2H-pyranyl, piperidinyl, piperazinyl, oxetanyl, cyano, C$_1$-C$_4$ alkyl, —S(O)—(C$_1$-C$_4$ alkyl), —S(O)$_2$—(C$_1$-C$_4$ alkyl), —C(O)—(C$_1$-C$_4$ alkyl), —C(O)-heterocyclyl, —O—(C$_1$-C$_4$ alkyl), halo, C$_3$-C$_6$ cycloalkyl, —O—(C$_3$-C$_6$ cycloalkyl), —N(CH$_3$)$_2$, Si(CH$_3$)$_2$OH, —NH—C(O)—CH$_3$, —O—(C$_0$-C$_4$ alkylene)-aryl, and morpholinyl, wherein:
  said piperidinyl is optionally substituted with one substituent chosen from morpholinyl, —O—(C$_1$-C$_4$ alkyl), C$_1$-C$_4$ alkyl, and C$_1$-C$_4$ haloalkyl or one or two substituents independently chosen from halo;
  said tetrahydropyranyl or tetrahydrofuranyl is optionally substituted with one substituent chosen from hydroxyl and —O—(C$_1$-C$_4$ alkyl);
  said oxetanyl is optionally substituted with one substitutent chosen from C$_1$-C$_4$ alkyl;
  said piperazinyl is optionally substituted with one substituent chosen from C$_1$-C$_4$ alkyl and halo;
  any said cycloalkyl portion of R$^1$ is optionally substituted with one substituent chosen from cyano and hydroxyl;
  any said alkyl portion of R$^1$ is optionally substituted with one to five substituents independently chosen from halo, cyano, hydroxyl, and —O—(C$_1$-C$_4$ alkyl).

In some embodiments, R$^3$ is chosen from C$_1$-C$_6$ alkyl, —(C$_0$-C$_3$ alkylene)-(C$_3$-C$_6$ carbocyclyl), and —(C$_0$-C$_3$ alkylene)-(monocyclic O- or S-containing heterocyclyl), wherein:
  any said alkyl or said alkylene portion of R$^3$ is optionally substituted with one to five substituents independently chosen from halo, cyano, and hydroxyl; and any said carbocyclyl or said heterocyclyl portion of $R^3$ is optionally substituted with one to four substituents independently chosen from halo, cyano, hydroxyl, $C_1$-$C_4$ alkyl, $C_1$-$C_4$ haloalkyl, —O—($C_1$-$C_4$ alkyl), —O—($C_1$-$C_4$ haloalkyl), —C(O)—($C_1$-$C_4$ alkyl), —C(O)—O—($C_1$-$C_4$ alkyl), —S(O)$_p$—($C_1$-$C_4$ alkyl), —O-phenyl, —($C_1$-$C_4$ alkyl)-phenyl, and morpholin-4-yl.

For example, in some embodiments, $R^3$ is chosen from cyclobutyl, cyclopropyl, cyclohexanyl, oxetanyl, thietanyl, tetrahydrofuranyl, and tetrahydropyranyl. In some embodiments, $R^3$ is chosen from —($C_1$ alkylene)-tetrahydropyranyl, —($C_1$ alkylene)-tetrahydrofuranyl, —($C_1$ or $C_2$ alkylene)-oxetanyl, —($C_1$ or $C_2$ alkylene)-cyclopropyl, —($C_1$ or $C_2$ alkylene)-cyclobutyl, and —($C_1$ or $C_2$ alkylene)-cyclohexanyl. In some embodiments, said cyclopropyl, said cylobutyl, or said cyclohexanyl group is independently substituted by one to four substituents independently chosen from halo, hydroxyl, and cyano.

In some embodiments, $R^3$ is chosen from cyclobutyl, cyclopropyl, and cyclohexanyl, wherein said cyclobutyl, said cyclopropyl, or said cyclohexanyl is independently substituted by one to four halo groups. In some embodiments, $R^3$ is chosen from cyclobutyl, cyclopropyl, and cyclohexanyl, wherein said cyclobutyl, said cyclopropyl, or said cyclohexanyl is substituted by one cyano or hydroxyl group. In some embodiments, $R^3$ is chosen from oxetanyl and —($C_1$ alkylene)-oxetanyl, wherein said oxetanyl portion of $R^3$ is substituted with $C_1$-$C_4$ alkyl.

In some embodiments, $R^3$ is $C_1$-$C_6$ alkyl. In some embodiments, $R^3$ is $C_1$-$C_6$ alkyl independently substituted with one to four halo groups.

In some embodiments, the compound is a compound of Formula (I) chosen from the compounds in Table 1.

In another aspect, the present disclosure features a pharmaceutical composition comprising a compound of Formula (I) (e.g., a compound in Table 1) or a pharmaceutically acceptable salt thereof, and a pharmaceutically acceptable carrier.

Table 1 below shows the structures of compounds described herein.

TABLE 1

| # | Structure | LCMS (M + 1) | $^1$H NMR |
|---|-----------|--------------|-----------|
| 1 | 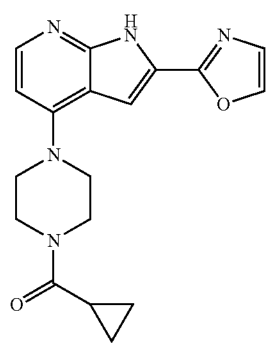 [SMILES: O=C(C1CC1)N1CCN(c2ccnc3[nH]c(-c4ncco4)cc23)CC1] | 338 | $^1$H NMR (400 MHz, DMSO-d6) δ 8.24 (d, J = 0.9 Hz, 1H), 8.06 (d, J = 5.5 Hz, 1H), 7.42 (d, J = 0.8 Hz, 1H), 7.18 (s, 1H), 6.48 (d, J = 5.6 Hz, 1H), 3.93 (s, 2H), 3.71 (s, 2H), 3.56 (s, 2H), 3.48 (s, 2H), 2.02 (tt, J = 7.7, 4.9 Hz, 1H), 0.82-0.69 (m, 4H). |
| 2 | 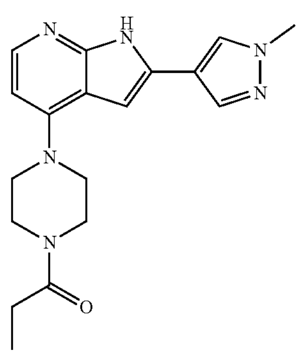 [SMILES: CCC(=O)N1CCN(c2ccnc3[nH]c(-c4cnn(C)c4)cc23)CC1] | 339 | $^1$H-NMR (400 MHz, DMSO-d$_6$) δ ppm 11.72 (s, 1H), 8.13 (s, 1H), 7.94-7.89 (m, 2H), 6.66 (d, 1H, J = 2.0 Hz), 6.41 (d, 1H, J = 5.2 Hz), 3.88 (s, 3H), 3.67-3.65 (m, 4H), 3.40-3.33 (m, 4H), 2.38 (q, 2H, J = 7.2 Hz), 1.02 (t, 3H, J = 7.2 Hz). |
| 3 | 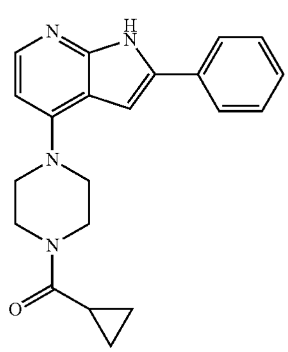 [SMILES: O=C(C1CC1)N1CCN(c2ccnc3[nH]c(-c4ccccc4)cc23)CC1] | 347 | $^1$H NMR (400 MHz, DMSO) δ 13.18 (s, 1H), 8.03 (d, J = 7.2 Hz, 1H), 7.96-7.91 (m, 2H), 7.52 (t, 3 = 7.7 Hz, 2H), 7.46 (d, J = 2.0 Hz, 1H), 7.41 (d, J = 7.4 Hz, 2H), 6.77 (d, J = 7.3 Hz, 1H), 4.05 (d, J = 24.2 Hz, 4H), 3.77 (s, 2H), 1.99 (s, 1H), 0.79 (dd, J = 10.7, 3.3 Hz, 4H). |

TABLE 1-continued

| # | Structure | LCMS (M + 1) | ¹H NMR |
|---|---|---|---|
| 4 | 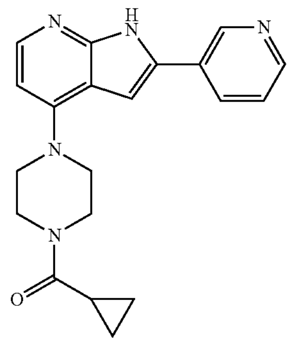 | 348 | ¹H NMR (400 MHz, DMSO) δ 13.28 (s, 1H), 9.21 (d, J = 1.9 Hz, 1H), 8.61 (dd, J = 4.8, 1.4 Hz, 1H), 8.40-8.32 (m, 1H), 8.07 (d, J = 7.2 Hz, 1H), 7.62 (dd, J = 8.1, 4.9 Hz, 2H), 6.78 (d, J = 7.2 Hz, 1H), 4.05 (d, J = 21.4 Hz, 7H), 3.78 (s, 3H), 2.00 (s, 1H), 0.87-0.69 (m, 4H). |
| 5 | 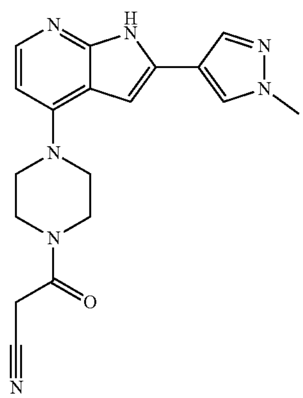 [SMILES: Cn1cc(-c2cc3c(N4CCN(C(=O)CC#N)CC4)ccnc3[nH]2)cn1] | 350 | ¹H NMR (400 MHz, DMSO) δ 12.99 (s, 1H), 8.20 (s, 1H), 8.03-7.97 (m, 2H), 7.10 (d, J = 2.0 Hz, 1H), 6.76 (d, J = 7.2 Hz, 1H), 4.14 (s, 2H), 4.01-3.94 (m, 4H), 3.92 (s, 3H), 3.78-3.72 (m, 2H), 3.71-3.62 (m, 2H). |
| 6 | 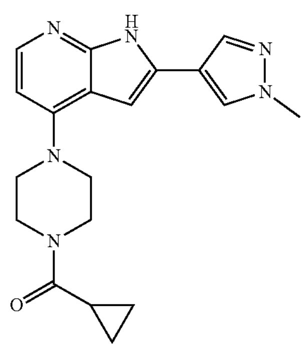 [SMILES: Cn1cc(-c2cc3c(N4CCN(C(=O)C5CC5)CC4)ccnc3[nH]2)cn1] | 351 | ¹H-NMR (400 MHz, DMSO-d₆) δ ppm 11.73 (s, 1H), 8.13 (s, 1H), 7.94 (s, 1H), 7.90 (d, 1H, J = 4.2 Hz), 6.67 (d, 1H, J = 1.6 Hz), 6.42 (d, 1H, J = 5.6 Hz), 3.90 (br. s., 2H), 3.88 (s, 3H), 3.69 (br. s., 2H), 3.44 (br. s., 2H), 3.34 (br. s., 2H), 2.05-2.02 (m, 1H), 0.79-0.73 (m, 4H). |
| 7 | 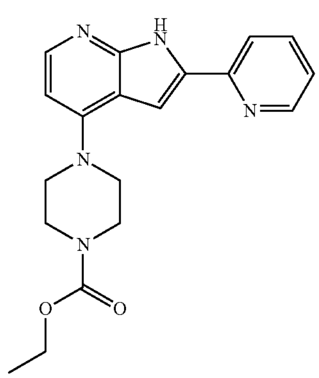 [SMILES: CCOC(=O)N1CCN(c2ccnc3[nH]c(-c4ccccn4)cc23)CC1] | 352 | ¹H-NMR (400 MHz, d₆-DMSO) δ ppm 11.98 (s, 1H), 8.60 (d, 1H, J = 4.0 Hz), 8.04 (d, 1H, J = 8.0 Hz), 8.00 (d, 1H, J = 6.0 Hz), 7.87-7.83 (m, 1H), 7.29-7.25 (m, 2H), 6.44 (d, 1H, J = 5.6 Hz), 4.08 (q, 2H, J = 7.2 Hz), 3.60-3.59 (m, 4H), 3.46-3.43 (m, 4H), 1.21 (t, 3H, J = 7.2 Hz). |

TABLE 1-continued

| # | Structure | LCMS (M + 1) | ¹H NMR |
|---|---|---|---|
| 8 | 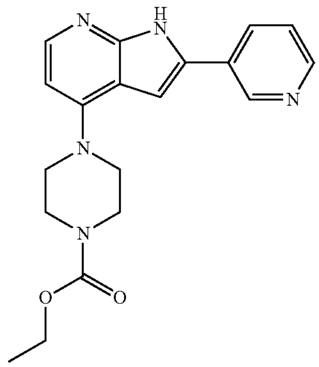 [SMILES: CCOC(=O)N1CCN(c2ccnc3[nH]c(-c4cccnc4)cc23)CC1] | 352 | ¹H-NMR (500 MHz, 6d-DMSO) δ ppm 12.10 (s, 1H), 9.18 (d, 1H, J = 2.0 Hz), 8.48 (dd, 1H, J = 5.0, 1.5 Hz), 8.31-8.28 (m, 1H), 8.00 (d, 1H, J = 5.5 Hz), 7.47 (dd, 1H, J = 8.0, 4.5 Hz), 7.22 (d, 1H, J = 5.5 Hz), 6.46 (d, 1H, J = 5.5 Hz), 4.08 (q, 2H, J = 7.0 Hz), 3.60-3.56 (m, 2H), 3.45-3.41 (m, 4H), 1.22 (t, 2H, J = 7.0 Hz). |
| 9 | 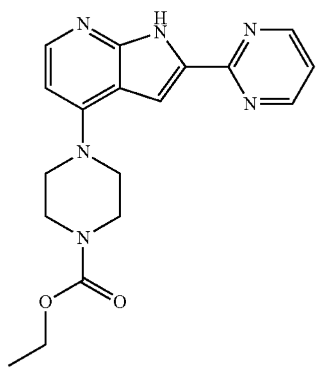 [SMILES: CCOC(=O)N1CCN(c2ccnc3[nH]c(-c4ncccn4)cc23)CC1] | 353 | ¹H-NMR (400 MHz, 6d-DMSO) δ ppm 12.14 (s, 1H), 8.84 (d, 2H, J = 5.2 Hz), 8.06 (d, 1H, J = 5.2 Hz), 7.39-7.35 (m, 2H), 6.46 (d, 1H, J = 5.2 Hz), 4.09 (q, 2H, J = 7.2 Hz), 3.63-3.58 (m, 4H), 3.51-3.46 (m, 4H), 1.22 (t, 3H, J = 7.2 Hz). |
| 10 | 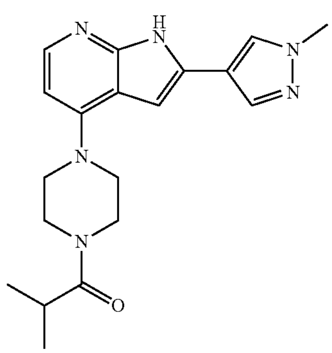 [SMILES: CC(C)C(=O)N1CCN(c2ccnc3[nH]c(-c4cnn(C)c4)cc23)CC1] | 353 | ¹H NMR (400 MHz, DMSO) δ 12.99 (s, 1H), 8.20 (s, 1H), 8.03-7.97 (m, 2H), 7.10 (d, J = 2.0 Hz, 1H), 6.76 (d, J = 7.2 Hz, 1H), 4.14 (s, 2H), 4.01-3.94 (m, 4H), 3.92 (s, 3H), 3.78-3.72 (m, 2H), 3.71-3.62 (m, 2H). |
| 11 | 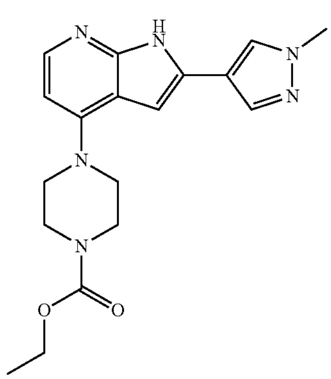 [SMILES: CCOC(=O)N1CCN(c2ccnc3[nH]c(-c4cnn(C)c4)cc23)CC1] | 355 | ¹H NMR (400 MHz, DMSO) δ 12.85 (s, 1H), 8.20 (s, 1H), 7.98 (t, J = 3.6 Hz, 2H), 7.10 (d, J = 1.9 Hz, 1H), 6.75 (d, J = 7.2 Hz, 1H), 4.14-4.08 (m, 3H), 3.95-3.90 (m, 8H), 3.65 (s, 4H), 1.23 (t, J = 7.1 Hz, 3H). |

TABLE 1-continued

| # | Structure | LCMS (M + 1) | ¹H NMR |
|---|---|---|---|
| 12 | 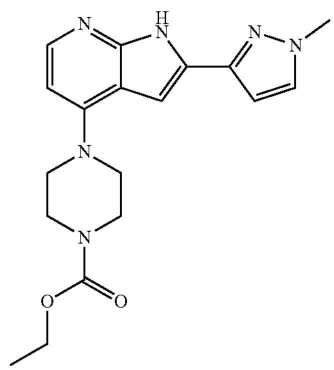 [SMILES: CCOC(=O)N1CCN(c2ccnc3[nH]c(-c4ccn(C)n4)cc23)CC1] | 355 | ¹H-NMR (500 MHz, 6d-DMSO) δ ppm 11.80 (s, 1H), 7.94 (d, 1H, J = 5.0 Hz), 7.74 (d, 1H, J = 2.0 Hz), 6.77-6.75 (m, 2H), 6.43 (d, 1H, J = 5.0 Hz), 4.08 (q, 2H, J = 7.0 Hz), 3.89 (s, 3H), 3.60-3.59 (m, 4H), 3.39-3.37 (m, 4H), 1.22 (t, 3H, J = 7.0 Hz). |
| 13 | 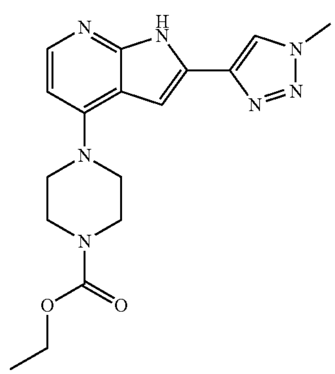 [SMILES: CCOC(=O)N1CCN(c2ccnc3[nH]c(-c4cn(C)nn4)cc23)CC1] | 356 | ¹H-NMR (400 MHz, 6d-DMSO) δ ppm 12.02 (br s, 1H), 8.37 (s, 1H), 8.15 (s, 1H), 7.98 (d, 1H, J = 5.6 Hz), 6.90 (s, 1H), 6.46 (d, 1H, J = 5.6 Hz), 4.13 (s, 3H), 4.09 (q, 2H, J = 7.2 Hz), 3.65-3.55 (m, 4H), 3.47-3.38 (m, 4H), 1.22 (t, 3H, J = 7.2 Hz). |
| 14 | 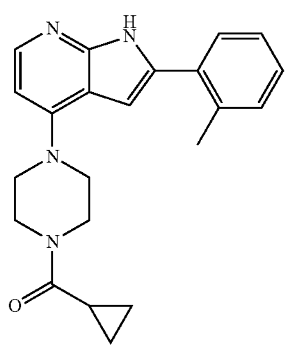 [SMILES: Cc1ccccc1-c1cc2c(N3CCN(C(=O)C4CC4)CC3)ccnc2[nH]1] | 361 | ¹H NMR (400 MHz, DMSO) δ 12.89 (s, 1H), 7.99 (d, J = 7.1 Hz, 1H), 7.87 (d, J = 8.8 Hz, 3H), 7.49 (d, J = 7.1 Hz, 3H), 7.45-7.34 (m, 4H), 7.30 (s, 1H), 7.17 (d, J = 8.9 Hz, 3H), 6.73 (d, J = 7.1 Hz, 1H), 5.19 (s, 2H), 3.98 (d, J = 17.4 Hz, 5H), 3.75 (s, 1H), 2.00 (s, 1H), 0.79 (t, J = 5.8 Hz, 5H). |
| 15 | 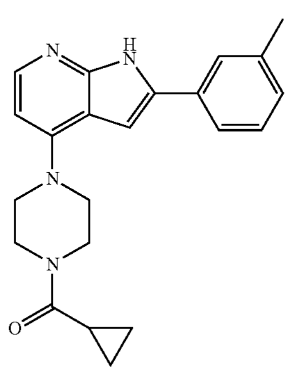 [SMILES: Cc1cccc(-c2cc3c(N4CCN(C(=O)C5CC5)CC4)ccnc3[nH]2)c1] | 361 | ¹H NMR (400 MHz, DMSO) δ 13.07 (s, 1H), 8.01 (d, J = 7.2 Hz, 1H), 7.78 (s, 2H), 7.45-7.37 (m, 2H), 7.23 (s, 1H), 6.76 (d, J = 7.3 Hz, 1H), 4.04 (d, J = 23.2 Hz, 4H), 2.44-2.37 (m, 3H), 1.99 (ddd, J = 12.6, 7.4, 5.3 Hz, 1H), 0.85-0.74 (m, 4H). |

TABLE 1-continued

| # | Structure | LCMS (M + 1) | ¹H NMR |
|---|-----------|--------------|--------|
| 16 | 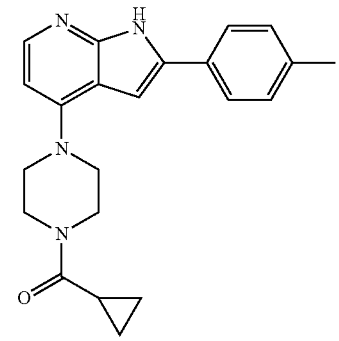 [SMILES: Cc1ccc(-c2cc3c(N4CCN(C(=O)C5CC5)CC4)ccnc3[nH]2)cc1] | 361 | ¹H NMR (400 MHz, DMSO) δ 13.11 (s, 1H), 8.02 (d, J = 7.2 Hz, 1H), 7.83 (d, J = 8.2 Hz, 2H), 7.39 (d, J = 1.7 Hz, 1H), 7.33 (d, J = 8.0 Hz, 2H), 6.75 (d, J = 7.2 Hz, 1H), 4.05 (s, 3H), 4.00 (s, 4H), 3.76 (s, 3H), 2.36 (s, 3H), 2.04-1.97 (m, 1H), 0.79 (t, J = 5.6 Hz, 5H). |
| 17 | 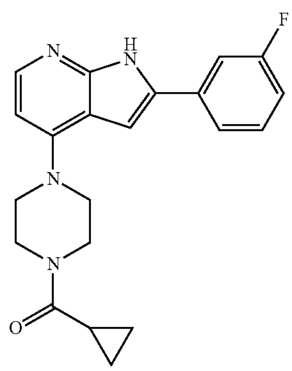 [SMILES: O=C(C1CC1)N1CCN(c2ccnc3[nH]c(-c4cccc(F)c4)cc23)CC1] | 365 | ¹H NMR (400 MHz, DMSO) δ 13.19 (s, 1H), 8.05 (d, J = 7.2 Hz, 1H), 7.86 (d, J = 10.6 Hz, 1H), 7.80 (d, J = 7.9 Hz, 1H), 7.57 (d, J = 6.2 Hz, 2H), 7.23 (d, J = 2.0 Hz, 1H), 6.77 (d, J = 7.2 Hz, 1H), 4.05 (d, J = 22.1 Hz, 6H), 3.77 (s, 2H), 2.00 (s, 1H), 0.79 (d, J = 7.5 Hz, 4H). |
| 18 | 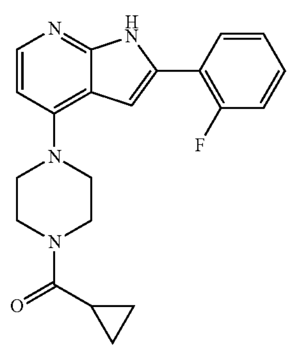 [SMILES: O=C(C1CC1)N1CCN(c2ccnc3[nH]c(-c4ccccc4F)cc23)CC1] | 365 | ¹H NMR (400 MHz, DMSO) δ 12.86 (s, 1H), 8.06 (d, J = 7.1 Hz, 1H), 7.94 (d, J = 1.5 Hz, 1H), 7.41 (ddd, J = 14.8, 12.9, 9.1 Hz, 3H), 7.30 (s, 1H), 6.75 (d, J = 7.1 Hz, 1H), 3.99 (d, J = 23.2 Hz, 6H), 3.76 (s, 2H), 2.51 (dt, J = 3.6, 1.8 Hz, 4H), 2.03-1.94 (m, 1H), 0.83-0.73 (m, 4H). |
| 19 | 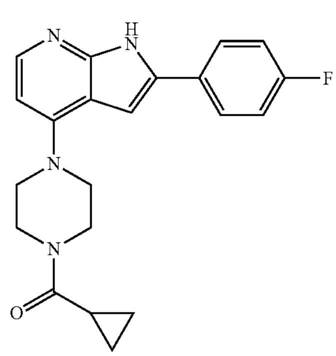 [SMILES: O=C(C1CC1)N1CCN(c2ccnc3[nH]c(-c4ccc(F)cc4)cc23)CC1] | 365 | |

TABLE 1-continued

| # | Structure | LCMS (M + 1) | $^1$H NMR |
|---|---|---|---|
| 20 | 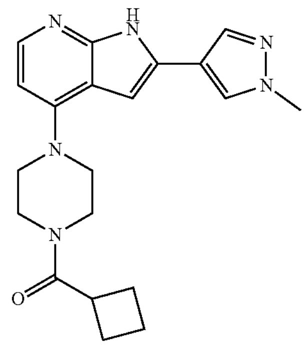 [SMILES: Cn1cc(-c2cc3c(N4CCN(C(=O)C5CCC5)CC4)ccnc3[nH]2)cn1] | 365 | $^1$H NMR (400 MHz, DMSO) δ 12.81 (s, 1H), 8.21 (s, 1H), 7.98 (d, J = 7.1 Hz, 2H), 7.10 (d, J = 1.6 Hz, 1H), 6.75 (d, J = 7.2 Hz, 1H), 3.92 (s, 6H), 3.71 (s, 2H), 3.61 (s, 2H), 3.42 (p, J = 8.3 Hz, 1H), 2.19 (ddd, J = 20.8, 16.4, 9.0 Hz, 2H), 1.94 (dd, J = 18.7, 9.4 Hz, 1H), 1.78 (dd, J = 19.4, 9.5 Hz, 1H). |
| 21 | 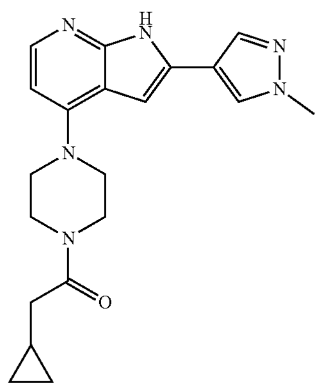 [SMILES: Cn1cc(-c2cc3c(N4CCN(C(=O)CC5CC5)CC4)ccnc3[nH]2)cn1] | 365 | $^1$H NMR (400 MHz, DMSO) δ 12.96 (s, 1H), 8.20 (s, 1H), 7.98 (dd, J = 6.4, 3.8 Hz, 2H), 7.10 (d, J = 2.0 Hz, 1H), 6.75 (d, J = 7.3 Hz, 1H), 3.95 (d, J = 4.7 Hz, 4H), 3.92 (s, 3H), 3.74 (s, 4H), 2.33 (d, J = 6.7 Hz, 2H), 1.01 (s, 1H), 0.51-0.46 (m, 2H), 0.18-0.12 (m, 2H). |
| 22 | 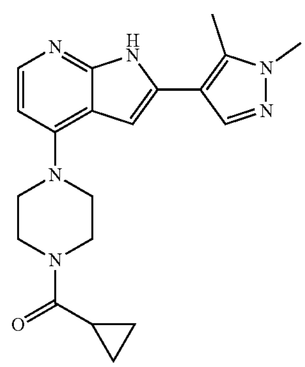 [SMILES: Cc1c(-c2cc3c(N4CCN(C(=O)C5CC5)CC4)ccnc3[nH]2)cnn1C] | 365 | |
| 23 | 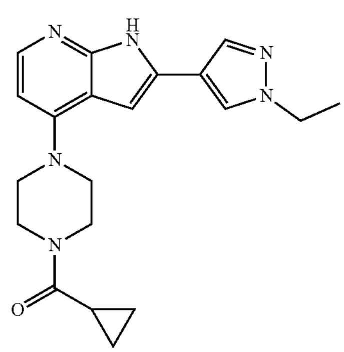 [SMILES: CCn1cc(-c2cc3c(N4CCN(C(=O)C5CC5)CC4)ccnc3[nH]2)cn1] | 365 | $^1$H NMR (400 MHz, DMSO-d$_6$) δ ppm 11.70 (s, 1H), 8.19 (s, 1H), 7.95 (s, 1H), 7.90 (d, 1H, J = 5.6 Hz), 6.67 (s, 1H), 6.42 (d, 1H, J = 5.6 Hz), 4.19-4.15 (q, 2H, J = 6.8 Hz), 3.90 (br. s., 2H), 3.69 (br. s., 2H), 3.43 (br. s., 2H), 3.41 (br. s., 2H), 2.05-2.01 (m, 1H), 1.41 (t, 1H, J = 7.2 Hz), 0.78-0.74 (m, 4H). |

TABLE 1-continued

| # | Structure | LCMS (M + 1) | ¹H NMR |
|---|---|---|---|
| 24 | 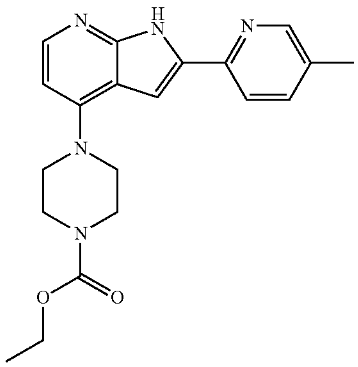 [SMILES: CCOC(=O)N1CCN(c2ccnc3[nH]c(-c4ccc(C)cn4)cc23)CC1] | 366 | ¹H-NMR (400 MHz, 6d-DMSO) δ ppm 11.94 (s, 1H), 8.45 (s, 1H), 8.19 (s, 1H), 7.99 (d, 1H, J = 5.2 Hz), 7.95 (d, 1H, J = 4.4 Hz), 7.70-7.67 (m, 1H), 7.20 (s, 1H), 6.44 (d, 1H, J = 5.6 Hz), 4.09 (q, 2H, J = 7.2 Hz), 3.61-3.58 (m, 4H), 3.46-3.42 (m, 4H), 2.33 (s, 3H), 1.22 (t, 3H, J = 7.2 Hz). |
| 25 | 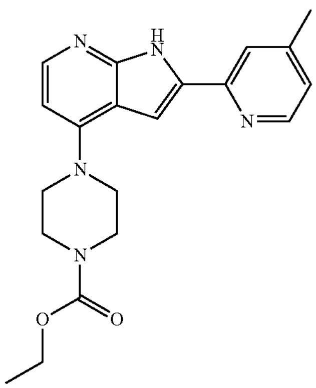 | 366 | ¹H-NMR (400 MHz, 6d-DMSO) δ ppm 11.91 (s, 1H), 8.46 (d, 1H, J = 5.2 Hz), 8.32 (s, 1H), 8.00 (d, 1H, J = 5.6 Hz), 7.92 (s, 1H), 7.24 (d, 1H, J = 2.0 Hz), 7.13 (d, 1H, J = 4.8 Hz), 6.45 (d, 1H, J = 5.6 Hz), 4.09 (q, 2H, J = 6.8 Hz), 3.61-3.60 (m, 4H), 3.46-3.44 (m, 4H), 2.38 (s, 3H), 1.22 (t, 3H, J = 6.8 Hz). |
| 26 | 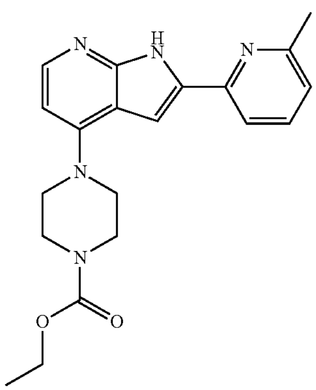 | 366 | ¹H-NMR (400 MHz, 6d-DMSO) δ ppm 11.93 (s, 1H), 8.14 (s, 1H), 8.02 (d, 1H, J = 4.0 Hz), 7.85 (d, 1H, J = 8.0 Hz), 7.76-7.72 (m, 1H), 7.22 (s, 1H), 7.15 (d, 1H, J = 3.6 Hz), 6.46 (d, 1H, J = 5.2 Hz), 4.09 (q, 2H, J = 7.2 Hz), 3.62-3.58 (m, 4H), 3.48-3.42 (m, 4H), 2.54 (s, 3H), 1.20 (t, 3H, J = 7.2 Hz). |
| 27 | 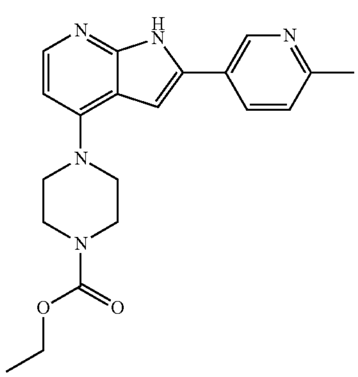 [SMILES: CCOC(=O)N1CCN(c2ccnc3[nH]c(-c4ccc(C)nc4)cc23)CC1] | 366 | ¹H-NMR (500 MHz, 6d-DMSO) δ ppm 12.03 (s, 1H), 9.03 (d, 1H, J = 2.5 Hz), 8.20-8.18 (m, 1H), 7.97 (d, 1H, J = 6.0 Hz), 7.31 (d, 1H, J = 8.5 Hz), 7.14 (d, 1H, J = 1.5 Hz), 6.45 (d, 1H, J = 5.5 Hz), 4.09 (q, 2H, J = 7.5 Hz), 3.61-3.58 (m, 4H), 3.46-3.42 (m, 4H), 2.01 (s, 3H), 1.22 (t, 3H, J = 7.0 Hz). |

TABLE 1-continued

| # | Structure | LCMS (M + 1) | ¹H NMR |
|---|-----------|--------------|--------|
| 29 | 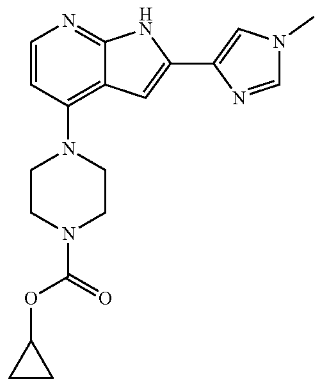 [SMILES: Cn1cnc(-c2cc3c(N4CCN(C(=O)OC5CC5)CC4)ccnc3[nH]2)c1] | 367 | ¹H-NMR (400 MHz, 6d-DMSO) δ ppm 11.66 (s, 1H), 7.89 (d, 1H, J = 5.2 Hz), 7.64 (s, 1H), 7.54 (d, 1H, J = 0.8 Hz), 6.60 (d, 1H, J = 2.0 Hz), 6.39 (d, 1H, J = 5.2 Hz), 4.02-4.01 (m, 1H), 3.69 (s, 3H), 3.58-3.52 (m, 4H), 3.34-3.31 (m, 4H), 0.66-0.63 (4H). |
| 30 | 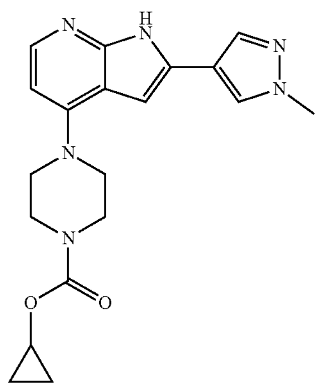 [SMILES: Cn1cc(-c2cc3c(N4CCN(C(=O)OC5CC5)CC4)ccnc3[nH]2)cn1] | 367 | |
| 31 | 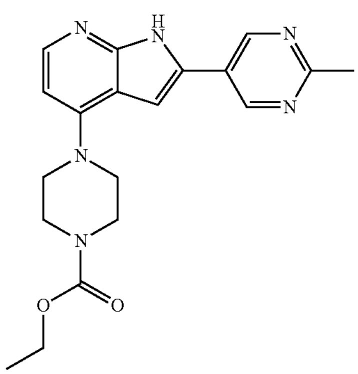 [SMILES: CCOC(=O)N1CCN(c2ccnc3[nH]c(-c4cnc(C)nc4)cc23)CC1] | 367 | ¹H-NMR (500 MHz, 6d-DMSO) δ ppm 12.16 (s, 1H), 9.23 (s, 2H), 8.01 (d, 1H, J = 5.5 Hz), 7.30 (s, 1H), 6.46 (d, 1H, J = 5.5 Hz), 4.08 (q, 2H, J = 7.0 Hz), 3.65-3.60 (m, 4H), 3.47-3.45 (m, 4H), 2.65 (s, 3H), 1.22 (t, 3H, J = 7.0 Hz). |
| 32 | 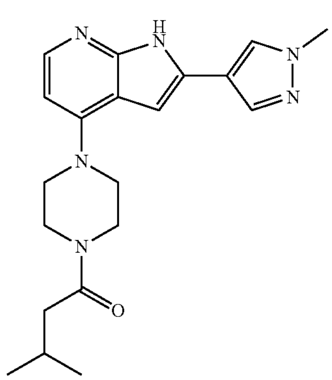 [SMILES: CC(C)CC(=O)N1CCN(c2ccnc3[nH]c(-c4cnn(C)c4)cc23)CC1] | 367 | ¹H NMR (400 MHz, DMSO) δ 12.97 (s, 1H), 8.19 (s, 1H), 8.02-7.96 (m, 2H), 7.10 (d, J = 2.0 Hz, 1H), 6.74 (d, J = 7.2 Hz, 1H), 3.95 (s, 4H), 3.91 (s, 3H), 3.75 (s, 4H), 2.26 (d, J = 6.9 Hz, 2H), 2.09-1.99 (m, 1H), 0.94 (d, J = 6.6 Hz, 6H). |

TABLE 1-continued

| # | Structure | LCMS (M + 1) | ¹H NMR |
|---|---|---|---|
| 33 | 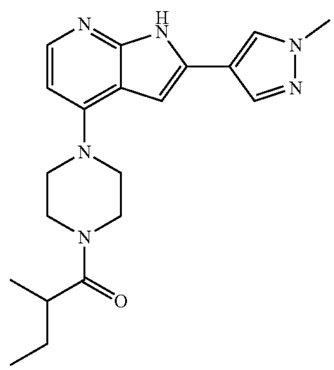 [SMILES: CCC(C)C(=O)N1CCN(c2ccnc3[nH]c(-c4cnn(C)c4)cc23)CC1] | 367 | ¹H NMR (400 MHz, DMSO) δ 12.95 (s, 1H), 8.20 (s, 1H), 7.99 (dd, J = 7.0, 3.9 Hz, 2H), 7.12 (d, J = 2.0 Hz, 1H), 6.75 (d, J = 7.2 Hz, 1H), 4.00-3.93 (m, 4H), 3.92 (s, 3H), 3.82 (s, 2H), 3.76 (d, J = 5.0 Hz, 2H), 2.74 (d, J = 6.8 Hz, 1H), 1.66-1.55 (m, 1H), 1.41-1.29 (m, 1H), 1.04 (d, J = 6.7 Hz, 3H), 0.86 (t, J = 7.4 Hz, 3H). |
| 34 | 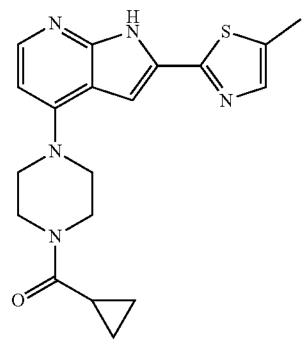 [SMILES: Cc1cnc(-c2cc3c(N4CCN(C(=O)C5CC5)CC4)ccnc3[nH]2)s1] | 368 | ¹H NMR (400 MHz, DMSO-d6) δ 12.18 (s, 1H), 8.00 (d, J = 5.5 Hz, 1H), 7.56 (s, 1H), 7.04 (s, 1H), 6.44 (d, J = 5.5 Hz, 1H), 3.90 (br. s, 2H), 3.68 (br. s, 2H), 3.47 (br. d, J = 29.8 Hz, 4H), 2.05-1.94 (m, 1H), 0.80-0.67 (m, 4H). |
| 35 | 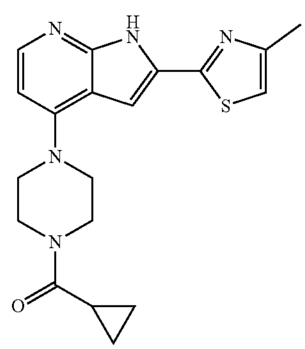 [SMILES: Cc1csc(-c2cc3c(N4CCN(C(=O)C5CC5)CC4)ccnc3[nH]2)n1] | 368 | ¹H NMR (400 MHz, DMSO-d6) δ 12.23 (s, 1H), 8.00 (d, J = 5.5 Hz, 1H), 7.27 (s, 1H), 7.09 (s, 1H), 6.44 (d, J = 5.5 Hz, 1H), 3.90 (br. s, 2H), 3.68 (br. s, 2H), 3.48 (br. d, J = 31.0 Hz, 4H), 2.41 (s, 3H), 2.08-1.89 (m, 1H), 0.82-0.65 (m, 4H). |
| 36 | 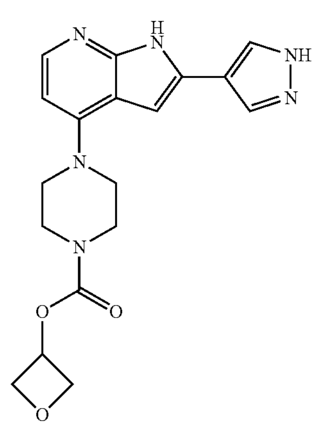 [SMILES: O=C(OC1COC1)N1CCN(c2ccnc3[nH]c(-c4cn[nH]c4)cc23)CC1] | 369 | ¹H-NMR (400 MHz, 6d-DMSO) δ ppm 12.91 (s, 1H), 11.70 (s, 1H), 8.20 (s, 1H), 8.00 (s, 1H), 7.91 (d, 1H, J = 5.2 Hz), 6.68 (s, 1H), 6.44 (d, 1H, J = 5.2 Hz), 5.34-5.30 (m, 1H), 4.80-4.78 (m, 2H), 4.54-4.51 (m, 2H), 3.68-3.66 (m, 2H), 3.59-3.57 (m, 2H), 3.40-3.38 (m, 4H). |

TABLE 1-continued

| # | Structure | LCMS (M + 1) | ¹H NMR |
|---|---|---|---|
| 37 | 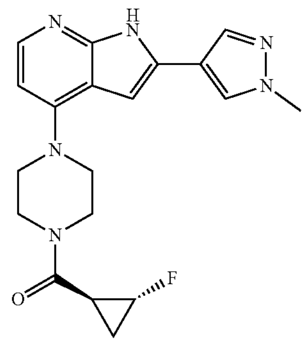 [SMILES: Cn1cc(-c2cc3c(N4CCN(C(=O)[C@@H]5C[C@H]5F)CC4)ccnc3[nH]2)cn1] | 368 | ¹H NMR (400 MHz, Methanol-d4) δ 8.01 (s, 1H), 7.95-7.87 (m, 2H), 6.71 (s, 1H), 6.54 (d, J = 5.9 Hz, 1H), 4.01 (t, J = 5.2 Hz, 2H), 3.95 (s, 3H), 3.82 (t, J = 5.2 Hz, 2H), 3.67 (q, J = 4.9 Hz, 2H), 3.58 (q, J = 6.0, 4.8 Hz, 2H), 2.54 (dddd, J = 17.7, 10.6, 6.6, 1.8 Hz, 1H), 1.47 (dddd, J = 21.7, 10.5, 6.4, 3.3 Hz, 1H), 1.30 (dq, J = 9.8, 6.3 Hz, 2H). |
| 38 | 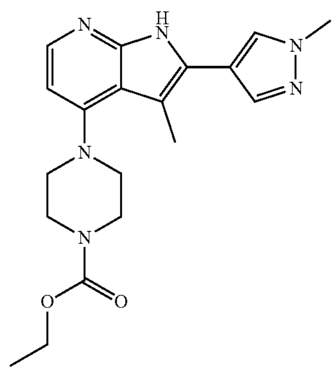 [SMILES: CCOC(=O)N1CCN(c2ccnc3[nH]c(-c4cnn(C)c4)c(C)c23)CC1] | 369 | ¹H-NMR (500 MHz, 6d-DMSO) δ ppm 11.56 (s, 1H), 8.10 (s, 1H), 7.96 (d, 1H, J = 5.5 Hz), 7.90 (s, 1H), 6.54 (d, 1H, J = 5.5 Hz), 4.08 (q, 2H, J = 7.0 Hz), 3.91 (s, 3H), 3.65-3.52 (m, 4H), 3.10-3.00 (m, 4H), 2.49 (s, 3H), 1.21 (t, 3H, J = 7.0 Hz). |
| 39 | 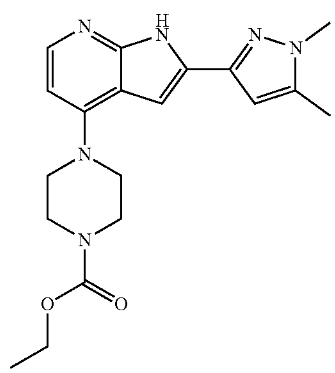 [SMILES: CCOC(=O)N1CCN(c2ccnc3[nH]c(-c4cc(C)n(C)n4)cc23)CC1] | 369 | ¹H-NMR (500 MHz, 6d-DMSO) δ ppm 11.74 (s, 1H), 7.92 (d, 1H, J = 5.5 Hz), 7.69 (d, 1H, J = 2.0 Hz), 6.55 (s, 1H), 6.41 (d, 1H, J = 5.5 Hz), 4.09 (q, 2H, J = 7.0 Hz), 3.77 (s, 3H), 3.61-3.58 (m, 4H), 3.40-3.35 (m, 4H), 2.29 (s, 3H), 1.21 (t, 3H, J = 6.5 Hz). |
| 40 | 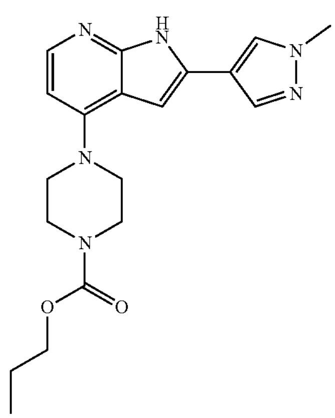 [SMILES: CCCOC(=O)N1CCN(c2ccnc3[nH]c(-c4cnn(C)c4)cc23)CC1] | 369 | ¹H-NMR (400 MHz, 6d-DMSO) δ ppm 11.71 (s, 1H), 8.12 (s, 1H), 7.93 (s, 1H), 7.90 (d, 1H, J = 5.2 Hz), 6.66 (d, 1H, J = 1.2 Hz), 6.41 (d, 1H, J = 5.6 Hz), 4.01 (t, 2H, J = 6.4 Hz), 3.87 (s, 3H), 3.60-3.58 (m, 4H), 3.37-3.35 (m, 4H), 1.63-1.58 (m, 2H), 0.91 (t, 3H, J = 7.2 Hz). |

TABLE 1-continued

| # | Structure | LCMS (M + 1) | ¹H NMR |
|---|-----------|--------------|--------|
| 41 | 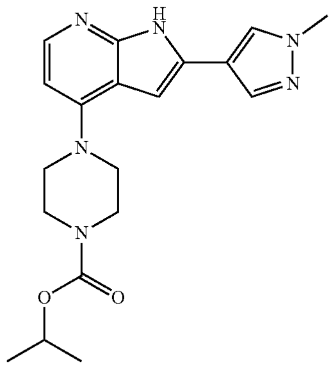 [SMILES: CC(C)OC(=O)N1CCN(c2ccnc3[nH]c(-c4cnn(C)c4)cc23)CC1] | 369 | ¹H-NMR (500 MHz, 6d-DMSO) δ ppm 11.70 (s, 1H), 8.12 (s, 1H), 7.93 (s, 1H), 7.90 (d, 1H, J = 5.0 Hz), 6.65 (d, 1H, J = 2.0 Hz), 6.41 (d, 1H, J = 6.0 Hz), 4.82 (heptet 1H, J = 6.0 Hz), 3.87 (s, 3H), 3.63-3.61 (m, 4H), 3.40-3.32 (m, 4H), 1.22 (d, 6H, J = 6.5 Hz). |
| 42 | 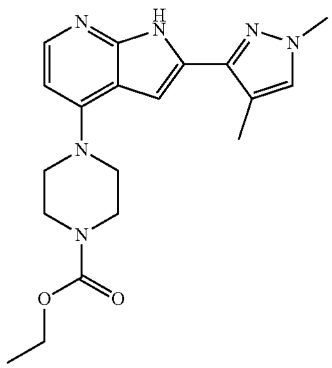 [SMILES: CCOC(=O)N1CCN(c2ccnc3[nH]c(-c4nn(C)cc4C)cc23)CC1] | 369 | ¹H-NMR (400 MHz, 6d-DMSO) δ ppm 11.55 (s, 1H), 7.94 (d, 1H, J = 5.2 Hz), 7.57 (s, 1H), 6.54 (d, 1H, J = 1.6 Hz), 6.44 (d, 1H, J = 5.6 Hz), 4.09 (q, 2H, J = 6.8 Hz), 3.85 (s, 3H), 3.62-3.58 (m, 4H), 3.40-3.37 (m, 4H), 2.22 (s, 1H), 1.21 (t, 3H, J = 6.8 Hz). |
| 43 | 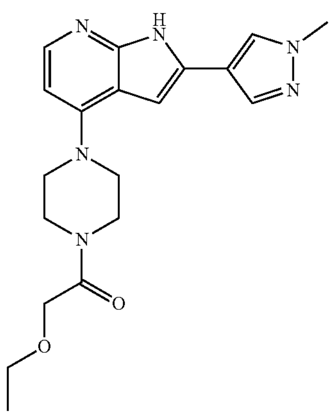 [SMILES: CCOCC(=O)N1CCN(c2ccnc3[nH]c(-c4cnn(C)c4)cc23)CC1] | 369 | ¹H NMR (400 MHz, DMSO) δ 12.89 (s, 1H), 8.20 (s, 1H), 7.99 (d, J = 6.1 Hz, 2H), 7.11 (d, J = 1.9 Hz, 1H), 6.76 (d, J = 7.2 Hz, 1H), 4.19 (s, 2H), 3.92 (s, 7H), 3.72 (s, 4H), 3.52 (q, J = 7.0 Hz, 2H), 1.16 (t, J = 7.0 Hz, 3H). |
| 44 | 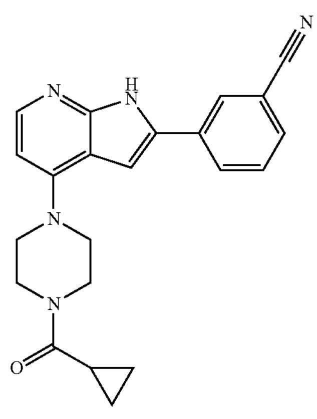 [SMILES: N#Cc1cccc(-c2cc3c(N4CCN(C(=O)C5CC5)CC4)ccnc3[nH]2)c1] | 372 | ¹H NMR (400 MHz, DMSO) δ 12.96 (s, 1H), 8.48 (s, 1H), 8.27 (d, J = 8.1 Hz, 1H), 8.05 (d, J = 6.9 Hz, 1H), 7.83 (d, J = 7.6 Hz, 1H), 7.72 (t, J = 7.9 Hz, 1H), 7.61 (s, 1H), 6.72 (d, J = 7.0 Hz, 1H), 3.97 (d, J = 26.3 Hz, 6H), 3.77 (s, 2H), 2.00 (d, J = 5.1 Hz, 1H), 0.79 (t, J = 5.9 Hz, 4H). |

TABLE 1-continued

| # | Structure | LCMS (M + 1) | ¹H NMR |
|---|---|---|---|
| 45 | 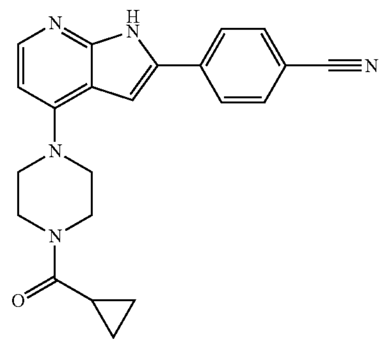 [SMILES: N#Cc1ccc(-c2cc3c(N4CCN(C(=O)C5CC5)CC4)ccnc3[nH]2)cc1] | 372 | ¹H NMR (400 MHz, DMSO) δ 13.25 (s, 1H), 13.25 (s, 1H), 8.14 (d, J = 8.6 Hz, 2H), 8.14 (d, J = 8.6 Hz, 2H), 8.06 (d, J = 7.1 Hz, 1H), 8.03 (dd, J = 25.4, 7.9 Hz, 3H), 8.00 (d, J = 8.6 Hz, 2H), 7.69 (s, 1H), 7.69 (s, 1H), 6.76 (d, J = 7.2 Hz, 1H), 6.76 (d, J = 7.2 Hz, 1H), 4.04 (d, J = 17.1 Hz, 8H), 4.04 (d, J = 17.1 Hz, 7H), 3.77 (s, 2H), 3.77 (s, 3H), 2.00 (dq, J = 7.4, 5.3 Hz, 1H), 2.00 (dq, J = 7.4, 5.3 Hz, 1H), 0.83-0.76 (m, 4H), 0.89-0.70 (m, 5H). |
| 46 | 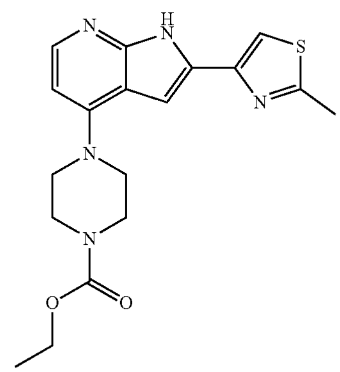 [SMILES: CCOC(=O)N1CCN(c2ccnc3[nH]c(-c4csc(C)n4)cc23)CC1] | 372 | ¹H-NMR (400 MHz, 6d-DMSO) δ ppm 11.98 (s, 1H), 7.97 (d, 1H, J = 5.6 Hz), 7.85 (s, 1H), 6.87 (d, 1H, J = 1.6 Hz), 6.44 (d, 1H, J = 5.2 Hz), 4.08 (q, 2H, J = 7.2 Hz), 3.65-3.50 (m, 4H), 3.45-3.45 (m, 4H), 2.71 (s, 3H), 1.21 (t, 3H, J = 7.2 Hz). |
| 47 | 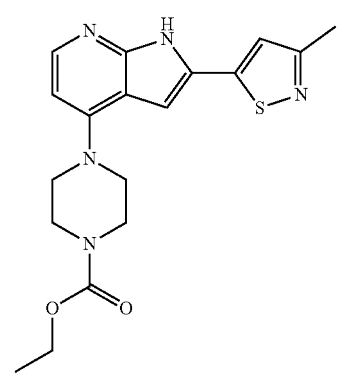 [SMILES: CCOC(=O)N1CCN(c2ccnc3[nH]c(-c4cc(C)ns4)cc23)CC1] | 372 | ¹H-NMR (400 MHz, 6d-DMSO) δ ppm 12.20 (s, 1H), 8.02 (d, 1H, J = 5.6 Hz), 7.60 (s, 1H,), 7.06 (s, 1H), 6.46 (d, 1H, J = 5.2 Hz), 4.08 (q, 2H, J = 6.8 Hz), 3.60-3.58 (m, 4H), 3.45-3.43 (m, 4H), 2.45 (s, 3H,), 1.22 (t, 3H, J = 6.8 Hz). |
| 48 | 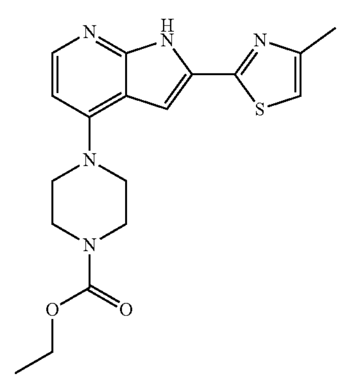 [SMILES: CCOC(=O)N1CCN(c2ccnc3[nH]c(-c4nc(C)cs4)cc23)CC1] | 372 | ¹H-NMR (400 MHz, d₆-DMSO) δ ppm 12.26 (s, 1H), 8.01 (d, 1H, J = 4.8 Hz), 7.29 (d, 1H, J = 0.8 Hz), 7.08 (s, 1H), 6.45 (d, 1H, J = 5.2 Hz), 4.07 (q, 2H, J = 7.2 Hz), 3.59-3.58 (m, 4H), 3.44-3.42 (m, 4H), 2.42 (s, 3H), 1.21 (t, 3H, J = 7.2 Hz). |

TABLE 1-continued

| # | Structure | LCMS (M + 1) | ¹H NMR |
|---|---|---|---|
| 49 | 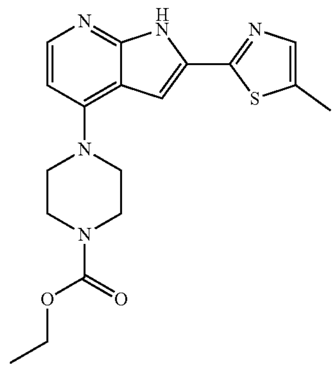 [SMILES: CCOC(=O)N1CCN(c2ccnc3[nH]c(-c4ncc(C)s4)cc23)CC1] | 372 | ¹H-NMR (400 MHz, d₆-DMSO) δ ppm 12.22 (br. s., 1H), 8.0 (d, 1H, J = 1.2 Hz), 7.57 (d, 1H, J = 0.8 Hz), 7.03 (s, 1H), 6.45 (d, 1H, J = 5.6 Hz), 4.07 (q, 2H, J = 7.2 Hz), 3.58-3.59 (m, 4H), 3.43-3.41 (m, 4H), 2.49 (s, 3H), 1.21 (t, 3H, J = 7.2 Hz). |
| 50 | 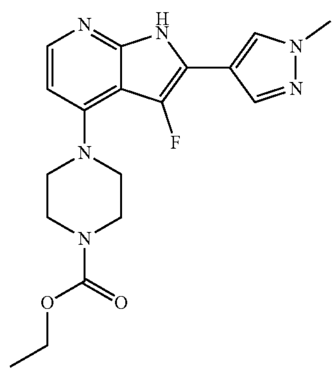 | 373 | ¹H-NMR (500 MHz, 6d-DMSO) δ ppm 11.76 (s, 1H), 8.12 (s, 1H), 7.97 (d, 1H, J = 5.5 Hz), 7.89 (s, 1H), 6.49 (d, 1H, J = 5.0 Hz), 4.08 (q, 2H, J = 7.5 Hz), 3.91 (s, 3H), 3.62-3.50 (m, 4H), 3.30-3.22 (m, 4H), 1.21 (t, 3H, J = 7.0 Hz). |
| 51 | 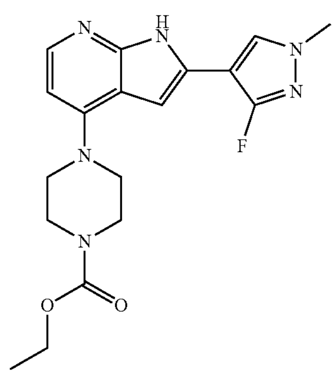 [SMILES: CCOC(=O)N1CCN(c2ccnc3[nH]c(-c4cn(C)nc4F)cc23)CC1] | 373 | ¹H-NMR (400 MHz, 6d-DMSO) δ ppm 11.78 (s, 1H), 8.04 (d, 1H, J = 2.0 Hz), 7.94 (d, 1H, J = 5.2 Hz), 6.48 (s, 1H), 6.44 (d, 1H, J = 5.6 Hz), 4.08 (q, 2H, J = 7.2 Hz), 3.79 (s, 3H), 3.60-3.57 (m, 4H), 3.39-3.34 (m, 4H), 1.21 (t, 3H, J = 7.2 Hz). |
| 52 | 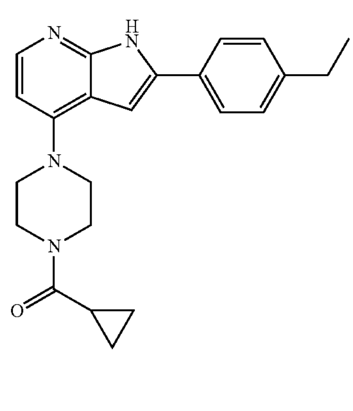 [SMILES: CCc1ccc(-c2cc3c(N4CCN(C(=O)C5CC5)CC4)ccnc3[nH]2)cc1] | 375 | ¹H NMR (400 MHz, DMSO) δ 12.98 (s, 1H), 8.00 (d, J = 7.1 Hz, 1H), 7.85 (d, J = 8.3 Hz, 2H), 7.37 (dd, J = 7.9, 5.1 Hz, 3H), 6.75 (d, J = 7.2 Hz, 1H), 4.02 (d, J = 17.4 Hz, 4H), 3.76 (s, 2H), 2.67 (d, J = 7.6 Hz, 2H), 2.00 (s, 1H), 1.23 (t, J = 7.6 Hz, 3H), 0.79 (t, J = 5.7 Hz, 4H). |

TABLE 1-continued

| # | Structure | LCMS (M + 1) | ¹H NMR |
|---|---|---|---|
| 53 | 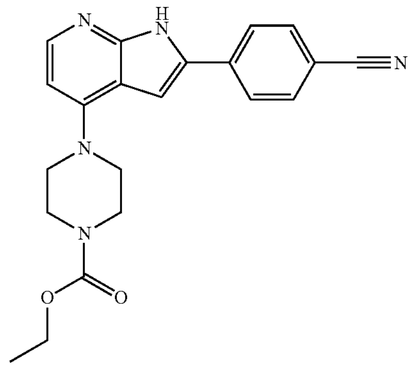 | 376 | ¹H-NMR (500 MHz, 6d-DMSO) δ ppm 12.17 (s, 1H), 8.15 (d, 2H, J = 8.0 Hz), 8.02 (d, 1H, J = 5.5 Hz), 7.90 (d, 2H, J = 8.0 Hz), 7.34 (s, 1H), 6.45 (d, 1H, J = 5.5 Hz), 4.10-4.08 (m, 2H), 3.62-3.55 (m, 4H), 3.51-3.46 (m, 4H), 1.24-1.20 (m, 3H). |
| 54 | 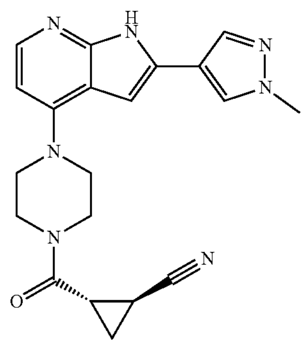 [SMILES: Cn1cc(-c2cc3c(N4CCN(C(=O)[C@H]5C[C@@H]5C#N)CC4)ccnc3[nH]2)cn1] | 376 | |
| 55 | 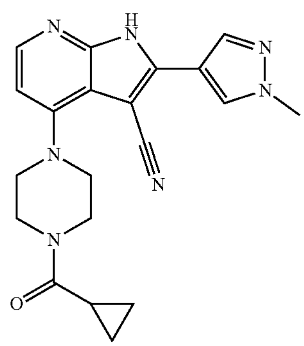 [SMILES: Cn1cc(-c2[nH]c3nccc(N4CCN(C(=O)C5CC5)CC4)c3c2C#N)cn1] | 376 | ¹H NMR (400 MHz, Methanol-d₄) δ 9.12 (d, J = 0.7 Hz, 1H), 8.92 (d, J = 0.7 Hz, 1H), 8.89 (d, J = 5.4 Hz, 1H), 7.49 (d, J = 5.4 Hz, 1H), 4.74 (s, 2H), 4.72 (s, 3H), 4.55 (s, 2H), 4.04 (s, 3H), 2.77 (tt, J = 7.9, 4.8 Hz, 1H), 1.99 (s, 1H), 1.64-1.55 (m, 2H), 1.53 (dt, J = 8.0, 2.6 Hz, 2H). |
| 56 | 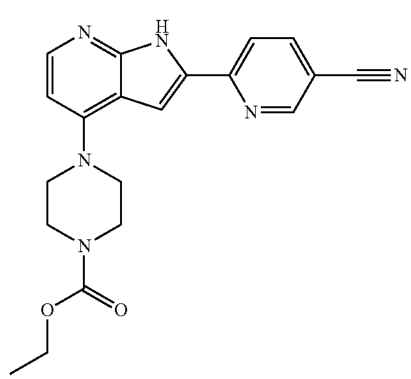 | 377 | ¹H-NMR (400 MHz, 6d-DMSO) δ ppm 12.25 (s, 1H), 9.01 (s, 1H), 8.35 (d, 1H, J = 8.0 Hz), 8.22 (d, 1H, J = 8.4 Hz), 8.05 (d, 1H, J = 4.8 Hz), 7.52 (s, 1H), 6.46 (d, 1H, J = 5.2 Hz), 4.10-4.06 (m, 2H), 3.61-3.60 (m, 4H), 3.50-3.49 (m, 4H), 1.22 (t, 3H, J = 6.8 Hz). |

TABLE 1-continued

| # | Structure | LCMS (M + 1) | ¹H NMR |
|---|---|---|---|
| 57 | 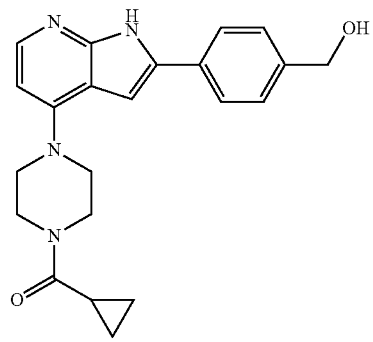 [SMILES: O=C(C1CC1)N1CCN(c2ccnc3[nH]c(-c4ccc(CO)cc4)cc23)CC1] | 377 | ¹H NMR (400 MHz, DMSO) δ 13.19 (s, 1H), 8.05-7.98 (m, 4H), 7.61 (d, J = 8.4 Hz, 3H), 7.51 (d, J = 2.0 Hz, 1H), 6.77 (d, J = 7.3 Hz, 2H), 5.49 (s, 2H), 4.05 (d, J = 24.9 Hz, 6H), 3.77 (s, 2H), 1.99 (s, 1H), 0.80 (s, 4H). |
| 58 | 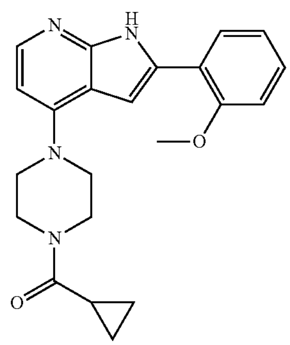 [SMILES: COc1ccccc1-c1cc2c(N3CCN(C(=O)C4CC4)CC3)ccnc2[nH]1] | 377 | ¹H NMR (400 MHz, DMSO) δ 12.44 (s, 1H), 8.05 (d, J = 7.2 Hz, 1H), 7.89 (dd, J = 7.7, 1.5 Hz, 1H), 7.44-7.36 (m, 2H), 7.22 (d, J = 8.2 Hz, 1H), 7.11 (t, J = 7.5 Hz, 1H), 6.76 (d, J = 7.3 Hz, 1H), 4.08 (s, 2H), 4.02 (s, 3H), 3.98 (s, 3H), 3.77 (s, 2H), 1.99 (s, 1H), 0.79 (t, J = 5.5 Hz, 4H). |
| 59 | 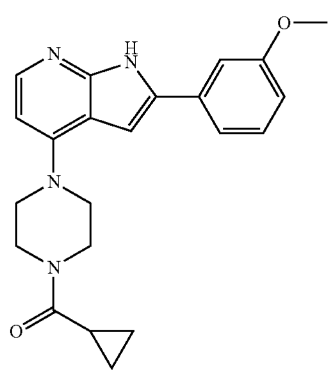 [SMILES: COc1cccc(-c2cc3c(N4CCN(C(=O)C5CC5)CC4)ccnc3[nH]2)c1] | 377 | ¹H NMR (400 MHz, DMSO) δ 13.08 (d, J = 29.6 Hz, 1H), 8.06-7.97 (m, 2H), 7.90 (d, J = 8.3 Hz, 1H), 7.61 (d, J = 8.4 Hz, 1H), 7.52-7.42 (m, 2H), 6.76 (dd, J = 7.3, 2.9 Hz, 1H), 4.05 (d, J = 23.4 Hz, 4H), 3.77 (s, 4H), 3.65 (s, 3H), 1.99 (ddd, J = 12.6, 7.3, 5.3 Hz, 1H), 0.85-0.76 (m, 4H). |
| 60 | 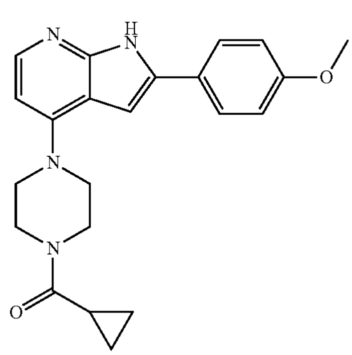 [SMILES: COc1ccc(-c2cc3c(N4CCN(C(=O)C5CC5)CC4)ccnc3[nH]2)cc1] | 377 | |

TABLE 1-continued

| # | Structure | LCMS (M + 1) | ¹H NMR |
|---|---|---|---|
| 61 | 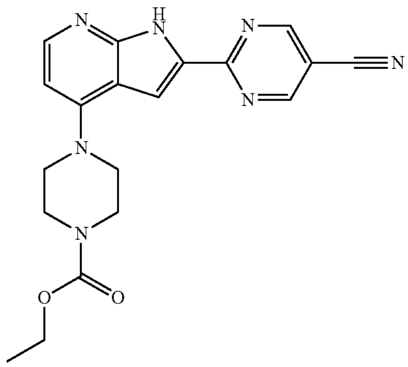 | 378 | ¹H-NMR (500 MHz, 6d-DMSO) δ ppm 12.36 (s, 1H), 9.26 (s, 2H), 8.09 (d, 1H, J = 6.5 Hz), 7.57 (s, 1H), 6.46 (d, 1H, J = 6.5 Hz), 4.08 (q, 2H, J = 7.5 Hz), 3.62-3.61 (m, 4H), 3.54-3.53 (m, 4H), 1.22 (t, 3H, J = 7.5 Hz). |
| 62 | 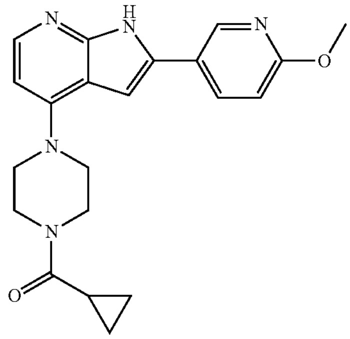 [SMILES: COc1ccc(-c2cc3c(N4CCN(C(=O)C5CC5)CC4)ccnc3[nH]2)cn1] | 378 | ¹H NMR (400 MHz, DMSO) δ 13.05 (s, 1H), 8.74 (d, J = 2.2 Hz, 1H), 8.25 (dd, J = 8.7, 2.5 Hz, 1H), 8.03 (d, J = 7.1 Hz, 1H), 7.42 (d, J = 1.8 Hz, 1H), 7.01 (d, J = 8.8 Hz, 1H), 6.76 (d, J = 7.2 Hz, 1H), 4.03 (d, J = 18.3 Hz, 6H), 3.92 (s, 3H), 3.80 (s, 2H), 2.00 (t, J = 5.1 Hz, 1H), 0.82-0.76 (m, 4H). |
| 63 | 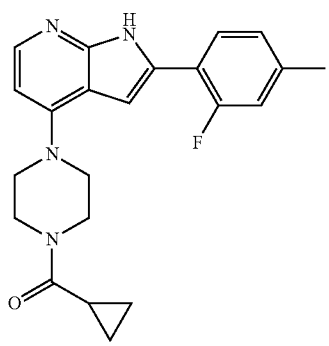 [SMILES: Cc1ccc(-c2cc3c(N4CCN(C(=O)C5CC5)CC4)ccnc3[nH]2)c(F)c1] | 379 | ¹H NMR (400 MHz, DMSO) δ 12.83 (s, 1H), 8.04 (d, J = 7.2 Hz, 0H), 7.82 (t, J = 8.2 Hz, 1H), 7.23 (dd, J = 20.4, 10.6 Hz, 3H), 6.77 (d, J = 7.3 Hz, 1H), 4.07 (s, 1H), 4.01 (s, 4H), 3.76 (s, 3H), 2.39 (s, 3H), 1.99 (s, 1H), 0.82-0.75 (m, 4H). |
| 64 | 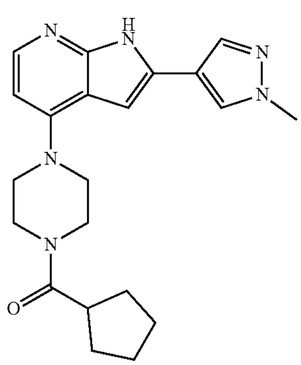 [SMILES: Cn1cc(-c2cc3c(N4CCN(C(=O)C5CCCC5)CC4)ccnc3[nH]2)cn1] | 379 | ¹H-NMR (400 MHz, DMSO-d₆) δ ppm 11.73 (s, 1H), 8.13 (s, 1H), 7.94-7.89 (m, 2H), 6.67 (d, 1H, J = 2.0 Hz), 6.41 (d, 1H, J = 5.6 Hz), 3.88 (s, 3H), 3.72-3.68 (m, 4H), 3.39-3.33 (m, 4H), 3.05-3.04 (m, 1H), 1.81-1.51 (m, 8H). |

TABLE 1-continued

| # | Structure | LCMS (M + 1) | ¹H NMR |
|---|-----------|--------------|--------|
| 65 | 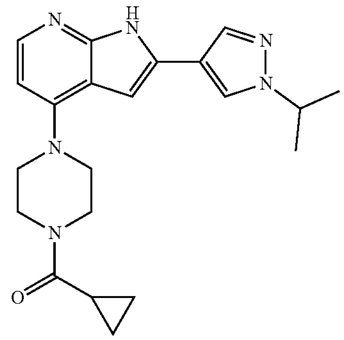 [SMILES: CC(C)n1cc(-c2cc3c(N4CCN(C(=O)C5CC5)CC4)ccnc3[nH]2)cn1] | 379 | ¹H NMR (400 MHz, DMSO-d₆) δ ppm 11.68 (s, 1H), 8.24 (s, 1H), 7.95 (s, 1H), 7.91 (d, 1H, J = 5.2 Hz), 6.69 (s, 1H), 6.42 (d, 1H, J = 5.2 Hz), 4.53-4.50 (m, 1H), 3.90 (br. s., 2H), 3.69 (br. s., 2H), 3.44 (br. s., 2H), 3.41 (br. s., 2H), 2.05-2.01 (m., 1H), 1.44 (d, 6H, J = 6.8 Hz), 0.78-0.74 (m, 4H). |
| 66 | 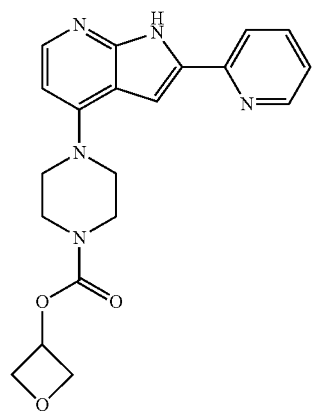 | 380 | ¹H-NMR (500 MHz, d₆-DMSO) δ ppm 12.02 (s, 1H), 8.62 (d, 1H, J = 4.0 Hz), 8.32 (s, 1H), 8.07-8.02 (m, 2H), 7.89-7.85 (m, 1H), 7.31-7.28 (m, 2H), 6.46 (d, 1H, J = 6.0 Hz), 5.36-5.33 (m, 1H), 4.81-4.78 (m, 2H), 4.55-4.53 (m, 2H), 3.71-3.61 (m, 4H), 3.50-3.48 (m, 4H). |
| 67 | 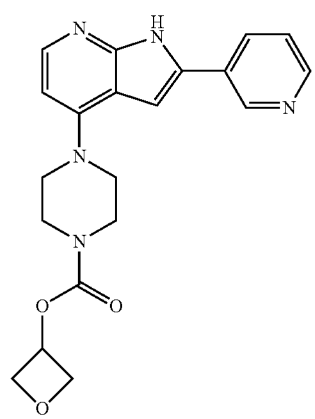 | 380 | ¹H-NMR (500 MHz, 6d-DMSO) δ ppm 12.11 (s, 1H), 9.18 (d, 1H, J = 2.0 Hz), 8.48 (dd, 1H, J = 5.0, 1.5 Hz), 8.31-8.28 (m, 1H), 8.00 (d, 1H, J = 6.0 Hz), 7.47 (dd, 1H, J = 8.0, 4.5 Hz), 7.24 (s, 1H), 6.46 (d, 1H, J = 5.0 Hz), 5.33 (quintet, 1H, J = 5.5 Hz), 4.78 (t, 2H, J = 7.5 Hz), 4.53 (dd, 2H, J = 7.5, 5.5 Hz), 3.70-3.69 (m, 2H), 3.68-3.58 (m, 2H), 3.48-3.42 (m, 4H). |
| 68 | 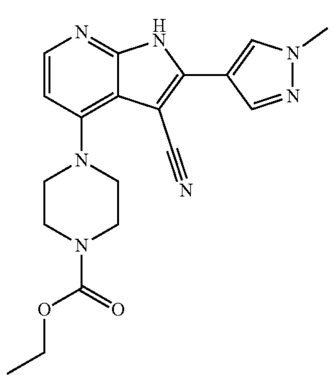 [SMILES: CCOC(=O)N1CCN(c2ccnc3[nH]c(-c4cnn(C)c4)c(C#N)c23)CC1] | 380 | ¹H-NMR (500 MHz, 6d-DMSO) δ ppm 12.94 (s, 1H), 8.41 (s, 1H), 8.20-8.10 (m, 2H), 6.74 (d, 1H, J = 5.5 Hz), 4.08 (q, 2H, J = 7.0 Hz), 3.97 (s, 3H), 3.65-3.52 (m, 4H), 3.20-3.08 (m, 4H), 1.22 (t, 3H, J = 7.0 Hz). |

TABLE 1-continued

| # | Structure | LCMS (M + 1) | ¹H NMR |
|---|---|---|---|
| 69 | 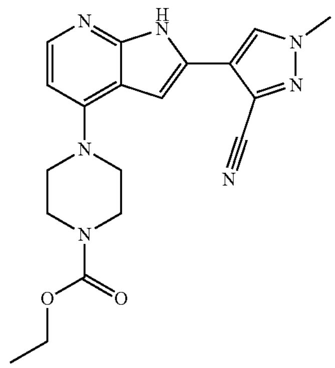 [SMILES: CCOC(=O)N1CCN(c2ccnc3[nH]c(-c4cn(C)nc4C#N)cc23)CC1] | 380 | ¹H-NMR (500 MHz, 6d-DMSO) δ ppm 11.98 (s, 1H), 8.32 (s, 1H), 8.00 (d, 1H, J = 5.5 Hz), 6.83 (s, 1H), 6.48 (d, 1H, J = 5.5 Hz), 4.08 (q, 2H, J = 7.0 Hz), 4.01 (s, 3H), 3.59-3.58 (m, 4H), 3.42-3.41 (m, 4H), 1.21 (t, 3H, J = 7.0 Hz). |
| 70 | 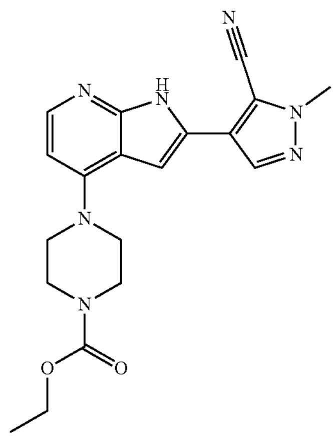 [SMILES: CCOC(=O)N1CCN(c2ccnc3[nH]c(-c4cnn(C)c4C#N)cc23)CC1] | 380 | ¹H-NMR (500 MHz, 6d-DMSO) δ ppm 12.09 (br. s, 1H), 8.17 (s, 1H), 8.02 (d, 1H, J = 5.5 Hz), 6.83 (s, 1H), 6.48 (d, 1H, J = 5.5 Hz), 4.08 (q, 2H, J = 7.0 Hz), 4.06 (s, 3H), 3.59-3.58 (m, 4H), 3.42-3.41 (m, 4H), 1.21 (t, 3H, J = 7.0 Hz). |
| 71 | 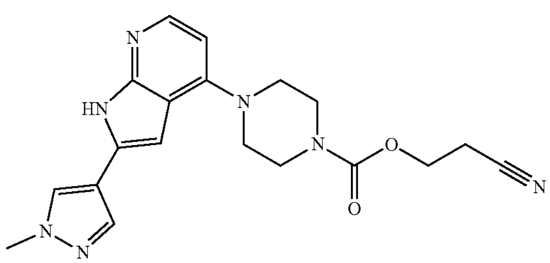 [SMILES: Cn1cc(-c2cc3c(N4CCN(C(=O)OCCC#N)CC4)ccnc3[nH]2)cn1] | 380 | ¹H-NMR (500 MHz, 6d-DMSO) δ ppm 11.71 (s, 1H), 8.12 (s, 1H), 7.94 (s, 1H), 7.90 (d, 1H, J = 5.0 Hz), 6.67 (d, 1H, J = 2.0 Hz), 6.42 (d, 1H, J = 5.5 Hz), 4.23 (t, 2H, J = 6.0 Hz), 3.87 (s, 3H), 3.63-3.61 (m, 4H), 3.34-3.32 (m, 4H), 2.92 (t, 2H, J = 6.0 Hz). |
| 72 | 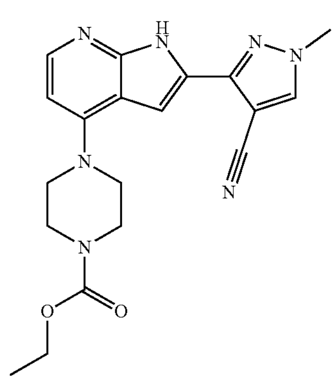 [SMILES: CCOC(=O)N1CCN(c2ccnc3[nH]c(-c4nn(C)cc4C#N)cc23)CC1] | 380 | ¹H-NMR (400 MHz, DMSO-d₆) δ ppm 12.18 (br. s., 1H), 8.17 (s, 1H), 8.08 (d, 1H, J = 5.6 Hz), 7.01 (s, 1H), 6.51 (d, 1H, J = 5.6 Hz.), 4.07 (q, 2H, J = 7.2 Hz.), 3.99 (s, 3H), 3.59-3.57 (m, 4H), 3.49-3.46 (m, 4H), 1.20 (t, 3H, J = 7.2 Hz). |

TABLE 1-continued

| # | Structure | LCMS (M + 1) | ¹H NMR |
|---|---|---|---|
| 73 | 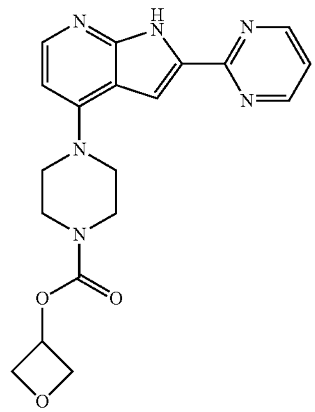 | 381 | ¹H-NMR (500 MHz, 6d-DMSO) δ ppm 12.11 (s, 1H), 8.85 (d, 2H, J = 4.5 Hz), 8.06 (d, 1H, J = 5.0 Hz), 7.38 (s, 1H), 7.37 (t, 1H, J = 4.5 Hz), 6.47 (d, 1H, J = 5.0 Hz), 5.34 (quintet, 1H, J = 5.5 Hz), 4.79 (t, 2H, J = 7.0 Hz), 4.54 (dd, 2H, J = 7.0, 5.5 Hz), 3.72-3.66 (m, 2H), 3.65-3.58 (m, 2H), 3.52-3.48 (m, 4H). |
| 74 | 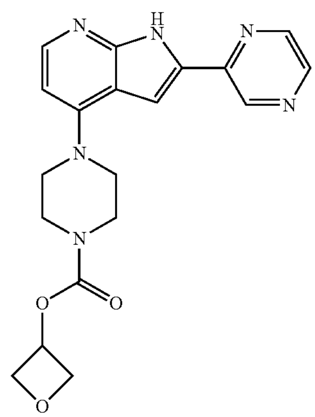 | 381 | ¹H-NMR (400 MHz, 6d-DMSO) δ ppm 12.41-12.05 (br., 1H), 9.33 (d, 1H, J = 1.2 Hz), 8.65 (s, 1H), 8.51 (d, 1H, J = 2.4 Hz), 8.05 (d, 1H, J = 5.6 Hz), 7.47 (s, 1H), 6.48 (d, 1H, J = 5.6 Hz), 5.34 (quintet, 1H, J = 5.2 Hz), 4.79 (t, 2H, J = 7.2 Hz), 4.54 (dd, 2H, J = 7.2, 5.2 Hz), 3.72-3.66 (m, 2H), 3.65-3.58 (m, 2H), 3.52-3.48 (m, 4H). |
| 75 | 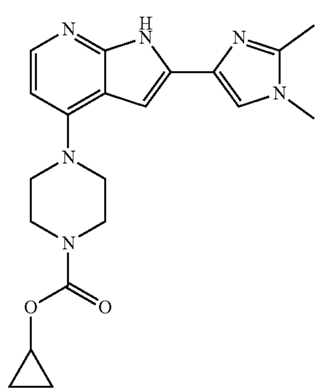 [SMILES: Cc1nc(-c2cc3c(N4CCN(C(=O)OC5CC5)CC4)ccnc3[nH]2)cn1C] | 381 | ¹H-NMR (500 MHz, 6d-DMSO) δ ppm 11.60 (s, 1H), 7.88 (d, 1H, J = 6.0 Hz), 7.45 (s, 1H), 6.55 (d, 1H, J = 2.0 Hz), 6.39 (d, 1H, J = 5.5 Hz), 4.10-4.00 (m, 1H), 3.59 (s, 3H), 3.59-3.50 (m, 4H), 3.33-3.20 (m, 4H), 2.31 (s, 3H), 0.70-0.65 (m, 4H). |

TABLE 1-continued
| # | Structure | LCMS (M + 1) | ¹H NMR |
|---|---|---|---|
| 76 | 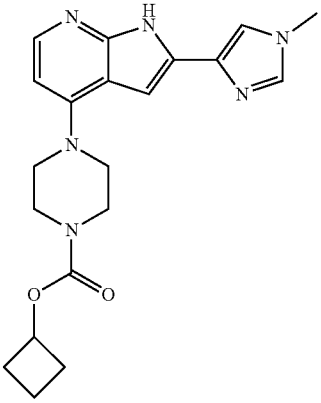 [SMILES: Cn1cnc(-c2cc3c(N4CCN(C(=O)OC5CCC5)CC4)ccnc3[nH]2)c1] | 381 | ¹H-NMR (400 MHz, 6d-DMSO) δ ppm 11.65 (s, 1H), 7.90 (d, 1H, J = 5.2 Hz), 7.65 (s, 1H), 7.54 (d, 1H, J = 1.2 Hz), 6.61 (d, 1H, J = 2.0 Hz), 6.40 (d, 1H, J = 5.6 Hz), 4.88-4.84 (m, 1H), 3.69 (s, 3H), 3.60-3.53 (m, 4H), 3.36-3.32 (m, 4H), 2.26-2.21 (m, 2H), 2.03-1.98 (m, 2H), 1.72-1.70 (m, 2H), 1.58-1.54 (m, 1H). |
| 77 | 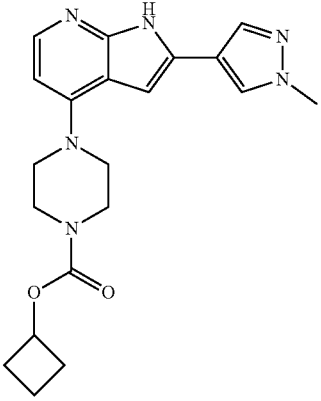 [SMILES: Cn1cc(-c2cc3c(N4CCN(C(=O)OC5CCC5)CC4)ccnc3[nH]2)cn1] | 381 | |
| 78 | 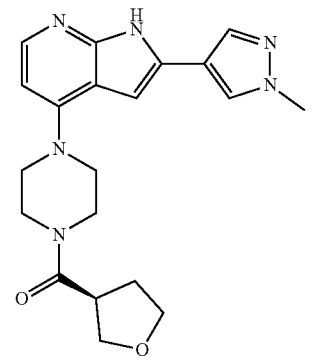 [SMILES: Cn1cc(-c2cc3c(N4CCN(C(=O)[C@H]5CCOC5)CC4)ccnc3[nH]2)cn1] | 381 | ¹H NMR (400 MHz, Methanol-d₄) δ 8.01 (d, J = 0.7 Hz, 1H), 7.91 (d, J = 0.7 Hz, 2H), 6.73 (s, 1H), 6.55 (d, J = 5.9 Hz, 1H), 4.01 (d, J = 8.2 Hz, 1H), 3.95 (s, 3H), 3.93-3.75 (m, 7H), 3.70-3.55 (m, 4H), 3.50 (tt, J = 8.3, 6.3 Hz, 1H), 2.27-2.06 (m, 2H). |
| 79 | 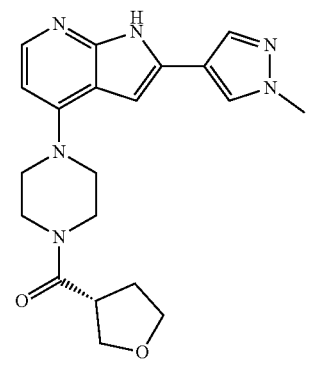 [SMILES: Cn1cc(-c2cc3c(N4CCN(C(=O)[C@@H]5CCOC5)CC4)ccnc3[nH]2)cn1] | 381 | ¹H NMR (400 MHz, Methanol-d₄) δ 8.01 (d, J = 0.7 Hz, 1H), 7.91 (d, J = 0.7 Hz, 2H), 6.73 (s, 1H), 6.55 (d, J = 5.9 Hz, 1H), 4.01 (d, J = 8.2 Hz, 1H), 3.95 (s, 3H), 3.93-3.75 (m, 7H), 3.70-3.55 (m, 4H), 3.50 (tt, J = 8.3, 6.3 Hz, 1H), 2.27-2.06 (m, 2H). |

TABLE 1-continued
| # | Structure | LCMS (M + 1) | ¹H NMR |
|---|---|---|---|
| 80 | 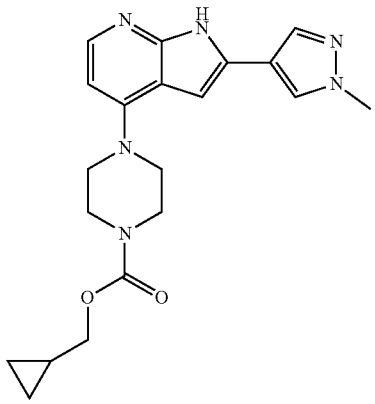 [SMILES: Cn1cc(-c2cc3c(N4CCN(C(=O)OCC5CC5)CC4)ccnc3[nH]2)cn1] | 381 | ¹H-NMR (500 MHz, 6d-DMSO) δ ppm 11.70 (s, 1H), 8.11 (s, 1H), 7.93 (s, 1H), 7.90 (d, 1H, J = 5.0 Hz), 6.65 (d, 1H, J = 1.0 Hz), 6.41 (d, 1H, J = 6.0 Hz), 3.90-3.86 (m, 2H), 3.87 (s, 3H), 3.60-3.58 (m, 4H), 3.38-3.32 (m, 4H), 1.12-1.01 (m, 1H), 0.53-0.51 (m, 2H), 0.30-0.27 (m, 2H). |
| 81 | 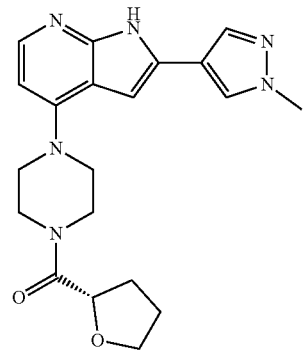 [SMILES: Cn1cc(-c2cc3c(N4CCN(C(=O)[C@@H]5CCCO5)CC4)ccnc3[nH]2)cn1] | 381 | ¹H NMR (400 MHz, Methanol-d₄) δ 8.01 (d, J = 0.7 Hz, 1H), 7.91 (d, J = 0.7 Hz, 2H), 6.73 (s, 1H), 6.55 (d, J = 5.9 Hz, 1H), 4.00 (t, J = 8.2 Hz, 1H), 3.95 (s, 3H), 3.91 (dd, J = 8.3, 5.9 Hz, 2H), 3.89-3.79 (m, 6H), 3.68-3.57 (m, 4H), 3.50 (tt, J = 8.3, 6.3 Hz, 1H), 2.26-2.09 (m, 2H). |
| 82 | 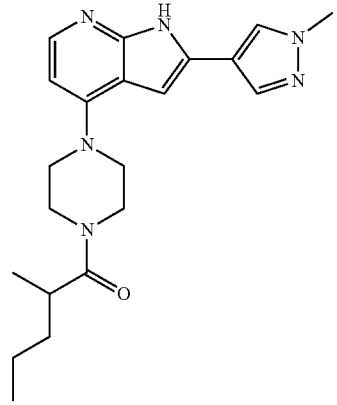 [SMILES: CCCC(C)C(=O)N1CCN(c2ccnc3[nH]c(-c4cnn(C)c4)cc23)CC1] | 381 | ¹H NMR (400 MHz, DMSO) δ 12.89 (s, 1H), 8.20 (s, 1H), 8.01-7.97 (m, 2H), 7.11 (d, J = 1.9 Hz, 1H), 6.74 (d, J = 7.2 Hz, 1H), 3.95 (s, 4H), 3.92 (s, 3H), 3.82 (s, 2H), 3.75 (s, 2H), 2.81 (dd, J = 12.9, 6.5 Hz, 1H), 1.62-1.53 (m, 1H), 1.33-1.22 (m, 3H), 1.04 (d, J = 6.7 Hz, 3H), 0.88 (t, J = 7.2 Hz, 3H). |
| 83 | 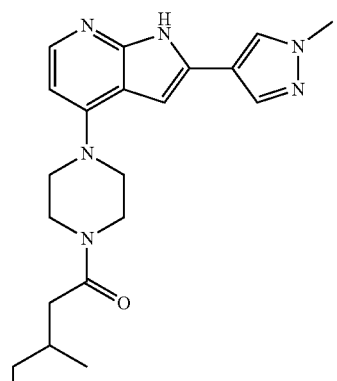 | 381 | ¹H NMR (400 MHz, DMSO) δ 12.91 (s, 1H), 8.20 (s, 1H), 7.99 (d, J = 7.8 Hz, 2H), 7.11 (d, J = 2.0 Hz, 1H), 6.74 (d, J = 7.2 Hz, 1H), 3.95 (s, 4H), 3.92 (s, 3H), 3.75 (s, 4H), 2.36 (dd, J = 15.2, 5.8 Hz, 1H), 2.18 (dd, J = 15.2, 8.0 Hz, 1H), 1.84 (d, J = 6.6 Hz, 1H), 1.44-1.33 (m, 1H), 1.26-1.14 (m, 1H), 0.89 (dd, J = 14.2, 7.0 Hz, 6H). |

TABLE 1-continued

| # | Structure | LCMS (M + 1) | ¹H NMR |
|---|---|---|---|
| 84 | 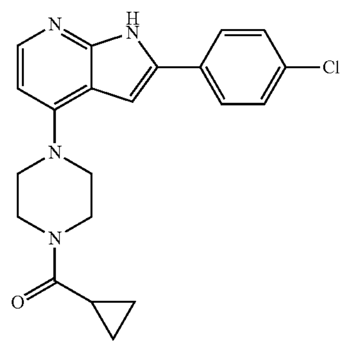 [SMILES: O=C(C1CC1)N1CCN(c2ccnc3[nH]c(-c4ccc(Cl)cc4)cc23)CC1] | 381 | ¹H NMR (400 MHz, DMSO) δ 13.08-12.93 (m, 1H), 8.05-7.95 (m, 3H), 7.60 (d, J = 8.7 Hz, 2H), 7.47 (s, 1H), 6.73 (d, J = 7.0 Hz, 1H), 3.98 (d, J = 21.8 Hz, 4H), 3.76 (s, 2H), 2.00 (s, 1H), 0.79 (t, J = 5.8 Hz, 4H). |
| 85 | 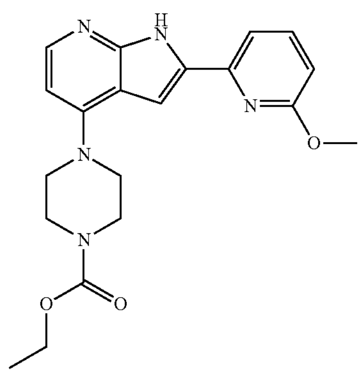 [SMILES: CCOC(=O)N1CCN(c2ccnc3[nH]c(-c4cccc(OC)n4)cc23)CC1] | 382 | ¹H-NMR (400 MHz, 6d-DMSO) δ ppm 11.92 (s, 1H), 8.01 (d, 1H, J = 5.6 Hz), 7.74 (t, 1H, J = 8.0 Hz), 7.63 (d, 1H, J = 7.6 Hz), 7.23 (s, 1H), 6.99 (d, 1H, J = 8.0 Hz), 6.43 (d, 1H, J = 5.6 Hz), 4.08 (q, 2H, J = 7.2 Hz), 4.01 (s, 3H), 3.70-3.50 (m, 4H), 3.48-3.40 (m, 4H), 1.21 (t, 3H, J = 7.2 Hz). |
| 86 | 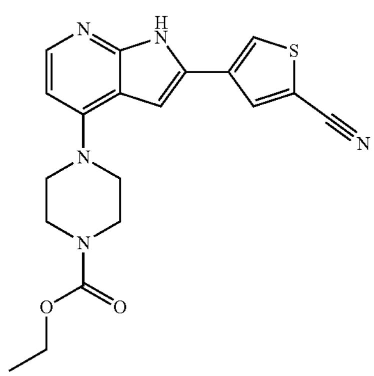 [SMILES: CCOC(=O)N1CCN(c2ccnc3[nH]c(-c4csc(C#N)c4)cc23)CC1] | 382 | ¹H-NMR (400 MHz, 6d-DMSO) δ ppm 12.06 (s, 1H), 8.55 (d, 1H, J = 1.2 Hz), 8.34 (d, 1H, J = 1.6 Hz), 7.98 (d, 1H, J = 5.6 Hz), 7.10 (d, 1H, J = 2.4 Hz), 6.45 (d, 1H, J = 5.2 Hz), 4.09 (q, 2H, J = 7.2 Hz ), 3.60-3.59 (m, 4H), 3.43-3.42 (m, 4H), 1.22 (t, 3H, J = 7.2 Hz). |
| 87 | 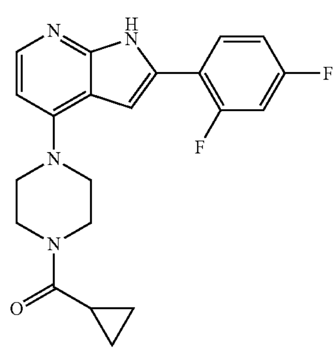 [SMILES: O=C(C1CC1)N1CCN(c2ccnc3[nH]c(-c4ccc(F)cc4F)cc23)CC1] | 383 | ¹H NMR (400 MHz, DMSO) δ 12.94 (s, 1H), 8.07 (d, J = 7.1 Hz, 1H), 7.97 (d, J = 6.4 Hz, 1H), 7.51 (s, 1H), 7.33 (d, J = 2.4 Hz, 1H), 7.28 (s, 1H), 6.76 (d, J = 7.2 Hz, 1H), 4.03 (d, J = 13.3 Hz, 6H), 3.76 (s, 3H), 1.98 (s, 1H), 0.83-0.73 (m, 4H). |

TABLE 1-continued

| # | Structure | LCMS (M + 1) | ¹H NMR |
|---|---|---|---|
| 88 | 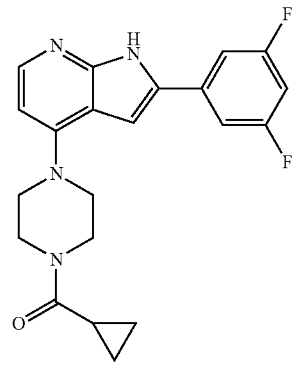 [SMILES: O=C(C1CC1)N1CCN(c2ccnc3[nH]c(-c4cc(F)cc(F)c4)cc23)CC1] | 383 | ¹H NMR (400 MHz, DMSO) δ 13.27 (s, 1H), 8.07 (d, J = 7.2 Hz, 1H), 7.76 (dd, J = 9.1, 2.1 Hz, 2H), 7.67 (s, 1H), 7.27 (dd, J = 6.8, 4.6 Hz, 1H), 6.77 (d, J = 7.3 Hz, 1H), 4.04 (d, J = 19.1 Hz, 4H), 3.78 (s, 2H), 2.00 (s, 1H), 0.88-0.73 (m, 4H). |
| 89 | 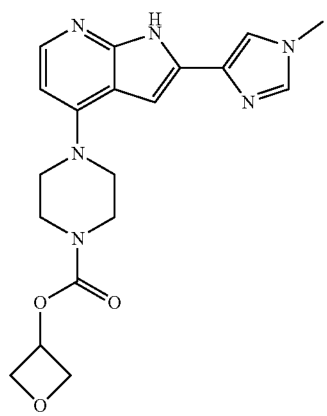 [SMILES: Cn1cnc(-c2cc3c(N4CCN(C(=O)OC5COC5)CC4)ccnc3[nH]2)c1] | 383 | ¹H-NMR (500 MHz, 6d-DMSO) δ ppm 11.70 (s, 1H), 7.91 (d, 1H, J = 5.5 Hz), 7.67 (s, 1H), 7.57 (d, 1H, J = 1.0 Hz), 6.64 (d, 1H, J = 2.0 Hz), 6.43 (d, 1H, J = 5.5 Hz), 5.36-5.31 (m, 1H), 4.81-4.78 (m, 2H), 4.55-4.52 (m, 2H), 3.71-3.69 (m, 7H), 3.40-3.38 (m, 4H). |
| 90 | 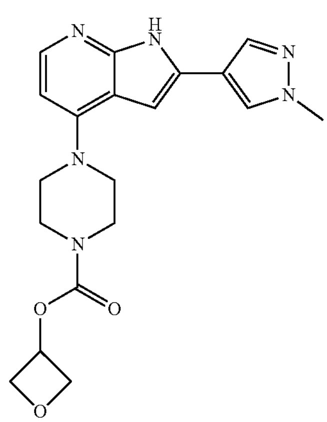 [SMILES: Cn1cc(-c2cc3c(N4CCN(C(=O)OC5COC5)CC4)ccnc3[nH]2)cn1] | 383 | ¹H-NMR (400 MHz, 6d-DMSO) δ ppm 11.73 (s, 1H), 8.12 (s, 1H), 7.94 (s, 1H), 7.91 (d, 1H, J = 5.2 Hz), 6.66 (d, 1H, J = 1.5 Hz), 6.42 (d, 1H, J = 5.2 Hz), 5.33 (quintet, 1H, J = 5.6 Hz), 4.78 (t, 2H, J = 7.2 Hz), 4.52 (dd, 2H, J = 7.2, 5.2 Hz), 3.89 (s, 3H), 3.66-3.62 (m, 2H), 3.62-3.58 (m, 2H), 3.40-3.38 (m, 4H). |

TABLE 1-continued

| # | Structure | LCMS (M + 1) | ¹H NMR |
|---|---|---|---|
| 91 | 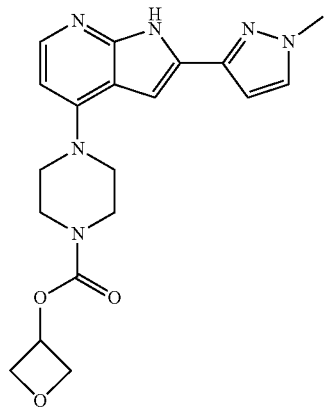 | 383 | ¹H-NMR (500 MHz, CDCl₃) δ ppm 9.99 (br. s, 1H), 8.14 (d, 1H, J = 5.0 Hz), 7.40 (d, 1H, J = 2.5 Hz), 6.67 (s, 1H), 6.57 (d, 1H, J = 2.5 Hz), 6.44 (d, 1H, J = 5.5 Hz), 5.45 (quintet, 1H, J = 5.5 Hz), 4.92 (t, 2H, J = 7.0 Hz), 4.70 (dd, 2H, J = 7.0, 5.5 Hz), 3.98 (s, 3H), 3.79-3.75 (m, 2H), 3.75-3.72 (m, 2H), 3.49-3.47 (m, 4 H). |
| 92 | 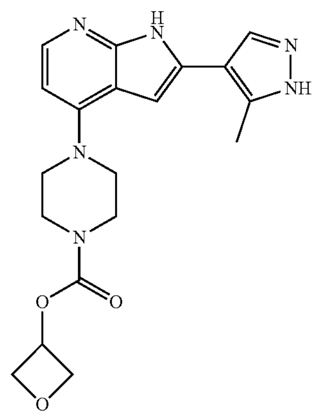 [SMILES: Cc1[nH]ncc1-c1cc2c(N3CCN(C(=O)OC4COC4)CC3)ccnc2[nH]1] | 383 | ¹H-NMR (400 MHz, 6d-DMSO and MeOH-d) δ ppm 7.90 (d, 1H, J = 5.2 Hz), 7.65 (s, 1H, HCOOH), 6.99 (s, 1H), 6.42 (d, 1H, J = 5.6 Hz), 6.38 (s, 1H), 5.34-5.28 (m, 1H), 4.78-4.74 (m, 2H), 4.53-4.49 (m, 2H), 3.67-3.57 (m, 4H), 3.42-3.34 (m, 4H), 2.42 (s, 1H) |
| 93 | 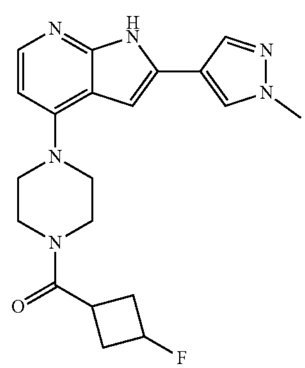 [SMILES: Cn1cc(-c2cc3c(N4CCN(C(=O)C5CC(F)C5)CC4)ccnc3[nH]2)cn1] | 383 | |
| 94 | 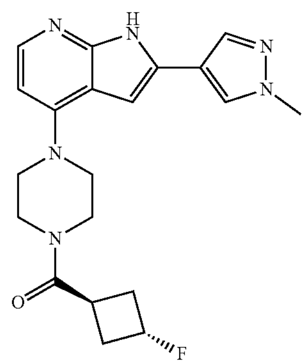 [SMILES: Cn1cc(-c2cc3c(N4CCN(C(=O)[C@H]5C[C@H](F)C5)CC4)ccnc3[nH]2)cn1] | 383 | ¹H NMR (400 MHz, Methanol-d₄) δ 8.00 (s, 1H), 7.94-7.84 (m, 2H), 6.65 (s, 1H), 6.50 (d, J = 5.7 Hz, 1H), 5.23-4.96 (m, 1H), 3.94 (s, 3H), 3.87-3.77 (m, 2H), 3.73-3.61 (m, 2H), 3.57-3.44 (m, 7H), 2.71-2.58 (m, 1H), 2.57-2.39 (m, 1H). |

TABLE 1-continued

| # | Structure | LCMS (M + 1) | ¹H NMR |
|---|---|---|---|
| 95 | 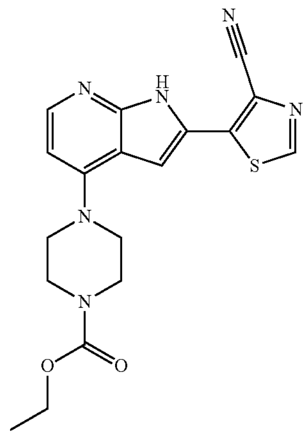 [SMILES: CCOC(=O)N1CCN(c2ccnc3[nH]c(-c4scnc4C#N)cc23)CC1] | 383 | ¹H-NMR (500 MHz, 6d-DMSO) δ ppm 12.34 (br s, 1H), 9.20 (s, 1H), 8.06 (d, 1H, J = 5.5 Hz), 7.26 (s, 1H), 6.51 (d, 1H, J = 5.5 Hz), 4.08 (q, 2H, J = 7.0 Hz ), 3.60-3.59 (m, 4H), 3.52-3.51 (m, 4H), 1.21 (t, 3H, J = 7.0 Hz). |
| 96 | 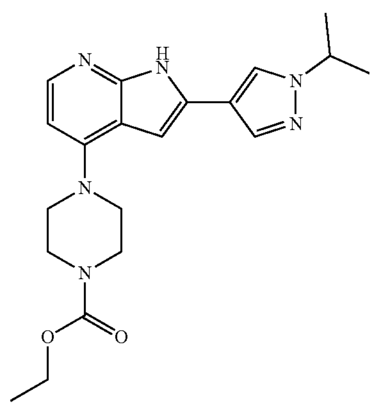 [SMILES: CCOC(=O)N1CCN(c2ccnc3[nH]c(-c4cnn(C(C)C)c4)cc23)CC1] | 383 | ¹H-NMR (500 MHz, 6d-DMSO) δ ppm 11.66 (s, 1H), 8.23 (s, 1H), 7.95 (s, 1H), 7.90 (d, 1H, J = 5.5 Hz), 6.65 (d, 1H, J = 2.0 Hz), 6.41 (d, 1H, J = 5.0 Hz), 4.53-4.49 (m, 1H), 4.09 (q, 2H, J = 7.0 Hz), 3.58 (m, 4H), 3.37-3.35 (m, 4H), 1.45 (d, 6H, J = 6.5 Hz), 1.22 (t, 3H, J = 7.0 Hz). |
| 97 | 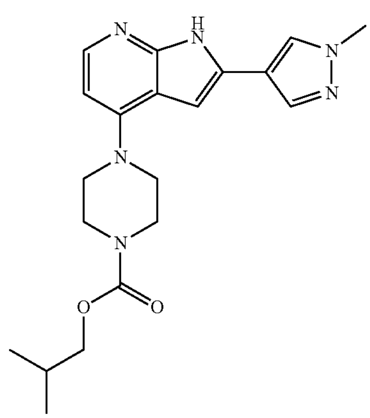 [SMILES: CC(C)COC(=O)N1CCN(c2ccnc3[nH]c(-c4cnn(C)c4)cc23)CC1] | 383 | ¹H-NMR (400 MHz, 6d-DMSO) δ ppm 11.71 (s, 1H), 8.19 (s, 1H), 7.93 (s, 1H), 7.90 (d, 1H, J = 5.2 Hz), 6.66 (d, 1H, J = 2.0 Hz), 6.42 (d, 1H, J = 2.0 Hz), 3.87 (s, 3H), 3.84 (d, 2H, J = 6.8 Hz), 3.62-3.57 (m, 4H), 3.40-3.35 (m, 4H), 1.91-1.88 (m, 1H), 0.91 (d, 6H, J = 6.4 Hz). |

TABLE 1-continued

| # | Structure | LCMS (M + 1) | ¹H NMR |
|---|---|---|---|
| 98 | 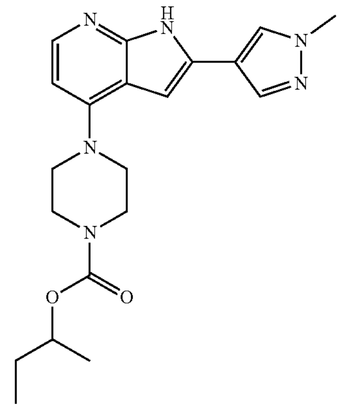 [SMILES: CCC(C)OC(=O)N1CCN(c2ccnc3[nH]c(-c4cnn(C)c4)cc23)CC1] | 383 | ¹H-NMR (500 MHz, 6d-DMSO) δ ppm 11.73 (s, 1H), 8.17 (s, 1H), 8.12 (s, 1H), 7.93 (s, 1H), 7.90 (d, 1H, J = 5.5 Hz), 6.66 (s, 1H), 6.41 (d, 1H, J = 4.4 Hz), 4.70-4.65 (m, 1H), 3.88 (s, 3H), 3.60-3.58 (m, 4H), 3.37-3.35 (m, 4H), 1.57-1.54 (m, 2H), 1.19 (d, 3H, J = 6.0 Hz), 0.88 (t, 3H, J = 7.0 Hz). |
| 99 | 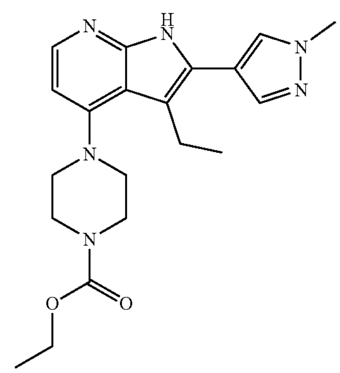 [SMILES: CCOC(=O)N1CCN(c2ccnc3[nH]c(-c4cnn(C)c4)c(CC)c23)CC1] | 383 | ¹H-NMR (400 MHz, 6d-DMSO) δ ppm 11.52 (s, 1H), 8.07 (s, 1H), 7.98 (d, 1H, J = 4.8 Hz), 7.85 (s, 1H), 6.63 (d, 1H, J = 5.2 Hz), 4.07 (q, 2H, J = 6.8 Hz), 3.90 (s, 3H), 3.65-3.55 (m, 4H), 3.05-2.95 (m, 4H), 2.91 (q, 2H, J = 7.2 Hz), 1.24-1.14 (m, 6H). |
| 100 | 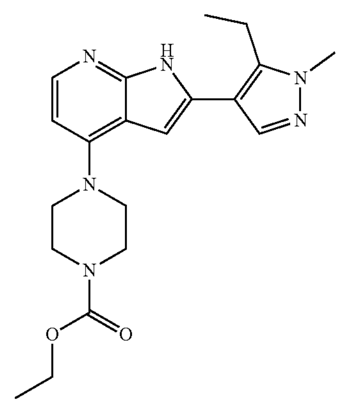 [SMILES: CCOC(=O)N1CCN(c2ccnc3[nH]c(-c4cnn(C)c4CC)cc23)CC1] | 383 | ¹H-NMR (400 MHz, 6d-DMSO) δ ppm 11.61 (s, 1H), 7.93 (d, 1H, J = 5.6 Hz), 7.80 (s, 1H), 6.44 (d, 1H, J = 5.6 Hz), 6.36 (d, 1H, J = 2.0 Hz), 4.09 (t, 2H, J = 7.2 Hz), 3.82 (s, 3H), 3.59-3.58 (m, 4H), 3.39-3.36 (m, 4H), 2.95 (t, 2H, J = 7.2 Hz), 1.23-1.15 (m, 6H). |
| 101 | 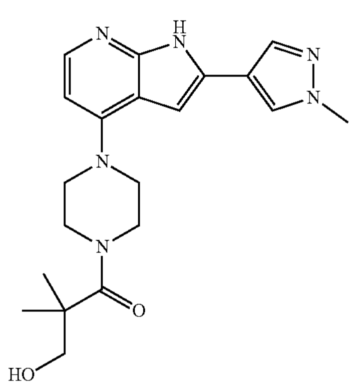 [SMILES: Cn1cc(-c2cc3c(N4CCN(C(=O)C(C)(C)CO)CC4)ccnc3[nH]2)cn1] | 383 | |

TABLE 1-continued
| # | Structure | LCMS (M + 1) | ¹H NMR |
|---|---|---|---|
| 102 | 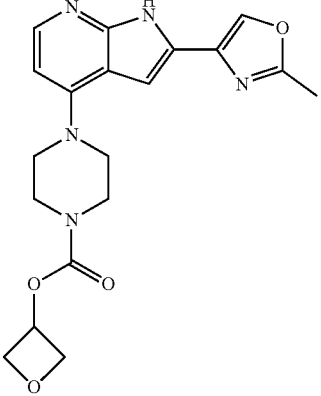 | 384 | ¹H-NMR (400 MHz, 6d-DMSO) δ ppm 11.88 (s, 1H), 8.28 (s, 1H), 7.95 (d, 1H, J = 5.2 Hz), 6.76 (d, 1H, J = 1.2 Hz), 6.44 (d, 1H, J = 5.2 Hz), 5.33-5.30 (m, 1H), 4.79-4.75 (m, 2H), 4.53-4.50 (m, 2H), 3.67-3.57 (m, 4H), 3.42-3.40 (m, 4H), 2.46 (s, 3H) |
| 103 | 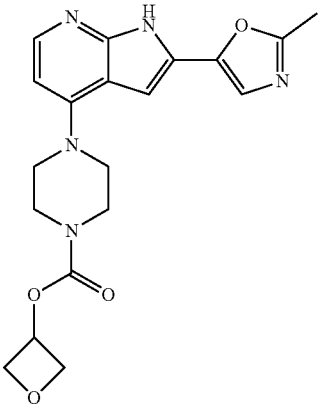 [SMILES: Cc1ncc(-c2cc3c(N4CCN(C(=O)OC5COC5)CC4)ccnc3[nH]2)o1] | 384 | ¹H-NMR (400 MHz, 6d-DMSO) δ ppm 12.07 (s, 1H), 7.98 (d, 1H, J = 5.6 Hz), 7.41 (s, 1H), 6.77 (s, 1H), 6.45 (d, 1H, J = 5.6 Hz), 5.34-5.30 (m, 1H), 4.79-4.76 (m, 2H), 4.53-4.50 (m, 2H), 3.66-3.57 (m, 4H), 3.44-3.41 (m, 4H), 2.48 (s, 3H). |
| 104 | 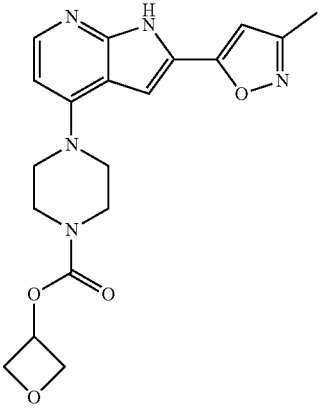 | 384 | ¹H-NMR (500 MHz, 6d-DMSO) δ ppm 12.32 (s, 1H), 8.05 (d, 1H, J = 5.5 Hz), 7.13 (s, 1H), 6.76 (s, 1H), 6.49 (d, 1H, J = 6.0 Hz), 5.35-5.32 (m, 1H), 4.81-4.77 (m, 2H), 4.55-4.51 (m, 2H), 3.80-3.50 (m, 4H), 3.50-3.40 (m, 4H), 2.30 (s, 3H). |

TABLE 1-continued

| # | Structure | LCMS (M + 1) | ¹H NMR |
|---|---|---|---|
| 105 | 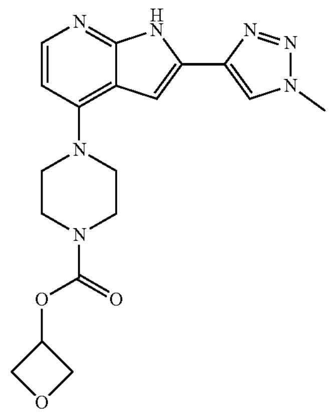 [SMILES: Cn1cc(-c2cc3c(N4CCN(C(=O)OC5COC5)CC4)ccnc3[nH]2)nn1] | 384 | ¹H-NMR (400 MHz, 6d-DMSO) δ ppm 12.03 (br s, 1H), 8.37 (s, 1H), 7.98 (d, 1H, J = 4.8 Hz), 6.91 (s, 1H), 6.47 (d, 1H, J = 5.6 Hz), 5.36-5.31 (m, 1H), 4.82-4.77 (m, 2H), 4.55-4.51 (m, 2H), 4.13 (s, 3H), 3.70-3.58 (m, 4H), 3.47-3.40 (m, 4H). |
| 106 | 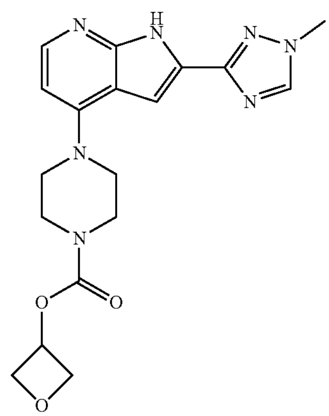 | 384 | ¹H-NMR (500 MHz, 6d-DMSO) δ ppm 12.03 (s, 1H), 8.56 (s, 1H), 8.00 (d, 1H, J = 5.0 Hz), 6.95 (d, 1H, J = 1.0 Hz), 6.45 (d, 1H, J = 5.5 Hz), 5.34-5.32 (m, 1H), 4.80-4.76 (m, 2H), 4.55-4.51 (m, 2H), 3.94 (s, 3H), 3.70-3.58 (m, 4 h), 3.45-3.43 (m, 4H). |
| 107 | 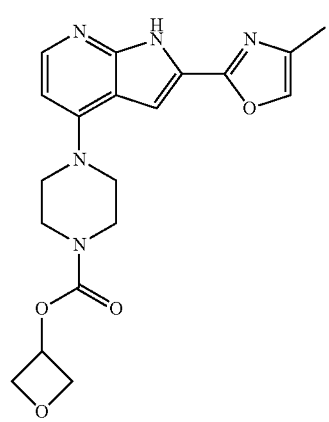 [SMILES: Cc1coc(-c2cc3c(N4CCN(C(=O)OC5COC5)CC4)ccnc3[nH]2)n1] | 384 | ¹H-NMR (400 MHz, 6d-DMSO) δ ppm 12.34 (s, 1H), 8.03 (d, 1H, J = 5.6 Hz), 7.91 (d, 1H, J = 0.8 Hz), 7.11 (s, 1H), 6.47 (d, 1H, J = 5.6 Hz), 5.33-5.30 (m, 1H), 4.79-4.75 (m, 2H), 4.53-4.50 (m, 2H), 3.67-3.57 (m, 4H), 3.47-3.45 (m, 4H), 2.17 (s, 3H) |

TABLE 1-continued

| # | Structure | LCMS (M + 1) | ¹H NMR |
|---|---|---|---|
| 108 | 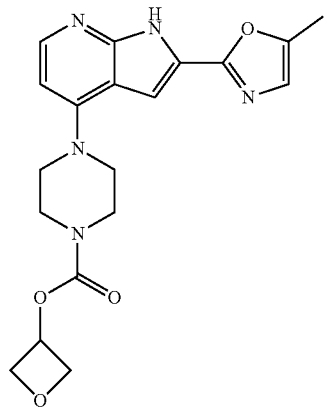 [SMILES: Cc1cnc(-c2cc3c(N4CCN(C(=O)OC5COC5)CC4)ccnc3[nH]2)o1] | 384 | ¹H-NMR (400 MHz, 6d-DMSO) δ ppm 12.31 (br s, 1H), 8.04 (d, 1H, J = 5.6 Hz), 7.07 (s, 1H), 7.01 (d, 1H, J = 1.2 Hz), 6.48 (d, 1H, J = 5.6 Hz), 5.36-5.30 (m, 1H), 4.80-4.77 (m, 2H), 4.54-4.51 (m, 2H), 3.69-3.67 (m, 2H), 3.60-3.58 (m, 2H), 3.53-3.51 (m, 4H), 2.39 (s, 1H). |
| 109 | 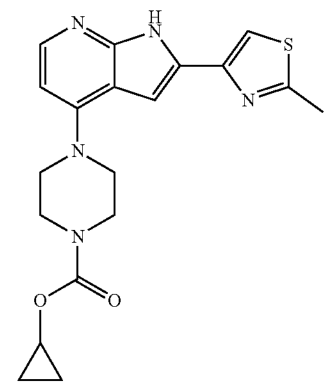 [SMILES: Cc1nc(-c2cc3c(N4CCN(C(=O)OC5CC5)CC4)ccnc3[nH]2)cs1] | 384 | ¹H-NMR (500 MHz, 6d-DMSO) δ ppm 12.00 (s, 1H), 7.98 (d, 1H, J = 5.5 Hz), 7.87 (s, 1H), 6.87 (d, 1H, J = 1.5 Hz), 6.44 (d, 1H, J = 5.5 Hz), 4.10-4.00 (m, 1H), 3.70-3.50 (m, 4H), 3.48-3.36 (m, 4H), 2.72 (s, 3H), 0.70-0.60 (m, 4H). |
| 110 | 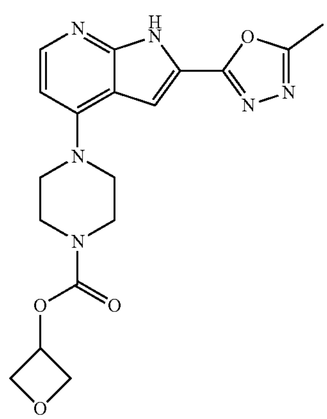 [SMILES: Cc1nnc(-c2cc3c(N4CCN(C(=O)OC5COC5)CC4)ccnc3[nH]2)o1] | 385 | ¹H-NMR (400 MHz, 6d-DMSO) δ ppm 12.60 (br. s., 1H), 8.24 (s, 1H), 8.10 (d, 1H, J = 5.6 Hz), 7.27 (s, 1H), 6.51 (d, 1H, J = 5.6 Hz), 5.34 (quintet, 1H, J = 5.2 Hz), 4.79 (t, 2H, J = 7.0 Hz), 4.53 (dd, 2H, J = 7.6, 5.2 Hz), 3.68-3.64 (m, 2H), 3.60-3.56 (m, 2H), 3.52-3.48 (m, 4H), 2.59 (s, 3H). |
| 111 | 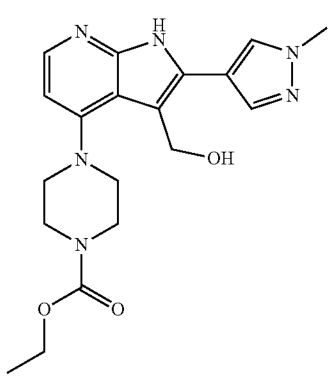 [SMILES: CCOC(=O)N1CCN(c2ccnc3[nH]c(-c4cnn(C)c4)c(CO)c23)CC1] | 385 | ¹H-NMR (500 MHz, DMSO-d₆) δ ppm 11.79 (br. s., 1H), 8.15 (s, 1H), 8.00 (s, 1H), 7.99 (d, 1H, J = 5.5 Hz), 6.58 (d, 1H, J = 5.5 Hz.), 4.90 (t, 1H, J = 3.5 Hz.), 4.72 (d, 2H, J = 3.5 Hz.), 4.09 (q, 2H, J = 7.0 Hz.), 3.92 (s, 3H), 3.62-3.58 (m, 4H), 3.18-3.16 (m, 4H), 1.22 (t, 3H, J = 7.0 Hz). |

TABLE 1-continued

| # | Structure | LCMS (M + 1) | ¹H NMR |
|---|---|---|---|
| 112 | 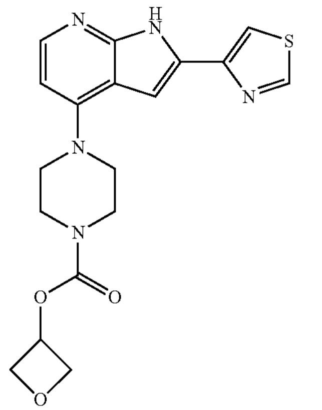 [SMILES: O=C(OC1COC1)N1CCN(c2ccnc3[nH]c(-c4cscn4)cc23)CC1] | 386 | ¹H-NMR (400 MHz, 6d-DMSO) δ ppm 12.06 (s, 1H), 9.20 (d, 1H, J = 1.6 Hz), 8.09 (d, 1H, J = 2.0 Hz), 8.00 (d, 1H, J = 5.2 Hz), 6.98 (s, 1H), 6.47 (d, 1H, J = 5.6 Hz), 5.35-5.32 (m, 1H), 4.80-4.77 (m, 2H), 4.54-4.51 (m, 2H), 3.69-3.67 (m, 2H), 3.60-3.58 (m, 2H), 3.46-3.43 (m, 4H). |
| 113 | 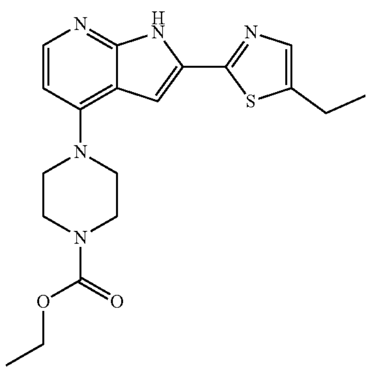 [SMILES: CCOC(=O)N1CCN(c2ccnc3[nH]c(-c4ncc(CC)s4)cc23)CC1] | 386 | ¹H-NMR (400 MHz, 6d-DMSO) δ ppm 8.02 (d, 1H, J = 4.8 Hz), 7.62 (s, 1H), 7.06 (s, 1H), 6.45 (d, 1H, J = 5.2 Hz), 4.08 (q, 2H, J = 7.2 Hz), 3.60-3.57 (m, 4H), 3.46-3.42 (m, 4H), 2.91 (q, 2H, J = 7.2 Hz), 1.29 (t, 3H, J = 7.2 Hz), 1.22 (t, 3H, J = 7.2 Hz). |
| 114 | 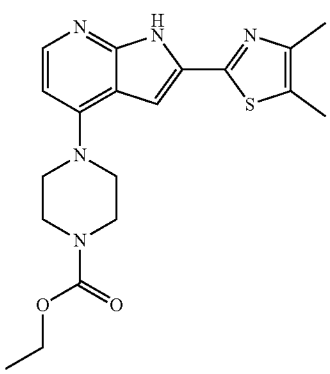 [SMILES: CCOC(=O)N1CCN(c2ccnc3[nH]c(-c4nc(C)c(C)s4)cc23)CC1] | 386 | ¹H-NMR (400 MHz, 6d-DMSO) δ ppm 8.00 (d, 1H, J = 5.6 Hz), 6.98 (s, 1H), 6.45 (d, 1H, J = 5.6 Hz), 4.08 (q, 2H, J = 6.8 Hz), 3.60-3.59 (m, 4H), 3.44-3.41 (m, 4H), 2.39 (s, 3H), 2.32 (s, 3H), 1.21 (t, 3H, J = 6.8 Hz). |
| 115 | 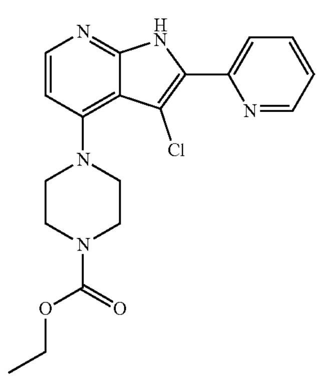 [SMILES: CCOC(=O)N1CCN(c2ccnc3[nH]c(-c4ccccn4)c(Cl)c23)CC1] | 386 | ¹H-NMR (400 MHz, 6d-DMSO) δ ppm 12.35 (s, 1H), 8.73 (d, 1H, J = 2.4 Hz), 8.20-8.15 (m, 2H), 7.98-7.94 (m, 1H), 7.43-7.40 (m, 1H), 6.66 (d, 1H, J = 5.2 Hz), 4.08 (q, 2H, J = 6.8 Hz), 3.63-3.60 (m, 4H), 3.17-3.16 (m, 4H), 1.21 (t, 3H, J = 6.8 Hz). |

TABLE 1-continued

| # | Structure | LCMS (M + 1) | ¹H NMR |
|---|---|---|---|
| 116 | 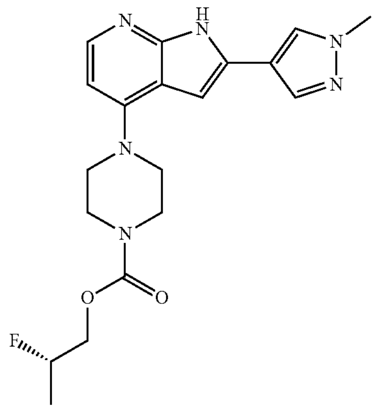 [SMILES: C[C@H](F)COC(=O)N1CCN(c2ccnc3[nH]c(-c4cnn(C)c4)cc23)CC1] | 387 | ¹H-NMR (400 MHz, 6d-DMSO) δ ppm 11.72 (s, 1H), 8.16 (s, 1H), 8.12 (s, 1H), 7.93 (s, 1H), 7.90 (d, 1H, J = 5.6 Hz), 6.66 (s, 1H), 6.42 (d, 1H, J = 5.6 Hz), 5.00-4.81 (m, 1H), 4.27-4.06 (m, 2H), 3.88 (s, 3H), 3.62-3.60 (m, 4H), 3.39-3.37 (m, 4H), 1.31 (dd, 3H, J = 23.6, 6.4 Hz). |
| 117 | 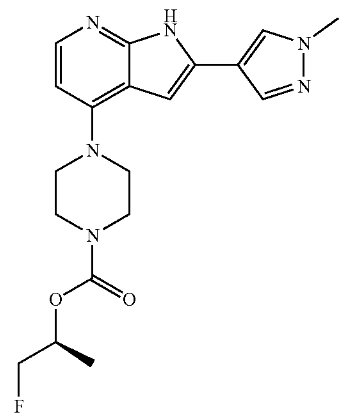 [SMILES: C[C@@H](CF)OC(=O)N1CCN(c2ccnc3[nH]c(-c4cnn(C)c4)cc23)CC1] | 387 | ¹H-NMR (400 MHz, 6d-DMSO) δ ppm 11.72 (s, 1H), 8.19 (s, 1H), 8.12 (s, 1H), 7.93 (s, 1H), 7.90 (d, 1H, J = 5.6 Hz), 6.66 (s, 1H), 6.42 (d, 1H, J = 5.2 Hz), 5.00-4.91 (m, 1H), 4.60-4.37 (m, 2H), 3.87 (s, 3H), 3.60-3.58 (m, 4H), 3.37-3.36 (m, 4H), 1.21 (d, 3H, J = 6.0 Hz). |
| 118 | 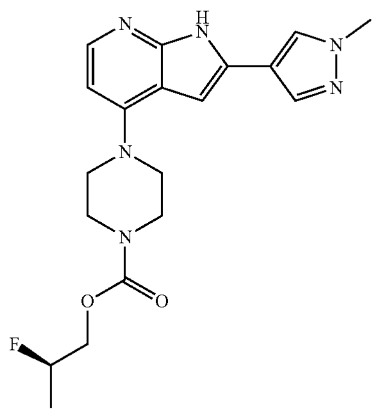 [SMILES: C[C@@H](F)COC(=O)N1CCN(c2ccnc3[nH]c(-c4cnn(C)c4)cc23)CC1] | 387 | ¹H-NMR (400 MHz, 6d-DMSO) δ ppm 11.72 (s, 1H), 8.16 (s, 1H), 8.12 (s, 1H), 7.93 (s, 1H), 7.90 (d, 1H, J = 5.6 Hz), 6.66 (s, 1H), 6.42 (d, 1H, J = 5.6 Hz), 5.00-4.81 (m, 1H), 4.27-4.06 (m, 2H), 3.88 (s, 3H), 3.62-3.60 (m, 4H), 3.39-3.37 (m, 4H), 1.31 (dd, 3H, J = 23.6, 6.4 Hz). |
| 119 | 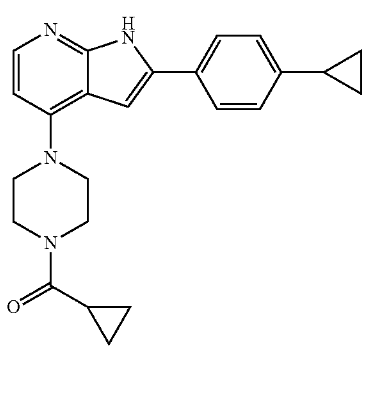 [SMILES: O=C(C1CC1)N1CCN(c2ccnc3[nH]c(-c4ccc(C5CC5)cc4)cc23)CC1] | 387 | |

TABLE 1-continued

| # | Structure | LCMS (M + 1) | ¹H NMR |
|---|---|---|---|
| 120 | 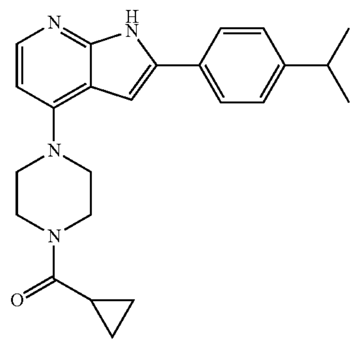 [SMILES: CC(C)c1ccc(-c2cc3c(N4CCN(C(=O)C5CC5)CC4)ccnc3[nH]2)cc1] | 389 | ¹H NMR (400 MHz, DMSO) δ 13.10 (s, 1H), 8.02 (d, J = 7.2 Hz, 1H), 7.85 (d, J = 8.3 Hz, 2H), 7.39 (d, J = 8.2 Hz, 3H), 6.76 (d, J = 7.3 Hz, 1H), 4.04 (d, J = 21.7 Hz, 15H), 3.77 (s, 2H), 2.94 (d, J = 6.9 Hz, 1H), 2.00 (dq, J = 7.4, 5.3 Hz, 1H), 1.25 (d, J = 6.9 Hz, 6H), 0.79 (t, J = 5.7 Hz, 4H). |
| 121 | 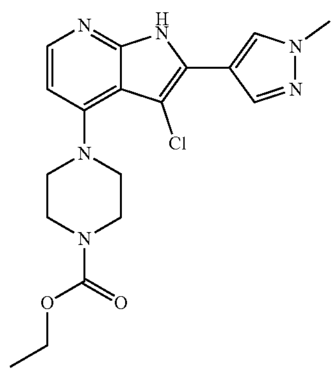 | 389 | ¹H NMR (400 MHz, Methanol-d4) δ 8.25 (s, 1H), 8.07 (d, J = 0.8 Hz, 1H), 8.02 (d, J = 5.5 Hz, 1H), 6.67 (d, J = 5.5 Hz, 1H), 4.17 (q, J = 7.1 Hz, 2H), 3.98 (s, 3H), 3.75 (t, J = 4.9 Hz, 4H), 3.23 (t, J = 5.0 Hz, 4H), 1.29 (t, J = 7.1 Hz, 3H). |
| 122 | 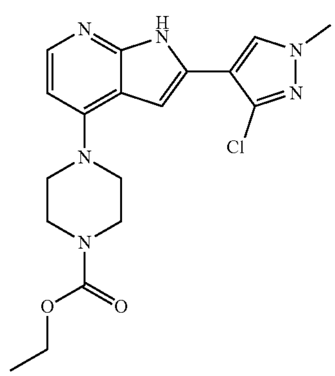 [SMILES: CCOC(=O)N1CCN(c2ccnc3[nH]c(-c4cn(C)nc4Cl)cc23)CC1] | 389 | ¹H-NMR (500 MHz, 6d-DMSO) δ ppm 11.75 (s, 1H), 8.19 (s, 1H), 7.96 (d, 1H, J = 5.0 Hz), 6.74 (s, 1H), 6.45 (d, 1H, J = 5.0 Hz), 4.08 (q, 2H, J = 7.0 Hz), 3.87 (s, 3H), 3.62-3.57 (m, 4H), 3.42-3.36 (m, 4H), 1.21 (t, 3H, J = 7.0 Hz). |
| 123 | 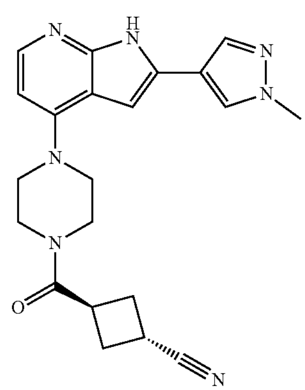 [SMILES: Cn1cc(-c2cc3c(N4CCN(C(=O)[C@H]5C[C@H](C#N)C5)CC4)ccnc3[nH]2)cn1] | 390 | ¹H-NMR (400 MHz, 6d-DMSO) δ ppm 11.71 (s, 1H), 8.11 (s, 1H), 7.92 (s, 1H), 7.89 (d, 1H, J = 5.2 Hz), 6.64 (d, 1H, J = 1.6 Hz), 6.39 (d, 1H, J = 5.2 Hz), 3.87 (s, 3H), 3.67-3.63 (m, 3H), 3.51-3.49 (m, 2H), 3.34-3.32 (m, 4H), 3.29-3.25 (m, 2H), 2.64-2.62 (m, 2H), 2.49-2.45 (m, 1H). |

TABLE 1-continued

| # | Structure | LCMS (M + 1) | ¹H NMR |
|---|---|---|---|
| 124 | 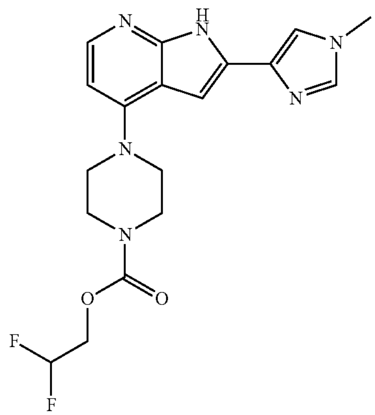 [SMILES: Cn1cnc(-c2cc3c(N4CCN(C(=O)OCC(F)F)CC4)ccnc3[nH]2)c1] | 391 | ¹H-NMR (400 MHz, 6d-DMSO) δ ppm 11.68 (s, 1H), 7.90 (d, 1H, J = 5.2 Hz), 7.65 (s, 3H), 7.55 (s, 3H), 6.63 (d, 1H, J = 1.6 Hz), 6.40 (d, 1H, J = 5.6 Hz), 6.27 (tt, 1H, J = 54.4 Hz, J = 3.2 Hz), 4.34 (td, 2H, J = 15.2 Hz, J = 3.2 Hz), 3.69 (s, 3H), 3.65-3.58 (m, 4H), 3.40-3.35 (m, 4H). |
| 125 | 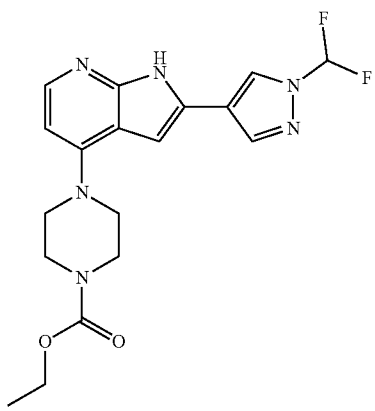 [SMILES: CCOC(=O)N1CCN(c2ccnc3[nH]c(-c4cnn(C(F)F)c4)cc23)CC1] | 391 | ¹H-NMR (400 MHz, 6d-DMSO) δ ppm 11.89 (s, 1H), 8.65 (s, 1H), 8.33 (s, 1H), 8.10-7.74 (m, 2H), 6.91 (d, 1H, J = 1.6 Hz), 6.44 (d, 1H, J = 5.6 Hz), 4.09 (q, 2H, J = 6.8 Hz), 3.61-3.57 (m, 4H), 3.41-3.38 (m, 4H), 1.22 (t, 3H, J = 6.8 Hz). |
| 126 | 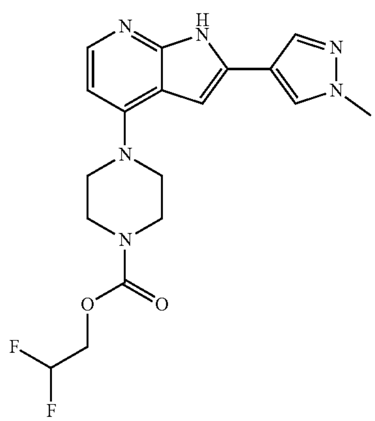 [SMILES: Cn1cc(-c2cc3c(N4CCN(C(=O)OCC(F)F)CC4)ccnc3[nH]2)cn1] | 391 | ¹H-NMR (500 MHz, 6d-DMSO) δ ppm 11.71 (s, 1H), 8.12 (s, 1H), 7.93 (s, 1H), 7.91 (d, 1H, J = 5.5 Hz), 6.66 (d, 1H, J = 2.0 Hz), 6.41 (d, 1H, J = 5.0 Hz), 6.28 (tt, 1H, J = 54.0, 13.0 Hz), 4.34 (t, 2H, J = 12.5 Hz), 3.87 (s, 3H), 3.63-3.61 (m, 4H), 3.40-3.32 (m, 4H). |
| 127 | 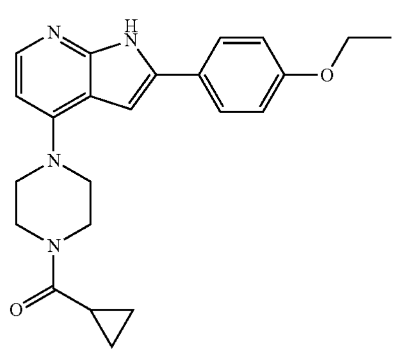 [SMILES: CCOc1ccc(-c2cc3c(N4CCN(C(=O)C5CC5)CC4)ccnc3[nH]2)cc1] | 391 | ¹H NMR (400 MHz, 6d-DMSO) δ ppm 11.84 (s, 1H), 7.93 (d, 1H, J = 5.2 Hz), 7.87 (d, 2H, J = 8.8 Hz), 6.98 (d, 2H, J = 8.8 Hz), 6.91 (s, 1H), 6.43 (d, 1H, J = 5.6 Hz), 4.08 (q., 2H, J = 7.2 Hz), 3.91 (br. s., 2H), 3.70 (br. s., 2H), 3.47 (br. s., 2H), 3.39 (br. s., 2H), 2.06-2.00 (m, 1H), 1.35 (t, 3H, J = 7.2 Hz), 0.78-0.74 (m, 4H). |

TABLE 1-continued

| # | Structure | LCMS (M + 1) | ¹H NMR |
|---|---|---|---|
| 128 | 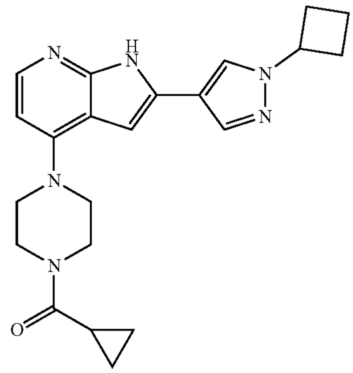 [SMILES: O=C(C1CC1)N1CCN(c2ccnc3[nH]c(-c4cnn(C5CCC5)c4)cc23)CC1] | 391 | ¹H NMR (400 MHz, DMSO-d$_6$) δ ppm 11.69 (s, 1H), 8.28 (s, 1H), 7.99 (s, 1H), 7.91 (d, 1H, J = 5.2 Hz), 6.69 (s, 1H), 6.42 (d, 1H, J = 5.2 Hz), 4.87-4.83 (m, 1H), 3.90 (br. s., 2H), 3.69 (br. s., 2H), 3.44 (br. s., 2H), 3.41 (br. s., 2H), 2.43-2.41 (m, 4H), 2.05-2.01 (m, 1H), 1.83-1.78 (m, 2H), 0.78-0.74 (m, 4H). |
| 129 | 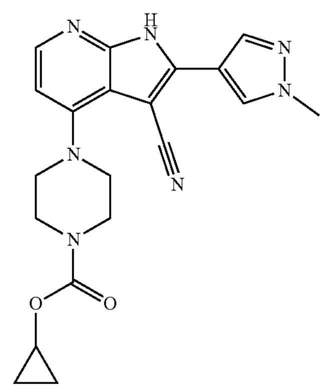 [SMILES: Cn1cc(-c2[nH]c3nccc(N4CCN(C(=O)OC5CC5)CC4)c3c2C#N)cn1] | 392 | ¹H-NMR (500 MHz, 6d-DMSO) δ ppm 12.92 (s, 1H), 8.40 (s, 1H), 8.19-8.13 (m, 2H), 6.73 (d, 1H, J = 5.0 Hz), 4.10-4.00 (m, 1H), 3.97 (s, 3H), 3.65-3.52 (m, 4H), 3.20-3.08 (m, 4H), 0.70-0.60 (m, 4H). |
| 130 | 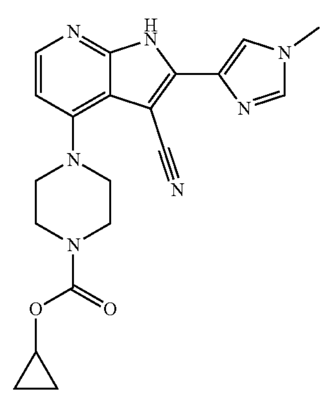 [SMILES: Cn1cnc(-c2[nH]c3nccc(N4CCN(C(=O)OC5CC5)CC4)c3c2C#N)c1] | 392 | ¹H-NMR (400 MHz, 6d-DMSO) δ ppm 12.85 (br. s., 1H), 8.14 (d, 1H, J = 6.0 Hz), 7.88 (s, 1H), 7.87 (s, 1H), 6.72 (d, 1H, J = 5.2 Hz), 4.06-4.00 (m, 1H), 3.79 (s, 3H), 3.65-3.55 (m, 4H), 3.20-3.10 (m, 4H), 0.68-0.62 (m, 4H). |
| 131 | 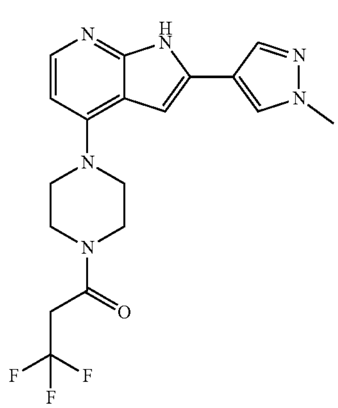 [SMILES: Cn1cc(-c2cc3c(N4CCN(C(=O)CC(F)(F)F)CC4)ccnc3[nH]2)cn1] | 393 | ¹H NMR (400 MHz, DMSO) δ 12.98 (s, 1H), 8.20 (s, 1H), 7.99 (dd, J = 10.1, 3.9 Hz, 2H), 7.10 (d, J = 2.0 Hz, 1H), 6.76 (d, J = 7.2 Hz, 1H), 3.97 (s, 4H), 3.92 (s, 3H), 3.80-3.70 (m, 6H). |

TABLE 1-continued
| # | Structure | LCMS (M + 1) | ¹H NMR |
|---|---|---|---|
| 132 | 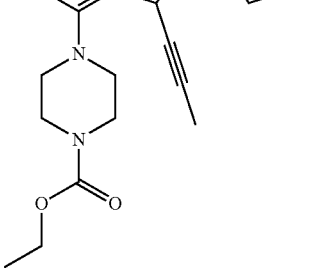 | 393 | ¹H-NMR (400 MHz, DMSO-d₆) δ ppm 12.04 (br. s., 1H), 8.34 (s, 1H), 8.17 (s, 1H), 8.00 (d, 1H, J = 5.2 Hz), 6.54 (d, 1H, J = 5.2 Hz.), 4.08 (q, 2H, J = 6.8 Hz.), 3.93 (s, 3H), 3.63-3.58 (m, 4H), 3.23-3.16 (m, 4H), 2.21 (s, 3H), 1.22 (t, 3H, J = 6.8 Hz). |
| 133 | 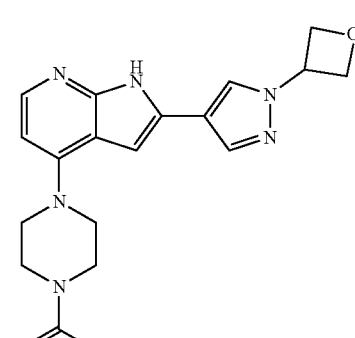 | 393 | |
| 134 | 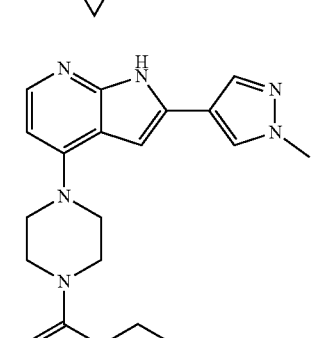 | 393 | ¹H NMR (400 MHz, DMSO) δ 12.94 (s, 1H), 8.20 (s, 1H), 8.02-7.96 (m, 2H), 7.11 (d, J = 2.0 Hz, 1H), 6.74 (d, J = 7.2 Hz, 1H), 3.94 (d, J = 19.9 Hz, 7H), 3.80 (s, 2H), 3.71 (s, 2H), 2.61 (t, J = 9.5 Hz, 1H), 1.70 (dd, J = 25.5, 12.5 Hz, 5H), 1.42-1.16 (m, 5H). |
| 135 | 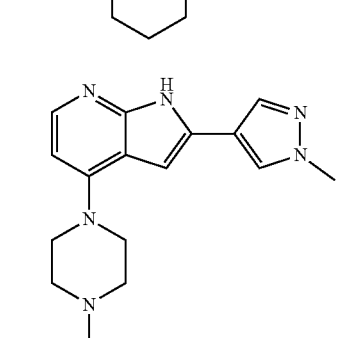 | 393 | ¹H NMR (400 MHz, DMSO) δ 12.98 (s, 1H), 8.19 (s, 1H), 7.98 (dd, J = 7.7, 3.9 Hz, 2H), 7.10 (d, J = 2.0 Hz, 1H), 6.74 (d, J = 7.3 Hz, 1H), 3.94 (d, J = 3.9 Hz, 3H), 3.92 (s, 3H), 3.75 (dd, J = 12.6, 8.2 Hz, 4H), 2.40 (d, J = 7.1 Hz, 2H), 2.24-2.12 (m, 1H), 1.79 (td, J = 11.4, 6.5 Hz, 2H), 1.56 (dddd, J = 18.5, 14.8, 10.0, 5.0 Hz, 4H), 1.16 (dt, J = 12.3, 7.5 Hz, 2H). |

TABLE 1-continued

| # | Structure | LCMS (M + 1) | ¹H NMR |
|---|---|---|---|
| 136 | 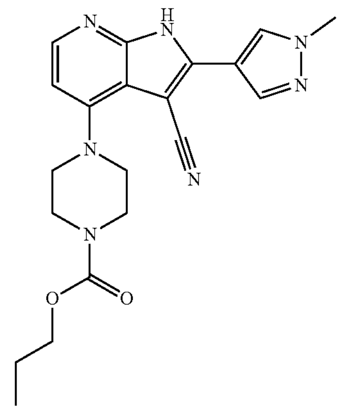 [SMILES: CCCOC(=O)N1CCN(c2ccnc3[nH]c(-c4cnn(C)c4)c(C#N)c23)CC1] | 394 | ¹H-NMR (500 MHz, 6d-DMSO) δ ppm 12.93 (s, 1H), 8.41 (s, 1H), 8.19-8.13 (m, 2H), 6.74 (d, 1H, J = 5.5 Hz), 4.00 (t, 2H, J = 6.5 Hz), 3.97 (s, 3H), 3.65-3.52 (m, 4H), 3.20-3.08 (m, 4H), 1.64-1.58 (m, 2H), 0.91 (t, 3H, J = 7.0 Hz). |
| 137 | 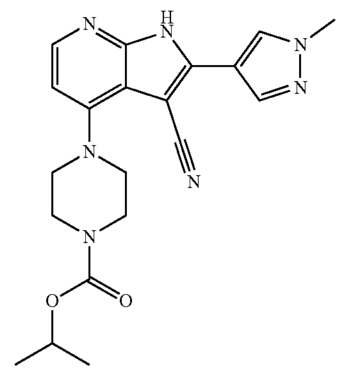 [SMILES: CC(C)OC(=O)N1CCN(c2ccnc3[nH]c(-c4cnn(C)c4)c(C#N)c23)CC1] | 394 | ¹H-NMR (500 MHz, 6d-DMSO) δ ppm 12.93 (s, 1H), 8.41 (s, 1H), 8.19-8.13 (m, 2H), 6.74 (d, 1H, J = 5.0 Hz), 4.84-4.80 (m, 1H), 3.97 (s, 3H), 3.65-3.52 (m, 4H), 3.25-3.10 (m, 4H), 1.22 (d, 6H, J = 6.5 Hz). |
| 138 | 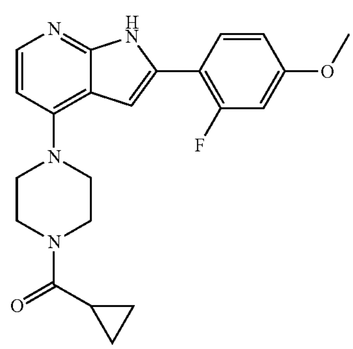 [SMILES: COc1ccc(-c2cc3c(N4CCN(C(=O)C5CC5)CC4)ccnc3[nH]2)c(F)c1] | 395 | ¹H NMR (400 MHz, DMSO) δ 12.81 (s, 1H), 8.03 (d, J = 7.2 Hz, 1H), 7.84 (t, J = 8.9 Hz, 1H), 7.20 (s, 1H), 7.07 (dd, J = 13.5, 2.4 Hz, 1H), 6.99 (dd, J = 8.8, 2.4 Hz, 1H), 6.77 (d, J = 7.3 Hz, 1H), 4.04 (d, J = 24.9 Hz, 7H), 3.85 (s, 4H), 3.76 (s, 3H), 2.02-1.94 (m, 1H), 0.78 (d, J = 7.9 Hz, 4H). |
| 139 | 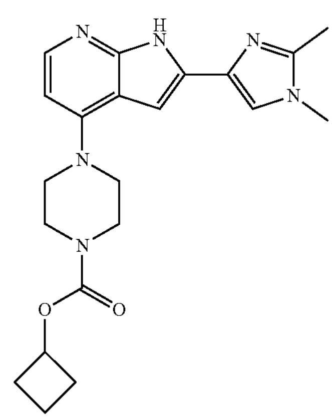 [SMILES: Cc1nc(-c2cc3c(N4CCN(C(=O)OC5CCC5)CC4)ccnc3[nH]2)cn1C] | 395 | ¹H-NMR (500 MHz, DMSO-d₆) δ ppm 11.58 (br. s., 1H), 7.89 (d, 1H, J = 5.0 Hz), 7.45 (s, 1H), 6.56 (d, 1H, J = 1.5 Hz), 6.40 (d, 1H, J = 5.5 Hz), 4.89-4.85(m, 1H), 3.63-3.59 (m, 4H), 3.69 (s, 3H), 3.36-3.33 (m, 4H), 2.32(s, 3H), 2.29-2.24(m, 2H), 2.05-2.00(m, 2H), 1.75-1.54(m, 2H). |

TABLE 1-continued
| # | Structure | LCMS (M + 1) | ¹H NMR |
|---|---|---|---|
| 140 | 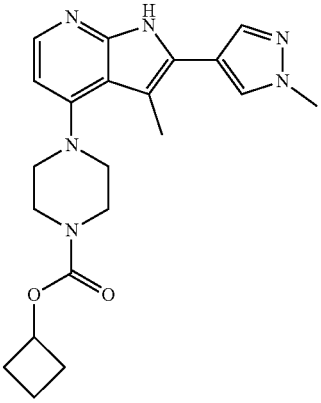 [SMILES: Cc1c(-c2cnn(C)c2)[nH]c2nccc(N3CCN(C(=O)OC4CCC4)CC3)c12] | 395 | ¹H-NMR (500 MHz, 6d-DMSO) δ ppm 11.57 (s, 1H), 8.10 (s, 1H), 7.96 (d, 1H, J = 5.0 Hz), 7.90 (s, 1H), 6.55 (d, 1H, J = 5.0 Hz), 4.90-4.84 (m, 1H), 3.91 (s, 3H), 3.69-3.52 (m, 4H), 3.15-3.00 (m, 4H), 2.45 (s, 3H), 2.30-2.20 (m, 2H), 2.10-1.95 (m, 2H), 1.80-1.65 (m, 1H), 1.65-1.50 (m, 1H). |
| 141 | 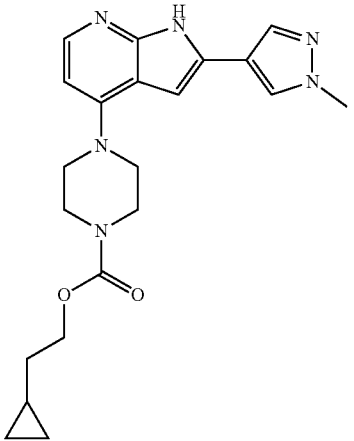 [SMILES: Cn1cc(-c2cc3c(N4CCN(C(=O)OCCC5CC5)CC4)ccnc3[nH]2)cn1] | 395 | |
| 142 | 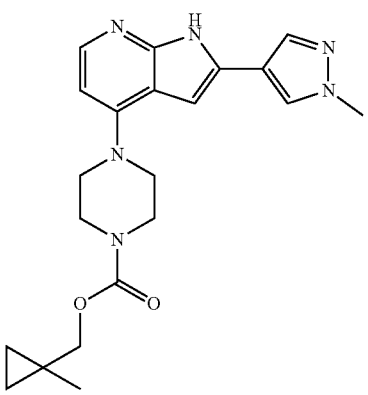 [SMILES: Cn1cc(-c2cc3c(N4CCN(C(=O)OCC5(C)CC5)CC4)ccnc3[nH]2)cn1] | 395 | ¹H-NMR (500 MHz, 6d-DMSO) δ ppm 11.72 (s, 1H), 8.13 (s, 1H), 7.94 (s, 1H), 7.91 (d, 1H, J = 5.5 Hz), 6.68 (d, 1H, J = 2.0 Hz), 6.42 (d, 1H, J = 5.5 Hz), 3.87 (s, 3H), 3.88 (s, 2H), 3.62-3.61 (m, 4H), 3.40-3.39 (m, 4H), 1.12 (s, 3H), 1.49-0.48 (m, 2H), 0.36-0.34 (m, 2H). |

TABLE 1-continued

| # | Structure | LCMS (M + 1) | ¹H NMR |
|---|---|---|---|
| 143 | 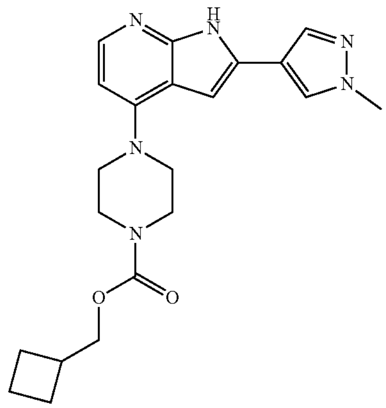 [SMILES: Cn1cc(-c2cc3c(N4CCN(C(=O)OCC5CCC5)CC4)ccnc3[nH]2)cn1] | 395 | ¹H-NMR (500 MHz, 6d-DMSO) δ ppm 11.72 (s, 1H), 8.13 (s, 1H), 7.94 (s, 1H), 7.91 (d, 1H, J = 5.5 Hz), 6.67 (s, 1H), 6.42 (d, 1H, J = 5.5 Hz), 4.02 (d, 2H, J = 6.5 Hz), 3.88 (s, 3H), 3.59-3.60 (m, 4H), 3.38-3.34 (m, 4H), 2.64-2.57 (m, 1H), 2.05-1.99 (m, 2H), 1.91-1.85 (m, 2H), 1.81-1.74 (m, 2H). |
| 144 | 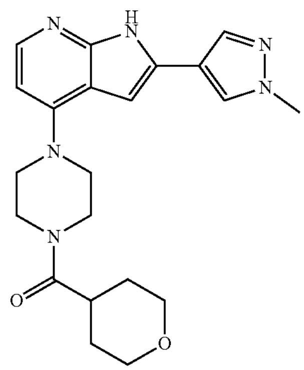 [SMILES: Cn1cc(-c2cc3c(N4CCN(C(=O)C5CCOCC5)CC4)ccnc3[nH]2)cn1] | 395 | ¹H NMR (400 MHz, DMSO) δ 12.95 (s, 1H), 8.19 (s, 1H), 8.01-7.97 (m, 2H), 7.10 (d, J = 2.0 Hz, 1H), 6.75 (d, J = 7.2 Hz, 1H), 4.02-3.81 (m, 12H), 3.72 (s, 2H), 3.41 (td, J = 11.2, 3.0 Hz, 2H), 2.93 (s, 1H), 1.68-1.54 (m, 4H). |
| 145 | 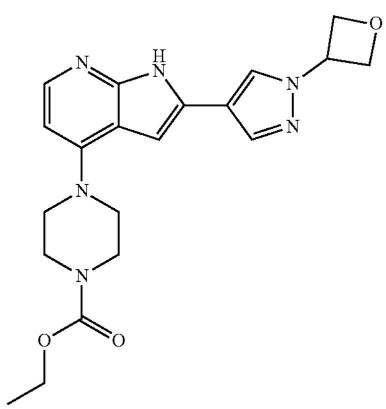 [SMILES: CCOC(=O)N1CCN(c2ccnc3[nH]c(-c4cnn(C5COC5)c4)cc23)CC1] | 397 | ¹H-NMR (500 MHz, 6d-DMSO) δ ppm 11.75 (s, 1H), 8.36 (s, 1H), 8.19 (s, 1H), 8.10 (s, 1H), 7.92 (d, 1H, J = 5.5 Hz), 6.72 (d, 1H, J = 1.5 Hz), 6.42 (d, 1H, J = 5.0 Hz), 5.61-5.59 (m, 1H), 4.97-4.94 (m, 2H), 4.91-4.88 (m, 2H), 4.01 (q, 2H, J = 7.5 Hz), 3.60-3.58 (m, 4H), 3.37-3.30 (m, 4H), 1.22 (t, 3H, J = 7.0 Hz). |
| 146 | 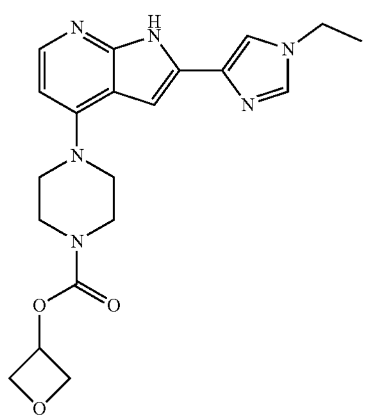 [SMILES: CCn1cnc(-c2cc3c(N4CCN(C(=O)OC5COC5)CC4)ccnc3[nH]2)c1] | 397 | ¹H-NMR (400 MHz, 6d-DMSO) δ ppm 11.66 (s, 1H), 7.91 (d, 1H, J = 5.6 Hz), 7.33 (s, 1H), 7.64 (s, 1H), 6.64 (s, 1H), 6.42 (d, 1H, J = 5.6 Hz), 5.35-5.31 (m, 1H), 4.80-4.76 (m, 2H), 4.54-4.51 (m, 2H), 4.04 (q, 2H, J = 7.2 Hz), 3.68-3.58 (m, 4H), 3.40-3.37 (m, 4H), 1.38 (t, 3H, J = 7.2 Hz). |

TABLE 1-continued

| # | Structure | LCMS (M + 1) | ¹H NMR |
|---|---|---|---|
| 147 | 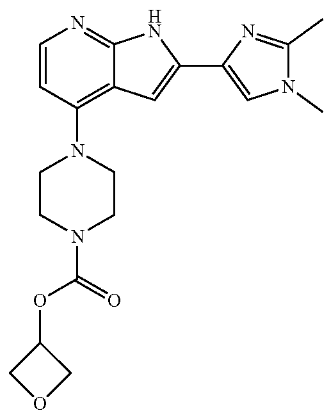 [SMILES: Cc1nc(-c2cc3c(N4CCN(C(=O)OC5COC5)CC4)ccnc3[nH]2)cn1C] | 397 | ¹H-NMR (500 MHz, d₆-DMSO) δ ppm 11.62 (s, 1H), 7.90 (d, 1H, J = 5.5 Hz), 7.47 (s, 1H), 6.58 (s, 1H), 6.41 (d, 1H, J = 5.5 Hz), 5.35-5.31 (m, 1H), 4.81-4.78 (m, 2H), 4.55-4.52 (m, 2H), 3.69-3.59 (m, 2H), 3.60-3.55 (m, 5H), 3.89-3.34 (m, 4H), 2.33 (s, 3H). |
| 148 | 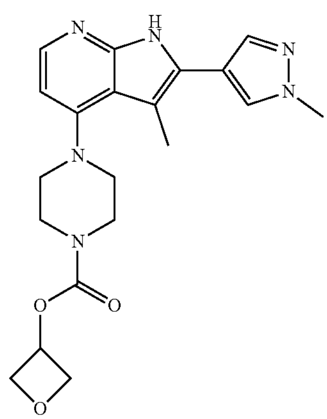 [SMILES: Cc1c(-c2cnn(C)c2)[nH]c2nccc(N3CCN(C(=O)OC4COC4)CC3)c12] | 397 | ¹H-NMR (500 MHz, 6d-DMSO) δ ppm 11.56 (s, 1H), 8.29 (s, 1H), 8.10 (s, 1H), 7.96 (d, 1H, J = 5.0 Hz), 7.90 (s, 1H), 6.55 (d, 1H, J = 5.0 Hz), 5.33 (quintet, 1H, J = 5.5 Hz), 4.78 (t, 2H, J = 7.5 Hz), 4.52 (dd, 2H, J = 7.5, 5.5 Hz), 3.93 (s, 3H), 3.75-3.70 (m, 2H), 3.70-3.65 (m, 2H), 3.15-3.00 (m, 4H), 2.51 (s, 3H). |
| 149 | 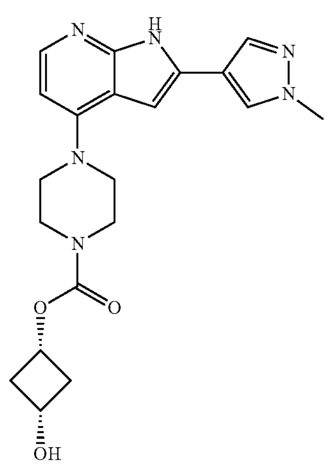 [SMILES: Cn1cc(-c2cc3c(N4CCN(C(=O)O[C@H]5C[C@@H](O)C5)CC4)ccnc3[nH]2)cn1] | 397 | ¹H-NMR (400 MHz, DMSO-d₆) δ ppm 11.72 (br. s., 1H), 8.12 (s, 1H), 7.93 (s, 1H), 7.90 (d, 1H, J = 5.2 Hz), 6.65 (s, 1H), 6.41 (d, 1H, J = 5.2 Hz.), 5.17 (d, 1H, J = 6.8 Hz.), 4.49-4.41 (m, 1H), 3.88 (s, 3H), 3.83-3.73 (m, 1H), 3.61-3.54 (m, 4H), 3.38-3.36 (m, 4H), 2.70-2.61 (m, 2H), 1.92-1.84 (m, 2H). |

TABLE 1-continued

| # | Structure | LCMS (M + 1) | ¹H NMR |
|---|---|---|---|
| 150 | 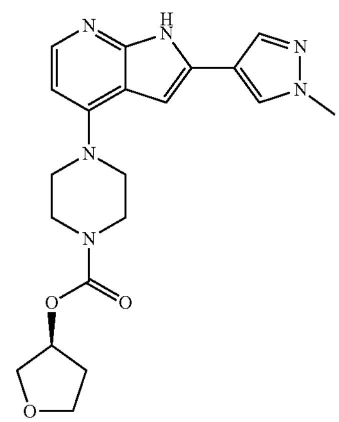 [SMILES: Cn1cc(-c2cc3c(N4CCN(C(=O)O[C@H]5CCOC5)CC4)ccnc3[nH]2)cn1] | 397 | ¹H-NMR (500 MHz, 6d-DMSO) δ ppm 11.72 (s, 1H), 8.12 (s, 1H), 7.93 (s, 1H), 7.90 (d, 1H, J = 5.5 Hz), 6.65 (d, 1H, J = 1.5 Hz), 6.41 (d, 1H, J = 5.5 Hz), 5.20-5.17 (m, 1H), 3.87 (s, 3H), 3.82-3.80 (m, 2H), 3.80-3.78 (m, 2H), 3.74-3.73 (m, 4H), 3.36-3.32 (m, 4H), 2.16-2.12 (m, 1H), 1.96-1.93 (m, 1H). |
| 151 | 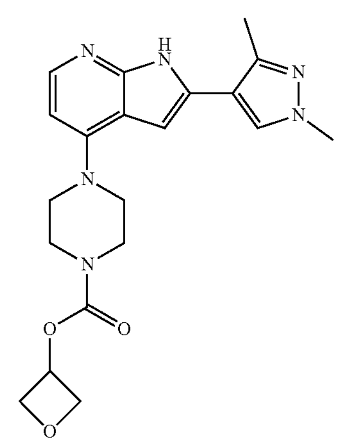 [SMILES: Cc1nn(C)cc1-c1cc2c(N3CCN(C(=O)OC4COC4)CC3)ccnc2[nH]1] | 397 | ¹H-NMR (500 MHz, 6d-DMSO) δ ppm 8.01 (s, 1H), 7.93 (d, 1H, J = 6.0 Hz), 6.44 (d, 1H, J = 5.0 Hz), 6.40 (s, 1H), 5.34 (quintet, 1H, J = 5.5 Hz), 4.79 (t, 2H, J = 7.0 Hz), 4.53 (dd, 2H, J = 7.0, 5.5 Hz), 3.80 (s, 3H), 3.69-3.64 (m, 2H), 3.60-3.55 (m, 2H), 3.42-3.38 (m, 4H), 2.38 (s, 3H). |
| 152 | 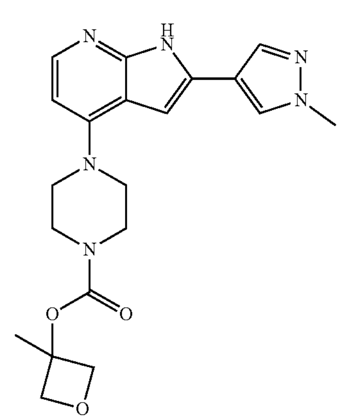 | 397 | ¹H-NMR (500 MHz, 6d-DMSO) δ ppm 11.72 (s, 1H), 8.12 (s, 1H), 7.93 (s, 1H), 7.90 (d, 1H, J = 5.5 Hz), 6.65 (d, 1H, J = 1.5 Hz), 6.41 (d, 1H, J = 5.5 Hz), 4.65 (d, 2H, J = 7.0 Hz), 4.42 (d, 1H, J = 7.0 Hz), 3.87 (s, 3H), 3.65-3.60 (m, 2H), 3.60-3.55 (m, 2H), 3.40-3.32 (m, 4H), 1.66 (s, 3H). |

TABLE 1-continued
| # | Structure | LCMS (M + 1) | ¹H NMR |
|---|---|---|---|
| 153 | 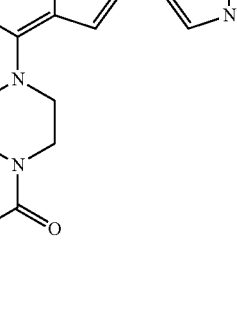 | 397 | ¹H-NMR (500 MHz, 6d-DMSO) δ ppm 11.71 (s, 1H), 8.17 (s, 1H), 8.12 (s, 1H), 7.93 (s, 1H), 7.90 (d, 1H, J = 5.5 Hz), 6.66 (d, 1H, J = 2.0 Hz), 6.41 (d, 1H, J = 5.5 Hz), 4.67-4.64 (m, 2H), 4.40-4.37 (m, 2H), 4.25-4.24 (m, 2H), 3.87 (s, 3H), 3.38-3.37 (m, 4H), 3.32-3.27 (m, 4H), 2.50-2.49 (m, 1H). |
| 154 | 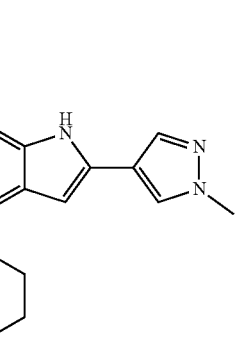 | 397 | ¹H-NMR (500 MHz, 6d-DMSO) δ ppm 11.72 (s, 1H), 8.12 (s, 1H), 7.93 (s, 1H), 7.90 (d, 1H, J = 5.5 Hz), 6.65 (d, 1H, J = 1.5 Hz), 6.41 (d, 1H, J = 5.5 Hz), 5.20-5.17 (m, 1H), 3.87 (s, 3H), 3.82-3.80 (m, 2H), 3.80-3.78 (m, 2H), 3.74-3.73 (m, 4H), 3.36-3.32 (m, 4H), 2.16-2.12 (m, 1H), 1.96-1.93 (m, 1H). |
| 155 | 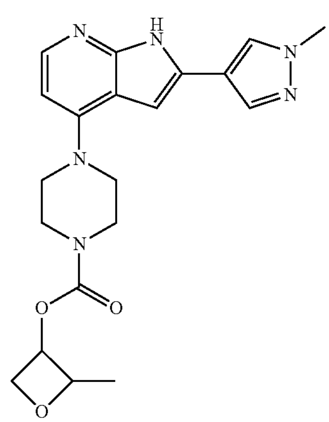 [SMILES: CC1OCC1OC(=O)N1CCN(c2ccnc3[nH]c(-c4cnn(C)c4)cc23)CC1] | 397 | ¹H-NMR (500 MHz, 6d-DMSO) δ ppm 14.35-14.16 (m, 0.25H), 13.17 (s, 0.75H), 8.30 (s, 1H), 8.04 (s, 1H), 7.92 (d, 1H, J = 6.5 Hz), 7.08 (s, 1H), 6.73 (d, 1H, J = 7.0 Hz), 5.40-5.30 (m, 0.25H), 5.10-5.00 (m, 0.25H), 5.00-4.90 (m, 0.75H), 4.80-4.70 (m, 1H), 4.70-4.60 (m, 0.75H), 4.45-4.35 (m, 1H), 4.00-3.80 (m, 7H), 3.80-3.55 (m, 4H), 1.45-1.25 (m, 3H). |

TABLE 1-continued

| # | Structure | LCMS (M + 1) | ¹H NMR |
|---|---|---|---|
| 156 | 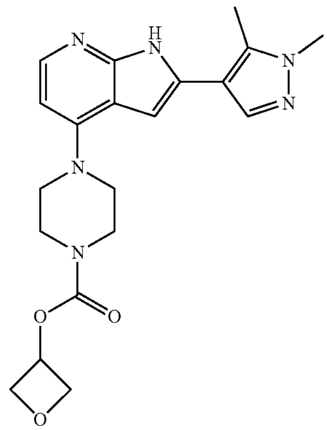 [SMILES: Cc1c(-c2cc3c(N4CCN(C(=O)OC5COC5)CC4)ccnc3[nH]2)cnn1C] | 397 | ¹H-NMR (500 MHz, 6d-DMSO) δ ppm 11.70-11.55 (br., 1H), 7.93 (d, 1H, J = 5.5 Hz), 7.80 (s, 1H), 6.45 (d, 1H, J = 6.0 Hz), 6.40 (s, 1H), 5.34 (quintet, 1H, J = 6.0 Hz), 4.79 (t, 2H, J = 7.0 Hz), 4.53 (dd, 2H, J = 7.0, 5.0 Hz), 3.80 (s, 3H), 3.69-3.64 (m, 2H), 3.60-3.55 (m, 2H), 3.42-3.38 (m, 4H), 2.47 (s, 3H). |
| 157 | 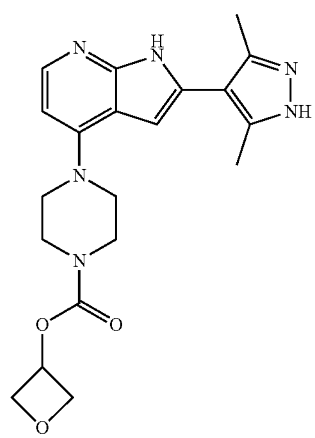 [SMILES: Cc1n[nH]c(C)c1-c1cc2c(N3CCN(C(=O)OC4COC4)CC3)ccnc2[nH]1] | 397 | ¹H-NMR (400 MHz, 6d-DMSO) δ ppm 12.34 (s, 1H), 11.31 (s, 1H), 7.94 (d, 1H, J = 5.6 Hz), 6.45 (d, 1H, J = 5.6 Hz), 6.33 (s, 1H), 5.34-5.30 (m, 1H), 4.79-4.76 (m, 2H), 4.54-4.51 (m, 2H), 3.67-3.65 (m, 2H), 3.57-3.55 (m, 2H), 3.39-3.37 (m, 4H), 2.28 (s, 6H). |
| 158 | 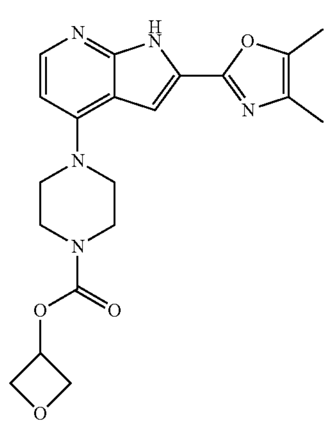 [SMILES: Cc1nc(-c2cc3c(N4CCN(C(=O)OC5COC5)CC4)ccnc3[nH]2)oc1C] | 398 | ¹H-NMR (400 MHz, CDCl₃) δ ppm 11.20-10.75 (br., 1H), 8.27 (d, 1H, J = 5.6 Hz), 7.02 (s, 1H), 6.45 (d, 1H, J = 5.6 Hz), 5.50-5.40 (m, 1H), 4.93 (t, 2H, J = 7.6 Hz), 4.70 (dd, 2H, J = 7.6, 5.6 Hz), 3.77-3.70 (m, 4H), 3.56-3.50 (m, 4H), 3.20-3.15 (m, 1H), 3.08-3.03 (m, 1H), 2.95-2.88 (m, 2H), 2.73-2.68 (m, 1H), 2.54-2.50 (m, 1H), 2.37 (s, 3H), 2.19 (s, 3H). |

TABLE 1-continued

| # | Structure | LCMS (M + 1) | ¹H NMR |
|---|---|---|---|
| 159 | 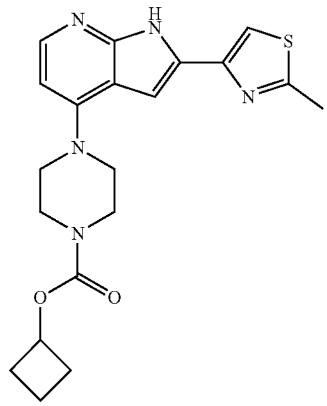 [SMILES: Cc1nc(-c2cc3c(N4CCN(C(=O)OC5CCC5)CC4)ccnc3[nH]2)cs1] | 398 | ¹H-NMR (400 MHz, 6d-DMSO) δ ppm 11.98 (s, 1H), 7.97 (d, 1H, J = 5.2 Hz), 7.87 (s, 1H), 6.88 (s, 1H), 6.44 (d, 1H, J = 5.2 Hz), 4.87 (quintet, 1H, J = 7.2 Hz), 3.60-3.51 (m, 4H), 3.45-3.38 (m, 4H), 2.72 (s, 3H), 2.28-2.23 (m, 2H), 2.05-1.98 (m, 2H), 1.75-1.70 (m, 1H), 1.59-1.54 (m, 1H). |
| 160 | 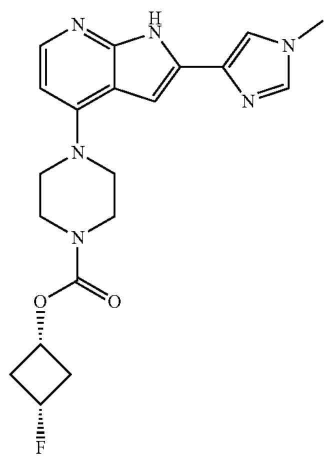 [SMILES: Cn1cnc(-c2cc3c(N4CCN(C(=O)O[C@H]5C[C@@H](F)C5)CC4)ccnc3[nH]2)c1] | 399 | ¹H-NMR (400 MHz, 6d-DMSO) δ ppm 11.66 (s, 1H), 7.90 (d, 1H, J = 5.2 Hz), 7.65 (s, 1H), 7.55 (d, 1H, J = 0.4 Hz), 6.62 (d, 1H, J = 1.6 Hz), 4.93-4.73 (m, 1H), 4.54-4.48 (m, 1H), 3.69 (s, 3H), 3.67-3.52 (m, 4H), 3.40-3.34 (m, 4H), 2.85-2.80 (m, 2H), 2.29-2.15 (m, 2H). |
| 161 | 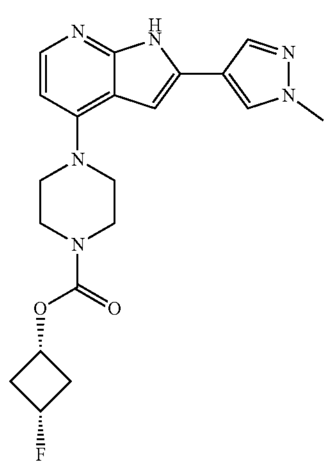 [SMILES: Cn1cc(-c2cc3c(N4CCN(C(=O)O[C@H]5C[C@@H](F)C5)CC4)ccnc3[nH]2)cn1] | 399 | ¹H NMR (400 MHz, DMSO-d6) δ 11.69 (s, 1H), 8.11 (d, J = 6.8 Hz, 1H), 7.98-7.75 (m, 2H), 6.63 (s, 1H), 6.40 (d, J = 5.5 Hz, 1H), 4.82 (dp, J = 56.7, 6.5 Hz, 1H), 4.50 (dq, J = 11.2, 6.8 Hz, 1H), 3.86 (s, 3H), 3.57 (s, 4H), 3.36 (t, J = 5.1 Hz, 4H), 2.94-2.72 (m, 2H), 2.32-2.11 (m, 2H). |

TABLE 1-continued

| # | Structure | LCMS (M + 1) | ¹H NMR |
|---|---|---|---|
| 162 | 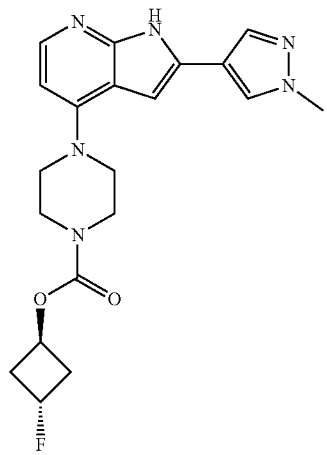 [SMILES: Cn1cc(-c2cc3c(N4CCN(C(=O)O[C@H]5C[C@H](F)C5)CC4)ccnc3[nH]2)cn1] | 399 | ¹H-NMR (500 MHz, 6d-DMSO) δ ppm 11.72 (s, 1H), 8.12 (s, 1H), 7.93 (s, 1H), 7.90 (d, 1H, J = 5.5 Hz), 6.65 (d, 1H, J = 1.5 Hz), 6.42 (d, 1H, J = 6.0 Hz), 5.25-5.23 (m, 1H), 5.09-5.08 (m, 1H), 3.88 (s, 3H), 4.59-4.51 (m, 4H), 3.38-3.33 (m, 4H), 2.57-2.43 (m, 4H). |
| 163 | 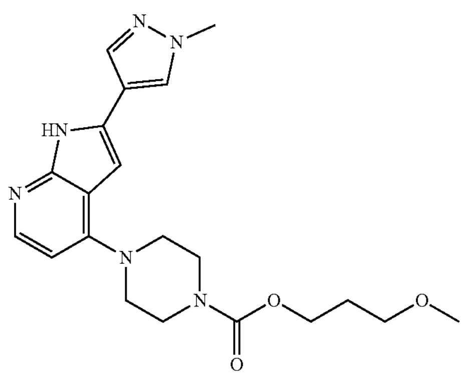 [SMILES: COCCCOC(=O)N1CCN(c2ccnc3[nH]c(-c4cnn(C)c4)cc23)CC1] | 399 | ¹H-NMR (400 MHz, 6d-DMSO) δ ppm 11.72 (s, 1H), 8.12 (s, 1H), 7.94 (s, 1H), 7.90 (d, 1H, J = 5.6 Hz), 6.66 (s, 1H), 6.41 (d, 1H, J = 5.6 Hz), 4.09 (t, 2H, J = 6.4 Hz), 3.87 (s, 3H), 3.60-3.58 (m, 4H), 3.40 (t, 2H, J = 6.4 Hz), 3.37-3.33 (m, 4H), 3.24 (s, 3H), 1.83 (quintet, 2H, J = 6.4 Hz). |
| 164 | 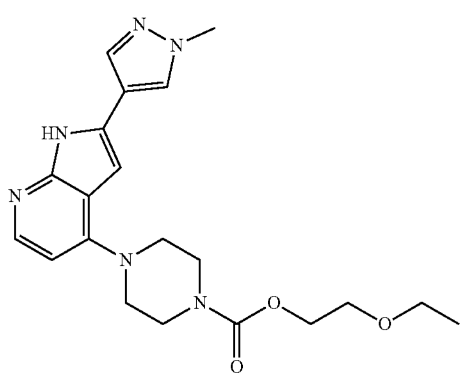 [SMILES: CCOCCOC(=O)N1CCN(c2ccnc3[nH]c(-c4cnn(C)c4)cc23)CC1] | 399 | ¹H-NMR (400 MHz, 6d-DMSO) δ ppm 11.72 (s, 1H), 8.12 (s, 1H), 7.94 (s, 1H), 7.90 (d, 1H, J = 5.6 Hz), 6.67 (d, 1H, J = 1.6 Hz), 6.42 (d, 1H, J = 5.6 Hz), 4.15 (t, 2H, J = 4.8 Hz), 3.88 (s, 3H), 3.62-3.56 (m, 4H), 3.58 (t, 2H, J = 4.8 Hz), 3.47 (q, 2H, J = 6.8 Hz), 3.38-3.32 (m, 4H), 1.12 (t, 3H, J = 6.8 Hz). |
| 165 | 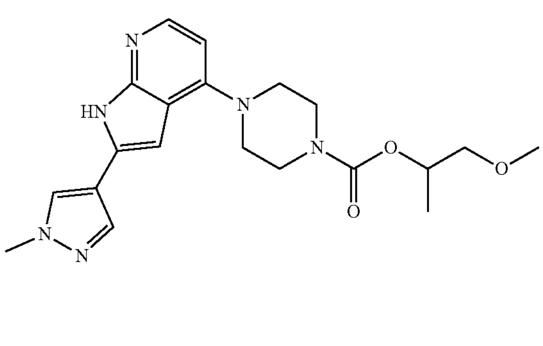 | 399 | ¹H-NMR (500 MHz, 6d-DMSO) δ ppm 11.72 (s, 1H), 8.12 (s, 1H), 7.94 (s, 1H), 7.90 (d, 1H, J = 5.0 Hz), 6.67 (d, 1H, J = 1.5 Hz), 6.42 (d, 1H, J = 6.0 Hz), 4.88-4.85 (m, 1H), 3.88 (s, 3H), 3.60-3.54 (m, 4H), 3.44-3.36 (m, 2H), 3.42-3.37 (m, 4H), 3.28 (s, 3H), 1.18 (d, 3H, J = 7.0 Hz). |

TABLE 1-continued

| # | Structure | LCMS (M + 1) | ¹H NMR |
|---|---|---|---|
| 166 | 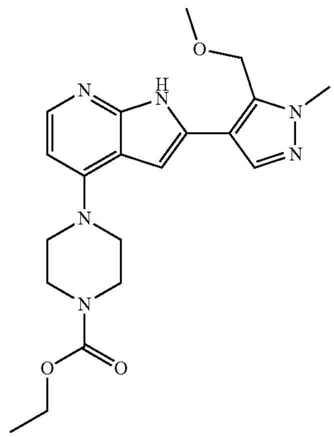 [SMILES: CCOC(=O)N1CCN(c2ccnc3[nH]c(-c4cnn(C)c4COC)cc23)CC1] | 399 | ¹H-NMR (400 MHz, 6d-DMSO) δ ppm 11.65 (s, 1H), 7.94 (d, 1H, J = 5.2 Hz), 7.84 (s, 1H), 6.46-6.40 (m, 2H), 4.65 (s, 2H), 4.07 (q, 2H, J = 6.8 Hz), 3.88 (s, 3H), 3.62-3.54 (m, 4H), 3.42-3.35 (m, 4H), 3.33 (s, 3H), 1.21 (t, 3H, J = 6.8 Hz). |
| 167 | 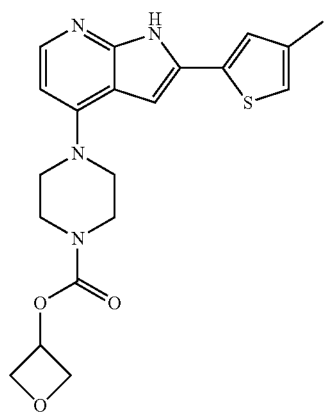 [SMILES: Cc1csc(-c2cc3c(N4CCN(C(=O)OC5COC5)CC4)ccnc3[nH]2)c1] | 399 | ¹H-NMR (400 MHz, 6d-DMSO) δ ppm 11.99 (br s, 1H), 7.96 (d, 1H, J = 4.8 Hz), 7.41 (s, 1H), 7.10 (s, 1H), 6.70 (s, 1H), 6.45 (d, 1H, J = 5.2 Hz), 5.34-5.31 (m, 1H), 4.80-4.77 (m, 2H), 4.54-4.51 (m, 2H), 3.68-3.66 (m, 2H), 3.59-3.57 (m, 2H), 3.42-3.41 (m, 4H), 2.23 (t, 3H). |
| 168 | 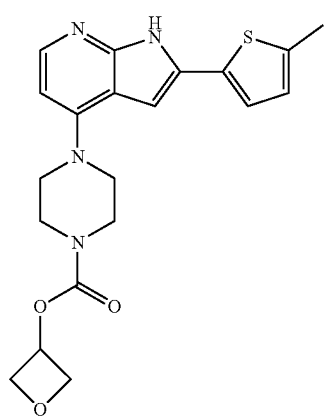 [SMILES: Cc1ccc(-c2cc3c(N4CCN(C(=O)OC5COC5)CC4)ccnc3[nH]2)s1] | 399 | ¹H-NMR (400 MHz, 6d-DMSO) δ ppm 11.95 (s, 1H), 7.95 (d, 1H, J = 5.2 Hz), 7.37 (d, 1H, J = 3.6 Hz), 6.81 (d, 1H, J = 3.6 Hz), 6.61 (s, 1H), 6.45 (d, 1H, J = 5.6 Hz), 5.33-5.31 (m, 1H), 4.80-4.76 (m, 2H), 4.55-4.51 (m, 2H), 3.69-3.67 (m, 2H), 3.58-3.56 (m, 2H), 3.41-3.40 (m, 4H), 2.47 (S, 3H). |

TABLE 1-continued

| # | Structure | LCMS (M + 1) | $^1$H NMR |
|---|---|---|---|
| 169 | 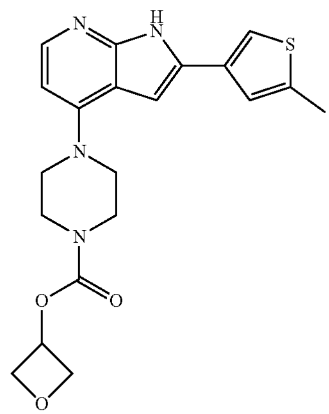 | 399 | $^1$H-NMR (400 MHz, 6d-DMSO) δ ppm 11.82 (s, 1H), 7.94 (d, 1H, J = 6 Hz), 7.68 (d, 1H, J = 1.6 Hz), 7.39 (s, 1H), 6.83 (d, 1H, J = 1.6 Hz), 6.43 (d, 1H, J = 5.6 Hz), 5.34 (q, 1H, J = 5.2, Hz), 4.79 (t, 2H, J = 7.2 Hz), 4.53 (q, 2H, J = 5.2 Hz), 3.67-3.58 (m, 4H), 3.44-3.41 (m, 4H), 2.48 (s, 3H). |
| 170 | 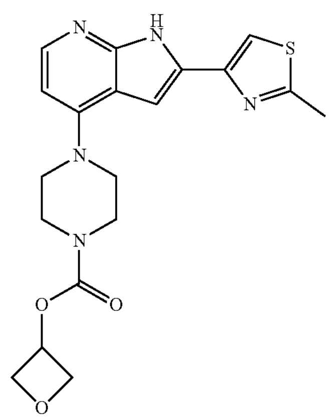 [SMILES: Cc1nc(-c2cc3c(N4CCN(C(=O)OC5COC5)CC4)ccnc3[nH]2)cs1] | 400 | $^1$H-NMR (400 MHz, 6d-DMSO) δ ppm 11.99 (s, 1H), 7.99 (d, 1H, J = 5.2 Hz), 7.87 (s, 1H), 6.89 (s, 1H), 6.46 (d, 1H, J = 5.2 Hz), 5.34 (quintet, 1H, J = 5.2 Hz), 4.79 (t, 2H, J = 7.0 Hz), 4.53 (dd, 2H, J = 7.6, 5.2 Hz), 3.69-3.67 (m, 2H), 3.62-3.58 (m, 2H), 3.46-3.42 (m, 4H), 2.72 (s, 3H). |
| 171 | 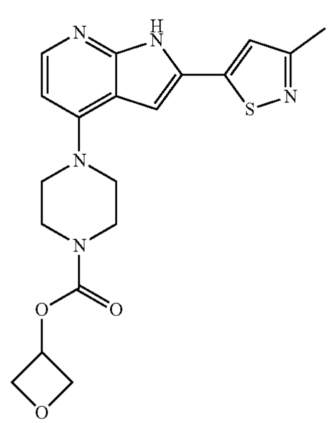 | 400 | $^1$H-NMR (400 MHz, 6d-DMSO) δ ppm 12.23 (s, 1H), 8.22 (s, 1H, HCOOH), 8.01 (d, 1H, J = 4.4 Hz), 7.59 (s, 1H), 7.06 (s, 1H), 6.45 (d, 1H, J = 5.2 Hz), 5.37-5.29 (m, 1H), 4.79-474 (m, 2H), 4.53-4.47 (m, 2H), 3.66-3.57 (m, 4H), 3.47-3.44 (m, 4H), 2.44 (s, 3H) |

TABLE 1-continued

| # | Structure | LCMS (M + 1) | ¹H NMR |
|---|---|---|---|
| 172 | 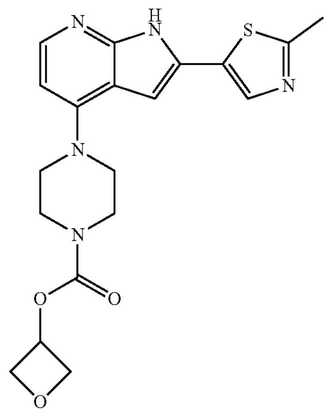 [SMILES: Cc1ncc(-c2cc3c(N4CCN(C(=O)OC5COC5)CC4)ccnc3[nH]2)s1] | 400 | ¹H-NMR (400 MHz, 6d-DMSO) δ ppm 12.10 (s, 1H), 8.06 (s, 1H), 7.97 (s, 1H), 6.75 (s, 1H), 6.44 (s, 1H), 5.35-5.25 (m, 1H), 4.82-4.72 (m, 2H), 4.55-4.46 (m, 2H), 3.66-3.55 (m, 4H), 3.47-3.38 (m, 4H), 2.67 (s, 3H) |
| 173 | 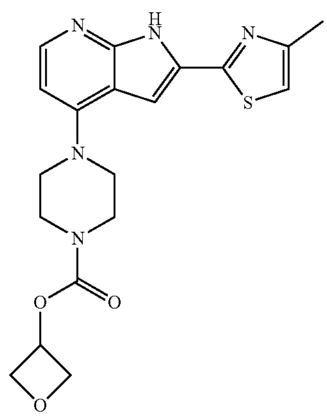 | 400 | ¹H-NMR (500 MHz, d₆-DMSO) δ ppm 12.28 (br. s, 1H), 8.03 (d, 1H, J = 5.5 Hz), 7.31 (s, 1H), 7.11 (s, 1H), 6.48 (d, 1H, J = 5.5 Hz), 5.35-5.33 (m, 1H), 4.81-4.78 (m, 2H), 4.55-4.52 (m, 2H), 3.70-3.59 (m, 4H), 3.49-3.348 (m, 4H), 2.44 (s, 3H). |
| 174 | 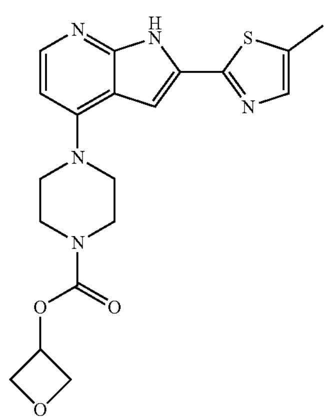 [SMILES: Cc1cnc(-c2cc3c(N4CCN(C(=O)OC5COC5)CC4)ccnc3[nH]2)s1] | 400 | ¹H-NMR (400 MHz, d₆-DMSO) δ ppm 12.22 (s, 1H), 8.01 (d, 1H, J = 5.2 Hz), 7.57 (d, 1H, J = 1.2 Hz), 7.04 (s, 1H), 6.46 (d, 1H, J = 5.2 Hz), 5.35-5.29 (m, 1H), 4.79-4.76 (m, 2H), 4.53-4.50 (m, 2H), 3.68-3.58 (m, 4H), 3.46-3.345 (m, 4H), 2.49 (s, 3H). |

TABLE 1-continued

| # | Structure | LCMS (M + 1) | ¹H NMR |
|---|---|---|---|
| 175 | 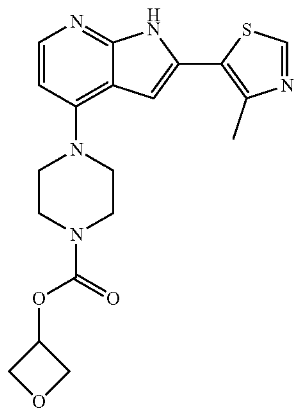 [SMILES: Cc1ncsc1-c1cc2c(N3CCN(C(=O)OC4COC4)CC3)ccnc2[nH]1] | 400 | ¹H-NMR (400 MHz, 6d-DMSO) δ ppm 11.90 (s, 1H), 9.01 (s, 1H), 8.00 (d, 1H, J = 5.2 Hz), 6.68 (s, 1H), 6.47 (d, 1H, J = 5.6 Hz), 5.32 (quintet, 1H, J = 5.2 Hz), 4.77 (t, 2H, J = 7.2 Hz), 4.51 (dd, 2H, J = 7.2, 5.2 Hz), 3.70-3.65 (m, 2H), 3.65-3.60 (m, 2H), 3.57-3.44 (m, 4H), 2.57 (s, 3H). |
| 177 | 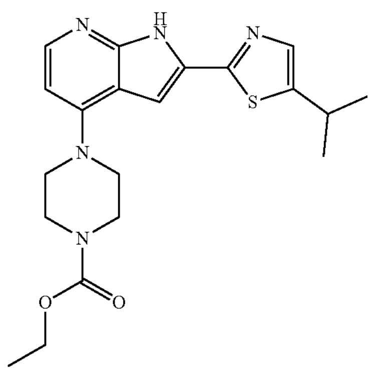 [SMILES: CCOC(=O)N1CCN(c2ccnc3[nH]c(-c4ncc(C(C)C)s4)cc23)CC1] | 400 | ¹H-NMR (400 MHz, 6d-DMSO) δ ppm 12.22 (s, 1H), 8.01 (d, 1H, J = 5.2 Hz), 7.62 (s, 1H,), 7.07 (s, 1H), 6.45 (d, 1H, J = 5.6 Hz), 4.08 (q, 2H, J = 7.2 Hz), 3.60-3.57 (m, 4H), 3.44-3.43 (m, 4H), 3.28 (t, 1H, J = 6.4 Hz) 1.33 (d, 6H, J = 6.8 Hz), 1.22 (t, 3H, J = 7.2 Hz). |
| 178 | 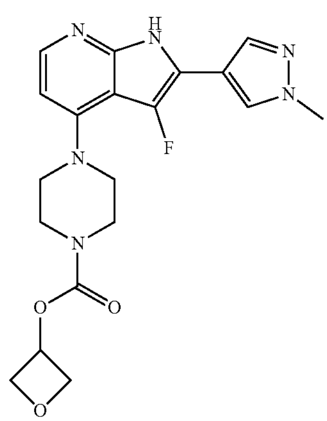 | 401 | |

TABLE 1-continued
| # | Structure | LCMS (M + 1) | ¹H NMR |
|---|---|---|---|
| 179 | 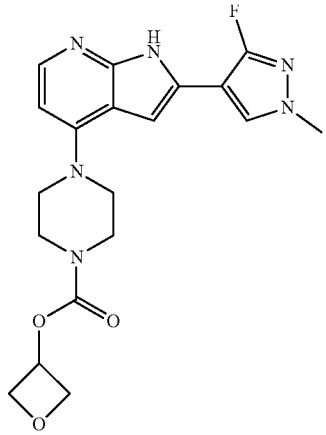 [SMILES: Cn1cc(-c2cc3c(N4CCN(C(=O)OC5COC5)CC4)ccnc3[nH]2)c(F)n1] | 401 | ¹H-NMR (400 MHz, 6d-DMSO) δ ppm 11.80 (s, 1H), 8.04 (d, 1H, J = 2.0 Hz), 7.95 (d, 1H, J = 5.6 Hz), 6.49 (s, 1H) 6.46 (d, 1H, J = 5.6 Hz), 5.35-5.30 (m, 1H), 4.81-4.76(m, 2H), 4.55-4.51 (m, 2H), 3.79 (s, 3H), 3.68-3.56 (m, 4H), 3.41-3.39 (m, 4H). |
| 180 | 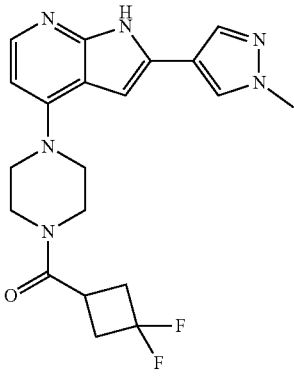 [SMILES: Cn1cc(-c2cc3c(N4CCN(C(=O)C5CC(F)(F)C5)CC4)ccnc3[nH]2)cn1] | 401 | |
| 181 | 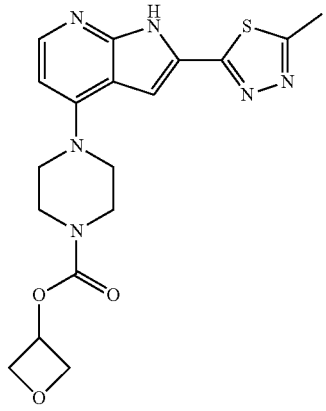 | 401 | ¹H-NMR (400 MHz, 6d-DMSO) δ ppm 12.47 (br s, 1H), 8.06 (d, 1H, J = 5.6 Hz), 7.25 (s, 1H), 6.49 (d, 1H, J = 5.6 Hz), 5.35-5.30 (m, 1H), 4.80-4.77 (m, 2H), 4.54-4.51 (m, 2H), 3.69-3.67 (m, 2H), 3.60-3.58 (m, 2H), 3.51-3.50 (m, 4H), 2.78 (s, 3H). |

TABLE 1-continued

| # | Structure | LCMS (M + 1) | ¹H NMR |
|---|---|---|---|
| 182 | 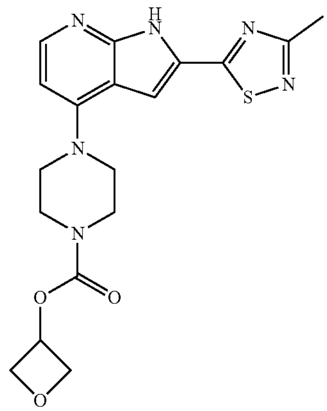 [SMILES: Cc1nsc(-c2cc3c(N4CCN(C(=O)OC5COC5)CC4)ccnc3[nH]2)n1] | 401 | ¹H-NMR (400 MHz, 6d-DMSO) δ ppm 12.60 (s, 1H), 8.06 (d, 1H, J = 5.2 Hz), 7.43 (s, 1H), 6.75 (s, 1H), 6.47 (d, 1H, J = 5.6 Hz), 5.34-5.29 (m, 1H), 4.79-4.76 (m, 2H), 4.53-4.50 (m, 2H), 3.67-3.59 (m, 4H), 3.55-3.52 (m, 4H), 2.62 (s, 3H) |
| 183 | 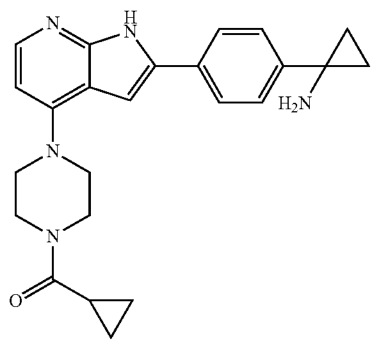 [SMILES: NC1(c2ccc(-c3cc4c(N5CCN(C(=O)C6CC6)CC5)ccnc4[nH]3)cc2)CC1] | 402 | |
| 184 | 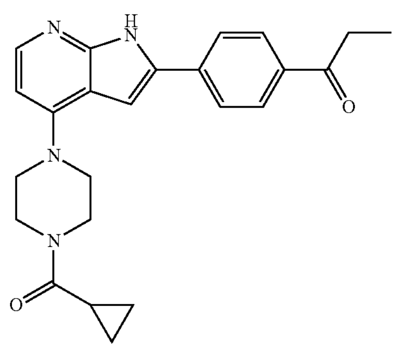 [SMILES: CCC(=O)c1ccc(-c2cc3c(N4CCN(C(=O)C5CC5)CC4)ccnc3[nH]2)cc1] | 403 | ¹H-NMR (400 MHz, 6d-DMSO) δ ppm 12.14 (s, 1H), 8.10 (d, 2H, J = 8.0 Hz), 8.02-8.01 (m, 1H), 8.01 (d, 2H, J = 8.0 Hz), 7.29 (s, 1H), 6.46 (d, 1H, J = 5.6 Hz), 3.98-3.88 (m, 2H), 3.98-3.88 (m, 2H), 3.76-3.66 (m, 2H), 3.60-3.55 (m, 2H), 3.45-3.40 (m, 2H), 3.08 (q, 2H, J = 7.2 Hz), 2.08-2.01 (m, 1H), 1.10 (t, 3H, J = 7.2 Hz), 0.85-0.71 (m, 4H). |
| 185 | 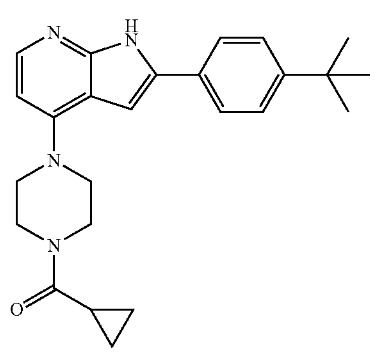 [SMILES: CC(C)(C)c1ccc(-c2cc3c(N4CCN(C(=O)C5CC5)CC4)ccnc3[nH]2)cc1] | 403 | ¹H NMR (400 MHz, DMSO) δ 13.09 (s, 1H), 8.02 (d, J = 7.2 Hz, 1H), 7.85 (d, J = 8.5 Hz, 2H), 7.53 (d, J = 8.5 Hz, 2H), 7.38 (d, J = 1.9 Hz, 1H), 6.76 (d, J = 7.2 Hz, 1H), 4.04 (d, J = 21.4 Hz, 6H), 3.77 (s, 2H), 2.04-1.96 (m, 1H), 1.33 (s, 10H), 0.79 (d, J = 7.7 Hz, 4H). |

TABLE 1-continued

| # | Structure | LCMS (M + 1) | ¹H NMR |
|---|---|---|---|
| 186 | 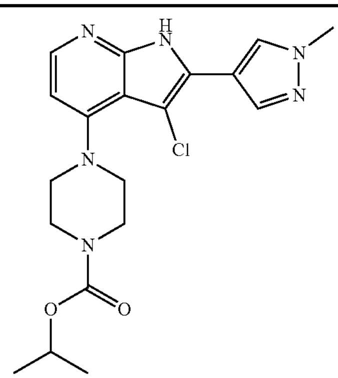 | 403 | ¹H-NMR (400 MHz, 6d-DMSO) δ ppm 12.17 (s, 1H), 8.34 (s, 1H), 8.09 (s, 1H), 8.04 (d, 1H, J = 5.6 Hz), 6.60 (d, 1H, J = 5.6 Hz), 4.82-4.78 (m, 1H), 3.92 (s, 3H), 3.60 (br. s, 4H), 3.11 (br. s, 4H), 1.20 (d, 6H, J = 6.4 Hz). |
| 187 | 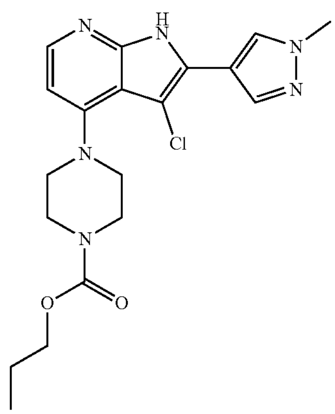 [SMILES: CCCOC(=O)N1CCN(c2ccnc3[nH]c(-c4cnn(C)c4)c(Cl)c23)CC1] | 403 | ¹H-NMR (400 MHz, 6d-DMSO) δ ppm 12.16 (s, 1H), 8.34 (s, 1H), 8.09 (s, 1H), 8.04 (d, 1H, J = 5.2 Hz), 6.60 (d, 1H, J = 5.2 Hz), 4.0-3.97 (m, 2H), 3.92 (s, 3H), 3.61-3.62 (m, 4H), 3.15-3.12 (m, 4H), 1.60 (q, 2H, J = 7.2 Hz), 0.90 (t, 3H, J = 7.2 Hz). |
| 188 | 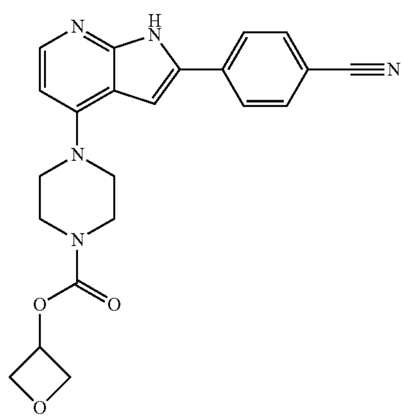 | 404 | ¹H-NMR (500 MHz, 6d-DMSO) δ ppm 12.18 (s, 1H), 8.15 (d, 2H, J = 8.5 Hz), 8.02 (d, 1H, J = 6.5 Hz), 7.90 (d, 2H, J = 8.5 Hz), 7.34 (s, 1H), 6.46 (d, 1H, J = 5.5 Hz), 5.41-5.30 (m, 1H), 4.81-4.77 (m, 2H), 4.55-4.51 (m, 2H), 3.50-3.48 (m, 4H), 3.42-3.33 (m, 4H). |
| 189 | 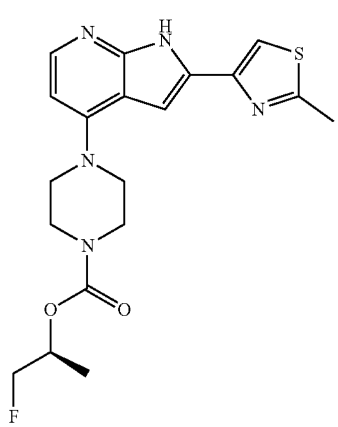 [SMILES: Cc1nc(-c2cc3c(N4CCN(C(=O)O[C@@H](C)CF)CC4)ccnc3[nH]2)cs1] | 404 | ¹H-NMR (400 MHz, 6d-DMSO) δ ppm 11.98 (s, 1H), 7.98 (d, 1H, J = 5.6 Hz), 7.86 (s, 1H), 6.89 (s, 1H), 6.45 (d, 1H, J = 1.6 Hz), 5.04-4.91 (m, 1H), 4.60-4.37 (m, 2H), 3.62-3.61 (m, 4H), 3.43-3.42 (m, 4H), 2.72 (s, 3H), 1.22 (d, 3H, J = 6.8 Hz). |

TABLE 1-continued

| # | Structure | LCMS (M + 1) | ¹H NMR |
|---|---|---|---|
| 190 | 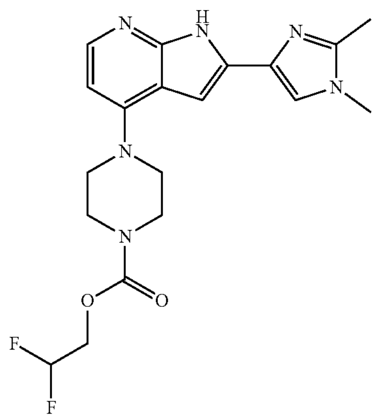 [SMILES: Cc1nc(-c2cc3c(N4CCN(C(=O)OCC(F)F)CC4)ccnc3[nH]2)cn1C] | 405 | ¹H-NMR (500 MHz, DMSO-d$_6$) δ ppm 11.62 (br. s., 1H), 7.89 (d, 1H, J = 5.0 Hz), 7.46 (s, 1H), 6.57 (d, 1H, J = 7.0 Hz), 6.41(d, 1H, J = 5.5 Hz), 6.29-6.18 (m, 1H), 4.38-4.31 (m, 2H), 3.66-3.60(m, 4H), 3.59(s, 3H), 3.40-3.34(m, 4H), 2.32(s, 3H). |
| 191 | 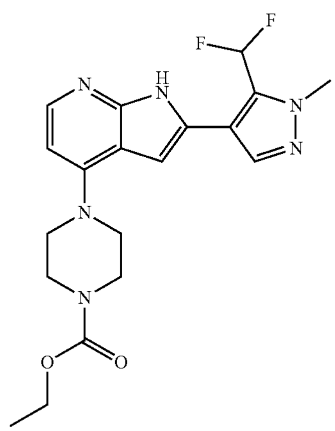 [SMILES: CCOC(=O)N1CCN(c2ccnc3[nH]c(-c4cnn(C)c4C(F)F)cc23)CC1] | 405 | ¹H-NMR (400 MHz, 6d-DMSO) δ ppm 11.85 (br s, 1H), 7.98 (d, 1H, J = 6.4 Hz), 7.95 (s, 1H), 7.50 (t, 1H, J = 51.2 Hz), 6.55 (s, 1H), 6.46 (d, 1H, J = 5.6 Hz), 4.08 (q, 2H, J = 7.2 Hz), 4.03 (s, 3H), 3.60-3.55 (m, 4H), 3.45-3.38 (m, 4H), 1.22 (t, 3H, J = 7.2 Hz). |
| 192 | 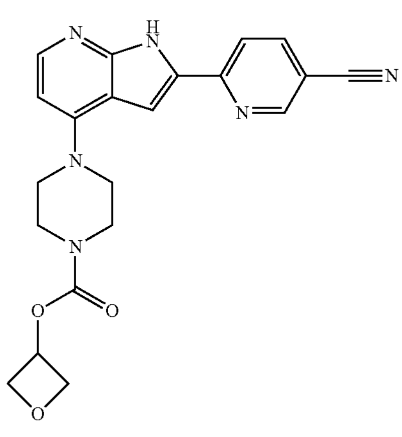 [SMILES: N#Cc1ccc(-c2cc3c(N4CCN(C(=O)OC5COC5)CC4)ccnc3[nH]2)nc1] | 405 | ¹H-NMR (400 MHz, 6d-DMSO) δ ppm 12.26 (br. s, 1H), 9.01 (d, 1H, J = 1.2 Hz), 8.38-8.33 (m, 1H), 8.22 (d, 1H, J = 8.4 Hz), 8.06 (d, 1H, J = 1.6 Hz), 7.53 (s, 1H), 6.47 (d, 1H, J = 5.6 Hz), 5.67-5.31 (m, 1H), 4.82-4.75 (m, 2H), 4.55-4.51 (m, 2H), 3.75-3.40 (m, 8H). |

TABLE 1-continued

| # | Structure | LCMS (M + 1) | ¹H NMR |
|---|---|---|---|
| 194 | 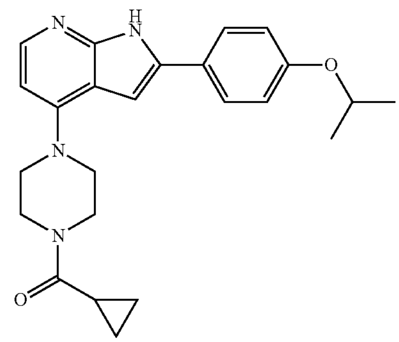 [SMILES: CC(C)Oc1ccc(-c2cc3c(N4CCN(C(=O)C5CC5)CC4)ccnc3[nH]2)cc1] | 405 | 1H NMR (400 MHz, DMSO) δ 12.95 (s, 1H), 7.96 (d, J = 7.1 Hz, 1H), 7.87 (d, J = 8.8 Hz, 2H), 7.28 (d, J = 1.6 Hz, 1H), 7.05 (d, J = 8.9 Hz, 2H), 6.73 (d, J = 7.2 Hz, 1H), 4.77-4.69 (m, 1H), 4.01 (s, 6H), 3.76 (s, 2H), 2.03-1.96 (m, 1H), 1.31 (d, J = 6.0 Hz, 6H), 0.79 (t, J = 5.8 Hz, 4H). |
| 195 | 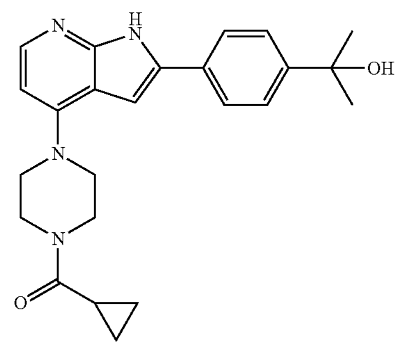 [SMILES: CC(C)(O)c1ccc(-c2cc3c(N4CCN(C(=O)C5CC5)CC4)ccnc3[nH]2)cc1] | 405 | ¹H-NMR (400 MHz, 6d-DMSO) δ ppm 11.89 (s, 1H), 7.95 (d, 1H, J = 5.2 Hz), 7.86 (d, 2H, J = 8.4 Hz), 7.50 (d, 2H, J = 8.4 Hz), 7.0 (d, 1H, J = 2.0 Hz), 7.42 (d, 1H, J = 5.2 Hz), 5.05 (s, 1H), 3.93-3.88 (m, 2H), 3.73-3.68 (m, 2H), 3.49-3.41 (m, 4H), 2.05-1.99 (m, 1H), 1.44 (s, 6H), 0.78-0.74 (m, 4H). |
| 196 | 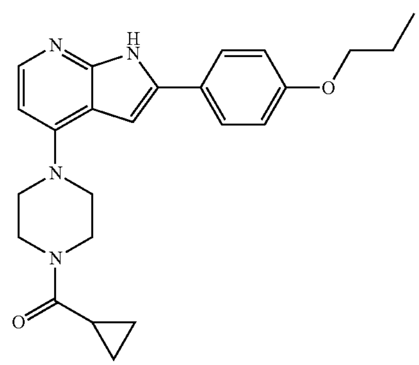 [SMILES: CCCOc1ccc(-c2cc3c(N4CCN(C(=O)C5CC5)CC4)ccnc3[nH]2)cc1] | 405 | 1H NMR (400 MHz, DMSO) δ 12.97 (s, 1H), 7.99 (d, J = 7.2 Hz, 1H), 7.86 (d, J = 8.9 Hz, 2H), 7.31 (d, J = 1.9 Hz, 1H), 7.08 (d, J = 8.9 Hz, 2H), 6.75 (d, J = 7.2 Hz, 1H), 4.09-3.73 (m, 8H), 1.78-1.75 (m, 2H), 1.01 (t, J = 7.4 Hz, 3H), 0.82-0.75 (m, 4H). |
| 197 | 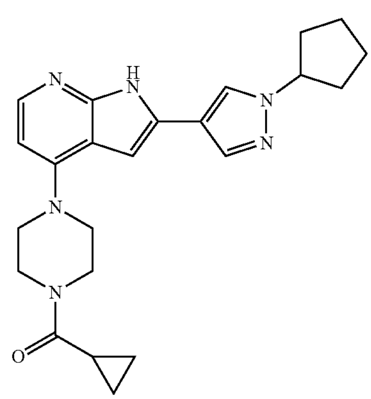 [SMILES: O=C(C1CC1)N1CCN(c2ccnc3[nH]c(-c4cnn(C5CCCC5)c4)cc23)CC1] | 405 | ¹H NMR (400 MHz, DMSO-d₆) δ ppm 11.69 (s, 1H), 8.24 (s, 1H), 7.95 (s, 1H), 7.90 (d, 1H, J = 5.2 Hz), 6.69 (s, 1H), 6.42 (d, 1H, J = 5.2 Hz), 4.74-4.68 (m, 1H), 3.90 (br. s., 2H), 3.69 (br. s., 2H), 3.44 (br. s., 2H), 3.41 (br. s., 2H), 2.16-2.01 (m, 3H), 1.98-1.90 (m, 2H), 1.84-1.77 (m, 2H), 1.71-1.63 (m, 2H), 0.78-0.74(m, 4H). |

TABLE 1-continued

| # | Structure | LCMS (M + 1) | ¹H NMR |
|---|---|---|---|
| 198 | 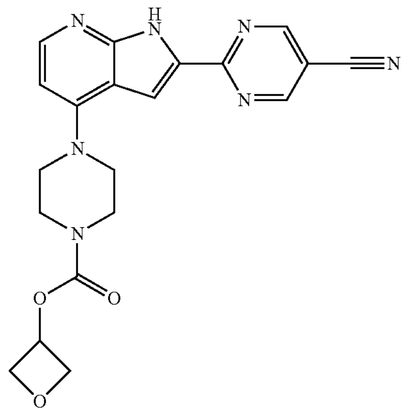 | 406 | ¹H-NMR (500 MHz, 6d-DMSO) δ ppm 12.39 (s, 1H), 9.27 (s, 2H), 8.11-8.08 (m, 1H), 7.58 (s, 1H), 6.49-6.47 (m, 1H), 5.35-5.32 (m, 1H), 4.79 (t, 2H, J = 7.0 Hz), 4.54-4.52 (m, 2H), 3.72-3.69 (m, 2H), 3.61-3.59 (m, 2H), 3.56-3.55 (m, 4H). |
| 199 | 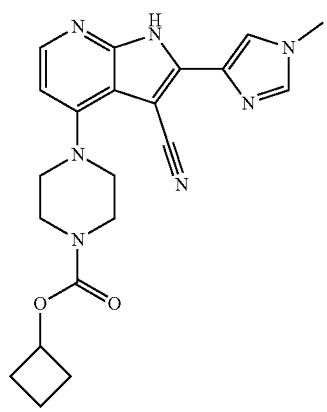 [SMILES: Cn1cnc(-c2[nH]c3nccc(N4CCN(C(=O)OC5CCC5)CC4)c3c2C#N)c1] | 406 | ¹H-NMR (400 MHz, 6d-DMSO) δ ppm 12.85 (br. s., 1H), 8.14 (d, 1H, J = 4.8 Hz), 7.88 (s, 1H), 7.87 (s, 1H), 6.72 (d, 1H, J = 5.6 Hz), 4.86 (quintet, 1H, J = 7.6 Hz), 3.79 (s, 3H), 3.70-3.60 (m, 4H), 3.20-3.10 (m, 4H), 2.30-2.23 (m, 2H), 2.08-1.98 (m, 2H), 1.76-1.68 (m, 1H), 1.61-1.53 (m, 1H). |
| 200 | 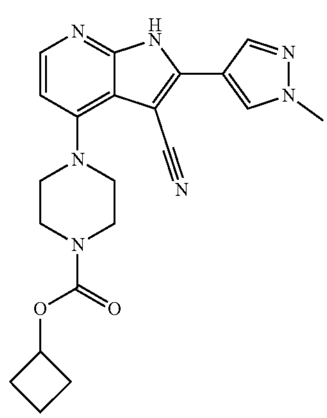 [SMILES: Cn1cc(-c2[nH]c3nccc(N4CCN(C(=O)OC5CCC5)CC4)c3c2C#N)cn1] | 406 | ¹H-NMR (500 MHz, 6d-DMSO) δ ppm 12.93 (s, 1H), 8.40 (s, 1H), 8.19-8.13 (m, 2H), 6.73 (d, 1H, J = 5.0 Hz), 5.00-4.75 (m, 1H), 3.97 (s, 3H), 3.69-3.52 (m, 4H), 3.30-3.08 (m, 4H), 2.40-2.20 (m, 2H), 2.20-1.95 (m, 2H), 1.80-1.50 (m, 2H). |

TABLE 1-continued

| # | Structure | LCMS (M + 1) | ¹H NMR |
|---|---|---|---|
| 201 | 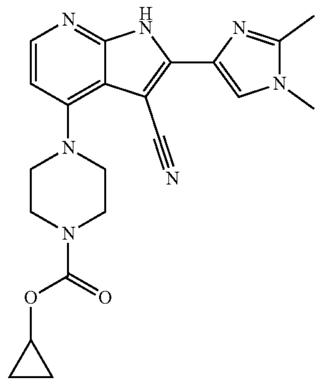 [SMILES: Cc1nc(-c2[nH]c3nccc(N4CCN(C(=O)OC5CC5)CC4)c3c2C#N)cn1C] | 406 | 1H-NMR (500 MHz, DMSO-d₆) δ ppm 12.79 (br. s., 1H), 8.11 (d, 1H, J = 5.0 Hz), 7.81 (s, 1H), 6.70 (d, 1H, J = 5.5 Hz), 4.04-4.02 (m, 1H), 3.68 (s, 3H), 3.64-3.55 (m, 4H), 3.18-3.11 (m, 4H), 2.39 (s, 3H), 0.66 (d, 4H, J = 5.0 Hz). |
| 202 | 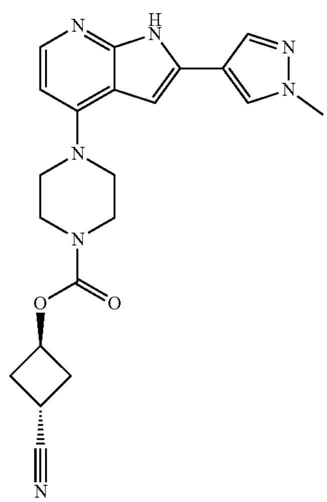 [SMILES: Cn1cc(-c2cc3c(N4CCN(C(=O)O[C@H]5C[C@H](C#N)C5)CC4)ccnc3[nH]2)cn1] | 406 | ¹H-NMR (400 MHz, 6d-DMSO) δ ppm 11.73 (s, 1H), 8.12 (s, 1H), 7.93 (s, 1H), 7.91 (d, 1H, J = 5.6 Hz), 6.65 (d, 1H, J = 1.2 Hz), 6.42 (d, 1H, J = 5.6 Hz), 5.12-5.06 (m, 1H), 3.88 (s, 3H), 3.60-3.50 (m, 4H), 3.48-3.40 (m, 4H), 2.69-2.62 (m, 2H), 2.53-2.50 (m, 2H). |
| 203 | 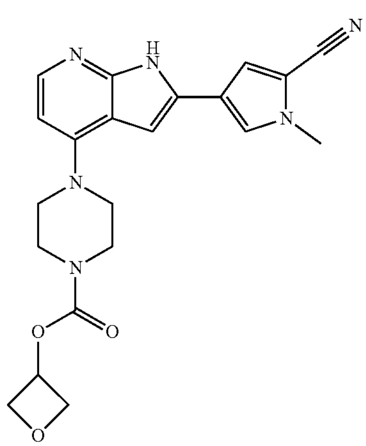 [SMILES: Cn1cc(-c2cc3c(N4CCN(C(=O)OC5COC5)CC4)ccnc3[nH]2)cc1C#N] | 407 | ¹H-NMR (400 MHz, 6d-DMSO) δ ppm 11.75 (s, 1H), 7.92 (d, 1H, J = 5.2 Hz), 7.69 (d, 1H, J = 1.6 Hz), 7.42 (d, 1H, J = 2.0 Hz), 6.71 (d, 1H, J = 2.4 Hz), 6.43 (d, 1H, J = 5.6 Hz), 5.36-5.31 (m, 1H), 4.81-4.77 (m, 2H), 4.55-4.51 (m, 2H), 3.81 (s, 3H), 3.68-3.56 (m, 4H), 3.42-3.36 (m, 4H). |

TABLE 1-continued

| # | Structure | LCMS (M + 1) | ¹H NMR |
|---|---|---|---|
| 204 | 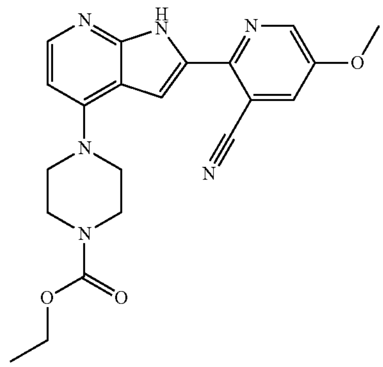 [SMILES: CCOC(=O)N1CCN(c2ccnc3[nH]c(-c4ncc(OC)cc4C#N)cc23)CC1] | 407 | ¹H-NMR (400 MHz, 6d-DMSO) δ ppm 12.03 (br. s., 1H), 8.64 (d, 1H, J = 3.2 Hz), 8.09-8.05 (m, 2H), 7.38 (s, 1H), 6.5 (d, 1H, J = 5.6 Hz), 4.08 (q, 2H, J = 7.2 Hz), 3.94 (s, 3H), 3.62-3.58 (m, 4H), 3.48-3.42 (m, 4H), 1.20 (t, 3H, J = 7.0 Hz). |
| 205 | 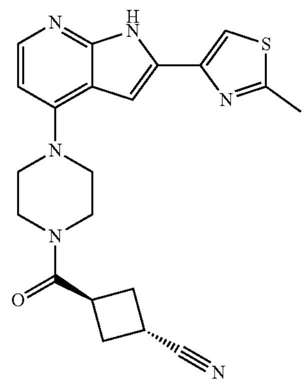 [SMILES: Cc1nc(-c2cc3c(N4CCN(C(=O)[C@H]5C[C@H](C#N)C5)CC4)ccnc3[nH]2)cs1] | 407 | ¹H-NMR (400 MHz, 6d-DMSO) δ ppm 11.98 (s, 1H), 7.97 (d, 1H, J = 5.6 Hz), 7.86 (s, 1H), 6.89 (s, 1H), 6.43 (d, 1H, J = 5.6 Hz), 3.70-3.66 (m, 3H), 3.54-3.53 (m, 2H), 3.44-3.40 (m, 4H), 3.28-3.27 (m, 1H), 2.72 (s, 3H,), 2.63-2.58 (m, 2H), 2.49-2.46 (d, 2H, J = 14 Hz). |
| 206 | 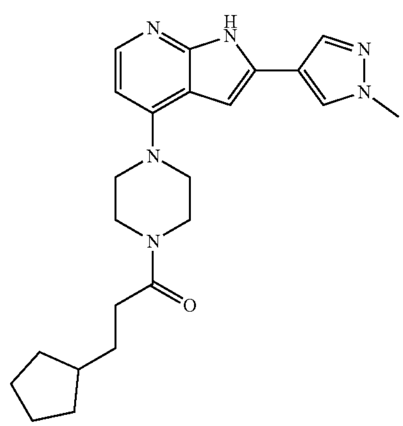 [SMILES: Cn1cc(-c2cc3c(N4CCN(C(=O)CCC5CCCC5)CC4)ccnc3[nH]2)cn1] | 407 | 1H NMR (400 MHz, DMSO) δ 12.94 (s, 1H), 8.20 (s, 1H), 7.99 (d, J = 8.6 Hz, 2H), 7.10 (d, J = 2.0 Hz, 1H), 6.74 (d, J = 7.2 Hz, 1H), 4.00-3.90 (m, 7H), 3.79-3.70 (m, 4H), 2.41-2.34 (m, 2H), 1.82-1.70 (m, 3H), 1.55 (tdd, J = 17.1, 7.3, 4.3 Hz, 7H), 1.16-1.04 (m, 2H). |
| 207 | 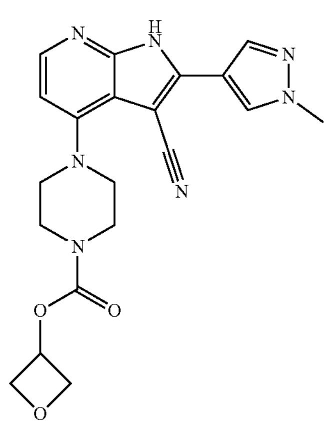 [SMILES: Cn1cc(-c2[nH]c3nccc(N4CCN(C(=O)OC5COC5)CC4)c3c2C#N)cn1] | 408 | ¹H-NMR (500 MHz, 6d-DMSO) δ ppm 12.93 (br. s, 1H), 8.41 (s, 1H), 8.17 (s, 1H), 8.16 (d, 1H, J = 5.5 Hz), 6.74 (d, 1H, J = 5.5 Hz), 5.33 (quintet, 1H, J = 5.5 Hz), 4.78 (t, 2H, J = 7.5 Hz), 4.53 (dd, 2H, J = 7.5, 5.5 Hz), 3.97 (s, 3H), 3.75-3.65 (m, 2H), 3.65-3.55 (m, 2H), 3.25-3.19 (m, 4H). |

TABLE 1-continued
| # | Structure | LCMS (M + 1) | ¹H NMR |
|---|---|---|---|
| 208 | 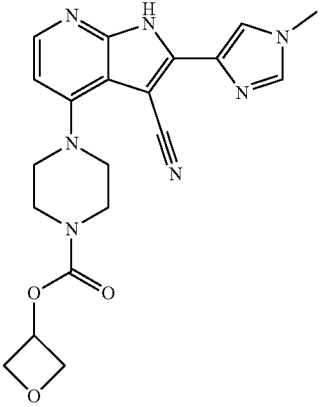 [SMILES: Cn1cnc(-c2[nH]c3nccc(N4CCN(C(=O)OC5COC5)CC4)c3c2C#N)c1] | 408 | |
| 209 | 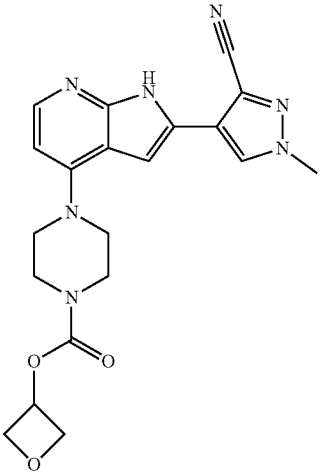 [SMILES: Cn1cc(-c2cc3c(N4CCN(C(=O)OC5COC5)CC4)ccnc3[nH]2)c(C#N)n1] | 408 | ¹H-NMR (500 MHz, 6d-DMSO) δ ppm 11.99 (s, 1H), 8.32 (s, 1H), 8.01 (d, 1H, J = 5.0 Hz), 6.84 (s, 1H), 6.49 (d, 1H, J = 5.5 Hz), 5.33 (quintet, 1H, J = 5.5 Hz), 4.78 (t, 2H, J = 7.5 Hz), 4.53 (dd, 2H, J = 7.5, 5.0 Hz), 4.01 (s, 3H), 3.70-3.64 (m, 2H), 3.64-3.57 (m, 2H), 3.49-3.42(m, 4H). |
| 210 | 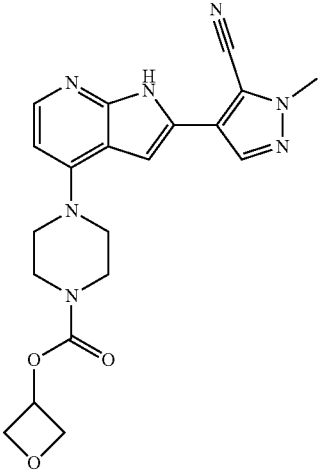 [SMILES: Cn1ncc(-c2cc3c(N4CCN(C(=O)OC5COC5)CC4)ccnc3[nH]2)c1C#N] | 408 | ¹H-NMR (500 MHz, 6d-DMSO) δ ppm 12.10 (s, 1H), 8.17 (s, 1H), 8.02 (d, 1H, J = 5.0 Hz), 6.83 (s, 1H), 6.49 (d, 1H, J = 6.0 Hz), 5.33 (quintet, 1H, J = 5.5 Hz), 4.78 (t, 2H, J = 7.5 Hz), 4.53 (dd, 1H, J = 7.5, 5.5 Hz), 4.06 (s, 3H), 3.70-3.65 (m, 2H), 3.60-3.55 (m, 2H), 3.45-3.44 (m, 4H). |

TABLE 1-continued

| # | Structure | LCMS (M + 1) | ¹H NMR |
|---|---|---|---|
| 211 | 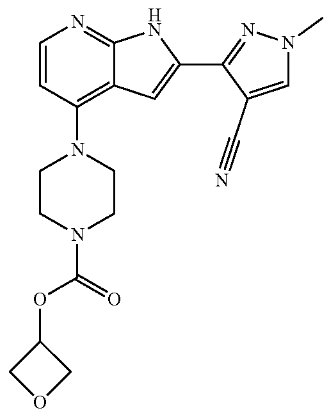 [SMILES: Cn1cc(C#N)c(-c2cc3c(N4CCN(C(=O)OC5COC5)CC4)ccnc3[nH]2)n1] | 408 | ¹H-NMR (400 MHz, 6d-DMSO) δ ppm 12.08-12.03 (br, 1H), 8.18 (s, 1H), 8.10 (d, 1H, J = 5.6 Hz), 7.03 (s, 1H), 6.54 (d, 1H, J = 5.6 Hz), 5.34-5.31 (m, 1H), 4.79-4.76 (m, 2H), 4.54-4.51 (m, 2H), 3.99 (s, 3H), 3.68-3.66 (m, 2H), 3.58-3.56 (m, 2H), 3.51-3.49 (m, 4H). |
| 212 | 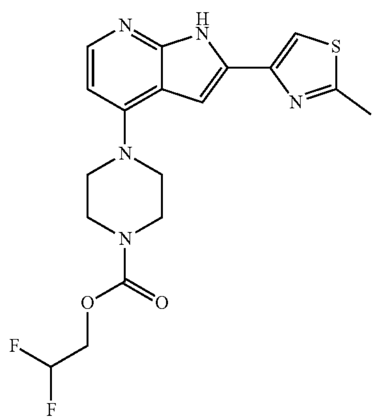 [SMILES: Cc1nc(-c2cc3c(N4CCN(C(=O)OCC(F)F)CC4)ccnc3[nH]2)cs1] | 408 | ¹H-NMR (400 MHz, 6d-DMSO) δ ppm 11.98 (s, 1H), 7.98 (d, 1H, J = 5.6 Hz), 7.86 (s, 1H), 6.89 (d, 1H, J = 1.6 Hz), 6.45 (d, 1H, J = 1.6 Hz), 6.42-6.14 (m, 1H), 4.39-4.31 (m, 2H), 3.64-3.63 (m, 4H), 3.44-3.43 (m, 4H), 2.72 (s, 3H). |
| 213 | 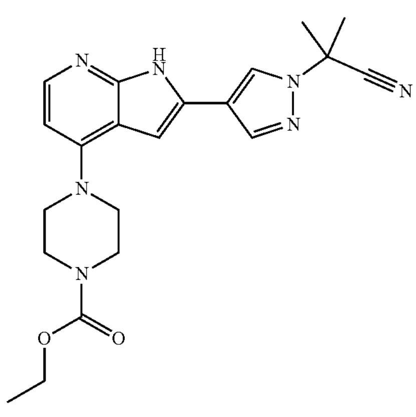 [SMILES: CCOC(=O)N1CCN(c2ccnc3[nH]c(-c4cnn(C(C)(C)C#N)c4)cc23)CC1] | 408 | ¹H-NMR (500 MHz, $d_6$-DMSO) δ ppm 11.78 (s, 1H), 8.54 (s, 1H), 8.17 (s, 1H), 7.93 (d, 1H, J = 5.5 Hz), 6.79 (d, 1H, J = 2.0 Hz), 6.44 (d, 1H, J = 5.5 Hz), 4.09 (q, 2H, J = 7.0 Hz), 3.60-3.61 (m, 4H), 3.39-3.34 (m, 4H), 2.02 (s, 6H), 1.22 (t, 3H, J = 7.0 Hz). |

TABLE 1-continued

| # | Structure | LCMS (M + 1) | ¹H NMR |
|---|---|---|---|
| 214 | 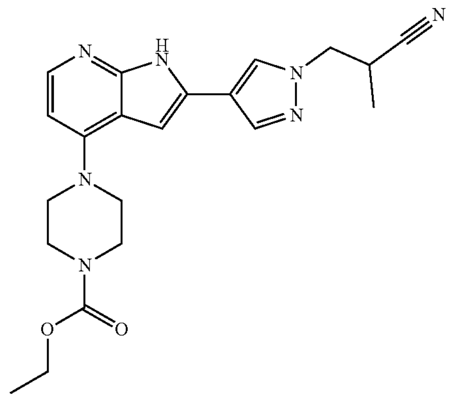 [SMILES: CCOC(=O)N1CCN(c2ccnc3[nH]c(-c4cnn(CC(C)C#N)c4)cc23)CC1] | 408 | ¹H-NMR (500 MHz, CDCl$_3$) δ ppm 8.04 (d, 1H, J = 5.5 Hz), 7.93 (s, 2H), 6.53 (s, 1H), 6.46 (d, 1H, J = 6.0 Hz), 4.43-4.33(m, 2H), 4.23 (q, 2H, J = 7.0 Hz), 3.81-3.74 (m, 4H), 3.59-3.51 (m, 4H), 3.40-3.33 (m, 1H), 1.42 (d, 3H, J = 7.0 Hz), 1.33 (t, 3H, J = 7.0 Hz). |
| 215 | 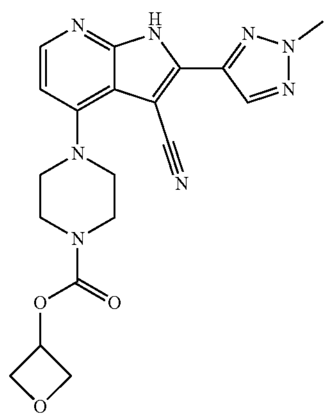 [SMILES: Cn1ncc(-c2[nH]c3nccc(N4CCN(C(=O)OC5COC5)CC4)c3c2C#N)n1] | 409 | ¹H-NMR (500 MHz, d$_6$-DMSO) δ ppm 13.37 (s, 1H), 8.36 (s, 1H), 8.24 (d, 1H, J = 5.0 Hz), 6.79 (d, 1H, J = 5.5 Hz), 5.36-5.31 (m, 1H), 4.80-4.78 (m, 2H), 4.56-4.53 (m, 2H), 4.31 (s, 3H), 3.75-3.66 (m, 4H), 3.18-3.17 (m, 4H). |
| 216 | 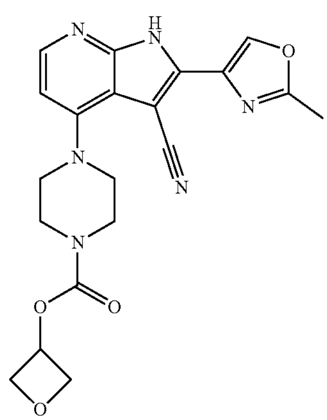 [SMILES: Cc1nc(-c2[nH]c3nccc(N4CCN(C(=O)OC5COC5)CC4)c3c2C#N)co1] | 409 | ¹H-NMR (400 MHz, 6d-DMSO) δ ppm 13.17 (s, 1H), 8.58 (s, 1H), 8.18 (d, 1H, J = 5.2 Hz), 6.74 (d, 1H, J = 5.2 Hz), 5.33-5.28 (m, 1H), 4.79-4.75 (m, 2H), 4.54-4.51 (m, 2H), 3.72-3.58 (m, 4H), 3.27-3.15 (m, 4H), 2.54 (s, 3H) |

TABLE 1-continued

| # | Structure | LCMS (M + 1) | ¹H NMR |
|---|---|---|---|
| 217 | 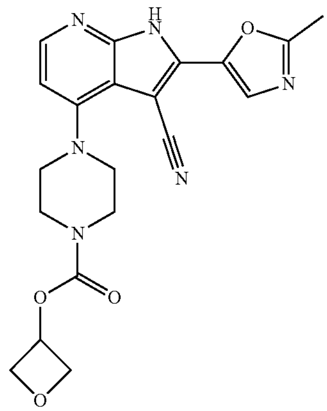 [SMILES: Cc1ncc(-c2[nH]c3nccc(N4CCN(C(=O)OC5COC5)CC4)c3c2C#N)o1] | 409 | ¹H-NMR (500 MHz, 6d-DMSO) δ ppm 8.21 (d, 1H, J = 5.5 Hz), 7.74 (s, 1H), 6.77 (d, 1H, J = 5.5 Hz), 5.34-5.32 (m, 1H), 4.80-4.77 (m, 2H), 4.55-4.53 (m, 2H), 3.74-3.63 (m, 4H), 3.28-3.15 (m, 4H), 2.57 (s, 3H). |
| 218 | 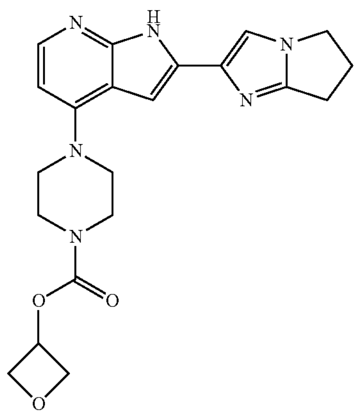 [SMILES: O=C(OC1COC1)N1CCN(c2ccnc3[nH]c(-c4cn5c(n4)CCC5)cc23)CC1] | 409 | |
| 219 | 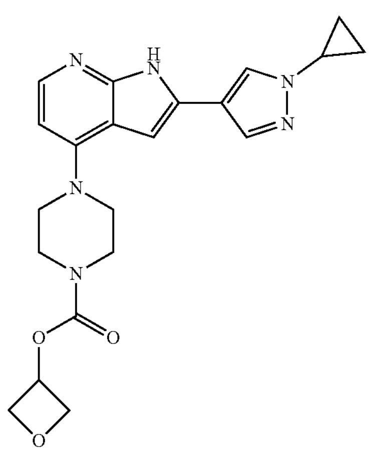 [SMILES: O=C(OC1COC1)N1CCN(c2ccnc3[nH]c(-c4cnn(C5CC5)c4)cc23)CC1] | 409 | ¹H-NMR (400 MHz, 6d-DMSO) δ ppm 11.69 (br s, 1H), 8.24 (s, 1H), 7.93 (s, 1H), 7.91 (d, 1H, J = 5.2 Hz), 6.68 (d, 1H, J = 2.4 Hz), 6.43 (d, 1H, J = 5.6 Hz), 5.35-5.31 (m, 1H), 4.81-4.77 (m, 2H), 4.55-4.51 (m, 2H), 3.78-3.73 (m, 1H), 3.68-3.56 (m, 4H), 3.45-3.36 (m, 4H), 1.06-0.98 (m, 4H). |

TABLE 1-continued
| # | Structure | LCMS (M + 1) | ¹H NMR |
|---|---|---|---|
| 220 | 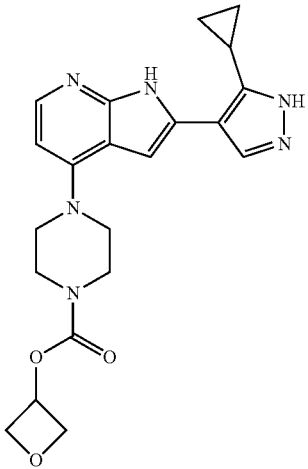 [SMILES: O=C(OC1COC1)N1CCN(c2ccnc3[nH]c(-c4cn[nH]c4C4CC4)cc23)CC1] | 409 | ¹H-NMR (400 MHz, 6d-DMSO) δ ppm 12.48 (s, 1H), 11.60 (s, 1H), 7.98 (br. s, 1H), 7.92 (d, 1H, J = 5.6 Hz), 6.60 (s, 1H), 6.43 (d, 1H, J = 5.2 Hz), 5.33 (quintet, 1H, J = 5.6 Hz), 4.79 (t, 2H, J = 7.2 Hz), 4.53 (dd, 2H, J = 7.2, 5.6 Hz), 3.67-3.60 (m, 2H), 3.60-3.52 (m, 2H), 3.48-3.40 (m, 4H), 2.14-2.12 (m, 1H), 0.99-0.93 (m, 2H), 0.81-0.76 (m, 2H). |
| 221 | 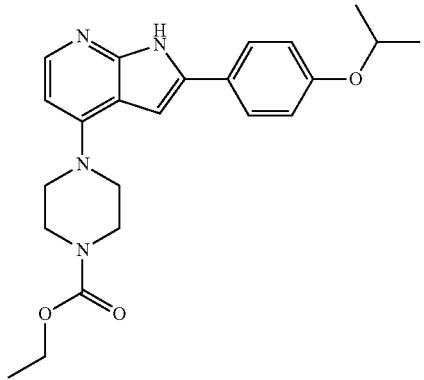 [SMILES: CCOC(=O)N1CCN(c2ccnc3[nH]c(-c4ccc(OC(C)C)cc4)cc23)CC1] | 409 | 1H NMR (400 MHz, DMSO) δ 13.42 (s, 1H), 9.25 (s, 2H), 8.11 (d, J = 7.1 Hz, 2H), 7.99 (s, 1H), 7.67 (s, 1H), 7.36 (s, 1H), 6.84 (d, J = 7.2 Hz, 1H), 4.16 (s, 2H), 3.95 (s, 2H), 3.74 (s, 2H), 2.69 (s, 2H). |
| 222 | 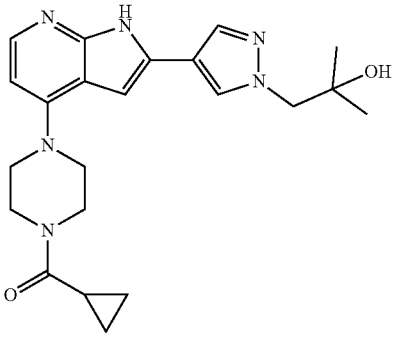 [SMILES: CC(C)(O)Cn1cc(-c2cc3c(N4CCN(C(=O)C5CC5)CC4)ccnc3[nH]2)cn1] | 409 | ¹H NMR (400 MHz, DMSO-d₆) δ 11.71 (s, 1H), 8.15 (s, 1H), 7.98-7.84 (m, 2H), 6.67 (d, J = 2.1 Hz, 1H), 6.41 (d, J = 5.5 Hz, 1H), 4.74 (s, 1H), 4.03 (s, 2H), 3.89 (s, 2H), 3.69 (s, 2H), 3.40 (d, J = 27.1 Hz, 4H), 2.01 (d, J = 5.1 Hz, 1H), 1.09 (s, 6H), 0.83-0.64 (m, 4H). |
| 223 | 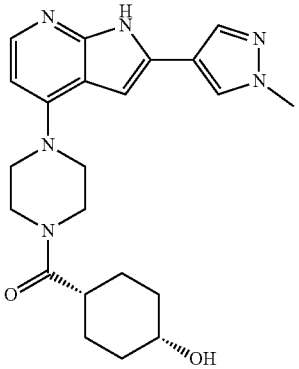 [SMILES: Cn1cc(-c2cc3c(N4CCN(C(=O)[C@H]5CC[C@@H](O)CC5)CC4)ccnc3[nH]2)cn1] | 409 | 1H NMR (400 MHz, DMSO) δ 13.06 (s, 1H), 8.18 (s, 1H), 8.02-7.95 (m, 2H), 7.10 (d, J = 1.7 Hz, 1H), 6.74 (dd, J = 7.1, 3.7 Hz, 1H), 3.91 (s, 6H), 3.86-3.67 (m, 6H), 2.61 (s, 1H), 1.85-1.38 (m, 8H). |

TABLE 1-continued

| # | Structure | LCMS (M + 1) | ¹H NMR |
|---|---|---|---|
| 224 | 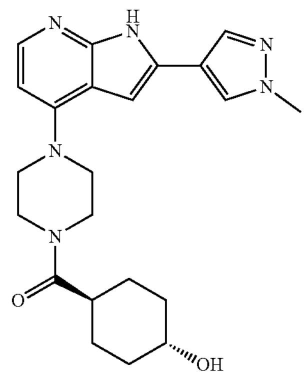 [SMILES: Cn1cc(-c2cc3c(N4CCN(C(=O)[C@H]5CC[C@H](O)CC5)CC4)ccnc3[nH]2)cn1] | 409 | 1H NMR (400 MHz, DMSO) δ 12.94 (s, 1H), 8.19 (s, 1H), 8.03-7.94 (m, 2H), 7.11 (d, J = 1.9 Hz, 1H), 6.74 (d, J = 7.2 Hz, 1H), 3.94 (d, J = 19.4 Hz, 8H), 3.80 (s, 2H), 3.70 (s, 2H), 3.42-3.34 (m, 1H), 1.87 (d, J = 12.5 Hz, 2H), 1.70 (d, J = 12.8 Hz, 2H), 1.41 (q, J = 10.6 Hz, 2H), 1.22 (dd, J = 24.5, 11.6 Hz, 2H). |
| 225 | 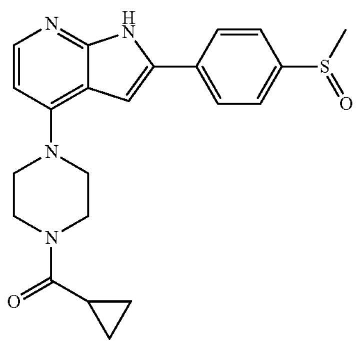 [SMILES: CS(=O)c1ccc(-c2cc3c(N4CCN(C(=O)C5CC5)CC4)ccnc3[nH]2)cc1] | 409 | |
| 226 | 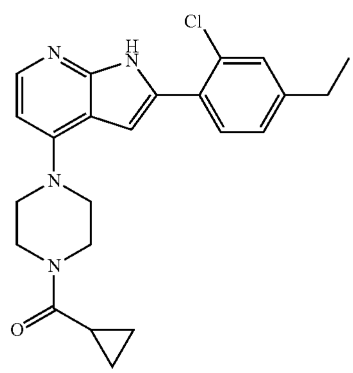 [SMILES: CCc1ccc(-c2cc3c(N4CCN(C(=O)C5CC5)CC4)ccnc3[nH]2)c(Cl)c1] | 409 | ¹H-NMR (400 MHz, 6d-DMSO) δ ppm 11.80 (s, 1H), 8.01 (d, 1H, J = 5.6 Hz), 7.63 (d, 1H, J = 8.0 Hz), 7.44 (s, 1H), 7.29 (d, 1H, J = 6.8 Hz), 6.86 (d, 1H, J = 2.0 Hz), 6.47 (d, 1H, J = 5.2 Hz), 3.95-3.88 (m, 2H), 3.70-3.65 (m, 2H), 3.52-3.48 (m, 2H), 3.45-3.40 (m, 2H), 2.65 (q, 2H, J = 7.6 Hz), 2.03-1.97 (m, 1H), 1.20 (t, 3H, J = 7.6 Hz), 0.80-0.73 (m, 4H). |
| 227 | 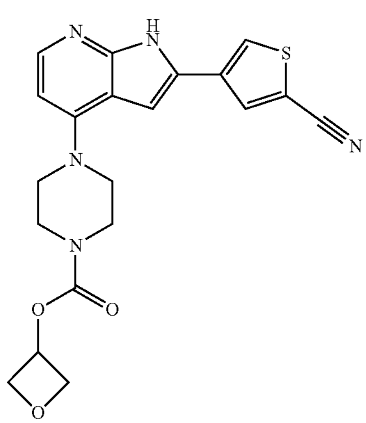 [SMILES: N#Cc1cc(-c2cc3c(N4CCN(C(=O)OC5COC5)CC4)ccnc3[nH]2)cs1] | 410 | |

TABLE 1-continued

| # | Structure | LCMS (M + 1) | ¹H NMR |
|---|---|---|---|
| 228 | 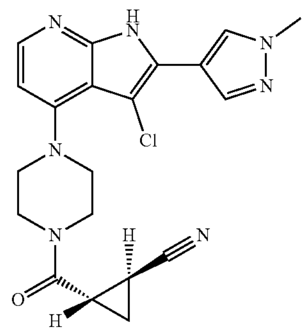 [SMILES: Cn1cc(-c2[nH]c3nccc(N4CCN(C(=O)[C@H]5C[C@@H]5C#N)CC4)c3c2Cl)cn1] | 410 | ¹H-NMR (400 MHz, 6d-DMSO) δ ppm 12.18 (s, 1H), 8.36 (s, 1H), 8.11 (s, 1H), 8.06 (d, 1H, J = 5.6 Hz), 6.62 (d, 1H, J = 5.2 Hz), 4.00-3.90 (m, 2H), 3.94 (s, 1H), 3.78-3.69 (m, 2H), 3.30-3.13 (m, 4H), 3.00-2.91 (m, 1H), 2.13-2.06 (m, 1H), 1.49-1.35 (m, 1H), 1.34-1.30 (m, 1H). |
| 229 | 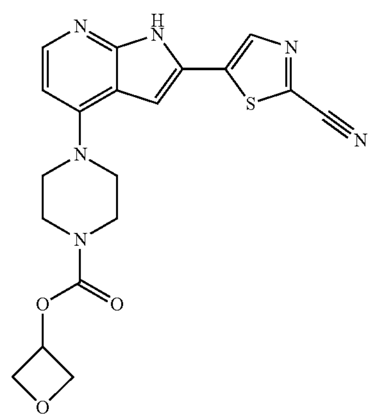 [SMILES: N#Cc1ncc(-c2cc3c(N4CCN(C(=O)OC5COC5)CC4)ccnc3[nH]2)s1] | 411 | ¹H-NMR (400 MHz, 6d-DMSO) δ ppm 12.46 (s, 1H), 8.61 (s, 1H), 8.05 (d, 1H, J = 5.2 Hz), 7.28 (s, 1H), 6.49 (d, 1H, J = 5.6 Hz), 5.34 (quintet, 1H, J = 5.2 Hz), 4.79 (t, 2H, J = 7.2 Hz), 4.53 (dd, 2H, J = 7.6, 5.2 Hz), 3.72-3.67 (m, 2H), 3.62-3.56 (m, 2H), 3.54-3.44 (m, 4H). |
| 230 | 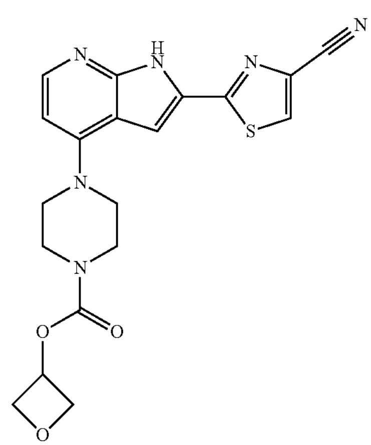 [SMILES: N#Cc1csc(-c2cc3c(N4CCN(C(=O)OC5COC5)CC4)ccnc3[nH]2)n1] | 411 | ¹H-NMR (500 MHz, 6d-DMSO) δ ppm 12.08 (br s, 1H), 8.83 (s, 1H), 8.06 (d, 1H, J = 6.0 Hz), 7.37 (s, 1H), 6.48 (d, 1H, J = 5.5 Hz), 5.34-5.32 (m, 1H), 4.80-4.77 (m, 2H), 4.54-4.51 (m, 2H), 3.69-3.67 (m, 2H), 3.59-3.57 (m, 2H), 3.53-3.51 (m, 4H). |

TABLE 1-continued
| # | Structure | LCMS (M + 1) | ¹H NMR |
|---|---|---|---|
| 231 | 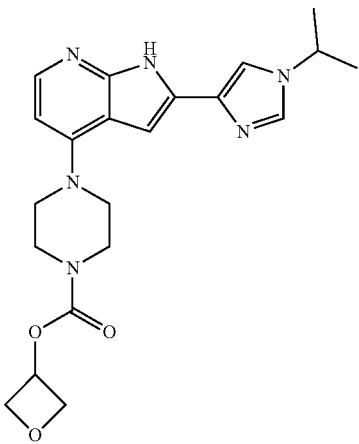 [SMILES: CC(C)n1cnc(-c2cc3c(N4CCN(C(=O)OC5COC5)CC4)ccnc3[nH]2)c1] | 411 | |
| 232 | 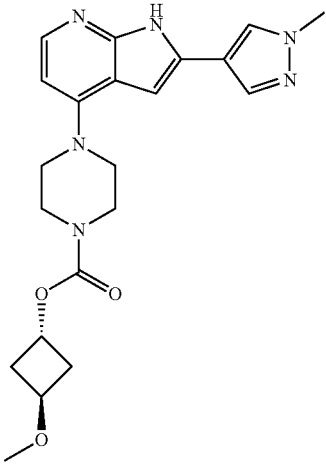 | 411 | ¹H-NMR (400 MHz, 6d-DMSO) δ ppm 11.72 (s, 1H), 8.12 (s, 1H), 7.93 (s, 1H), 7.90 (d, 1H, J = 5.6 Hz), 6.65 (d, 1H, J = 2.0 Hz), 6.42 (d, 1H, J = 6.4 Hz), 5.00-4.94 (m, 1H), 4.05-4.00 (m, 1H), 3.88 (s, 3H), 3.59-3.58 (m, 4H), 3.38-3.35 (m, 4H), 3.15 (s, 3H), 2.32-2.22 (m, 4H). |
| 233 | 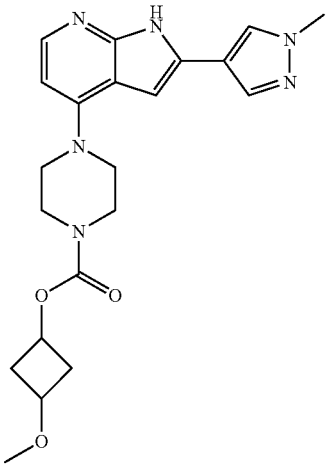 | 411 | ¹H-NMR (400 MHz, 6d-DMSO) δ ppm 11.70 (d, 1H, J = 5.2 Hz), 8.11 (s, 1H), 7.92 (s, 1H), 7.89 (d, 1H, J = 5.6 Hz), 6.60 (d, 1H, J = 1.6 Hz), 6.40 (d, 1H, J = 5.6 Hz), 4.59-4.52 (m, 1H), 3.87 (s, 3H), 3.58-3.53 (m, 5H), 3.36-3.32 (m, 4H), 3.13 (s, 3H), 2.72-2.65 (m, 2H), 1.91-1.84 (m, 2H). |

TABLE 1-continued

| # | Structure | LCMS (M + 1) | ¹H NMR |
|---|---|---|---|
| 234 | 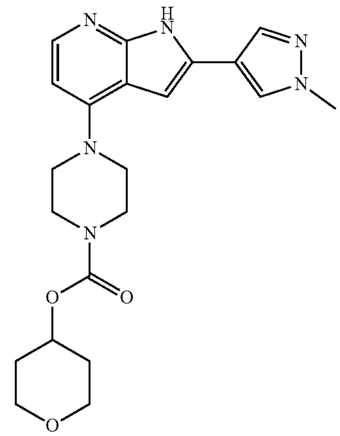 [SMILES: Cn1cc(-c2cc3c(N4CCN(C(=O)OC5CCOCC5)CC4)ccnc3[nH]2)cn1] | 411 | |
| 235 | 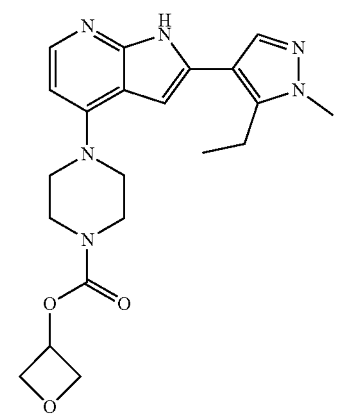 [SMILES: CCc1c(-c2cc3c(N4CCN(C(=O)OC5COC5)CC4)ccnc3[nH]2)cnn1C] | 411 | ¹H-NMR (400 MHz, 6d-DMSO) δ ppm 11.65 (s, 1H), 8.23 (br. s., 1H), 7.94 (br. s., 1H), 7.80 (s, 1H), 6.46 (s, 1H), 6.38 (s, 1H), 5.36-5.31 (m, 1H), 4.80-4.76 (m, 2H), 4.54-4.51 (m, 2H), 3.82 (s, 3H), 3.76-3.73 (m, 2H), 3.60-3.57 (m, 2H), 3.40-3.38 (m, 4H), 2.95 (q, 2H, J = 7.6 Hz), 1.28 (t, 3H, J = 7.2 Hz). |
| 236 | 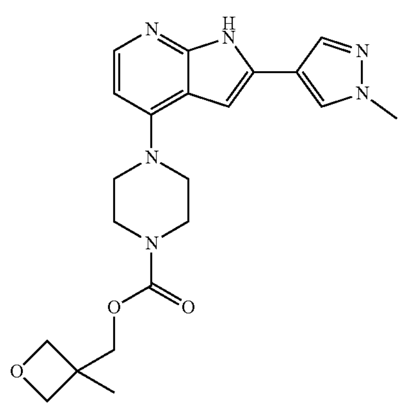 [SMILES: Cn1cc(-c2cc3c(N4CCN(C(=O)OCC5(C)COC5)CC4)ccnc3[nH]2)cn1] | 411 | ¹H-NMR (400 MHz, 6d-DMSO) δ ppm 11.76 (s, 1H), 8.17 (s, 1H), 8.12 (s, 1H), 7.94 (s, 1H), 7.90 (d, 1H, J = 4.8 Hz), 6.67 (s, 1H), 6.40 (d, 1H, J = 5.6 Hz), 4.42 (d, 2H, J = 6.0 Hz), 4.25 (d, 2H, J = 6.0 Hz), 4.12 (s, 2H), 3.87 (s, 3H), 3.70-3.50 (m, 4H), 3.40-3.30 (m, 4H), 1.27 (s, 3H). |

TABLE 1-continued

| # | Structure | LCMS (M + 1) | ¹H NMR |
|---|---|---|---|
| 237 | 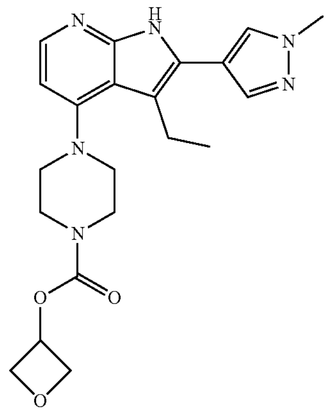 [SMILES: CCc1c(-c2cnn(C)c2)[nH]c2nccc(N3CCN(C(=O)OC4COC4)CC3)c12] | 411 | ¹H-NMR (500 MHz, 6d-DMSO) δ ppm 11.55 (s, 1H), 8.28 (s, 1H), 8.09 (s, 1H), 8.0 (d, 1H, J = 5.5 Hz), 7.87 (s, 1H), 6.65 (d, 1H, J = 5.5 Hz), 5.35-5.32 (m, 1H), 4.80-4.78 (m, 2H), 4.53 (q, 2H, J = 7.0 Hz), 3.92 (s, 3H), 3.69-3.55 (m, 4H), 3.04-3.05 (m, 4H), 2.95-2.91(m, 2H), 1.21 (t, 3H, J = 7.0 Hz). |
| 238 | 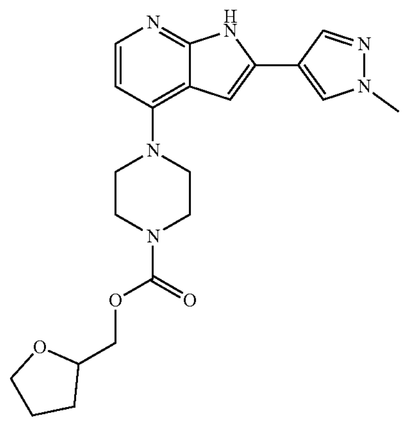 [SMILES: Cn1cc(-c2cc3c(N4CCN(C(=O)OCC5CCCO5)CC4)ccnc3[nH]2)cn1] | 411 | ¹H-NMR (500 MHz, 6d-DMSO) δ ppm 11.72 (s, 1H), 8.20-8.18 (m, 1H), 8.02-7.92 (m, 2H), 6.75-6.63 (m, 1H), 6.50-6.38 (m, 1H), 4.11-3.94 (m, 4H), 3.87 (s, 3H), 3.79-3.67 (m, 2H), 3.52-3.38 (m, 4H), 2.34-2.25 (m, 3H), 2.01-1.93 (m, 1H), 1.90-1.65 (m, 2H), 1.60-1.51 (m, 1H). |
| 239 | 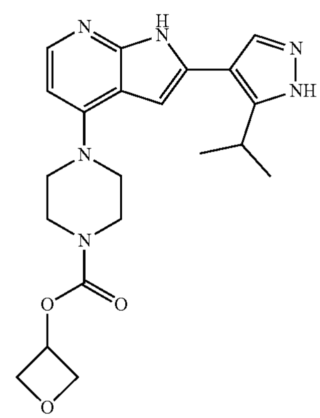 [SMILES: CC(C)c1[nH]ncc1-c1cc2c(N3CCN(C(=O)OC4COC4)CC3)ccnc2[nH]1] | 411 | ¹H-NMR (500 MHz, d₆-DMSO) δ ppm 12.80-12.63 (br, 1H), 11.58 (s, 1H), 8.05-7.95 (br, 1H), 7.94 (d, 1H, J = 5.5 Hz), 6.45 (d, 1H, J = 5.0 Hz), 6.38 (s, 1H), 5.35-5.32 (m, 1H), 4.80-4.78 (m, 2H), 4.55-4.52 (m, 2H), 3.69-3.58 (m, 4H), 3.48-3.40 (m, 4H), 12.9 (d, 6H, J = 7.0 Hz). |
| 240 | 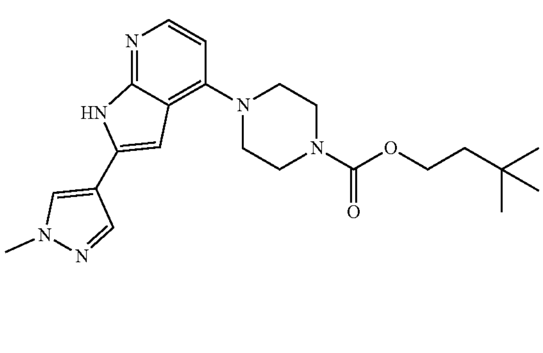 [SMILES: Cn1cc(-c2cc3c(N4CCN(C(=O)OCCC(C)(C)C)CC4)ccnc3[nH]2)cn1] | 411 | ¹H-NMR (400 MHz, 6d-DMSO) δ ppm 11.72 (s, 1H), 8.21 (br. s., 1H), 8.12 (s, 1H), 7.93 (s, 1H), 7.90 (d, 1H, J = 4.8 Hz), 6.65 (s, 1H), 6.42 (d, 1H, J = 5.2 Hz), 4.12 (t, 2H, J = 7.2 Hz), 3.87 (s, 3H), 3.58-3.57 (m, 4H), 3.36-3.35 (m, 4H), 1.55 (t, 2H, J = 7.2 Hz), 0.93 (s, 9H). |

TABLE 1-continued

| # | Structure | LCMS (M + 1) | ¹H NMR |
|---|---|---|---|
| 241 | 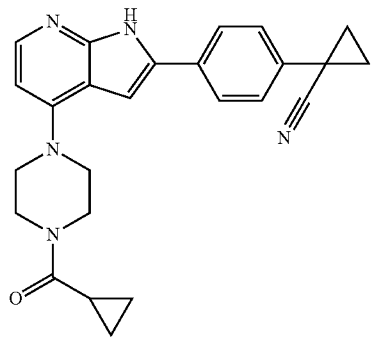 [SMILES: N#CC1(c2ccc(-c3cc4c(N5CCN(C(=O)C6CC6)CC5)ccnc4[nH]3)cc2)CC1] | 412 | |
| 242 | 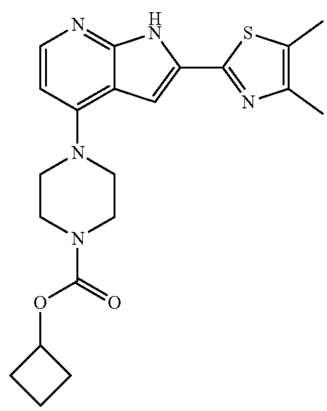 [SMILES: Cc1nc(-c2cc3c(N4CCN(C(=O)OC5CCC5)CC4)ccnc3[nH]2)sc1C] | 412 | ¹H-NMR (400 MHz, 6d-DMSO) δ ppm 12.18 (br s, 1H), 8.01 (d, 1H, J = 5.2 Hz), 6.98 (s, 1H), 6.45 (d, 1H, J = 5.6 Hz), 4.89-4.85 (m, 1H), 3.59-3.57 (m, 4H), 3.43-3.42 (m, 4H), 2.39 (s, 3H), 2.32 (s, 3H), 2.30-2.23 (m, 2H), 2.06-1.96 (m, 2H), 1.74-1.70 (m, 1H), 1.59-1.52 (m, 1H). |
| 243 | 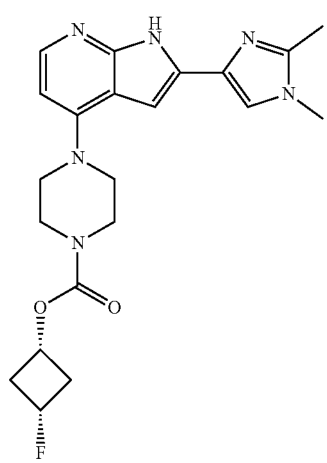 [SMILES: Cc1nc(-c2cc3c(N4CCN(C(=O)O[C@H]5C[C@@H](F)C5)CC4)ccnc3[nH]2)cn1C] | 413 | 1H-NMR (500 MHz, DMSO-d₆) δ ppm 11.59 (br. s., 1H), 7.89 (d, 1H, J = 7.0 Hz), 7.46 (s, 1H), 6.56 (d, 1H, J = 2.0 Hz), 6.41(d, 1H, J = 10.5 Hz), 4.92-4.75 (m, 1H), 4.54-4.84 (m, 1H), 3.64-3.60(m, 4H), 3.59(s, 3H), 3.37-3.34(m, 4H), 2.89-2.82(m, 2H), 2.32(s, 3H), 2.26-2.18(m, 2H). |

TABLE 1-continued

| # | Structure | LCMS (M + 1) | ¹H NMR |
|---|---|---|---|
| 244 | 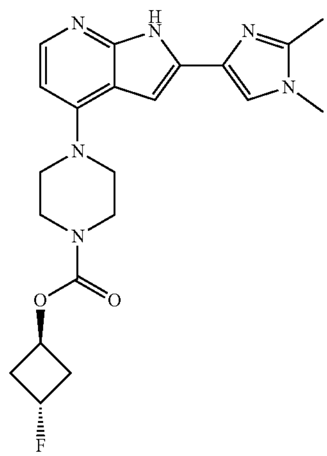 [SMILES: Cc1nc(-c2cc3c(N4CCN(C(=O)O[C@H]5C[C@H](F)C5)CC4)ccnc3[nH]2)cn1C] | 413 | ¹H-NMR (500 MHz, 6d-DMSO) δ ppm 11.60 (s, 1H), 7.88 (d, 1H, J = 5.5 Hz), 7.45 (s, 1H), 6.56 (d, 1H, J = 1.5 Hz), 6.39 (d, 1H, J = 5.5 Hz), 5.35-5.20 (m, 1H), 5.11-5.05 (m, 1H), 3.65-3.50 (m, 7H), 3.40-3.32 (m, 4H), 2.65-2.35 (m, 4H), 2.31 (s, 3H). |
| 245 | 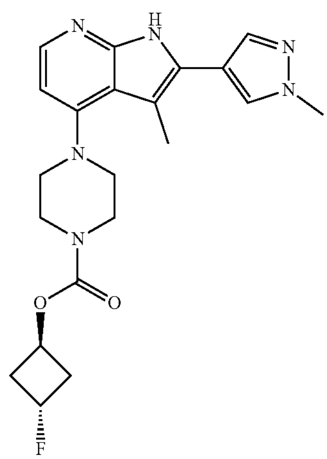 [SMILES: Cc1c(-c2cnn(C)c2)[nH]c2nccc(N3CCN(C(=O)O[C@H]4C[C@H](F)C4)CC3)c12] | 413 | ¹H-NMR (500 MHz, 6d-DMSO) δ ppm 11.57 (s, 1H), 8.10 (s, 1H), 7.96 (d, 1H, J = 4.5 Hz), 7.90 (s, 1H), 6.55 (d, 1H, J = 5.5 Hz), 5.40-5.20 (m, 1H), 5.12-5.05 (m, 1H), 3.91 (s, 3H), 3.69-3.52 (m, 4H), 3.20-3.00 (m, 4H), 2.65-2.50 (m, 2H), 2.50 (s, 3H), 2.50-2.40 (m, 2H). |
| 246 | 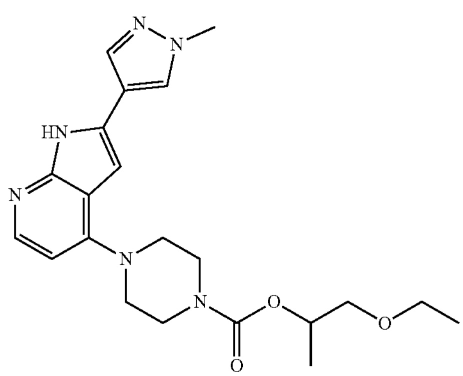 [SMILES: CCOCC(C)OC(=O)N1CCN(c2ccnc3[nH]c(-c4cnn(C)c4)cc23)CC1] | 413 | ¹H-NMR (400 MHz, 6d-DMSO) δ ppm 11.72 (s, 1H), 8.18 (br. s., 1H), 8.12 (s, 1H), 7.94 (s, 1H), 7.91 (d, 1H, J = 4.8 Hz), 6.66 (s, 1H), 6.42 (d, 1H, J = 5.6 Hz), 4.86-4.82 (m, 1H), 3.87 (s, 3H), 3.59-3.58 (m, 4H), 3.48-3.42 (m, 4H), 3.37-3.36 (m, 4H), 1.19 (d, 3H, J = 6.4 Hz), 1.11 (t, 3H, J = 7.2 Hz). |
| 247 | 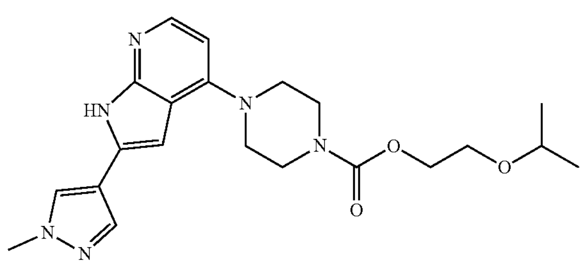 [SMILES: CC(C)OCCOC(=O)N1CCN(c2ccnc3[nH]c(-c4cnn(C)c4)cc23)CC1] | 413 | ¹H-NMR (400 MHz, 6d-DMSO) δ ppm 11.75 (br. s., 1H), 8.17 (br. s., 1H), 8.12 (s, 1H), 7.95 (s, 1H), 7.91 (d, 1H, J = 5.2 Hz), 6.67 (s, 1H), 6.42 (d, 1H, J = 5.6 Hz), 4.13 (t, 2H, J = 4.8 Hz), 3.88 (s, 3H), 3.61-3.53 (m, 7H), 3.38-3.36 (m, 4H), 1.10 (d, 6H, J = 6.4 Hz). |

TABLE 1-continued

| # | Structure | LCMS (M + 1) | ¹H NMR |
|---|---|---|---|
| 248 | 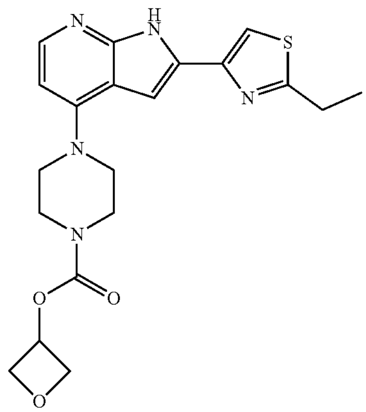 | 414 | ¹H-NMR (400 MHz, 6d-DMSO) δ ppm 11.98 (s, 1H), 7.98 (d, 1H, J = 5.6 Hz), 7.88 (s, 1H), 6.88 (s, 1H), 6.45 (d, 1H, J = 5.6 Hz), 5.40-5.25 (m, 1H), 4.80-4.75 (m, 2H), 4.60-4.50 (m, 2H), 3.80-3.52 (m, 4H), 3.50-3.40 (m, 4H), 3.04 (q, 2H, J = 7.6 Hz), 1.34 (t, 3H, J = 7.6 Hz). |
| 249 | 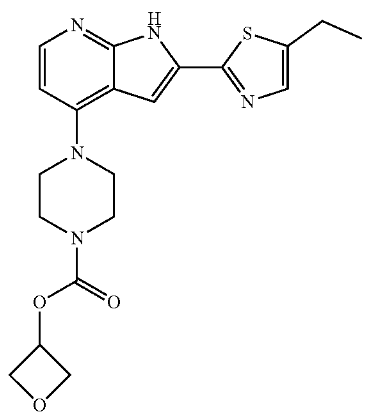 [SMILES: CCc1cnc(-c2cc3c(N4CCN(C(=O)OC5COC5)CC4)ccnc3[nH]2)s1] | 414 | ¹H-NMR (400 MHz, 6d-DMSO) δ ppm 12.22-12.18 (br, 1H), 8.03 (d, 1H, J = 5.6 Hz), 7.61 (s, 1H), 7.06 (s, 1H), 6.47 (d, 1H, J = 5.6 Hz), 5.34-5.32 (m, 1H), 4.80-4.77 (m, 2H), 4.54-4.51 (m, 2H), 3.69-3.67 (m, 2H), 3.60-3.58 (m, 2H), 3.47-3.46 (m, 4H), 2.90 (q, 2H, J = 7.6 Hz), 1.29 (t, 3H, J = 7.2 Hz). |
| 250 | 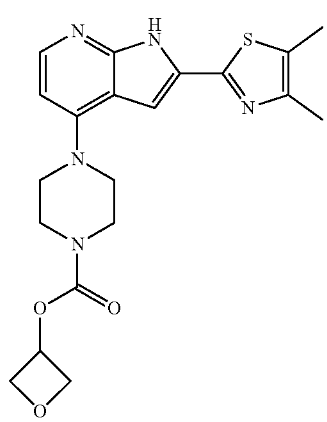 [SMILES: Cc1nc(-c2cc3c(N4CCN(C(=O)OC5COC5)CC4)ccnc3[nH]2)sc1C] | 414 | ¹H-NMR (400 MHz, 6d-DMSO) δ ppm 12.17 (s, 1H), 8.00 (d, 1H, J = 5.6 Hz), 6.99 (s, 1H), 6.45 (d, 1H, J = 5.6 Hz), 5.35-5.31 (m, 1H), 4.80-4.76 (m, 2H), 4.54-4.51 (m, 2H), 3.68-3.63 (m, 2H), 3.61-3.58 (m, 2H), 3.46-3.42 (m, 4H), 2.39 (s, 3H), 2.32 (s, 3H). |

TABLE 1-continued

| # | Structure | LCMS (M + 1) | ¹H NMR |
|---|---|---|---|
| 251 | 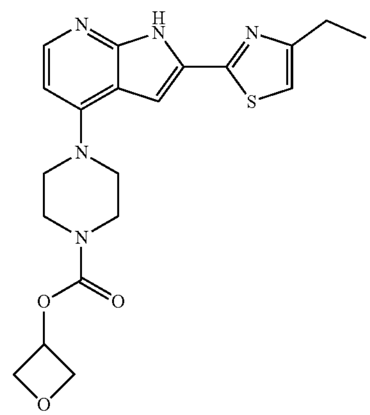 [SMILES: CCc1csc(-c2cc3c(N4CCN(C(=O)OC5COC5)CC4)ccnc3[nH]2)n1] | 414 | ¹H-NMR (500 MHz, 6d-DMSO) δ ppm 12.35-12.28 (br, 1H), 8.21 (s, 0.29H), 8.04 (d, 1H, J = 5.5 Hz), 7.30 (s, 1H), 7.10 (s, 1H), 6.47 (d, 1H, J = 5.5 Hz), 5.34-5.31 (m, 1H), 4.80-4.77 (m, 2H), 4.54-4.51 (m, 2H), 3.69-3.67 (m, 2H), 3.64-3.62 (m, 2H), 3.60-3.58 (m, 4H), 2.80 (q, 2H, J = 7.5 Hz), 1.28 (t, 3H, J = 7.5 Hz). |
| 252 | 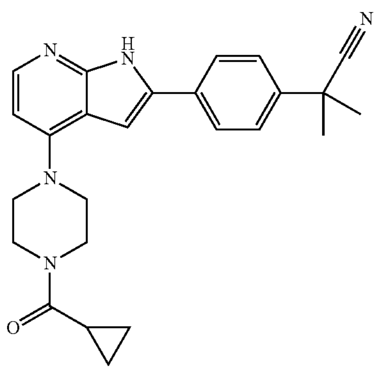 [SMILES: CC(C)(C#N)c1ccc(-c2cc3c(N4CCN(C(=O)C5CC5)CC4)ccnc3[nH]2)cc1] | 414 | |
| 253 | 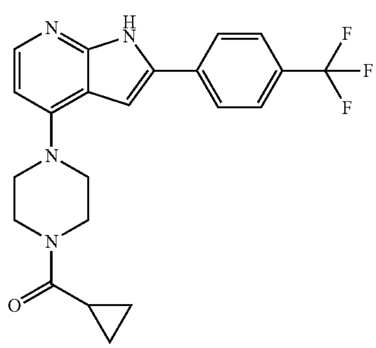 [SMILES: O=C(C1CC1)N1CCN(c2ccnc3[nH]c(-c4ccc(C(F)(F)F)cc4)cc23)CC1] | 415 | 1H NMR (400 MHz, DMSO) δ 13.19 (s, 1H), 8.17 (d, J = 8.2 Hz, 2H), 8.06 (d, J = 7.1 Hz, 1H), 7.89 (d, J = 8.4 Hz, 2H), 7.63 (s, 1H), 6.75 (d, J = 7.1 Hz, 1H), 4.03 (d, J = 14.3 Hz, 7H), 3.77 (s, 5H), 2.00 (dq, J = 7.4, 5.2 Hz, 1H), 0.80 (t, J = 5.6 Hz, 4H). |
| 254 | 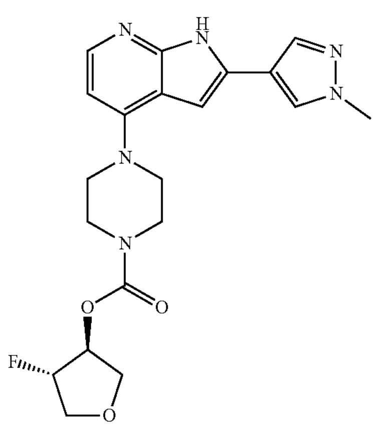 [SMILES: Cn1cc(-c2cc3c(N4CCN(C(=O)O[C@H]5COC[C@@H]5F)CC4)ccnc3[nH]2)cn1] | 415 | |

TABLE 1-continued

| # | Structure | LCMS (M + 1) | ¹H NMR |
|---|---|---|---|
| 255 | 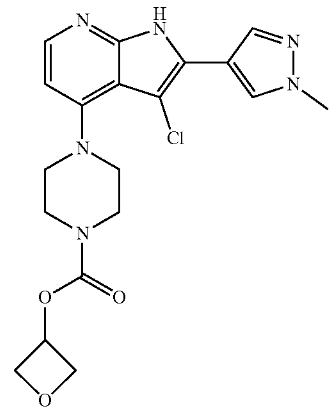 [SMILES: Cn1cc(-c2[nH]c3nccc(N4CCN(C(=O)OC5COC5)CC4)c3c2Cl)cn1] | 415 | ¹H-NMR (400 MHz, 6d-DMSO) δ ppm 12.17 (s, 1H), 8.35 (s, 1H), 8.10 (s, 1H), 8.04 (d, 1H, J = 5.2 Hz), 6.61 (d, 1H, J = 5.6 Hz), 4.90-4.84 (m, 1H), 3.93 (s, 1H), 3.70-3.60 (m, 4H), 3.18-3.08 (m, 4H), 2.35-2.21 (m, 2H), 2.09-1.90 (m, 2H), 1.75-1.70 (m, 1H), 1.62-1.55 (m, 1H). |
| 256 | 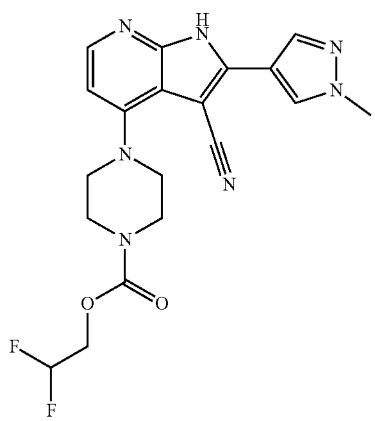 [SMILES: Cn1cc(-c2[nH]c3nccc(N4CCN(C(=O)OCC(F)F)CC4)c3c2C#N)cn1] | 416 | ¹H-NMR (500 MHz, 6d-DMSO) δ ppm 12.93 (s, 1H), 8.41 (s, 1H), 8.19-8.13 (m, 2H), 6.74 (d, 1H, J = 5.5 Hz), 6.28 (tt, 1H, J = 55.0, 3.0 Hz), 4.39-4.30 (m, 2H), 3.97 (s, 3H), 3.69-3.52 (m, 4H), 3.25-3.10 (m, 4H). |
| 257 | 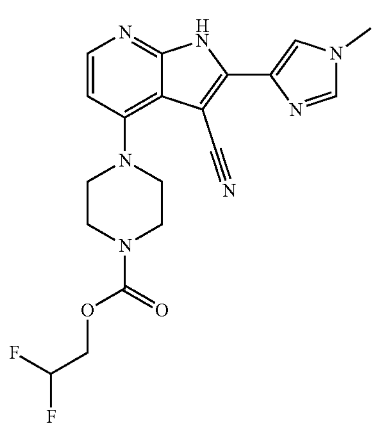 [SMILES: Cn1cnc(-c2[nH]c3nccc(N4CCN(C(=O)OCC(F)F)CC4)c3c2C#N)c1] | 416 | ¹H-NMR (400 MHz, 6d-DMSO) δ ppm 12.85 (br. s., 1H), 8.14 (d, 1H, J = 5.2 Hz), 7.88 (s, 1H), 7.87 (s, 1H), 6.73 (d, 1H, J = 5.2 Hz), 6.44-6.14 (m, 1H), 4.35 (td, 2H, J = 15.4, 3.6 Hz), 3.79 (s, 3H), 3.70-3.60 (m, 4H), 3.25-3.15 (m, 4H). |

TABLE 1-continued

| # | Structure | LCMS (M + 1) | ¹H NMR |
|---|---|---|---|
| 258 | 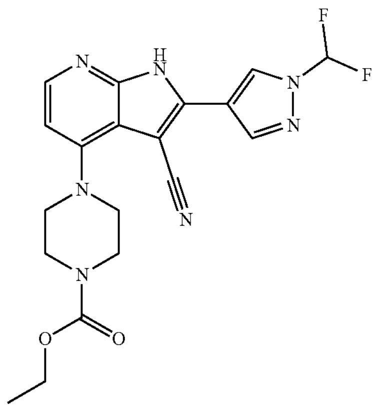 [SMILES: CCOC(=O)N1CCN(c2ccnc3[nH]c(-c4cnn(C(F)F)c4)c(C#N)c23)CC1] | 416 | ¹H-NMR (400 MHz, 6d-DMSO) δ ppm 13.14 (s, 1H), 8.88 (s, 1H), 8.47 (s, 1H), 8.20 (d, 1H, J = 5.6 Hz), 8.18-7.88 (m, 1H), 6.76 (d, 1H, J = 5.6 Hz), 4.09 (q, 2H, J = 7.2 Hz), 3.68-3.62 (m, 4H), 3.23-3.17 (m, 4H), 1.22 (t, 3H, J = 7.2 Hz). |
| 259 | 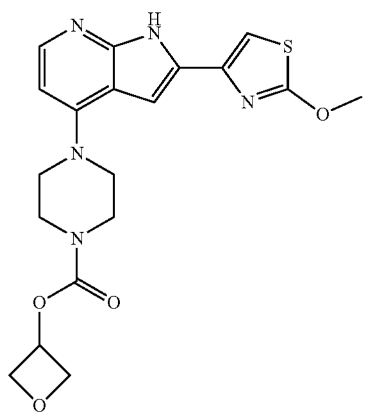 [SMILES: COc1nc(-c2cc3c(N4CCN(C(=O)OC5COC5)CC4)ccnc3[nH]2)cs1] | 416 | ¹H-NMR (500 MHz, 6d-DMSO) δ ppm 11.94 (s, 1H), 8.17 (s, 1H), 7.99 (d, 1H, J = 5.5 Hz), 7.43 (s, 1H), 6.81 (s, 1H), 6.46 (d, 1H, J = 5.5 Hz), 5.34 (quintet, 1H, J = 6.0 Hz), 4.79 (t, 2H, J = 7.0 Hz), 4.53 (dd, 2H, J = 8.0, 5.5 Hz), 4.12 (s, 3H), 3.68-3.64 (m, 2H), 3.60-3.56 (m, 2H), 3.45-3.43 (m, 4H). |
| 260 | 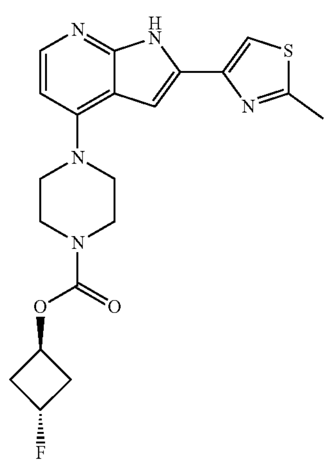 [SMILES: Cc1nc(-c2cc3c(N4CCN(C(=O)O[C@H]5C[C@H](F)C5)CC4)ccnc3[nH]2)cs1] | 416 | ¹H-NMR (500 MHz, 6d-DMSO) δ ppm 12.01 (s, 1H), 7.99 (d, 1H, J = 5.5 Hz), 7.87 (s, 1H), 6.89 (s, 1H), 6.45 (d, 1H, J = 5.5 Hz), 5.40-5.30 (m, 0.5H), 5.28-5.20 (m, 0.5H), 5.15-5.05 (m, 1H), 3.70-3.50 (m, 4H), 3.46-3.38 (m, 4H), 2.73 (s, 3H), 2.60-2.40 (m, 4H). |

TABLE 1-continued
| # | Structure | LCMS (M + 1) | ¹H NMR |
|---|---|---|---|
| 261 | 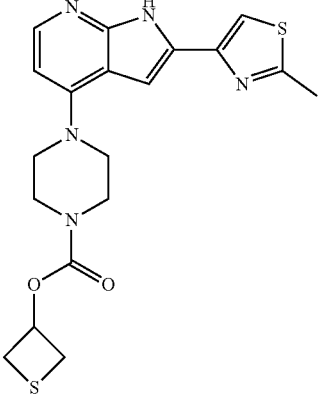 | 416 | ¹H-NMR (400 MHz, 6d-DMSO) δ ppm 11.99 (s, 1H), 7.98 (d, 1H, J = 4.8 Hz), 7.86 (s, 1H), 6.88 (d, 1H, J = 1.2 Hz), 6.45 (d, 1H, J = 4.0 Hz), 5.49-5.45 (m, 1H), 3.62-3.57 (m, 4H), 3.48-3.42 (m, 6H), 3.31-3.28 (m, 2H), 2.72 (s, 3H). |
| 262 | 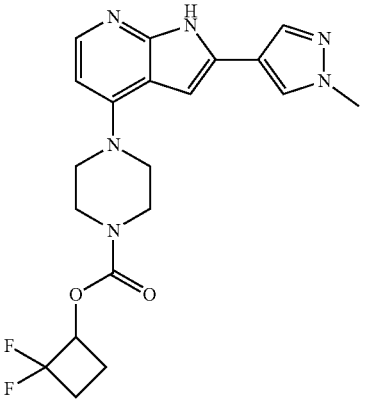 | 417 | ¹H-NMR (500 MHz, 6d-DMSO) δ ppm 11.73 (s, 1H), 8.12 (s, 1H), 7.93 (s, 1H), 7.91 (d, 1H, J = 6.0 Hz), 6.67 (d, 1H, J = 2.0 Hz), 6.43 (d, 1H, J = 5.5 Hz), 5.25-5.20 (m, 1H), 3.87 (s, 3H), 3.69-3.52 (m, 4H), 3.40-3.33 (m, 4H), 2.50-2.20 (m, 3H), 1.85-1.75 (m, 2H). |
| 263 | 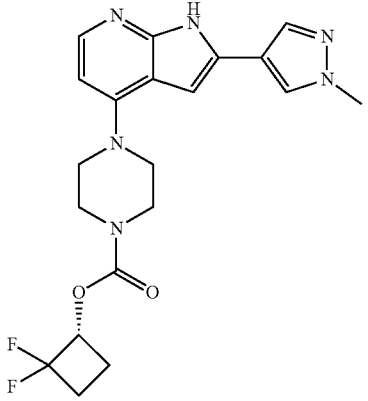 | 417 | ¹H-NMR (500 MHz, 6d-DMSO) δ ppm 11.76 (s, 1H), 8.12 (s, 1H), 7.93 (s, 1H), 7.91 (d, 1H, J = 5.5 Hz), 6.68 (s, 1H), 6.43 (d, 1H, J = 6.0 Hz), 5.25-5.20 (m, 1H), 3.88 (s, 3H), 3.69-3.52 (m, 4H), 3.40-3.33 (m, 4H), 2.50-2.20 (m, 3H), 1.85-1.75 (m, 2H). |

TABLE 1-continued

| # | Structure | LCMS (M + 1) | ¹H NMR |
|---|---|---|---|
| 264 | 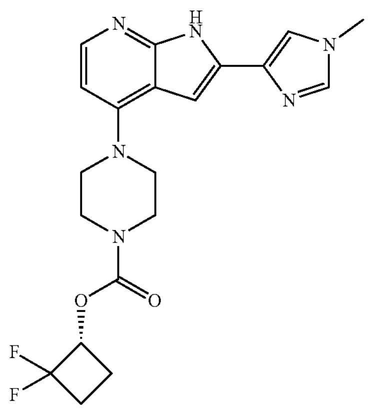 [SMILES: Cn1cnc(-c2cc3c(N4CCN(C(=O)O[C@@H]5CCC5(F)F)CC4)ccnc3[nH]2)c1] | 417 | ¹H-NMR (500 MHz, 6d-DMSO) δ ppm 11.67 (s, 1H), 7.91 (d, 1H, J = 5.5 Hz), 7.66 (s, 1H), 7.56 (d, 1H, J = 1.0 Hz), 6.65 (d, 1H, J = 1.5 Hz), 6.42 (d, 1H, J = 5.5 Hz), 5.25-5.20 (m, 1H), 3.70 (s, 3H), 3.69-3.52 (m, 4H), 3.45-3.33 (m, 4H), 2.50-2.20 (m, 3H), 1.85-1.75 (m, 1H). |
| 265 | 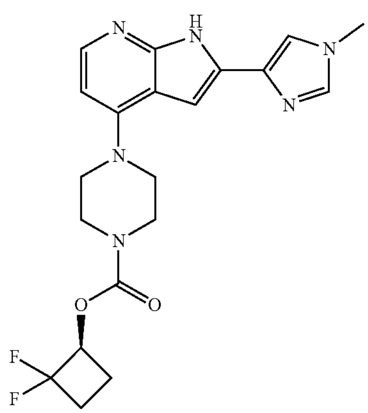 | 417 | ¹H-NMR (500 MHz, 6d-DMSO) δ ppm 11.67 (s, 1H), 7.91 (d, 1H, J = 5.0 Hz), 7.66 (s, 1H), 7.56 (d, 1H, J = 1.5 Hz), 6.65 (s, 1H), 6.43 (d, 1H, J = 6.0 Hz), 5.25-5.20 (m, 1H), 3.70 (s, 3H), 3.69-3.52 (m, 4H), 3.45-3.33 (m, 4H), 2.50-2.20 (m, 3H), 1.85-1.75 (m, 1H). |
| 266 | 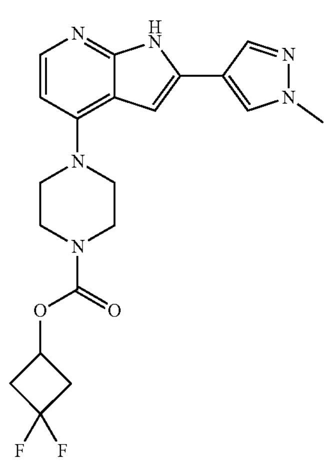 [SMILES: Cn1cc(-c2cc3c(N4CCN(C(=O)OC5CC(F)(F)C5)CC4)ccnc3[nH]2)cn1] | 417 | ¹H-NMR (400 MHz, 6d-DMSO) δ ppm 11.71 (s, 1H), 8.10 (s, 1H), 7.93 (s, 1H), 7.89 (d, 1H, J = 5.6 Hz), 6.64 (d, 1H, J = 1.6 Hz), 6.40 (d, 1H, J = 5.6 Hz), 4.86-4.83 (m, 1H), 3.87 (s, 3H), 3.60-3.58 (m, 4H), 3.39-3.36 (m, 4H), 3.07-2.99 (m, 2H), 2.77-2.66 (m, 2H). |

TABLE 1-continued

| # | Structure | LCMS (M + 1) | ¹H NMR |
|---|---|---|---|
| 267 | 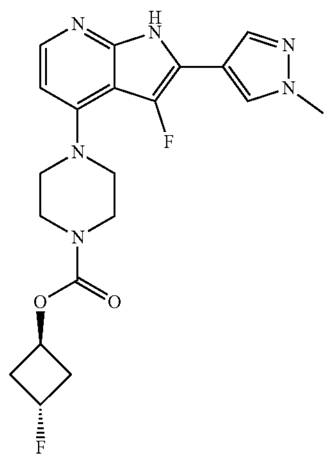 | 417 | ¹H-NMR (500 MHz, 6d-DMSO) δ ppm 11.76 (s, 1H), 8.12 (s, 1H), 7.98 (d, 1H, J = 5.5 Hz), 7.89 (s, 1H), 66.49 (d, 1H, J = 5.5 Hz), 5.35-5.22 (m, 1H), 5.11-5.05 (m, 1H), 3.91 (s, 3H), 3.65-3.50 (m, 4H), 3.30-3.20 (m, 4H), 2.60-2.40 (m, 4H). |
| 268 | 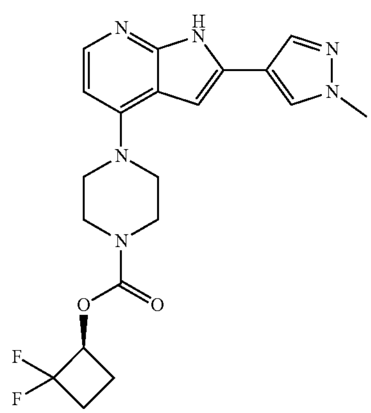 | 417 | ¹H-NMR (500 MHz, 6d-DMSO) δ ppm 11.71 (s, 1H), 8.12 (s, 1H), 7.93 (s, 1H), 7.91 (d, 1H, J = 5.5 Hz), 6.66 (d, 1H, J = 1.5 Hz), 6.42 (d, 1H, J = 5.5 Hz), 5.25-5.20 (m, 1H), 3.87 (s, 3H), 3.69-3.52 (m, 4H), 3.40-3.33 (m, 4H), 2.50-2.20 (m, 3H), 1.85-1.75 (m, 2H). |
| 269 | 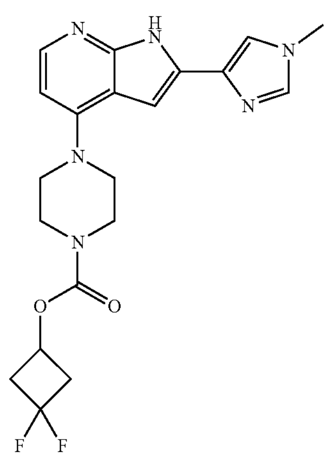 [SMILES: Cn1cnc(-c2cc3c(N4CCN(C(=O)OC5CC(F)(F)C5)CC4)ccnc3[nH]2)c1] | 417 | ¹H-NMR (400 MHz, 6d-DMSO) δ ppm 11.65 (s, 1H), 7.90 (d, 1H, J = 5.6 Hz), 7.65 (s, 1H), 7.55 (d, 1H, J = 1.2 Hz), 6.63 (s, 1H), 6.41 (d, 1H, J = 5.6 Hz), 4.90-4.80 (m, 1H), 3.69 (s, 3H), 3.67-3.53 (m, 4H), 3.41-3.34 (m, 4H), 3.08-3.01 (m, 2H), 2.74-2.65 (m, 2H). |

TABLE 1-continued

| # | Structure | LCMS (M + 1) | ¹H NMR |
|---|---|---|---|
| 270 | 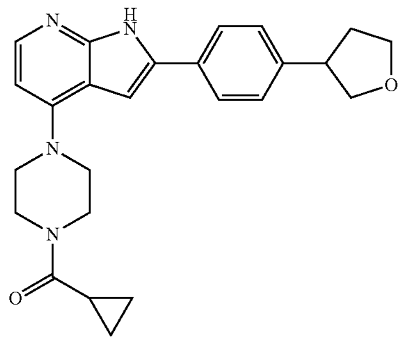 [SMILES: O=C(C1CC1)N1CCN(c2ccnc3[nH]c(-c4ccc(C5CCOC5)cc4)cc23)CC1] | 417 | ¹H-NMR (400 MHz, 6d-DMSO) δ ppm 11.92 (s, 1H), 7.96 (d, 1H, J = 5.6 Hz), 7.88 (d, 2H, J = 8.4 Hz), 7.33 (d, 2H, J = 8.4 Hz), 7.01 (d, 1H, J = 1.6 Hz), 6.43 (d, 1H, J = 5.6 Hz), 4.06-4.02 (m, 1H), 3.99-3.95 (m, 1H), 3.95-3.90 (m, 2H), 3.83-3.78 (m, 1H), 3.70-3.65 (m, 2H), 3.58-3.54 (m, 1H), 3.41-3.37 (m, 2H), 3.36-3.32 (m, 3H), 3.33-3.29 (m, 1H), 2.04-2.00 (m, 1H), 1.99-1.92 (m, 1H), 0.78-0.73 (m, 4H). |
| 271 | 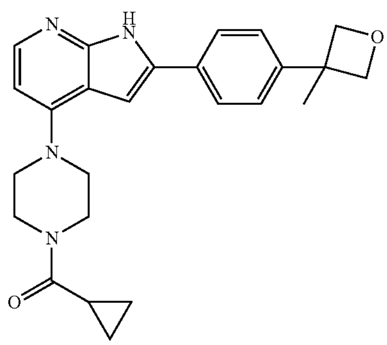 [SMILES: CC1(c2ccc(-c3cc4c(N5CCN(C(=O)C6CC6)CC5)ccnc4[nH]3)cc2)COC1] | 417 | ¹H-NMR (400 MHz, CDCl₃) δ ppm 11.80 (br s, 1H), 8.12 (d, 1H, J = 1.2 Hz), 7.81 (d, 2H, J = 8.4 Hz), 7.35 (d, 2H, J = 8.4 Hz), 6.76 (s, 1H), 6.48 (d, 1H, J = 5.6 Hz), 5.03 (d, 2H, J = 5.6 Hz), 4.71 (d, 1H, J = 5.6 Hz), 4.01-3.96 (m, 2H), 3.93-3.87 (m, 2H), 3.67-3.60 (m, 2H), 3.59-3.51 (m, 2H), 1.84-1.77 (m, 1H), 1.80 (s, 3H), 1.08-1.03 (m, 2H), 0.87-0.81 (m, 2H). |
| 272 | 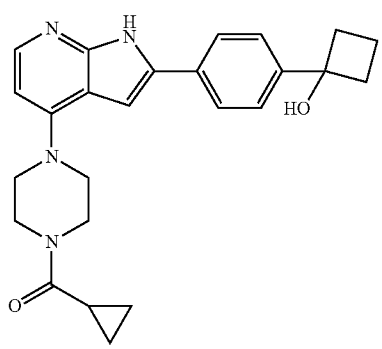 [SMILES: O=C(C1CC1)N1CCN(c2ccnc3[nH]c(-c4ccc(C5(O)CCC5)cc4)cc23)CC1] | 417 | ¹H-NMR (400 MHz, 6d-DMSO) δ ppm 11.93 (s, 1H), 7.96 (d, 1H, J = 5.6 Hz), 7.90 (d, 2H, J = 8.4 Hz), 7.52 (d, 2H, J = 8.4 Hz), 7.03 (d, 1H, J = 2.0 Hz), 6.43 (d, 1H, J = 5.6 Hz), 5.52 (s, 1H), 3.93-3.90 (m, 2H), 3.71-3.68 (m, 2H), 3.50-3.45 (m, 2H), 3.44-3.40 (m, 2H), 2.44-2.38 (m, 2H), 2.31-2.24 (m, 2H), 2.07-1.99 (m, 1H), 1.96-1.90 (m, 1H), 1.72-1.61 (m, 1H). |
| 273 | 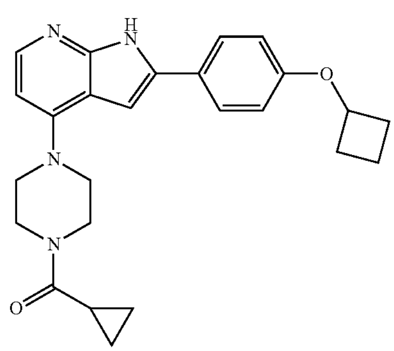 [SMILES: O=C(C1CC1)N1CCN(c2ccnc3[nH]c(-c4ccc(OC5CCC5)cc4)cc23)CC1] | 417 | 1H NMR (400 MHz, DMSO) δ 13.07 (s, 1H), 7.96 (d, J = 7.2 Hz, 1H), 7.87 (d, J = 8.8 Hz, 2H), 7.29 (d, J = 1.9 Hz, 1H), 6.98 (d, J = 8.9 Hz, 2H), 6.74 (d, J = 7.2 Hz, 1H), 4.78 (s, 1H), 4.01 (d, J = 16.8 Hz, 5H), 3.76 (s, 2H), 2.49-2.43 (m, 12H), 2.14-2.03 (m, 2H), 1.99 (s, 1H), 1.81 (dd, J = 20.3, 10.2 Hz, 1H), 1.69 (dt, J = 18.5, 8.1 Hz, 1H), 0.79 (t, J = 5.7 Hz, 4H). |

| # | Structure | LCMS (M + 1) | ¹H NMR |
|---|-----------|--------------|--------|
| 274 | 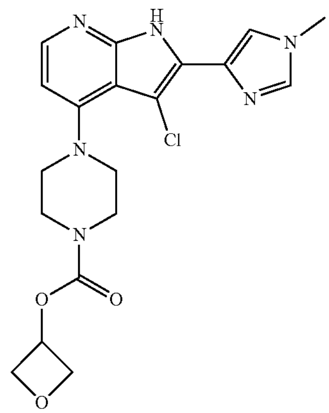 [SMILES: Cn1cnc(-c2[nH]c3nccc(N4CCN(C(=O)OC5COC5)CC4)c3c2Cl)c1] | 417 | |
| 275 | 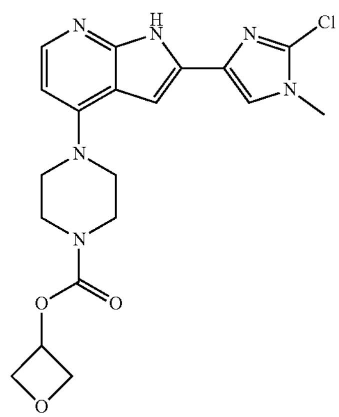 [SMILES: Cn1cc(-c2cc3c(N4CCN(C(=O)OC5COC5)CC4)ccnc3[nH]2)nc1Cl] | 417 | ¹H-NMR (400 MHz, 6d-DMSO) δ ppm 11.77 (s, 1H), 7.94 (d, 1H, J = 5.6 Hz), 7.67 (s, 1H), 6.67 (d, 1H, J = 2.0 Hz), 6.44 (d, 1H, J = 5.6 Hz), 5.34 (quintet, 1H, J = 5.2 Hz), 4.79 (t, 2H, J = 7.2 Hz), 4.53 (dd, 2H, J = 7.6, 5.2 Hz), 3.72-3.67 (m, 2H), 3.65 (s, 3H), 3.62-3.58 (m, 2H), 3.42-3.38 (m, 4H). |
| 276 | 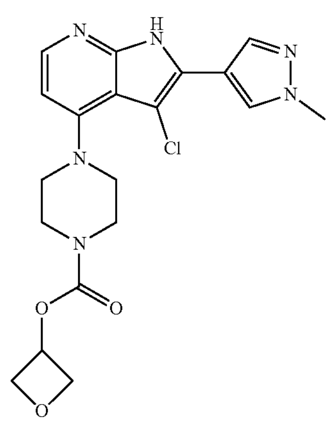 | 417 | ¹H-NMR (500 MHz, 6d-DMSO) δ ppm 12.17 (s, 1H), 8.35 (s, 1H), 8.09 (s, 1H), 8.05 (d, 1H, J = 5.0 Hz), 6.62 (d, 1H, J = 5.0 Hz), 5.33 (quintet, 1H, J = 5.5 Hz), 4.78 (t, 2H, J = 7.5 Hz), 4.53 (dd, 2H, J = 7.5, 5.5 Hz), 3.93 (s, 3H), 3.80-3.70 (m, 2H), 3.70-3.60 (m, 2H), 3.29-3.15 (m, 4H). |

TABLE 1-continued
| # | Structure | LCMS (M + 1) | ¹H NMR |
|---|---|---|---|
| 277 | 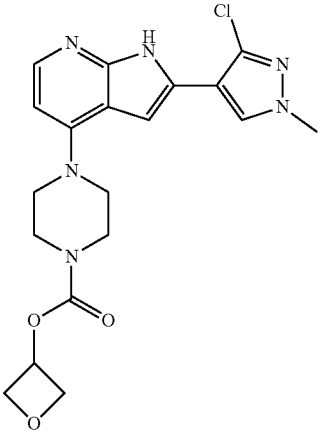 [SMILES: Cn1cc(-c2cc3c(N4CCN(C(=O)OC5COC5)CC4)ccnc3[nH]2)c(Cl)n1] | 417 | ¹H-NMR (400 MHz, 6d-DMSO) δ ppm 11.77 (s, 1H), 8.19 (s, 1H), 7.97 (d, 1H, J = 5.6 Hz), 6.75 (d, 1H, J = 1.6 Hz), 6.47 (d, 1H, J = 5.6 Hz), 5.35-5.30 (m, 1H), 4.81-4.76(m, 2H), 4.55-4.51 (m, 2H), 3.88 (s, 3H), 3.70-3.56 (m, 4H), 3.43-3.41 (m, 4H). |
| 278 | 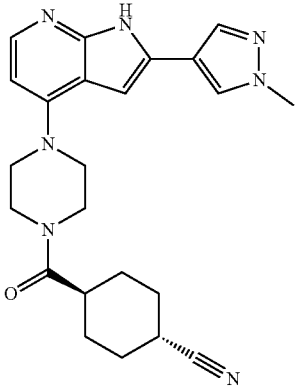 [SMILES: Cn1cc(-c2cc3c(N4CCN(C(=O)[C@H]5CC[C@H](C#N)CC5)CC4)ccnc3[nH]2)cn1] | 418 | ¹H NMR (400 MHz, 6d-DMSO) δ ppm 11.72(s, 1H), 8.12 (s, 1H), 7.93 (s, 1H), 7.90 (d, 1H, J = 5.2 Hz), 6.66 (d, 1H, J = 1.6 Hz), 6.41 (d, 1H, J = 5.2 Hz), 3.88 (s, 3H), 3.75-3.70 (m, 2H), 3.68-3.64 (m, 2H), 3.41-3.37 (m, 2H), 3.35-3.30 (m, 2H), 2.06-2.02 (m, 2H), 1.74-1.71 (m, 2H), 1.61-1.58 (m, 2H), 1.56-1.43 (m, 2H). |
| 279 | 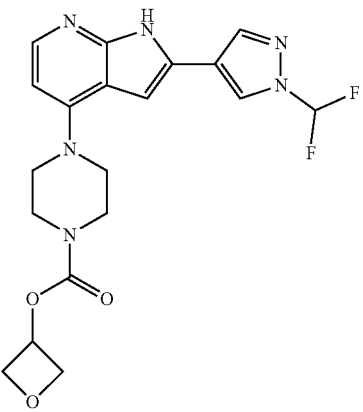 [SMILES: O=C(OC1COC1)N1CCN(c2ccnc3[nH]c(-c4cnn(C(F)F)c4)cc23)CC1] | 419 | ¹H-NMR (400 MHz, 6d-DMSO) δ ppm 11.89 (br s, 1H), 8.65 (s, 1H), 8.34 (s, 1H), 8.16 (s, 1H), 7.90 (t, 1H, J = 59.2 Hz), 7.96 (d, 1H, J = 4.8 Hz), 6.93 (s, 1H), 6.45 (d, 1H, J = 5.6 Hz), 5.36-5.31 (m, 1H), 4.82-4.76 (m, 2H), 4.55-4.51 (m, 2H), 3.80-3.55 (m, 4H), 3.51-3.48 (m, 4H). |

TABLE 1-continued
| # | Structure | LCMS (M + 1) | ¹H NMR |
|---|---|---|---|
| 280 | 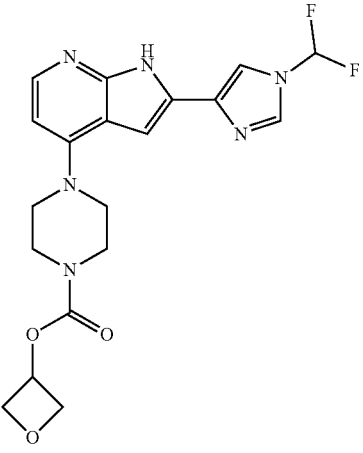 [SMILES: O=C(OC1COC1)N1CCN(c2ccnc3[nH]c(-c4cn(C(F)F)cn4)cc23)CC1] | 419 | ¹H-NMR (400 MHz, 6d-DMSO) δ ppm 11.86 (s, 1H), 8.25 (d, 1H, J = 0.8 Hz), 7.99 (d, 1H, J = 1.2 Hz), 7.96 (d, 1H, J = 5.6 Hz), 7.88 (t, 1H, J = 60.0 Hz), 6.82 (d, 1H, J = 1.6 Hz), 6.45 (d, 1H, J = 5.2 Hz), 5.36-5.31 (m, 1H), 4.81-4.76 (m, 2H), 4.56-4.51 (m, 2H), 3.71-3.58 (m, 4H), 3.45-3.40 (m, 4H). |
| 281 | 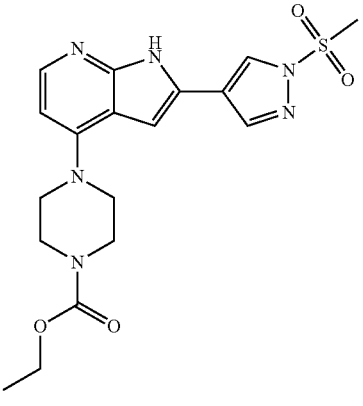 [SMILES: CCOC(=O)N1CCN(c2ccnc3[nH]c(-c4cnn(S(C)(=O)=O)c4)cc23)CC1] | 419 | ¹H-NMR (400 MHz, 6d-DMSO) δ ppm 11.90 (s, 1H), 8.78 (s, 1H), 8.52 (s, 1H), 7.95 (d, 1H, J = 5.6 Hz), 7.04 (s, 1H), 6.44 (d, 1H, J = 5.6 Hz), 4.08 (q, 2H, J = 6.8 Hz), 3.65-3.60 (m, 4H), 3.60 (s, 3H), 3.42-3.40 (m, 4H), 1.22 (t, 3H, J = 6.8 Hz). |
| 282 | 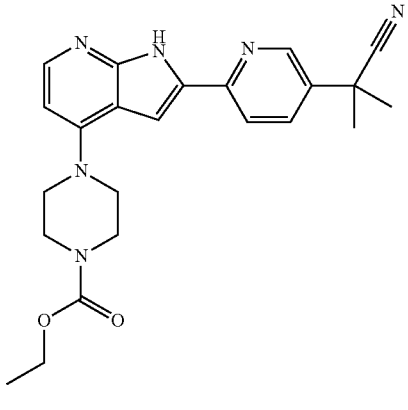 [SMILES: CCOC(=O)N1CCN(c2ccnc3[nH]c(-c4ccc(C(C)(C)C#N)cn4)cc23)CC1] | 419 | ¹H-NMR (400 MHz, CDCl₃) δ ppm 11.63 (br. s., 1H), 8.79 (s, 1H), 8.29 (d, 1H, J = 5.6 Hz), 7.85-7.82 (m, 2H), 7.00 (s, 1H), 6.47 (d, 1H, J = 5.6 Hz), 4.20 (q, 2H, J = 7.2 Hz), 3.78-3.72 (m, 4H), 3.55-3.50 (m, 4H), 1.81 (s, 6H), 1.31 (t, 3H, J = 7.2 Hz). |
| 283 | 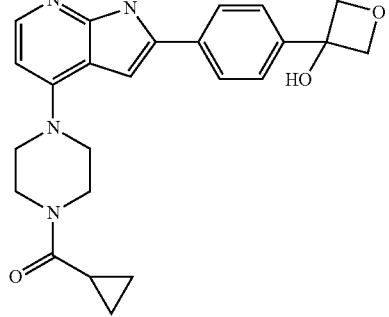 | 419 | ¹H-NMR (400 MHz, 6d-DMSO) δ ppm 11.99 (s, 1H), 7.98 (d, 2H, J = 8.0 Hz), 7.65 (d, 2H, J = 8.0 Hz), 7.09 (s, 1H), 6.45 (d, 1H, J = 5.2 Hz), 4.79 (d, 2H, J = 6.4 Hz), 4.72 (d, 2H, J = 6.4 Hz), 3.93-3.92 (m, 2H), 3.71-3.70 (m, 2H), 3.52-3.49 (m, 4H), 2.06-2.02 (m, 1H), 0.79-0.75 (m, 4H). |

TABLE 1-continued

| # | Structure | LCMS (M + 1) | ¹H NMR |
|---|---|---|---|
| 284 | 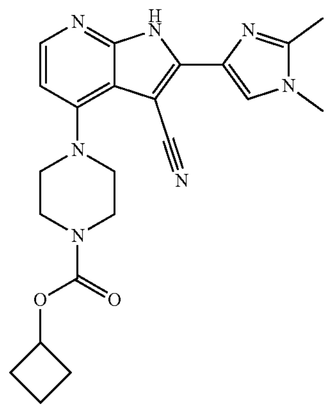 [SMILES: Cc1nc(-c2[nH]c3nccc(N4CCN(C(=O)OC5CCC5)CC4)c3c2C#N)cn1C] | 420 | 1H-NMR (500 MHz, DMSO-d$_6$) δ ppm 12.78 (br. s., 1H), 8.11 (d, 1H, J = 5.5 Hz), 7.82 (s, 1H), 6.71 (d, 1H, J = 5.5 Hz), 4.90-4.84 (m, 1H), 3.68 (s, 3H), 3.66-3.60 (m, 4H), 3.18-2.14 (m, 4H), 2.39 (s, 3H), 2.30-2.24(m, 2H), 2.05-2.00(m, 2H), 1.75-1.70(m, 1H), 1.60-1.54(m, 1H). |
| 285 | 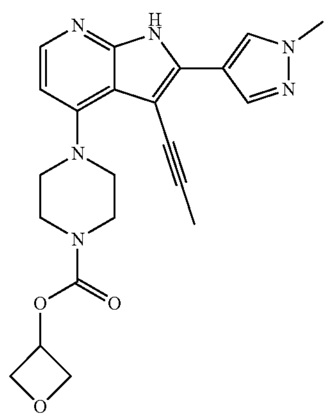 [SMILES: CC#Cc1c(-c2cnn(C)c2)[nH]c2nccc(N3CCN(C(=O)OC4COC4)CC3)c12] | 421 | 1H-NMR (500 MHz, DMSO-d$_6$) δ ppm 12.05 (br. s., 1H), 8.34 (s, 1H), 8.17 (s, 1H), 8.01 (d, 1H, J = 5.5 Hz), 6.56(d, 1H, J = 5.5 Hz), 5.35-5.31(m, 1H), 4.80-4.77 (m, 2H), 4.55-4.52 (m, 2H), 3.93 (s, 3H), 3.73-3.57(m, 4H), 3.25-3.19(m, 4H), 2.22(s, 3H). |
| 286 | 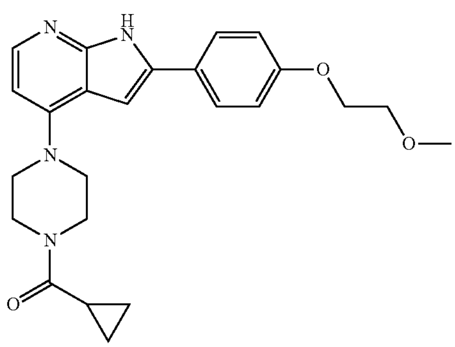 [SMILES: COCCOc1ccc(-c2cc3c(N4CCN(C(=O)C5CC5)CC4)ccnc3[nH]2)cc1] | 421 | |
| 287 | 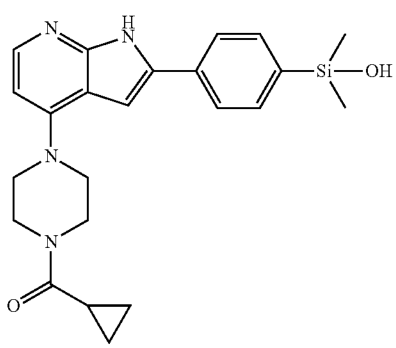 [SMILES: C[Si](C)(O)c1ccc(-c2cc3c(N4CCN(C(=O)C5CC5)CC4)ccnc3[nH]2)cc1] | 421 | ¹H NMR (400 MHz, DMSO-d$_6$) δ 11.97 (d, J = 2.0 Hz, 1H), 7.97 (d, J = 5.5 Hz, 1H), 7.92 (d, J = 8.0 Hz, 2H), 7.58 (d, J = 8.0 Hz, 2H), 7.08 (d, J = 2.1 Hz, 1H), 6.43 (d, J = 5.5 Hz, 1H), 5.93 (s, 1H), 3.91 (s, 2H), 3.70 (s, 2H), 3.49 (s, 2H), 3.42 (s, 2H), 2.03 (td, J = 7.8, 3.9 Hz, 1H), 0.86-0.63 (m, 4H), 0.26 (s, 6H). |

TABLE 1-continued

| # | Structure | LCMS (M + 1) | ¹H NMR |
|---|-----------|--------------|--------|
| 288 | 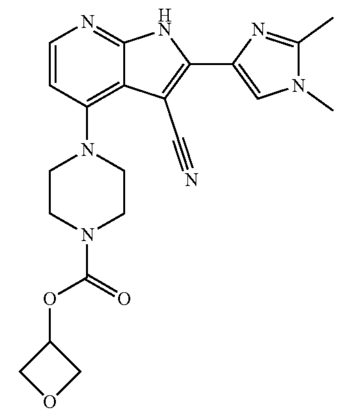 [SMILES: Cc1nc(-c2[nH]c3nccc(N4CCN(C(=O)OC5COC5)CC4)c3c2C#N)cn1C] | 422 | 1H-NMR (500 MHz, DMSO-d$_6$) δ ppm 12.79 (s, 1H), 8.12 (d, 1H, J = 5.0 Hz), 7.82 (d, 1H, J = 3 Hz), 6.72 (d, 1H, J = 5.5 Hz), 5.35-5.30(m, 1H), 4.80-4.76 (m, 2H), 4.55-4.52 (m, 2H), 3.72-3.62(m, 4H), 3.68(s, 3H), 3.20-3.17(m, 4H), 2.39(s, 3H). |
| 289 | 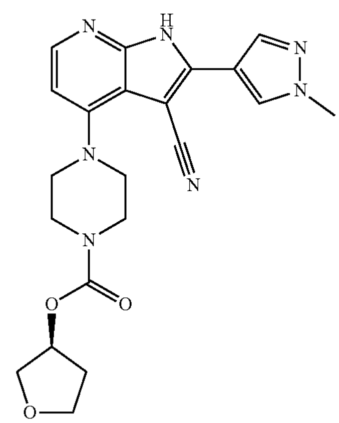 [SMILES: Cn1cc(-c2[nH]c3nccc(N4CCN(C(=O)O[C@H]5CCOC5)CC4)c3c2C#N)cn1] | 422 | ¹H-NMR (500 MHz, 6d-DMSO) δ ppm 12.93 (s, 1H), 8.40 (s, 1H), 8.19-8.13 (m, 2H), 6.73 (d, 1H, J = 5.5 Hz), 5.19-5.15 (m, 1H), 3.97 (s, 3H), 3.83-3.82 (m, 2H), 3.74-3.70 (m, 2H), 3.69-3.52 (m, 4H), 3.20-3.08 (m, 4H), 2.20-2.10 (m, 1H), 1.96-1.92 (m, 1H). |
| 290 | 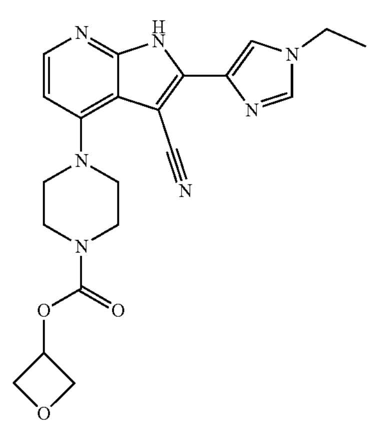 [SMILES: CCn1cnc(-c2[nH]c3nccc(N4CCN(C(=O)OC5COC5)CC4)c3c2C#N)c1] | 422 | ¹H-NMR (400 MHz, 6d-DMSO) δ ppm 12.84 (s, 1H), 8.14 (d, 1H, J = 5.6 Hz), 7.95 (d, 1H, J = 4.4 Hz), 6.73 (d, 1H, J = 6.0 Hz), 6.64 (s, 1H), 5.35-5.31 (m, 1H), 4.80-4.76 (m, 2H), 4.55-4.51 (m, 2H), 4.14 (q, 2H, J = 7.2 Hz), 3.73-3.63 (m, 4H), 3.33-3.20 (m, 4H), 1.41 (t, 3H, J = 7.2 Hz). |

TABLE 1-continued

| # | Structure | LCMS (M + 1) | ¹H NMR |
|---|---|---|---|
| 291 | 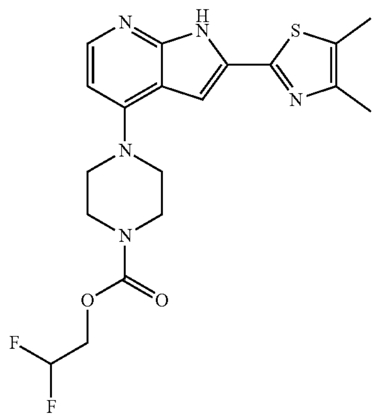 [SMILES: Cc1nc(-c2cc3c(N4CCN(C(=O)OCC(F)F)CC4)ccnc3[nH]2)sc1C] | 422 | ¹H-NMR (400 MHz, 6d-DMSO) δ ppm 12.14 (br s, 1H), 8.01 (d, 1H, J = 5.6 Hz), 7.00 (s, 1H), 6.46 (d, 1H, J = 5.6 Hz), 6.42-6.13 (m, 1H), 4.39-4.30 (m, 2H), 3.64-3.62 (m, 4H), 3.46-3.45 (m, 4H), 2.39 (s, 3H), 2.32 (s, 3H). |
| 292 | 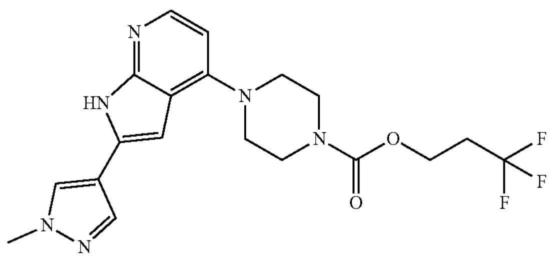 [SMILES: Cn1cc(-c2cc3c(N4CCN(C(=O)OCCC(F)(F)F)CC4)ccnc3[nH]2)cn1] | 423 | ¹H-NMR (400 MHz, 6d-DMSO) δ ppm 11.72 (s, 1H), 8.19 (br. s., 1H), 8.12 (s, 1H), 7.94 (s, 1H), 7.91 (d, 1H, J = 5.6 Hz), 6.66 (s, 1H), 6.42 (d, 1H, J = 5.6 Hz), 4.26 (t, 2H, J = 5.6 Hz), 3.87 (s, 3H), 3.59-3.58 (m, 4H), 3.37-3.36 (m, 4H), 2.71-2.66 (m, 2H). |
| 293 | 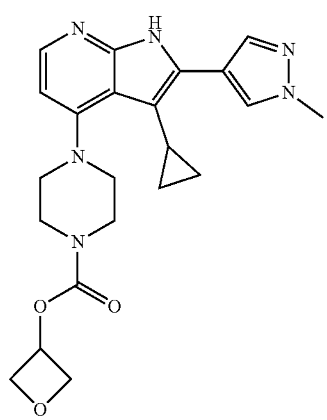 [SMILES: Cn1cc(-c2[nH]c3nccc(N4CCN(C(=O)OC5COC5)CC4)c3c2C2CC2)cn1] | 423 | ¹H-NMR (500 MHz, 6d-DMSO) δ ppm 11.57 (s, 1H), 8.16 (s, 1H), 8.00 (s, 1H), 7.93 (d, 1H, J = 5.5 Hz), 6.51 (d, 1H, J = 5.5 Hz), 5.35-5.30 (m, 1H), 4.80-4.76 (m, 2H), 4.54-4.50 (m, 2H), 3.93 (s, 3H), 3.80-3.52 (m, 4H), 3.25-3.08 (m, 4H), 2.00-1.90 (m, 1H), 1.07-1.02 (m, 2H), 0.35-0.30 (m, 2H). |
| 294 | 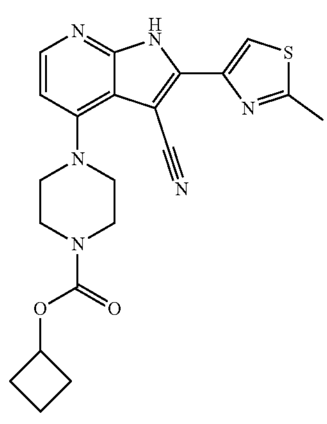 [SMILES: Cc1nc(-c2[nH]c3nccc(N4CCN(C(=O)OC5CCC5)CC4)c3c2C#N)cs1] | 423 | ¹H-NMR (400 MHz, 6d-DMSO) δ ppm 8.23 (s, 1H), 8.21 (d, 1H, J = 5.6 Hz), 6.76 (d, 1H, J = 5.6 Hz), 4.91-4.84 (m, 1H), 3.65-3.63 (m, 4H), 3.21-3.18 (m, 4H), 2.77 (s, 3H), 2.30-2.24 (m, 2H), 2.07-2.00 (m, 2H), 1.76-1.69 (m, 1H), 1.61-1.53 (m, 1H). |

TABLE 1-continued

| # | Structure | LCMS (M + 1) | ¹H NMR |
|---|---|---|---|
| 295 | 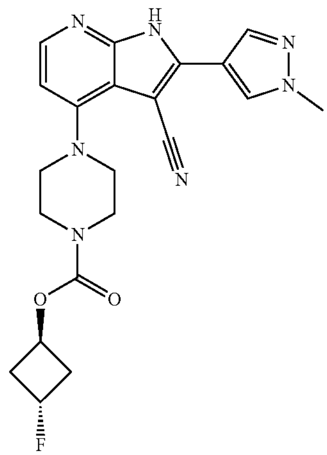 [SMILES: Cn1cc(-c2[nH]c3nccc(N4CCN(C(=O)O[C@H]5C[C@H](F)C5)CC4)c3c2C#N)cn1] | 424 | ¹H-NMR (500 MHz, 6d-DMSO) δ ppm 12.94 (s, 1H), 8.40 (s, 1H), 8.17-8.15 (m, 2H), 6.74 (d, 1H, J = 5.5 Hz), 5.35-5.24 (m, 1H), 5.09-5.08 (m, 1H), 3.97 (s, 3H), 3.65-3.62 (m, 4H), 3.19-3.14 (m, 4H), 2.57-2.42 (m, 4H). |
| 296 | 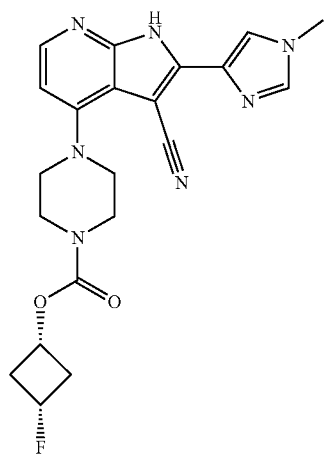 [SMILES: Cn1cnc(-c2[nH]c3nccc(N4CCN(C(=O)O[C@H]5C[C@@H](F)C5)CC4)c3c2C#N)c1] | 424 | ¹H-NMR (400 MHz, 6d-DMSO) δ ppm 12.84 (br. s., 1H), 8.14 (d, 1H, J = 5.2 Hz), 7.88 (s, 1H), 7.87 (s, 1H), 6.73 (d, 1H, J = 5.2 Hz), 4.92-4.74 (m, 1H), 4.54-4.48 (m, 1H), 3.79 (s, 3H), 3.70-3.60 (m, 4H), 3.25-3.15 (m, 4H), 2.89-2.81 (m, 2H), 2.30-2.18 (m, 2H). |
| 297 | 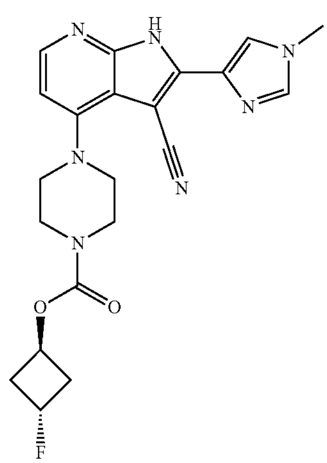 [SMILES: Cn1cnc(-c2[nH]c3nccc(N4CCN(C(=O)O[C@H]5C[C@H](F)C5)CC4)c3c2C#N)c1] | 424 | ¹H-NMR (400 MHz, 6d-DMSO) δ ppm 12.84 (br. s., 1H), 8.14 (d, 1H, J = 5.2 Hz), 7.88 (s, 1H), 7.87 (s, 1H), 6.73 (d, 1H, J = 5.2 Hz), 5.38-5.20 (m, 1H), 5.10-5.06 (m, 1H), 3.79 (s, 3H), 3.70-3.60 (m, 4H), 3.25-3.15 (m, 4H), 2.62-2.56 (m, 2H), 2.46-2.40 (m, 2H). |

TABLE 1-continued

| # | Structure | LCMS (M + 1) | ¹H NMR |
|---|---|---|---|
| 299 | 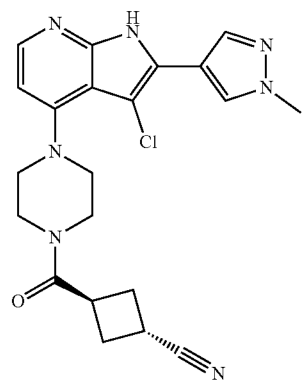 [SMILES: Cn1cc(-c2[nH]c3nccc(N4CCN(C(=O)[C@H]5C[C@H](C#N)C5)CC4)c3c2Cl)cn1] | 424 | ¹H-NMR (400 MHz, 6d-DMSO) δ ppm 12.18 (s, 1H), 8.35 (s, 1H), 8.10 (s, 1H), 8.05 (d, 1H, J = 5.2 Hz), 6.59 (d, 1H, J = 5.6 Hz), 3.93 (s, 3H), 3.74-3.71 (m, 2H), 3.71-3.69 (m, 1H), 3.57-3.53 (m, 2H), 3.28-3.26 (m, 1H), 3.12-3.07 (m, 4H), 2.63-3.60 (m, 3H), 2.51-3.49 (m, 1H). |
| 300 | 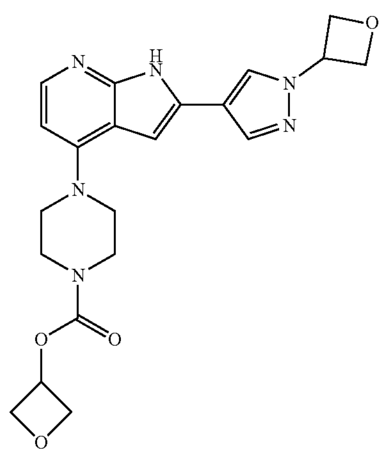 [SMILES: O=C(OC1COC1)N1CCN(c2ccnc3[nH]c(-c4cnn(C5COC5)c4)cc23)CC1] | 425 | ¹H-NMR (500 MHz, 6d-DMSO) δ ppm 11.76 (s, 1H), 8.37 (s, 1H), 8.19 (s, 1H), 8.10 (s, 1H), 7.92 (d, 1H, J = 5.0 Hz), 6.79 (s, 1H), 6.43 (d, 1H, J = 5.5 Hz), 5.63-5.58 (m, 1H), 5.36-5.31 (m, 1H), 4.97-4.91 (m, 2H), 4.91-4.88 (m, 2H), 4.78-4.77 (m, 2H), 4.54-4.51 (m, 2H), 3.68-3.53 (m, 2H), 3.47-3.46 (m, 2H), 3.34-3.22 (m, 4H). |
| 301 | 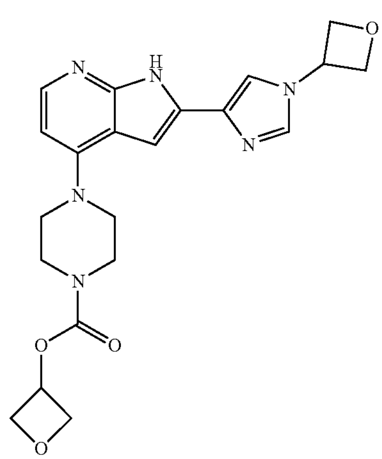 [SMILES: O=C(OC1COC1)N1CCN(c2ccnc3[nH]c(-c4cn(C5COC5)cn4)cc23)CC1] | 425 | 1H-NMR (500 MHz, DMSO-d₆) δ ppm 11.69 (br. s., 1H), 8.02 (d, 1H, J = 1.0 Hz), 7.92 (d, 1H, J = 5.5 Hz), 7.91 (d, 1H, J = 6 Hz), 6.71 (d, 1H, J = 7.5 Hz), 6.43 (d, 1H, J = 5.0 Hz), 5.52-5.48 (m, 1H), 5.36-5.31 (m, 1H), 5.02-4.99 (m, 2H), 4.80-4.75 (m, 4H), 4.54-4.51(m, 2H), 3.71-3.55 (m, 4H), 3.42-3.38(m, 4H). |

TABLE 1-continued
| # | Structure | LCMS (M + 1) | ¹H NMR |
|---|---|---|---|
| 302 | 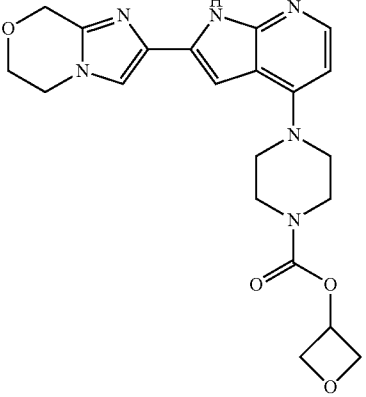 | 425 | |
| 303 | 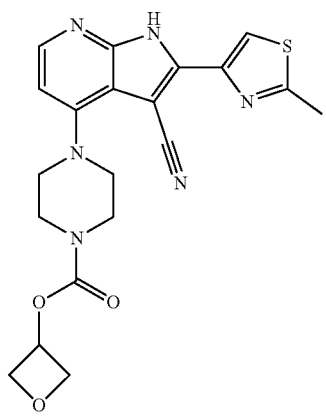 [SMILES: Cc1nc(-c2[nH]c3nccc(N4CCN(C(=O)OC5COC5)CC4)c3c2C#N)cs1] | 425 | ¹H-NMR (400 MHz, 6d-DMSO) δ ppm 13.12 (s, 1H), 8.24 (s, 1H), 8.21 (d, 1H, J = 5.6 Hz), 6.77 (d, 1H, J = 5.2 Hz), 5.36-5.30 (m, 1H), 4.80-4.77 (m, 2H), 4.55-4.52 (m, 2H), 3.73-3.64 (m, 4H), 3.23-3.21 (m, 4H), 2.77 (s, 3H). |
| 304 | 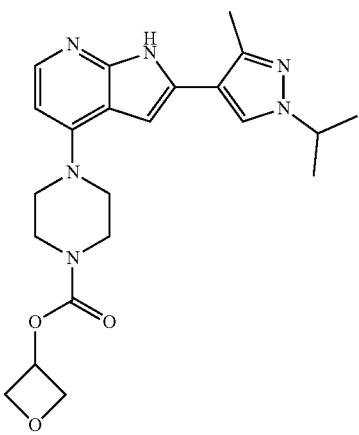 [SMILES: Cc1nn(C(C)C)cc1-c1cc2c(N3CCN(C(=O)OC4COC4)CC3)ccnc2[nH]1] | 425 | ¹H-NMR (400 MHz, 6d-DMSO) δ ppm 11.51 (s, 1H), 8.13 (s, 1H), 7.92 (d, 1H, J = 5.2 Hz), 6.44 (d, 1H, J = 5.2 Hz), 6.40 (s, 1H), 5.34-5.31 (m, 1H), 4.80-4.78 (m, 2H), 4.54-4.51 (m, 2H), 4.41-4.40 (m, 1H), 3.68-3.66 (m, 2H), 3.59-3.57 (m, 2H), 3.40-3.38 (m, 4H), 2.39 (s, 3H), 1.43 (d, 6H, J = 6.4 Hz). |

TABLE 1-continued
| # | Structure | LCMS (M + 1) | ¹H NMR |
|---|---|---|---|
| 305 | 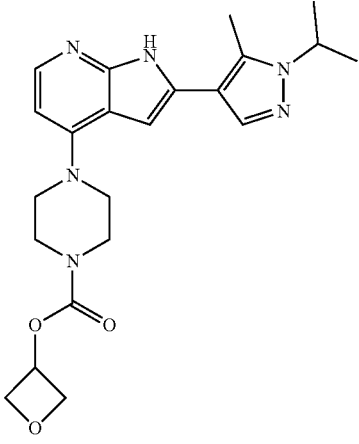 [SMILES: Cc1c(-c2cc3c(N4CCN(C(=O)OC5COC5)CC4)ccnc3[nH]2)cnn1C(C)C] | 425 | ¹H-NMR (400 MHz, 6d-DMSO) δ ppm 11.60 (s, 1H), 7.93 (d, 1H, J = 5.2 Hz), 7.83 (s, 1H), 6.44 (d, 1H, J = 5.2 Hz), 6.40 (s, 1H), 5.34-5.31 (m, 1H), 4.80-4.76 (m, 2H), 4.63-4.60 (m, 1H), 4.52-4.51 (m, 2H), 3.68-3.66 (m, 2H), 3.59-3.57 (m, 2H), 3.40-3.38 (m, 4H), 2.47 (s, 3H), 1.40 (d, 6H, J = 6.8 Hz). |
| 306 | 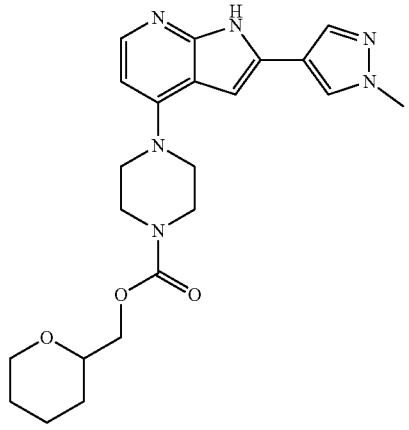 [SMILES: Cn1cc(-c2cc3c(N4CCN(C(=O)OCC5CCCCO5)CC4)ccnc3[nH]2)cn1] | 425 | ¹H-NMR (400 MHz, 6d-DMSO) δ ppm 11.71 (s, 1H), 8.15 (s, 1H), 8.11 (s, 1H), 7.93 (s, 1H), 7.89 (d, 1H, J = 5.2 Hz), 6.66 (s, 1H), 6.41 (d, 1H, J = 5.2 Hz), 3.97 (d, 2H, J = 5.2 Hz), 3.90-3.80 (m, 4H), 3.64-3.54 (m, 4H), 3.52-3.44 (m, 1H), 3.40-3.30 (m, 5H), 1.84-1.72 (m, 1H), 1.60-1.52 (m, 1H), 1.50-1.36 (m, 3H), 1.30-1.16 (m, 1H). |
| 307 | 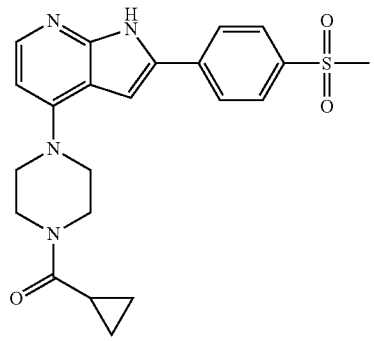 [SMILES: CS(=O)(=O)c1ccc(-c2cc3c(N4CCN(C(=O)C5CC5)CC4)ccnc3[nH]2)cc1] | 425 | |

TABLE 1-continued
| # | Structure | LCMS (M + 1) | ¹H NMR |
|---|---|---|---|
| 308 | 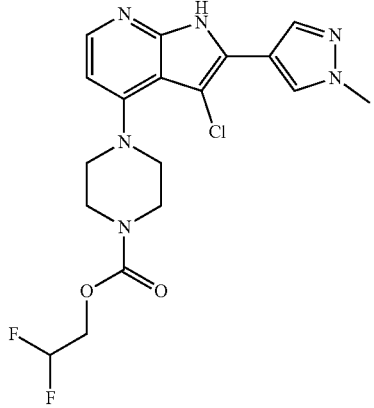 [SMILES: Cn1cc(-c2[nH]c3nccc(N4CCN(C(=O)OCC(F)F)CC4)c3c2Cl)cn1] | 425 | ¹H-NMR (500 MHz, 6d-DMSO) δ ppm 12.19-12.18 (m, 1H), 8.36 (s, 1H), 8.10 (s, 1H), 8.06 (d, 1H, J = 5.5 Hz), 6.62 (d, 1H, J = 5.5 Hz), 6.40-6.17 (m, 1H), 4.39-4.32 (m, 2H), 3.94 (s, 3H), 3.72-3.66 (m, 4H), 3.15-3.16 (m, 4H). |
| 309 | 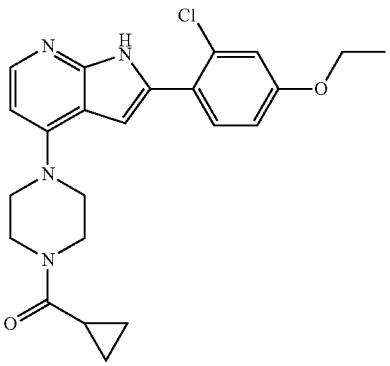 [SMILES: CCOc1ccc(-c2cc3c(N4CCN(C(=O)C5CC5)CC4)ccnc3[nH]2)c(Cl)c1] | 425 | ¹H-NMR (400 MHz, 6d-DMSO) δ ppm 11.72 (s, 1H), 7.98 (d, 1H, J = 5.2 Hz), 7.61 (d, 1H, J = 8.8 Hz), 7.14 (d, 1H, J = 2.4 Hz), 7.02 (dd, 1H, J = 8.8, 2.4 Hz), 6.78 (d, 1H, J = 2.0 Hz), 6.50 (d, 1H, J = 6.0 Hz), 4.10 (q, 2H, J = 7.2 Hz), 3.91-3.87 (m, 2H), 3.71-3.67 (m, 2H), 3.50-3.45 (m, 2H), 3.43-3.38 (m, 2H), 2.04-1.98 (m, 1H), 1.34 (t, 3H, J = 7.2 Hz), 0.76-0.72 (m, 4H). |
| 310 | 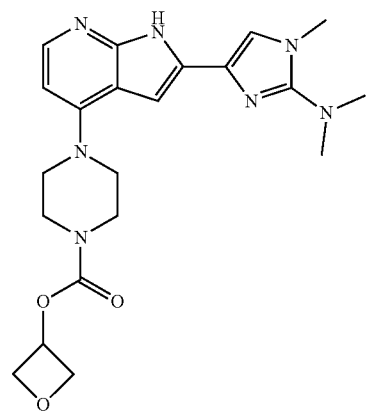 [SMILES: CN(C)c1nc(-c2cc3c(N4CCN(C(=O)OC5COC5)CC4)ccnc3[nH]2)cn1C] | 426 | ¹H-NMR (500 MHz, 4d-MeOD) δ ppm 7.91 (d, 1H, J = 5.5 Hz), 7.27 (s, 1H), 6.79 (s, 1H), 6.51 (d, 1H, J = 5.5 Hz), 4.62 (quintet, 1H, J = 5.5 Hz), 4.12-4.10 (m, 2H), 3.90-3.86 (m, 2H), 3.02-2.98 (m, 2H), 2.92-2.88 (m, 2H), 2.80 (s, 3H), 2.76-2.68 (m, 4H), 2.05 (s, 6H). |
| 311 | 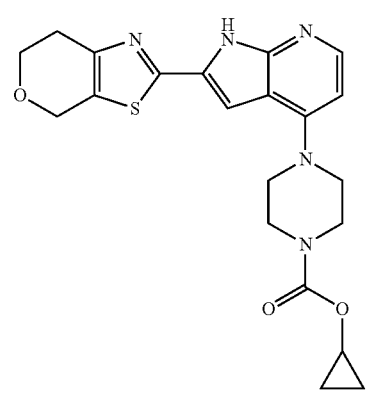 [SMILES: O=C(OC1CC1)N1CCN(c2ccnc3[nH]c(-c4nc5c(s4)COCC5)cc23)CC1] | 426 | ¹H-NMR (400 MHz, 6d-DMSO) δ ppm 12.29 (s, 1H), 8.0 (d, 1H, J = 5.2 Hz), 7.07 (s, 1H), 6.44 (d, 1H, J = 5.6 Hz), 4.83 (s, 2H), 4.05-3.96 (m, 3H), 3.54-3.56 (m, 4H), 3.42-3.43 (m, 4H), 2.87-2.85 (m, 2H), 0.66-0.63 (m, 4H). |

TABLE 1-continued

| # | Structure | LCMS (M + 1) | ¹H NMR |
|---|-----------|--------------|--------|
| 312 | 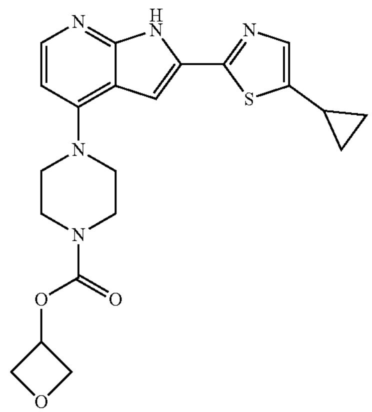 [SMILES: O=C(OC1COC1)N1CCN(c2ccnc3[nH]c(-c4ncc(C5CC5)s4)cc23)CC1] | 426 | ¹H-NMR (400 MHz, 6d-DMSO) δ ppm 12.25 (s, 1H), 8.14 (s, 1H, HCOOH), 8.00 (d, 1H, J = 5.2 Hz), 7.61 (s, 1H), 7.04 (s, 1H), 6.45 (d, 1H, J = 5.6 Hz), 5.33-5.31 (m, 1H), 4.79-4.76 (m, 2H), 4.53-4.50 (m, 2H), 3.66-3.57 (m, 4H), 3.46-3.43 (m, 4H), 2.24-2.18 (m, 1H), 1.09-1.05 (m, 2H), 0.76-0.72 (m, 2H) |
| 313 | 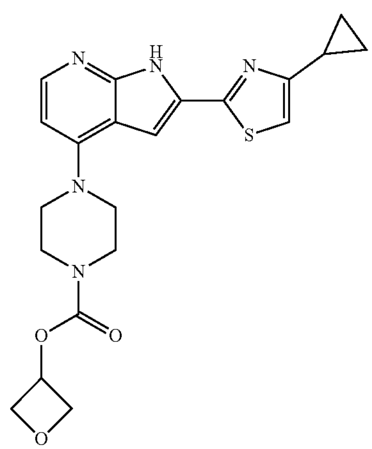 [SMILES: O=C(OC1COC1)N1CCN(c2ccnc3[nH]c(-c4nc(C5CC5)cs4)cc23)CC1] | 426 | ¹H-NMR (400 MHz, 6d-DMSO) δ ppm 12.44-12.00 (br, 1H), 8.18 (s, 1H), 8.05 (d, 1H, J = 5.6 Hz), 7.26 (s, 1H), 7.07 (s, 1H), 6.47 (d, 1H, J = 5.6 Hz), 5.35-5.32 (m, 1H), 4.80-4.77 (m, 2H), 4.54-4.51 (m, 2H), 3.69-3.67 (m, 2H), 3.59-3.57 (m, 2H), 3.48-3.47 (m, 4H), 2.14-2.10 (m, 1H), 0.94-0.92 (m, 4H). |
| 314 | 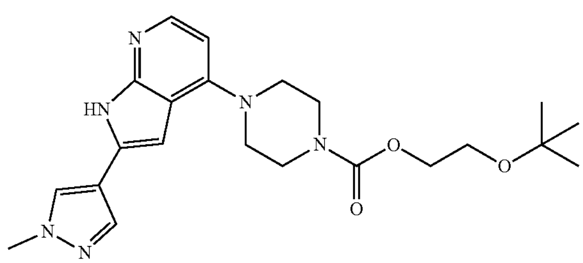 [SMILES: Cn1cc(-c2cc3c(N4CCN(C(=O)OCCOC(C)(C)C)CC4)ccnc3[nH]2)cn1] | 427 | ¹H-NMR (400 MHz, 6d-DMSO) δ ppm 11.71 (s, 1H), 8.15 (s, 1H), 8.11 (s, 1H), 7.93 (s, 1H), 7.89 (d, 1H, J = 5.2 Hz), 6.65 (s, 1H), 6.41 (d, 1H, J = 5.2 Hz), 4.07 (t, 2H, J = 4.8 Hz), 3.87 (s, 3H), 3.64-3.54 (m, 4H), 3.51 (t, 2H, J = 4.8 Hz), 3.40-3.30 (m, 4H), 11.35 (s, 9H). |
| 315 | 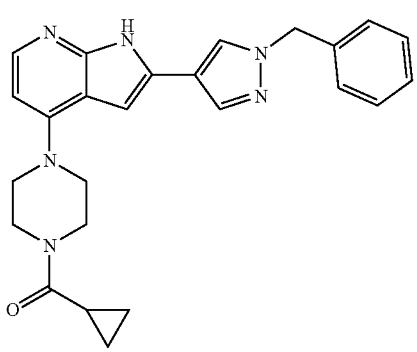 [SMILES: O=C(C1CC1)N1CCN(c2ccnc3[nH]c(-c4cnn(Cc5ccccc5)c4)cc23)CC1] | 427 | 1H NMR (400 MHz, DMSO) δ 12.90 (s, 1H), 8.30 (s, 1H), 8.04 (s, 1H), 7.99 (d, J = 7.2 Hz, 1H), 7.43-7.28 (m, 5H), 7.14 (d, J = 1.9 Hz, 1H), 6.74 (d, J = 7.2 Hz, 1H), 5.42 (s, 2H), 4.06-3.93 (m, 6H), 3.74 (s, 2H), 1.99 (s, 1H), 0.79 (t, J = 5.7 Hz, 4H). |

TABLE 1-continued

| # | Structure | LCMS (M + 1) | ¹H NMR |
|---|---|---|---|
| 316 | 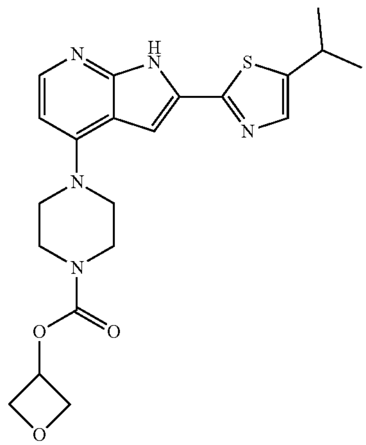 [SMILES: CC(C)c1cnc(-c2cc3c(N4CCN(C(=O)OC5COC5)CC4)ccnc3[nH]2)s1] | 428 | ¹H-NMR (500 MHz, 6d-DMSO) δ ppm 12.23 (s, 1H), 8.02 (d, 1H, J = 5.5 Hz), 7.62 (d, 1H, J = 0.5 Hz), 7.08 (s, 1H), 6.46 (d, 1H, J = 6.0 Hz), 5.35-5.32 (m, 1H), 4.80-4.77 (m, 2H), 4.54-4.51 (m, 2H), 3.69-3.67 (m, 2H), 3.58-3.48 (m, 2H), 3.47-3.45 (m, 4H), 3.30-3.27 (m, 1H), 1.33 (d, 6H, J = 6.5 Hz). |
| 317 | 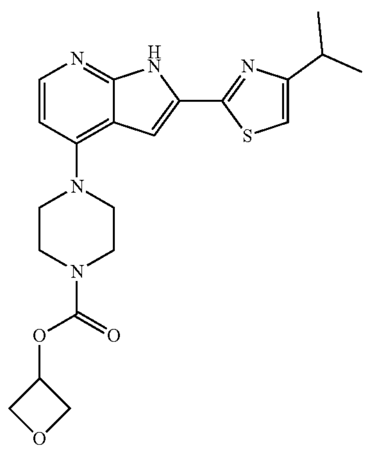 [SMILES: CC(C)c1csc(-c2cc3c(N4CCN(C(=O)OC5COC5)CC4)ccnc3[nH]2)n1] | 428 | ¹H-NMR (400 MHz, 6d-DMSO) δ ppm 12.34-12.30 (br, 1H), 8.19 (s, 1H), 8.05 (d, 1H, J = 5.6 Hz), 7.29 (s, 1H), 7.09 (s, 1H), 6.48 (d, 1H, J = 5.6 Hz), 5.35-5.32 (m, 1H), 4.80-4.77 (m, 2H), 4.54-4.51 (m, 2H), 3.69-3.67 (m, 2H), 3.65-3.63 (m, 2H), 3.48-3.47 (m, 4H), 3.11-3.06 (m, 1H), 1.31 (d, 6H, J = 6.8 Hz). |
| 318 | 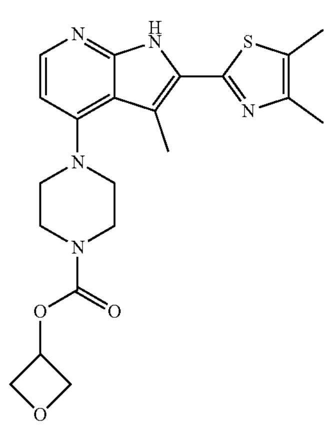 [SMILES: Cc1nc(-c2[nH]c3nccc(N4CCN(C(=O)OC5COC5)CC4)c3c2C)sc1C] | 428 | ¹H-NMR (400 MHz, 6d-DMSO) δ ppm 11.90 (s, 1H), 8.07 (d, 1H, J = 5.6 Hz), 6.60 (d, 1H, J = 5.6 Hz), 5.35-5.30 (m, 1H), 4.79-4.75 (m, 2H), 4.53-4.49 (m, 2H), 3.69-3.56 (m, 4H), 3.10-3.01 (m, 4H), 2.66 (s, 3H), 2.41 (s, 3H), 2.34 (s, 3H). |

| # | Structure | LCMS (M + 1) | ¹H NMR |
|---|---|---|---|
| 319 | 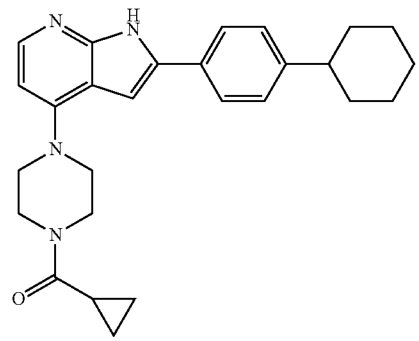 | 429 | 1H NMR (400 MHz, DMSO) δ 12.92 (s, 1H), 8.01 (d, J = 7.0 Hz, 1H), 7.85 (d, J = 8.3 Hz, 2H), 7.41-7.31 (m, 3H), 6.72 (d, J = 7.0 Hz, 1H), 3.97 (d, J = 25.9 Hz, 6H), 3.76 (s, 2H), 2.00 (td, J = 7.3, 2.3 Hz, 1H), 1.82 (d, J = 10.0 Hz, 4H), 1.73 (d, J = 12.3 Hz, 1H), 1.54-1.12 (m, 4H), 0.79 (t, J = 6.0 Hz, 4H). |
| 320 | 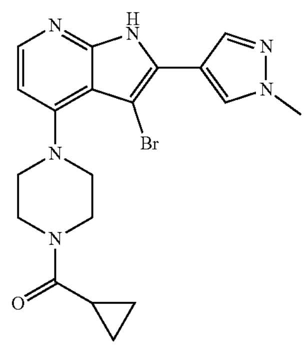 [SMILES: Cn1cc(-c2[nH]c3nccc(N4CCN(C(=O)C5CC5)CC4)c3c2Br)cn1] | 430 | 1H NMR (400 MHz, Methanol-d4) δ 8.44 (d, J = 0.7 Hz, 1H), 8.21 (d, J = 0.8 Hz, 1H), 8.14 (d, J = 5.4 Hz, 1H), 6.76 (d, J = 5.4 Hz, 1H), 5.67 (s, 1H), 4.11 (d, J = 10.3 Hz, 2H), 4.04 (s, 3H), 3.91 (s, 2H), 3.23 (s, 3H), 2.11 (tt, J = 7.8, 4.8 Hz, 1H), 1.00-0.91 (m, 2H), 0.91-0.76 (m, 3H). |
| 321 | 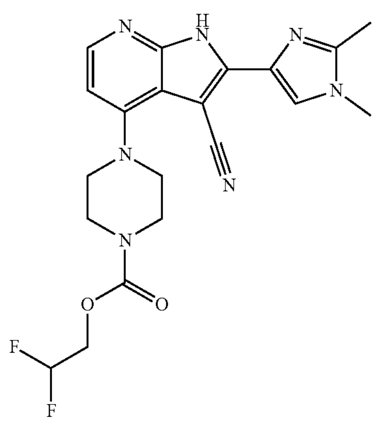 [SMILES: Cc1nc(-c2[nH]c3nccc(N4CCN(C(=O)OCC(F)F)CC4)c3c2C#N)cn1C] | 430 | 1H-NMR (400 MHz, DMSO-d₆) δ ppm 12.79 (br. s., 1H), 8.11 (d, 1H, J = 5.2 Hz), 7.82 (s, 1H), 6.72 (d, 1H, J = 5.2 Hz), 6.42-6.15 (m, 1H), 4.39-4.30 (m, 2H), 3.68 (s, 3H), 3.67-3.62 (m, 4H), 3.21-2.15 (m, 4H), 2.39 (s, 3H). |
| 322 | 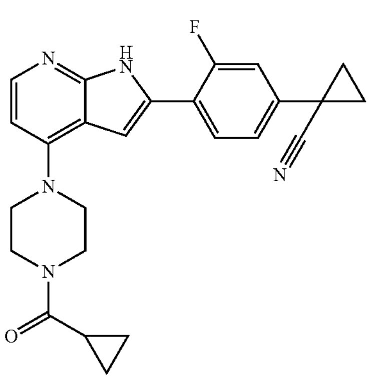 [SMILES: N#CC1(c2ccc(-c3cc4c(N5CCN(C(=O)C6CC6)CC5)ccnc4[nH]3)c(F)c2)CC1] | 430 | |

TABLE 1-continued

| # | Structure | LCMS (M + 1) | ¹H NMR |
|---|---|---|---|
| 323 | 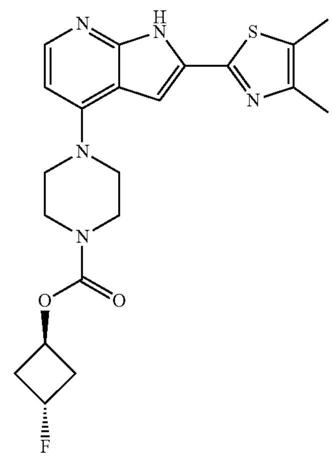 [SMILES: Cc1nc(-c2cc3c(N4CCN(C(=O)O[C@H]5C[C@H](F)C5)CC4)ccnc3[nH]2)sc1C] | 430 | ¹H-NMR (400 MHz, 6d-DMSO) δ ppm 11.18 (s, 1H), 8.00 (d, 1H, J = 5.6 Hz), 6.98 (s, 1H), 6.44 (d, 1H, J = 5.6 Hz), 5.37-5.20 (m, 1H), 5.10-5.05 (m, 1H), 3.60-3.56 (m, 4H), 3.43-3.41 (m, 4H), 2.60-2.52 (m, 2H), 2.49-2.43 (m, 2H), 2.38 (s, 3H), 2.31 (s, 3H) |
| 324 | 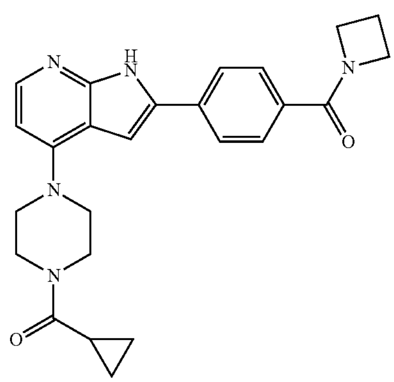 [SMILES: O=C(c1ccc(-c2cc3c(N4CCN(C(=O)C5CC5)CC4)ccnc3[nH]2)cc1)N1CCC1] | 430 | ¹H-NMR (400 MHz, DMSO-d₆) δ ppm 12.06 (s, 1H), 8.02-7.98 (m, 3H), 7.66 (d, 2H, J = 8.8 Hz), 7.20 (d, 1H, J = 1.6 Hz), 6.44 (d, 1H, J = 5.6 Hz), 4.35 (t, 2H, J = 7.6 Hz), 4.05 (t, 2H, J = 7.2 Hz), 3.91(br. s., 2H), 3.70 (br. s., 2H), 3.51 (br. s., 2H), 3.45 (br. s., 2H), 2.29-2.25 (m, 2H), 2.08-2.0 (m, 1H), 0.78-0.73 (m, 4H). |
| 325 | 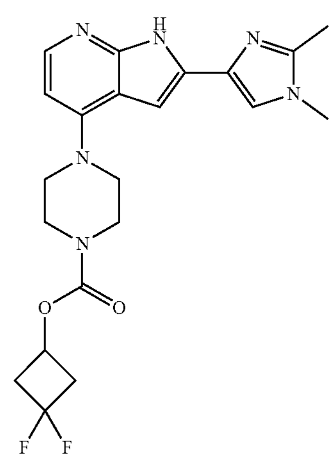 [SMILES: Cc1nc(-c2cc3c(N4CCN(C(=O)OC5CC(F)(F)C5)CC4)ccnc3[nH]2)cn1C] | 431 | 1H-NMR (500 MHz, DMSO-d₆) δ ppm 11.59 (br. s., 1H), 7.89 (d, 1H, J = 5.0 Hz), 7.46 (s, 1H), 6.57 (d, 1H, J = 2 Hz), 6.41(d, 1H, J = 2 Hz), 4.88-4.82 (m, 1H), 3.65-3.60 (m, 4H), 3.59(s, 3H), 3.39-3.35(m, 4H), 3.06-3.04(m, 2H), 2.74-2.70(m, 2H), 2.32(s, 3H). |

TABLE 1-continued

| # | Structure | LCMS (M + 1) | ¹H NMR |
|---|---|---|---|
| 326 | 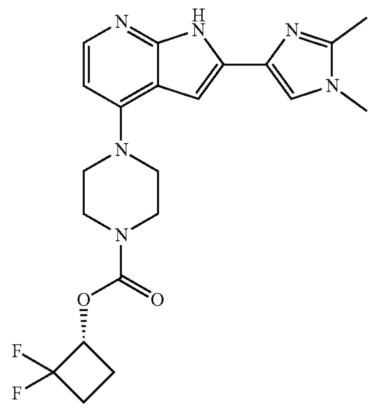 [SMILES: Cc1nc(-c2cc3c(N4CCN(C(=O)O[C@@H]5CCC5(F)F)CC4)ccnc3[nH]2)cn1C] | 431 | ¹H-NMR (500 MHz, 6d-DMSO) δ ppm 11.60 (s, 1H), 7.89 (d, 1H, J = 6.0 Hz), 7.46 (s, 1H), 6.57 (d, 1H, J = 2.0 Hz), 6.40 (d, 1H, J = 6.0 Hz), 5.25-5.20 (m, 1H), 3.75-3.50 (m, 7H), 3.48-3.30 (m, 4H), 2.50-2.15 (m, 6H), 1.85-1.75 (m, 1H). |
| 327 | 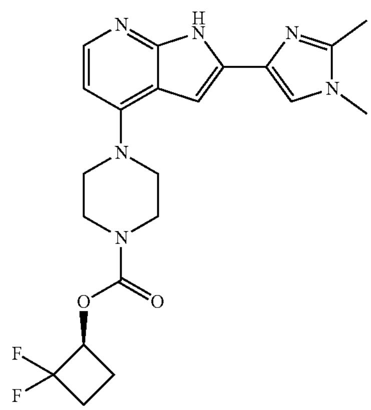 [SMILES: Cc1nc(-c2cc3c(N4CCN(C(=O)O[C@H]5CCC5(F)F)CC4)ccnc3[nH]2)cn1C] | 431 | ¹H-NMR (500 MHz, 6d-DMSO) δ ppm 11.60 (s, 1H), 7.89 (d, 1H, J = 6.0 Hz), 7.46 (s, 1H), 6.57 (d, 1H, J = 2.0 Hz), 6.40 (d, 1H, J = 6.0 Hz), 5.25-5.20 (m, 1H), 3.75-3.50 (m, 7H), 3.48-3.25 (m, 4H), 2.50-2.15 (m, 6H), 1.85-1.75 (m, 1H). |
| 328 | 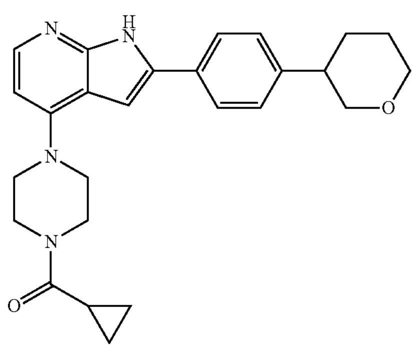 | 431 | ¹H-NMR (400 MHz, 6d-DMSO) δ ppm 11.91 (s, 1H), 7.95 (d, 1H, J = 5.6 Hz), 7.87 (d, 2H, J = 8.4 Hz), 7.32 (d, 2H, J = 8.4 Hz), 7.01 (d, 1H, J = 1.6 Hz), 6.43 (d, 1H, J = 5.6 Hz), 3.91-3.89 (m, 2H), 3.88-3.83 (m, 2H), 3.71-3.65 (m, 2H), 3.50-3.45 (m, 2H), 3.44-3.40 (m, 2H), 3.35-3.30 (m, 2H), 2.80-2.75 (m, 1H), 2.10-2.04 (m, 1H), 1.98-1.95 (m, 1H), 1.77-1.70 (m, 1H), 1.68-1.63 (m, 2H), 0.77-0.73 (m, 4H). |
| 329 | 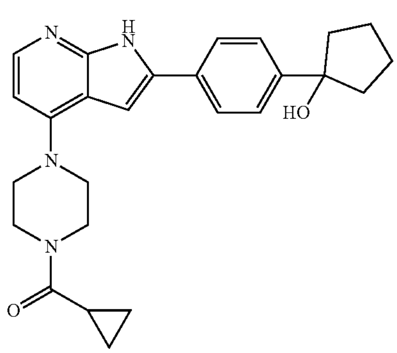 [SMILES: O=C(C1CC1)N1CCN(c2ccnc3[nH]c(-c4ccc(C5(O)CCCC5)cc4)cc23)CC1] | 431 | ¹H-NMR (400 MHz, 6d-DMSO) δ ppm 11.92 (s, 1H), 7.97 (d, 1H, J = 5.2 Hz), 7.88 (d, 2H, J = 8.4 Hz), 7.52 (d, 2H, J = 8.4 Hz), 7.02 (s, 1H), 6.44 (d, 1H, J = 5.2 Hz), 4.83 (s, 1H), 3.98-3.85 (m, 2H), 3.77-3.64 (m, 2H), 3.53-3.46 (m, 2H), 3.44-3.37 (m, 2H), 2.09-1.99 (m, 1H), 1.91-1.85 (m, 6H), 1.80-1.68 (m, 2H), 0.82-0.68 (m, 4H). |

TABLE 1-continued
| # | Structure | LCMS (M + 1) | ¹H NMR |
|---|---|---|---|
| 330 | 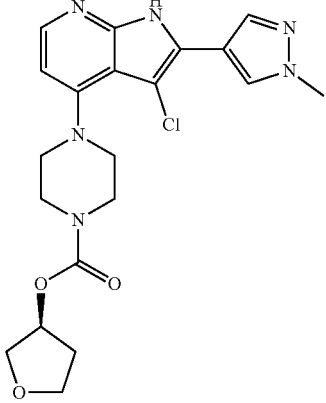 | 431 | ¹H-NMR (400 MHz, 6d-DMSO) δ ppm 12.17 (s, 1H), 8.34 (s, 1H), 8.08 (s, 1H), 8.04 (d, 1H, J = 5.2 Hz), 6.60 (d, 1H, J = 5.6 Hz), 6.17-6.15 (m, 1H), 3.92 (s, 3H), 3.82-3.79 (m, 2H), 3.75-3.71 (m, 2H), 3.64-3.60 (m, 4H), 3.16-3.12 (m, 4H), 2.14-1.96 (m, 1H), 1.95-1.91 (m, 1H). |
| 331 | 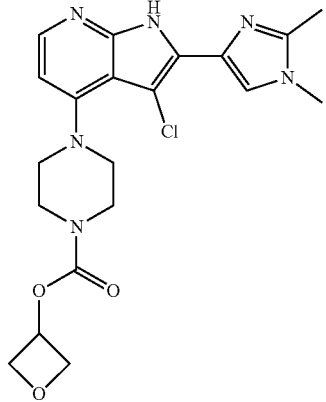 [SMILES: Cc1nc(-c2[nH]c3nccc(N4CCN(C(=O)OC5COC5)CC4)c3c2Cl)cn1C] | 431 | 1H-NMR (500 MHz, DMSO-d₆) δ ppm 11.93 (s, 1H), 8.01 (d, 1H, J = 5.5 Hz), 7.73 (s, 1H), 6.59 (d, 1H, J = 5.0 Hz), 5.35-5.30(m, 1H), 4.80-4.76 (m, 2H), 4.54-4.51 (m, 2H), 3.72-3.59(m, 4H), 3.65(s, 3H), 3.16-3.12(m, 4H), 2.37(s, 3H). |
| 332 | 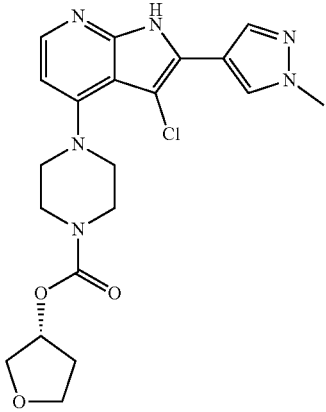 [SMILES: Cn1cc(-c2[nH]c3nccc(N4CCN(C(=O)O[C@@H]5CCOC5)CC4)c3c2Cl)cn1] | 431 | ¹H-NMR (500 MHz, 6d-DMSO) δ ppm 12.18 (s, 1H), 8.36 (s, 1H), 8.10 (s, 1H), 8.06 (d, 1H, J = 5.5 Hz), 6.62 (d, 1H, J = 5.5 Hz), 6.19-6.17 (m, 1H), 3.94 (s, 3H), ), 3.83-3.79 (m, 2H), ), 3.75-3.71 (m, 2H), 3.62-3.63 (m, 4H), 3.13-3.14 (m, 4H), 2.16-1.97 (m, 1H), 1.96-1.92 (m, 1H). |

TABLE 1-continued

| # | Structure | LCMS (M + 1) | ¹H NMR |
|---|---|---|---|
| 333 | 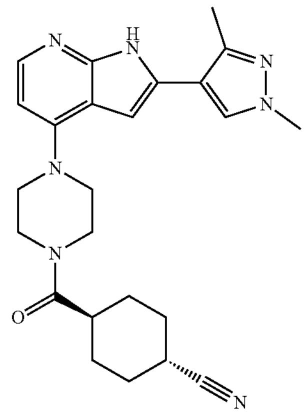 [SMILES: Cc1nn(C)cc1-c1cc2c(N3CCN(C(=O)[C@H]4CC[C@H](C#N)CC4)CC3)ccnc2[nH]1] | 432 | ¹H-NMR (400 MHz, 6d-DMSO) δ ppm 11.56 (s, 1H), 8.00 (s, 1H), 7.92 (d, 1H, J = 5.6 Hz), 6.43 (d, 1H, J = 5.6 Hz), 6.40 (d, 1H, J = 2.0 Hz), 3.80 (s, 3H), 3.74-3.72 (m, 2H), 3.67-3.65 (m, 2H), 3.42-3.40 (m, 2H), 2.72-2.70 (m, 2H), 2.52-2.50 (m, 2H), 2.46 (s, 3H), 2.05-2.03 (m, 2H), 1.73-1.71 (m, 2H), 1.60-1.57 (m, 2H), 1.42-1.39 (m, 2H). |
| 334 | 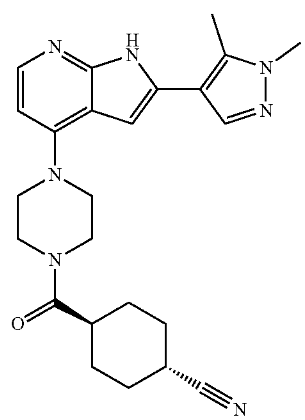 [SMILES: Cc1c(-c2cc3c(N4CCN(C(=O)[C@H]5CC[C@H](C#N)CC5)CC4)ccnc3[nH]2)cnn1C] | 432 | ¹H-NMR (500 MHz, 6d-DMSO) δ ppm 11.61 (s, 1H), 7.93 (d, 1H, J = 5.5 Hz), 7.79 (s, 1H), 6.43 (d, 1H, J = 5.5 Hz), 6.40 (d, 1H, J = 2.0 Hz), 3.80 (s, 3H), 3.74-3.72 (m, 2H), 3.67-3.65 (m, 2H), 3.42-3.40 (m, 2H), 3.40-3.30 (m, 2H), 2.72-2.70 (m, 2H), 2.46 (s, 3H), 2.05-2.03 (m, 2H), 1.73-1.71 (m, 2H), 1.60-1.57 (m, 2H), 1.42-1.39 (m, 2H). |
| 335 | 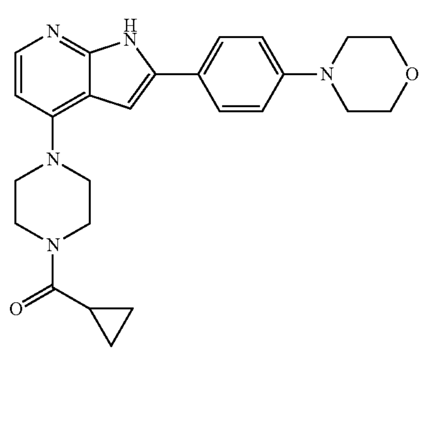 [SMILES: O=C(C1CC1)N1CCN(c2ccnc3[nH]c(-c4ccc(N5CCOCC5)cc4)cc23)CC1] | 432 | ¹H-NMR (400 MHz, DMSO-$d_6$) δ ppm 11.79 (s, 1H), 7.92 (d, 1H, J = 5.2 Hz), 7.83-7.80 (m, 2H), 7.01-6.99 (m, 2H), 6.87 (d, 1H, J = 1.6 Hz), 6.42 (d, 1H, J = 5.6 Hz), 3.92 (br. s., 2H), 3.76 (t, 4H, J = 4.4 Hz), 3.70 (br. s., 2H), 3.47 (br. s., 2H), 3.39 (br. s., 2H), 3.17 (t, 4H, J = 4.8 Hz), 2.06-1.99 (m, 1H), 0.80-0.72 (m, 4H). |

TABLE 1-continued

| # | Structure | LCMS (M + 1) | ¹H NMR |
|---|---|---|---|
| 336 | 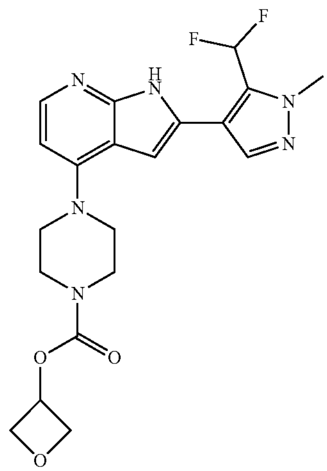 [SMILES: Cn1ncc(-c2cc3c(N4CCN(C(=O)OC5COC5)CC4)ccnc3[nH]2)c1C(F)F] | 433 | ¹H-NMR (400 MHz, 6d-DMSO) δ ppm 11.86 (br s, 1H), 7.98 (d, 1H, J = 5.6 Hz), 7.95 (s, 1H), 7.51 (t, 1H, J = 51.2 Hz), 6.56 (s, 1H), 6.47 (d, 1H, J = 5.6 Hz), 5.36-5.31 (m, 1H), 4.81-4.76 (m, 2H), 4.55-4.51 (m, 2H), 4.03 (s, 3H), 3.69-3.56 (m, 4H), 3.45-3.42 (m, 4H). |
| 337 | 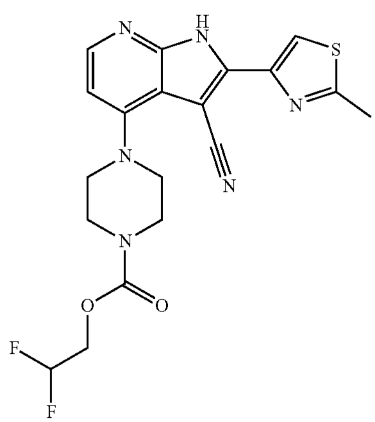 [SMILES: Cc1nc(-c2[nH]c3nccc(N4CCN(C(=O)OCC(F)F)CC4)c3c2C#N)cs1] | 433 | ¹H-NMR (400 MHz, 6d-DMSO) δ ppm 13.14 (s, 1H), 8.24-8.21 (m, 2H), 6.77 (d, 1H, J = 5.6 Hz), 6.43-6.14 (m, 1H), 4.39-4.31 (m, 2H), 3.69-3.68 (m, 4H), 3.23-3.22 (m, 4H), 2.77 (s, 3H). |
| 338 | 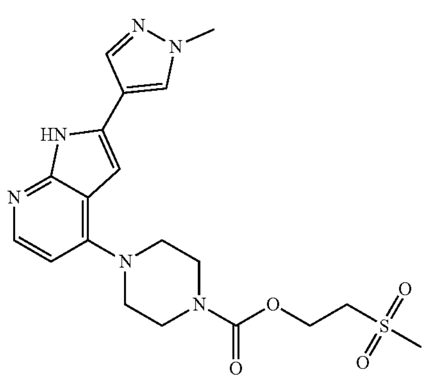 [SMILES: Cn1cc(-c2cc3c(N4CCN(C(=O)OCCS(C)(=O)=O)CC4)ccnc3[nH]2)cn1] | 433 | ¹H-NMR (400 MHz, 6d-DMSO) δ ppm 11.71 (s, 1H), 8.15 (s, 1H), 8.11 (s, 1H), 7.93 (s, 1H), 7.89 (d, 1H, J = 5.2 Hz), 6.65 (s, 1H), 6.41 (d, 1H, J = 5.2 Hz), 4.41 (t, 2H, J = 4.8 Hz), 3.87 (s, 3H), 3.66-3.56 (m, 4H), 3.52 (t, 2H, J = 4.8 Hz), 3.40-3.30 (m, 4H), 3.04 (s, 3H). |

TABLE 1-continued

| # | Structure | LCMS (M + 1) | ¹H NMR |
|---|---|---|---|
| 339 | 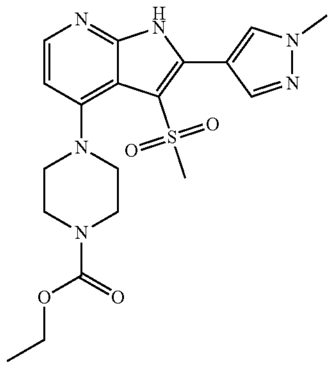 [SMILES: CCOC(=O)N1CCN(c2ccnc3[nH]c(-c4cnn(C)c4)c(S(C)(=O)=O)c23)CC1] | 433 | ¹H-NMR (500 MHz, 6d-DMSO) δ ppm 11.61 (s, 1H), 8.17 (s, 1H), 8.06 (s, 1H), 7.99 (d, 1H, J = 6.0 Hz), 6.92 (s, 1H), 6.46 (d, 1H, J = 5.5 Hz), 4.17 (s, 3H), 4.08 (q, 2H, J = 7.0 Hz), 3.60-3.57 (m, 4H), 3.46 (s, 3H), 3.34-3.32 (m, 4H), 1.21 (d, 1H, J = 7.0 Hz). |
| 340 | 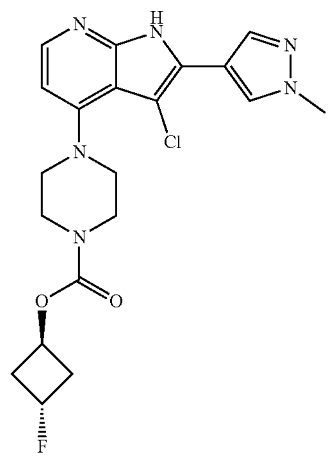 [SMILES: Cn1cc(-c2[nH]c3nccc(N4CCN(C(=O)O[C@H]5C[C@H](F)C5)CC4)c3c2Cl)cn1] | 433 | ¹H-NMR (400 MHz, 6d-DMSO) δ ppm 8.36 (s, 1H), 8.10 (s, 1H), 8.05 (d, 1H, J = 5.6 Hz), 6.61 (d, 1H, J = 5.2 Hz), 5.37-5.22 (m, 1H), 5.10-5.06 (m, 1H), 3.93 (s, 3H), 3.65-3.62 (m, 4H), 3.14-3.12 (m, 4H), 2.57-2.42 (m, 4H). |
| 341 | 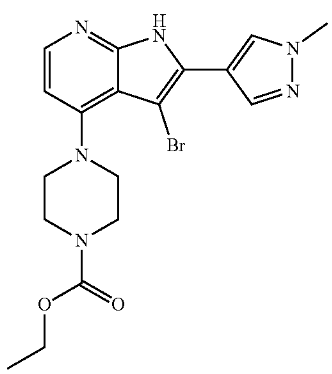 [SMILES: CCOC(=O)N1CCN(c2ccnc3[nH]c(-c4cnn(C)c4)c(Br)c23)CC1] | 434 | ¹H-NMR (500 MHz, 6d-DMSO) δ ppm 12.24 (s, 1H), 8.40 (s, 1H), 8.12 (s, 1H), 8.06 (d, 1H, J = 5.0 Hz), 6.65 (d, 1H, J = 5.0 Hz), 4.09-4.07 (m, 2H), 3.93 (s, 3H), 3.62-3.55 (m, 4H), 3.14-3.08 (m, 4H), 1.23-1.19 (m, 3H). |
| 342 | 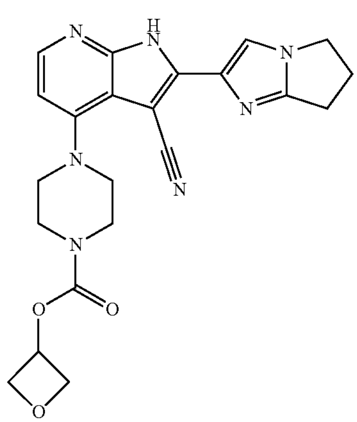 [SMILES: N#Cc1c(-c2cn3c(n2)CCC3)[nH]c2nccc(N3CCN(C(=O)OC4COC4)CC3)c12] | 434 | |

| # | Structure | LCMS (M + 1) | ¹H NMR |
|---|---|---|---|
| 343 | 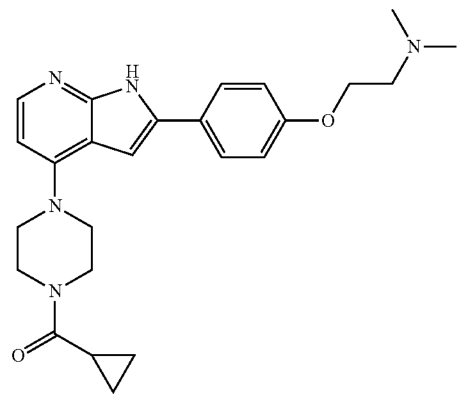 [SMILES: CN(C)CCOc1ccc(-c2cc3c(N4CCN(C(=O)C5CC5)CC4)ccnc3[nH]2)cc1] | 434 | 1H NMR (400 MHz, DMSO) δ 13.03 (s, 1H), 8.01 (d, J = 7.0 Hz, 1H), 7.91 (d, J = 8.9 Hz, 2H), 7.31 (s, 1H), 7.14 (d, J = 8.9 Hz, 2H), 6.73 (d, J = 7.1 Hz, 1H), 4.43-4.36 (m, 2H), 3.97 (d, J = 18.0 Hz, 6H), 3.76 (s, 2H), 3.55 (d, J = 3.1 Hz, 2H), 2.89 (s, 6H), 1.99 (ddd, J = 12.6, 7.4, 5.2 Hz, 1H), 0.79 (t, J = 5.7 Hz, 4H) |
| 344 | 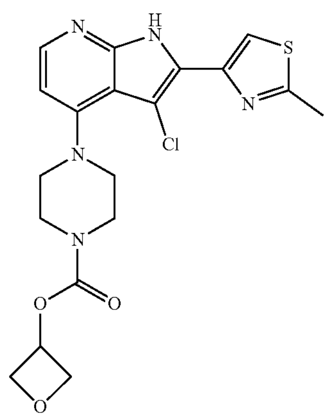 [SMILES: Cc1nc(-c2[nH]c3nccc(N4CCN(C(=O)OC5COC5)CC4)c3c2Cl)cs1] | 434 | ¹H-NMR (400 MHz, 6d-DMSO) δ ppm 12.29 (s, 1H), 8.13-8.09 (m, 2H), 6.64 (d, 1H, J = 5.2 Hz), 5.34-5.31 (m, 1H), 4.80-4.77 (m, 2H), 4.54-4.51 (m, 2H), 3.72-3.62 (m, 4H), 3.18-3.17 (m, 4H), 2.76 (s, 3H). |
| 345 | 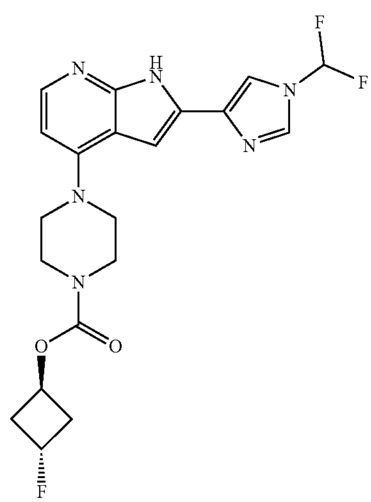 [SMILES: O=C(O[C@H]1C[C@H](F)C1)N1CCN(c2ccnc3[nH]c(-c4cn(C(F)F)cn4)cc23)CC1] | 435 | ¹H-NMR (400 MHz, 6d-DMSO) δ ppm 11.85 (s, 1H), 8.25 (d, 1H, J = 0.8 Hz), 7.99 (d, 1H, J = 1.2 Hz), 7.96 (d, 1H, J = 5.6 Hz), 7.88 (t, 1H, J = 60.0 Hz), 6.82 (d, 1H, J = 1.6 Hz), 6.44 (d, 1H, J = 5.2 Hz), 5.39-5.20 (m, 1H), 5.12-5.05 (m, 1H), 3.70-3.55 (m, 4H), 3.45-3.40 (m, 4H), 2.65-2.52 (m, 2H), 2.50-2.35 (m, 2H). |

TABLE 1-continued

| # | Structure | LCMS (M + 1) | ¹H NMR |
|---|---|---|---|
| 346 | 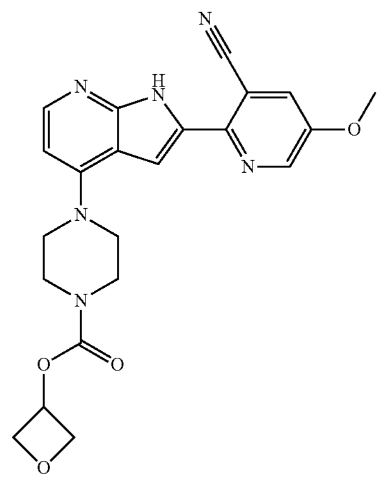 [SMILES: COc1cnc(-c2cc3c(N4CCN(C(=O)OC5COC5)CC4)ccnc3[nH]2)c(C#N)c1] | 435 | ¹H-NMR (400 MHz, 6d-DMSO) δ ppm 12.02 (s, 1H), 8.62 (d, 1H, J = 3.2 Hz), 8.06 (d, 1H, J = 3.2 Hz), 8.05 (d, 1H, J = 5.6 Hz), 7.38 (s, 3H), 6.49 (d, 1H, J = 5.2 Hz), 5.32-5.31 (m, 1H), 4.79-4.75 (m, 2H), 4.54-4.51 (m, 2H), 3.93 (s, 3H), 3.67-3.58 (m, 4H), 3.51-3.49 (m, 4H) |
| 347 | 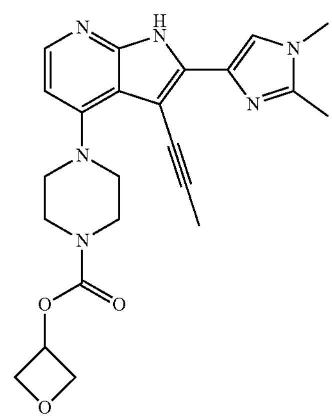 [SMILES: CC#Cc1c(-c2cn(C)c(C)n2)[nH]c2nccc(N3CCN(C(=O)OC4COC4)CC3)c12] | 435 | ¹H-NMR (400 MHz, 6d-DMSO) δ ppm 11.78 (s, 1H), 7.96 (d, 1H, J = 5.6 Hz), 7.78 (s, 1H), 5.53 (d, 1H, J = 5.6 Hz), 5.33 (s, 1H), 4.8-4.76 (m, 2H), 4.55-4.51 (m, 2H), 3.75-3.58 (m, 6H), 3.23-3.20 (m, 4H), 2.37 (s, 3H), 2.22 (s, 3H). |
| 348 | 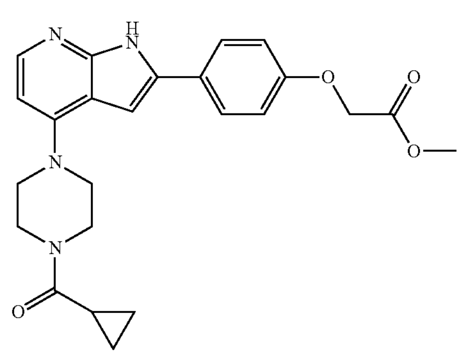 [SMILES: COC(=O)COc1ccc(-c2cc3c(N4CCN(C(=O)C5CC5)CC4)ccnc3[nH]2)cc1] | 435 | 1H NMR (400 MHz, DMSO) δ 13.17 (d, J = 10.0 Hz, 1H), 7.98-7.87 (m, 3H), 7.33 (d, J = 2.2 Hz, 1H), 7.09 (d, J = 9.0 Hz, 2H), 6.76 (d, J = 7.3 Hz, 1H), 4.90 (s, 1H), 4.77 (s, 1H), 4.03 (d, J = 22.4 Hz, 2H), 3.81 (s, 2H), 3.73 (s, 4H), 1.99 (s, 2H), 0.79 (dd, J = 9.4, 1.7 Hz, 4H). |

TABLE 1-continued

| # | Structure | LCMS (M + 1) | ¹H NMR |
|---|---|---|---|
| 349 | 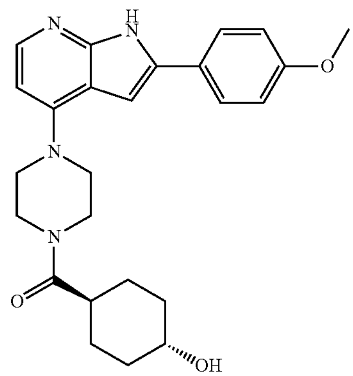 [SMILES: COc1ccc(-c2cc3c(N4CCN(C(=O)[C@H]5CC[C@H](O)CC5)CC4)ccnc3[nH]2)cc1] | 435 | ¹H-NMR (400 MHz, 6d-DMSO) δ ppm 11.83 (s, 1H), 7.93 (d, 1H, J = 5.6 Hz), 7.87 (d, 2H, J = 8.8 Hz), 6.99 (d, 2H, J = 8.8 Hz), 6.91 (s, 1H), 6.40 (d, 1H, J = 5.6 Hz), 4.56 (d, 1H, J = 4.4 Hz), 3.79 (s, 3H), 3.75-3.70 (m, 2H), 3.69-3.64 (m, 2H), 3.48-3.44 (m, 2H), 3.44-3.40 (m, 2H), 3.40-3.38 (m, 1H), 2.54-2.50 (m, 1H), 1.87-1.84 (m, 2H), 1.70-1.67 (m, 2H), 1.41-1.37 (m, 2H), 1.23-1.19 (m, 2H). |
| 350 | 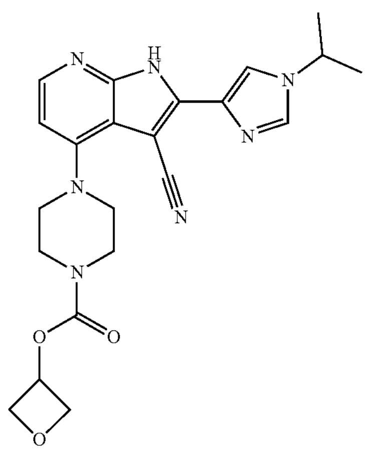 [SMILES: CC(C)n1cnc(-c2[nH]c3nccc(N4CCN(C(=O)OC5COC5)CC4)c3c2C#N)c1] | 436 | ¹H-NMR (400 MHz, 6d-DMSO) δ ppm 12.83 (br s, 1H), 8.15 (d, 1H, J = 5.2 Hz), 8.03 (s, 1H), 7.98 (s, 1H), 6.73 (d, 1H, J = 5.2 Hz), 5.36-5.31 (m, 1H), 4.81-4.76 (m, 2H), 4.60-4.51 (m, 3H), 3.78-3.61 (m, 4H), 3.25-3.15 (m, 4H), 1.48 (d, 6H, J = 6.8 Hz). |
| 351 | 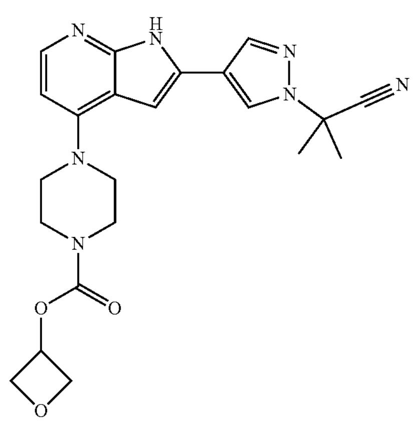 [SMILES: CC(C)(C#N)n1cc(-c2cc3c(N4CCN(C(=O)OC5COC5)CC4)ccnc3[nH]2)cn1] | 436 | ¹H-NMR (500 MHz, d₆-DMSO) δ ppm 11.78 (s, 1H), 8.54 (s, 1H), 8.17 (s, 1H), 7.94 (d, 1H, J = 5.5 Hz), 6.79 (d, 1H, J = 2.0 Hz), 6.44 (d, 1H, J = 5.5 Hz), 5.35-5.33 (m, 1H), 4.81-4.78 (m, 2H), 4.55-4.52 (m, 2H), 3.69-3.59 (m, 4H), 3.43-3.34 (m, 4H), 2.03 (s, 6H). |

TABLE 1-continued

| # | Structure | LCMS (M + 1) | ¹H NMR |
|---|---|---|---|
| 352 | 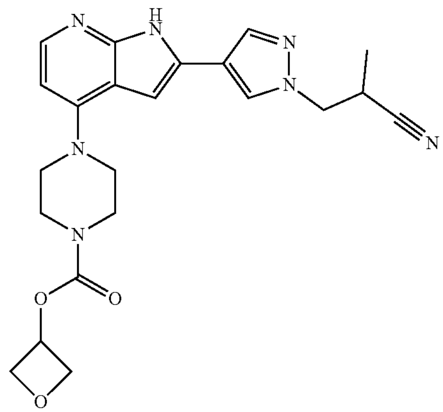 [SMILES: CC(C#N)Cn1cc(-c2cc3c(N4CCN(C(=O)OC5COC5)CC4)ccnc3[nH]2)cn1] | 436 | ¹H-NMR (500 MHz, CDCl₃) δ ppm 8.10 (d, 1H, J = 5.5 Hz), 7.96 (s, 1H), 7.92 (s, 1H), 6.53 (s, 1H), 6.48 (d, 1H, J = 6.0 Hz), 5.51-5.46 (m, 1H), 4.95 (t, 2H, J = 7.0 Hz), 4.72 (dd, 2H, J = 7.0, 5.5 Hz), 4.44-4.33 (m, 2H), 3.80-3.77 (m, 4H), 3.55-3.53 (m, 4H), 3.40-3.35 (m, 1H), 1.43 (d, 3H, J = 7.5 Hz). |
| 353 | 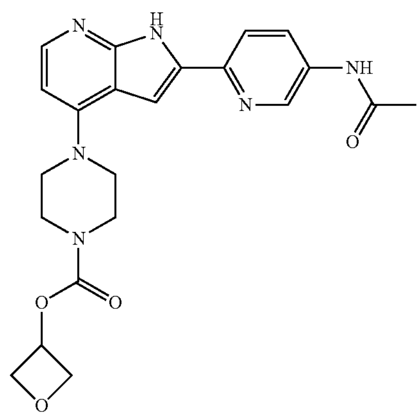 [SMILES: CC(=O)Nc1ccc(-c2cc3c(N4CCN(C(=O)OC5COC5)CC4)ccnc3[nH]2)nc1] | 437 | ¹H NMR (400 MHz, 6d-DMSO) δ ppm 11.92 (s, 1H), 10.27 (s, 1H), 8.75 (d, 1H, J = 2.0 Hz), 8.09 (d, 1H, J = 2.4 Hz), 8.00 (s, 1H), 7.98 (d, 1H, J = 2.4 Hz), 7.15 (d, 1H, J = 2.0 Hz), 6.46 (d, 1H, J = 5.6 Hz), 5.33 (quintet, 1H, J = 5.6 Hz), 4.79 (t, 2H, J = 7.2 Hz), 4.54 (dd, 2H, J = 7.2, 5.6 Hz), 3.70-3.60 (m, 2H), 3.60-3.52 (m, 2H), 3.50-3.43 (m, 4H), 2.08 (s, 3H). |
| 354 | 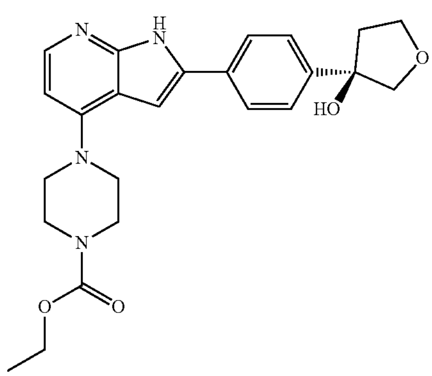 [SMILES: CCOC(=O)N1CCN(c2ccnc3[nH]c(-c4ccc([C@]5(O)CCOC5)cc4)cc23)CC1] | 437 | ¹H NMR (500 MHz, 6d-DMSO) δ ppm 11.93 (s, 1H), 7.97 (d, 1H, J = 5.5 Hz), 7.92 (d, 2H, J = 8.0 Hz), 7.54 (d, 2H, J = 8.0 Hz), 7.02 (d, 1H, J = 2.0 Hz), 6.44 (d, 1H, J = 5.0 Hz), 5.42 (s, 1H), 4.08 (q, 2H, J = 7.0 Hz), 4.03-4.00 (m, 2H), 3.82-3.80 (m, 1H), 3.78-3.75 (m, 1H), 3.62-3.58 (m, 4H), 3.48-3.43 (m, 4H), 2.31-2.25 (m, 1H), 2.16-2.12 (m, 1H), 1.22 (t, 3H, J = 7.0 Hz). |
| 355 | 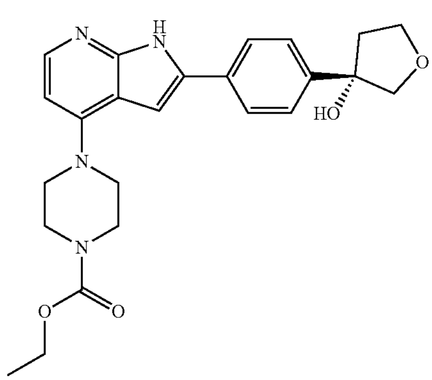 [SMILES: CCOC(=O)N1CCN(c2ccnc3[nH]c(-c4ccc([C@@]5(O)CCOC5)cc4)cc23)CC1] | 437 | ¹H NMR (500 MHz, 6d-DMSO) δ ppm 11.93 (s, 1H), 7.97 (d, 1H, J = 5.5 Hz), 7.92 (d, 2H, J = 8.0 Hz), 7.54 (d, 2H, J = 8.0 Hz), 7.02 (d, 1H, J = 2.0 Hz), 6.44 (d, 1H, J = 5.0 Hz), 5.42 (s, 1H), 4.08 (q, 2H, J = 7.0 Hz), 4.03-4.00 (m, 2H), 3.82-3.80 (m, 1H), 3.78-3.75 (m, 1H), 3.62-3.58 (m, 4H), 3.48-3.43 (m, 4H), 2.31-2.25 (m, 1H), 2.16-2.12 (m, 1H), 1.22 (t, 3H, J = 7.0 Hz). |

TABLE 1-continued
| # | Structure | LCMS (M + 1) | ¹H NMR |
|---|---|---|---|
| 356 | 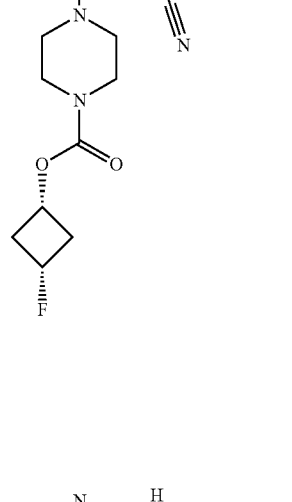 | 438 | 1H-NMR (500 MHz, DMSO-d₆) δ ppm 12.80 (br. s., 1H), 8.11 (d, 1H, J = 5.5 Hz), 7.82 (s, 1H), 6.71 (d, 1H, J = 6.0 Hz), 4.91-4.76 (m, 1H), 4.53-4.49 (m, 1H), 3.68 (s, 3H), 3.65-3.62 (m, 4H), 3.18-3.16 (m, 4H), 2.88-2.82 (m, 2H), 2.39 (s, 3H), 2.25-2.20 (m, 2H). |
| 357 | 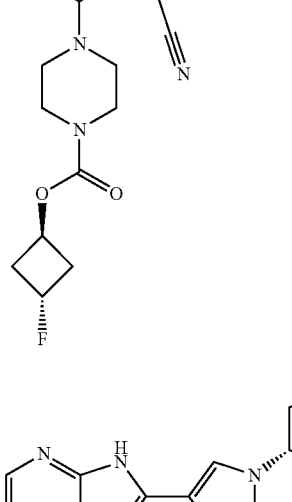 | 438 | 1H-NMR (500 MHz, DMSO-d₆) δ ppm 12.78 (br. s., 1H), 8.11 (d, 1H, J = 5.5 Hz.), 7.82 (s, 1H,), 6.71 (d, 1H, J = 5.5 Hz.), 5.36-5.22 (m, 1H), 5.10-5.06 (m, 1H), 3.68 (s, 3H), 3.67-3.60 (m, 4H), 3.18-3.14 (m, 4H), 2.58-2.53 (m, 2H), 2.47-2.40 (m, 2H), 2.39 (s, 3H). |
| 358 | 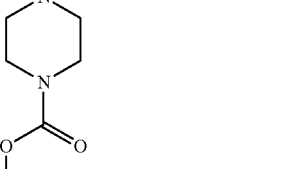 | 439 | ¹H-NMR (400 MHz, 6d-DMSO) δ ppm 11.64 (s, 1H), 7.91 (d, 1H, J = 5.2 Hz), 7.79 (s, 1H), 7.71 (s, 1H), 6.66 (s, 1H), 6.42 (d, 1H, J = 5.6 Hz), 5.38-5.27 (m, 1H), 5.05-4.93 (m, 1H), 4.85-4.73 (m, 2H), 4.58-4.47 (m, 2H), 4.11-4.03 (m, 1H), 3.95-3.85 (m, 3H), 3.80-3.58 (m, 4H), 3.45-3.37 (m, 4H), 2.49-2.45 (m, 1H), 2.15-2.03 (m, 1H). |

TABLE 1-continued
| # | Structure | LCMS (M + 1) | ¹H NMR |
|---|-----------|--------------|--------|
| 359 | 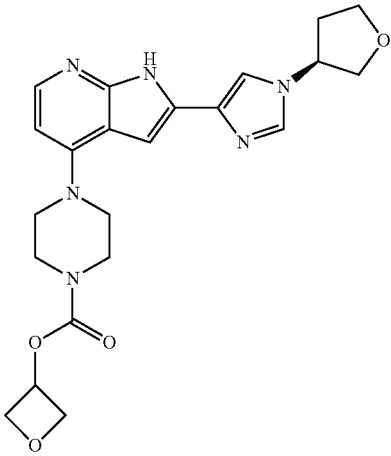 [SMILES: O=C(OC1COC1)N1CCN(c2ccnc3[nH]c(-c4cn([C@H]5CCOC5)cn4)cc23)CC1] | 439 | ¹H-NMR (400 MHz, 6d-DMSO) δ ppm 11.64 (s, 1H), 7.91 (d, 1H, J = 5.2 Hz), 7.79 (s, 1H), 7.71 (s, 1H), 6.66 (s, 1H), 6.43 (d, 1H, J = 5.6 Hz), 5.38-5.28 (m, 1H), 5.06-4.94 (m, 1H), 4.87-4.72 (m, 2H), 4.56-4.50 (m, 2H), 4.11-4.03 (m, 1H), 3.95-3.85 (m, 3H), 3.80-3.58 (m, 4H), 3.45-3.37 (m, 4H), 2.49-2.45 (m, 1H), 2.14-2.03 (m, 1H). |
| 360 | 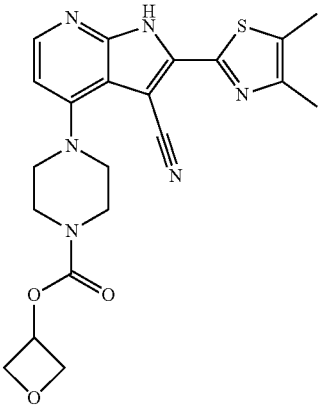 [SMILES: Cc1nc(-c2[nH]c3nccc(N4CCN(C(=O)OC5COC5)CC4)c3c2C#N)sc1C] | 439 | ¹H-NMR (400 MHz, 6d-DMSO) δ ppm 13.48 (br. s., 1H), 8.24 (d, 1H, J = 5.2 Hz), 6.78 (d, 1H, J = 5.2 Hz), 5.34 (quintet, 1H, J = 5.2 Hz), 4.79 (t, 2H, J = 6.8 Hz), 4.53 (dd, 2H, J = 7.6, 5.2 Hz), 3.74-3.72 (m, 2H), 3.66-3.62 (m, 2H), 3.28-3.22 (m, 4H), 2.48 (s, 3H), 2.39 (s, 3H). |
| 361 | 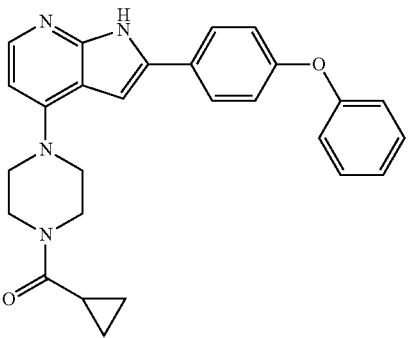 [SMILES: O=C(C1CC1)N1CCN(c2ccnc3[nH]c(-c4ccc(Oc5ccccc5)cc4)cc23)CC1] | 439 | 1H NMR (400 MHz, DMSO) δ 13.09 (s, 1H), 8.02 (d, J = 7.2 Hz, 3H), 7.95 (d, J = 8.8 Hz, 2H), 7.48-7.37 (m, 3H), 7.23-7.14 (m, 3H), 7.09 (dd, J = 8.6, 1.0 Hz, 2H), 6.76 (d, J = 7.3 Hz, 1H), 4.04 (d, J = 22.3 Hz, 51H), 2.03-1.93 (m, 1H), 0.79 (t, J = 5.6 Hz, 4H). |
| 362 | 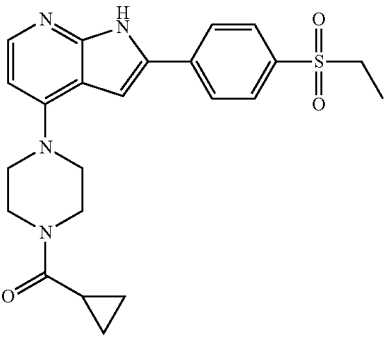 [SMILES: CCS(=O)(=O)c1ccc(-c2cc3c(N4CCN(C(=O)C5CC5)CC4)ccnc3[nH]2)cc1] | 439 | 1H NMR (400 MHz, DMSO) δ 13.26 (s, 1H), 8.21 (d, J = 8.6 Hz, 2H), 8.07 (d, J = 7.1 Hz, 1H), 8.01 (d, J = 8.6 Hz, 2H), 7.68 (s, 1H), 6.76 (d, J = 7.2 Hz, 1H), 4.04 (d, J = 17.0 Hz, 6H), 3.78 (s, 3H), 3.39-3.34 (m, 3H), 2.00 (s, 1H), 1.14 (t, J = 7.3 Hz, 3H), 0.83-0.76 (m, 4H). |

TABLE 1-continued

| # | Structure | LCMS (M + 1) | ¹H NMR |
|---|---|---|---|
| 363 | 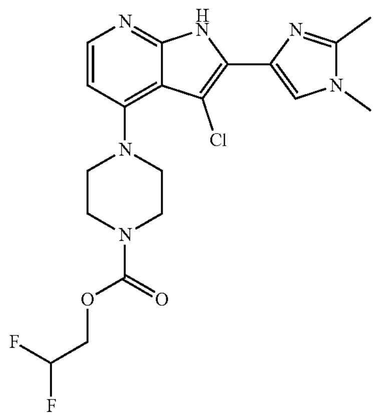 [SMILES: Cc1nc(-c2[nH]c3nccc(N4CCN(C(=O)OCC(F)F)CC4)c3c2Cl)cn1C] | 439 | 1H-NMR (500 MHz, DMSO-d$_6$) δ ppm 11.93 (br. s., 1H), 8.01 (d, 1H, J = 5.0 Hz), 7.73 (s, 1H), 6.59 (d, 1H, J = 5.5 Hz), 6.38-6.17(m, 1H), 4.39-4.31(m, 2H), 3.68-3.63 (m, 4H), 3.65(s, 3H), 3.16-3.13(m, 4H), 2.37(s, 3H). |
| 364 | 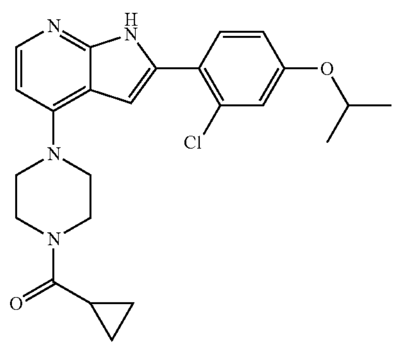 [SMILES: CC(C)Oc1ccc(-c2cc3c(N4CCN(C(=O)C5CC5)CC4)ccnc3[nH]2)c(Cl)c1] | 439 | 1H NMR (400 MHz, DMSO) δ 12.76 (s, 1H), 8.02 (s, 1H), 7.60 (d, J = 8.6 Hz, 1H), 7.21 (d, J = 2.5 Hz, 1H), 7.15-7.05 (m, 2H), 6.78-6.73 (m, 1H), 4.82-4.73 (m, 1H), 4.02 (d, J = 18.1 Hz, 6H), 3.75 (s, 20H), 1.98 (t, J = 5.1 Hz, 1H), 1.31 (d, J = 6.0 Hz, 6H), 0.81-0.75 (m, 4H). |
| 365 | 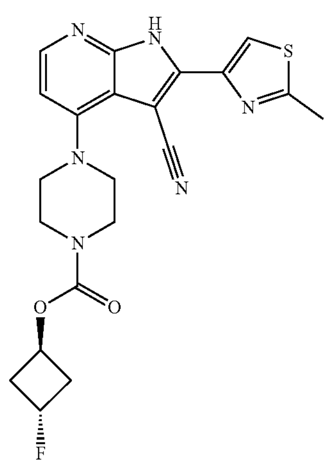 [SMILES: Cc1nc(-c2[nH]c3nccc(N4CCN(C(=O)O[C@H]5C[C@H](F)C5)CC4)c3c2C#N)cs1] | 441 | ¹H-NMR (400 MHz, 6d-DMSO) δ ppm 8.19-8.17 (m, 2H), 6.71 (d, 1H, J = 5.2 Hz), 5.39-5.21 (m, 1H), 5.11-5.06 (m, 1H), 3.66-3.64 (m, 4H), 3.20-3.18 (m, 4H), 2.76 (s, 3H), 2.61-2.53 (m, 2H), 2.49-2.41 (m, 4H). |

TABLE 1-continued

| # | Structure | LCMS (M + 1) | ¹H NMR |
|---|---|---|---|
| 366 | 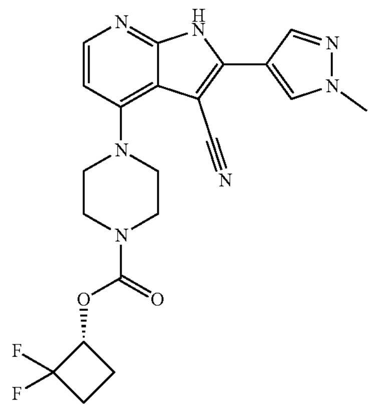 [SMILES: Cn1cc(-c2[nH]c3nccc(N4CCN(C(=O)O[C@@H]5CCC5(F)F)CC4)c3c2C#N)cn1] | 442 | ¹H-NMR (500 MHz, 6d-DMSO) δ ppm 12.94 (s, 1H), 8.40 (s, 1H), 8.17 (s, 1H), 8.15 (d, 1H, J = 5.5 Hz), 6.73 (d, 1H, J = 5.5 Hz), 5.25-5.20 (m, 1H), 3.97 (s, 3H), 3.69-3.60 (m, 4H), 3.25-3.15 (m, 4H), 2.50-2.20 (m, 3H), 1.85-1.80 (m, 1H). |
| 367 | 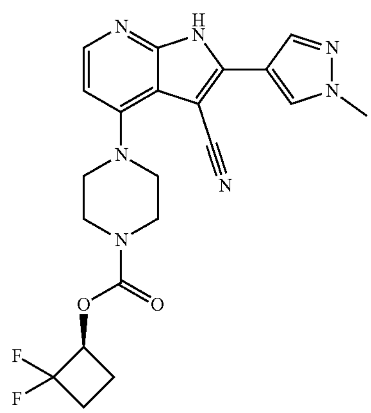 | 442 | ¹H-NMR (500 MHz, 6d-DMSO) δ ppm 12.95 (s, 1H), 8.40 (s, 1H), 8.16 (s, 1H), 8.15 (d, 1H, J = 5.5 Hz), 6.73 (d, 1H, J = 5.5 Hz), 5.25-5.20 (m, 1H), 3.97 (s, 3H), 3.69-3.60 (m, 4H), 3.25-3.15 (m, 4H), 2.50-2.20 (m, 3H), 1.85-1.80 (m, 1H). |
| 368 | 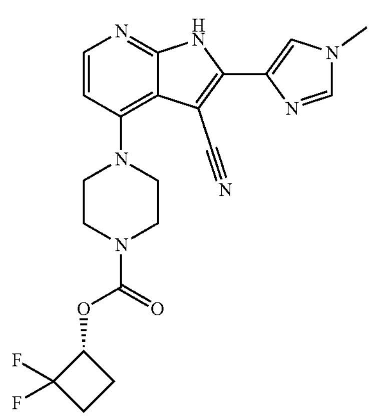 [SMILES: Cn1cnc(-c2[nH]c3nccc(N4CCN(C(=O)O[C@@H]5CCC5(F)F)CC4)c3c2C#N)c1] | 442 | ¹H-NMR (400 MHz, 6d-DMSO) δ ppm 12.85 (s, 1H), 8.14 (d, 1H, J = 5.2 Hz), 7.88 (s, 1H), 7.87(s, 1H), 6.73 (d, 1H, J = 5.6 Hz), 5.25-5.20 (m, 1H), 3.79 (s, 3H), 3.69-3.60 (m, 4H), 3.25-3.15 (m, 4H), 2.50-2.20 (m, 3H), 1.85-1.80 (m, 1H). |

TABLE 1-continued

| # | Structure | LCMS (M + 1) | ¹H NMR |
|---|---|---|---|
| 369 | 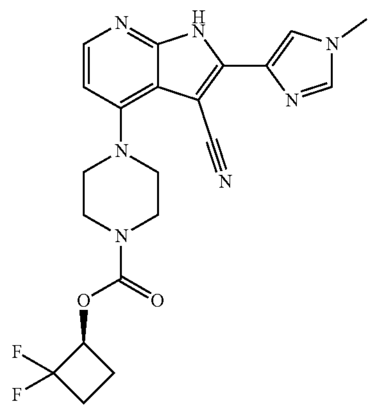 [SMILES: Cn1cnc(-c2[nH]c3nccc(N4CCN(C(=O)O[C@H]5CCC5(F)F)CC4)c3c2C#N)c1] | 442 | ¹H-NMR (500 MHz, 6d-DMSO) δ ppm 12.85 (s, 1H), 8.15 (d, 1H, J = 5.5 Hz), 7.88 (s, 1H), 7.87(s, 1H), 6.73 (d, 1H, J = 5.5 Hz), 5.25-5.20 (m, 1H), 3.79 (s, 3H), 3.69-3.60 (m, 4H), 3.25-3.15 (m, 4H), 2.50-2.20 (m, 3H), 1.85-1.80 (m, 1H). |
| 370 | 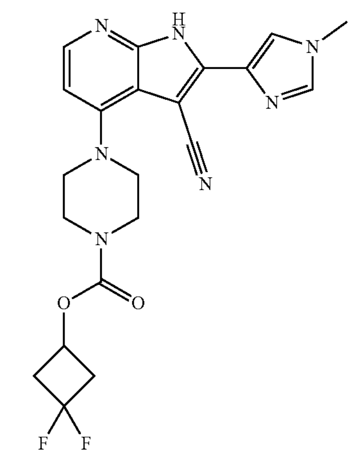 [SMILES: Cn1cnc(-c2[nH]c3nccc(N4CCN(C(=O)OC5CC(F)(F)C5)CC4)c3c2C#N)c1] | 442 | ¹H-NMR (400 MHz, 6d-DMSO) δ ppm 12.85 (br. s., 1H), 8.14 (d, 1H, J = 5.2 Hz), 7.88 (s, 1H), 7.87 (s, 1H), 6.73 (d, 1H, J = 5.2 Hz), 4.88-4.82 (m, 1H), 3.79 (s, 3H), 3.70-3.60 (m, 4H), 3.25-3.15 (m, 4H), 3.10-3.00 (m, 2H), 2.80-2.68 (m, 2H). |
| 371 | 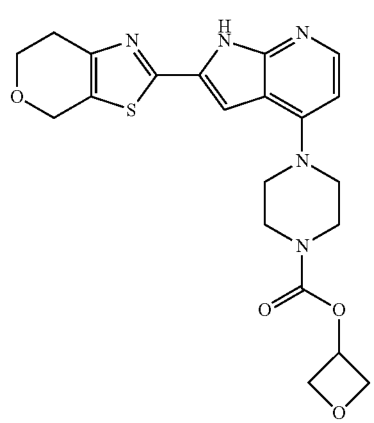 [SMILES: O=C(OC1COC1)N1CCN(c2ccnc3[nH]c(-c4nc5c(s4)COCC5)cc23)CC1] | 442 | ¹H-NMR (500 MHz, d₆-DMSO) δ ppm 12.31 (s, 1H), 8.03 (d, 1H, J = 5.6 Hz), 7.10 (d, 1H, J = 5.0 Hz), 6.47 (d, 1H, J = 5.2 Hz), 5.35-5.32 (m, 1H), 4.85-4.81 (m, 2H), 4.79-4.78 (m, 2H), 4.55-4.52 (m, 2H), 4.0-3.98 (m, 2H), 3.71-3.59 (m, 4H), 3.48-3.47 (m, 4H), 2.89-2.88 (m, 2H). |

TABLE 1-continued

| # | Structure | LCMS (M + 1) | ¹H NMR |
|---|---|---|---|
| 372 | 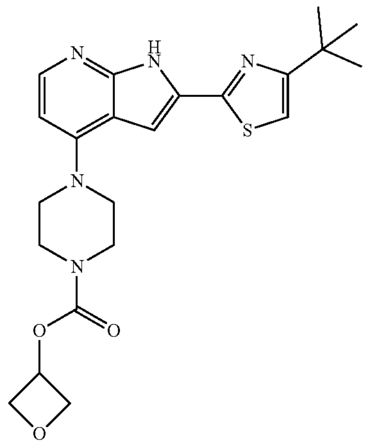 [SMILES: CC(C)(C)c1csc(-c2cc3c(N4CCN(C(=O)OC5COC5)CC4)ccnc3[nH]2)n1] | 442 | ¹H-NMR (400 MHz, 6d-DMSO) δ ppm 12.22-12.19 (m, 1H), 8.15 (s, 1H), 8.02 (d, 1H, J = 5.6 Hz), 7.42 (s, 1H), 7.08 (s, 1H), 6.47 (d, 1H, J = 5.6 Hz), 5.53-5.31 (m, 1H), 4.80-4.76 (m, 2H), 4.54-4.51 (m, 2H), 3.71-3.70 (m, 2H), 3.68-3.64 (m, 2H), 3.61-3.52 (m, 4H), 1.34 (s, 9H). |
| 373 | 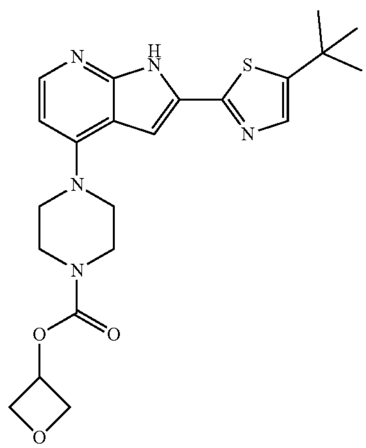 [SMILES: CC(C)(C)c1cnc(-c2cc3c(N4CCN(C(=O)OC5COC5)CC4)ccnc3[nH]2)s1] | 442 | ¹H-NMR (400 MHz, 6d-DMSO) δ ppm 12.17-12.15 (m, 1H), 8.20 (s, 1H), 8.03 (d, 1H, J = 5.2 Hz), 7.78 (s, 1H), 7.05 (s, 1H), 6.47 (d, 1H, J = 5.2 Hz), 5.36-5.30 (m, 1H), 4.80-4.76 (m, 2H), 4.56-4.51 (m, 2H), 3.71-3.68 (m, 2H), 3.64-3.62 (m, 2H), 3.61-3.52 (m, 4H), 1.34 (s, 9H). |
| 374 | 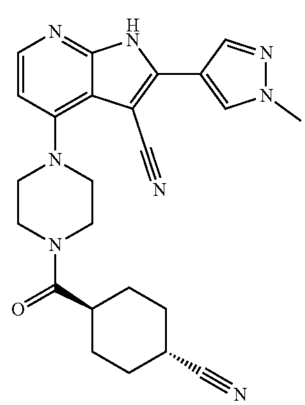 [SMILES: Cn1cc(-c2[nH]c3nccc(N4CCN(C(=O)[C@H]5CC[C@H](C#N)CC5)CC4)c3c2C#N)cn1] | 443 | ¹H-NMR (400 MHz, 6d-DMSO) δ ppm 12.90 (s, 1H), 8.40 (s, 1H), 8.17-8.15 (m, 2H), 6.74 (d, 1H, J = 5.2 Hz), 3.97 (s, 3H), 3.77-3.71 (m, 4H), 3.32-3.14 (m, 4H), 2.75-2.67 (m, 2H), 2.06-2.01 (m, 2H), 1.74-1.55 (m, 6H). |

| # | Structure | LCMS (M + 1) | ¹H NMR |
|---|---|---|---|
| 375 | 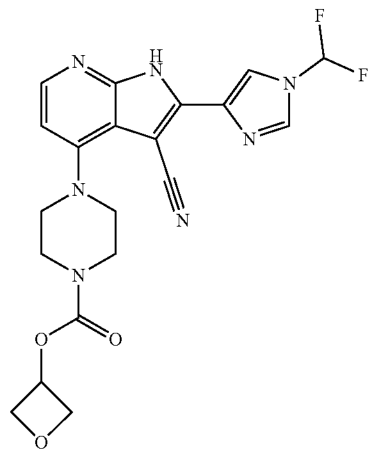 [SMILES: N#Cc1c(-c2cn(C(F)F)cn2)[nH]c2nccc(N3CCN(C(=O)OC4COC4)CC3)c12] | 444 | ¹H-NMR (400 MHz, 6d-DMSO) δ ppm 13.10 (s, 1H), 8.48 (s, 1H), 8.26 (s, 1H), 8.20 (d, 1H, J = 5.6 Hz), 7.98 (t, 1H, J = 60.0 Hz), 6.77 (d, 1H, J = 4.8 Hz), 5.36-5.31 (m, 1H), 4.81-4.76 (m, 2H), 4.57-4.52 (m, 2H), 3.80-3.60 (m, 4H), 3.30-3.20 (m, 4H). |
| 376 | 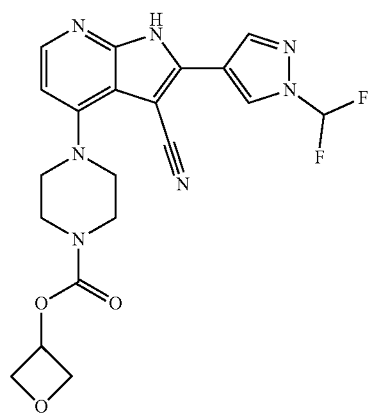 [SMILES: N#Cc1c(-c2cnn(C(F)F)c2)[nH]c2nccc(N3CCN(C(=O)OC4COC4)CC3)c12] | 444 | ¹H-NMR (400 MHz, 6d-DMSO) δ ppm 13.15 (s, 1H), 8.89 (s, 1H), 8.48 (s, 1H), 8.21 (d, 1H, J = 5.2 Hz), 8.18-7.88 (m, 1H), 6.77 (d, 1H, J = 5.2 Hz), 5.36-5.29 (m, 1H), 4.81-4.76 (m, 2H), 4.56-4.52 (m, 2H), 3.76-3.63 (m, 4H), 3.29-3.19 (m, 4H). |
| 377 | 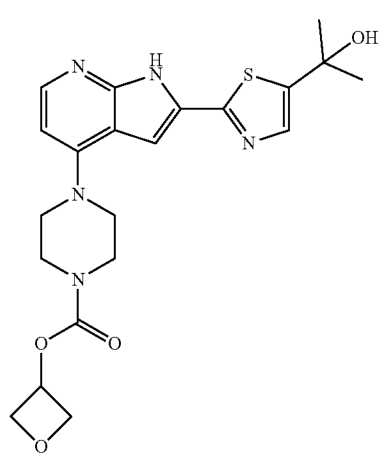 [SMILES: CC(C)(O)c1cnc(-c2cc3c(N4CCN(C(=O)OC5COC5)CC4)ccnc3[nH]2)s1] | 444 | ¹H-NMR (400 MHz, 6d-DMSO) δ ppm 12.23 (br s, 1H), 8.02 (d, 1H, J = 5.6 Hz), 7.65 (s, 1H), 7.10 (s, 1H), 6.47 (d, 1H, J = 5.6 Hz), 5.72 (s, 1H), 5.36-5.31 (m, 1H), 4.82-4.75 (m, 2H), 4.55-4.51 (m, 2H), 3.75-3.51 (m, 4H), 3.50-3.41 (m, 4H), 1.57 (s, 1H). |

TABLE 1-continued
| # | Structure | LCMS (M + 1) | ¹H NMR |
|---|---|---|---|
| 378 | 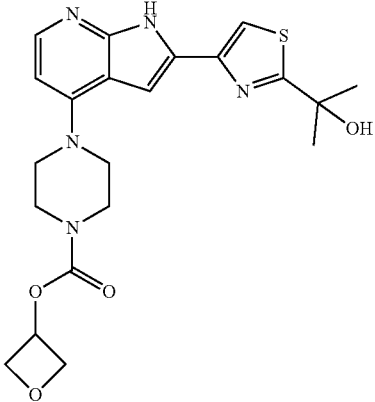 [SMILES: CC(C)(O)c1nc(-c2cc3c(N4CCN(C(=O)OC5COC5)CC4)ccnc3[nH]2)cs1] | 444 | ¹H-NMR (400 MHz, 6d-DMSO) δ ppm 11.95 (s, 1H), 7.97 (d, 1H, J = 5.6 Hz), 7.88 (s, 1H), 6.84 (d, 1H, J = 1.6 Hz), 6.44 (d, 1H, J = 5.2 Hz), 6.04 (s, 1H), 5.36-5.29 (m, 1H), 4.79-4.76 (m, 2H), 4.53-4.50 (m, 2H), 3.68-3.58 (m, 4H), 3.45-3.42 (m, 4H), 1.57 (s, 6H). |
| 379 | 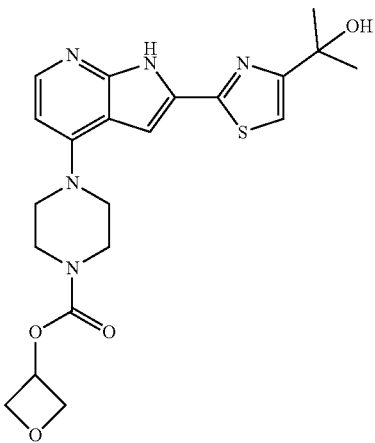 [SMILES: CC(C)(O)c1csc(-c2cc3c(N4CCN(C(=O)OC5COC5)CC4)ccnc3[nH]2)n1] | 444 | ¹H-NMR (400 MHz, 6d-DMSO) δ ppm 12.20 (s, 1H), 8.06 (d, 1H, J = 5.6 Hz), 7.38 (s, 1H), 7.09 (s, 1H), 6.48 (d, 1H, J = 5.6 Hz), 5.34 (quintet, 1H, J = 5.2 Hz), 5.18 (s, 1H), 4.79 (t, 2H, J = 7.2 Hz), 4.53 (dd, 2H, J = 7.6, 5.2 Hz), 3.68-3.64 (m, 2H), 3.60-3.58 (m, 2H), 3.48-3.44 (m, 4H), 1.53 (s, 6H). |
| 380 | 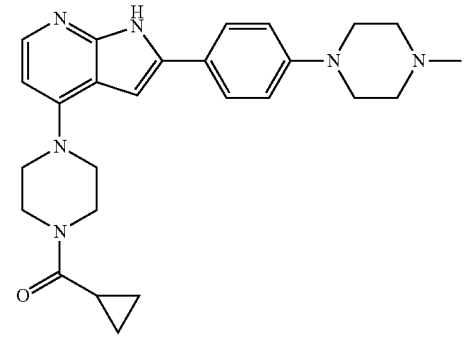 [SMILES: CN1CCN(c2ccc(-c3cc4c(N5CCN(C(=O)C6CC6)CC5)ccnc4[nH]3)cc2)CC1] | 445 | ¹H NMR (400 MHz, DMSO-d₆) δ ppm 11.77 (s, 1H), 7.93 (d, 1H, J = 5.6 Hz), 7.78 (d, 2H, J = 8.4 Hz), 6.98 (d, 2H, J = 8.8 Hz), 6.85 (s, 1H), 6.42 (d, 1H, J = 5.6 Hz), 3.91 (br. s., 2H), 3.70 (br. s., 2H), 3.46 (br. s., 2H), 3.39 (br. s., 2H), 3.21-3.19 (m, 4H), 2.50-2.44 (m, 4H), 2.30 (s, 3H), 2.06-2.00 (m, 1H), 0.78-0.74 (m, 4H). |
| 381 | 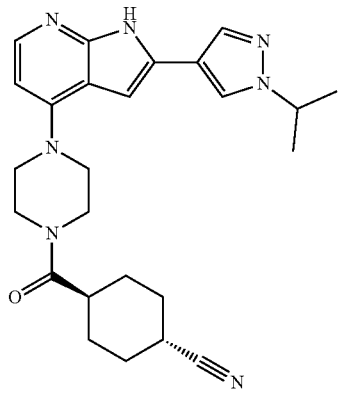 [SMILES: CC(C)n1cc(-c2cc3c(N4CCN(C(=O)[C@H]5CC[C@H](C#N)CC5)CC4)ccnc3[nH]2)cn1] | 446 | ¹H-NMR (500 MHz, 6d-DMSO) δ ppm 11.80-11.70 (br., 1H), 8.24 (s, 1H), 7.92 (s, 1H), 7.90 (d, 1H, J = 5.5 Hz), 6.66 (s, 1H), 6.41 (d, 1H, J = 5.5 Hz), 4.52-4.49 (m, 1H), 3.73-3.68 (m, 2H), 3.68-3.64 (m, 2H), 3.39-3.33 (m, 4H), 2.73-2.69 (m, 2H), 2.06-2.03 (m, 2H), 1.74-1.72 (m, 2H), 1.61-1.57 (m, 2H), 1.46-1.42 (m, 6H), 1.41-1.22 (m, 2H). |

TABLE 1-continued

| # | Structure | LCMS (M + 1) | ¹H NMR |
|---|---|---|---|
| 382 | 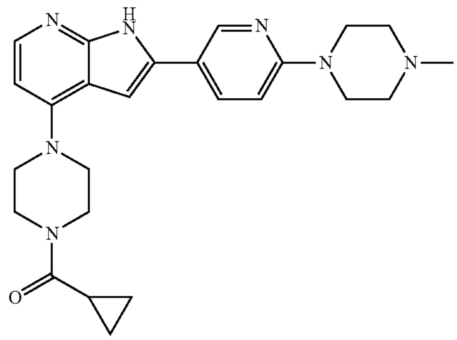 | 446 | ¹H-NMR (400 MHz, DMSO-d$_6$) δ ppm 11.88 (s, 1H), 8.72 (s, 1H), 8.14-8.09 (m, 2H), 7.94 (d, 1H, J = 5.2 Hz), 6.98-6.94 (m, 2H), 6.43 (d, 1H, J = 5.2 Hz), 3.91 (br. s., 2H), 3.69-3.63 (m, 6H), 3.55-3.40 (m, 4H), 2.68 (br. s., 4H), 2.41 (s, 3H), 2.05-1.99 (m, 1H), 0.78-0.72 (m, 4H). |
| 383 | 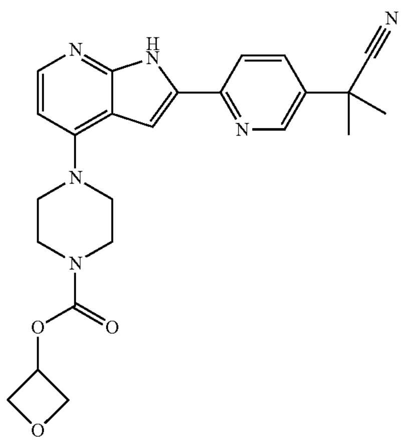 [SMILES: CC(C)(C#N)c1ccc(-c2cc3c(N4CCN(C(=O)OC5COC5)CC4)ccnc3[nH]2)nc1] | 447 | ¹H-NMR (500 MHz, 6d-DMSO) δ ppm 12.08 (s, 1H), 8.76 (d, 1H, J = 2.0 Hz), 8.12 (d, 1H, J = 8.5 Hz), 8.04-8.00 (m, 2H), 7.31 (s, 1H), 6.48 (d, 1H, J = 6.0 Hz), 5.34 (quintet, 1H, J = 6.0 Hz), 4.79 (t, 2H, J = 7.0 Hz), 4.53 (dd, 2H, J = 8.0, 5.5 Hz), 3.71-3.69 (m, 2H), 3.61-3.59 (m, 2H), 3.50-3.48 (m, 4H), 1.77 (s, 6H). |
| 384 | 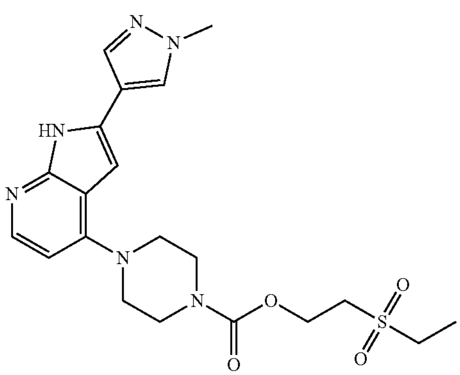 [SMILES: CCS(=O)(=O)CCOC(=O)N1CCN(c2ccnc3[nH]c(-c4cnn(C)c4)cc23)CC1] | 447 | ¹H-NMR (400 MHz, 6d-DMSO) δ ppm 11.73 (s, 1H), 8.13 (s, 1H), 7.95 (s, 1H), 7.91 (d, 1H, J = 5.6 Hz), 6.67 (s, 1H), 6.42 (d, 1H, J = 5.6 Hz), 4.42 (t, 2H, J = 5.6 Hz), 3.88 (s, 3H), 3.66-3.56 (m, 4H), 3.51 (t, 2H, J = 5.6 Hz), 3.42-3.30 (m, 4H), 3.14 (q, 2H, J = 7.2 Hz), 1.25 (t, 3H, J = 7.2 Hz). |
| 385 | 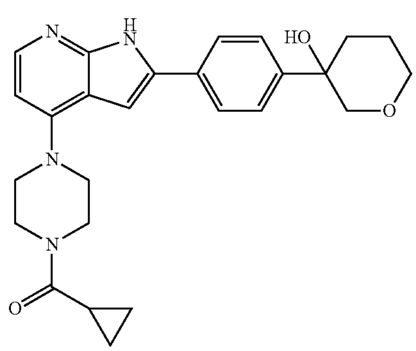 [SMILES: O=C(C1CC1)N1CCN(c2ccnc3[nH]c(-c4ccc(C5(O)CCCOC5)cc4)cc23)CC1] | 447 | ¹H-NMR (400 MHz, 6d-DMSO) δ ppm 11.93 (s, 1H), 7.96 (d, 1H, J = 5.2 Hz), 7.89 (d, 1H, J = 8.4 Hz), 7.57 (d, 2H, J = 8.4 Hz), 7.03 (s, 1H), 6.43 (d, 1H, J = 5.2 Hz), 5.14 (s, 1H), 3.92-3.80 (m, 2H), 3.78-3.70 (m, 1H), 3.70-3.66 (m, 1H), 3.65-3.60 (m, 1H), 3.52-3.35 (m, 5H), 2.07-1.99 (m, 2H), 1.94-1.87 (m, 1H), 1.74-1.71 (m, 1H), 1.42-1.38 (m, 1H), 1.24-1.22 (m, 2H), 0.77-0.73 (m, 4H). |

TABLE 1-continued

| # | Structure | LCMS (M + 1) | ¹H NMR |
|---|---|---|---|
| 386 | 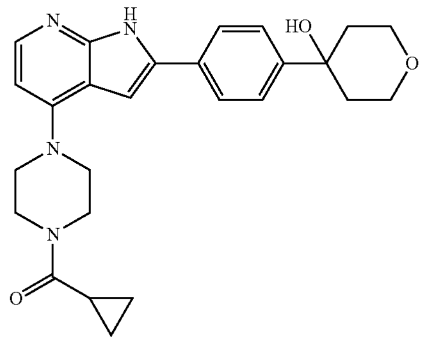 [SMILES: O=C(C1CC1)N1CCN(c2ccnc3[nH]c(-c4ccc(C5(O)CCOCC5)cc4)cc23)CC1] | 447 | ¹H-NMR (400 MHz, 6d-DMSO) δ ppm 11.94 (s, 1H), 7.97 (d, 1H, J = 5.6 Hz), 7.91 (d, 2H, J = 8.8 Hz), 7.54 (d, 2H, J = 8.8 Hz), 7.04 (d, 1H, J = 2.0 Hz), 6.44 (d, 1H, J = 5.6 Hz), 5.10 (s, 1H), 3.95-3.90 (m, 2H), 3.83-3.71 (m, 6H), 3.50-3.45 (m, 2H), 3.44-3.40 (m, 2H), 2.05-1.98 (m, 3H), 1.56 (d, 2H, J = 12.4 Hz), 0.79-0.74 (m, 4H). |
| 387 | 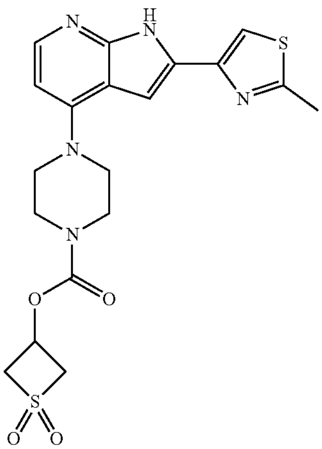 [SMILES: Cc1nc(-c2cc3c(N4CCN(C(=O)OC5CS(=O)(=O)C5)CC4)ccnc3[nH]2)cs1] | 448 | ¹H-NMR (400 MHz, 6d-DMSO) δ ppm 11.99 (s, 1H), 7.98 (d, 1H, J = 5.6 Hz), 7.86 (s, 1H), 6.89 (s, 1H), 6.45 (d, 1H, J = 6.0 Hz), 5.24-5.21 (m, 1H), 4.71-4.65 (m, 2H), 4.29-4.24 (m, 2H), 3.67-3.61 (m, 4H), 3.45-3.44 (m, 4H), 2.72 (s, 3H). |
| 388 | 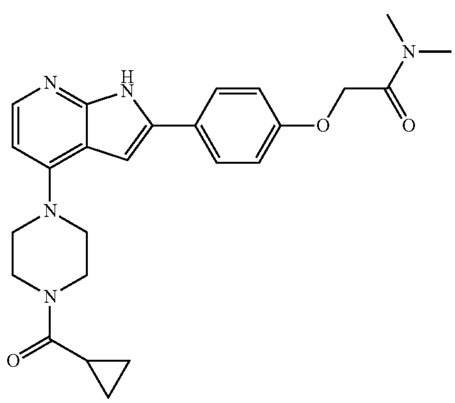 [SMILES: CN(C)C(=O)COc1ccc(-c2cc3c(N4CCN(C(=O)C5CC5)CC4)ccnc3[nH]2)cc1] | 448 | ¹H-NMR (400 MHz, 6d-DMSO) δ ppm 11.84 (s, 1H), 7.94 (d, 1H, J = 5.2 Hz), 7.84 (d, 2H, J = 8.8 Hz), 6.98 (d, 2H, J = 8.8 Hz), 6.91 (d, 1H, J = 1.6 Hz), 6.42 (d, 1H, J = 5.2 Hz), 4.85 (s, 2H), 3.95-3.85 (m, 2H), 3.75-3.65 (m, 2H), 3.50-3.45 (m, 2H), 3.44-3.40 (m, 2H), 3.01 (s, 3H), 2.85 (s, 3H), 2.04-2.00 (m, 1H), 0.78-0.72 (m, 4H). |
| 389 | 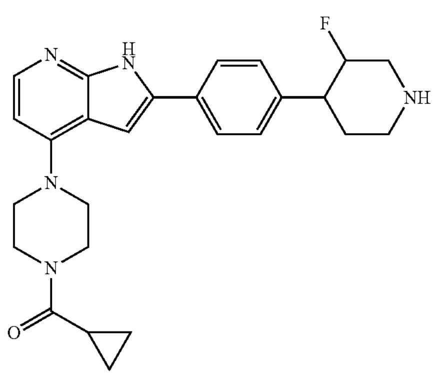 [SMILES: O=C(C1CC1)N1CCN(c2ccnc3[nH]c(-c4ccc(C5CCNCC5F)cc4)cc23)CC1] | 448 | ¹H-NMR (400 MHz, DMSO-d₆) δ ppm 11.92 (s, 1H), 7.95 (d, 1H, J = 5.2 Hz), 7.88 (d, 2H, J = 8.4 Hz), 7.34 (d, 2H, J = 8.4 Hz), 7.01 (d, 1H, J = 2.0 Hz), 6.42 (d, 1H, J = 5.2 Hz), 4.67-4.51 (m, 1H), 3.91 (br. s., 2H), 3.67 (br. s., 2H), 3.49 (br. s., 2H), 3.41 (br. s., 2H), 3.30-3.26 (m, 1H), 2.90-2.88 (m, 1H), 2.79-2.66 (m, 1H), 2.54-2.45 (m, 2H), 2.00-1.97 (m, 1H), 1.78-1.75 (m, 1H), 1.68-1.58 (m, 1H), 0.79-0.71 (m, 4H). |

TABLE 1-continued

| # | Structure | LCMS (M + 1) | ¹H NMR |
|---|---|---|---|
| 390 | 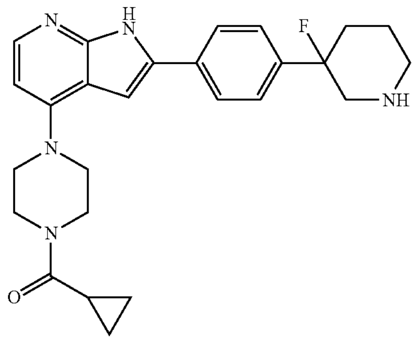 [SMILES: O=C(C1CC1)N1CCN(c2ccnc3[nH]c(-c4ccc(C5(F)CCCNC5)cc4)cc23)CC1] | 448 | ¹H-NMR (400 MHz, 6d-DMSO) δ ppm 9.80-9.67 (m, 1H), 8.94-8.73 (m, 1H), 8.06 (d, 2H, J = 8.0 Hz), 7.98 (d, 1H, J = 6.8 Hz), 7.60 (d, 2H, J = 8.4 Hz), 7.47 (s, 1H), 6.73 (d, 1H, J = 6.4 Hz), 4.10-3.40 (m, 10H), 3.16-2.94 (m, 1H), 2.33-1.81 (m, 6H), 0.80-0.77 (m, 4H). |
| 391 | 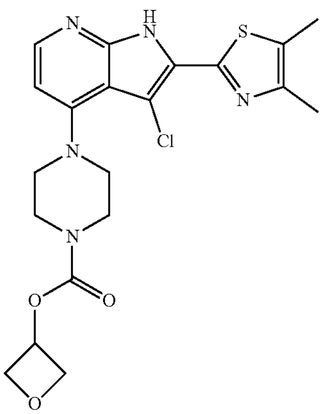 [SMILES: Cc1nc(-c2[nH]c3nccc(N4CCN(C(=O)OC5COC5)CC4)c3c2Cl)sc1C] | 448 | ¹H-NMR (400 MHz, 6d-DMSO) δ ppm 12.66 (br. s., 1H), 8.16 (d, 1H, J = 4.8 Hz), 6.67 (d, 1H, J = 5.2 Hz), 5.34 (quintet, 1H, J = 5.2 Hz), 4.79 (t, 2H, J = 6.8 Hz), 4.53 (dd, 2H, J = 7.6, 5.2 Hz), 3.74-3.72 (m, 2H), 3.66-3.62 (m, 2H), 3.20-3.16 (m, 4H), 2.44 (s, 3H), 2.38 (s, 3H). |
| 392 | 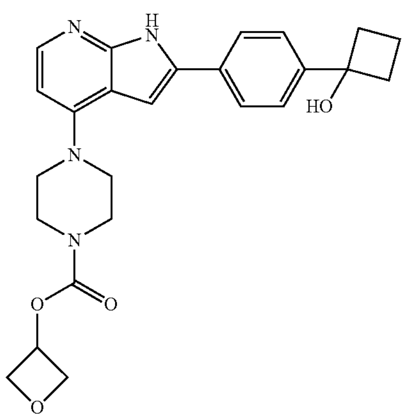 [SMILES: O=C(OC1COC1)N1CCN(c2ccnc3[nH]c(-c4ccc(C5(O)CCC5)cc4)cc23)CC1] | 449 | ¹H-NMR (400 MHz, 6d-DMSO) δ ppm 11.93 (d, 1H, J = 1.2 Hz), 7.97 (d, 1H, J = 5.2 Hz), 7.90 (d, 2H, J = 8.4 Hz), 7.53 (d, 2H, J = 8.4 Hz), 7.01 (d, 1H, J = 2.0 Hz), 6.45 (d, 1H, J = 5.6 Hz), 5.52 (s, 1H), 5.37-5.31 (m, 1H), 4.81-4.77 (m, 2H), 4.55-4.52 (m, 2H), 3.69-3.59 (m, 4H), 3.46-3.43 (m, 4H), 2.42-2.38 (m, 2H), 2.33-2.27 (m, 2H), 1.97-1.89 (m, 1H), 1.70-1.64 (m, 1H). |
| 393 | 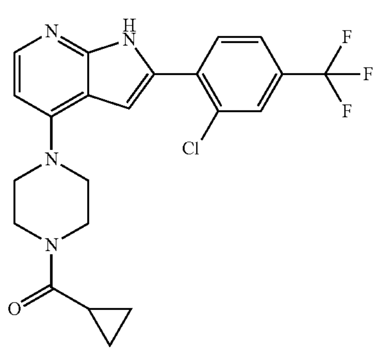 [SMILES: O=C(C1CC1)N1CCN(c2ccnc3[nH]c(-c4ccc(C(F)(F)F)cc4Cl)cc23)CC1] | 449 | 1H NMR (400 MHz, DMSO) δ 12.95 (s, 1H), 8.09 (d, J = 6.9 Hz, 2H), 7.94 (dd, J = 17.8, 8.3 Hz, 2H), 7.37 (s, 1H), 6.77 (d, J = 7.1 Hz, 1H), 4.03 (d, J = 9.5 Hz, 6H), 3.76 (s, 8H), 2.03-1.95 (m, 1H), 0.81-0.74 (m, 4H). |

TABLE 1-continued

| # | Structure | LCMS (M + 1) | ¹H NMR |
|---|---|---|---|
| 394 | 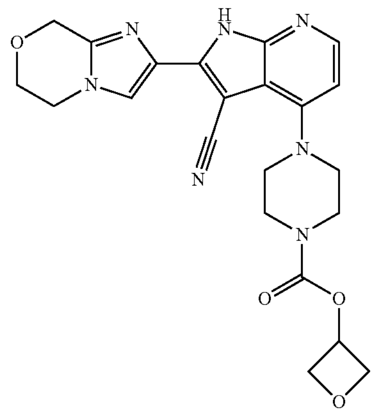 [SMILES: N#Cc1c(-c2cn3c(n2)COCC3)[nH]c2nccc(N3CCN(C(=O)OC4COC4)CC3)c12] | 450 | ¹H-NMR (400 MHz, 6d-DMSO) δ ppm 12.88-12.75 (br., 1H), 8.13 (d, 1H, J = 5.6 Hz), 7.90 (s, 1H), 6.72 (d, 1H, J = 5.6 Hz), 5.35-5.28 (m, 1H), 4.84 (s, 2H), 4.77 (1, 2H, J = 7.2 Hz), 4.53 (dd, 2H, J = 7.2, 5.2 Hz), 4.17 (t, 2H, J = 4.4 Hz), 4.06 (t, 2H, J = 4.4 Hz), 3.73-3.63 (m, 2H), 3.63-3.53 (m, 2H), 3.30-3.15 (m, 4H). |
| 395 | 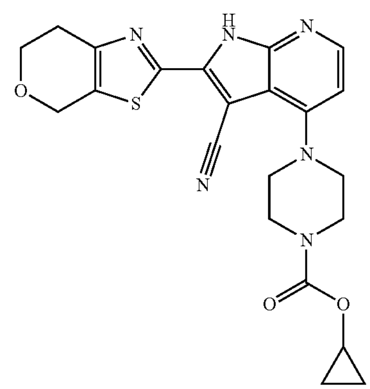 [SMILES: N#Cc1c(-c2nc3c(s2)COCC3)[nH]c2nccc(N3CCN(C(=O)OC4CC4)CC3)c12] | 451 | ¹H-NMR (500 MHz, 6d-DMSO) δ ppm 13.60 (s, 1H), 8.22 (d, 1H, J = 9.5 Hz), 6.77 (d, 1H, J = 10.5 Hz), 5.01 (s, 2H), 4.04-4.01 (m, 3H), 3.614-3.58 (m, 4H), 3.19-3.17 (m, 4H), 2.64 (s, 2H), 0.67-0.64 (m, 4H). |
| 396 | 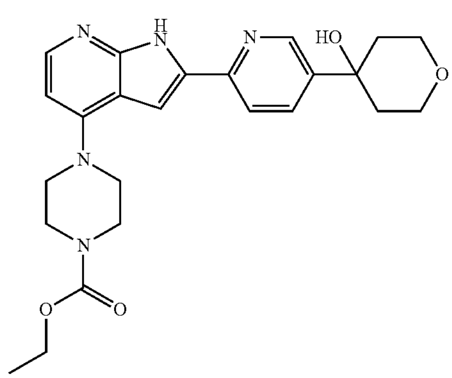 [SMILES: CCOC(=O)N1CCN(c2ccnc3[nH]c(-c4ccc(C5(O)CCOCC5)cn4)cc23)CC1] | 452 | ¹H-NMR (500 MHz, 6d-DMSO) δ ppm 11.99 (s, 1H), 8.73 (d, 1H, J = 1.5 Hz), 8.02 (d, 1H, J = 8.0 Hz), 8.03-8.00 (m, 1H), 7.94-7.91 (dd, 1H, J = 8.0, 2.0 Hz), 7.23 (s, 1H), 6.44 (d, 1H, J = 5.5 Hz), 5.40-5.25 (br., 1H), 4.09 (q, 2H, J = 7.0 Hz), 3.84-3.77 (m, 2H), 3.76-3.71 (m, 2H), 3.74-3.73 (m, 4H), 3.61-3.56 (m, 4H), 2.08-2.02 (m, 2H), 1.61-1.59 (m, 2H), 1.22 (t, 3H, J = 7.0 Hz). |
| 397 | 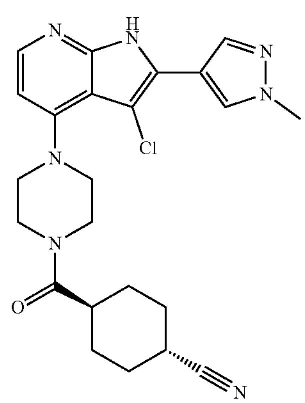 [SMILES: Cn1cc(-c2[nH]c3nccc(N4CCN(C(=O)[C@H]5CC[C@H](C#N)CC5)CC4)c3c2Cl)cn1] | 452 | ¹H-NMR (400 MHz, 6d-DMSO) δ ppm 12.17 (s, 1H), 8.35 (s, 1H), 8.10 (s, 1H), 8.05 (d, 1H, J = 5.6 Hz), 6.61 (d, 1H, J = 5.6 Hz), 3.93 (s, 3H), 3.80-3.68 (m, 4H), 3.18-3.08 (m, 4H), 2.75-2.70 (m, 2H), 2.08-2.00 (m, 2H), 1.75-1.70 (m, 2H), 1.62-1.57 (m, 2H), 1.44-1.38 (m, 2H). |

TABLE 1-continued

| # | Structure | LCMS (M + 1) | ¹H NMR |
|---|---|---|---|
| 398 | 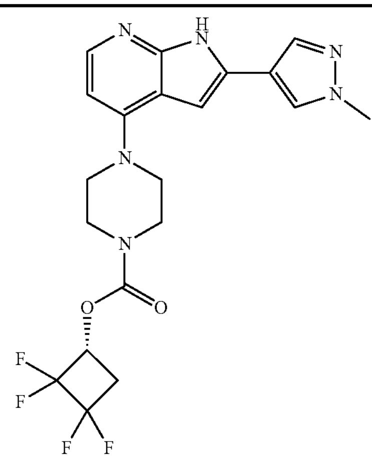 | 453 | ¹H-NMR (400 MHz, 6d-DMSO) δ ppm 11.73 (s, 1H), 8.12 (s, 1H), 7.92 (d, 1H, J = 6.4 Hz), 6.66 (d, 1H, J = 2.0 Hz), 6.43 (d, 1H, J = 5.2 Hz), 5.34-5.28 (m, 1H), 3.88 (s, 3H), 3.66-3.61 (m, 4H), 3.40-3.37 (m, 4H), 3.23-3.20 (m, 1H), 2.91-2.84 (m, 1H). |
| 399 | 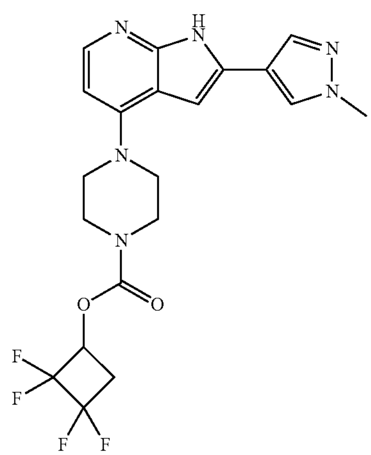 [SMILES: Cn1cc(-c2cc3c(N4CCN(C(=O)OC5CC(F)(F)C5(F)F)CC4)ccnc3[nH]2)cn1] | 453 | ¹H-NMR (400 MHz, 6d-DMSO) δ ppm 11.73 (s, 1H), 8.12 (s, 1H,), 7.93 (s, 1H), 7.91 (d, 1H, J = 5.6 Hz), 6.67 (d, 1H, J = 1.6 Hz), 6.43 (d, 1H, J = 5.2 Hz), 5.34-5.30 (m, 1H), 3.87 (s, 3H), 3.67-3.61 (m, 4H), 3.40-3.37 (m, 4H), 3.23-3.20 (m, 1H), 2.90-2.86 (m, 1H). |
| 400 | 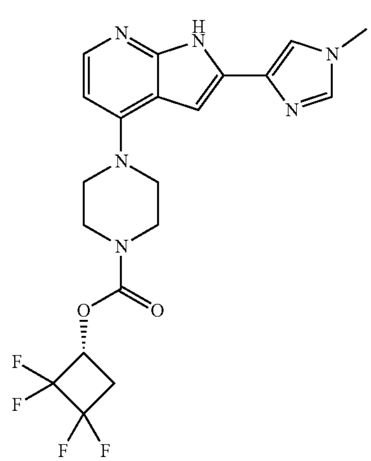 [SMILES: Cn1cnc(-c2cc3c(N4CCN(C(=O)O[C@@H]5CC(F)(F)C5(F)F)CC4)ccnc3[nH]2)c1] | 453 | ¹H-NMR (400 MHz, 6d-DMSO) δ ppm 11.67 (s, 1H), 7.91 (d, 1H, J = 5.2 Hz), 7.65 (s, 1H), 7.55 (d, 1H, J = 0.4 Hz), 6.64 (d, 1H, J = 2 Hz), 6.42 (d, 1H, J = 5.2 Hz), 5.33-5.28 (m, 1H), 3.69 (s, 3H), 3.68-3.62 (m, 4H), 3.42-3.37 (m, 4H), 3.27-3.13 (m, 1H), 2.94-2.80 (m, 1H). |

TABLE 1-continued
| # | Structure | LCMS (M + 1) | ¹H NMR |
|---|---|---|---|
| 401 | 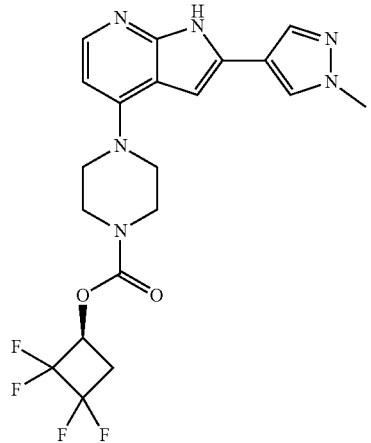 | 453 | ¹H-NMR (400 MHz, 6d-DMSO) δ ppm 11.74 (s, 1H), 8.12 (s, 1H), 7.92 (d, 1H, J = 6.4 Hz), 6.67 (d, 1H, J = 2.0 Hz), 6.43 (d, 1H, J = 5.2 Hz), 5.34-5.28 (m, 1H), 3.88 (s, 3H), 3.66-3.61 (m, 4H), 3.40-3.37 (m, 4H), 3.23-3.20 (m, 1H), 2.91-2.84 (m, 1H). |
| 402 | 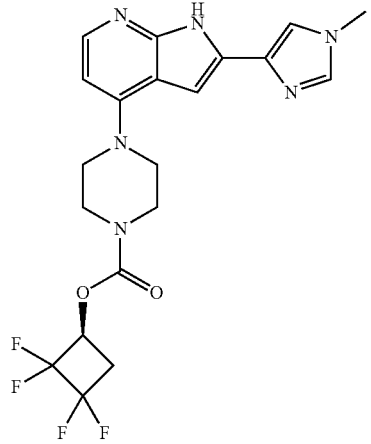 [SMILES: Cn1cnc(-c2cc3c(N4CCN(C(=O)O[C@H]5CC(F)(F)C5(F)F)CC4)ccnc3[nH]2)c1] | 453 | ¹H-NMR (400 MHz, 6d-DMSO) δ ppm 11.68 (s, 1H), 7.91 (d, 1H, J = 5.6 Hz), 7.66 (s, 1H), 7.56 (d, 1H, J = 1.2 Hz), 6.64 (d, 1H, J = 2.4 Hz), 6.43 (d, 1H, J = 5.6 Hz), 5.33-5.28 (m, 1H), 3.69 (s, 3H), 3.68-3.62 (m, 4H), 3.42-3.37 (m, 4H), 3.27-3.13 (m, 1H), 2.94-2.80 (m, 1H) |
| 403 | 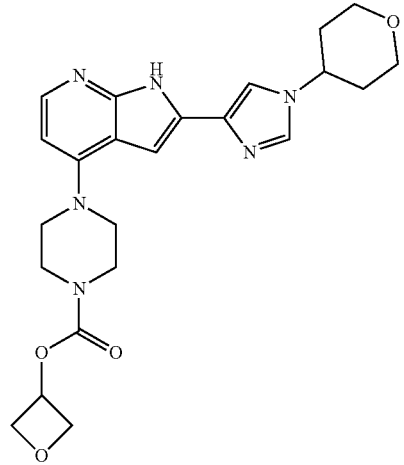 [SMILES: O=C(OC1COC1)N1CCN(c2ccnc3[nH]c(-c4cn(C5CCOCC5)cn4)cc23)CC1] | 453 | ¹H-NMR (500 MHz, d₆-DMSO) δ ppm 11.65 (s, 1H), 8.23 (s, 1H), 7.92 (d, 1H, J = 5.5 Hz), 7.84 (d, 1H, J = 1.0 Hz), 7.75 (d, 1H, J = 1.0 Hz), 6.66 (s, 1H), 6.43 (d, 1H, J = 5.5 Hz), 5.35-5.32 (m, 1H), 4.81-4.78 (m, 2H), 4.55-4.52 (m, 2H), 4.38-4.34 (m, 1H), 4.01-3.98 (m, 2H), 3.69-3.59 (m, 4H), 3.54-3.45 (m, 2H), 3.35-3.31 (m, 4H), 2.03-2.0 (m, 2H), 1.93-1.86 (m, 2H). |

TABLE 1-continued

| # | Structure | LCMS (M + 1) | ¹H NMR |
|---|---|---|---|
| 404 | 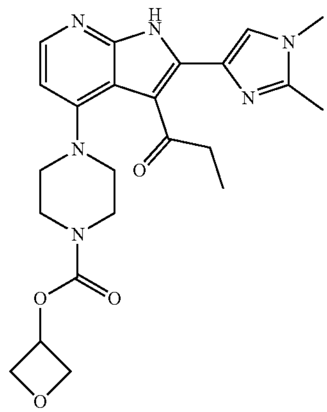 [SMILES: CCC(=O)c1c(-c2cn(C)c(C)n2)[nH]c2nccc(N3CCN(C(=O)OC4COC4)CC3)c12] | 453 | ¹H-NMR (500 MHz, CDCl₃) δ ppm 10.1 (s, 1H), 8.20 (d, 1H, J = 5.0 Hz), 7.83 (s, 1H), 6.66 (d, 1H, J = 5.0 Hz), 5.44-5.40 (m, 1H), 4.92-4.88 (m, 2H), 4.69-4.66 (m, 2H), 3.60-3.64 (m, 7H), 3.18-3.17 (m, 4H), 3.13-3.09 (m, 2H), 2.43 (s, 3H), 1.10 (t, 3H, J = 7.0 Hz). |
| 405 | 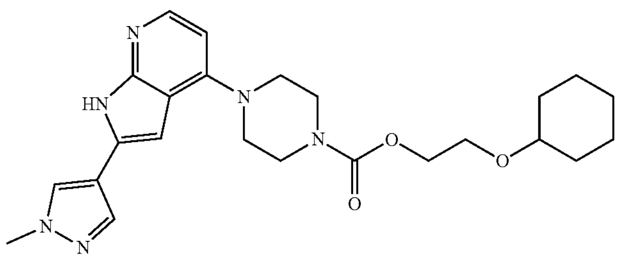 [SMILES: Cn1cc(-c2cc3c(N4CCN(C(=O)OCCOC5CCCCC5)CC4)ccnc3[nH]2)cn1] | 453 | ¹H-NMR (400 MHz, 6d-DMSO) δ ppm 11.73 (s, 1H), 8.20 (br. s., 1H), 8.12 (s, 1H), 7.94 (s, 1H), 7.91 (d, 1H, J = 5.2 Hz), 6.66 (s, 1H), 6.42 (d, 1H, J = 5.2 Hz), 4.14 (t, 2H, J = 4.8 Hz), 3.87 (s, 3H), 3.61-3.59 (m, 6H), 3.37-3.35 (m, 4H), 3.29-3.25 (m, 1H), 1.84-1.79 (m, 2H), 1.65-1.64 (m, 2H), 1.47-1.45 (m, 1H), 1.24-1.18 (m, 5H). |
| 406 | 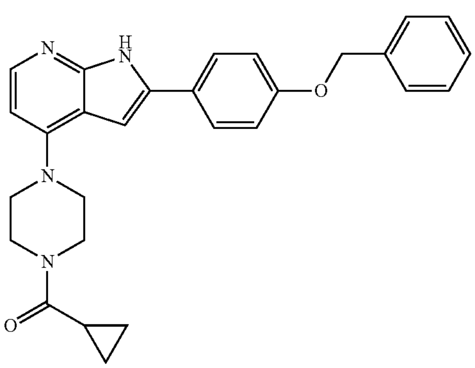 [SMILES: O=C(C1CC1)N1CCN(c2ccnc3[nH]c(-c4ccc(OCc5ccccc5)cc4)cc23)CC1] | 453 | 1H NMR (400 MHz, DMSO) δ 12.84 (s, 1H), 8.04 (d, J = 7.2 Hz, 1H), 7.53-7.50 (m, 1H), 7.41-7.35 (m, 3H), 7.02 (d, J = 1.9 Hz, 1H), 6.77 (d, J = 7.2 Hz, 1H), 4.03 (d, J = 27.0 Hz, 18H), 3.75 (s, 2H), 2.45 (s, 3H), 1.98 (s, 1H), 0.80-0.76 (m, 4H). |
| 407 | 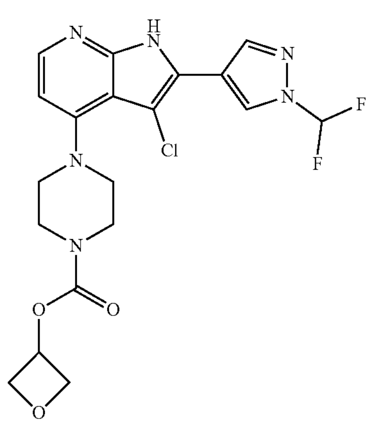 [SMILES: O=C(OC1COC1)N1CCN(c2ccnc3[nH]c(-c4cnn(C(F)F)c4)c(Cl)c23)CC1] | 453 | ¹H-NMR (400 MHz, 6d-DMSO) δ ppm 13.37 (s, 1H), 8.82 (s, 1H), 8.45 (s, 1H), 8.11 (d, 1H, J = 5.6 Hz), 8.10-7.80 (m, 1H), 6.64 (d, 1H, J = 5.2 Hz), 5.36-5.29 (m, 1H), 4.81-4.75 (m, 2H), 4.56-4.51 (m, 2H), 3.73-3.60 (m, 4H), 3.19-3.15 (m, 4H). |

TABLE 1-continued

| # | Structure | LCMS (M + 1) | ¹H NMR |
|---|---|---|---|
| 408 | 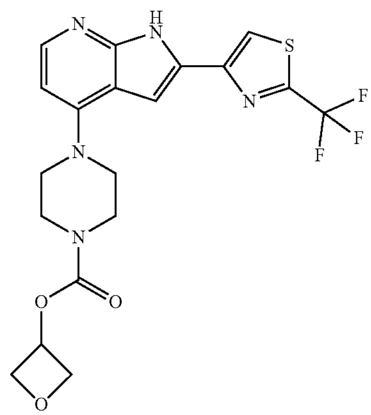 [SMILES: O=C(OC1COC1)N1CCN(c2ccnc3[nH]c(-c4csc(C(F)(F)F)n4)cc23)CC1] | 454 | ¹H-NMR (400 MHz, 6d-DMSO) δ ppm 12.27 (s, 1H), 8.43 (s, 1H), 8.03 (d, 1H, J = 5.6 Hz), 7.04 (s, 1H), 6.48 (d, 1H, J = 5.6 Hz), 5.36-5.30 (m, 1H), 4.80-4.77 (m, 2H), 4.54-4.51 (m, 2H), 3.70-3.59 (m, 4H), 3.49-3.46 (m, 4H). |
| 409 | 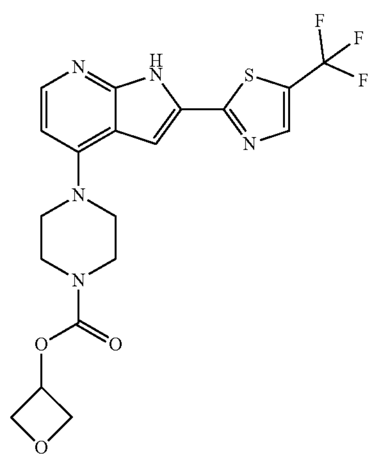 [SMILES: O=C(OC1COC1)N1CCN(c2ccnc3[nH]c(-c4ncc(C(F)(F)F)s4)cc23)CC1] | 454 | ¹H-NMR (400 MHz, 6d-DMSO) δ ppm 12.66-12.62 (br, 1H), 8.49 (d, 1H, J = 1.2 Hz), 8.07 (d, 1H, J = 5.2 Hz), 7.43 (s, 1H), 6.49 (d, 1H, J = 5.2 Hz), 5.36-5.30 (m, 1H), 4.80-4.77 (m, 2H), 4.54-4.51 (m, 2H), 3.69-3.67 (m, 2H), 3.60-3.58 (m, 2H), 3.54-3.53 (m, 4H). |
| 410 | 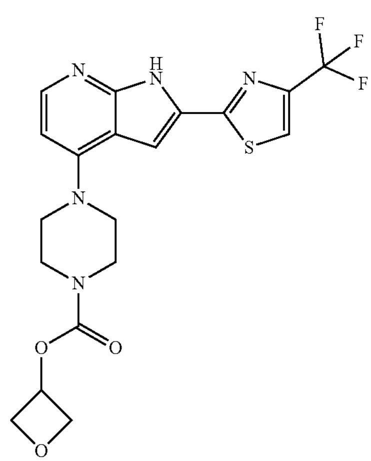 [SMILES: O=C(OC1COC1)N1CCN(c2ccnc3[nH]c(-c4nc(C(F)(F)F)cs4)cc23)CC1] | 454 | ¹H-NMR (500 MHz, 6d-DMSO) δ ppm 12.28 (s, 1H), 8.49 (s, 1H), 8.02 (d, 1H, J = 5.0 Hz), 7.32 (s, 1H), 6.49 (d, 1H, J = 5.0 Hz), 5.32-5.30 (m, 1H), 4.81-4.77 (m, 2H), 4.55-4.51 (m, 2H), 3.70-3.58 (m, 4H), 3.56-3.51 (m, 4H). |

TABLE 1-continued

| # | Structure | LCMS (M + 1) | ¹H NMR |
|---|---|---|---|
| 412 | 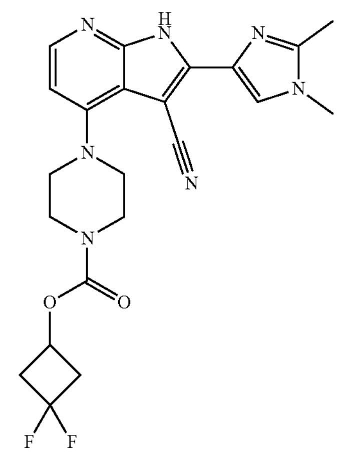 [SMILES: Cc1nc(-c2[nH]c3nccc(N4CCN(C(=O)OC5CC(F)(F)C5)CC4)c3c2C#N)cn1C] | 456 | 1H-NMR (400 MHz, DMSO-d$_6$) δ ppm 12.79 (br. s., 1H), 8.11 (d, 1H, J = 5.2 Hz), 7.82 (s, 1H), 6.71 (d, 1H, J = 5.2 Hz), 4.87-4.83 (m, 1H), 3.68 (s, 3H), 3.66-3.61 (m, 4H), 3.20-3.13 (m, 4H), 3.08-3.01 (m, 2H), 2.76-2.68 (m, 2H), 2.39(s, 3H). |
| 413 | 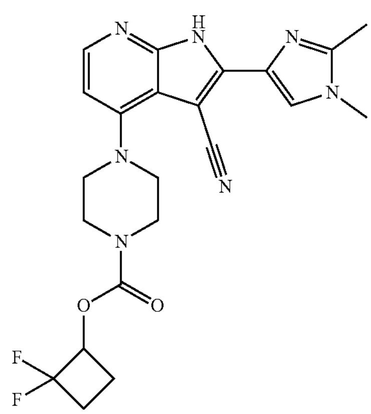 [SMILES: Cc1nc(-c2[nH]c3nccc(N4CCN(C(=O)OC5CCC5(F)F)CC4)c3c2C#N)cn1C] | 456 | ¹H-NMR (500 MHz, 6d-DMSO) δ ppm 12.78 (s, 1H), 8.12 (d, 1H, J = 5.0 Hz), 7.82 (s, 1H), 6.72 (d, 1H, J = 5.0 Hz), 5.25-5.20 (m, 1H), 3.75-3.50 (m, 7H), 3.32-3.10 (m, 4H), 2.50-2.20 (m, 6H), 1.85-1.75 (m, 1H). |
| 414 | 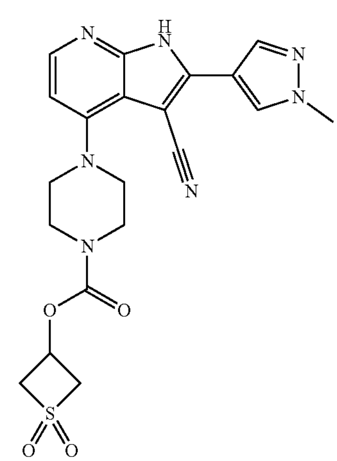 [SMILES: Cn1cc(-c2[nH]c3nccc(N4CCN(C(=O)OC5CS(=O)(=O)C5)CC4)c3c2C#N)cn1] | 456 | ¹H-NMR (500 MHz, d$_6$-DMSO) δ ppm 12.96 (s, 1H), 8.41 (s, 1H), 8.18-8.16 (m, 2H), 6.75 (d, 1H, J = 5.5 Hz), 5.24-5.21 (m, 1H), 4.70-4.66 (m, 2H), 4.32-4.28 (m, 2H), 3.98 (s, 3H), 3.72-3.66 (m, 4H), 3.23-3.22 (m, 4H). |

TABLE 1-continued

| # | Structure | LCMS (M + 1) | ¹H NMR |
|---|---|---|---|
| 415 | 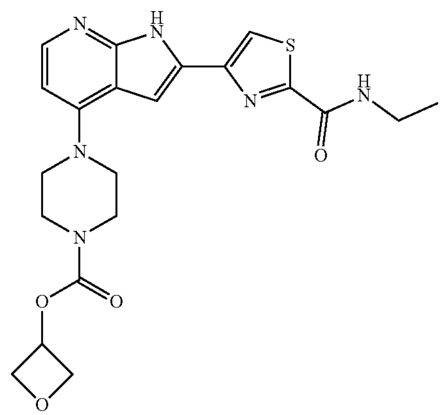 [SMILES: CCNC(=O)c1nc(-c2cc3c(N4CCN(C(=O)OC5COC5)CC4)ccnc3[nH]2)cs1] | 457 | ¹H-NMR (400 MHz, 6d-DMSO) δ ppm 12.60 (br s, 1H), 8.80 (t, 1H, J = 5.6 Hz), 8.32 (s, 1H), 8.05 (d, 1H, J = 6.0 Hz), 7.25 (s, 1H), 6.64 (d, 1H, J = 6.4 Hz), 5.36-5.33 (m, 1H), 4.81-4.78 (m, 2H), 4.55-4.51 (m, 2H), 3.75-3.73 (m, 6H), 3.70-3.68 (m, 2H), 3.40-3.33 (m, 2H), 1.20 (t, 3H, J = 6.8 Hz). |
| 416 | 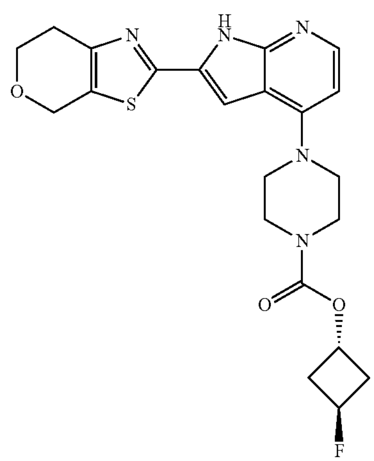 [SMILES: O=C(O[C@H]1C[C@H](F)C1)N1CCN(c2ccnc3[nH]c(-c4nc5c(s4)COCC5)cc23)CC1] | 458 | ¹H-NMR (500 MHz, 6d-DMSO) δ ppm 12.30 (s, 1H), 8.03 (s, 1H), 7.09 (s, 1H), 6.48 (d, 1H, J = 5.0 Hz), 5.36-5.10 (m, 2H), 4.84 (s, 2H), 4.0-3.98 (m, 2H), 3.61-3.58 (m, 4H), 3.44-3.46 (m, 4H), 2.88 (s, 2H), 2.60-2.56 (m, 4H). |
| 417 | 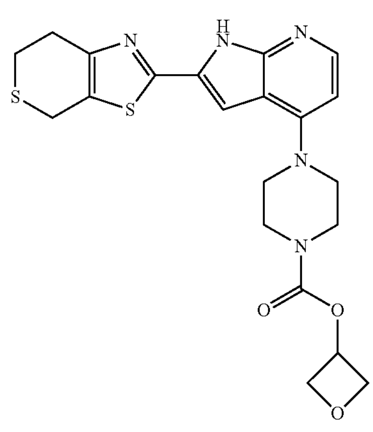 [SMILES: O=C(OC1COC1)N1CCN(c2ccnc3[nH]c(-c4nc5c(s4)CSCC5)cc23)CC1] | 458 | ¹H-NMR (400 MHz, 6d-DMSO) δ ppm 12.40-12.18 (br., 1H), 8.02 (d, 1H, J = 5.2 Hz), 7.07 (s, 1H), 6.46 (d, 1H, J = 5.2 Hz), 5.55 (quintet, 1H, J = 5.6 Hz), 4.79 (t, 2H, J = 6.8 Hz), 4.53 (dd, 2H, J = 6.8, 5.6 Hz), 3.98-3.94 (m, 2H), 3.70-3.60 (m, 2H), 3.60-3.50 (m, 2H), 3.50-3.41 (m, 4H), 3.09-2.98 (m, 4H). |

TABLE 1-continued

| # | Structure | LCMS (M + 1) | ¹H NMR |
|---|---|---|---|
| 418 | 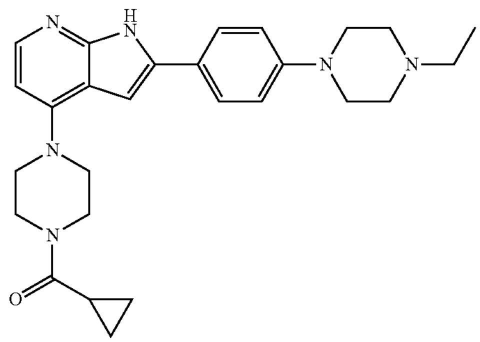 | 459 | ¹H NMR (400 MHz, DMSO-d₆) δ ppm 11.76 (s, 1H), 7.92 (d, 1H, J = 4.4 Hz), 7.79 (d, 2H, J = 7.2 Hz), 6.98 (d, 2H, J = 7.2 Hz), 6.85 (s, 1H), 6.42 (d, 1H, J = 4.4 Hz), 3.91 (br. s., 2H), 3.70 (br. s., 2H), 3.46 (br. s., 2H), 3.39 (br. s., 2H), 3.22-3.18 (m, 4H), 2.37 (q, 2H, J = 5.6 Hz), 2.06-2.00 (m, 1H), 1.04 (t, 3H, J = 5.6 Hz), 0.78-0.74 (m, 4H). |
| 420 | 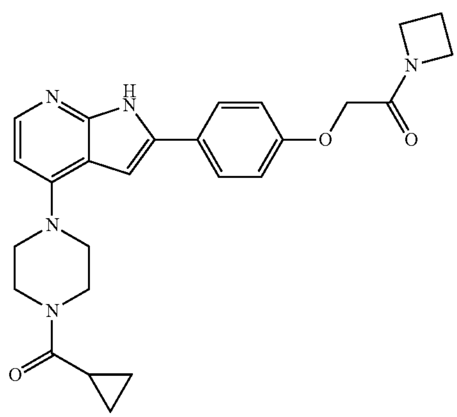 [SMILES: O=C(COc1ccc(-c2cc3c(N4CCN(C(=O)C5CC5)CC4)ccnc3[nH]2)cc1)N1CCC1] | 460 | ¹H-NMR (400 MHz, 6d-DMSO) δ ppm 11.85 (s, 1H), 7.94 (d, 1H, J = 5.2 Hz), 7.87 (d, 2H, J = 8.8 Hz), 6.99 (d, 2H, J = 8.8 Hz), 6.93 (d, 1H, J = 1.6 Hz), 6.43 (d, 1H, J = 5.2 Hz), 4.63 (s, 2H), 4.25 (t, 2H, J = 7.6 Hz), 3.92 (t, 2H, J = 7.6 Hz), 3.95-3.88 (m, 2H), 3.75-3.68 (m, 2H), 3.52-3.45 (m, 2H), 3.44-3.39 (m, 2H), 2.24 (quintet, 2H, J = 7.6 Hz), 2.05-2.00 (m, 1H), 0.79-0.73 (m, 4H). |
| 421 | 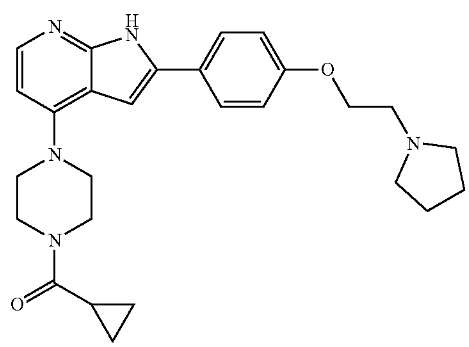 [SMILES: O=C(C1CC1)N1CCN(c2ccnc3[nH]c(-c4ccc(OCCN5CCCC5)cc4)cc23)CC1] | 460 | 1H NMR (400 MHz, DMSO) δ 13.22 (s, 1H), 8.02 (d, J = 7.2 Hz, 1H), 7.93 (d, J = 8.8 Hz, 2H), 7.35 (d, J = 1.9 Hz, 1H), 7.16 (d, J = 8.9 Hz, 2H), 6.76 (d, J = 7.2 Hz, 1H), 4.42-4.37 (m, 2H), 4.05 (s, 2H), 4.01 (s, 4H), 3.76 (s, 2H), 3.63 (d, J = 4.4 Hz, 4H), 3.18-3.11 (m, 2H), 2.09-1.96 (m, 3H), 1.91 (dd, J = 7.3, 5.0 Hz, 2H), 0.85-0.71 (m, 4H) |
| 422 | 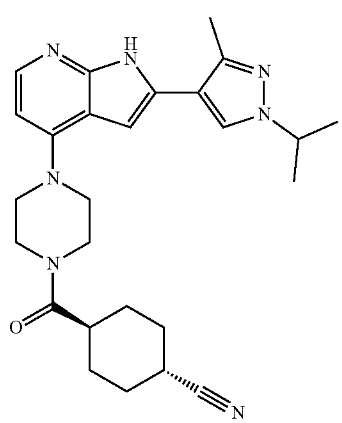 [SMILES: Cc1nn(C(C)C)cc1-c1cc2c(N3CCN(C(=O)[C@H]4CC[C@H](C#N)CC4)CC3)ccnc2[nH]1] | 460 | ¹H-NMR (400 MHz, 6d-DMSO) δ ppm 11.49 (s, 1H), 8.13 (s, 1H), 7.92 (d, 1H, J = 5.2 Hz), 6.43 (d, 1H, J = 5.2 Hz), 6.40 (d, 1H, J = 2.0 Hz), 4.44-4.40 (m, 1H), 3.73-3.71 (m, 2H), 3.67-3.65 (m, 2H), 3.41-3.40 (m, 2H), 3.36-3.35 (m, 2H), 2.73-2.70 (m, 2H), 2.39 (s, 3H) 2.06-2.02 (m, 2H), 1.74-1.70 (m, 2H), 1.61-1.57 (m, 2H), 1.43-1.42 (m, 2H), 1.42 (d, 6H, J = 6.8 Hz). |

TABLE 1-continued

| # | Structure | LCMS (M + 1) | ¹H NMR |
|---|---|---|---|
| 423 | 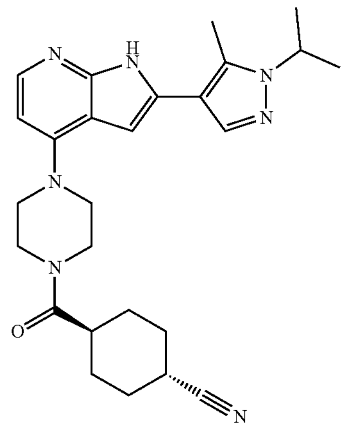 [SMILES: Cc1c(-c2cc3c(N4CCN(C(=O)[C@H]5CC[C@H](C#N)CC5)CC4)ccnc3[nH]2)cnn1C(C)C] | 460 | ¹H-NMR (400 MHz, 6d-DMSO) δ ppm 11.56 (s, 1H), 7.93 (d, 1H, J = 5.6 Hz), 7.82 (s, 1H), 6.43 (d, 1H, J = 5.2 Hz), 6.40 (d, 1H, J = 2.0 Hz), 4.62-4.60 (m, 1H), 3.73-3.71 (m, 2H), 3.67-3.65 (m, 2H), 3.41-3.38 (m, 4H), 2.72-2.70 (m, 2H), 2.48 (s, 3H), 2.05-2.02 (m, 2H), 1.73-1.71 (m, 2H), 1.60-1.57 (m, 2H), 1.42-1.39 (m, 2H), 1.40 (d, 6H, J = 6.4 Hz). |
| 424 | 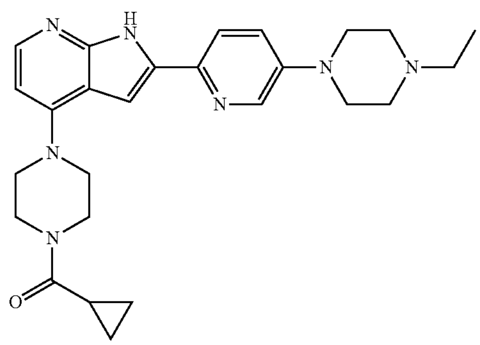 | 460 | ¹H-NMR (400 MHz, 6d-DMSO) δ ppm 11.79 (s, 1H), 8.32 (d, 1H, J = 2.4 Hz), 7.96 (d, 1H, J = 5.2 Hz), 7.88 (d, 1H, J = 8.8 Hz), 7.42 (dd, 1H, J = 8.8, 2.0 Hz), 7.05 (s, 1H), 6.43 (d, 1H, J = 5.2 Hz), 3.94-3.90 (m, 2H), 3.74-3.69 (m, 2H), 3.51-3.47 (m, 2H), 3.44-3.39 (m, 2H), 3.33-3.25 (m, 4H), 2.50-2.35 (m, 6H), 2.03-1.97 (m, 1H), 1.05 (t, 3H, J = 6.8 Hz), 0.80-0.73 (m, 4H). |
| 425 | 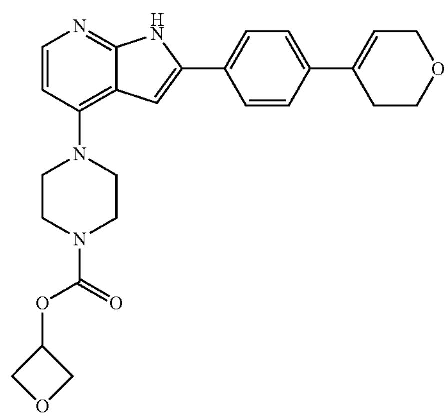 [SMILES: O=C(OC1COC1)N1CCN(c2ccnc3[nH]c(-c4ccc(C5=CCOCC5)cc4)cc23)CC1] | 461 | ¹H-NMR (400 MHz, 6d-DMSO) δ ppm 11.96 (s, 1H), 7.98-7.92 (m, 3H), 7.52 (d, 2H, J = 8.4 Hz), 7.06 (d, 1H, J = 2.0 Hz), 6.45 (d, 1H, J = 6.0 Hz), 6.36 (s, 1H), 5.35-5.32 (m, 1H), 4.81-4.77 (m, 2H), 4.55-4.52 (m, 2H), 4.25 (d, 2H, J = 5.2 Hz), 3.84 (t, 2H, J = 5.6 Hz), 3.68-3.60 (m, 4H), 3.46-3.44 (m, 4H), 2.50-2.49 (m, 2H). |
| 426 | 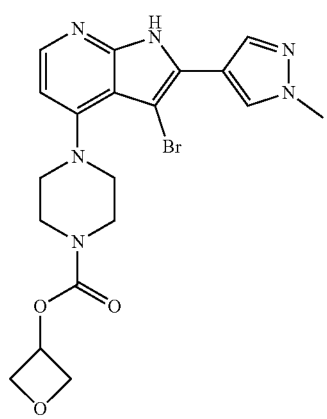 [SMILES: Cn1cc(-c2[nH]c3nccc(N4CCN(C(=O)OC5COC5)CC4)c3c2Br)cn1] | 462 | ¹H-NMR (500 MHz, 6d-DMSO) δ ppm 12.25 (s, 1H), 8.40 (s, 1H), 8.13 (s, 1H), 8.07 (d, 1H, J = 5.5 Hz), 6.66 (d, 1H, J = 5.0 Hz), 5.40-5.30 (m, 1H), 4.78 (t, 2H, J = 7.0 Hz), 4.60-4.49 (m, 2H), 3.93 (s, 3H), 3.80-3.70 (m, 2H), 3.70-3.60 (m, 2H), 3.20-3.10 (m, 4H). |

| # | Structure | LCMS (M + 1) | ¹H NMR |
|---|---|---|---|
| 427 | 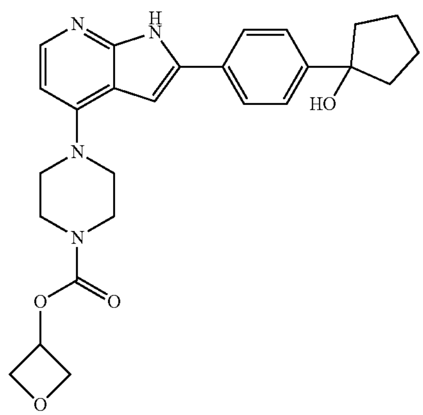 [SMILES: O=C(OC1COC1)N1CCN(c2ccnc3[nH]c(-c4ccc(C5(O)CCCC5)cc4)cc23)CC1] | 463 | ¹H-NMR (500 MHz, 6d-DMSO) δ ppm 11.91 (s, 1H), 7.97 (d, 1H, J = 5.5 Hz), 7.87 (d, 2H, J = 8.0 Hz), 7.51 (d, 2H, J = 8.5 Hz), 6.99 (s, 1H), 6.44 (d, 1H, J = 5.5 Hz), 5.35-5.33 (m, 1H), 4.81 (s, 1H), 4.80-4.78 (m, 2H), 4.54-4.52 (m, 2H), 3.71-3.59 (m, 4H), 3.44-3.43 (m, 4H), 1.87-1.83 (m, 6H), 1.75-1.71 (m, 2H). |
| 428 | 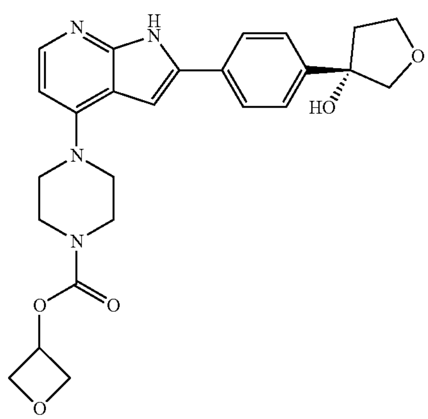 [SMILES: O=C(OC1COC1)N1CCN(c2ccnc3[nH]c(-c4ccc([C@@]5(O)CCOC5)cc4)cc23)CC1] | 465 | ¹H NMR (500 MHz, 6d-DMSO) δ ppm 11.93(s, 1H), 7.97 (d, 1H, J = 5.5 Hz), 7.92 (d, 2H, J = 8.0 Hz), 7.53(d, 2H, J = 8.0 Hz), 7.03 (d, 1H, J = 2.0 Hz), 6.45 (d, 1H, J = 5.5 Hz), 5.42 (s, 1H), 5.34 (quintet, 1H, J = 5.0 Hz), 4.79 (t, 2H, J = 7.0 Hz), 4.54 (dd, 2H, J = 7.0, 5.0 Hz), 4.03-3.99 (m, 2H), 3.85-3.80 (m, 1H), 3.80-3.75 (m, 1H), 3.70-3.62 (m, 2H), 3.62-3.55 (m, 2H), 3.45-3.38(m, 4H), 2.35-2.30 (m, 1H), 2.20-2.15 (m, 1H). |
| 429 | 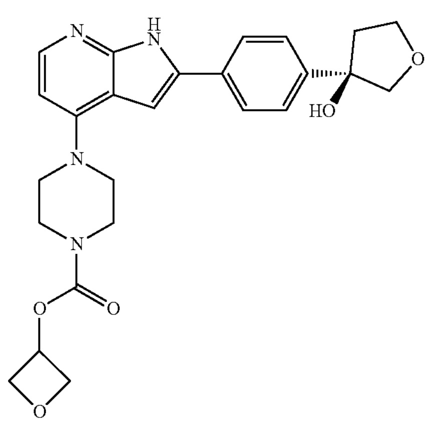 [SMILES: O=C(OC1COC1)N1CCN(c2ccnc3[nH]c(-c4ccc([C@]5(O)CCOC5)cc4)cc23)CC1] | 465 | ¹H NMR (500 MHz, 6d-DMSO) δ ppm 11.93 (s, 1H), 7.97 (d, 1H, J = 5.0 Hz), 7.91 (d, 2H, J = 8.5 Hz), 7.53(d, 2H, J = 8.5 Hz), 7.03 (s, 1H), 6.45 (d, 1H, J = 5.5 Hz), 5.42 (s, 1H), 5.34 (quintet, 1H, J = 5.0 Hz), 4.79 (t, 2H, J = 7.0 Hz), 4.54 (dd, 2H, J = 7.0, 5.0 Hz), 4.03-3.99 (m, 2H), 3.85-3.80 (m, 1H), 3.80-3.75 (m, 1H), 3.70-3.62 (m, 2H), 3.62-3.55 (m, 2H), 3.45-3.38(m, 4H), 2.35-2.30 (m, 1H), 2.20-2.15 (m, 1H). |

TABLE 1-continued

| # | Structure | LCMS (M + 1) | ¹H NMR |
|---|---|---|---|
| 430 | 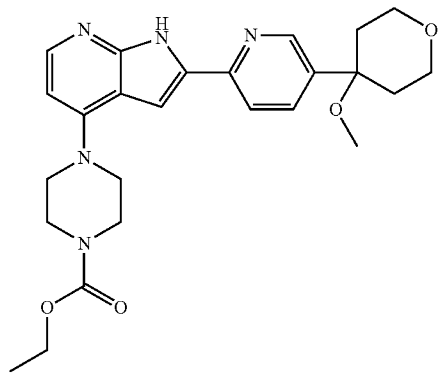 [SMILES: CCOC(=O)N1CCN(c2ccnc3[nH]c(-c4ccc(C5(OC)CCOCC5)cn4)cc23)CC1] | 466 | ¹H-NMR (500 MHz, 6d-DMSO) δ ppm 12.02 (s, 1H), 8.62 (d, 1H, J = 1.5 Hz), 8.06 (d, 1H, J = 8.5 Hz), 8.01 (d, 1H, J = 5.5 Hz), 7.86 (dd, 1H, J = 8.5, 2.5 Hz), 7.27 (d, 1H, J = 2.0 Hz), 6.45 (d, 1H, J = 5.5 Hz), 4.08 (q, 2H, J = 7.0 Hz), 3.73-3.72 (m, 4H), 3.64-3.60 (m, 4H), 3.48-3.42 (m, 4H), 2.02-1.97 (m, 4H), 1.22 (t, 3H, J = 7.0 Hz). |
| 431 | 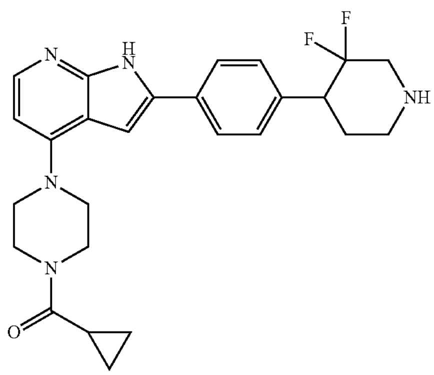 [SMILES: O=C(C1CC1)N1CCN(c2ccnc3[nH]c(-c4ccc(C5CCNCC5(F)F)cc4)cc23)CC1] | 466 | ¹H-NMR (400 MHz, DMSO-d₆/D₂O) δ ppm 11.94 (br. s., 1H), 8.22 (s, 2H), 7.94 (d, 1H, J = 4.8 Hz), 7.87 (d, 2H, J = 8.4 Hz), 7.34 (d, 2H, J = 7.6 Hz), 7.02 (s, 1H), 6.43 (d, 1H, J = 5.2 Hz), 3.92-3.42 (m, 8H), 3.28-3.18 (m, 1H), 3.13-3.08 (m, 1H), 3.00-2.98 (m, 1H), 2.89-2.78 (m, 1H), 2.65-2.59 (m, 1H), 2.05-1.97 (m, 2H), 1.79-1.76 (m, 1H), 0.75-0.73 (m, 4H). |
| 432 | 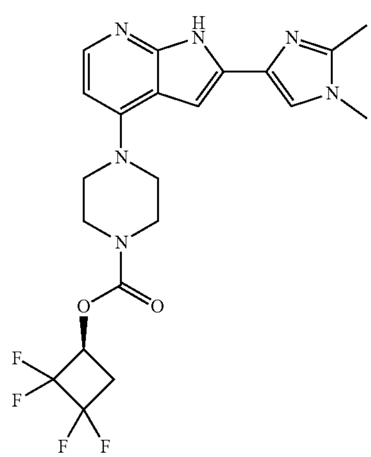 [SMILES: Cc1nc(-c2cc3c(N4CCN(C(=O)O[C@H]5CC(F)(F)C5(F)F)CC4)ccnc3[nH]2)cn1C] | 467 | ¹H-NMR (400 MHz, 6d-DMSO) δ ppm 11.61 (s, 1H), 7.90 (d, 1H, J = 5.6 Hz), 7.45 (s, 1H), 6.58 (s, 1H), 6.42 (d, 1H, J = 5.2 Hz), 5.32-5.29 (m, 1H), 3.67-3.59 (m, 4H), 3.59 (s, 3H) 3.39-3.35 (m, 4H), 3.26-3.20 (m, 1H), 2.90-2.85 (m, 2H), 2.30 (s, 3H). |

TABLE 1-continued

| # | Structure | LCMS (M + 1) | ¹H NMR |
|---|---|---|---|
| 433 | 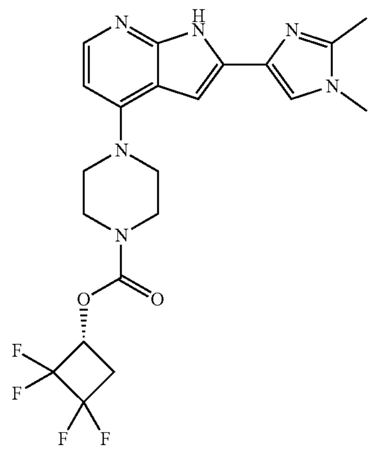 [SMILES: Cc1nc(-c2cc3c(N4CCN(C(=O)O[C@@H]5CC(F)(F)C5(F)F)CC4)ccnc3[nH]2)cn1C] | 467 | ¹H-NMR (400 MHz, 6d-DMSO) δ ppm 11.62 (s, 1H), 7.90 (d, 1H, J = 5.6 Hz), 7.46 (s, 1H), 6.58 (s, 1H), 6.42 (d, 1H, J = 5.2 Hz), 5.37-5.25 (m, 1H), 3.72-3.60 (m, 4H), 3.59 (s, 3H) 3.46-3.35 (m, 4H), 3.27-3.14 (m, 1H), 2.96-2.79 (m, 2H), 2.32 (s, 3H). |
| 434 | 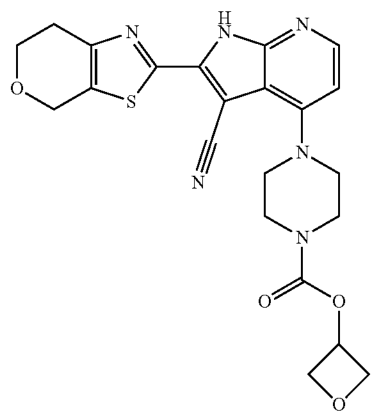 [SMILES: N#Cc1c(-c2nc3c(s2)COCC3)[nH]c2nccc(N3CCN(C(=O)OC4COC4)CC3)c12] | 467 | ¹H-NMR (500 MHz, 6d-DMSO) δ ppm 13.66 (s, 1H), 8.24 (d, 1H, J = 4.5 Hz), 6.79 (d, 1H, J = 5.5 Hz), 5.35-5.33 (m, 1H), 4.91 (s, 2H), 4.81-4.78 (m, 2H), 4.56-4.53 (m, 2H), 4.03-4.01 (m, 2H), 3.74-3.65 (m, 4H), 3.30-3.29 (m, 4H), 2.95-2.94(m, 2H). |
| 436 | 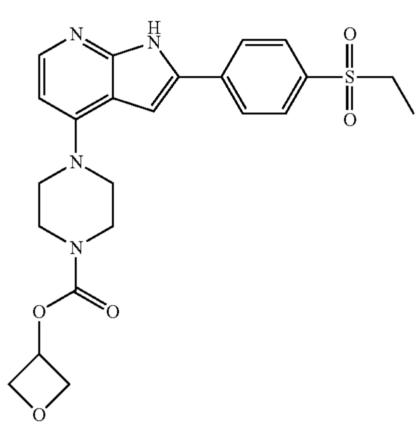 [SMILES: CCS(=O)(=O)c1ccc(-c2cc3c(N4CCN(C(=O)OC5COC5)CC4)ccnc3[nH]2)cc1] | 471 | 1H NMR (400 MHz, DMSO-d6) δ 12.16 (s, 1H), 8.25-8.11 (m, 2H), 8.01 (d, J = 5.5 Hz, 1H), 7.96-7.80 (m, 2H), 7.31 (d, J = 1.6 Hz, 1H), 6.46 (d, J = 5.6 Hz, 1H), 5.39-5.30 (m, 1H), 4.77 (ddd, J = 7.3, 6.3, 1.0 Hz, 2H), 4.52 (ddd, J = 7.4, 5.1, 0.9 Hz, 2H), 3.63 (d, J = 31.0 Hz, 5H), 3.49 (dd, J = 6.7, 3.7 Hz, 4H), 3.33 (d, J = 7.3 Hz, 1H), 1.11 (t, J = 7.3 Hz, 3H). |

TABLE 1-continued

| # | Structure | LCMS (M + 1) | ¹H NMR |
|---|---|---|---|
| 437 | 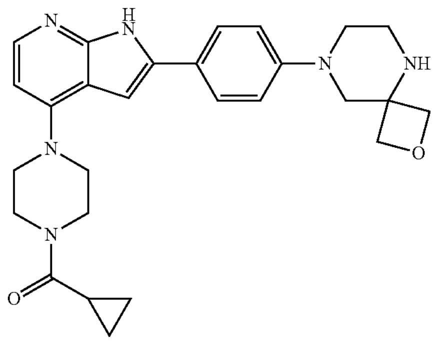 [SMILES: O=C(C1CC1)N1CCN(c2ccnc3[nH]c(-c4ccc(N5CCNC6(COC6)C5)cc4)cc23)CC1] | 473 | ¹H-NMR (400 MHz, 6d-DMSO) δ ppm 11.77 (s, 1H), 7.92 (d, 1H, J = 6.0 Hz), 7.80 (d, 2H, J = 8.8 Hz), 7.04 (d, 2H, J = 8.8 Hz), 6.85 (d, 1H, J = 2.0 Hz), 6.42 (d, 1H, J = 5.2 Hz), 4.40-4.30 (m, 4H), 4.00-3.80 (m, 2H), 3.75-3.60 (m, 2H), 3.50-3.40 (m, 6H), 3.10-3.00 (m, 2H), 2.82-2.70 (m, 2H), 2.10-1.95 (m, 1H), 0.80-0.60 (m, 4H). |
| 438 | 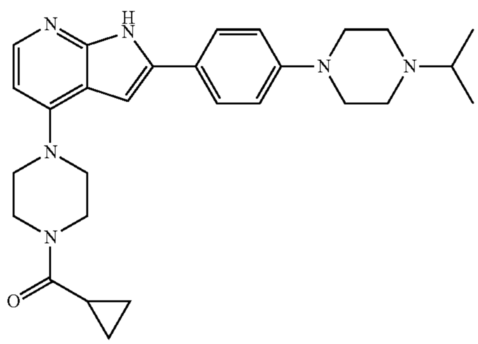 [SMILES: CC(C)N1CCN(c2ccc(-c3cc4c(N5CCN(C(=O)C6CC6)CC5)ccnc4[nH]3)cc2)CC1] | 473 | ¹H NMR (400 MHz, DMSO-d₆) δ ppm 11.77 (s, 1H), 7.92 (d, 1H, J = 4.0 Hz), 7.79 (d, 2H, J = 6.8 Hz), 6.98 (d, 2H, J = 6.8 Hz), 6.85 (s, 1H), 6.42 (d, 1H, J = 4.4 Hz), 3.91 (br. s., 2H), 3.70 (br. s., 2H), 3.46 (br. s., 2H), 3.39 (br. s., 2H), 3.18 (br. s., 4H), 2.58 (br. s., 4H), 2.06-2.00 (m, 1H), 1.02 (br. s., 6H), 0.78-0.74 (m, 4H). |
| 439 | 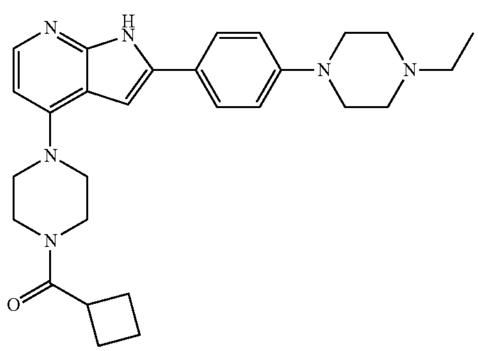 [SMILES: CCN1CCN(c2ccc(-c3cc4c(N5CCN(C(=O)C6CCC6)CC5)ccnc4[nH]3)cc2)CC1] | 473 | ¹H-NMR (400 MHz, DMSO-d₆) δ ppm 11.79 (s, 1H), 7.90 (d, 1H, J = 4.4 Hz), 7.78 (d, 1H, J = 8.4 Hz), 6.98 (d, 2H, J = 8.4 Hz), 6.83 (s, 1H), 6.39 (d, 1H, J = 5.2 Hz), 3.66 (br. s., 2H), 3.53 (br. s., 2H), 3.41-2.36 (m, 5H), 3.21 (br. s., 4H), 2.55 (br. s., 4H), 2.44-2.39 (m, 2H), 2.22-2.07 (m, 4H), 1.94-1.87 (m, 1H), 1.76-1.73 (m, 1H), 1.04 (t, 3H, J = 7.2 Hz). |
| 440 | 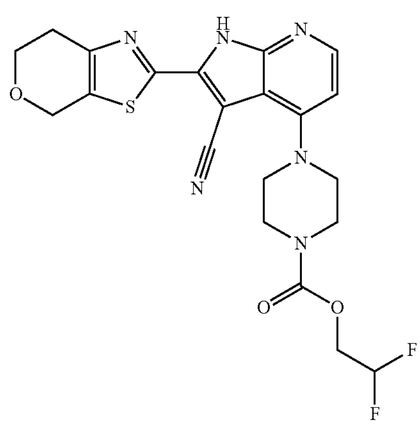 [SMILES: N#Cc1c(-c2nc3c(s2)COCC3)[nH]c2nccc(N3CCN(C(=O)OCC(F)F)CC3)c12] | 475 | ¹H-NMR (500 MHz, 6d-DMSO) δ ppm 13.64 (s, 1H), 8.24 (d, 1H, J = 8.0 Hz), 6.79 (d, 1H, J = 5.0 Hz), 6.41-6.18 (m, 1H), 4.92 (s, 2H), 4.39-4.32 (m, 2H), 4.03-4.01 (m, 2H), 3.69-3.65 (m, 4H), 3.30-3.22 (m, 4H), 2.65-2.64 (m, 2H). |

TABLE 1-continued

| # | Structure | LCMS (M + 1) | ¹H NMR |
|---|---|---|---|
| 441 | 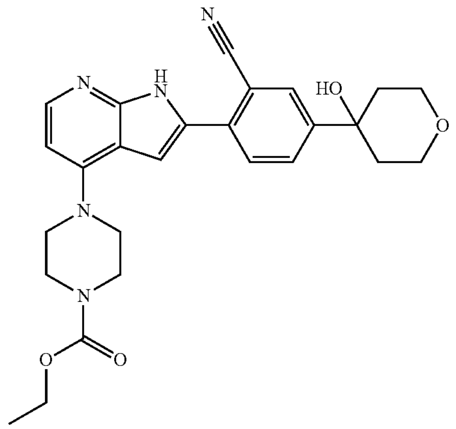 [SMILES: CCOC(=O)N1CCN(c2ccnc3[nH]c(-c4ccc(C5(O)CCOCC5)cc4C#N)cc23)CC1] | 476 | ¹H-NMR (500 MHz, 6d-DMSO) δ ppm 12.10 (s, 1H), 8.06 (d, 1H, J = 5.5 Hz), 8.01 (d, 1H, J = 1.5 Hz), 7.90-7.88 (m, 2H), 7.14 (d, 1H, J = 1.5 Hz), 6.51 (d, 1H, J = 6.0 Hz), 5.36 (s, 1H), 4.09 (q, 2H, J = 7.0 Hz), 3.84-3.78 (m, 2H), 3.78-3.72 (m, 2H), 3.60-3.48 (m, 4H), 3.47-3.46 (m, 4H), 2.08-2.04 (m, 2H), 1.57-1.54 (m, 2H), 1.22 (t, 3H, J = 7.0 Hz). |
| 442 | 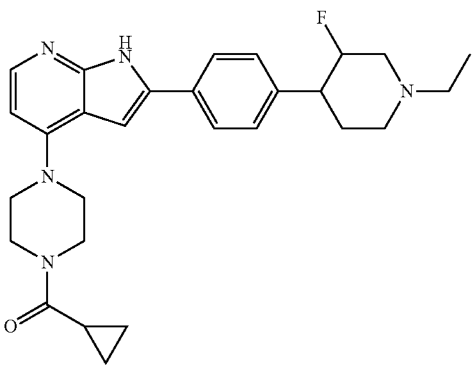 [SMILES: CCN1CCC(c2ccc(-c3cc4c(N5CCN(C(=O)C6CC6)CC5)ccnc4[nH]3)cc2)C(F)C1] | 476 | ¹H-NMR (400 MHz, DMSO-d₆) δ ppm 11.93 (s, 1H), 7.95 (d, 1H, J = 5.2 Hz), 7.88 (d, 2H, J = 8.4 Hz), 7.37 (d, 2H, J = 8.4 Hz), 7.03 (d, 1H, J = 2.0 Hz), 6.42 (d, 1H, J = 5.2 Hz), 4.84-4.63 (m, 1H), 3.91 (br. s., 2H), 3.70 (br. s., 2H), 3.48 (br. s., 2H), 3.41 (br. s., 2H), 2.90-2.88 (m, 1H), 2.69-2.66 (m, 1H), 2.02-1.99 (m, 3H), 1.79-1.70 (m, 2H), 1.04 (d, 3H, J = 7.2 Hz), 0.77-0.73 (m, 4H). |
| 443 | 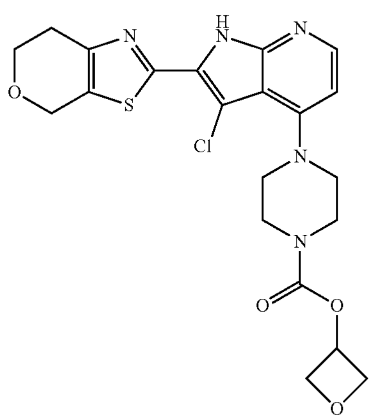 | 476 | ¹H-NMR (500 MHz, 6d-DMSO) δ ppm 12.72 (d, 1H, J = 4.0 Hz), 8.18 (d, 1H, J = 6.0 Hz), 6.68 (d, 1H, J = 5.5 Hz), 5.36-5.31 (m, 1H), 4.90 (s, 2H), 4.80-4.78 (m, 2H), 4.54-4.52 (m, 2H), 4.02-4.0 (m, 2H), 3.77-3.59 (m, 4H), 3.20-3.18 (m, 4H), 2.96-2.91(m, 2H). |
| 444 | 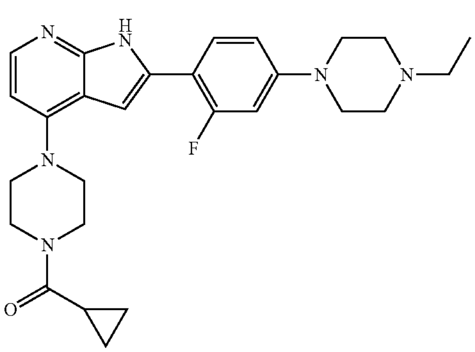 | 477 | ¹H-NMR (400 MHz, 6d-DMSO) δ ppm 11.74 (s, 1H), 7.97 (d, 1H, J = 6.0 Hz), 7.79-7.77 (m, 1H), 6.89-6.85 (m, 2H), 6.74 (s, 1H), 6.45 (d, 1H, J = 5.2 Hz), 3.91 (br. s., 2H), 3.69 (br. s., 2H), 3.48-3.25 (m, 14H), 2.05-1.98 (m., 1H), 1.06(br. s., 3H), 0.78-0.74 (m, 4H). |

TABLE 1-continued

| # | Structure | LCMS (M + 1) | ¹H NMR |
|---|---|---|---|
| 445 | 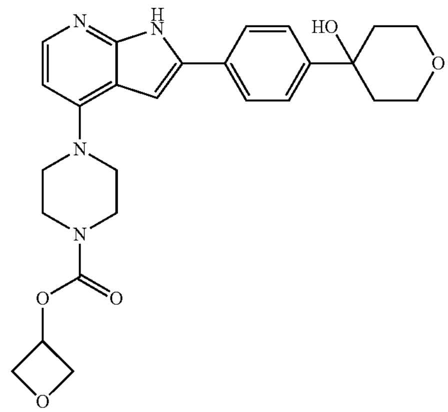 [SMILES: O=C(OC1COC1)N1CCN(c2ccnc3[nH]c(-c4ccc(C5(O)CCOCC5)cc4)cc23)CC1] | 479 | ¹H-NMR (400 MHz, 6d-DMSO) δ ppm 11.93 (s, 1H), 7.97 (d, 1H, J = 5.2 Hz), 7.90 (d, 2H, J = 8.4 Hz), 7.54 (d, 2H, J = 8.4 Hz), 7.02 (s, 1H), 6.45 (d, 1H, J = 5.6 Hz), 5.37-5.31 (m, 1H), 5.07 (s, 1H), 4.81-4.77 (m, 2H), 4.55-4.52 (m, 2H), 3.83-3.60 (m, 8H), 3.45-3.43 (m, 4H), 2.04-2.01 (m, 2H), 1.57-1.54 (m, 2H). |
| 446 | 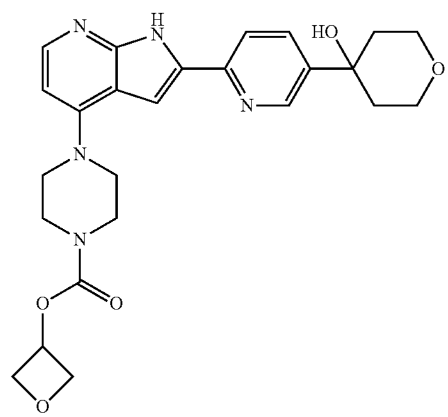 [SMILES: O=C(OC1COC1)N1CCN(c2ccnc3[nH]c(-c4ccc(C5(O)CCOCC5)cn4)cc23)CC1] | 480 | ¹H-NMR (500 MHz, 6d-DMSO) δ ppm 11.98 (s, 1H), 8.74 (d, 1H, J = 2.0 Hz), 8.02-8.00 (m, 2H), 7.93 (dd, 1H, J = 8.5, 2.5 Hz), 7.24 (d, 1H, J = 2.0 Hz), 6.46 (d, 1H, J = 5.0 Hz), 5.33 (quintet, 1H, J = 5.5 Hz), 5.27 (s, 1H), 4.79 (t, 2H, J = 7.5 Hz), 4.53 (dd, 1H, J = 7.5, 5.5 Hz), 3.82-3.75 (m, 2H), 3.74-3.72 (m, 4H), 3.71-3.70 (m, 2H), 3.61-3.60 (m, 4H), 2.05-2.04 (m, 2H), 1.62-1.59 (m, 2H). |
| 447 | 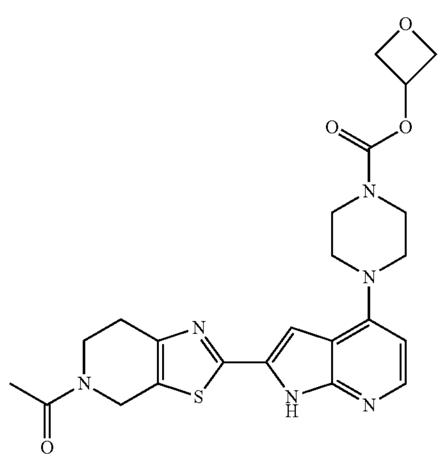 [SMILES: CC(=O)N1CCc2nc(-c3cc4c(N5CCN(C(=O)OC6COC6)CC5)ccnc4[nH]3)sc2C1] | 483 | ¹H-NMR (500 MHz, 6d-DMSO) δ ppm 12.29 (s, 1H), 8.03 (d, 1H, J = 5.5 Hz), 7.10 (d, 1H, J = 6.0 Hz), 6.47 (d, 1H, J = 5.5 Hz), 5.35-5.33 (m, 1H), 4.81-4.76 (m, 4H), 4.55-4.52 (m, 2H), 3.85-3.79 (m, 2H), 3.69-3.66 (m, 4H), 3.48-3.47 (m, 4H), 2.94-2.81 (m, 2H), 2.13 (d, 3H, J = 17.5 Hz). |

TABLE 1-continued

| # | Structure | LCMS (M + 1) | ¹H NMR |
|---|---|---|---|
| 448 | 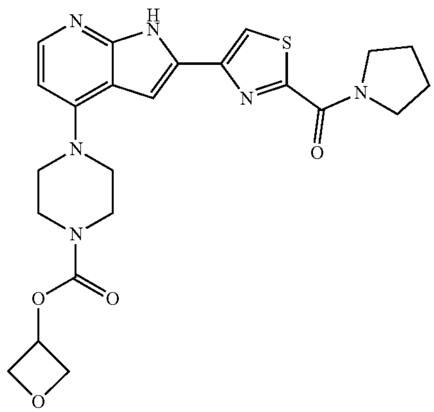 [SMILES: O=C(OC1COC1)N1CCN(c2ccnc3[nH]c(-c4csc(C(=O)N5CCCC5)n4)cc23)CC1] | 483 | ¹H-NMR (400 MHz, 6d-DMSO) δ ppm 12.10 (s, 1H), 8.27 (s, 1H), 8.02 (d, 1H, J = 5.6 Hz), 7.01 (s, 1H), 6.48 (d, 1H, J = 5.6 Hz), 5.35-5.32 (m, 1H), 4.80-4.77 (m, 2H), 4.54-4.51 (m, 2H), 4.18-4.15 (m, 2H), 3.59-3.57 (m, 2H), 3.55-3.53 (m, 4H), 3.47-3.45 (m, 4H), 2.01-1.97 (m, 2H), 1.89-1.86 (m, 2H). |
| 449 | 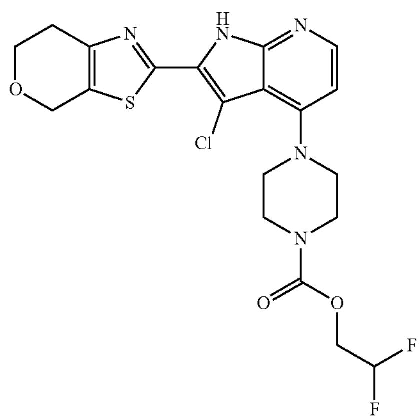 [SMILES: O=C(OCC(F)F)N1CCN(c2ccnc3[nH]c(-c4nc5c(s4)COCC5)c(Cl)c23)CC1] | 484 | ¹H-NMR (500 MHz, 6d-DMSO) δ ppm 12.74 (s, 1H), 8.18 (d, 1H, J = 6.0 Hz), 6.68 (d, 1H, J = 5.5 Hz), 5.40-5.19 (m, 1H), 4.90 (s, 2H), 4.38-4.32 (m, 2H), 4.01-4.0 (m, 2H), 3.68-3.67 (m, 4H), 3.18-3.19 (m, 4H), 2.92-2.93 (m, 2H). |
| 450 | 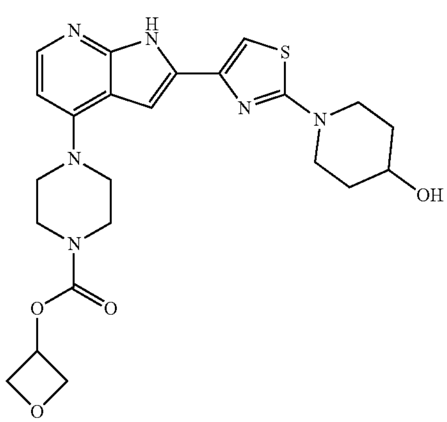 [SMILES: O=C(OC1COC1)N1CCN(c2ccnc3[nH]c(-c4csc(N5CCC(O)CC5)n4)cc23)CC1] | 485 | ¹H-NMR (400 MHz, 6d-DMSO) δ ppm 11.79 (br. s., 1H), 7.97 (d, 1H, J = 6.0 Hz), 7.22 (s, 1H), 6.76 (d, 1H, J = 1.6 Hz), 6.45 (d, 1H, J = 5.6 Hz), 5.34 (quintet, 1H, J = 5.2 Hz), 4.81 (d, 1H, J = 4.4 Hz), 4.79 (t, 2H, J = 7.2 Hz), 4.53 (dd, 2H, J = 7.6, 5.2 Hz), 3.82-3.66 (m, 5H), 3.62-3.56 (m, 2H), 3.44-3.40 (m, 4H), 3.27-3.21 (m, 2H), 1.88-1.82 (m, 2H), 1.52-1.46 (m, 2H). |
| 451 | 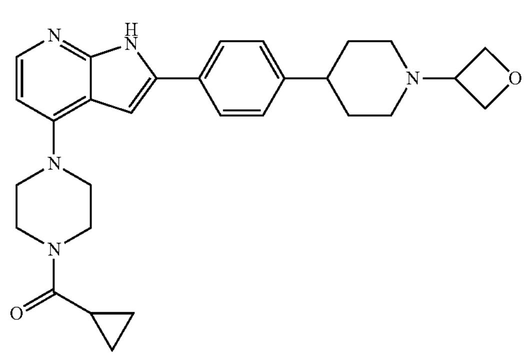 | 486 | ¹H-NMR (400 MHz, DMSO-d₆) δ ppm 11.90 (s, 1H), 8.45 (s, 1H), 7.95 (d, 1H, J = 5.6 Hz), 7.85 (d, 2H, J = 8.0 Hz), 7.31 (d, 2H, J = 8.4 Hz), 7.00 (s, 1H), 6.42 (d, 2H, J = 5.6 Hz), 4.54 (t, 2H, J = 6.4 Hz), 4.44 (t, 2H, J = 6.4 Hz), 3.91 (br. s., 2H), 3.70 (br. s., 2H), 3.47 (br. s., 2H), 3.41-3.38 (m, 3H), 2.81-2.79 (m, 2H), 2.04-2.01 (m, 1H), 1.88-1.66 (m, 6H), 0.77-0.73 (m, 4H). |

TABLE 1-continued

| # | Structure | LCMS (M + 1) | ¹H NMR |
|---|---|---|---|
| 452 | 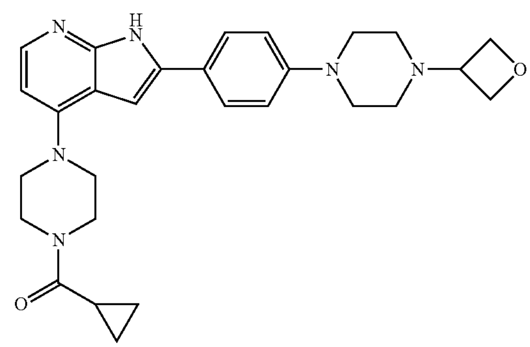 [SMILES: O=C(C1CC1)N1CCN(c2ccnc3[nH]c(-c4ccc(N5CCN(C6COC6)CC5)cc4)cc23)CC1] | 487 | ¹H NMR (400 MHz, DMSO-d₆) δ ppm 11.78 (s, 1H), 7.92 (d, 1H, J = 5.2 Hz), 7.79 (d, 2H, J = 8.8 Hz), 6.98 (d, 2H, J = 8.8 Hz), 6.85 (s, 1H), 6.42 (d, 1H, J = 5.6 Hz), 3.91 (br. s., 2H), 3.70 (br. s., 2H), 3.46 (br. s., 2H), 3.39 (br. s., 2H), 3.25-3.21 (m, 4H), 2.47-2.43 (m, 4H), 2.06-2.00 (m, 1H), 0.78-0.74 (m, 4H). |
| 453 | 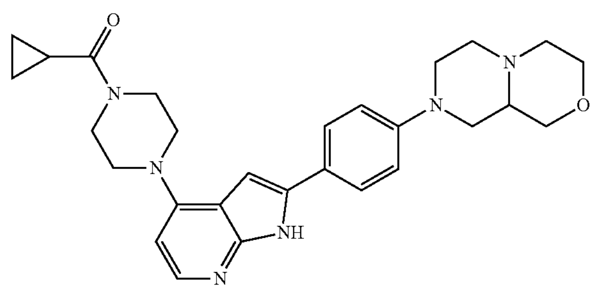 [SMILES: O=C(C1CC1)N1CCN(c2ccnc3[nH]c(-c4ccc(N5CCN6CCOCC6C5)cc4)cc23)CC1] | 487 | ¹H-NMR (400 MHz, 6d-DMSO) δ ppm 11.93 (s, 1H), 7.92 (d, 1H, J = 5.6 Hz), 7.79 (d, 2H, J = 8.0 Hz), 7.00 (d, 2H, J = 8.0 Hz), 6.92 (s, 1H), 6.46 (d, 1H, J = 5.6 Hz), 3.94-3.90 (m, 2H), 3.80-3.45 (m, 12H), 2.23-2.19 (m, 1H), 2.94-2.78 (m, 3H), 2.39-2.27 (m, 3H), 2.05-1.99 (m, 1H), 0.77-0.74 (m, 4H). |
| 454 | 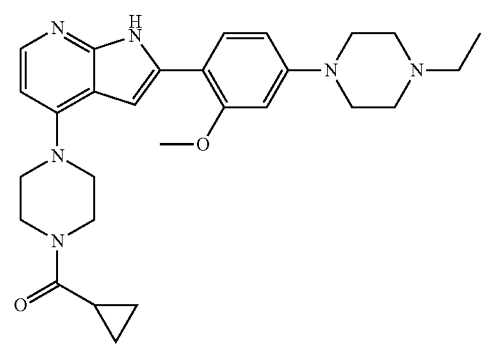 | 489 | ¹H-NMR (400 MHz, 6d-DMSO) δ ppm 11.31 (s, 1H), 8.22 (s, 2H), 7.92 (d, 1H, J = 5.6 Hz), 7.68 (d, 1H, J = 8.8 Hz), 6.83 (s, 1H), 6.62-6.58 (m, 2H), 6.41 (d, 1H, J = 5.6 Hz), 4.00-3.89 (m, 5H), 3.71-3.65 (m, 2H), 3.45-3.39 (m, 2H), 3.35-3.3 (m, 2H), 3.30-3.22 (m, 4H), 2.50-2.40 (m, 2H), 2.38 (q, 2H, J = 7.2 Hz), 2.08-1.95 (m, 1H), 1.05 (t, 3H, J = 7.2 Hz), 0.79-0.73 (m, 4H). |
| 455 | 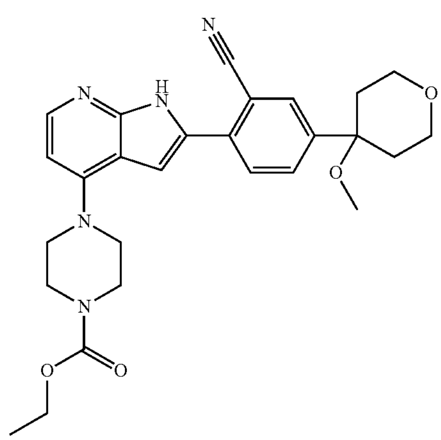 [SMILES: CCOC(=O)N1CCN(c2ccnc3[nH]c(-c4ccc(C5(OC)CCOCC5)cc4C#N)cc23)CC1] | 490 | ¹H-NMR (500 MHz, 6d-DMSO) δ ppm 12.10 (s, 1H), 8.06 (d, 1H, J = 5.0 Hz), 7.94 (d, 1H, J = 8.5 Hz), 7.91 (d, 1H, J = 2.0 Hz), 7.83 (dd, 1H, J = 8.5, 2.0 Hz), 7.19 (s, 1H), 6.51 (d, 1H, J = 5.0 Hz), 4.09 (q, 2H, J = 7.0 Hz), 3.75-3.68 (m, 4H), 3.60-3.49 (m, 4H), 3.47-3.33 (m, 4H), 2.95 (s, 3H), 2.01-1.95 (m, 4H), 1.22 (t, 3H, J = 7.0 Hz). |

TABLE 1-continued

| # | Structure | LCMS (M + 1) | ¹H NMR |
|---|---|---|---|
| 456 | 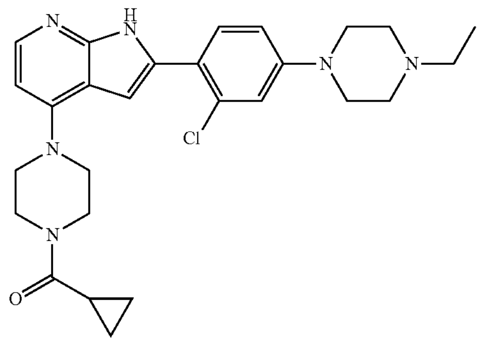 | 494 | ¹H-NMR (400 MHz, 6d-DMSO) δ ppm 11.69 (s, 1H), 7.97 (d, 1H, J = 5.6 Hz), 7.55 (d, 1H, J = 8.8 Hz), 7.07 (s, 1H), 7.01 (dd, 1H, J = 8.8, 2.0 Hz), 6.77 (s, 1H), 6.44 (d, 1H, J = 5.6 Hz), 3.90(br. s., 2H), 3.68 (br. s., 2H), 3.48 (br. s., 2H), 3.39 (br. s., 2H), 3.27 (br. s., 4H), 2.57 (br. s., 4H), 2.49 (br. s., 2H), 2.05-1.96 (m, 1H), 1.07 (t, 3H, J = 6.4 Hz), 0.77-0.71 (m, 4H). |
| 457 | 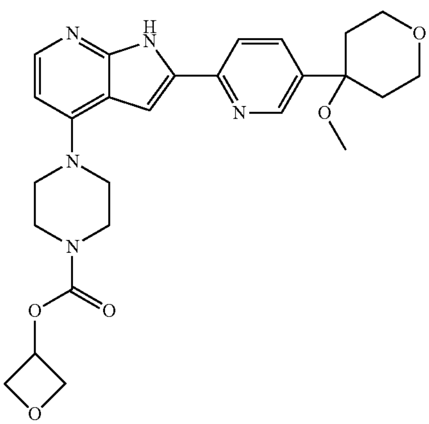 [SMILES: COC1(c2ccc(-c3cc4c(N5CCN(C(=O)OC6COC6)CC5)ccnc4[nH]3)nc2)CCOCC1] | 494 | ¹H-NMR (500 MHz, 6d-DMSO) δ ppm 12.06 (s, 1H), 8.62 (d, 1H, J = 1.5 Hz), 8.06 (d, 1H, J = 8.0 Hz), 8.02 (d, 1H, J = 5.5 Hz), 7.86 (dd, 1H, J = 8.0, 2.5 Hz), 7.28 (d, 1H, J = 2.0 Hz), 6.46 (d, 1H, J = 5.5 Hz), 5.34 (quintet, 1H, J = 5.0 Hz), 4.79 (t, 2H, J = 7.0 Hz), 4.53 (dd, 2H, J = 7.5, 5.0 Hz), 3.73-3.72 (m, 4H), 3.72-3.71 (m, 2H), 3.71-3.70 (m, 2H), 3.61-3.60 (m, 4H), 2.96 (s, 3H), 2.01-1.98 (m, 4H). |
| 458 | 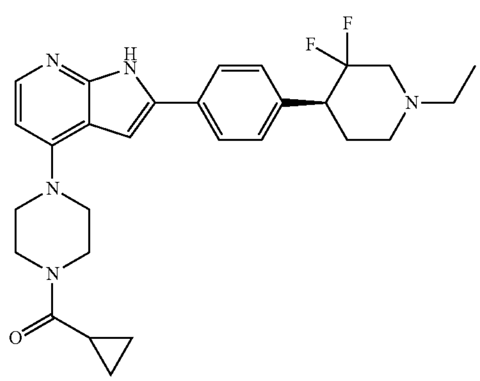 [SMILES: CCN1CC[C@@H](c2ccc(-c3cc4c(N5CCN(C(=O)C6CC6)CC5)ccnc4[nH]3)cc2)C(F)(F)C1] | 494 | ¹H-NMR (400 MHz, 6d-DMSO) δ ppm 11.94 (s, 1H), 7.96 (d, 1H, J = 5.2 Hz), 7.88 (d, 2H, J = 8.0 Hz), 7.35 (d, 2H, J = 8.4 Hz), 7.03 (d, 1H, J = 2.0 Hz), 6.42 (d, 1H, J = 5.2 Hz), 3.91 (s, 2H), 3.70 (s, 2H), 3.48 (s, 2H), 3.42 (s, 2H), 3.19-2.99 (m, 4H), 2.37-2.27 (m, 2H), 2.13-2.02 (m, 3H), 1.82 (s, 1H), 1.03 (t, 2H, J = 6.4 Hz), 0.76-0.74 (m, 4H). |
| 459 | 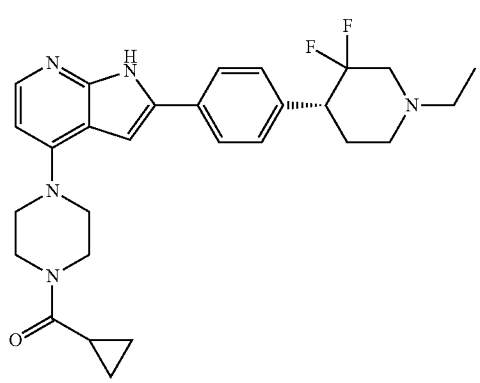 [SMILES: CCN1CC[C@H](c2ccc(-c3cc4c(N5CCN(C(=O)C6CC6)CC5)ccnc4[nH]3)cc2)C(F)(F)C1] | 494 | ¹H-NMR (400 MHz, 6d-DMSO) δ ppm 11.94 (s, 1H), 7.96 (d, 1H, J = 5.2 Hz), 7.88 (d, 2H, J = 8.0 Hz), 7.35 (d, 2H, J = 8.4 Hz), 7.03 (d, 1H, J = 2.0 Hz), 6.42 (d, 1H, J = 5.2 Hz), 3.91 (s, 2H), 3.70 (s, 2H), 3.48 (s, 2H), 3.42 (s, 2H), 3.19-2.99 (m, 4H), 2.37-2.27 (m, 2H), 2.13-2.02 (m, 3H), 1.82 (s, 1H), 1.03 (t, 2H, J = 6.4 Hz), 0.76-.074 (m, 4H). |

TABLE 1-continued

| # | Structure | LCMS (M + 1) | ¹H NMR |
|---|-----------|--------------|--------|
| 460 | 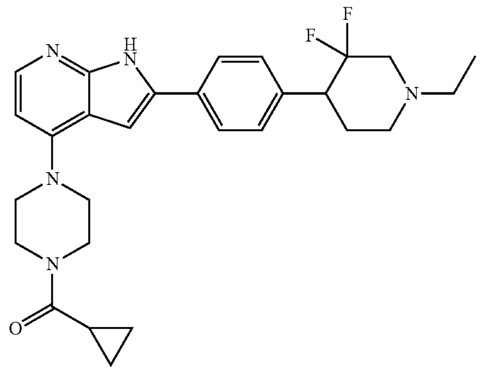 [SMILES: CCN1CCC(c2ccc(-c3cc4c(N5CCN(C(=O)C6CC6)CC5)ccnc4[nH]3)cc2)C(F)(F)C1] | 494 | ¹H-NMR (400 MHz, DMSO-d₆) δ ppm 11.94 (s, 1H), 7.96 (d, 1H, J = 5.2 Hz), 7.88 (d, 2H, J = 8.0 Hz), 7.35 (d, 2H, J = 8.4 Hz), 7.03 (d, 1H, J = 2.0 Hz), 6.42 (d, 1H, J = 5.2 Hz), 3.91 (br. s., 2H), 3.70 (br. s., 2H), 3.48 (br. s., 2H), 3.42 (br. s., 2H), 3.19-3.06 (m, 2H), 3.00-2.98 (m, 1H), 2.48-2.44 (m, 2H), 2.37-2.26 (m, 1H), 2.13-2.08 (m, 2H), 2.05-1.99 (m, 1H), 1.82-1.81 (m, 1H), 1.04 (t, 3H, J = 7.2 Hz), 0.79-0.71 (m, 4H) |
| 461 | 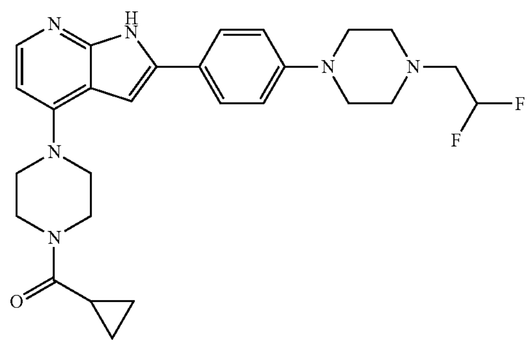 [SMILES: O=C(C1CC1)N1CCN(c2ccnc3[nH]c(-c4ccc(N5CCN(CC(F)F)CC5)cc4)cc23)CC1] | 495 | ¹H-NMR (400 MHz, DMSO-d₆) δ ppm 11.77 (s, 1H), 7.92 (d, 1H, J = 5.6 Hz), 7.80-7.78 (m, 2H), 7.01-6.98 (m, 2H), 6.85 (d, 1H, J = 1.2 Hz), 6.42 (d, 1H, J = 5.6 Hz), 6.20 (tt, 1H, J = 56 Hz, 4.4 Hz), 3.91 (br. s., 2H), 3.70 (br. s., 2H), 3.46 (br. s., 2H), 3.39 (br. s., 2H), 3.22-3.16 (m, 4H), 2.84-2.75 (m, 2H), 2.69-2.67 (m, 4H), 2.08-1.99 (m, 1H), 0.78-0.72 (m, 4H). |
| 462 | 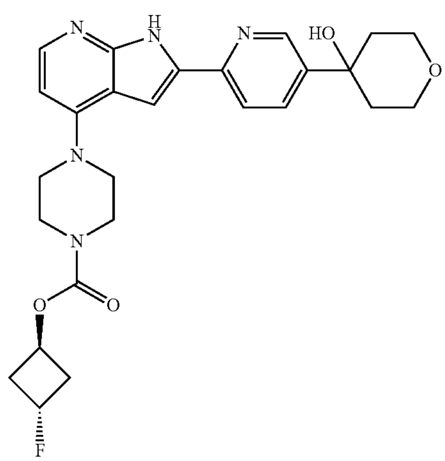 [SMILES: O=C(O[C@H]1C[C@H](F)C1)N1CCN(c2ccnc3[nH]c(-c4ccc(C5(O)CCOCC5)cn4)cc23)CC1] | 496 | ¹H-NMR (400 MHz, 6d-DMSO) δ ppm 11.96 (s, 1H), 8.73 (d, 1H, J = 2.4 Hz), 8.02-7.96 (m, 2H), 7.92 (dd, 1H, J = 8.4, 2.4 Hz), 7.23 (s, 1H), 6.44 (d, 1H, J = 5.6 Hz), 5.40-5.32 (m, 0.5H), 5.27 (s, 1H), 5.24-5.18 (m, 0.5H), 5.14-5.02 (m, 1H), 3.90-3.70 (m, 4H), 3.68-3.54 (m, 4H), 3.50-3.40 (m, 4H), 2.70-2.52 (m, 2H), 2.46-2.38 (m, 2H), 2.10-1.98 (m, 2H), 1.64-1.56 (m, 2H). |
| 463 | 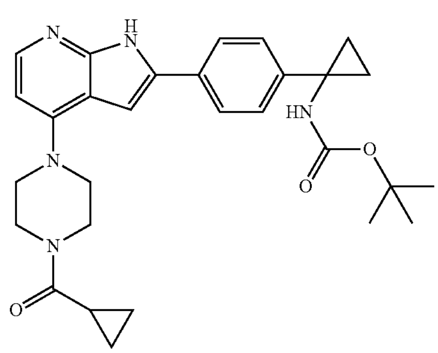 [SMILES: CC(C)(C)OC(=O)NC1(c2ccc(-c3cc4c(N5CCN(C(=O)C6CC6)CC5)ccnc4[nH]3)cc2)CC1] | 502 | |

TABLE 1-continued

| # | Structure | LCMS (M + 1) | ¹H NMR |
|---|---|---|---|
| 464 | 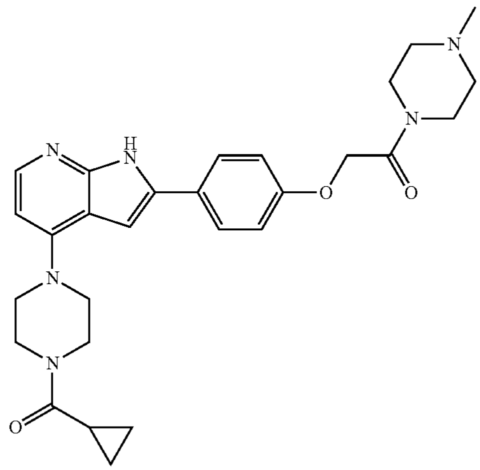 [SMILES: CN1CCN(C(=O)COc2ccc(-c3cc4c(N5CCN(C(=O)C6CC6)CC5)ccnc4[nH]3)cc2)CC1] | 503 | ¹H-NMR (400 MHz, 6d-DMSO) δ ppm 11.84 (s, 1H), 7.94 (d, 1H, J = 5.2 Hz), 7.85 (d, 2H, J = 8.8 Hz), 6.98 (d, 2H, J = 8.8 Hz), 6.92 (d, 1H, J = 2.4 Hz), 6.42 (d, 1H, J = 5.2 Hz), 4.86 (s, 2H), 3.95-3.85 (m, 2H), 3.75-3.65 (m, 2H), 3.46-3.40 (m, 8H), 2.40-2.30 (m, 2H), 2.30-2.20 (m, 2H), 2.18 (s, 3H), 2.04-2.00 (m, 1H), 0.78-0.73 (m, 4H). |
| 465 | 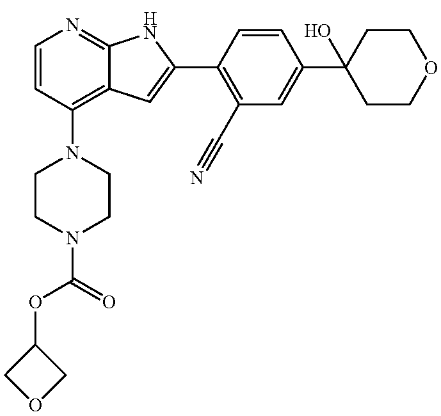 [SMILES: N#Cc1cc(C2(O)CCOCC2)ccc1-c1cc2c(N3CCN(C(=O)OC4COC4)CC3)ccnc2[nH]1] | 504 | ¹H-NMR (500 MHz, 6d-DMSO) δ ppm 12.18-12.01 (br., 1H), 8.07-8.01 (m, 1H), 8.01 (s, 1H), 7.90-7.89 (m, 2H), 7.15 (s, 1H), 6.52(d, 1H, J = 6.0 Hz), 5.36 (s, 1H), 5.33 (quintet, 1H, J = 5.5 Hz), 4.78 (t, 2H, J = 7.5 Hz), 4.53 (dd, 1H, J = 7.5, 5.5 Hz), 3.83-3.78 (m, 4H), 3.75-3.70 (m, 2H), 3.70-3.65 (m, 2H), 3.59-3.50 (m, 4H), 2.09-2.03 (m, 2H), 1.58-1.55 (m, 2H). |
| 466 | 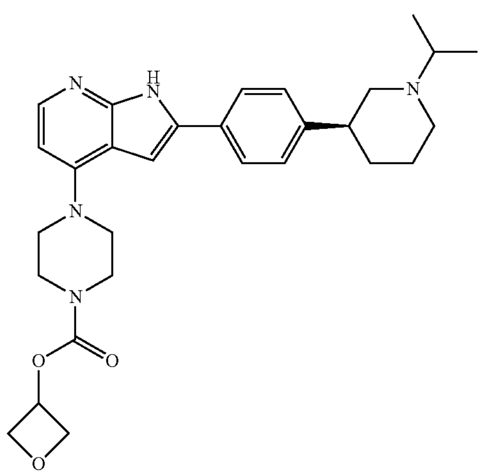 [SMILES: CC(C)N1CCC[C@@H](c2ccc(-c3cc4c(N5CCN(C(=O)OC6COC6)CC5)ccnc4[nH]3)cc2)C1] | 504 | ¹H-NMR (500 MHz, 6d-DMSO) δ ppm 11.92 (s, 1H), 7.97 (d, 1H, J = 5.5 Hz), 7.76 (d, 2H, J = 8.5 Hz), 7.33 (d, 2H, J = 8.5 Hz), 6.99 (d, 1H, J = 1.5 Hz), 6.45 (d, 1H, J = 5.5 Hz), 5.34 (quintet, 1H, J = 5.5 Hz), 4.80 (t, 2H, J = 7.0 Hz), 4.54 (dd, 2H, J = 8.0, 5.5 Hz), 3.72-3.67 (m, 2H), 3.65-3.60 (m, 2H), 3.46-3.44 (m, 4H), 2.85-2.80 (m, 2H), 2.75-2.73 (m, 2H), 2.22-2.14 (m, 2H), 1.88-1.84 (m, 1H), 1.79-1.73 (m, 1H), 1.60-1.54 (m, 1H), 1.50-1.42 (m, 1H), 1.00-0.98 (m, 6H). |

TABLE 1-continued

| # | Structure | LCMS (M + 1) | ¹H NMR |
|---|---|---|---|
| 467 | 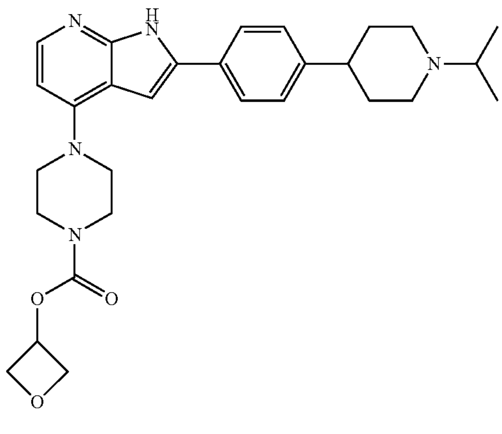 | 504 | ¹H-NMR (400 MHz, 6d-DMSO) δ ppm 11.91 (s, 1H), 7.97 (d, 1H, J = 5.2 Hz), 7.86 (d, 2H, J = 8.0 Hz), 7.31 (d, 2H, J = 8.0 Hz), 6.99 (s, 1H), 6.45 (d, 1H, J = 5.2 Hz), 5.34 (quintet, 1H, J = 5.2 Hz), 4.80 (t, 2H, J = 7.2 Hz), 4.54 (dd, 2H, J = 7.6, 5.2 Hz), 3.72-3.68 (m, 2H), 3.67-3.61 (m, 2H), 3.50-3.40 (m, 4H), 3.32-3.28 (m, 1H), 2.94-2.84 (m, 2H), 2.76-2.66 (m, 1H), 2.28-2.16 (m, 2H), 1.82-1.72 (m, 2H), 1.70-1.56 (m, 2H), 1.00 (d, 6H, J = 6.8 Hz). |
| 468 | 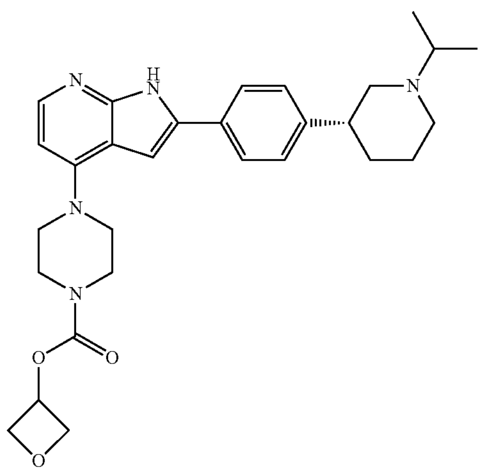 [SMILES: CC(C)N1CCC[C@H](c2ccc(-c3cc4c(N5CCN(C(=O)OC6COC6)CC5)ccnc4[nH]3)cc2)C1] | 504 | ¹H-NMR (500 MHz, 6d-DMSO) δ ppm 11.93 (s, 1H), 8.20 (s, 2H), 7.98 (d, 1H, J = 5.5 Hz), 7.87 (d, 2H, J = 8.5 Hz), 7.33 (d, 2H, J = 8.5 Hz), 6.99 (s, 1H), 6.44 (d, 1H, J = 5.5 Hz), 5.34 (quintet, 1H, J = 5.5 Hz), 4.79 (t, 2H, J = 7.0 Hz), 4.53 (dd, 2H, J = 7.5, 5.5 Hz), 3.70-3.65 (m, 2H), 3.62-3.57 (m, 2H), 3.59-3.48 (m, 4H), 2.97-2.92 (m, 3H), 2.85-2.82 (m, 1H), 2.45-2.40 (m, 1H), 2.40-2.36 (m, 1H), 1.86-1.78 (m, 2H), 1.68-1.61 (m, 1H), 1.55-1.51 (m, 1H), 1.07-1.05 (m, 6H). |
| 469 | 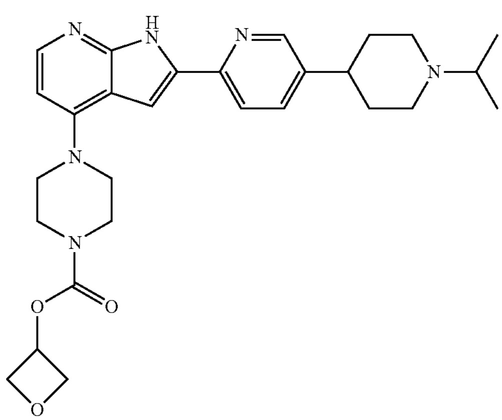 | 505 | ¹H-NMR (400 MHz, 6d-DMSO) δ ppm 11.97 (s, 1H), 8.51 (s, 1H), 8.01-7.97 (m, 2H), 7.76 (d, 1H, J = 8.0 Hz), 7.21 (s, 1H), 6.45 (d, 1H, J = 5.6 Hz), 5.34 (quintet, 1H, J = 5.6 Hz), 4.79 (t, 2H, J = 7.2 Hz), 4.54 (dd, 2H, J = 7.2, 5.6 Hz), 3.73-3.68 (m, 2H), 3.68-3.62 (m, 2H), 3.49-3.46 (m, 4H), 2.94-2.92 (m, 2H), 2.74-2.72 (m, 1H), 2.55-2.51 (m, 1H), 2.33-2.32 (m, 2H), 1.83-1.78 (m, 2H), 1.75-1.69 (m, 2H), 1.02 (d, 6H J = 6.0 Hz). |

TABLE 1-continued

| # | Structure | LCMS (M + 1) | ¹H NMR |
|---|---|---|---|
| 470 | 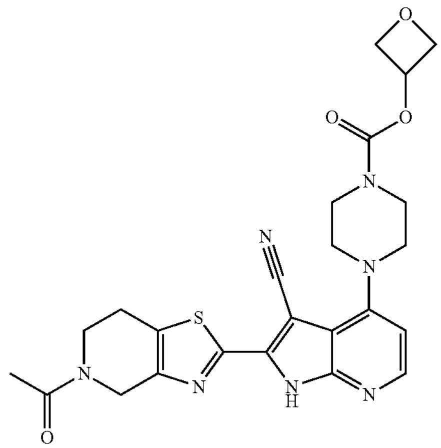 [SMILES: CC(=O)N1CCc2sc(-c3[nH]c4nccc(N5CCN(C(=O)OC6COC6)CC5)c4c3C#N)nc2C1] | 508 | ¹H-NMR (500 MHz, 6d-DMSO) δ ppm 12.95 (brs, 1H), 8.34 (s, 1H), 8.10-8.00 (m, 1H), 6.60-6.49 (m, 1H), 5.35-5.29 (m, 1H), 4.81-4.77 (m, 2H), 4.76-4.66 (m, 2H), 4.55-4.50 (m, 2H), 3.92-3.50 (m, 6H), 3.32-3.20 (m, 4H), 3.02-2.80 (m, 2H), 2.13 (s, 3H). |
| 471 | 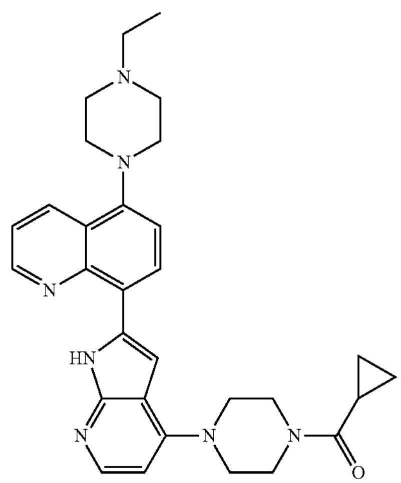 [SMILES: CCN1CCN(c2ccc(-c3cc4c(N5CCN(C(=O)C6CC6)CC5)ccnc4[nH]3)c3ncccc23)CC1] | 510 | ¹H-NMR (400 MHz, 6d-DMSO) δ ppm 12.88 (s, 1H), 8.96 (dd, 1H, J = 4.0, 1.6 Hz), 8.61-8.58 (m, 1H), 8.28 (d, 1H, J = 8.0 Hz), 8.14 (d, 1H, J = 5.6 Hz), 7.49-7.45 (m, 1H), 7.23 (d, 1H, J = 7.6 Hz), 6.99 (d, 1H, J = 1.6 Hz), 6.45 (d, 1H, J = 5.6 Hz), 4.011-3.98 (m, 2H), 3.96-3.93 (m, 2H), 3.60-3.55 (m, 2H), 3.55-3.50 (m, 2H), 3.20-3.18 (m, 4H), 2.77-2.75 (m, 4H), 2.57 (q, 2H, J = 7.2 Hz), 1.83-1.81 (m, 1H), 1.18 (t, 3H, J = 7.2 Hz), 1.07-1.04 (m, 2H), 0.86-0.82 (m, 2H). |
| 472 | 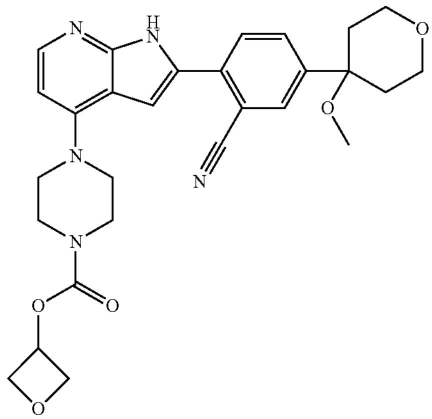 [SMILES: COC1(c2ccc(-c3cc4c(N5CCN(C(=O)OC6COC6)CC5)ccnc4[nH]3)c(C#N)c2)CCOCC1] | 518 | ¹H-NMR (400 MHz, 6d-DMSO) δ ppm 12.14 (s, 1H), 8.07 (d, 1H, J = 5.6 Hz), 7.94 (d, 1H, J = 8.0 Hz), 7.91 (d, 1H, J = 1.6 Hz), 7.83 (dd, 1H, J = 8.0, 1.6 Hz), 7.19 (s, 1H), 6.52 (d, 1H, J = 5.6 Hz), 5.34 (quintet, 1H, J = 5.2 Hz), 4.79 (t, 2H, J = 7.2 Hz), 4.54 (dd, 2H, J = 7.2, 5.2 Hz), 3.75-3.69 (m, 4H), 3.69-3.65 (m, 2H), 3.63-3.57 (m, 2H), 3.52-3.49 (m, 4H), 2.95 (s, 3H), 2.01-1.98 (m, 4H). |

TABLE 1-continued

| # | Structure | LCMS (M + 1) | ¹H NMR |
|---|---|---|---|
| 473 | 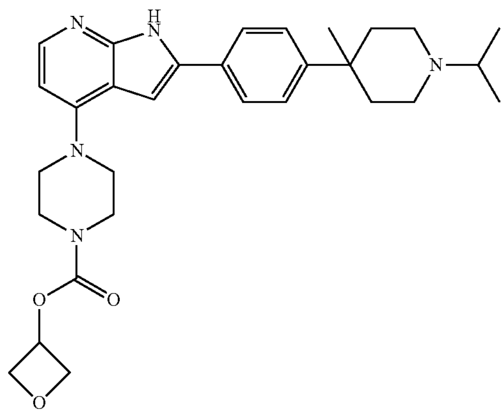 [SMILES: CC(C)N1CCC(C)(c2ccc(-c3cc4c(N5CCN(C(=O)OC6COC6)CC5)ccnc4[nH]3)cc2)CC1] | 518 | ¹H-NMR (400 MHz, 6d-DMSO) δ ppm 11.92 (s, 1H), 7.97 (d, 1H, J = 5.2 Hz), 7.88 (d, 2H, J = 8.4 Hz), 7.43 (d, 2H, J = 8.4 Hz), 6.98 (s, 1H), 6.45 (d, 1H, J = 5.2 Hz), 5.34 (quintet, 1H, J = 5.2 Hz), 4.79 (t, 2H, J = 6.8 Hz), 4.53 (dd, 2H, J = 7.6, 5.2 Hz), 3.69-3.64 (m, 2H), 3.64-3.59 (m, 2H), 3.46-3.43 (m, 4H), 2.63-2.59 (m, 1H), 2.49-2.46 (m, 2H), 2.42-2.38 (m, 2H), 2.05-2.00 (m, 2H), 1.74-1.69 (m, 2H), 1.18 (s, 3H), 0.93 (d, 6H, J = 6.8 Hz). |
| 474 | 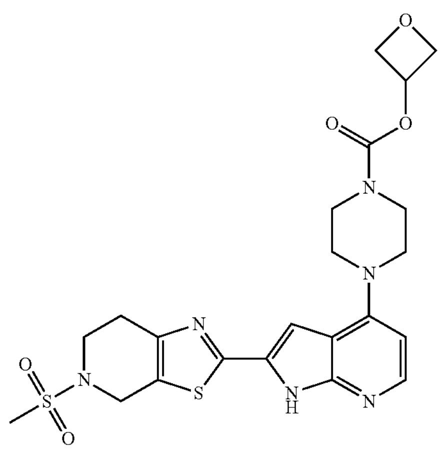 [SMILES: CS(=O)(=O)N1CCc2nc(-c3cc4c(N5CCN(C(=O)OC6COC6)CC5)ccnc4[nH]3)sc2C1] | 519 | ¹H-NMR (400 MHz, 6d-DMSO) δ ppm 12.32 (s, 1H), 8.02 (d, 1H, J = 5.6 Hz), 7.11 (s, 1H), 6.46 (d, 1H, J = 5.6 Hz), 5.34-5.31 (m, 1H), 4.80-4.76 (m, 2H), 4.57-4.54 (m, 2H), 4.50-4.53 (m, 2H), 3.68-3.67 (m, 2H), 3.61-3.58 (m, 4H), 3.47-3.46 (m, 4H), 3.0 (s, 3H), 2.97-2.94(m, 2H). |
| 475 | 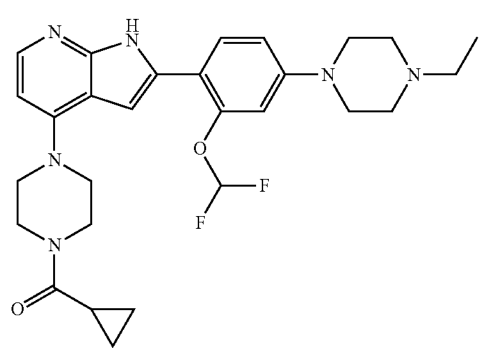 [SMILES: CCN1CCN(c2ccc(-c3cc4c(N5CCN(C(=O)C6CC6)CC5)ccnc4[nH]3)c(OC(F)F)c2)CC1] | 525 | ¹H-NMR (400 MHz, DMSO-d₆) δ ppm 11.63 (s, 1H), 7.95 (d, 1H, J = 6.0 Hz), 7.76 (d, 1H, J = 8.8 Hz), 7.26 (t, 1H, J = 74.4 Hz), 6.90 (dd, 1H, J = 8.4 Hz, 1.6 Hz), 6.82 (s, 1H), 6.75 (s, 1H), 6.43 (d, 1H, J = 5.6 Hz), 3.89 (br. s., 2H), 3.68 (br. s., 2H), 3.46 (br. s., 2H), 3.39 (br. s., 2H), 3.23-3.22 (m, 4H), 2.49-2.45 (m, 4H), 2.36 (q, 2H, J = 6.8 Hz), 2.06-1.99 (m, 1H), 1.03 (t, 3H, J = 7.2 Hz), 0.78-0.70 (m, 4H). |

US 11,236,086 B2
281  282
TABLE 1-continued
| # | Structure | LCMS (M + 1) | ¹H NMR |
|---|---|---|---|
| 476 | 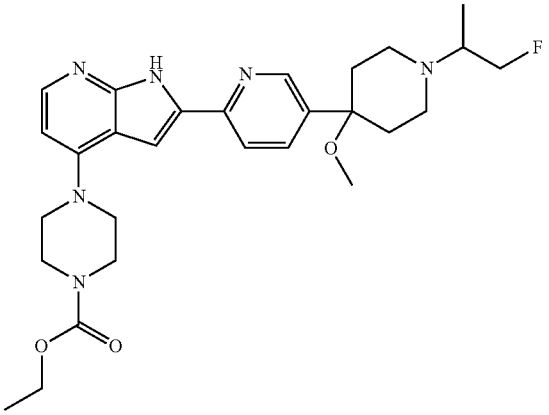 [SMILES: CCOC(=O)N1CCN(c2ccnc3[nH]c(-c4ccc(C5(OC)CCN(C(C)CF)CC5)cn4)cc23)CC1] | 525 | ¹H-NMR (500 MHz, 6d-DMSO) δ ppm 12.06 (br. s, 1H), 8.62 (s, 1H), 8.07 (br. s, 2H), 8.05-8.01 (m, 2H), 7.84 (dd, 1H, J = 8.0, 2.0 Hz), 7.27 (s, 1H), 6.46 (d, 1H, J = 5.0 Hz), 4.55-4.37 (m, 2H), 4.09 (q, 2H, J = 7.0 Hz), 3.61-3.60 (m, 4H), 3.46-3.45 (m, 4H), 2.99-2.97 (m, 1H), 2.94 (s, 3H), 2.71-2.68 (m, 4H), 2.06-2.03 (m, 2H), 1.96-1.91 (m, 2H), 1.22 (t, 3H, J = 7.0 Hz), 1.03 (d, 3H, J = 6.0 Hz). |
| 477 | 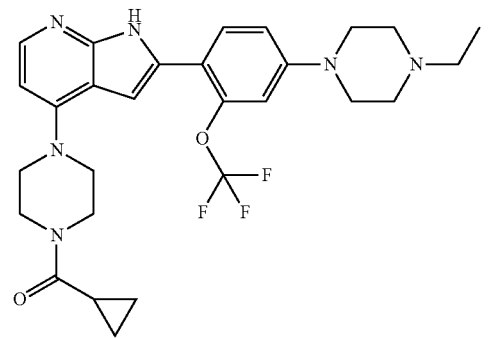 [SMILES: CCN1CCN(c2ccc(-c3cc4c(N5CCN(C(=O)C6CC6)CC5)ccnc4[nH]3)c(OC(F)(F)F)c2)CC1] | 543 | ¹H-NMR (400 MHz, 6d-DMSO) δ ppm 11.76 (s, 1H), 7.98 (d, 1H, J = 5.2 Hz), 7.80 (d, 1H, J = 8.8 Hz), 7.06 (dd, 1H, J = 8.8, 2.0 Hz), 6.91 (br. s., 1H), 6.45 (d, 1H, J = 5.6 Hz), 3.94-3.90 (m, 2H), 3.71-3.68 (m, 2H), 3.51-3.47 (m, 2H), 3.42-3.38 (m, 2H), 3.35-3.28 (m, 4H), 3.28-3.24 (m, 4H), 2.38 (q, 2H, J = 7.2 Hz), 2.07-2.0 (m, 1H), 1.04 (t, 3H, J = 7.2 Hz), 0.80-0.70 (m, 4H). |
| 478 | 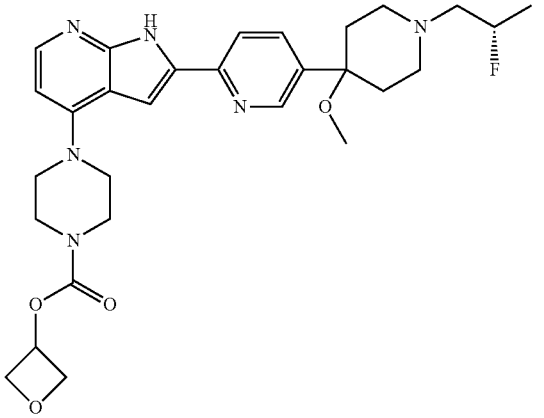 [SMILES: COC1(c2ccc(-c3cc4c(N5CCN(C(=O)OC6COC6)CC5)ccnc4[nH]3)nc2)CCN(C[C@H](C)F)CC1] | 553 | ¹H-NMR (400 MHz, 6d-DMSO) δ ppm 12.05 (s, 1H), 8.62 (d, 1H, J = 2.0 Hz), 8.06-8.01 (m, 1H), 8.02 (d, 1H, J = 5.6 Hz), 7.85 (dd, 1H, J = 8.4, 2.0 Hz), 7.27 (d, 1H, J = 1.2 Hz), 6.46 (d, 1H, J = 5.6 Hz), 5.33 (quintet, 1H, J = 5.6 Hz), 4.95-4.90 (m, 1H), 4.79 (t, 2H, J = 7.2 Hz), 4.53 (dd, 2H, J = 7.2, 5.6 Hz), 3.75-3.65 (m, 2H), 3.65-3.58 (m, 2H), 3.51-3.45 (m, 4H), 2.93 (s, 3H), 2.75-2.69 (m, 2H), 2.62-2.54 (m, 1H), 2.48-2.40 (m, 3H), 2.03-1.92 (m, 4H), 1.31-1.23 (dd, 3H, J = 24.0, 6.4 Hz). |

| # | Structure | LCMS (M + 1) | ¹H NMR |
|---|---|---|---|
| 479 | 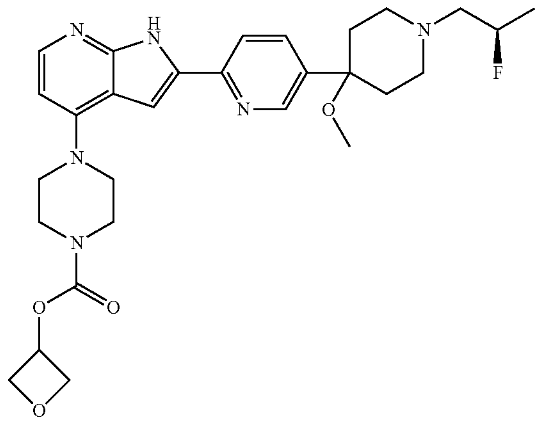 [SMILES: COC1(c2ccc(-c3cc4c(N5CCN(C(=O)OC6COC6)CC5)ccnc4[nH]3)nc2)CCN(C[C@@H](C)F)CC1] | 553 | ¹H-NMR (400 MHz, 6d-DMSO) δ ppm 12.05 (s, 1H), 8.62 (d, 1H, J = 2.0 Hz), 8.06-8.01 (m, 1H), 8.02 (d, 1H, J = 5.6 Hz), 7.85 (dd, 1H, J = 8.4, 2.0 Hz), 7.27 (d, 1H, J = 1.2 Hz), 6.46 (d, 1H, J = 5.6 Hz), 5.33 (quintet, 1H, J = 5.6 Hz), 4.95-4.90 (m, 1H). 4.79 (t, 2H, J = 7.2 Hz), 4.53 (dd, 2H, J = 7.2, 5.6 Hz), 3.75-3.65 (m, 2H), 3.65-3.58 (m, 2H), 3.51-3.45 (m, 4H), 2.93 (s, 3H), 2.75-2.69 (m, 2H), 2.62-2.54 (m, 1H), 2.48-2.40 (m, 3H), 2.03-1.92 (m, 4H), 1.31-1.23 (dd, 3H, J = 24.0, 6.4 Hz). |
| 480 | 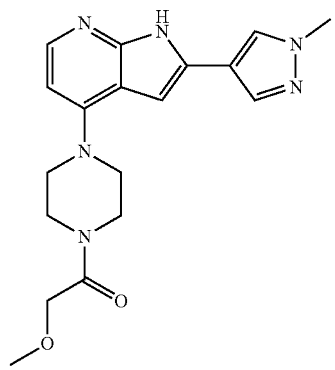 | | |

In another aspect, the present disclosure features a method of treating or ameliorating fibrodysplasia ossificans progressiva in a subject, comprising administering to the subject a pharmaceutically effective amount of a compound described herein (e.g., a compound in Table 1) or a pharmaceutically acceptable salt thereof, or a pharmaceutical composition thereof.

In another aspect, the present disclosure features a method of treating or ameliorating diffuse intrinsic pontine glioma in a subject, comprising administering to the subject a pharmaceutically effective amount of a compound described herein (e.g., a compound in Table 1) or a pharmaceutically acceptable salt thereof, or a pharmaceutical composition thereof.

In another aspect, the present disclosure features a method of inhibiting aberrant ALK2 activity in a subject, comprising administering to the subject a therapeutically effective amount of a compound described herein (e.g., a compound in Table 1) or a pharmaceutically acceptable salt thereof, or a pharmaceutical composition thereof.

Pharmaceutically acceptable salts of these compounds are also contemplated for the uses described herein.

"Pharmaceutically acceptable salt" refers to any salt of a compound of the disclosure which retains its biological properties and which is not toxic or otherwise undesirable for pharmaceutical use. Pharmaceutically acceptable salts may be derived from a variety of organic and inorganic counter-ions. Such salts include one or more of: (1) acid addition salts formed with organic or inorganic acids such as hydrochloric, hydrobromic, sulfuric, nitric, phosphoric, sulfamic, acetic, trifluoroacetic, trichloroacetic, propionic, hexanoic, cyclopentylpropionic, glycolic, glutaric, pyruvic, lactic, malonic, succinic, sorbic, ascorbic, malic, maleic, fumaric, tartaric, citric, benzoic, 3-(4-hydroxybenzoyl)benzoic, picric, cinnamic, mandelic, phthalic, lauric, methanesulfonic, ethanesulfonic, 1,2-ethane-disulfonic, 2-hydroxyethanesulfonic, benzenesulfonic, 4-chlorobenzenesulfonic, 2-naphthalenesulfonic, 4-toluenesulfonic, camphoric, camphorsulfonic, 4-methylbicyclo[2.2.2]-oct-2-ene-1-carboxylic, glucoheptonic, 3-phenylpropionic, trimethylacetic, tert-butylacetic, lauryl sulfuric, gluconic, benzoic, glutamic, hydroxynaphthoic, salicylic, stearic, cyclohexylsulfamic, quinic, muconic acid and the like acids; or (2) salts formed when an acidic proton present in the parent compound either (a) is replaced by a metal ion, e.g., an alkali metal ion, an alkaline earth ion, or an aluminum ion, or alkali metal or alkaline earth metal hydroxides, such as sodium, potassium, calcium, magnesium, aluminum, lithium, zinc, and barium hydroxide, ammonia or (b) coordinates with an organic base, such as aliphatic, alicyclic, or aromatic organic amines, such as ammonia, methylamine, dimethylamine, diethylamine, picoline, ethanolamine, diethanolamine, triethanolamine, ethylenediamine, lysine, arginine, ornithine, choline, N,N-dibenzylethylene-diamine, chloroprocaine, diethanolamine, procaine, N-benzylphenethyl amine, N-methylglucamine piperazine, tris(hydroxymethyl)-aminomethane, tetramethylammonium hydroxide, and the like. Pharmaceutically acceptable salts further include, by way of example only, sodium, potassium, calcium, magnesium, ammonium, tetraalkylammonium and the like, and when the compound contains a basic functionality, salts of non-toxic organic or inorganic acids, such as hydrochloride, hydrobromide, tartrate, mesylate, besylate, acetate, maleate, oxalate and the like. A pharmaceutically acceptable salt according to the disclosure includes at least one salt, and also may be mixtures of more than one salt.

Pharmaceutical compositions of the disclosure comprise one or more compounds of the disclosure and one or more pharmaceutically acceptable carrier(s). The term "pharmaceutically acceptable carrier" refers to a pharmaceutically-acceptable material, composition, or vehicle, such as a liquid or solid filler, diluent, excipient, solvent, or encapsulating material, involved in carrying or transporting any subject composition or component thereof. Each carrier must be "acceptable" in the sense of being compatible with the subject composition and its components and not injurious to the patient. Some examples of materials which may serve as pharmaceutically acceptable carriers include: (1) sugars, such as lactose, glucose, and sucrose; (2) starches, such as corn starch and potato starch; (3) cellulose and its derivatives, such as sodium carboxymethyl cellulose, ethyl cellulose, and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil, and soybean oil; (10) glycols, such as propylene glycol; (11) polyols, such as glycerin, sorbitol, mannitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compositions of the disclosure may be administered orally, parenterally, by inhalation spray, topically, rectally, nasally, buccally, vaginally, or via an implanted reservoir. The term "parenteral" as used herein includes subcutaneous, intravenous, intramuscular, intra-articular, intra-synovial, intrasternal, intrathecal, intrahepatic, intralesional, and intracranial injection or infusion techniques. In some embodiments, the compositions of the disclosure are administered orally, intraperitoneally, or intravenously. Sterile injectable forms of the compositions of this disclosure may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives, are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tween, Spans, and other emulsifying agents or bioavailability enhancers which are commonly used in the manufacture of pharmaceutically acceptable solid, liquid, or other dosage forms may also be used for the purposes of formulation.

The pharmaceutically acceptable compositions of this disclosure may be orally administered in any orally acceptable dosage form including, but not limited to, capsules, tablets, aqueous suspensions, or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring, or coloring agents may also be added.

Alternatively, the pharmaceutically acceptable compositions of this disclosure may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax, and polyethylene glycols.

The pharmaceutically acceptable compositions of this disclosure may also be administered topically, especially when the target of treatment includes areas or organs readily accessible by topical application, including diseases of the eye, the skin, or the lower intestinal tract. Suitable topical formulations are readily prepared for each of these areas or organs. Topical application for the lower intestinal tract can be effected in a rectal suppository formulation (see above) or in a suitable enema formulation.

Topically-transdermal patches may also be used.

For topical applications, the pharmaceutically acceptable compositions may be formulated in a suitable ointment containing the active component suspended or dissolved in one or more carriers. Carriers for topical administration of the compounds of this disclosure include, but are not limited to, mineral oil, liquid petrolatum, white petrolatum, propylene glycol, polyoxyethylene, polyoxypropylene compound, emulsifying wax, and water. Alternatively, the pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol, and water.

The pharmaceutically acceptable compositions of this disclosure may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of the compounds of the present disclosure that may be combined with the carrier to produce a composition in a single dosage form will vary depending upon the host treated, the particular mode of administration, and other factors determined by the person administering the single dosage form.

Toxicity and therapeutic efficacy of compounds of the disclosure, including pharmaceutically acceptable salts and deuterated variants, can be determined by standard pharmaceutical procedures in cell cultures or experimental animals. The $LD_{50}$ is the dose lethal to 50% of the population. The $ED_{50}$ is the dose therapeutically effective in 50% of the population. The dose ratio between toxic and therapeutic effects ($LD_{50}/ED_{50}$) is the therapeutic index. Compounds that exhibit large therapeutic indexes are preferred. While compounds that exhibit toxic side effects may be used, care should be taken to design a delivery system that targets such compounds to the site of affected tissue in order to minimize potential damage to uninfected cells and, thereby, reduce side effects.

Data obtained from the cell culture assays and animal studies can be used in formulating a range of dosage for use in humans. The dosage of such compounds may lie within a range of circulating concentrations that include the $ED_{50}$ with little or no toxicity. The dosage may vary within this range depending upon the dosage form employed and the route of administration utilized. For any compound, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

It should also be understood that a specific dosage and treatment regimen for any particular patient will depend upon a variety of factors, including, but not limited to, the activity of the specific compound employed, the age, body weight, general health, sex, diet, time of administration, rate of excretion, drug combination, and the judgment of the treating physician and the severity of the particular disease being treated. The amount of a compound of the present disclosure in the composition will also depend upon the particular compound in the composition.

Mutations in ALK2 cause the kinase to be inappropriately active and are associated with various diseases. The disclosure provides compounds that inhibit a mutant ALK2 gene, e.g., a mutant ALK2 gene that results in the expression of an ALK2 enzyme having an amino acid modification. In another aspect, the disclosure provides compounds that inhibit both wild type (WT) ALK2 protein and mutant forms of ALK2 protein. For the purposes of this disclosure, sequence information for ALK2 is found on the National Center for Biological Information (NCBI) webpage (https://www.ncbi.nlm.nih.gov/) under ACVR1 activin A receptor type 1 [*Homo sapiens* (human)]; Entrez Gene ID (NCBI): 90. It is also known as: FOP; ALK2; SKR1; TSRI; ACTRI; ACVR1A; ACVRLK2, said sequence information is incorporated by reference herein.

In some embodiments, the disclosure provides a method of inhibiting aberrant ALK2 activity in a subject comprising the step of administering to the subject in need thereof a pharmaceutically effective amount of at least one compound or pharmaceutical composition described herein. In some embodiments, the aberrant ALK2 activity is caused by a mutation in an ALK2 gene that results in the expression of an ALK2 enzyme having an amino acid modification chosen from one or more of L196P, PF197-8L, R202I, R206H, Q207E, R258S, R258G, G328A, G328V, G328W, G328E, G328R, G356D, and R375P. In some embodiments, the ALK2 enzyme has the amino acid modification R206H.

Because of their activity against ALK2, the compounds described herein can be used to treat a patient with a condition associated with aberrant ALK2 activity. In some embodiments, the condition associated with aberrant ALK2 activity is fibrodysplasia ossificans progressiva. FOP diagnosis is based on the presence of congenital malformations of the great toes (hallux valgus) and the formation of fibrous nodules in soft tissues. The nodules may or may not transform into heterotopic bone. These soft tissue lesions are often first noted in the head, neck back. Approximately 97% of FOP patients have the same c.617G>A; R206H mutation in the ACVR1 (Alk2) gene. There is a genetic test available through the University of Pennsylvania (Kaplan et al., Pediatrics 2008, 121(5): e1295-e1300).

Other common congenital anomalies include malformations of the thumbs, short broad femoral necks, tibial osteochondromas, and fused facet joints of the cervical spine. The fused facet joints in the neck often cause toddlers to scoot on their buttocks rather than crawl. FOP is commonly misdiagnosed (approximately 80%; cancer or fibromatosis), and patients are frequently subjected to inappropriate diagnostic procedures such as biopsies that exacerbate disease and cause permanent disability.

In some embodiments, the present disclosure provides a method of treating or ameliorating fibrodysplasia ossificans progressiva in a subject, said method comprising administering to said subject in need thereof a pharmaceutically effective amount of a compound or pharmaceutical composition described herein.

In some embodiments, the condition associated with aberrant ALK2 activity is fibrodysplasia ossificans progressiva (FOP) and the subject has a mutation in an ALK2 gene that results in the expression of an ALK2 enzyme having an amino acid modification chosen from one or more of L196P, PF197-8L, R202I, R206H, Q207E, R258S, R258G, G328A, G328W, G328E, 0328R, G356D, and R375P. In some embodiments, the ALK2 enzyme has the amino acid modification R206H.

The present disclosure includes methods of identifying and/or diagnosing patients for treatment with one or more of the compounds or pharmaceutical compositions described herein. In some embodiments, the disclosure provides a method of detecting a condition associated with aberrant ALK2 activity e.g., FOB in a subject, wherein the method includes (a) obtaining a sample e.g., plasma from the subject e.g., a human patient; and (b) detecting whether one or more mutations in an ALK2 gene as described herein are present in the sample. In another embodiment, the disclosure provides a method of diagnosing a condition associated with aberrant ALK2 activity in a subject, said method comprising: (a) obtaining a sample from the subject; (b) detecting whether one or more mutations in an ALK2 gene as described herein are present in the sample using a detection method described herein; and (c) diagnosing the subject with the condition when the presence of the one or more mutations is detected. Methods for detecting a mutation include but are not limited to hybridization-based methods, amplification-based methods, microarray analysis, flow cytometry analysis, DNA sequencing, next-generation sequencing (NGS), primer extension, PCR, in situ hybridization, dot blot, and Southern blot. In some embodiments, the present disclosure provides a method of diagnosing and treating a condition associated with aberrant ALK2 activity in a subject, said method comprising: (a) obtaining a sample from a subject; (b) detecting whether one or more mutations in an ALK2 gene as described herein are present in the sample; (c) diagnosing the subject with the condition when the one or more mutations in the sample are detected; and (d) administering an effective amount of one or more of the compounds or a pharmaceutical composition described herein to the diagnosed patient. In some embodiments, the disclosure provides a method of treating a condition associated with aberrant ALK2 activity in a subject, said method comprising a. determining if, having determined if, or receiving information that said subject has one or more mutations in an ALK2 gene as described herein; (b) identifying the subject as responsive to one or more compounds or a pharmaceutical composition described herein; and (c) administering an effective amount of the one or more compounds or pharmaceutical compositions to the subject.

In some embodiments, the condition associated with aberrant ALK2 activity is a brain tumor, e.g., glial tumor. In some embodiments, the glial tumor is diffuse intrinsic pontine glioma (DIPG). In some embodiments, the disclosure provides a method of treating or ameliorating diffuse intrinsic pontine glioma in a subject in need thereof, said method comprising administering to said subject a pharmaceutically effective amount of a compound or pharmaceutical composition as described herein.

In some embodiments, the condition associated with aberrant ALK2 activity is diffuse intrinsic pontine glioma and the subject has a mutation in an ALK2 gene that results in the expression of an ALK2 enzyme having at least one amino acid modification chosen from R206H, G328V, G328W, G328E, and G356D. In some embodiments, the ALK2 enzyme has the amino acid modification R206H.

In some embodiments, the condition associated with aberrant ALK2 activity is anemia associated with inflammation, cancer, or chronic disease.

In some embodiments, the condition associated with aberrant ALK2 activity is trauma- or surgery-induced heterotopic ossification.

In some embodiments, a compound of the disclosure is co-administered (either as part of a combination dosage form or as a separate dosage form administered prior to, sequentially with, or after administration) with a second therapeutic agent useful in treating the disease to be treated e.g., FOP. In some embodiments, a compound of the disclosure is co-administered with a steroid (e.g., prednisone) or other anti-allergenic agents such as omalizumab.

In some embodiments, a compound of the disclosure is co-administered with a RAR-γ agonist or an antibody against Activin-A for treating the disease to be treated, e.g., FOP. In some embodiments, the RAR-γ agonist to be co-administered is palovarotene. In some embodiments, the antibody against Activin- to be co-administered is REGN2477.

In some embodiments, a compound of the disclosure is co-administered with therapies that target mast cells useful in treating FOP. In some embodiments, a compound of the disclosure is co-administered with a mast cell inhibitor including, but not limited, to a KIT inhibitor. In some embodiments, the mast cell inhibitor to be co-administered is chosen from cromolyn sodium (or sodium cromoglicate), brentuximab (ADCETRIS®), ibrutinib (IMBRUVICA®), omalizumab (XOLAIR®), anti-leukotriene agents (e.g., montelukast (SINGULAIR®) or zileuton (ZYFLO® or ZYFLO CR®)), and KIT inhibitors (e.g., imatinib (GLEEVEC®), midostaurin (PKC412A), masitinib (MASIVET® or KINAVET®), BLU-285, DCC-2618, PLX9486).

Compounds of the disclosure, including salts and N-oxides thereof, can be prepared using known organic synthesis techniques and can be synthesized according to any of numerous possible synthetic routes, such as those in the Schemes below. The reactions for preparing compounds of the disclosure can be carried out in suitable solvents which can be readily selected by one of skill in the art of organic synthesis. Suitable solvents can be substantially non-reactive with the starting materials (reactants), the intermediates, or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the disclosure can involve the protection and deprotection of various chemical groups. The need for protection and deprotection, and the selection of appropriate protecting groups, can be readily determined by one skilled in the art. The chemistry of protecting groups can be found, for example, in Wuts and Greene, Protective Groups in Organic Synthesis, 4th ed., John Wiley & Sons: New Jersey, (2006), which is incorporated herein by reference in its entirety.

Reactions can be monitored according to any suitable method known in the art. For example, product formation can be monitored by spectroscopic means, such as nuclear magnetic resonance (NMR) spectroscopy (e.g., $^1$H or $^{13}$C), infrared (IR) spectroscopy, spectrophotometry (e.g., UV-visible), mass spectrometry (MS), or by chromatographic methods such as high performance liquid chromatography (HPLC) or thin layer chromatography (TLC).

LC-MS/HPLC:

Unless otherwise indicated, all liquid chromatography-mass spectrometry (LC-MS) data (sample analyzed for purity and identity) were obtained with one of the following instruments and mobile phases:

Agilent model-1260 LC system (or 1200 model) using an Agilent model 6120 (or 1956) mass spectrometer utilizing ES-API ionization fitted with an Agilent Poroshel 120 (EC-C18, 2.7 μm particle size, 3.0×50 mm dimensions) reverse-phase column at 22.4 degrees Celsius. The mobile phase consisted of a mixture of solvent 0.1% formic acid in water and 0.1% formic acid in acetonitrile. A constant gradient from 95% aqueous/5% organic to 5% aqueous/95% organic mobile phase over the course of 4 minutes was utilized. The flow rate was constant at 1 mL/min.

LC-MS: Basic Mobile Phase: A: water (10 mM NH$_4$HCO$_3$) B: ACN; Gradient: 5% B increase to 95% B within 1.2 min, 95% B for 1.3 min, back to 5% B within 0.01 min; Flow Rate: 2 mL/min; Column: XBridge, 3.5 um, 50*4.6 mm; Oven Temperature: 50° C. Acidic Mobile Phase: A: water (0.01% TFA) B: CAN (0.01% TPA); Gradient: 5% B increase to 95% B within 1.2 min, 95% B for 1.3 min, back to 5% B within 0.01 min; Flow Rate: 2 mL/min; Column: Sunfire, 3.5 um, 50*4.6 mm; Oven Temperature: 50° C.

HPLC: Basic Mobile Phase: A: water (10 mM NH$_4$HCO$_3$) B: ACN; Gradient: 5% B increase to 95% B within 1.2 min, 95% B for 1.3 min, back to 5% B within 0.01 min; Flow Rate: 2 mL/min; Column: XBridge, 3.5 um, 50*4.6 mm; Oven Temperature: 50° C. Acidic Mobile Phase: A: water (0.01% TFA) B: ACN (0.01% TFA); Gradient: 0 min 5% B, 3 min 5% B, 10 min 95% B, 15 min 95% B; Flow Rate: 1.2 mL/min; Column: Eclipse XDB-C18, 4.6*150 mm, 5 um; Oven Temperature: 40° C.

Prep LC-MS Method 1:

Preparative HPLC was performed on a Shimadzu Discovery VP® Preparative system fitted with a Luna 5u C18(2) 100A, AXIA packed, 250×212 mm reverse-phase column at 22.4 degrees Celsius. The mobile phase consisted of a mixture of solvent 0.1% formic acid in water and 0.1% formic acid in acetonitrile. A constant gradient from 95% aqueous/5% organic to 5% aqueous/95% organic mobile phase over the course of 25 minutes was utilized. The flow rate was constant at 20 mL/min. Reactions carried out in a microwave were done so in a Biotage Initiator microwave unit.

Prep LC-MS Method 2:

MS method: Capillary (kv): 3.5; Cone (v): 20; Extractor (v): 3; RF lens (v): 0.5; Source Temp(° C.): 100; Desolation Temp(° C.): 400

Inlet method: Solvent: CH$_3$OH, H$_2$O, 0.001 TFA/5-95 NH$_3$/CAN/5-95TFA/CAN; Gradient: 10-70; Run time: 3.5 mins; Flow rate: 60 mL/min Fraction method: Fraction trigger: mass; Split/collector delay (secs): 10.5; Maximum tube fill (%) 85; Positive ion detection—min. intensity threshold(mit):2000000; Column id: X-bridge, C18, 20 mm*50 mm, 10 um Chiral HPLC:

Preparative HPLC to resolve chiral mixtures was performed on the following instruments using one of the columns, and sets of general conditions listed below.

SFC Details:

Instrument: SFC-80 (Thar, Waters) or SFC-200 (Thar, Waters)

Column: AD-H 20*250 mm, 5um (Daicel)

Column temperature: 35° C.

Mobile phase: CO$_2$/Methanol(0.1% NH$_4$OH)=40/60-90/10

Flow rate: 80-180 g/min

Back pressure: 100 bar

Detection wavelength: 214-360 nm

HPLC Details:
Instrument: Gilson-281
Column: AD-H 20*250, 10 um (Daicel)
Mobile Phase: Hexane(0.1% DEA): EtOH (0.1% DEA)=0/100-100/0
Column temperature: 40° C.
Injection: 1 mL
Detection wavelength: 214-360 nm
Column:

| | | | | |
|---|---|---|---|---|
| AD-H | DAICEL | 10 um | Φ2,5 cm * 2 | Φ5.0 cm * 2 |
| OD-H | | | Φ2.5 cm * 2 | Φ5.0 cm * 1 |
| OJ-H | | | Φ2.5 cm * 2 | Φ5.0 cm * 1 |
| AS-H | | | Φ2.5 cm * 1 | Φ5.0 cm * 1 |
| OZ-H | | | Φ2.5 cm * 1 | Φ5.0 cm * 1 |
| AY-H | | | Φ2.5 cm * 2 | Φ5.0 cm * 1 |
| IC | | | Φ2.5 cm * 1 | |
| IA | | | Φ2.5 cm * 1 | |
| RegisCell | | | Φ2.5 cm * 1 | |
| (R,R)-Whelk-O1 | | | Φ2.5 cm * 1 | Φ5.0 cm * 1 |
| Cellulose-SC | | | Φ2.5 cm * 1 | |
| Amylose-C | | | Φ2.5 cm * 1 | |

Silica Gel Chromatography:
Silica gel chromatography was performed on either a Teledyne Isco CombiFlash® Rf unit or a Biotage® Isolera Four unit.

Proton NMR:
Unless otherwise indicated, all $^1$H NMR spectra were obtained with a Varian 400 MHz Unity Inova 400 MHz NMR instrument (acquisition time=3.5 seconds with a 1 second delay; 16 to 64 scans), Bruker, AVANCE III 500 MHz UltraShield-Plus digital NMR spectrometer, or a Bruker, AVANCE III 400 MHz UltraShield-Plus digital NMR spectrometer. Where characterized, all protons were reported in DMSO-$d_6$ solvent as parts-per million (ppm) with respect to residual DMSO (2.50 ppm).

EXAMPLES

The following examples are intended to be illustrative, and are not meant in any way to be limiting.

The below Schemes are meant to provide general guidance in connection with preparing the compounds of the invention. One skilled in the art would understand that the preparations shown in the Schemes can be modified or optimized using general knowledge of organic chemistry to prepare various compounds of the invention.

Synthetic Protocol A

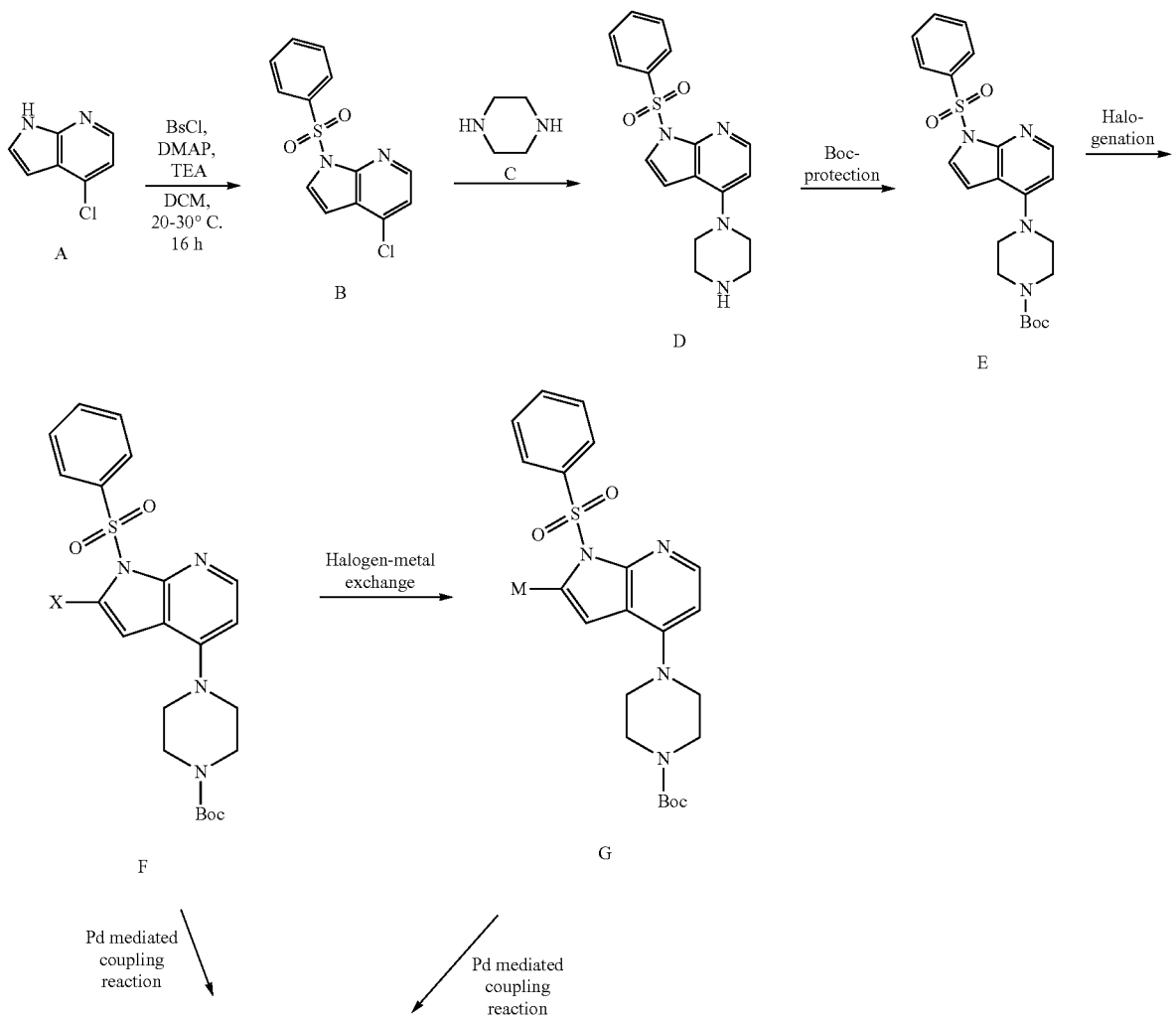

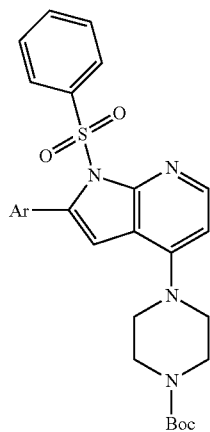
H

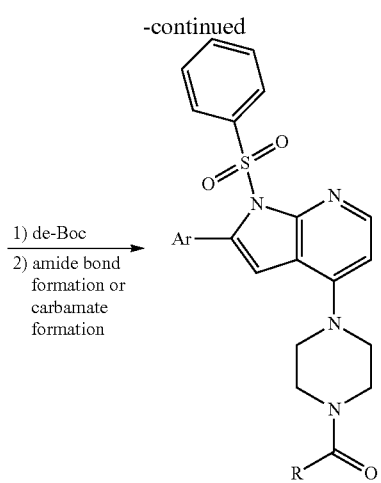
I

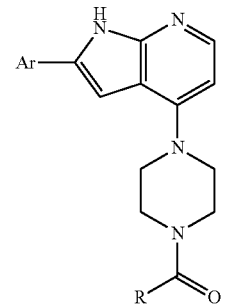
J

The pyrrolopyridine A can be protected with a sufonyl group to provide intermediate B. The intermediate B can be functionalized with a piperazine C via a substitution reaction to provide intermediate D. Intermediate D can be protected with a group, such as Boc (intermediate E), and then specifically halogenated to provide intermediate F. The intermediate F can undergo a halogen-metal exchange reaction to provide intermediate G as a boronate or tin-containing intermediate. Intermediate F can also be coupled to a boronate, boronate ester, trialkyltin, or alkylzinc reagent via a palladium-mediated coupling reaction, e.g., Suzuki, Stille, or Negishi coupling to provide intermediate H. These transformations are also possible for intermediate G to undergo to also provide intermediate H. Deprotection (de-Boc) of H followed by a capping reaction such as amide bond formation or carbamate formation provides intermediate I. Final compounds J can be achieved by deprotection (sulfonyl group) of intermediate I. As shown below, compounds 20, 262, and 410 of Tables 1, 2, and 3 were prepared using synthetic protocol A.

Example 1. Synthesis of tert-butyl 4-(2-iodo-1-(phenylsulfonyl)-1H-pyrrolo[2,3-b]pyridin-4-yl)piperazine-1-carboxylate

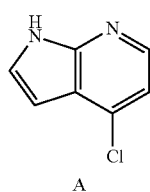
A

Step 1
BsCl, DMAP, TEA
―――――――――――→
DCM, 20-30° C. 16 h
86%

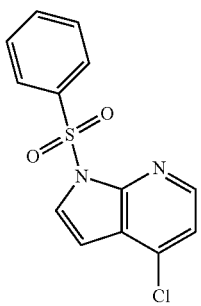
B

Step 2
C
―――――――――→
NMP, 140° C.,
3 h

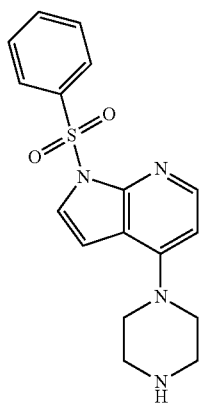
D

Step 3
Boc₂O, 20-30° C.
16 h
―――――――――――→
51% two steps

295
-continued

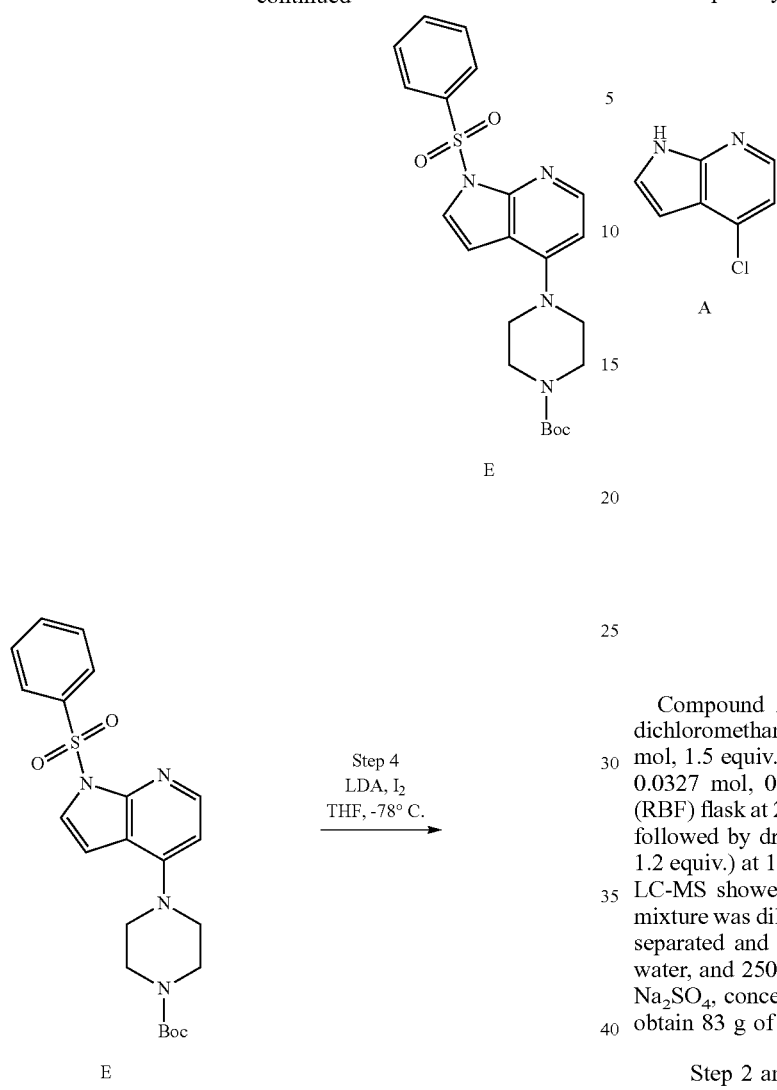

E

Step 4
LDA, I₂
THF, -78° C.

F

Step 1. Synthesis of 4-chloro-1-(phenylsulfonyl)-1H-pyrrolo[2,3-b]pyridine

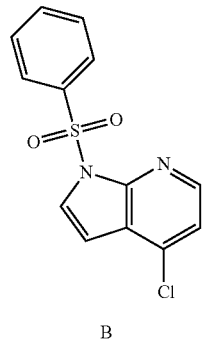

A

Step 1
1. Add A, DMAP, TEA and DCM.
2. Cool to 10° C.
3. Add BsCl dropwise.
4. Stir at 20° C.
5. Wash with water, Na₂CO₃, brine.
6. Concetrate, slurry with petroleum ether

B

Compound A (50 g, 0.3276 mol, 1 equiv.), 500 mL dichloromethane (DCM), triethylamine (TEA) (50 g, 0.4941 mol, 1.5 equiv.), and dimethylaminopyridine (DMAP) (4 g, 0.0327 mol, 0.1 equiv.) combined in a 1L round bottom (RBF) flask at 20° C. The mixture was then cooled to 10° C., followed by dropwise addition of BsCl (70 g, 0.3963 mol, 1.2 equiv.) at 10-20° C. After stirring at 20° C. for 18 hours, LC-MS showed a ratio of A/BsCl/B=0/8/84. The reaction mixture was diluted in 250 mL water. The organic phase was separated and washed with 250 mL sat.Na₂CO₃, 250 mL water, and 250 mL brine. The organic layer was dried over Na₂SO₄, concentrated, and slurried with petroleum ether to obtain 83 g of the title product (99% purity, 86% yield).

Step 2 and 3. Synthesis of tert-butyl 4-(1-(phenylsulfonyl)-1H-pyrrolo[2,3-b]pyridin-4-yl)piperazine-1-carboxylate

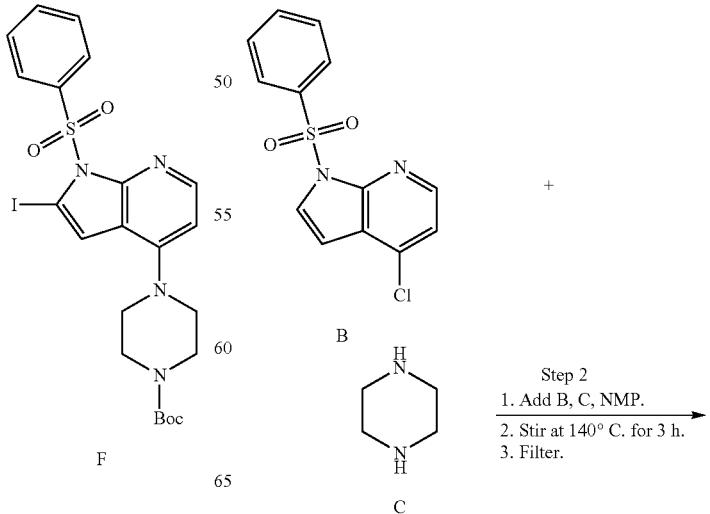

Step 2
1. Add B, C, NMP.
2. Stir at 140° C. for 3 h.
3. Filter.

297

-continued

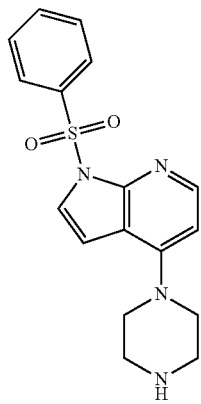

D

Step 3
1. Add Boc₂O dropwise at 10-25° C.
2. Stir at 15° C. for 18 h.
3. Add ethyl acetate, filter.
4. Wash with water, NaHSO₄.
5. Wash with water.
6. Concentrate.
7. Recrystallize with DCM and petroleum ether

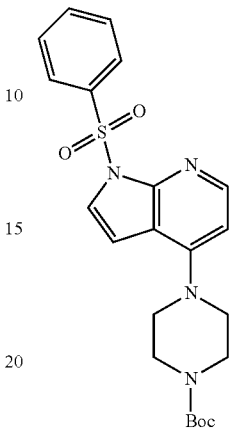

4

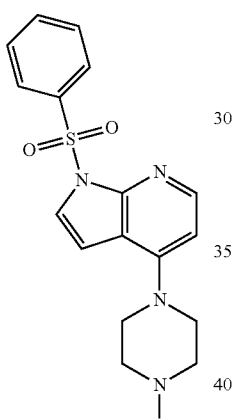

E

Compound B (27 g, 0.0631 mol, 1.0 equiv.), Compound C (24 g, 0.2786 mol, 3.0 equiv.), and 190 mL N-methylpyrrolidone (NMP) were added to 500 mL RBF at 15° C. The mixture was heated to 140° C. and stirred for 3 hours. LC-MS showed the ratio of B/D was 0/83. The mixture was cooled to 15° C. and stirred for an additional 18 hours. The insoluble solid was then filtered off, and Boc₂O (85 g, 0.3895 mol, 4.2 equiv.) was added dropwise at 10-25° C. The mixture was stirred for 18 hours at 15° C.; LS-MS showed the D/E ratio was 0/81. 540 mL ethyl acetate was then added to the mixture, followed by filtering. The filtrate was washed three times with 200 mL of water, and the resulting organic phase was washed with aq. NaHSO₄ (12.5 g in 150 mL water) and water (200 mL). The organic layer was dried over Na₂SO₄ and concentrated to obtain crude product. The crude product was dissolved with 150 mL DCM, followed by dropwise addition of 750 mL petroleum ether at 15° C. over the course of 30 minutes. The solution was then stirred for 30 minutes at 15° C. to form precipitate. 21 g of the title product as a white solid was obtained following filtration (99% purity, 51% yield (two steps)).

298

Step 4. Synthesis of tert-butyl 4-(2-iodo-1-(phenylsulfonyl)-1H-pyrrolo[2,3-b]pyridin-4-yl)piperazine-1-carboxylate

LDA, I₂
THF, -78° C.

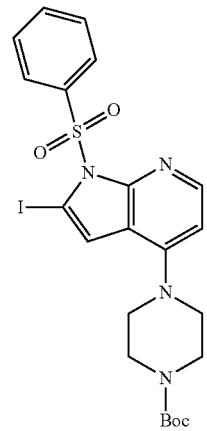

5

Lithium diisopropylamide (LDA) (2 M, 62 mL, 124 mmol) was added dropwise to a mixture of tert-butyl 4-(1-(phenylsulfonyl)-1H-pyrrolo[2,3-b]pyridin-4-yl)piperazine-1-carboxylate (50 g, 113 mmol) in THF (600 mL) at -78° C. The mixture was stirred at -78° C. for 1 h. I₂ (31 g, 122 mmol) in THF (100 mL) was added at -78° C., and the mixture was stirred at -78° C. for 1 h. The mixture was warmed to 0° C. and stirred for 0.5 h. The reaction was quenched with aq. Na₂S₂O₃ and aq. NH₄Cl, extracted with ethyl acetate. Concentrated and purified by silica gel chromatography (petroleum ether:ethyl acetate=1:1) to give the title product (45 g, 70%) as a light yellow solid. MS (ES+) $C_{22}H_{25}IN_4O_4S$ requires: 568, found: 569 [M+H]⁺.

Example 2. Synthesis of oxetan-3-yl 4-(2-(4-(trifluoromethyl)thiazol-2-yl)-1H-pyrrolo[2,3-b]pyridin-4-yl)piperazine-1-carboxylate

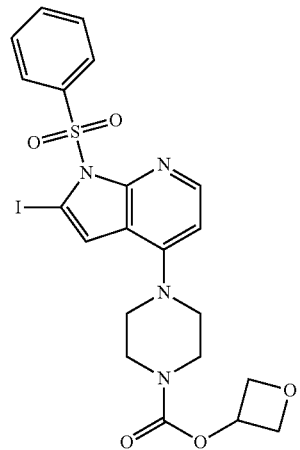

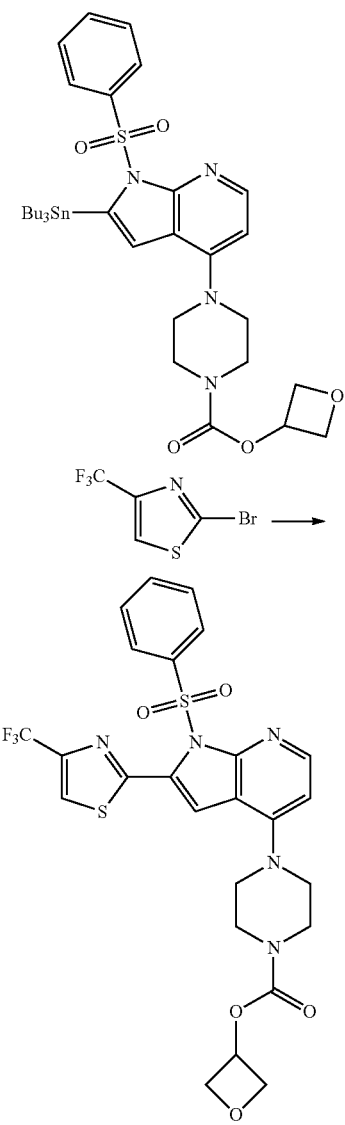

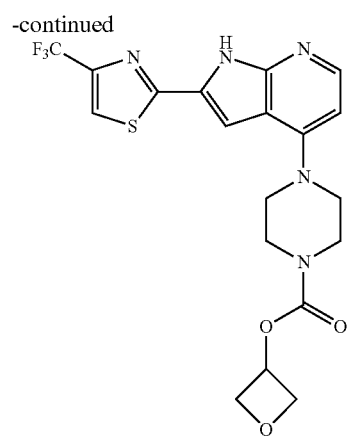

Step 1. Synthesis of oxetan-3-yl 4-(1-(phenylsulfonyl)-2-(tributylstannyl)-1H-pyrrolo[2,3-b]pyridin-4-yl)piperazine-1-carboxylate n-BuLi (21.2 mmol, 2.5 M) was added to a solution of oxetan-3-yl 4-(2-iodo-1-(phenylsulfonyl)-1H-pyrrolo[2,3-b]pyridin-4-yl)piperazine-1-carboxylate (10 g, 17.6 mmol) in THF (150 mL) at −78° C. After stirring at −78° C. for 1 h, Bu₃SnCl (6.9 g, 21.2 mmol) was added. The reaction was stirred at −78° C. for another 1 h and then stirred at room temperature overnight. The reaction mixture was extracted with ethyl acetate (200 mL), washed with brine, dried over Na$_2$SO$_4$, filtrated, and concentrated. The residue was purified by silica gel chromatography (petroleum ether:ethyl acetate=10:3) to give the title product (5 g, 92%), yield: 39%. MS (ES+) C$_{33}$H$_{48}$N$_4$O$_5$SSn requires: 731, found 732 [M+H]$^+$.

Step 2. Synthesis of oxetan-3-yl 4-(1-(phenylsulfonyl)-2-(4-(trifluoromethyl)thiazol-2-yl)-1H-pyrrolo[2,3-b]pyridin-4-yl)piperazine-1-carboxylate

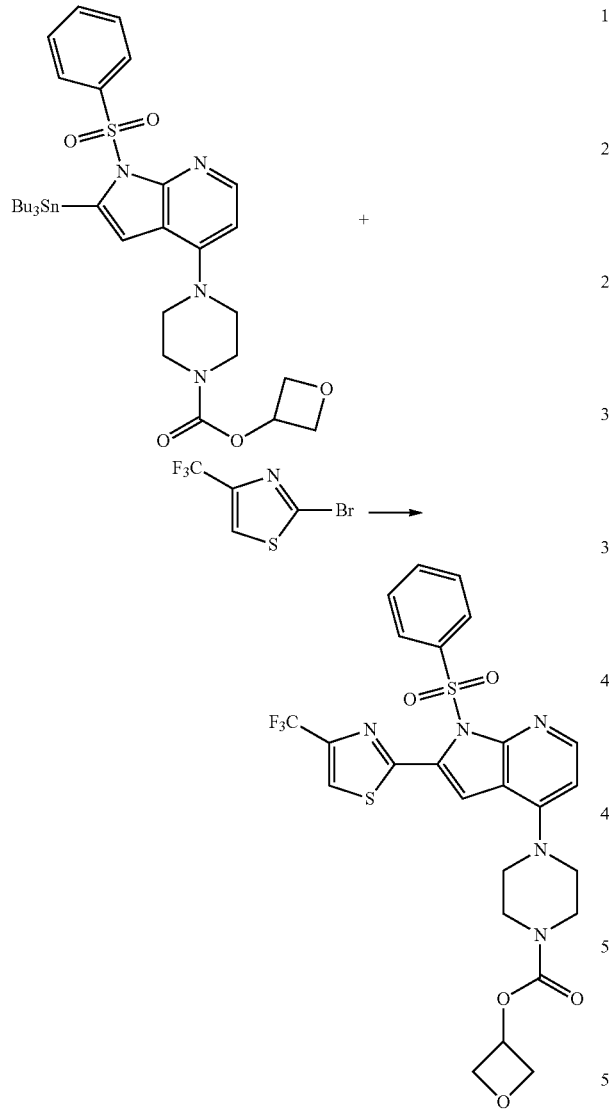

A mixture of oxetan-3-yl 4-(1-(phenylsulfonyl)-2-(tributylstannyl)-1H-pyrrolo[2,3-b]pyridin-4-yl)piperazine-1-carboxylate (250 mg, 342 µmol), 2-bromo-4-(trifluoromethyl)thiazole (120 mg, 513 µcool), CuI (65 mg, 342 mmol), and Pd(PPh$_3$)$_4$ (197 mg, 171 µmol) in toluene (10 mL) was degassed with N$_2$, and then stirred at 100° C. for 16 h under N$_2$. The mixture was cooled to room temperature and concentrated. The residue was directly purified by silica gel chromatography (ethyl acetate:petroleum ether=3:10) to give the title product (70 mg, yield 35%) as a light yellow solid. MS (ES+) C$_{25}$H$_{22}$F$_3$N$_5$O$_5$S$_2$ requires: 593, found: 594 [M+H]$^+$.

Step 3. Synthesis of oxetan-3-yl 4-(2-(4-(trifluoromethyl)thiazol-2-yl)-1H-pyrrolo[2,3-b]pyridin-4-yl)piperazine-1-carboxylate

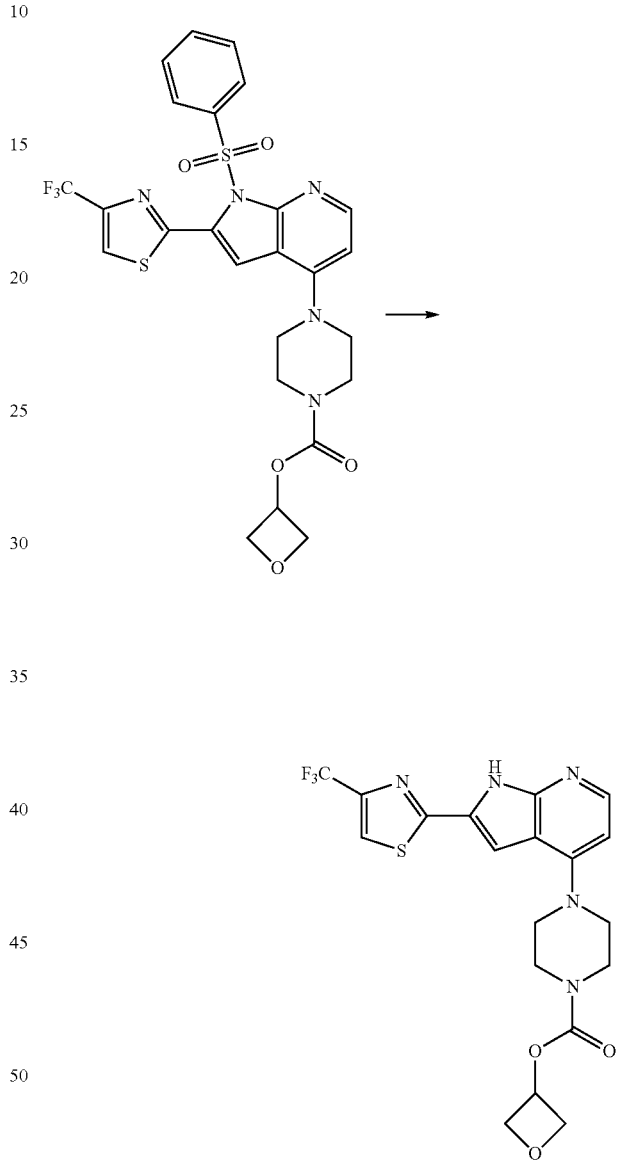

Tetrabutylammonium fluoride hydrate (IBAF) (2 mL, 1 M, 2.0 mmol) was added to a solution of oxetan-3-yl 4-(1-(phenylsulfonyl)-2-(4-(trifluoromethyl)thiazol-2-yl)-1H-pyrrolo[2,3-b]pyridin-4-yl)piperazine-1-carboxylate (70 mg, 118 µmol) in THF (5 mL). The reaction mixture was stirred at 60° C. for 6 h. LC-MS showed the reaction was completed. The mixture was diluted with DCM, washed with water and brine, and concentrated. The residue was directly purified by silica gel column (MeOH:DCM=1:15) and Prep-HPLC to give the title product (13.9 mg, yield 26%) as a white solid. MS (ES+) C$_{19}$H$_{18}$F$_3$N$_5$O$_3$S requires: 453, found: 454 [M+H]$^+$.

Example 3. Synthesis of 2,2-difluorocyclobutyl 4-(2-(1-methyl-1H-pyrazol-4-yl)-1H-pyrrolo[2,3-b]pyridin-4-yl)piperazine-1-carboxylate

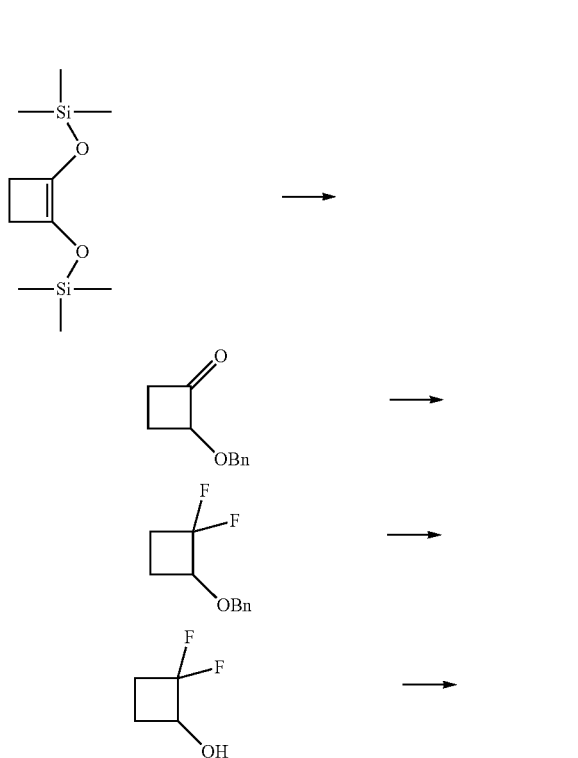

Step 1. Synthesis of 2-(benzyloxy)cyclobutanone

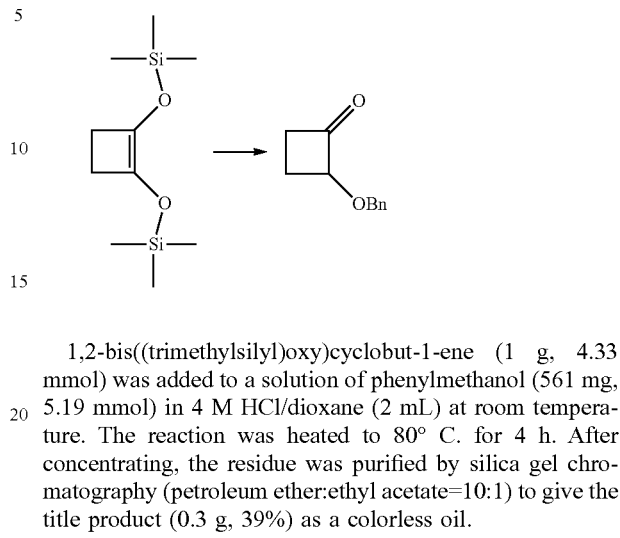

1,2-bis((trimethylsilyl)oxy)cyclobut-1-ene (1 g, 4.33 mmol) was added to a solution of phenylmethanol (561 mg, 5.19 mmol) in 4 M HCl/dioxane (2 mL) at room temperature. The reaction was heated to 80° C. for 4 h. After concentrating, the residue was purified by silica gel chromatography (petroleum ether:ethyl acetate=10:1) to give the title product (0.3 g, 39%) as a colorless oil.

Step 2. Synthesis of ((2,2-difluorocyclobutoxy)methyl)benzene

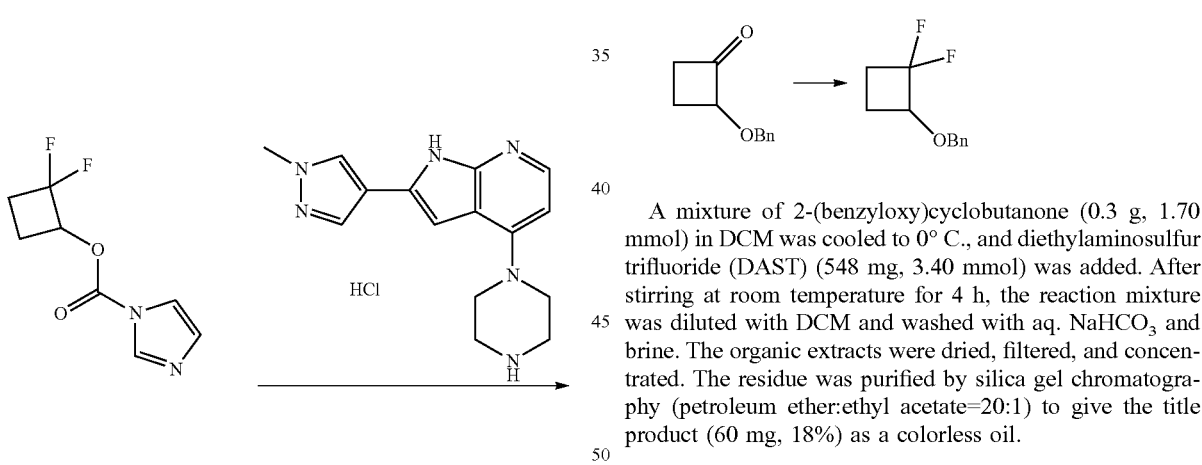

A mixture of 2-(benzyloxy)cyclobutanone (0.3 g, 1.70 mmol) in DCM was cooled to 0° C., and diethylaminosulfur trifluoride (DAST) (548 mg, 3.40 mmol) was added. After stirring at room temperature for 4 h, the reaction mixture was diluted with DCM and washed with aq. NaHCO$_3$ and brine. The organic extracts were dried, filtered, and concentrated. The residue was purified by silica gel chromatography (petroleum ether:ethyl acetate=20:1) to give the title product (60 mg, 18%) as a colorless oil.

Step 3. Synthesis of 2,2-difluorocyclobutanol

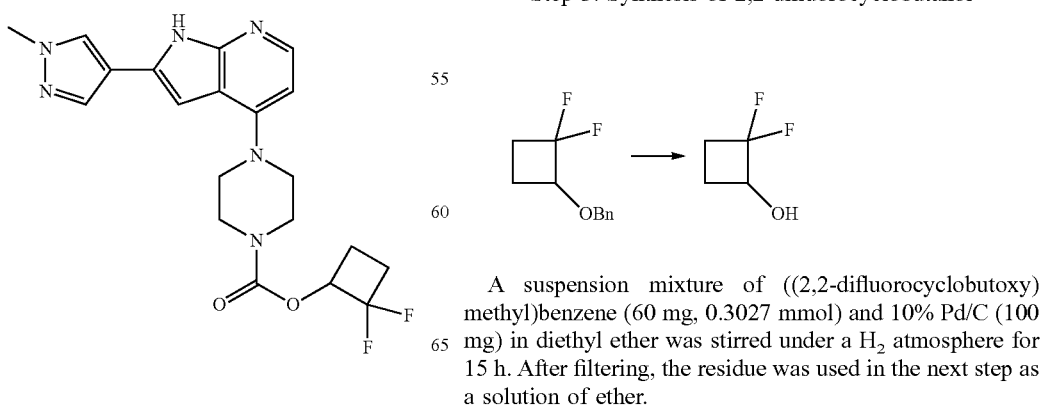

A suspension mixture of ((2,2-difluorocyclobutoxy)methyl)benzene (60 mg, 0.3027 mmol) and 10% Pd/C (100 mg) in diethyl ether was stirred under a H$_2$ atmosphere for 15 h. After filtering, the residue was used in the next step as a solution of ether.

Step 4. Synthesis of 2,2-difluorocyclobutyl 1H-imidazole-1-carboxylate

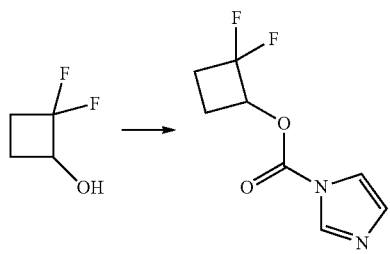 [SMILES: OC1CCC1(F)F ; O=C(OC1CCC1(F)F)n1ccnc1]

A mixture of 2,2-difluorocyclobutanol (above ether solution, 0.3027 mmol assumed) and CDI (50 mg, 0.305 mmol) in DCM was stirred at room temperature for 4 h. The resulting solution was used in the next step without any further purification. MS (ES+) $C_8H_8F_2N_2O_2$ requires: 202, found 203 $[M+H]^+$.

Step 5. Synthesis of 2,2-difluorocyclobutyl 4-(2-(1-methyl-1H-pyrazol-4-yl)-1H-pyrrolo[2,3-b]pyridin-4-yl)piperazine-1-carboxylate

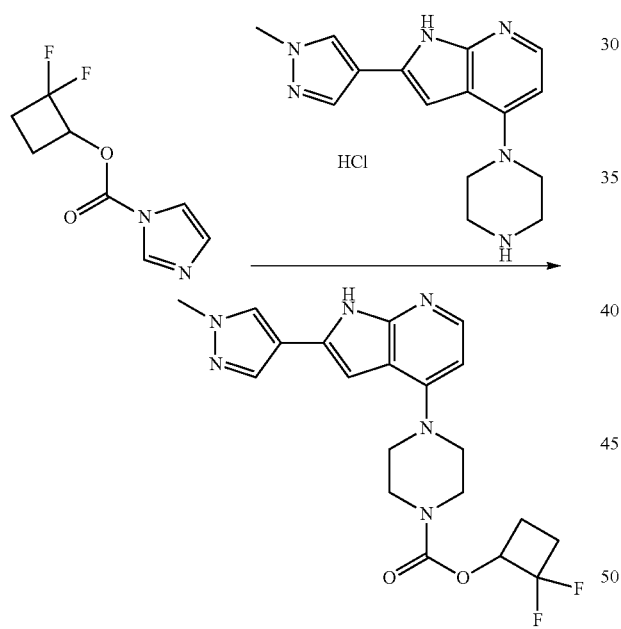

Triethylamine (60.0 mg, 0.5934 mmol) was added to a mixture of 2-(1-methyl-1H-pyrazol-4-yl)-4-(piperazin-1-yl)-1H-pyrrolo[2,3-b]pyridine hydrochloride (94.5 mg, 0.2967 mmol) in DCM and stirred for 10 min at room temperature, followed by addition of a solution of 2,2-difluorocyclobutyl 1H-imidazole-1-carboxylate (60 mg, 0.2967 mmol) in DCM. After stirring at room temperature for 15 h, the reaction mixture was diluted with DCM and washed with water. The organic layer was dried, filtered, and concentrated. The residue was purified by silica gel chromatography (DCM:MeOH=10:1) and then purified by Prep-HPLC to give the title product (14.4 mg, 12%) as a white solid. MS (ES+) $C_{20}H_{22}F_2N_6O_2$ requires: 416, found 417 $[M+H]^+$.

Example 4. Synthesis of cyclobutyl(4-(2-(1-methyl-1H-pyrazol-4-yl)-1H-pyrrolo[2,3-b]pyridin-4-yl)piperazin-1-yl)methanone

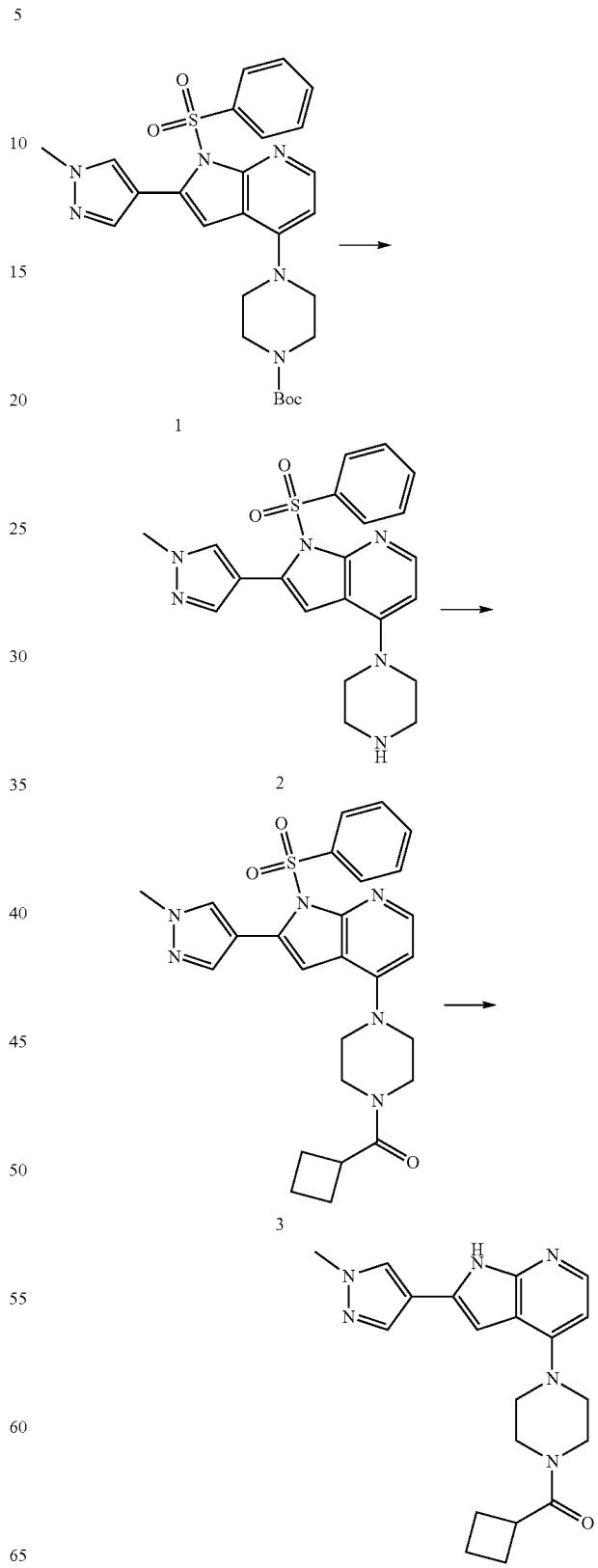

307

Step 1. Synthesis of 2-(1-methyl-1H-pyrazol-4-yl)-1-(phenylsulfonyl)-4-(piperazin-1-yl)-1H-pyrrolo[2,3-b]pyridine

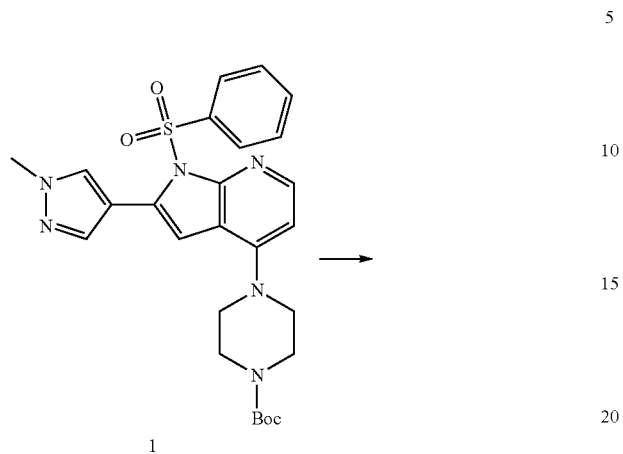

1

To compound 1 (200 mg, 0.45 mmol) was added MeOH/HCl(5 mL). The mixture was stirred at 30° C. for 5 hours. The mixture was concentrated under vacuum to obtain the target compound.

Step 2. Synthesis of cyclobutyl(4-(2-(1-methyl-1H-pyrazol-4-yl)-1-(phenylsulfonyl)-1H-pyrrolo[2,3-b]pyridin-4-yl)piperazin-1-yl)methanone

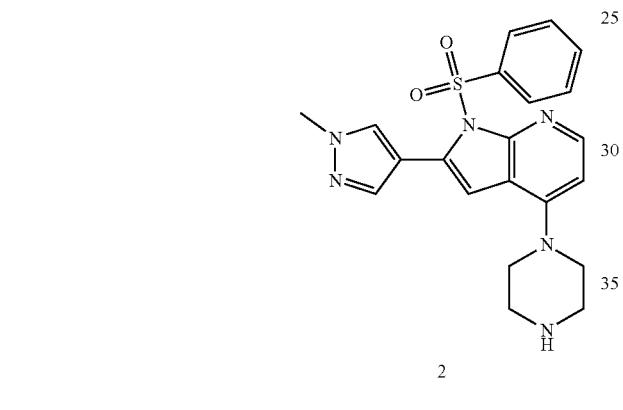

2

308

-continued

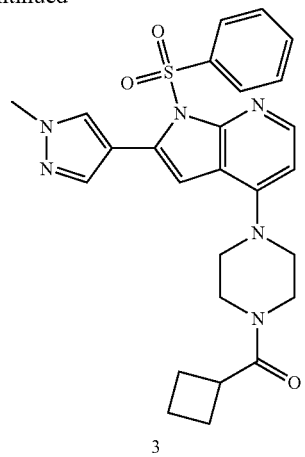

3

Cyclobutanecarboxylic acid (14 mg, 0.14 mmol), N-methylmorpholine (NMM) (61 mg, 0.60 mmol), and HBTU (49 mg, 0.13 mmol) were added to the mixture of compound 2 (50 mg, 0.12 mmol) in DMF (1.5 mL). The mixture was stirred at 25° C. for 5 hours. The mixture was used directly in the next step.

Step 3. Synthesis of cyclobutyl(4-(2-(1-methyl-1H-pyrazol-4-yl)-1H-pyrrolo[2,3-b]pyridin-4-yl)piperazin-1-yl)methanone

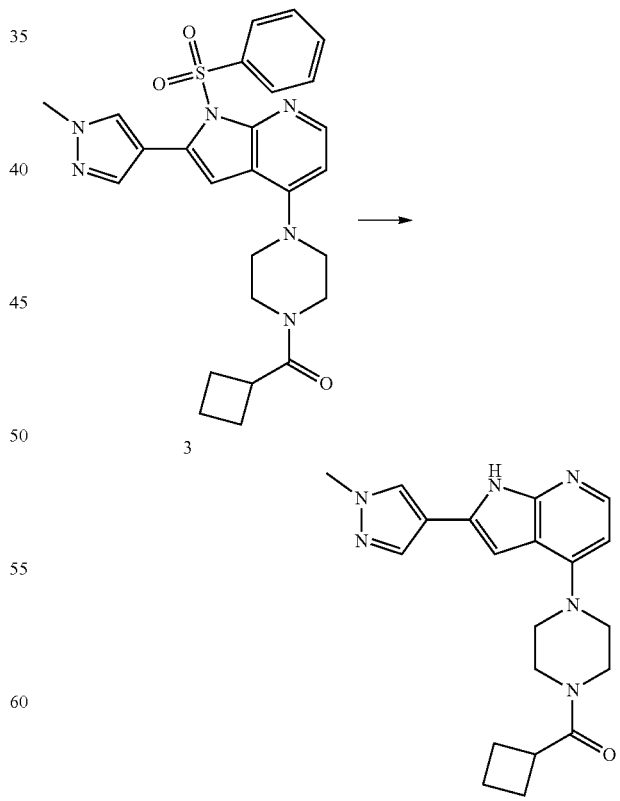

KOH (10 eq.) was added to compound 3 (1.0 eq.) in 2 mL MeOH. The mixture was stirred at room temperature for 3 hours. Acetic acid was added to the mixture to adjust pH to 7, and the mixture was purified by prep-HPLC to obtain the target compound.

Synthetic Protocol B

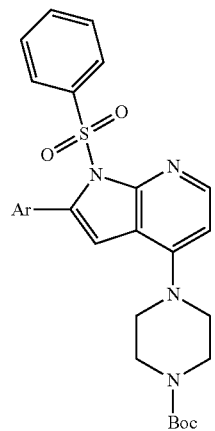

H

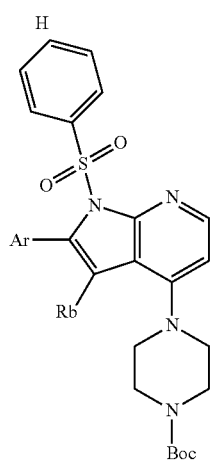

K

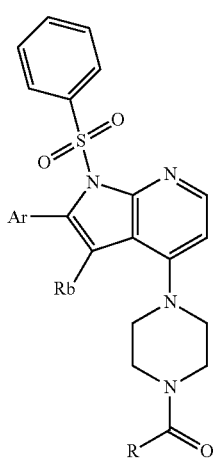

L

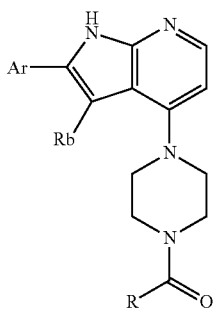

M

Intermediate H was prepared using the methods described in synthetic protocol A. Intermediate H can be further functionalized via halogenation, halogenation followed by a palladium-mediated coupling reaction (e.g. Suzuki, Stille, Sonogashira, or Negishi coupling), or metalation followed by reaction with an electrophile to yield intermediate K. Deprotection (de-Boc) of K followed by a capping reaction, such as amide bond formation or carbamate formation, provides intermediate L. Final compounds M can be achieved by deprotection (sulfonyl group) of intermediate L. As shown below, compounds 132, 258, and 267 of Tables 1, 2, and 3 were prepared using synthetic protocol B.

Example 5. Synthesis of (1r,3r)-3-fluorocyclobutyl 4-(3-fluoro-2-(1-methyl-1H-pyrazol-4-yl)-1.H-pyrrolo[2,3-b]pyridin-4-yl)piperazine-1-carboxylate

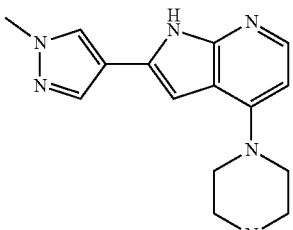

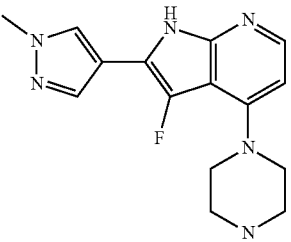

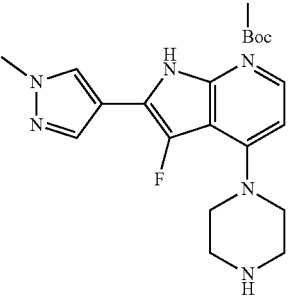

311
-continued

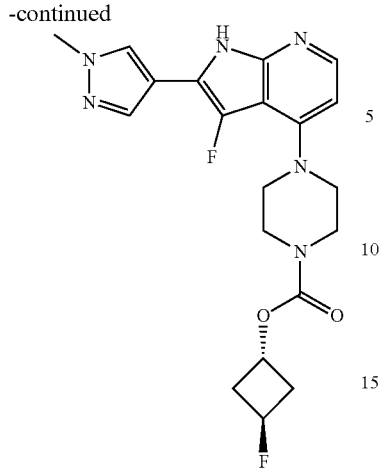

Step 1. Synthesis of (tert-butyl 4-(3 fluoro-2-(1-methyl-1H-pyrazol-4-yl)-1H-pyrrolo[2,3-b]pyridin-4-yl)piperazine-1-carboxylate N-fluoro-N-(phenylsulfonyl)benzenesulfonamide (82.4 mg, 0.2614 mmol) was added to a solution of tert-butyl 4-(2-(1-methyl-1H-pyrazol-4-yl)-1H-pyrrolo[2,3-b]pyridin-4-yl)piperazine-1-carboxylate (100 mg, 0.2614 mmol) in DCM. After stirring at room temperature for 1.5 h, the reaction mixture was diluted with DCM and washed with aq. NaHCO₃. The organic layer was dried, filtered, and concentrated. The residue was purified by silica gel chromatography (DCM:MeOH=20:1) to give the title product (30 mg, 40% purity, 12%) as a yellow solid. MS (ES+) $C_{20}H_{25}FN_6O_2$ requires: 400, found 401 [M+H]⁺.

312

Step 2. Synthesis of 3 fluoro-2-(1-methyl-1H-pyrazol-4-yl)-4-(piperazin-1-yl)-1H-pyrrolo[2,3-b]pyridine

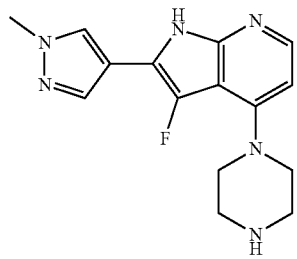

4 M HCl/dioxane was added to a solution of tert-butyl 4-(3-fluoro-2-(1-methyl-1H-pyrazol-4-yl)-1H-pyrrolo[2,3-b]pyridin-4-yl)piperazine-1-carboxylate (60 mg, 0.1498 mmol) in DCM. After stirring at room temperature for 3 h, the reaction mixture was concentrated to give the title product (crude HCl salt, 45 mg, quantitative) as a yellow solid. MS (ES+) $C_{15}H_{17}FN_6$ requires: 300, found 301 [M+H]⁺.

Step 3. Synthesis of (1r,3r)-3-fluorocyclobutyl 4-(3-fluoro-2-(1-methyl-1H-pyrazol-4-yl)-1H-pyrrolo[2,3-b]pyridin-4-yl)piperazine-1-carboxylate

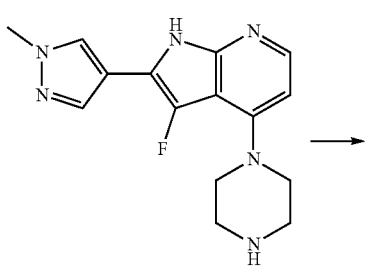

-continued

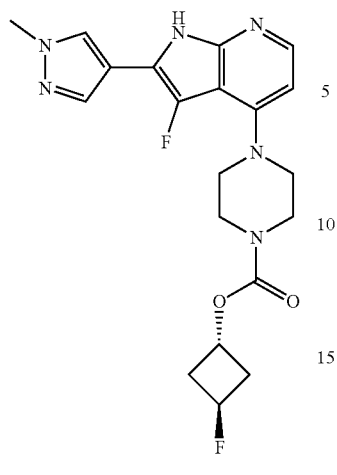

CDI (72.8 mg, 0.4494 mmol) was added to a solution of (1r,3r)-3-fluorocyclobutanol (40.4 mg, 0.4494 mmol) in DCM (3 mL). After stirring for 6 h at room temperature, the resulting solution was added to a mixture of 3-fluoro-2-(1-methyl-1H-pyrazol-4-yl)-4-(piperazin-1-yl)-1H-pyrrolo[2,3-b]pyridine (45 mg, 0.1498 mmol) and TEA (30 mg, 0.30 mmol) in DCM. After stirring at room temperature for another 15 h, the reaction mixture was diluted with DCM and washed with water. The organic layer was dried, filtered, and concentrated. The resulting precipitate was washed with MeOH to give the title product (34.8 mg, 56%) as a yellow solid. MS (ES+) $C_{20}H_{22}F_2N_6O_2$ requires: 416, found 417 [M+H]$^+$.

Example 6. Synthesis of ethyl 4-(3-cyano-2-(1-(difluoromethyl)-1H-pyrazol-4-yl)-1H-pyrrolo[2,3-b]pyridin-4-yl)piperazine-1-carboxylate Step 1. Synthesis of tert-butyl 4-(2-(1-(difluoromethyl)-1H-pyrazol-4-yl)-1-((2-(trimethylsilyl)ethoxy)methyl)-1H-pyrrolo[2,3-b]pyridin-4-yl)piperazine-1-carboxylate

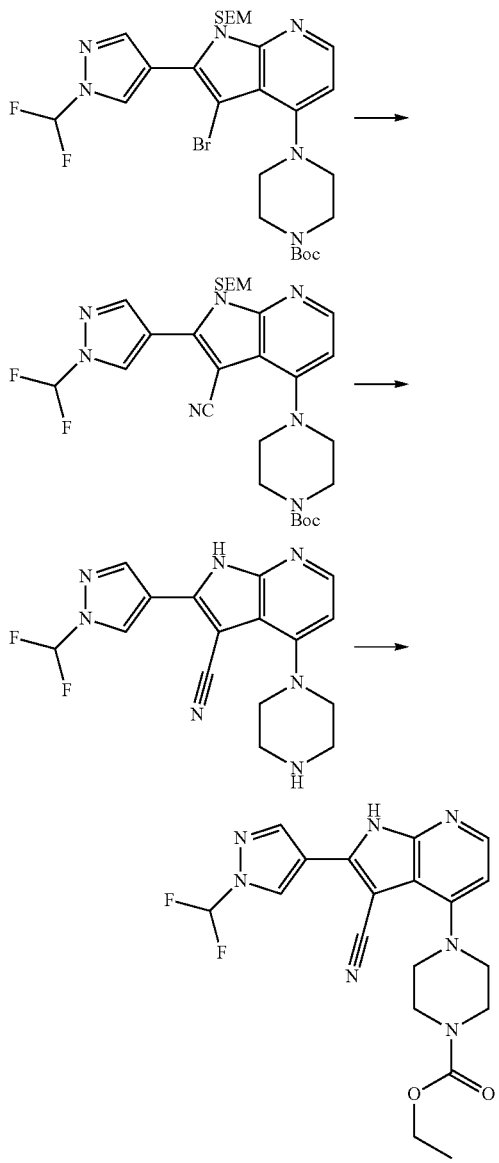

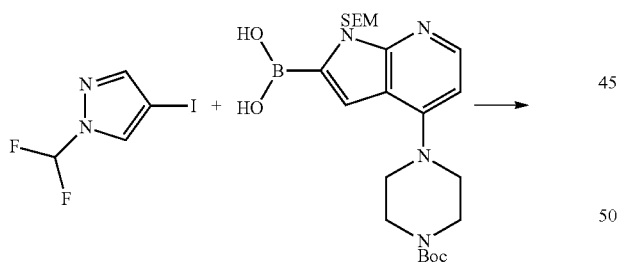

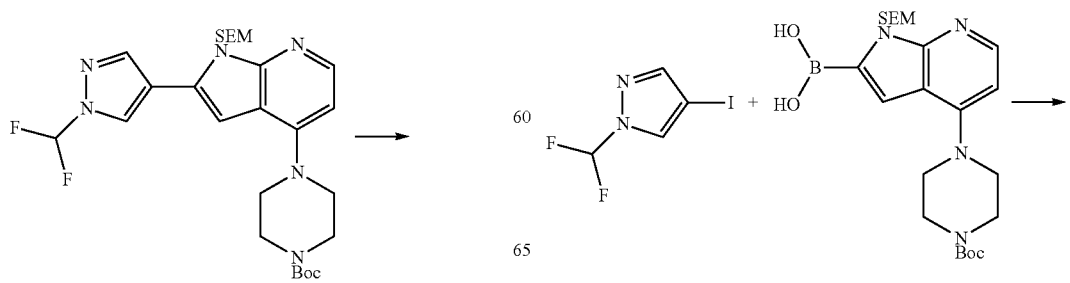

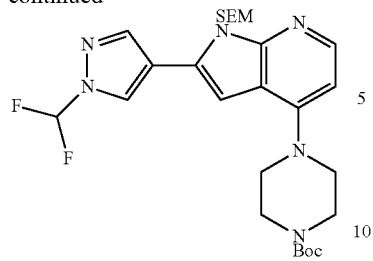

A mixture of 1-(difluoromethyl)-4-iodo-1H-pyrazole (200 mg, 819 µmol) and (4-(4-(tert-butoxycarbonyl)piperazin-1-yl)-1-((2-(trimethylsilyl)ethoxy)methyl)-1H-pyrrolo[2,3-b]pyridin-2-yl)boronic acid (390 mg, 819 µmol), Na$_2$CO$_3$ (259 mg, 2.45 mmol), and Pd(dppf)Cl$_2$ (60 mg, 82 µmol) in THF (20 mL)/H$_2$O (2 mL) was stirred at 75° C. under N$_2$ for 1 h. LC-MS showed the reaction was completed. The reaction mixture was cooled, concentrated, and directly purified by silica gel column (ethyl acetate/petroleum ether=1/5-5/1) to give the title compound (312 mg, yield 69%) as a colorless oil. MS (ES+) C$_{26}$H$_{38}$F$_2$N$_6$O$_3$Si requires: 548, found 549 [M+H]$^+$.

Step 2. Synthesis of tert-butyl 4-(3-bromo-2-(1-(difluoromethyl)-1H-pyrazol-4-yl)-1-((2-(trimethylsilyl)ethoxy)methyl)-1H-pyrrolo[2,3-b]pyridin-4-yl)piperazine-1-carboxylate

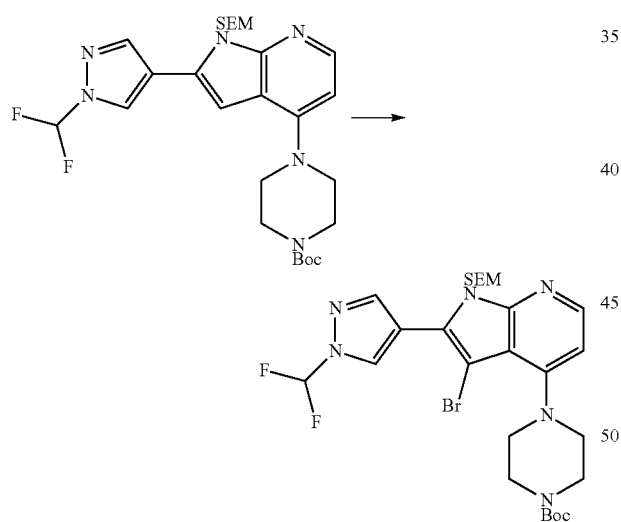

N-Bromosuccinimide (NBS) (101 mg, 568 µmol) was added to a solution of tert-butyl 4-(2-(1-(difluoromethyl)-1H-pyrazol-4-yl)-1-((2-(trimethylsilyl)ethoxy)methyl)-1H-pyrrolo[2,3-b]pyridin-4-yl)piperazine-1-carboxylate (312 mg, 568 µmol) in DCM (20 mL) at room temperature, and then stirred at RT for 1 h. LC-MS showed the reaction was completed. The reaction mixture was concentrated, and the residue was directly purified by silica gel column (ethyl acetate/petroleum ether=1/5-5/1) to afford the title compound (281 mg, yield 79%) as a colorless oil. MS (ES+) C$_{26}$H$_{37}$BrF$_2$N$_6$O$_3$Si requires: 626, 628, found 627, 629 [M+H]$^+$.

Step 3. Synthesis of tert-butyl 4-(3-cyano-2-(1-(difluoromethyl)-1H-pyrazol-4-yl)-1-((2-(trimethylsilyl)ethoxy)methyl)-1H-pyrrolo[2,3-b]pyridin-4-yl)piperazine-1-carboxylate

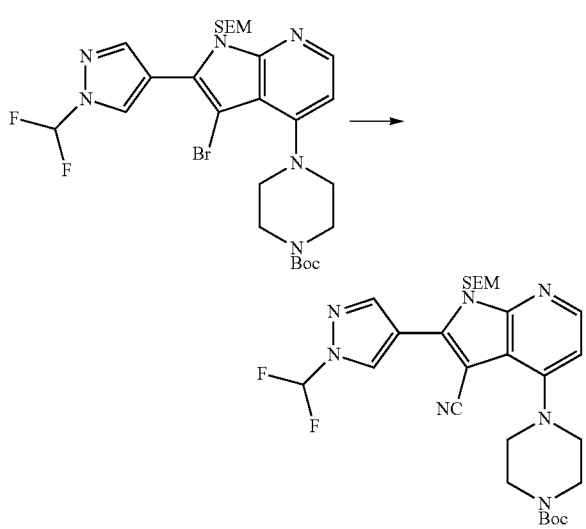

A mixture of tert-butyl 4-(3-bromo-2-(1-(difluoromethyl)-1H-pyrazol-4-yl)-1-((2-(trimethylsilyl)ethoxy)methyl)-1H-pyrrolo[2,3-b]pyridin-4-yl)piperazine-1-carboxylate (281 mg, 447 µmol), dicyanozinc (104 mg, 894 µmol), and Pd(PPh$_3$)$_4$ (51.6 mg, 44.7 µmol) in DMA (2 mL) was stirred at 120° C. for 1 h. LC-MS showed the reaction was completed. The reaction mixture was cooled and concentrated. The residue was purified by silica gel column (ethyl acetate/petroleum ether=3/10-3:1) to afford the title compound (223 mg, yield 86%) as a white solid. MS (ES+) C$_{27}$H$_{37}$F$_2$N$_7$O$_3$Si requires: 573, found 574 [M+H]$^+$.

Step 4. Synthesis of 2-(1-(difluoromethyl)-1H-pyrazol-4-yl)-4-(piperazin-1-yl)-1H-pyrrolo[2,3-b]pyridine-3-carbonitrile

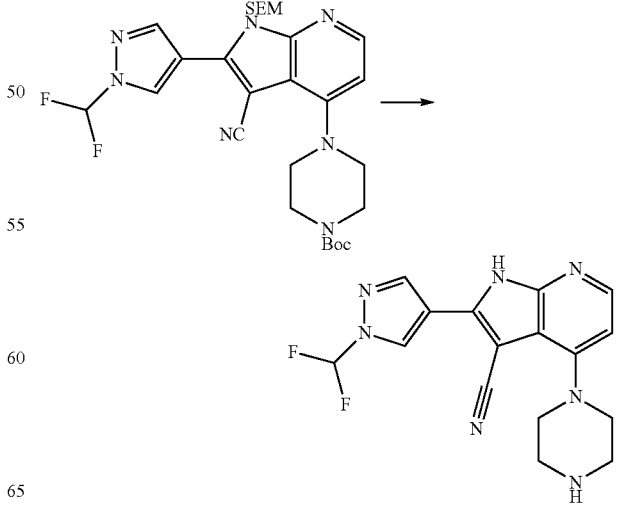

317

TFA (1 mL) was added to a solution of tert-butyl 4-(3-cyano-2-(1-(difluoromethyl)-1H-pyrazol-4-yl)-1-((2-(trimethylsilyl)ethoxy)methyl)-1H-pyrrolo[2,3-b]pyridin-4-yl)piperazine-1-carboxylate (225 mg, 392 μmol) in DCM (2 mL) at room temperature, and then stirred for 16 h. LC-MS showed the reaction was completed. The reaction mixture was concentrated to afford the crude product (130 mg) as a yellow oil. MS (ES+) $C_{16}H_{15}F_2N_7$ requires: 343, found 344 [M+H]$^+$.

Step 5. Synthesis of ethyl 4-(3-cyano-2-(1-(difluoromethyl)-1H-pyrazol-4-yl)-1H-pyrrolo[2,3-b]pyridin-4-yl)piperazine-1-carboxylate

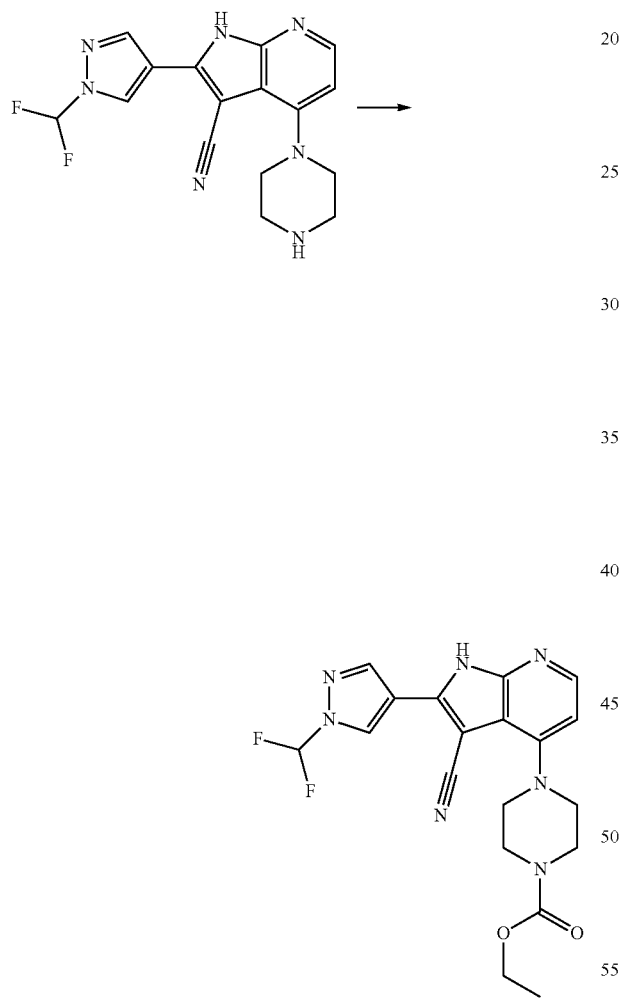

Ethyl chloroformate (38 mg, 348 μmol) was added to a solution of 2-(1-(difluoromethyl)-1H-pyrazol-4-yl)-4-(piperazin-1-yl)-1H-pyrrolo[2,3-b]pyridine-3-carbonitrile (60 mg, 174 μcool) and triethylamine (522 mg, 522 μmol) in DMF (2 mL), and then stirred at room temperature for 1 h. LC-MS showed the reaction was completed. The reaction mixture was concentrated and purified by Prep-HPLC to give the title compound (33.1 mg, 45%) as a white solid. MS (ES+) $C_{19}H_{19}F_2N_7O_2$ requires: 415, found 416 [M+H]$^+$.

318

Example 7. Synthesis of ethyl 4-(2-(1-methyl-1H-pyrazol-4-yl)-3-(prop-1-yn-1-yl)-1H-pyrrolo[2,3-b]pyridin-4-yl)piperazine-1-carboxylate

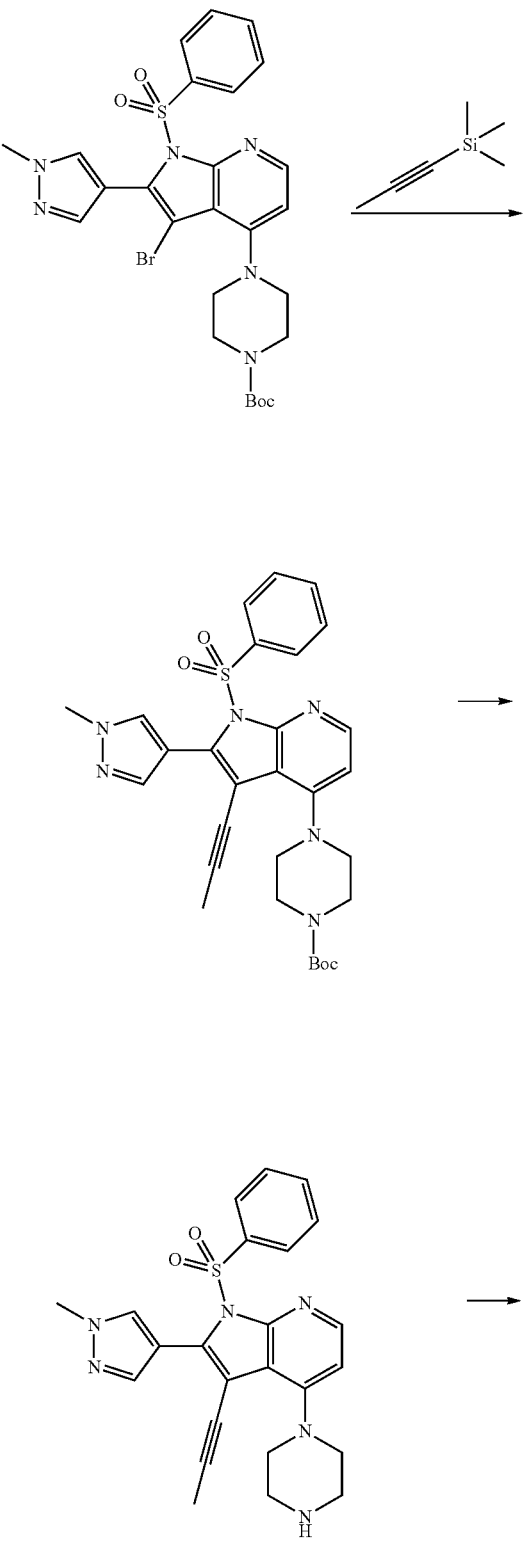

319

-continued

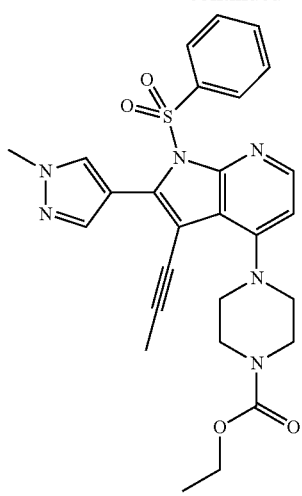

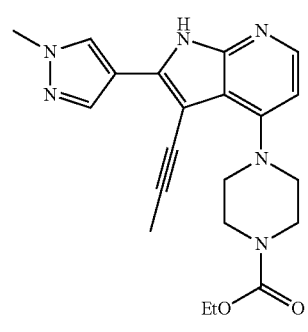 [SMILES: CC#Cc1c(-c2cnn(C)c2)[nH]c2nccc(N3CCN(C(=O)OCC)CC3)c12]

Step 1. Synthesis of tert-butyl 4-(2-(1-methyl-1H-pyrazol-4-yl)-1-(phenylsulfonyl)-3-(prop-1-yn-1-yl)-1H-pyrrolo[2,3-b]pyridin-4-yl)piperazine-1-carboxylate

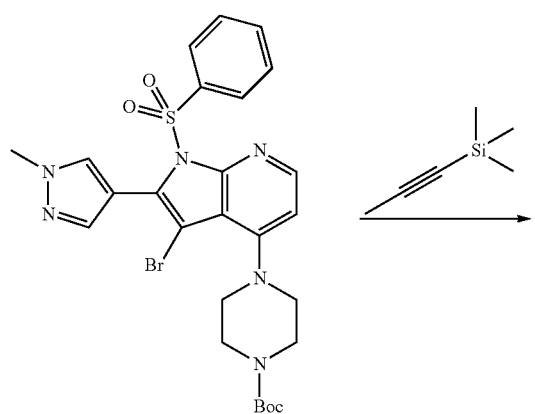

320

-continued

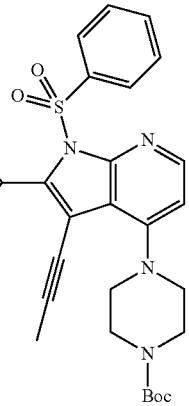

A mixture of tert-butyl 4-(3-bromo-2-(1-methyl-1H-pyrazol-4-yl)-1-(phenylsulfonyl)-1H-pyrrolo[2,3-b]pyridin-4-yl)piperazine-1-carboxylate (600 mg, 1.0 mmol), trimethyl (prop-1-yn-1-yl)silane (560 mg, 5.0 mmol), Pd(t-Bu$_3$P)$_2$ (100 mg, 0.20 mmol), CuI (38 mg, 0.20 mmol), triethylamine (500 mg, 5.0 mmol), and K$_2$CO$_3$ (408 mg, 3.0 mmol) in DMF (10 mL) was degassed with nitrogen and then stirred at 100° C. for 3 hours. The reaction mixture was evaporated to dryness. The residue was purified by flash column chromatography (petroleum ether:ethyl acetate=10:1-1:5) to give the title compound (200 mg, yield 35%) as a yellow solid. MS (ES+) C$_{29}$H$_{32}$N$_6$O$_4$S requires: 560, found 561 [M+H]$^+$.

Step 2. Synthesis of 2-(1-methyl-1H-pyrazol-4-yl)-1-(phenylsulfonyl)-4-(piperazin-1-yl)-3-(prop-1-yn-1-yl)-1H-pyrrolo[2,3-b]pyridine

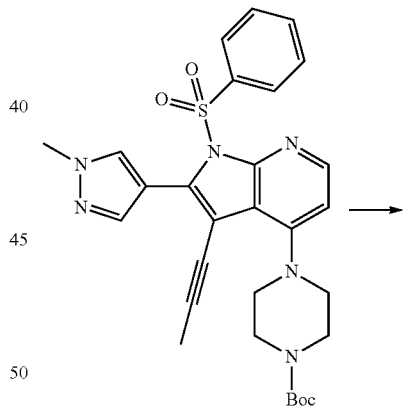

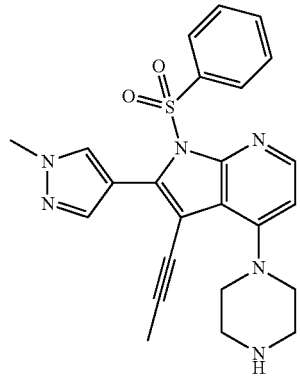

TFA (1 mL) was added to a solution of tert-butyl 4-(2-(1-methyl-1H-pyrazol-4-yl)-1-(phenylsulfonyl)-3-(prop-1-yn-1-yl)-1H-pyrrolo[2,3-b]pyridin-4-yl)piperazine-1-carboxylate (200 mg, 0.35 mmol) in DCM (3 mL), and then stirred at room temperature for 4 hours. LC-MS showed the start material was completely consumed. The reaction mixture was evaporated to dryness to give crude product without further purification. MS (ES+) $C_{24}H_{24}N_6O_2S$ requires: 460, found 461 $[M+H]^+$.

Step 3. Synthesis of ethyl 4-(2-(1-methyl-1H-pyrazol-4-yl)-1-(phenylsulfonyl)-3-(prop-1-yn-1-yl)-1H-pyrrolo[2,3-b]pyridin-4-yl)piperazine-1-carboxylate

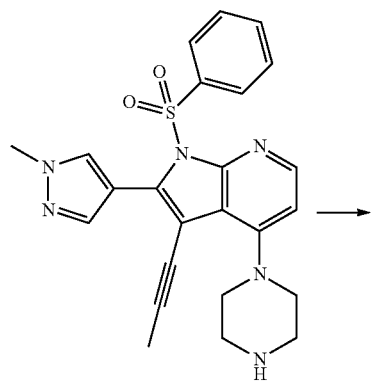

Ethyl chloroformate (57 mg, 0.53 mmol) was added to a solution of 2-(1-methyl-1H-pyrazol-4-yl)-1-(phenylsulfonyl)-4-(piperazin-1-yl)-3-(prop-1-yn-1-yl)-1H-pyrrolo[2,3-b]pyridine (crude, 0.35 mmol) and triethylamine (350 mg, 3.5 mmol) in DCM (3 mL), and then stirred at room temperature for 2 hours. The reaction mixture was diluted with DCM, and washed with water and brine. The organic layer was evaporated to dryness to give crude product without further purification. MS (ES+) $C_{27}H_{28}N_6O_4S$ requires: 532, found 533 $[M+H]^+$.

Step 4. Synthesis of ethyl 4-(2-(1-methyl-1H-pyrazol-4-yl)-3-(prop-1-yn-1-yl)-1H-pyrrolo[2,3-b]pyridin-4-yl)piperazine-1-carboxylate

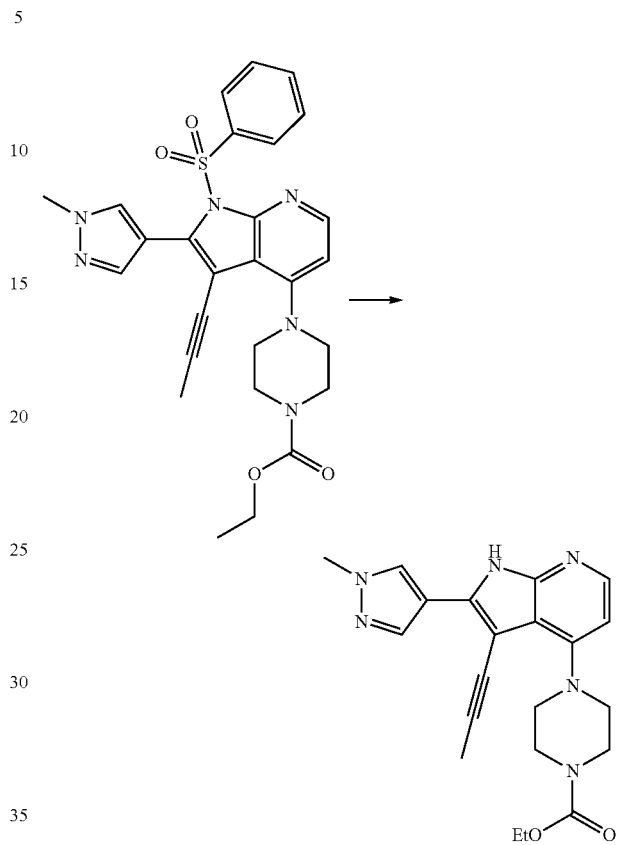

TBAF (1.0 M in THF, 1.0 mL, 1.0 mmol) was added to a solution of ethyl 4-(2-(1-methyl-1H-pyrazol-4-yl)-1-(phenylsulfonyl)-3-(prop-1-yn-1-yl)-1H-pyrrolo[2,3-b]pyridin-4-yl)piperazine-1-carboxylate (crude, assumed 0.35 mmol) in THF (2 mL), and then stirred at 60° C. for 2 hours. The reaction mixture was cooled, concentrated, and directly purified by Prep-HPLC to give the title compound (23 mg, yield 16%) as a white solid. MS (ES+) $C_{21}H_{24}N_6O_2$ requires: 392, found: 393 $[M+H]^+$.

Synthetic Protocol C

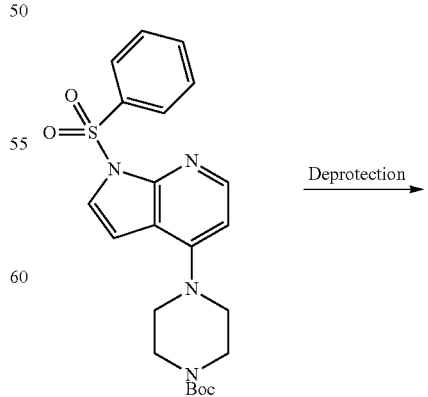

E

-continued

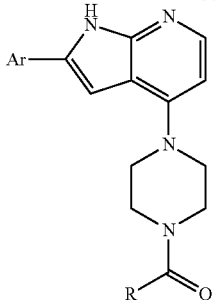

I

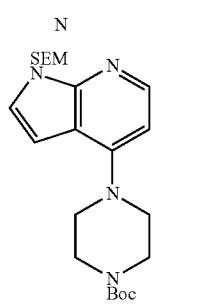

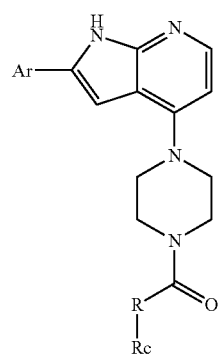

J

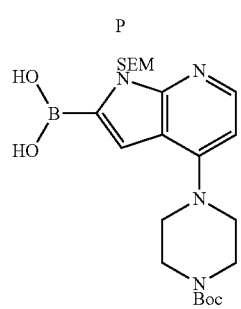

Intermediate E was prepared using the methods described in synthetic protocol A. The intermediate E can be selectively deprotected to provide intermediate N, followed by re-protection yields intermediate P. Intermediate P can be further functionalized via metalation/borylation to provide boronic acid/ester intermediate Q. Intermediate Q can be functionalized by a palladium-mediated coupling reaction (e.g., Suzuki, Stille, Sonogashira, or Negishi coupling) to yield intermediate R. Double deprotection of R followed by a capping reaction, such as amide bond formation or carbamate formation, provides intermediate I. Final compounds J can be achieved by substitution, halogenation, or other capping reactions of intermediate I. As shown below, compound 205 of Tables 1, 2, and 3 was prepared using synthetic protocol C.

Example 8. Synthesis of (1r,3r)-3-(4-(2-(2-methylthiazol-4-yl)-1H-pyrrolo[2,3-b]pyridin-4-yl)piperazine-1-carbonyl)cyclobutanecarbonitrile

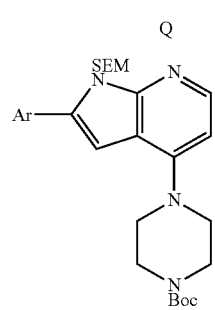

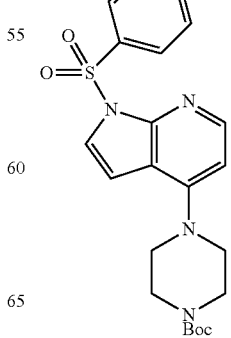

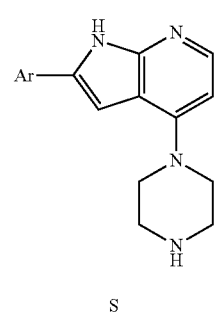

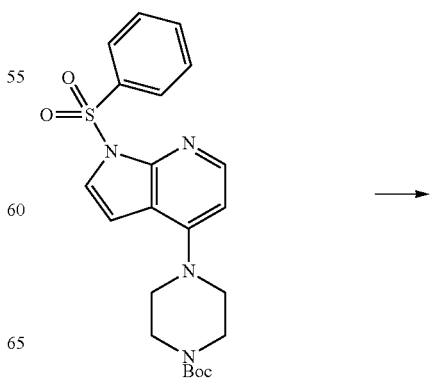

325
-continued

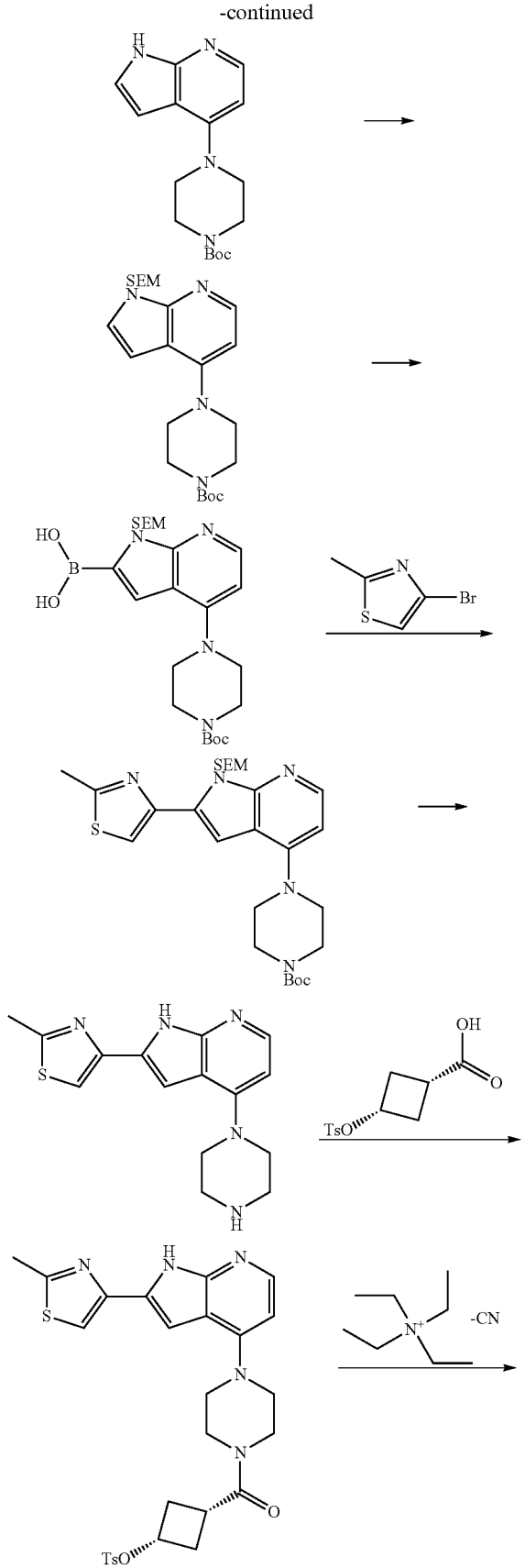

326
-continued

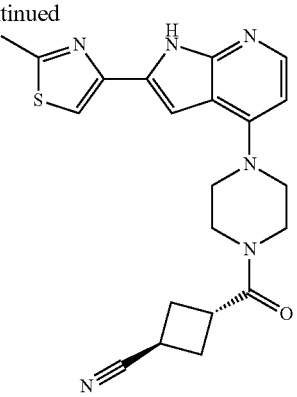

Step 1. Synthesis of tert-butyl tert-butyl 4-(1H-pyrrolo[2,3-b]pyridin-4-yl)piperazine-1-carboxylate Sodium hydroxide (170 mL, 2.0 M) was added to a solution of tert-butyl 4-(1-(phenylsulfonyl)-1H-pyrrolo[2,3-b]pyridin-4-yl)piperazine-1-carboxylate (50 g, 112.0 mmol) in MeOH (170 mL). Then, the resulting mixture was heated at 70° C. for 16 hours. After cooling to room temperature, the precipitate solid was collected by filtration, which was then dried to give the title compound (30.0 g, 89%) as a white solid. MS (ES+) $C_{16}H_{22}N_4O_2$ requires: 302, found: 303 [M+H]$^+$.

Step 2. Synthesis of tert-butyl 4-(1-((2-(trimethylsilyl)ethoxy)methyl)-1H-pyrrolo[2,3-b]pyridin-4-yl)piperazine-1-carboxylate Sodium hydride (1.18 g, 49.5 mmol) was slowly added to a solution of tert-butyl 4-(1H-pyrrolo[2,3-b]pyridin-4-yl)

piperazine-1-carboxylate (10 g, 33 mmol) in DMF (150 mL), and stirred at 0° C. for 30 minutes. 2-(trimethylsilyl)ethoxymethyl chloride (SEMCl) (5.5 g, 33 mmol) was added, and then stirred for another 2 hours. LC-MS showed the reaction was sufficiently clean. The reaction was quenched with H$_2$O and extracted with EtOAc. The organic layer was washed with H$_2$O and brine, dried over Na$_2$SO$_4$, and then concentrated to afford crude product, which was purified by flash chromatography on silica gel eluting with petroleum ether/ethyl acetate (3:1) to obtain the title compound (12.0 g, 84%) as a yellow solid. MS (ES+) C$_{22}$H$_{36}$N$_4$O$_3$Si requires: 432, found: 433 [M+H]$^+$.

Step 3. Synthesis of 4-(4-(tert-butoxycarbonyl)piperazin-1-yl)-1-((2-(trimethylsilyl)ethoxy)methyl)-1H-pyrrolo[2,3-b]pyridin-2-ylboronic Acid

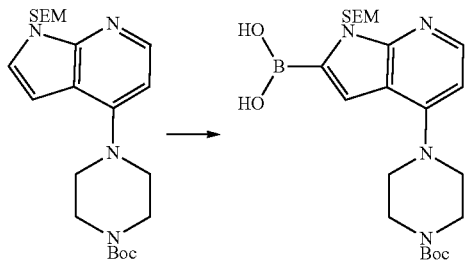

LDA (29.5 g, 276 mmol, 2.0 M) was added dropwise to a solution of tert-butyl 4-(1-((2-(trimethylsilyl)ethoxy)methyl)-1H-pyrrolo[2,3-b]pyridin-4-yl)piperazine-1-carboxylate (23 g, 53.1 mmol) in dry THF (300 mL) at −7° C., and then stirred at −78° C. for 30 minutes. Then triisopropyl borate (64.8 g, 345.0 mmol) was added at −78° C. dropwise. Subsequently, the reaction was stirred at −78° C. for another 1 hour, LC-MS showed that the reaction was completed. The cold bath was removed. The reaction was quenched by aqueous NH$_4$C$_1$ and extracted with EA. The organic layer was washed with water and brine, dried over Na$_2$SO$_4$, and then concentrated to obtain the title compound (17.66 g, 70%) as a yellow solid. MS (ES+) C$_{22}$H$_{37}$BN$_4$O$_5$Si requires: 476, found: 477 [M+H]$^+$.

Step 4. Synthesis of tert-butyl 4-(2-(2-methylthiazol-4-yl)-1-((2-(trimethylsilyl)ethoxy)methyl)-1H-pyrrolo[2,3-b]pyridin-4-yl)piperazine-1-carboxylate

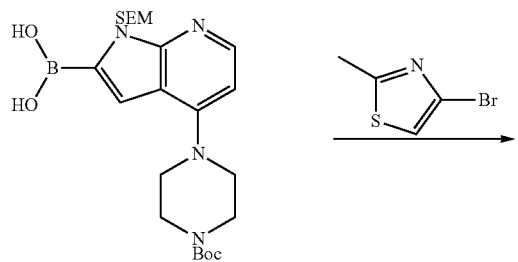

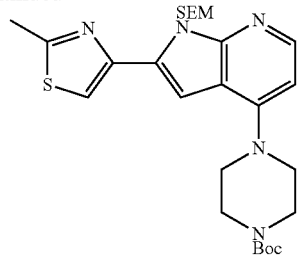

A mixture of 4-bromo-2-methylthiazole (600 mg, 3.36 mmol), (4-(4-(ethoxycarbonyl)piperazin-1-yl)-1-((2-(trimethylsilyl)ethoxy)methyl)-1H-pyrrolo[2,3-b]pyridin-2-yl)boronic acid (1.60 g, 3.36 mmol), Pd(dppf)Cl$_2$ (245 mg, 336 µmol), and triethylamine (1.01 g, 10.0 mmol) in dioxane (20 mL) and H$_2$O (5 mL) was stirred at 70° C. for 2 h. After that, the reaction mixture was cooled and concentrated. The residue was purified by silica gel column (petroleum ether/ethyl acetate=2/1) to obtain the title compound as a yellow solid (1.5 g, 84%). MS (ES+) C$_{26}$H$_{39}$N$_5$O$_3$SSi requires: 529, found: 530 [M+H]$^+$.

Step 5. Synthesis of 2-methyl-4-(4-(piperazin-1-yl)-1H-pyrrolo[2,3-b]pyridin-2-yl)thiazole

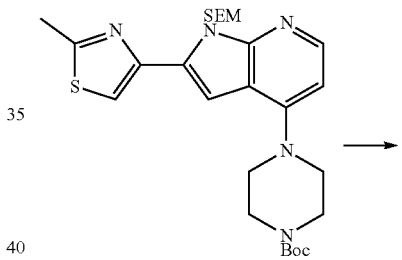

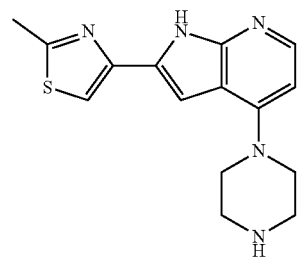

TFA (5 mL) was added to a solution of tert-butyl 4-(2-(2-methylthiazol-4-yl)-1-((2-(trimethylsilyl)ethoxy)methyl)-1H-pyrrolo[2,3-b]pyridin-4-yl)piperazine-1-carboxylate (1.5 g, 2.83 mmol) in DCM (5 mL), and then the solution was stirred at 40° C. for 12 h. Next, the solution was concentrated at 40-50° C. The residue was purified by reversed-phase column and then triturated with CH$_3$OH (15 mL) to obtain the title compound as a white solid (620 mg, 73%). MS (ES+) C$_{15}$H$_{17}$N$_5$S requires: 299, found: 300 [M+H]$^+$.

Step 6. Synthesis of (1s,3s)-3-(4-(2-(2-methylthiazol-4-yl)-1H-pyrrolo[2,3-b]pyridin-4-yl)piperazine-1-carbonyl)cyclobutyl 4-methylbenzenesulfonate

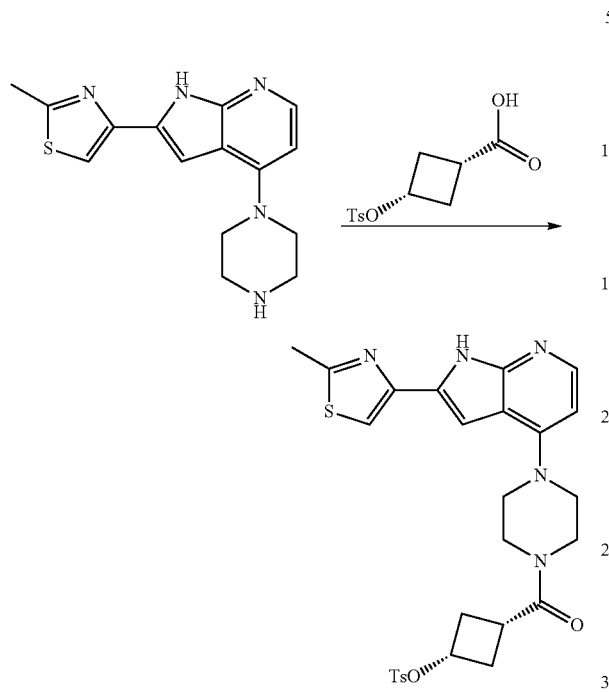

HATU (306 mg, 805 μmol) was added to a mixture of 2-methyl-4-(4-(piperazin-1-yl)-1H-pyrrolo[2,3-b]pyridin-2-yl)thiazole (201 mg, 671 μmol), (1s,3s)-3-(tosyloxy)cyclobutanecarboxylic acid (200 mg, 738 umol), and DIEA (260 mg, 2.01 mmol) in DMF (5 mL), and then stirred at room temperature for 16 h. The reaction mixture was diluted with ethyl acetate, and washed with water and brine. The organic layer was dried, filtered, and concentrated. The residue was purified by silica gel column (MeOH/EtOAc=1/10) to obtain the title compound (226 mg, 55%) as a colorless oil. MS (ES+) $C_{27}H_{29}N_5O_4S_2$ requires: 551, found 552 $[M+H]^+$.

Step 7. Synthesis of (1r,3r)-3-(4-(2-(2-methylthiazol-4-yl)-1H-pyrrolo[2,3-b]pyridin-4-yl)piperazine-1-carbonyl)cyclobutanecarbonitrile

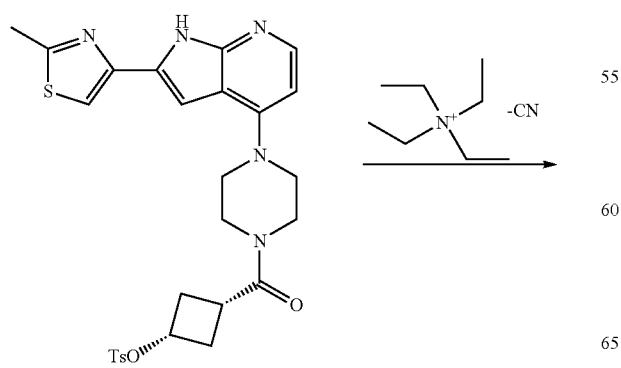

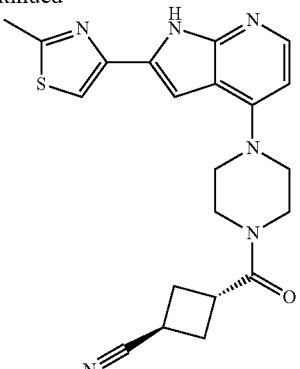

Tetraethylammonium cyanide (32 mg, 2.05 umol) was added to a mixture of (1s,3s)-3-(4-(2-(2-methylthiazol-4-yl)-1H-pyrrolo[2,3-b]pyridin-4-yl)piperazine-1-carbonyl)cyclobutyl 4-methylbenzenesulfonate (226 mg, 409 μmol) in $CH_3CN$ (10 mL), and then stirred at 80° C. for 16 h. The reaction mixture was cooled and concentrated. The residue was directly purified by Prep-HPLC to give the title compound (44.3 mg, 36%) as a white solid. MS (ES+) $C_{21}H_{22}N_6OS$ requires: 406, found 407 $[M+H]^+$.

Example 9. Synthesis of Other Example Compounds

Table 2 indicates which Synthetic Protocol A, B, or C described in the disclosure was used to synthesize various compounds described herein. Blank values indicate that a synthetic scheme other than one of Synthetic Protocols A, B, or C was used and that the synthetic scheme for such compound is set forth in the Examples.

TABLE 2

Synthetic Protocols Used for Example Compounds

| # | Synthetic Protocol |
|---|---|
| 1 | A |
| 2 | A |
| 3 | A |
| 4 | A |
| 5 | A |
| 6 | A |
| 7 | A |
| 8 | A |
| 9 | A |
| 10 | A |
| 11 | A |
| 12 | A |
| 13 | A |
| 14 | A |
| 15 | A |
| 16 | A |
| 17 | A |
| 18 | A |
| 19 | A |
| 20 | A |
| 21 | A |
| 22 | A |
| 23 | A |
| 24 | A |
| 25 | A |
| 26 | A |
| 27 | A |
| 29 | A |
| 30 | A |

TABLE 2-continued

Synthetic Protocols Used for Example Compounds

| # | Synthetic Protocol |
|---|---|
| 31 | A |
| 32 | A |
| 33 | A |
| 34 | A |
| 35 | A |
| 36 | A |
| 37 | A |
| 38 | B |
| 39 | A |
| 40 | A |
| 41 | A |
| 42 | A |
| 43 | A |
| 44 | A |
| 45 | A |
| 46 | A |
| 47 | A |
| 48 | A |
| 49 | A |
| 50 | B |
| 51 | A |
| 52 | A |
| 53 | A |
| 54 | A |
| 55 | B |
| 56 | A |
| 57 | A |
| 58 | A |
| 59 | A |
| 60 | A |
| 61 | A |
| 62 | A |
| 63 | A |
| 64 | A |
| 65 | A |
| 66 | A |
| 67 | A |
| 68 | B |
| 69 | A |
| 70 | A |
| 71 | A |
| 72 | A |
| 73 | A |
| 74 | A |
| 75 | A |
| 76 | A |
| 77 | A |
| 78 | A |
| 79 | A |
| 80 | A |
| 81 | A |
| 82 | A |
| 83 | A |
| 84 | A |
| 85 | A |
| 86 | A |
| 87 | A |
| 88 | A |
| 89 | A |
| 90 | A |
| 91 | A |
| 92 | A |
| 93 | A |
| 94 | A |
| 95 | A |
| 96 | A |
| 97 | A |
| 98 | A |
| 99 | B |
| 100 | A |
| 101 | A |
| 102 | A |
| 103 | A |
| 104 | A |
| 105 | A |
| 106 | A |
| 107 | A |
| 108 | A |
| 109 | A |
| 110 | A |
| 111 | B |
| 112 | A |
| 113 | A |
| 114 | A |
| 115 | B |
| 116 | A |
| 117 | A |
| 118 | A |
| 119 | A |
| 120 | A |
| 121 | B |
| 122 | A |
| 123 | C |
| 124 | A |
| 125 | A |
| 126 | A |
| 127 | A |
| 128 | A |
| 129 | B |
| 130 | B |
| 131 | A |
| 132 | B |
| 133 | A |
| 134 | A |
| 135 | A |
| 136 | B |
| 137 | B |
| 138 | A |
| 139 | A |
| 140 | B |
| 141 | A |
| 142 | A |
| 143 | A |
| 144 | A |
| 145 | A |
| 146 | A |
| 147 | A |
| 148 | B |
| 149 | A |
| 150 | A |
| 151 | A |
| 152 | A |
| 153 | A |
| 154 | A |
| 155 | A |
| 156 | A |
| 157 | A |
| 158 | A |
| 159 | A |
| 160 | A |
| 161 | A |
| 162 | A |
| 163 | A |
| 164 | A |
| 165 | A |
| 166 | A |
| 167 | A |
| 168 | A |
| 169 | A |
| 170 | A |
| 171 | A |
| 172 | A |
| 173 | A |
| 174 | A |
| 175 | A |
| 177 | A |
| 178 | B |
| 179 | A |
| 180 | A |
| 181 | A |

TABLE 2-continued

Synthetic Protocols Used for Example Compounds

| # | Synthetic Protocol |
|---|---|
| 182 | A |
| 183 | A |
| 184 | A |
| 185 | A |
| 186 | B |
| 187 | B |
| 188 | A |
| 189 | A |
| 190 | A |
| 191 | A |
| 192 | A |
| 194 | A |
| 195 | A |
| 196 | A |
| 197 | A |
| 198 | A |
| 199 | B |
| 200 | B |
| 201 | B |
| 202 | A |
| 203 | A |
| 204 | A |
| 205 | C |
| 206 | A |
| 207 | B |
| 208 | B |
| 209 | A |
| 210 | A |
| 211 | A |
| 212 | A |
| 213 | A |
| 214 | A |
| 215 | B |
| 216 | B |
| 217 | B |
| 218 | A |
| 219 | A |
| 220 | A |
| 221 | A |
| 222 | A |
| 223 | A |
| 224 | A |
| 225 | A |
| 226 | A |
| 227 | A |
| 228 | B |
| 229 | A |
| 230 | A |
| 231 | A |
| 232 | A |
| 233 | A |
| 234 | A |
| 235 | A |
| 236 | A |
| 237 | B |
| 238 | A |
| 239 | A |
| 240 | A |
| 241 | A |
| 242 | A |
| 243 | A |
| 244 | A |
| 245 | B |
| 246 | A |
| 247 | A |
| 248 | A |
| 249 | A |
| 250 | A |
| 251 | A |
| 252 | A |
| 253 | A |
| 254 | A |
| 255 | B |
| 256 | B |
| 257 | B |
| 258 | B |
| 259 | A |
| 260 | A |
| 261 | A |
| 262 | A |
| 263 | A |
| 264 | A |
| 265 | A |
| 266 | A |
| 267 | B |
| 268 | A |
| 269 | A |
| 270 | A |
| 271 | A |
| 272 | A |
| 273 | A |
| 274 | B |
| 275 | A |
| 276 | B |
| 277 | A |
| 278 | A |
| 279 | A |
| 280 | A |
| 281 | A |
| 282 | A |
| 283 | A |
| 284 | B |
| 285 | B |
| 286 | A |
| 287 | A |
| 288 | B |
| 289 | B |
| 290 | B |
| 291 | A |
| 292 | A |
| 293 | B |
| 294 | B |
| 295 | B |
| 296 | B |
| 297 | B |
| 299 | C |
| 300 | A |
| 301 | A |
| 302 | A |
| 303 | B |
| 304 | A |
| 305 | A |
| 306 | A |
| 307 | A |
| 308 | B |
| 309 | A |
| 310 | A |
| 311 | A |
| 312 | A |
| 313 | A |
| 314 | A |
| 315 | A |
| 316 | A |
| 317 | A |
| 318 | B |
| 319 | A |
| 320 | B |
| 321 | B |
| 322 | A |
| 323 | A |
| 324 | A |
| 325 | A |
| 326 | A |
| 327 | A |
| 328 | A |
| 329 | A |
| 330 | B |
| 331 | B |
| 332 | B |
| 333 | A |

TABLE 2-continued

Synthetic Protocols Used for Example Compounds

| # | Synthetic Protocol |
|---|---|
| 334 | A |
| 335 | A |
| 336 | A |
| 337 | B |
| 338 | A |
| 339 | B |
| 340 | B |
| 341 | B |
| 342 | B |
| 343 | A |
| 344 | B |
| 345 | A |
| 346 | A |
| 347 | B |
| 348 | A |
| 349 | A |
| 350 | B |
| 351 | A |
| 352 | A |
| 353 | A |
| 354 | A |
| 355 | A |
| 356 | B |
| 357 | B |
| 358 | A |
| 359 | A |
| 360 | B |
| 361 | A |
| 362 | A |
| 363 | B |
| 364 | A |
| 365 | B |
| 366 | B |
| 367 | B |
| 368 | B |
| 369 | B |
| 370 | B |
| 371 | A |
| 372 | A |
| 373 | A |
| 374 | B |
| 375 | B |
| 376 | B |
| 377 | A |
| 378 | A |
| 379 | A |
| 380 | A |
| 381 | A |
| 382 | A |
| 383 | A |
| 384 | A |
| 385 | A |
| 386 | A |
| 387 | A |
| 388 | A |
| 389 | A |
| 390 | A |
| 391 | B |
| 392 | A |
| 393 | A |
| 394 | B |
| 395 | B |
| 396 | A |
| 397 | B |
| 398 | A |
| 399 | A |
| 400 | A |
| 401 | A |
| 402 | A |
| 403 | A |
| 404 | B |
| 405 | A |
| 406 | A |
| 407 | B |
| 408 | A |
| 409 | A |
| 410 | A |
| 412 | B |
| 413 | B |
| 414 | B |
| 415 | A |
| 416 | A |
| 417 | A |
| 418 | A |
| 420 | A |
| 421 | A |
| 422 | A |
| 423 | A |
| 424 | A |
| 425 | A |
| 426 | B |
| 427 | A |
| 428 | A |
| 429 | A |
| 430 | A |
| 431 | A |
| 432 | A |
| 433 | A |
| 434 | B |
| 436 | A |
| 437 | A |
| 438 | A |
| 439 | A |
| 440 | B |
| 441 | B |
| 442 | A |
| 443 | B |
| 444 | A |
| 445 | A |
| 446 | A |
| 447 | A |
| 448 | A |
| 449 | B |
| 450 | A |
| 451 | A |
| 452 | A |
| 453 | A |
| 454 | A |
| 455 | A |
| 456 | A |
| 457 | A |
| 458 | A |
| 459 | A |
| 460 | A |
| 461 | A |
| 462 | A |
| 463 | A |
| 464 | A |
| 465 | B |
| 466 | A |
| 467 | A |
| 468 | A |
| 469 | A |
| 470 | B |
| 471 | A |
| 472 | A |
| 473 | A |
| 474 | A |
| 475 | A |
| 476 | A |
| 477 | A |
| 478 | A |
| 479 | A |

Example 10 ALK Binding Assays

Binding assays were conducted using the LAN-THASCREEN® technology (ThermoFisher Scientific).

LANTHASCREEN® is a competitive binding, displacement assay where the assumed steady state occupancy of the binding site is measured using a time-resolved, fluorescence energy transfer (TR-FRET) readout between a fluorescent tracer and Europium (Eu)-tagged antibody specific for the kinase or expression tag (e.g., GST) of interest. Displacement of the tracer by a compound of the disclosure reduces, and is directly proportional to, the TR-FRET between the tracer and the antibody. Tracer was used at a concentration equal to or near to its Kd for the kinase. The Eu-tagged antibody was typically used in excess to ensure sampling of all competent protein capable of binding the tracer.

For these assays, a mutant ALK2 was used that was N-terminally tagged with GST (ALK2R206H Carna Bioscience (09-148) or ALK2R206H ThermoFisher (PV6232)); a Eu-tagged anti-GST antibody (ThermoFisher) and Kinase Tracer 178 (ThermoFisher).

In all cases, the kinase (2-5 nM) was mixed with Eu-tagged antibody (4-10 nM) mix and tracer (50 nM) were incubated with test compound titrations prepared in 100% DMSO (1% DMSO final) for 30 minutes at room temperature. All reagents and compounds were dissolved in Kinase Buffer A (ThermoFisher) to achieve the final concentration. The plates were read on a PerkinElmer EnVision® multilabel plate reader or a BioTek Synergy Neo plate reader, and the assay signal was represented as a ratio of the TR-FRET emission ($\lambda_{ex}$ 330 nm, $\lambda^{em}$ 662 nm and $\lambda^{em}$ 665 nm). This readout was normalized to 0% and 100% inhibited control wells, plotted against inhibitor concentration, and fitted to a 4-parameter log dose response curve.

The results of this assay are shown in Table 3 in the column labelled "Binding Assay" wherein "A" represents an $IC_{50}$ of less than or equal to 10 nM; "B" represents an $IC_{50}$ of greater than 10 nM and less than or equal to 50 nM; and "C" represents an $IC_{50}$ of greater than 50 nM. Blank values in the table indicate that the particular compound was not tested in this assay.

Example 11. Cell-Based ALK2-R206H Cell Activity Assay

A. Cell Line HEK293-ALK2-R206H

A HEK293 (ATCC, Cat No. CRL1573) based stable cell line expressing human ALK2 R206H cDNA (synthesized by GeneScript, Piscataway, N.J.) and a FLAG tag at the C-terminus was generated by lentivirus transduction and subsequent blasticidin (Life Technologies, Cat No. A1113902) selection at 10 µg/ml for >2 wks. This cell line was named HEK293-ALK2-R206H.

B. Measurement of Smad1-Ser463/Ser465 Phosphorylation by AlphaLISA

HEK293-ALK2-R206H cells were grown, harvested, and then resuspended in serum-free, phenol red-free DMEM high glucose media (Life Technologies, Cat No. 31053). The media also contained 50 units/ml penicillin and 50 µg/ml streptomycin (Life Technologies, Cat. No. 15070-063). HEK293-ALK2-R206H cells were then plated in white opaque 384-wells microplates (2×104/well) (OptiPlate-384, PerkinElmer, Waltham, Mass., Cat No. 6007299) overnight (>16h) at 37° C. 5% CO2 for use in the assay.

Test compounds were first diluted to 4 mM or 0.4 mM and then serially diluted 3-fold into 10 different concentrations using DMSO. Each concentration of compound was further diluted 40-fold with phenol red-free DMEM (Life Technologies, Cat No. 31053). 2 µl of the diluted compounds were then dispensed into the HEK293-ALK2-R206H cell-containing wells of the microplates in duplicates. In this way, each compound was tested in 10 doses (3-fold serial dilution with the top concentration being 10 µM or 1 µM). Liquid handling was achieved using a Bravo Automated Liquid Handling Platform (Agilent Technologies). DMSO without compound was used as a negative control. The positive control was 1 µM LDN193189, a known bone morphogenetic protein (BMP inhibitor).

After 2-3 hours of incubation with test compound or control, the cells were lysed and signal was developed using ALPHASCREEN® SUREFIRE® SMAD1 (p-Ser463/465) cellular kinase assay kit (PerkinElmer, Cat No. TGRSM1S10K) following the manufacturer's recommended protocol. The microplates were read using Perkin Elmer ENVISION® plate reader (emission 520-620 nM). The signal reflected the level of phospho-Ser/463/465-Smad1 in the lysate. The raw data were plotted using the DMSO negative and LDN193189 positive controls as the 0% and 100% inhibition, respectively. The 10-point dose response curve was used to calculate the IC50 values.

The results of this assay are shown in Table 3 in the column labeled "Cell Assay" wherein "A" represents an IC50 of less than or equal to 100 nM; "B" an IC50 of greater than 100 nM and less than or equal to 500 nM; "C" an IC50 of greater than 500 nM. Blank values in the table indicate that the particular compound was not tested in this assay.

In Table 3, the following designations are used:

For "Binding Assay" data: ≤10 nM=A; ≥10-50 nM=B; >50 nM=C; and a blank value in the table indicates that the particular compound was not tested in this assay.

For "Cell Line" data: ≤100 nM=A; ≥100-500 nM=B; >500 nM=C; and a blank value in the table indicates that the particular compound was not tested in this assay.

TABLE 3

ALK2 Inhibitory Activity of Example Compounds of the Disclosure

| # | Binding Assay | Cell Line |
|---|---|---|
| 1 | B | C |
| 2 | A | C |
| 3 | B | |
| 4 | B | |
| 5 | B | |
| 6 | A | B |
| 7 | A | A |
| 8 | A | B |
| 9 | A | |
| 10 | B | |
| 11 | A | B |
| 12 | A | B |
| 13 | A | B |
| 14 | C | |
| 15 | B | |
| 16 | B | |
| 17 | B | |
| 18 | B | |
| 19 | A | B |
| 20 | A | |
| 21 | A | B |
| 22 | B | |
| 23 | A | B |
| 24 | A | B |
| 25 | A | |
| 26 | A | B |
| 27 | A | |
| 29 | A | A |
| 30 | A | A |
| 31 | B | |
| 32 | B | B |
| 33 | B | B |
| 34 | A | B |

TABLE 3-continued

ALK2 Inhibitory Activity of Example Compounds of the Disclosure

| # | Binding Assay | Cell Line |
|---|---|---|
| 35 | A | B |
| 36 | A | |
| 37 | A | A |
| 38 | A | A |
| 39 | A | B |
| 40 | A | B |
| 41 | A | B |
| 42 | B | |
| 43 | C | |
| 44 | B | |
| 45 | A | A |
| 46 | A | A |
| 47 | A | |
| 48 | A | B |
| 49 | A | B |
| 50 | A | A |
| 51 | A | B |
| 52 | B | B |
| 53 | A | A |
| 54 | A | B |
| 55 | A | B |
| 56 | A | B |
| 57 | A | |
| 58 | C | |
| 59 | A | B |
| 60 | A | B |
| 61 | A | |
| 62 | B | |
| 63 | B | |
| 64 | A | B |
| 65 | A | A |
| 66 | A | B |
| 67 | A | B |
| 68 | A | A |
| 69 | A | A |
| 70 | A | A |
| 71 | A | B |
| 72 | B | |
| 73 | A | |
| 74 | B | |
| 75 | A | A |
| 76 | A | A |
| 77 | A | A |
| 78 | A | |
| 79 | A | |
| 80 | A | |
| 81 | B | |
| 82 | A | C |
| 83 | B | |
| 84 | B | |
| 85 | A | |
| 86 | A | A |
| 87 | B | |
| 88 | A | |
| 89 | A | A |
| 90 | A | A |
| 91 | A | B |
| 92 | A | |
| 93 | A | A |
| 94 | A | |
| 95 | A | |
| 96 | A | A |
| 97 | A | B |
| 98 | A | B |
| 99 | A | |
| 100 | A | B |
| 101 | B | |
| 102 | A | B |
| 103 | A | B |
| 104 | A | B |
| 105 | A | B |
| 106 | B | |
| 107 | B | |
| 108 | B | |
| 109 | A | A |
| 110 | B | |
| 111 | A | B |
| 112 | A | A |
| 113 | A | A |
| 114 | A | A |
| 115 | A | A |
| 116 | A | A |
| 117 | A | A |
| 118 | A | B |
| 119 | C | |
| 120 | A | B |
| 121 | A | A |
| 172 | A | B |
| 123 | A | B |
| 124 | A | A |
| 125 | A | A |
| 126 | A | A |
| 127 | B | B |
| 128 | A | B |
| 129 | A | A |
| 130 | A | A |
| 131 | B | C |
| 132 | A | A |
| 133 | A | B |
| 134 | A | B |
| 135 | A | B |
| 136 | A | A |
| 137 | A | A |
| 138 | A | |
| 139 | A | A |
| 140 | A | A |
| 141 | A | |
| 142 | A | |
| 143 | A | |
| 144 | A | C |
| 145 | A | A |
| 146 | A | A |
| 147 | A | A |
| 148 | A | B |
| 149 | A | B |
| 150 | A | B |
| 151 | A | B |
| 152 | A | B |
| 153 | A | B |
| 154 | A | |
| 155 | A | C |
| 156 | A | |
| 157 | C | |
| 158 | A | |
| 159 | A | A |
| 160 | A | A |
| 161 | A | A |
| 162 | A | A |
| 163 | A | |
| 164 | A | |
| 165 | B | |
| 166 | B | |
| 167 | A | A |
| 168 | A | |
| 169 | A | A |
| 170 | A | A |
| 171 | A | B |
| 172 | A | B |
| 173 | A | B |
| 174 | A | B |
| 175 | A | B |
| 177 | A | A |
| 178 | A | B |
| 179 | A | B |
| 180 | A | B |
| 181 | A | |
| 182 | B | |
| 183 | A | A |

TABLE 3-continued

ALK2 Inhibitory Activity of Example Compounds of the Disclosure

| # | Binding Assay | Cell Line |
|---|---|---|
| 184 | A | |
| 185 | A | B |
| 186 | A | B |
| 187 | A | A |
| 188 | A | A |
| 189 | A | A |
| 190 | A | A |
| 191 | A | B |
| 192 | A | B |
| 194 | A | A |
| 195 | A | A |
| 196 | B | |
| 197 | A | A |
| 198 | A | B |
| 199 | A | A |
| 200 | A | A |
| 201 | A | A |
| 202 | A | A |
| 203 | A | A |
| 204 | A | B |
| 205 | A | A |
| 206 | B | |
| 207 | A | A |
| 208 | A | A |
| 209 | A | |
| 210 | A | B |
| 211 | C | |
| 212 | A | A |
| 213 | A | B |
| 214 | A | B |
| 215 | A | B |
| 216 | A | |
| 217 | A | |
| 218 | A | A |
| 219 | A | A |
| 220 | B | C |
| 221 | A | B |
| 222 | A | |
| 223 | B | |
| 224 | A | C |
| 225 | A | B |
| 226 | B | |
| 227 | A | B |
| 228 | A | A |
| 229 | A | |
| 230 | A | |
| 231 | A | A |
| 232 | A | A |
| 233 | A | B |
| 234 | A | B |
| 235 | A | |
| 236 | A | |
| 237 | A | |
| 238 | A | |
| 239 | C | |
| 240 | B | |
| 241 | A | A |
| 242 | A | A |
| 243 | A | A |
| 244 | A | A |
| 245 | A | A |
| 246 | A | |
| 247 | A | |
| 248 | A | A |
| 249 | A | A |
| 250 | A | A |
| 251 | A | B |
| 252 | A | A |
| 253 | B | |
| 254 | A | B |
| 255 | A | A |
| 256 | A | A |
| 257 | A | A |
| 258 | A | A |
| 259 | A | B |
| 260 | A | A |
| 261 | A | |
| 262 | A | A |
| 263 | A | A |
| 264 | A | A |
| 265 | A | A |
| 266 | A | A |
| 267 | A | A |
| 268 | A | A |
| 269 | A | A |
| 270 | A | A |
| 271 | A | A |
| 272 | A | A |
| 273 | A | B |
| 274 | A | A |
| 275 | A | A |
| 276 | A | A |
| 277 | A | A |
| 278 | A | A |
| 279 | A | A |
| 280 | A | A |
| 281 | A | B |
| 282 | A | A |
| 283 | A | B |
| 284 | A | A |
| 285 | A | A |
| 286 | A | B |
| 287 | A | B |
| 288 | A | A |
| 289 | A | A |
| 290 | A | A |
| 291 | A | A |
| 292 | A | B |
| 293 | A | |
| 294 | A | A |
| 295 | A | A |
| 296 | A | A |
| 297 | A | A |
| 299 | A | A |
| 300 | A | B |
| 301 | A | B |
| 302 | A | A |
| 303 | A | A |
| 304 | A | A |
| 305 | A | B |
| 306 | A | |
| 307 | A | B |
| 308 | A | A |
| 309 | C | |
| 310 | A | A |
| 311 | A | A |
| 312 | A | A |
| 313 | A | B |
| 314 | A | |
| 315 | A | A |
| 316 | A | A |
| 317 | A | B |
| 318 | A | |
| 319 | B | |
| 320 | A | B |
| 321 | A | A |
| 322 | A | A |
| 323 | A | A |
| 324 | A | B |
| 325 | A | A |
| 326 | A | A |
| 327 | A | |
| 328 | A | A |
| 329 | A | A |
| 330 | A | A |
| 331 | A | A |
| 332 | A | B |
| 333 | A | B |

TABLE 3-continued

ALK2 Inhibitory Activity of Example Compounds of the Disclosure

| # | Binding Assay | Cell Line |
|---|---|---|
| 334 | A | B |
| 335 | A | A |
| 336 | A | B |
| 337 | A | A |
| 338 | B | |
| 339 | B | |
| 340 | A | A |
| 341 | A | A |
| 342 | A | A |
| 343 | A | A |
| 344 | A | A |
| 345 | A | A |
| 346 | A | |
| 347 | A | A |
| 348 | A | C |
| 349 | A | A |
| 350 | A | A |
| 351 | A | B |
| 352 | A | B |
| 353 | B | |
| 354 | A | A |
| 355 | A | A |
| 356 | A | A |
| 357 | A | A |
| 358 | A | B |
| 359 | A | A |
| 360 | A | |
| 361 | B | |
| 362 | A | A |
| 363 | A | A |
| 364 | B | |
| 365 | A | A |
| 366 | A | A |
| 367 | A | A |
| 368 | A | A |
| 369 | A | A |
| 370 | A | A |
| 371 | A | A |
| 372 | A | A |
| 373 | B | |
| 374 | A | A |
| 375 | A | A |
| 376 | A | A |
| 377 | A | A |
| 378 | A | B |
| 379 | A | |
| 380 | A | A |
| 381 | A | A |
| 382 | A | A |
| 383 | A | A |
| 384 | B | |
| 385 | A | A |
| 386 | A | A |
| 387 | A | A |
| 388 | A | B |
| 389 | A | A |
| 390 | A | A |
| 391 | A | |
| 392 | A | A |
| 393 | C | |
| 394 | A | A |
| 395 | A | A |
| 396 | A | A |
| 397 | A | A |
| 398 | A | A |
| 399 | A | B |
| 400 | A | |
| 401 | A | A |
| 402 | A | |
| 403 | A | A |
| 404 | B | |
| 405 | A | |
| 406 | B | |
| 407 | A | A |
| 408 | A | B |
| 409 | A | |
| 410 | B | |
| 412 | A | A |
| 413 | A | A |
| 414 | A | A |
| 415 | A | B |
| 416 | A | A |
| 417 | A | A |
| 418 | A | A |
| 420 | A | B |
| 421 | A | A |
| 422 | A | A |
| 423 | A | A |
| 424 | A | A |
| 425 | A | A |
| 426 | A | B |
| 427 | A | A |
| 428 | A | A |
| 429 | A | A |
| 430 | A | |
| 431 | A | A |
| 432 | A | A |
| 433 | A | A |
| 434 | A | A |
| 436 | A | A |
| 437 | A | A |
| 438 | A | A |
| 439 | A | A |
| 440 | A | A |
| 441 | A | A |
| 442 | A | A |
| 443 | A | |
| 444 | A | A |
| 445 | A | A |
| 446 | A | A |
| 447 | A | A |
| 448 | A | |
| 449 | A | A |
| 450 | A | B |
| 451 | A | A |
| 452 | A | A |
| 453 | A | A |
| 454 | B | |
| 455 | A | A |
| 456 | A | A |
| 457 | A | |
| 458 | A | A |
| 459 | A | A |
| 460 | A | A |
| 461 | A | B |
| 462 | A | A |
| 463 | A | |
| 464 | A | B |
| 465 | A | |
| 466 | A | A |
| 467 | A | A |
| 468 | A | A |
| 469 | A | A |
| 470 | A | A |
| 471 | A | |
| 472 | A | A |
| 473 | A | A |
| 474 | A | A |
| 475 | A | A |
| 476 | A | A |
| 477 | A | A |
| 478 | A | A |
| 479 | A | A |

INCORPORATION BY REFERENCE

All publications and patents mentioned herein are hereby incorporated by reference in their entirety as if each individual publication or patent was specifically and individually indicated to be incorporated by reference.

EQUIVALENTS

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The disclosure includes embodiments in which exactly one member of the group is present in, employed in, or otherwise relevant to a given product or process. The disclosure includes embodiments in which more than one, or all of the group members are present in, employed in, or otherwise relevant to a given product or process.

Furthermore, the disclosure encompasses all variations, combinations, and permutations in which one or more limitations, elements, clauses, and descriptive terms from one or more of the listed claims are introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the disclosure, or aspects of the disclosure, is/are referred to as comprising particular elements and/or features, certain embodiments of the disclosure or aspects of the disclosure consist, or consist essentially of, such elements and/or features. For purposes of simplicity, those embodiments have not been specifically set forth in haec verba herein. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the disclosure, to the tenth of the unit of the lower limit of the range, unless the context clearly dictates otherwise.

Those skilled in the art will recognize, or be able to ascertain using no more than routine experimentation, many equivalents to the specific embodiments of the disclosure described and claimed herein. Such equivalents are intended to be encompassed by the following claims.

The invention claimed is:

1. A compound of Formula (I):

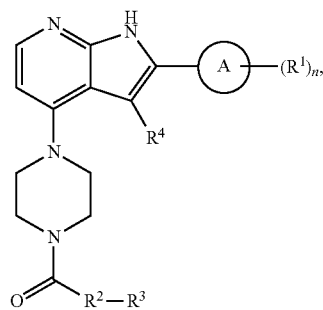

(I)

or a pharmaceutically acceptable salt thereof, wherein:
ring A is chosen from monocyclic aryl, monocyclic heteroaryl, quinolinyl, and bicyclic heterocyclyl, wherein only one ring of said bicyclic heterocyclyl is aromatic;
each $R^1$ is independently chosen from halo, cyano, oxo, $C_1$-$C_4$ alkyl, —O—($C_1$-$C_4$ alkyl), —C(O)—($C_1$-$C_4$ alkyl), —C(O)—O—($C_1$-$C_4$ alkyl), —C(O)—N($R^8$)—($C_1$-$C_4$ alkyl), —N($R^8$)$_2$, —N($R^8$)—C(O)—($C_1$-$C_4$ alkyl), —S(O)$_p$—($C_1$-$C_4$ alkyl), —O—($C_1$-$C_4$ alkylene)-C(O)—O—($C_1$-$C_4$ alkyl), —O—($C_1$-$C_4$ alkylene)-N($R^8$)$_2$, —O—($C_1$-$C_4$ alkylene)-C(O)—N($R^8$)$_2$, —Si($R^9$)($C_1$-$C_4$ alkyl)$_2$, $C_3$-$C_8$ carbocyclyl, —C(O)—($C_3$-$C_5$ carbocyclyl), —O—($C_0$-$C_4$ alkylene)-($C_3$-$C_8$ carbocyclyl), —O—($C_0$-$C_4$ alkylene)-C(O)—($C_3$-$C_5$ carbocyclyl), —($C_0$-$C_4$ alkylene)-aryl, —O—($C_0$-$C_4$ alkylene)-aryl, heterocyclyl, —C(O)-heterocyclyl, —O—($C_0$-$C_4$ alkylene)-heterocyclyl, and —O—($C_0$-$C_4$ alkylene)-C(O)-heterocyclyl, wherein:
any said alkyl or said alkylene portion of $R^1$ is optionally substituted with one to five substituents independently chosen from halo, cyano, hydroxyl, and O—($C_1$-$C_4$ alkyl); and
any said carbocyclyl, said aryl, or said heterocyclyl portion of $R^1$ is optionally substituted with one to five substituents independently chosen from halo, $C_1$-$C_4$ alkyl, $C_1$-$C_4$ haloalkyl, cyano, hydroxyl, —O—($C_1$-$C_4$ alkyl), heterocyclyl, —N($R^8$)$_2$, and —N($R^8$)—C(O)—O—($C_1$-$C_4$ alkyl);
$R^2$ is a bond or —O—;
$R^3$ is chosen from $C_1$-$C_6$ alkyl, —($C_0$-$C_6$ alkylene)-($C_3$-$C_8$ carbocyclyl), and —($C_0$-$C_6$ alkylene)-(monocyclic —O— or S-containing heterocyclyl), wherein:
a carbon atom of said monocylic heterocyclyl is the attachment point for said monocyclic heterocyclyl;
any said alkyl or said alkylene portion of $R^3$ is optionally substituted with one to five substituents independently chosen from halo, cyano, hydroxyl, $C_1$-$C_4$ alkyl, —O—($C_1$-$C_4$ alkyl), —O—($C_3$-$C_8$ cycloalkyl), and —S(O)$_p$—($C_1$-$C_4$ alkyl); and
any said carbocyclyl or said heterocyclyl portion of $R^3$ is optionally substituted with one to five substituents independently chosen from halo, cyano, oxo, hydroxyl, $C_1$-$C_4$ alkyl, $C_1$-$C_4$ haloalkyl, —O—($C_1$-$C_4$—O—($C_1$-$C_4$ haloalkyl), —C(O)—($C_1$-$C_4$ alkyl), —C(O)—O—($C_1$-$C_4$—S(O)$_p$—($C_1$-$C_4$ alkyl), —O-phenyl, —($C_1$-$C_4$ alkyl)-phenyl, and morpholin-4-yl;
$R^4$ is chosen from hydrogen, $C_1$-$C_4$ alkyl, $C_2$-$C_4$ alkenyl, $C_2$-$C_4$ alkynyl, $C_3$-$C_6$ cycloalkyl, —C(O)—($C_1$-$C_4$ alkyl), halo, and cyano, wherein:
any said alkyl portion of $R^4$ is optionally substituted with hydroxyl;
each $R^8$ is independently chosen from hydrogen and $C_1$-$C_4$ alkyl, or two $R^8$ together with the nitrogen atom to which they are joined form a heterocyclyl;
each $R^9$ is independently chosen from hydrogen, $C_1$-$C_4$ alkyl, and hydroxyl;
n is 0, 1, 2, 3, 4, 5, or 6; and
p is 0, 1, or 2.

2. The compound of claim 1 or a pharmaceutically acceptable salt thereof, wherein ring A is chosen from 6-membered monocyclic aryl, 5-membered heteroaryl, 6-membered monocyclic heteroaryl, 9-membered bicyclic heterocyclyl, and 10-membered bicyclic heterocyclyl.

3. The compound of claim 1 or a pharmaceutically acceptable salt thereof, wherein ring A is chosen from phenyl, pyrrolyl, pyrazolyl, imidazolyl, thiazolyl, isothiazolyl, oxazolyl, isoxazolyl, thiophenyl, 1,2,4-thiadiazolyl, 1,3,4-thiadiazolyl, 1,2,3-triazolyl, pyridinyl, pyrimidinyl, pyrazinyl,

[structures]

4. The compound of claim 1 or a pharmaceutically acceptable salt thereof, wherein ring A is chosen from

[structures]

wherein:
X is chosen from O, N, and $S(O)_p$;
Y is CH or N;
W is chosen from CH, N, S, and O;
Z is chosen from CH, NH, S, and O; and
p is 0, 1, or 2.

5. The compound of claim 1 or a pharmaceutically acceptable salt thereof, wherein ring A is chosen from

[structures]

wherein:
$R^{1B}$ is chosen from hydrogen, halo, cyano, $C_1$-$C_4$ alkyl, —O—($C_1$-$C_4$—C(O)—($C_1$-$C_4$ alkyl), —C(O)—($C_3$-$C_6$ cycloalkyl), —C(O)—O—($C_1$-$C_4$ alkyl), —N($R^8$)—C(O)—($C_1$-$C_4$—S(O)$_p$—($C_1$-$C_4$ alkyl), $C_3$-$C_6$ cycloalkyl, and 3- to 6-membered heterocyclyl, wherein:
any said alkyl portion of $R^{1B}$ is optionally substituted with one to five substituents independently chosen from halo and cyano;
any said cycloalkyl or said heterocyclyl portion of $R^{1B}$ is optionally substituted with one to five substituents independently chosen from halo, —N($R^8$)$_2$, $C_1$-$C_4$ alkyl, heterocyclyl, and $C_1$-$C_4$ haloalkyl;
p is 0, 1, or 2; and
when $R^{18}$ is hydrogen, then n1 is 0, 1, 2, 3, 4, or 5 and, when $R^{18}$ is not hydrogen, then n1 is 0, 1, 2, 3, or 4.

6. The compound of claim 1 or a pharmaceutically acceptable salt, wherein ring A is chosen from

[structures]

wherein:
$R^{18}$ is chosen from hydrogen, $C_1$-$C_4$ alkyl, $C_3$-$C_6$ cycloalkyl, —($C_0$-$C_4$ alkylene)-aryl, heterocyclyl, and —S(O)$_p$—($C_1$-$C_4$ alkyl), wherein:
any said alkyl portion of $R^{1B}$ is optionally substituted with one to five substituents independently chosen from halo and cyano;
p is 0, 1, or 2;
each $R^1$ is independently chosen from $C_1$-$C_4$ alkyl, $C_3$-$C_6$ cycloalkyl, halo, cyano, and —N($R^8$)$_2$, wherein:
any said alkyl portion of $R^{1B}$ is optionally substituted with one to five substituents independently chosen from halo and cyano;
each $R^8$ is independently chosen from $C_1$-$C_4$ alkyl; and
when $R^{18}$ is hydrogen, then n1 is 0, 1, 2, or 3, and, when $R^{18}$ is not hydrogen, then n1 is 0, 1, or 2.

7. The compound of claim 1 or a pharmaceutically acceptable salt thereof, wherein ring A is chosen from

[structures]

wherein:
  each $R^1$ is independently chosen from $C_1$-$C_4$ alkyl, $C_3$-$C_6$ cycloalkyl, —O—($C_1$-$C_4$ alkyl), —C(O)-heterocyclyl, and cyano, wherein:
    any said alkyl portion of $R^1$ is optionally substituted with one to five substituents independently chosen from halo, hydroxyl, and cyano.

8. The compound of claim 1 or a pharmaceutically acceptable salt thereof, wherein ring A is chosen from

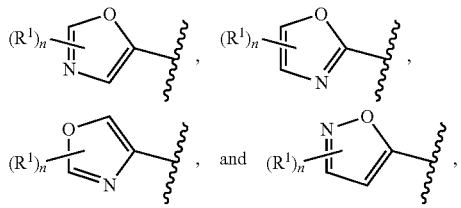

wherein:
  each $R^1$ is independently chosen from $C_1$-$C_4$ alkyl optionally substituted with one to five substituents independently chosen from halo, hydroxyl, and cyano.

9. The compound of claim 1 or a pharmaceutically acceptable salt thereof, wherein ring A is chosen from

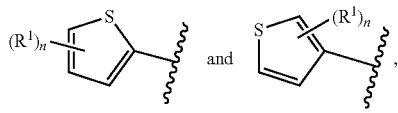

wherein:
  each $R^1$ is independently chosen from $C_1$-$C_4$ alkyl and cyano, wherein:
    any said alkyl portion of $R^1$ is optionally substituted with one to five substituents independently chosen from halo, hydroxyl, and cyano.

10. The compound of claim 1 or a pharmaceutically acceptable salt thereof, wherein each $R^1$ is independently chosen from tetrahydropyranyl, tetrahydrofuranyl, 3,6-dihydro-2H-pyranyl, piperidinyl, piperazinyl, oxetanyl, cyano, $C_1$-$C_4$ alkyl, —S(O)—($C_1$-$C_4$ alkyl), —S(O)$_2$—($C_1$-$C_4$ alkyl), —C(O)—($C_1$-$C_4$ alkyl), —C(O)-heterocyclyl, —O—($C_1$-$C_4$ alkyl), halo, $C_3$-$C_6$ cycloalkyl, —O—($C_3$-$C_6$ cycloalkyl), —N(CH$_3$)$_2$, Si(CH$_3$)$_2$OH, —NH—C(O)—CH$_3$, —O—($C_0$-$C_4$ alkylene)-aryl, and morpholinyl, wherein
  said piperidinyl is optionally substituted with one substituent chosen from morpholinyl, —O—($C_1$-$C_4$ alkyl), $C_1$-$C_4$ alkyl, and $C_1$-$C_4$ haloalkyl or one or two substituents independently chosen from halo;
  said tetrahydropyranyl or tetrahydrofuranyl is optionally substituted with one substituent chosen from hydroxyl and —O—($C_1$-$C_4$ alkyl);
  said oxetanyl is optionally substituted with one substituent chosen from $C_1$-$C_4$ alkyl;
  said piperazinyl is optionally substituted with one substituent chosen from $C_1$-$C_4$ alkyl and halo;
  any said cycloalkyl portion of $R^1$ is optionally substituted with one substituent chosen from cyano and hydroxyl;
  any said alkyl portion of $R^1$ is optionally substituted with one to five substituents independently chosen from halo, hydroxyl, cyano, and —O—($C_1$-$C_4$ alkyl).

11. The compound of claim 10 or a pharmaceutically acceptable salt thereof, wherein $R^3$ is chosen from $C_1$-$C_6$ alkyl, —($C_0$-$C_3$ alkylene)-($C_3$-$C_6$ carbocyclyl), and —($C_0$-$C_3$ alkylene)-(monocyclic 0- or S-heterocyclyl), wherein:
  any said alkyl or said alkylene portion of $R^3$ is optionally substituted with one to five substituents independently chosen from halo, cyano, and hydroxyl; and
  any said carbocyclyl or said heterocyclyl portion of $R^3$ is optionally substituted with one to four substituents independently chosen from halo, cyano, hydroxyl, $C_1$-$C_4$ alkyl, $C_1$-$C_4$ haloalkyl, —O—($C_1$-$C_4$ alkyl), —O—($C_1$-$C_4$ haloalkyl), —C(O)—($C_1$-$C_4$ alkyl), —C(O)—O—($C_1$-$C_4$ alkyl), —S(O)$_p$—($C_1$-$C_4$ alkyl), —O-phenyl, —($C_1$-$C_4$ alkyl)-phenyl, and morpholin-4-yl.

12. A pharmaceutical composition comprising at least one compound chosen from the compounds of claim 1 and pharmaceutically acceptable salts thereof and at least one pharmaceutically acceptable excipient.

13. A method of inhibiting aberrant ALK2 activity in a subject in need thereof, the method comprising the step of administering to the subject a pharmaceutically effective amount of at least one compound chosen from the compounds of claim 1 and pharmaceutically acceptable salts thereof.

14. The method of claim 13, wherein the aberrant ALK2 activity is caused by a mutation in an ALK2 gene that results in the expression of an ALK2 enzyme having at least one amino acid modification chosen from L196P, PF197-8L, R202I, R206H, Q207E, R258S, R258G, G328A, G328V, G328W, G328E, G328R, G356D, and R375P.

15. A compound chosen from any one of the following compounds

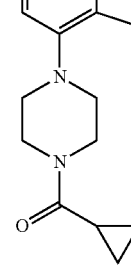

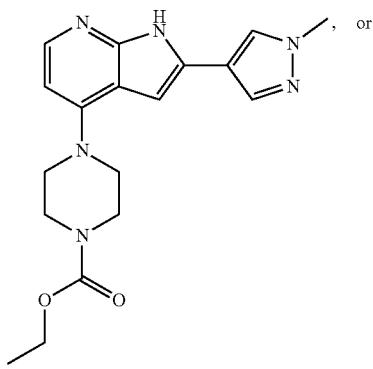

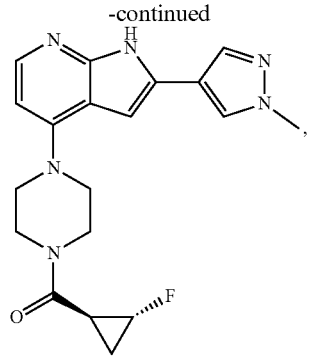

or a pharmaceutically acceptable salt thereof.

16. The compound of claim 15, wherein the compound is

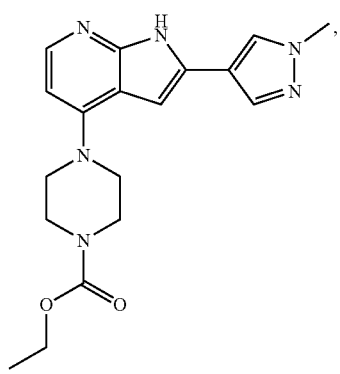 [SMILES: CCOC(=O)N1CCN(c2ccnc3[nH]c(-c4cnn(C)c4)cc23)CC1]

or a pharmaceutically acceptable salt thereof.

17. The compound of claim 15, wherein the compound is or a pharmaceutically acceptable salt thereof.

18. The compound of claim 15, wherein the compound is

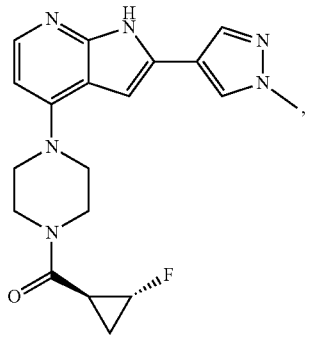 [SMILES: Cn1cc(-c2cc3c(N4CCN(C(=O)[C@@H]5C[C@H]5F)CC4)ccnc3[nH]2)cn1]

or a pharmaceutically acceptable salt thereof.

19. A compound chosen from any one of the following compounds:

| # | Structure |
|---|---|
| 1 | 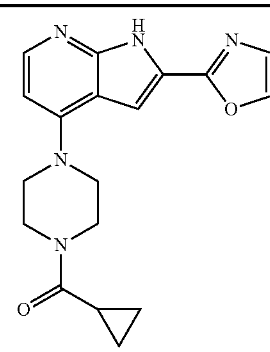 |
| 2 | 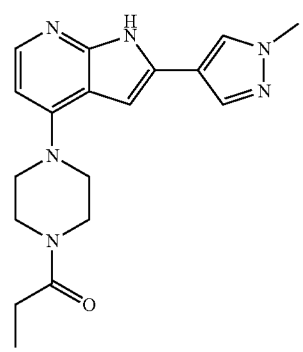 [SMILES: CCC(=O)N1CCN(c2ccnc3[nH]c(-c4cnn(C)c4)cc23)CC1] |
| 3 | 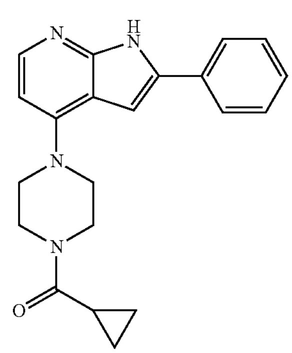 [SMILES: O=C(C1CC1)N1CCN(c2ccnc3[nH]c(-c4ccccc4)cc23)CC1] |

| # | Structure |
|---|---|
| 4 | 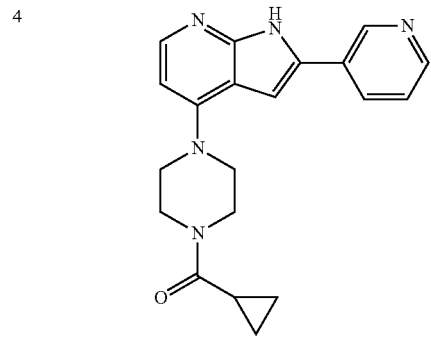 |
| 5 | 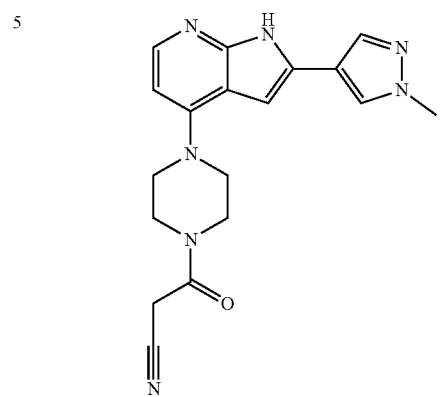 |
| 6 | 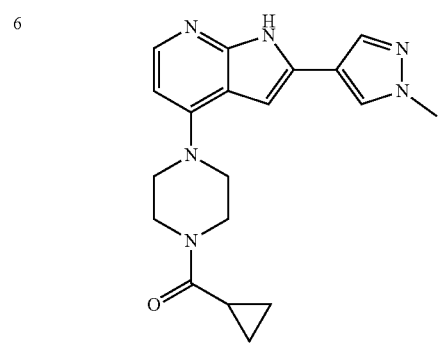 |
| 7 | 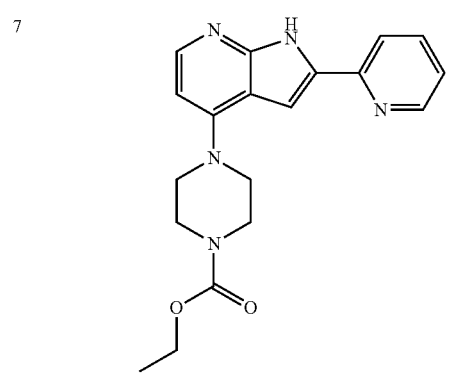 |
| # | Structure |
|---|---|
| 8 | 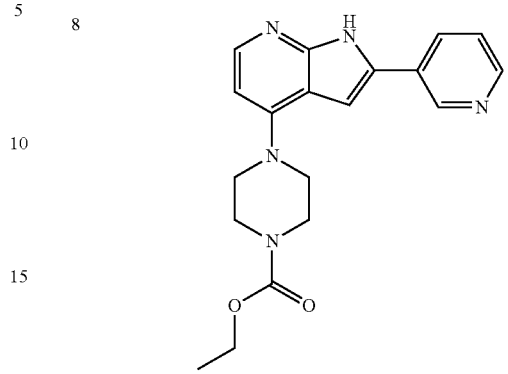 |
| 9 | 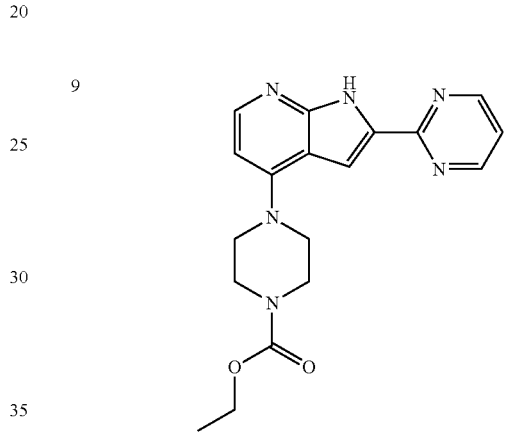 |
| 10 | 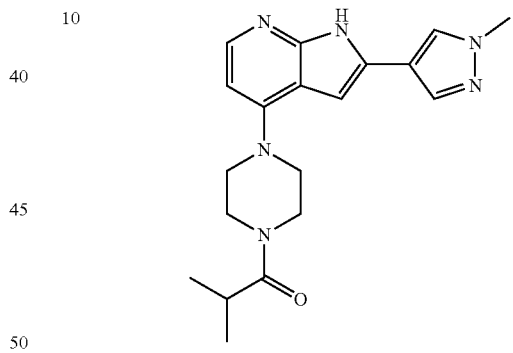 |
| 11 | 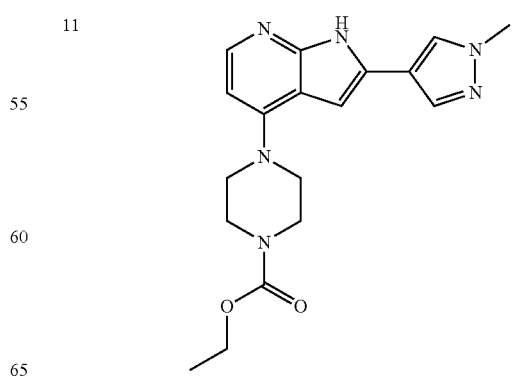 |

| # | Structure |
|---|---|
| 12 | 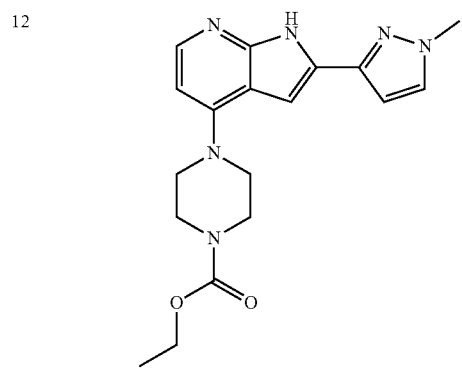 |
| 13 | 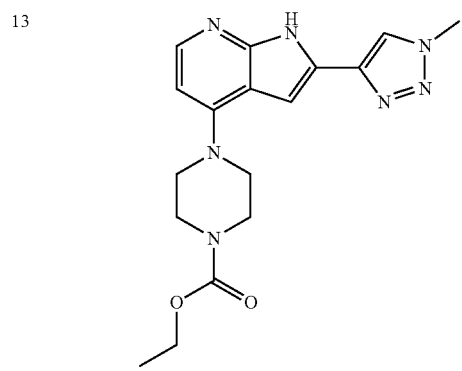 |
| 14 | 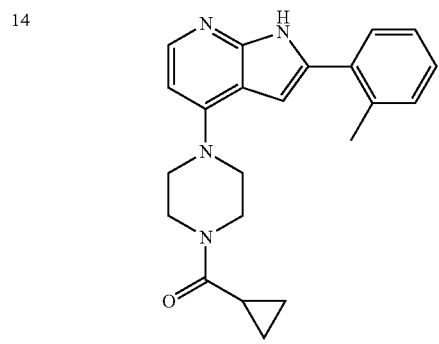 |
| 15 | 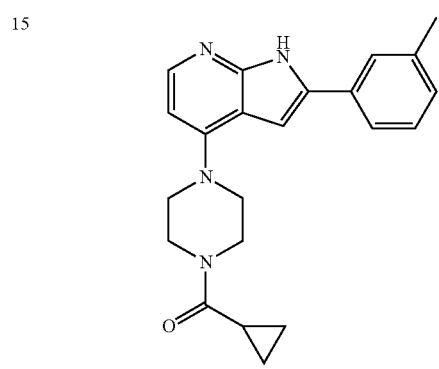 |
| # | Structure |
|---|---|
| 16 | 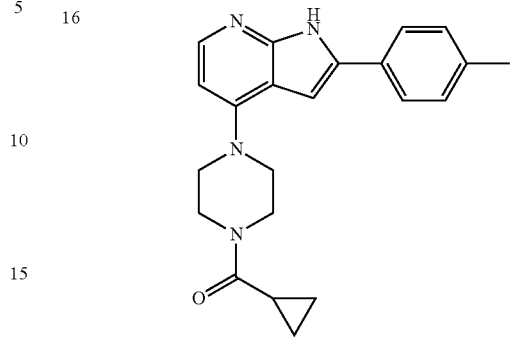 |
| 17 | 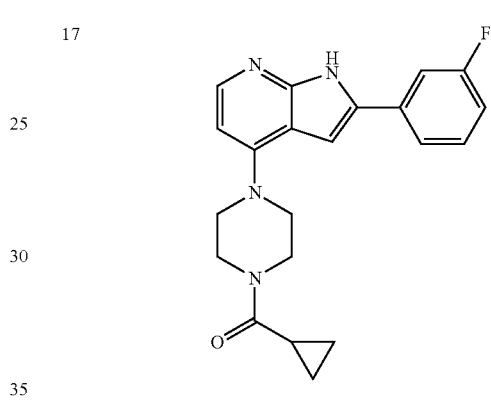 |
| 18 | 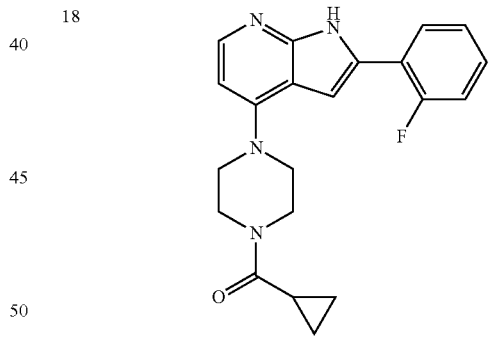 |
| 19 | 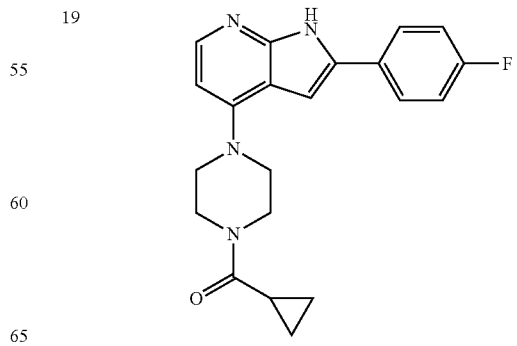 |

| # | Structure |
|---|---|
| 20 | 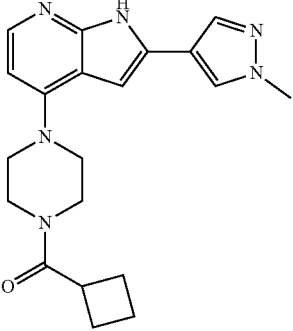 |
| 21 | 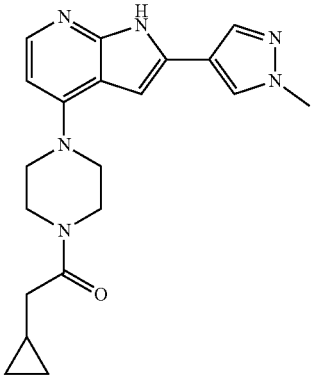 |
| 22 | 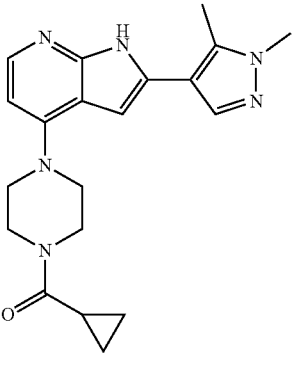 [SMILES: Cc1c(-c2cc3c(N4CCN(C(=O)C5CC5)CC4)ccnc3[nH]2)cnn1C] |
| 23 | 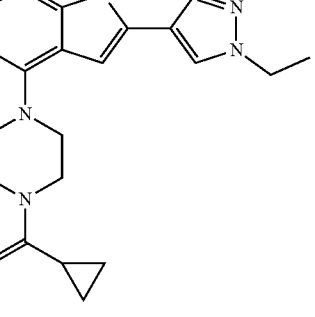 |
| # | Structure |
|---|---|
| 24 | 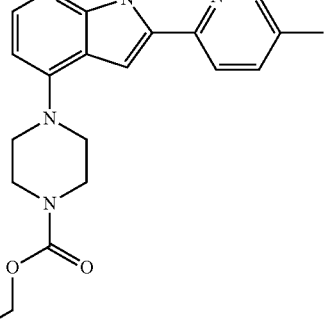 |
| 25 | 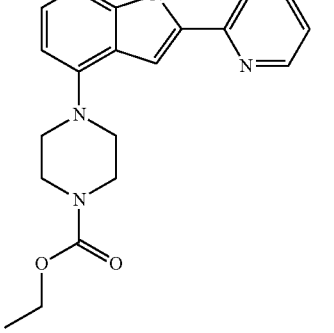 |
| 26 | 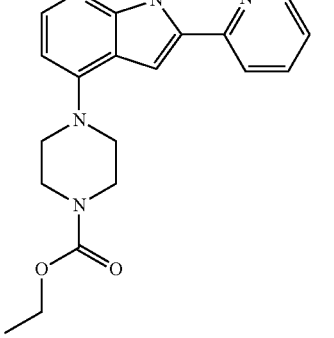 |
| 27 | 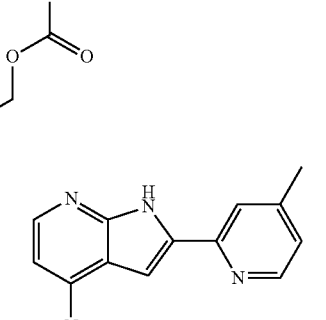 |

-continued
| # | Structure |
|---|---|
| 29 | 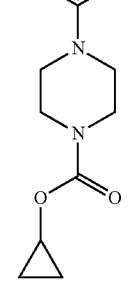 |
| 30 | 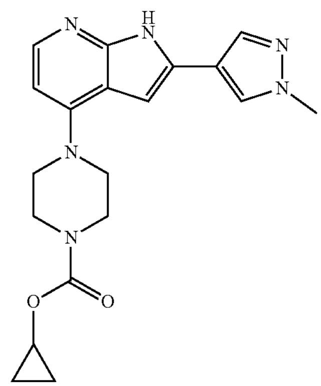 |
| 31 | 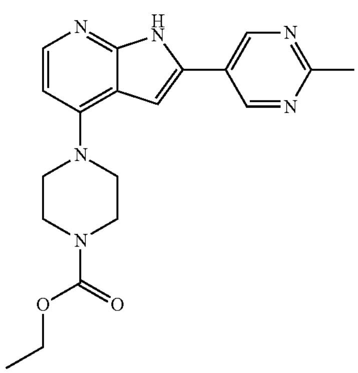 |
| 32 | 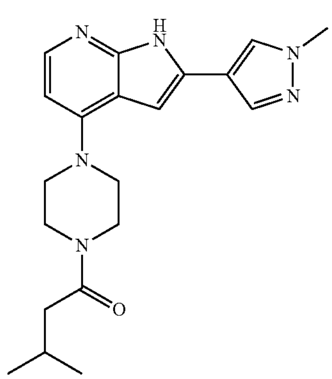 [SMILES: CC(C)CC(=O)N1CCN(c2ccnc3[nH]c(-c4cnn(C)c4)cc23)CC1] |
-continued
| # | Structure |
|---|---|
| 33 | 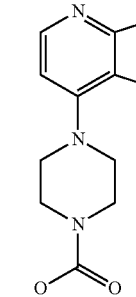 |
| 34 | 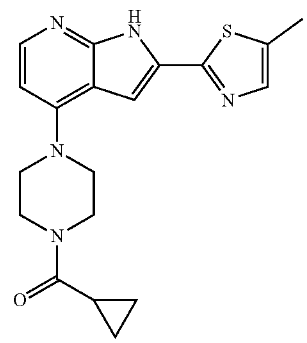 [SMILES: Cc1cnc(-c2cc3c(N4CCN(C(=O)C5CC5)CC4)ccnc3[nH]2)s1] |
| 35 | 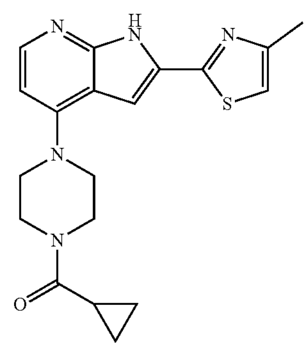 [SMILES: Cc1csc(-c2cc3c(N4CCN(C(=O)C5CC5)CC4)ccnc3[nH]2)n1] |
| 36 | 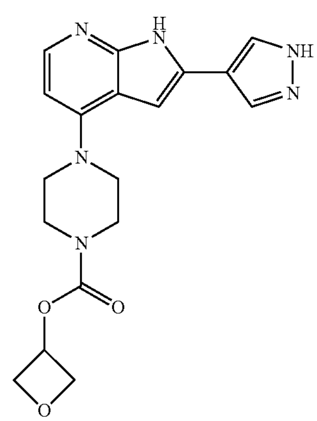 [SMILES: O=C(OC1COC1)N1CCN(c2ccnc3[nH]c(-c4cn[nH]c4)cc23)CC1] |

| # | Structure |
|---|---|
| 37 | 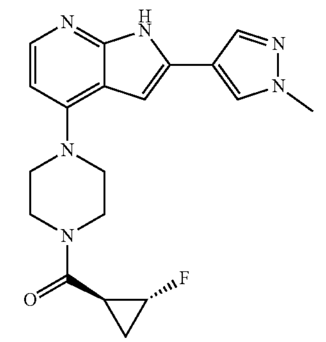 [SMILES: Cn1cc(-c2cc3c(N4CCN(C(=O)[C@@H]5C[C@H]5F)CC4)ccnc3[nH]2)cn1] |
| 38 | 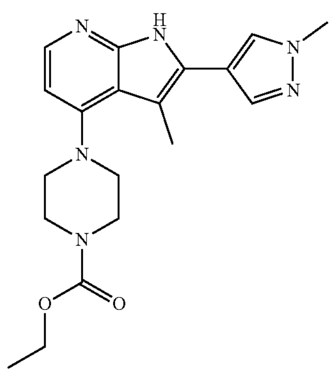 [SMILES: CCOC(=O)N1CCN(c2ccnc3[nH]c(-c4cnn(C)c4)c(C)c23)CC1] |
| 39 | 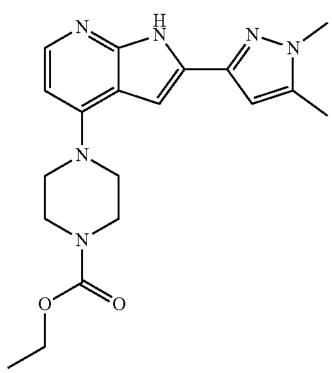 [SMILES: CCOC(=O)N1CCN(c2ccnc3[nH]c(-c4cc(C)n(C)n4)cc23)CC1] |
| 40 | 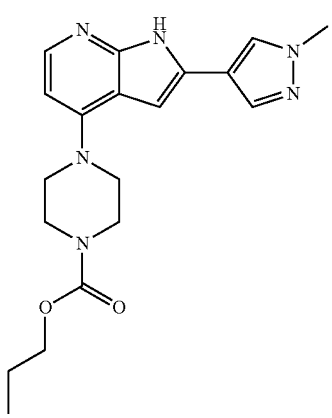 |
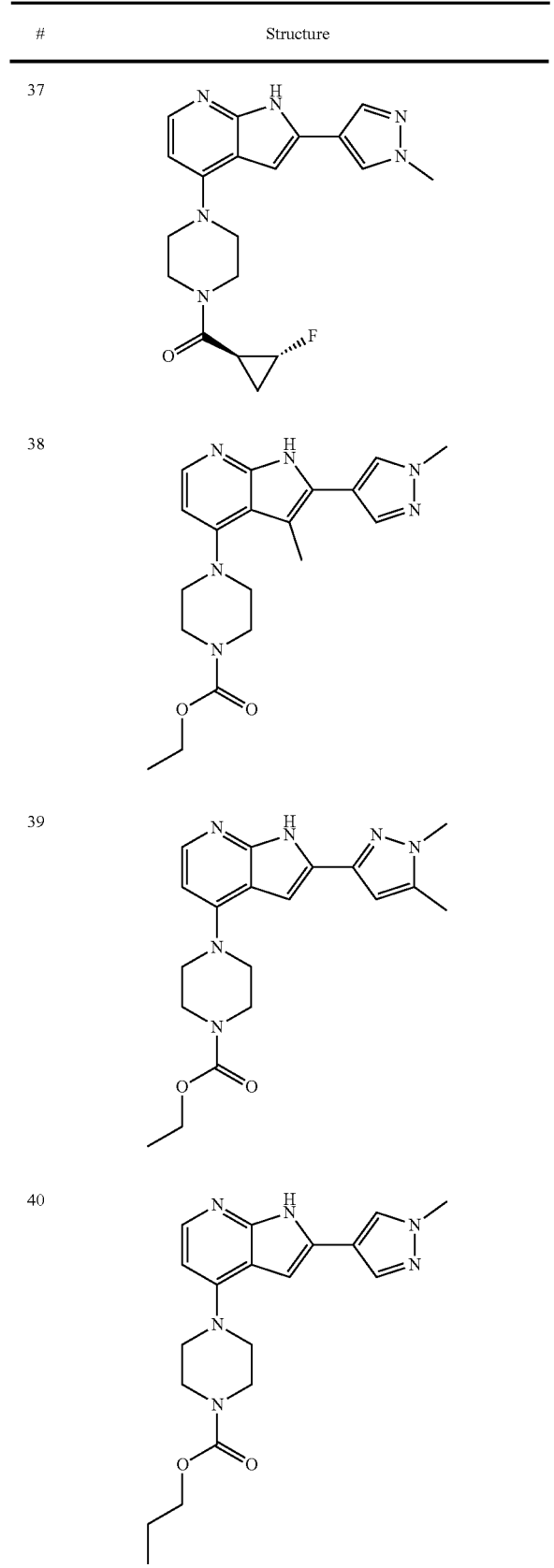
| # | Structure |
|---|---|
| 41 | 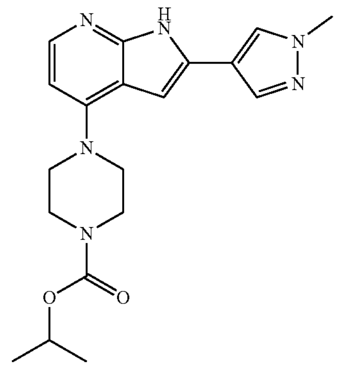 [SMILES: CC(C)OC(=O)N1CCN(c2ccnc3[nH]c(-c4cnn(C)c4)cc23)CC1] |
| 42 | 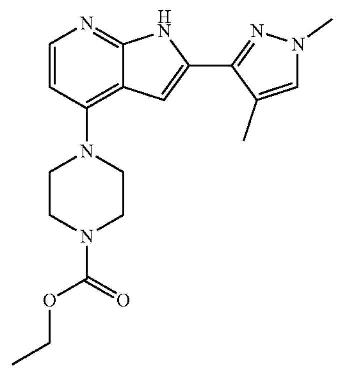 [SMILES: CCOC(=O)N1CCN(c2ccnc3[nH]c(-c4nn(C)cc4C)cc23)CC1] |
| 43 | 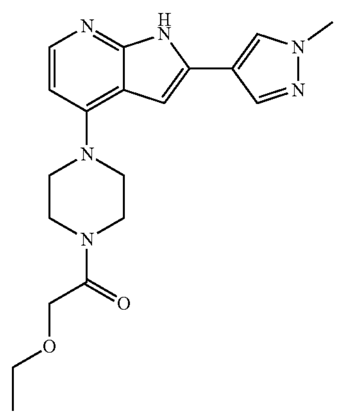 |
| 44 | 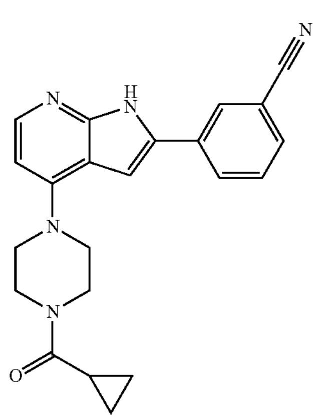 [SMILES: N#Cc1cccc(-c2cc3c(N4CCN(C(=O)C5CC5)CC4)ccnc3[nH]2)c1] |
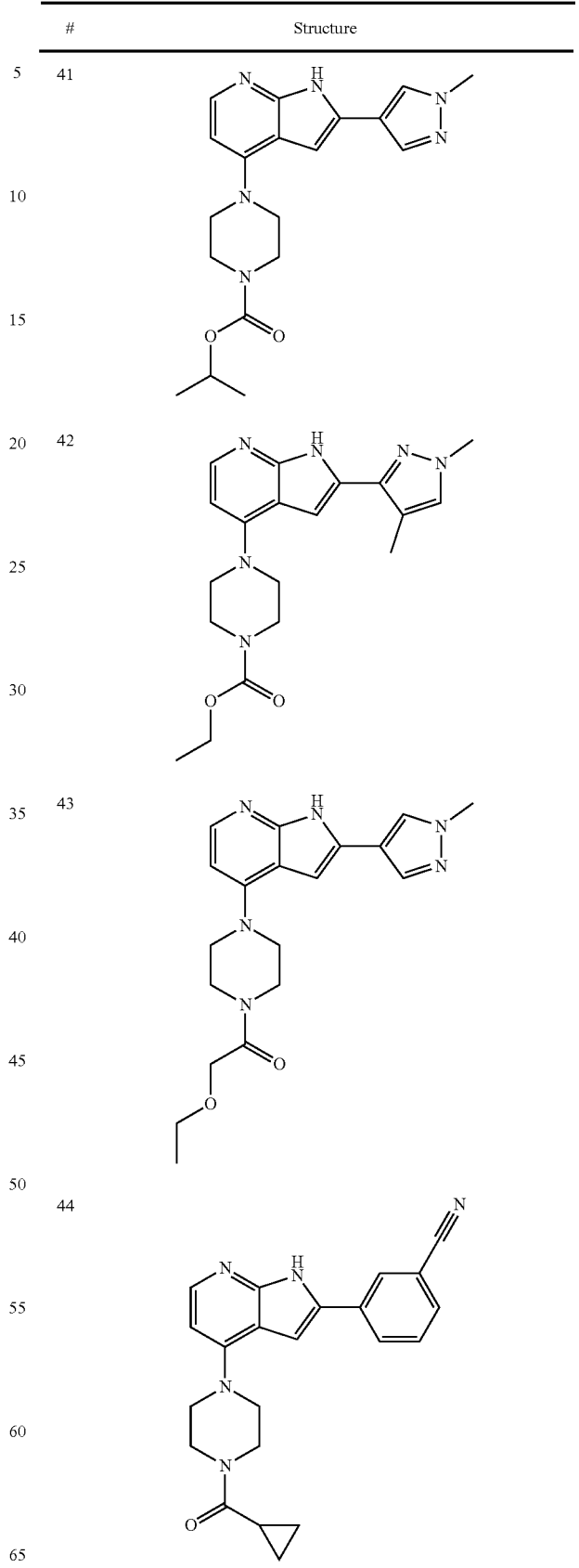

| # | Structure |
|---|---|
| 45 | 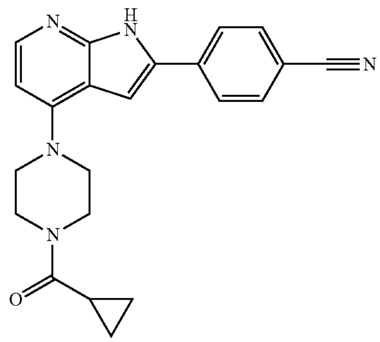 [SMILES: N#Cc1ccc(-c2cc3c(N4CCN(C(=O)C5CC5)CC4)ccnc3[nH]2)cc1] |
| 46 | 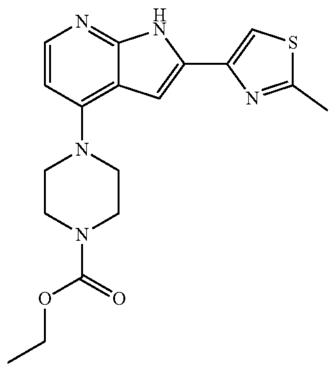 [SMILES: CCOC(=O)N1CCN(c2ccnc3[nH]c(-c4csc(C)n4)cc23)CC1] |
| 47 | 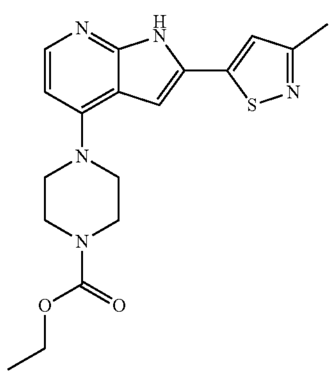 [SMILES: CCOC(=O)N1CCN(c2ccnc3[nH]c(-c4cc(C)ns4)cc23)CC1] |
| 48 | 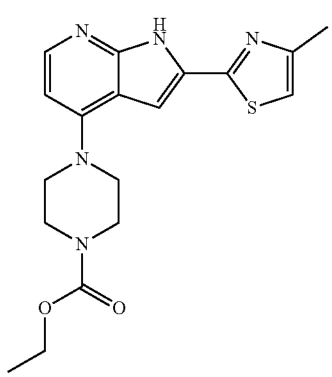 [SMILES: CCOC(=O)N1CCN(c2ccnc3[nH]c(-c4nc(C)cs4)cc23)CC1] |
| 49 | |
| 50 | |
| 51 | |
| 52 | |

-continued
| # | Structure |
|---|---|
| 53 | 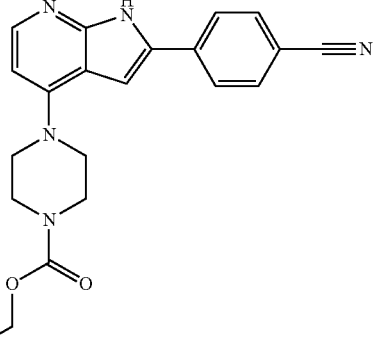 |
| 54 | 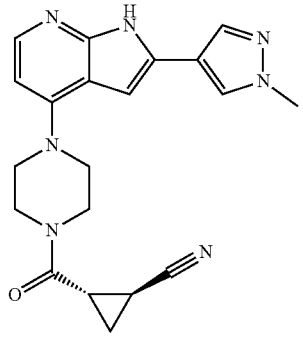 [SMILES: Cn1cc(-c2cc3c(N4CCN(C(=O)[C@H]5C[C@@H]5C#N)CC4)ccnc3[nH]2)cn1] |
| 55 | 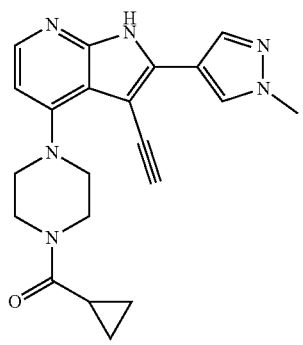 |
| 56 | 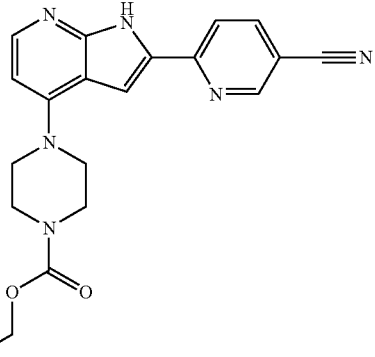 |
-continued
| # | Structure |
|---|---|
| 57 | 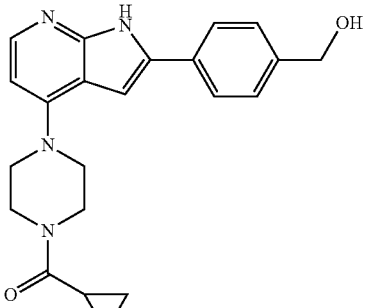 |
| 58 | 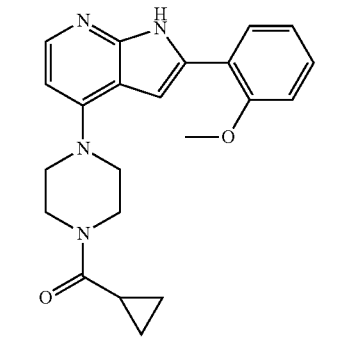 |
| 59 | 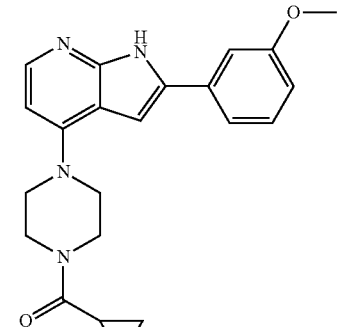 |
| 60 | 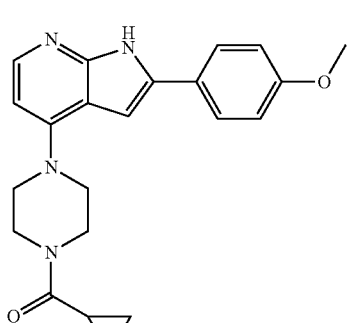 |

367
-continued

| # | Structure |
|---|---|
| 61 | 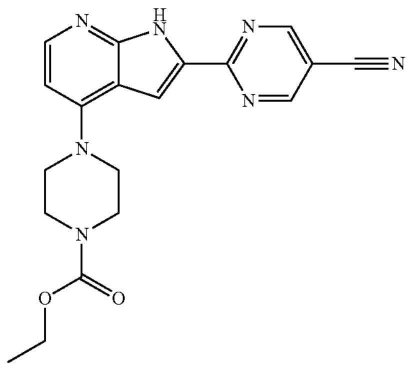 [SMILES: CCOC(=O)N1CCN(c2ccnc3[nH]c(-c4ccc(C#N)cn4)cc23)CC1] |
| 62 | 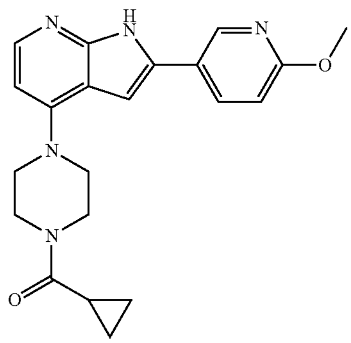 |
| 63 | 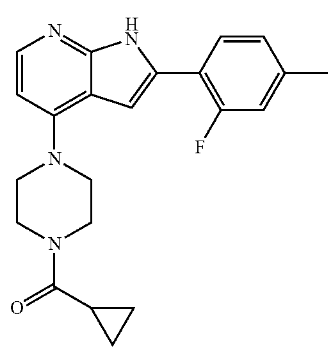 [SMILES: Cc1ccc(-c2cc3c(N4CCN(C(=O)C5CC5)CC4)ccnc3[nH]2)c(F)c1] |
| 64 | 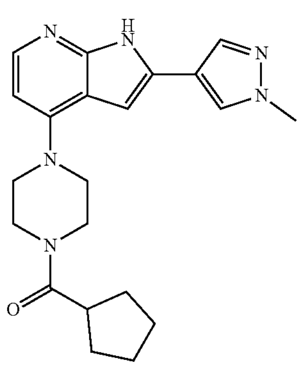 |

368
-continued

| # | Structure |
|---|---|
| 65 | 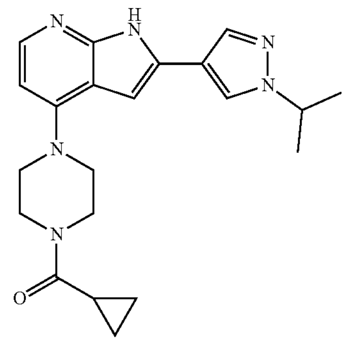 [SMILES: CC(C)n1cc(-c2cc3c(N4CCN(C(=O)C5CC5)CC4)ccnc3[nH]2)cn1] |
| 66 | 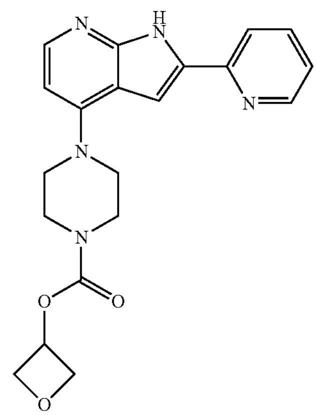 [SMILES: O=C(OC1COC1)N1CCN(c2ccnc3[nH]c(-c4ccccn4)cc23)CC1] |
| 67 | 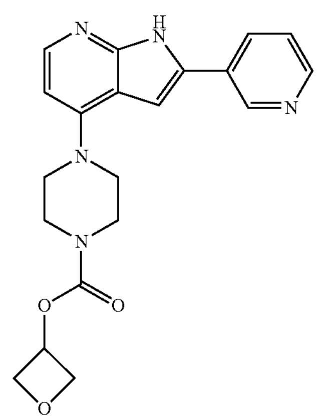 [SMILES: O=C(OC1COC1)N1CCN(c2ccnc3[nH]c(-c4cccnc4)cc23)CC1] |
| 68 | 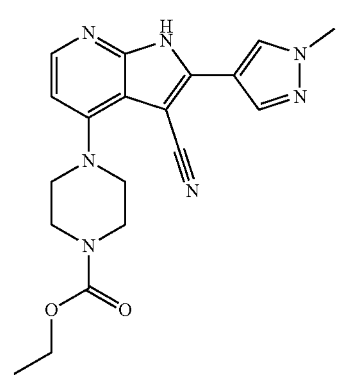 [SMILES: CCOC(=O)N1CCN(c2ccnc3[nH]c(-c4cnn(C)c4)c(C#N)c23)CC1] |

| # | Structure |
|---|---|
| 69 | 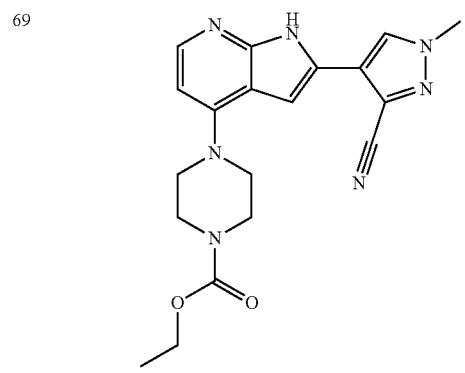 |
| 70 | 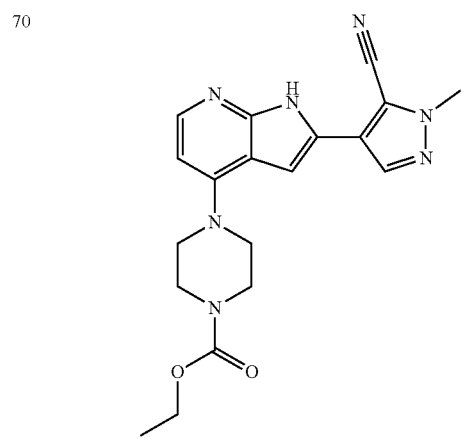 |
| 71 | 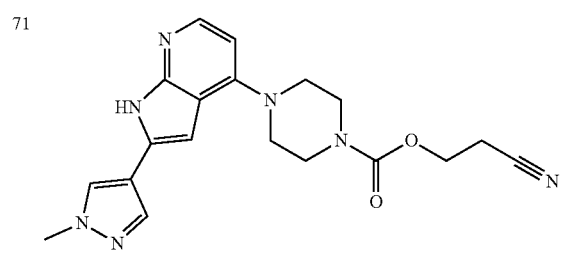 |
| 72 | 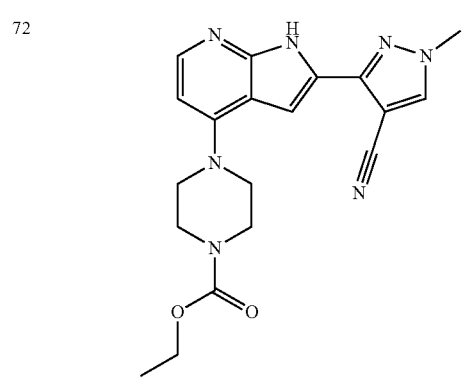 |
| # | Structure |
|---|---|
| 73 | 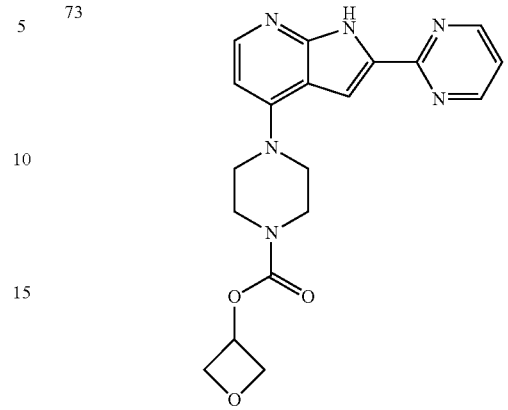 |
| 74 | 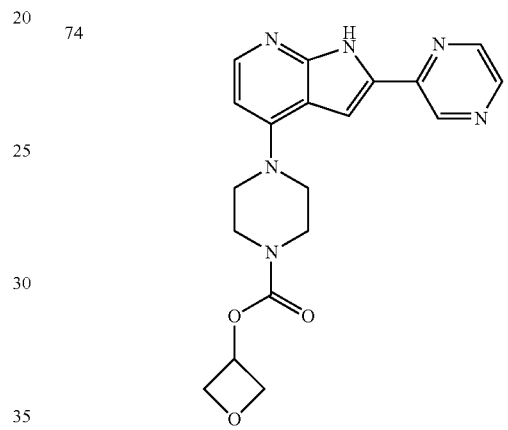 |
| 75 | 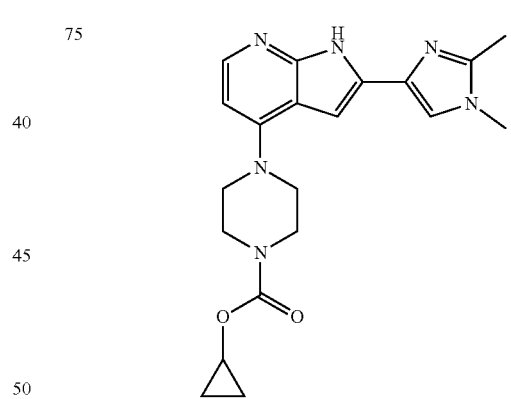 |
| 76 | 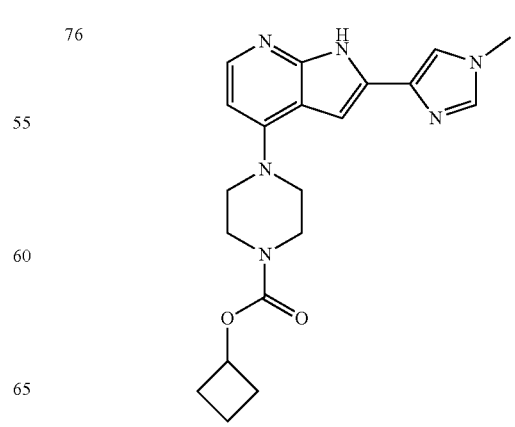 |

| # | Structure |
|---|---|
| 77 | 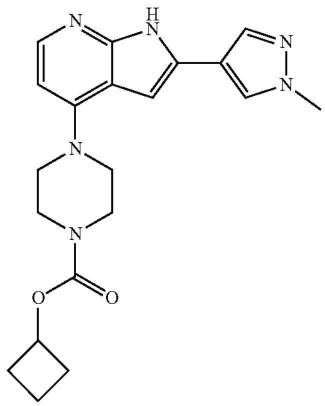 [SMILES: Cn1cc(-c2cc3c(N4CCN(C(=O)OC5CCC5)CC4)ccnc3[nH]2)cn1] |
| 78 | 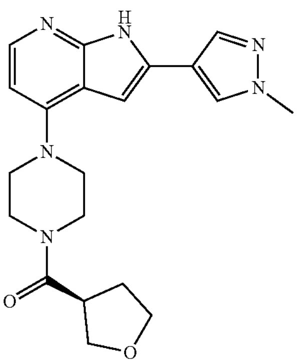 [SMILES: Cn1cc(-c2cc3c(N4CCN(C(=O)[C@H]5CCOC5)CC4)ccnc3[nH]2)cn1] |
| 79 | 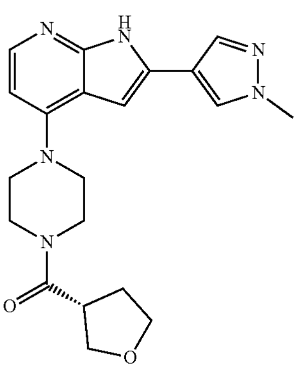 [SMILES: Cn1cc(-c2cc3c(N4CCN(C(=O)[C@@H]5CCOC5)CC4)ccnc3[nH]2)cn1] |
| 80 | 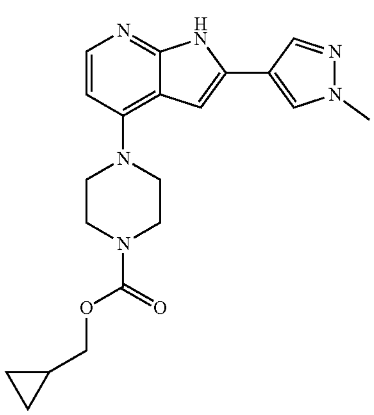 [SMILES: Cn1cc(-c2cc3c(N4CCN(C(=O)OCC5CC5)CC4)ccnc3[nH]2)cn1] |
| 81 | |
| 82 | |
| 83 | |
| 84 | |

| # | Structure |
|---|---|
| 85 | 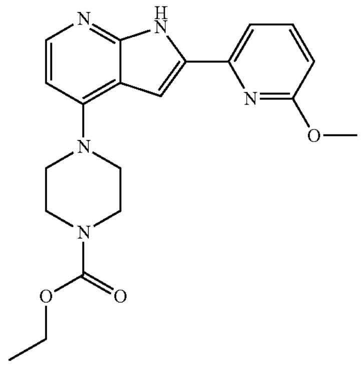 [SMILES: CCOC(=O)N1CCN(c2ccnc3[nH]c(-c4cccc(OC)n4)cc23)CC1] |
| 86 | 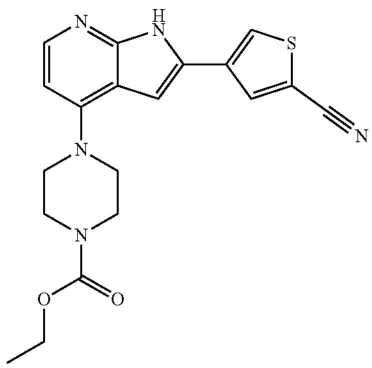 [SMILES: CCOC(=O)N1CCN(c2ccnc3[nH]c(-c4csc(C#N)c4)cc23)CC1] |
| 87 | 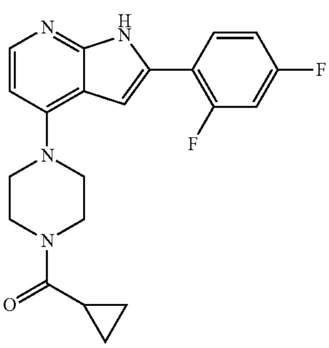 |
| 88 | 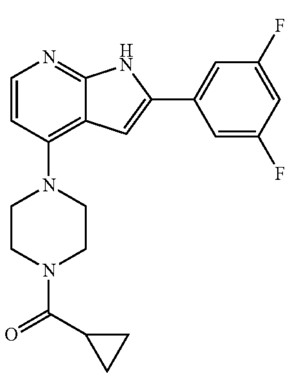 [SMILES: O=C(C1CC1)N1CCN(c2ccnc3[nH]c(-c4cc(F)cc(F)c4)cc23)CC1] |

| # | Structure |
|---|---|
| 89 | 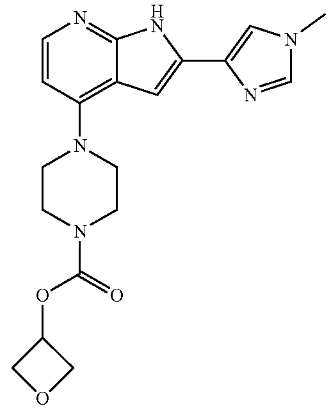 [SMILES: Cn1cnc(-c2cc3c(N4CCN(C(=O)OC5COC5)CC4)ccnc3[nH]2)c1] |
| 90 | 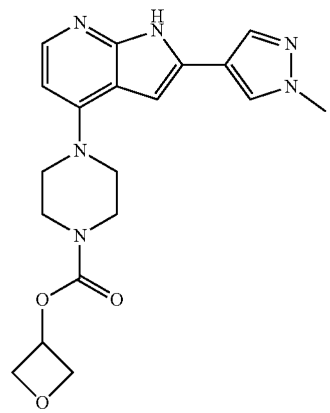 [SMILES: Cn1cc(-c2cc3c(N4CCN(C(=O)OC5COC5)CC4)ccnc3[nH]2)cn1] |
| 91 | 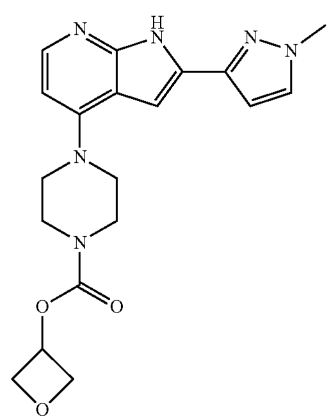 [SMILES: Cn1ccc(-c2cc3c(N4CCN(C(=O)OC5COC5)CC4)ccnc3[nH]2)n1] |

| # | Structure |
|---|---|
| 92 | 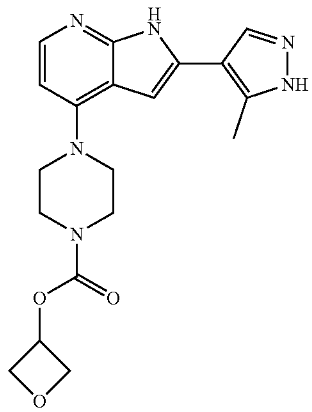 [SMILES: Cc1[nH]ncc1-c1cc2c(N3CCN(C(=O)OC4COC4)CC3)ccnc2[nH]1] |
| 93 | 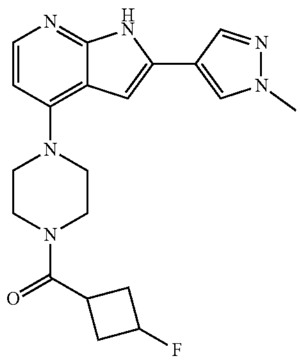 [SMILES: Cn1cc(-c2cc3c(N4CCN(C(=O)C5CC(F)C5)CC4)ccnc3[nH]2)cn1] |
| 94 | 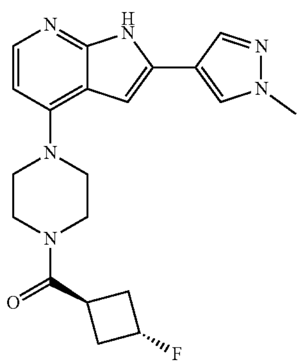 [SMILES: Cn1cc(-c2cc3c(N4CCN(C(=O)[C@H]5C[C@H](F)C5)CC4)ccnc3[nH]2)cn1] |
| 95 | 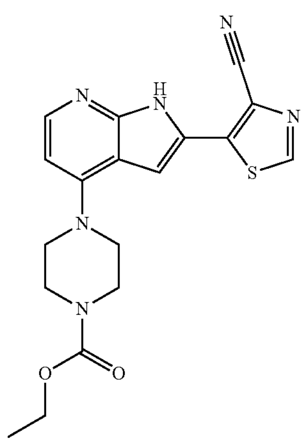 [SMILES: CCOC(=O)N1CCN(c2ccnc3[nH]c(-c4scnc4C#N)cc23)CC1] |

| # | Structure |
|---|---|
| 96 | |
| 97 | |
| 98 | |
| 99 | |

| # | Structure |
|---|---|
| 100 | 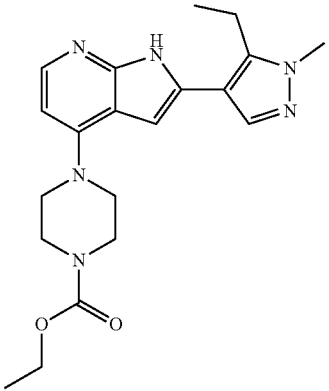 [SMILES: CCOC(=O)N1CCN(c2ccnc3[nH]c(-c4cnn(C)c4CC)cc23)CC1] |
| 101 | 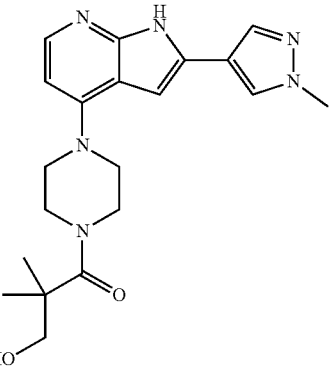 |
| 102 | 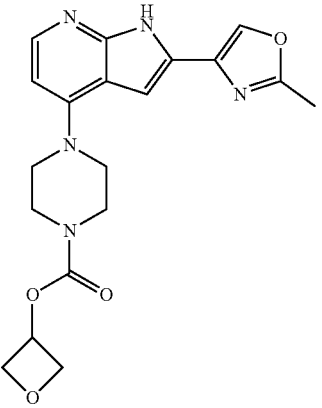 |
| 103 | 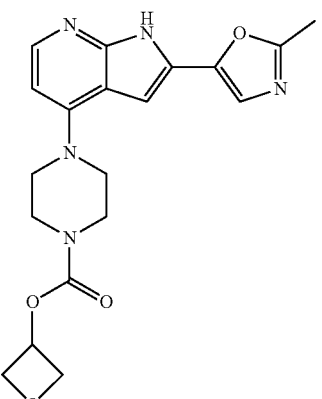 |
| # | Structure |
|---|---|
| 104 | 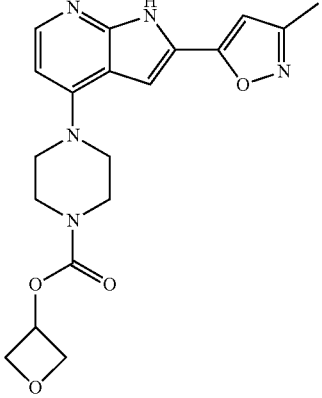 |
| 105 | 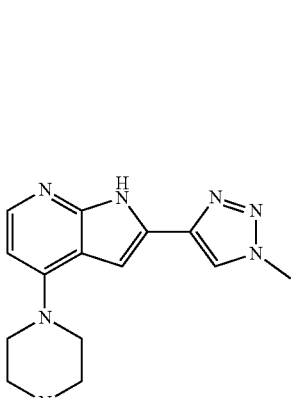 |
| 106 | 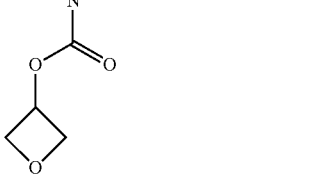 |

-continued

| # | Structure |
|---|---|
| 107 | 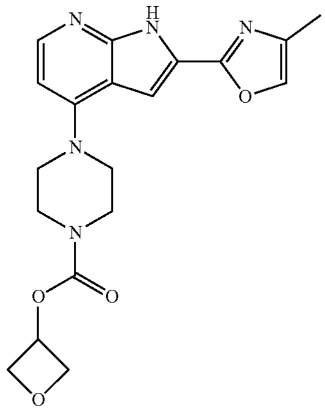 |
| 108 | 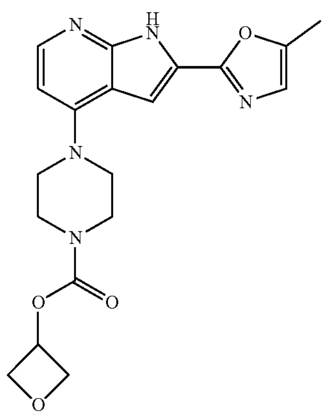 |
| 109 | 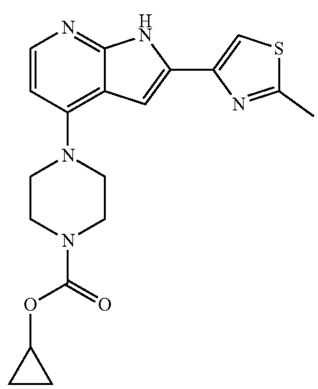 [SMILES: Cc1nc(-c2cc3c(N4CCN(C(=O)OC5CC5)CC4)ccnc3[nH]2)cs1] |
| 110 | 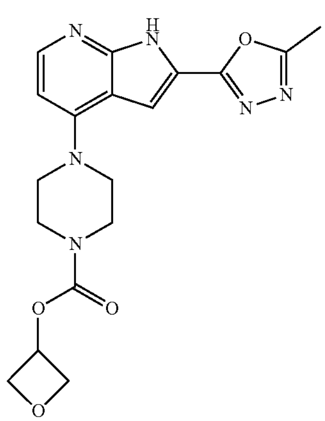 |

-continued

| # | Structure |
|---|---|
| 111 | 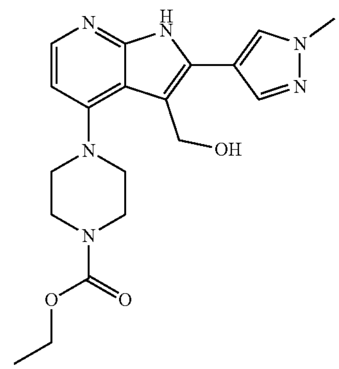 [SMILES: CCOC(=O)N1CCN(c2ccnc3[nH]c(-c4cnn(C)c4)c(CO)c23)CC1] |
| 112 | 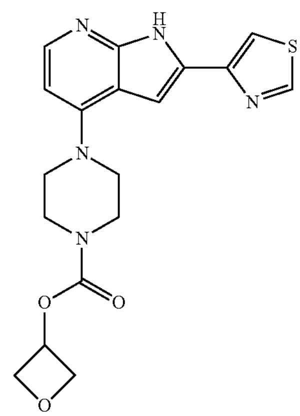 [SMILES: O=C(OC1COC1)N1CCN(c2ccnc3[nH]c(-c4cscn4)cc23)CC1] |
| 113 | 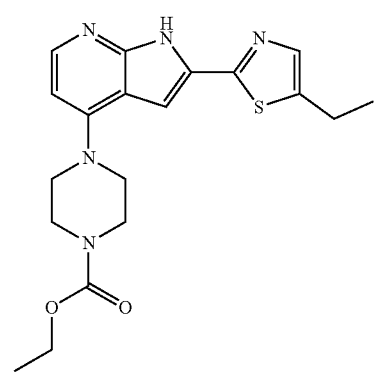 [SMILES: CCOC(=O)N1CCN(c2ccnc3[nH]c(-c4ncc(CC)s4)cc23)CC1] |
| 114 | 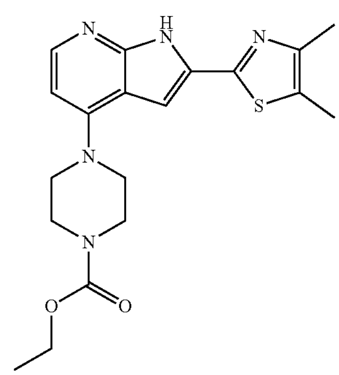 [SMILES: CCOC(=O)N1CCN(c2ccnc3[nH]c(-c4nc(C)c(C)s4)cc23)CC1] |

| # | Structure |
|---|---|
| 115 | 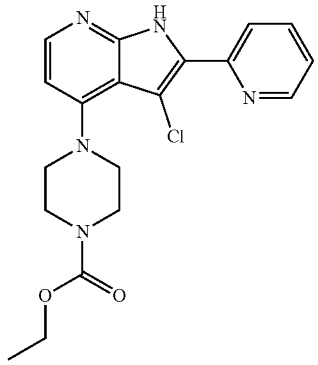 [SMILES: CCOC(=O)N1CCN(c2ccnc3[nH]c(-c4ccccn4)c(Cl)c23)CC1] |
| 116 | 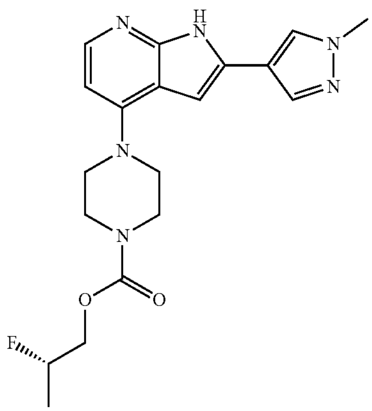 [SMILES: C[C@H](F)COC(=O)N1CCN(c2ccnc3[nH]c(-c4cnn(C)c4)cc23)CC1] |
| 117 | 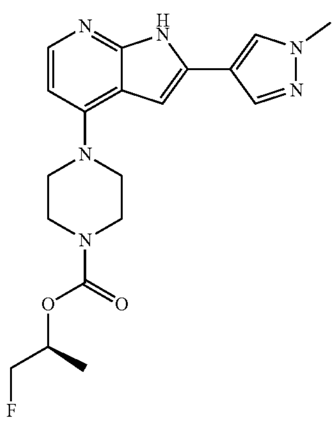 [SMILES: C[C@@H](CF)OC(=O)N1CCN(c2ccnc3[nH]c(-c4cnn(C)c4)cc23)CC1] |
| 118 | 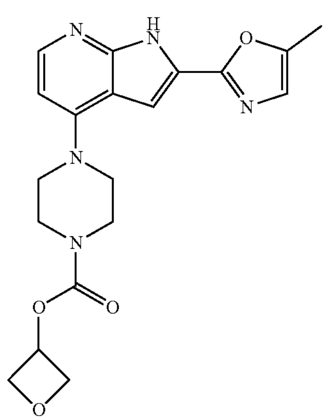 |
| 119 | |
| 120 | |
| 121 | |
| 122 | |

383
-continued
| # | Structure |
|---|---|
| 123 | 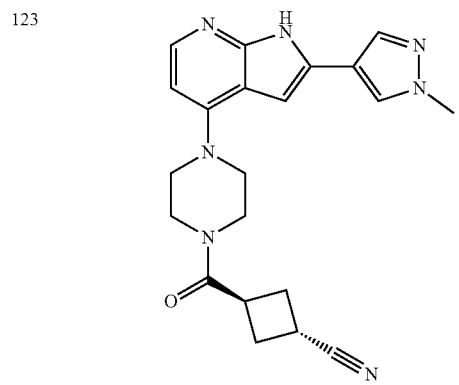 |
| 124 | 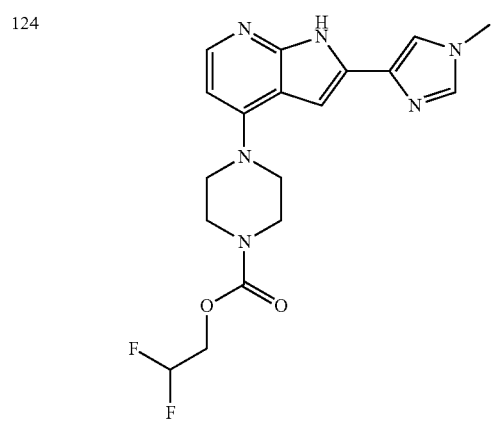 |
| 125 | 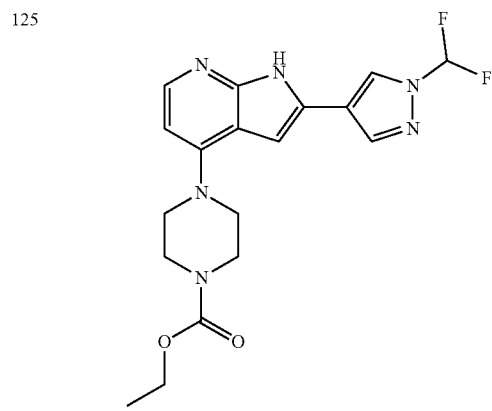 |
384
-continued
| # | Structure |
|---|---|
| 126 | 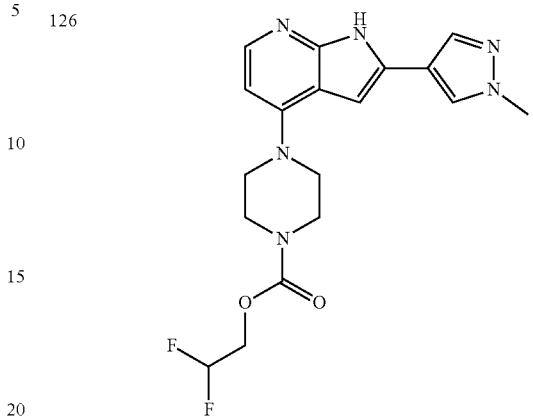 |
| 127 | 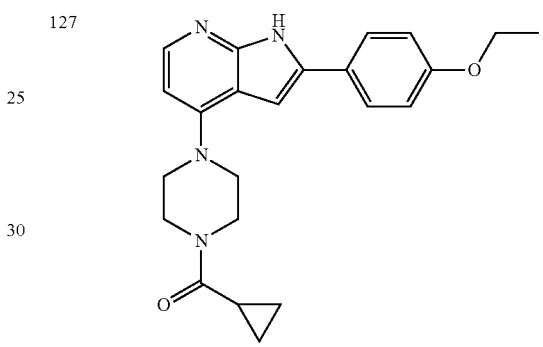 |
| 128 | 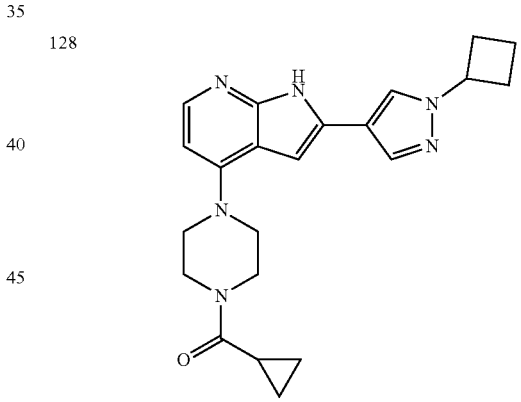 |
| 129 | 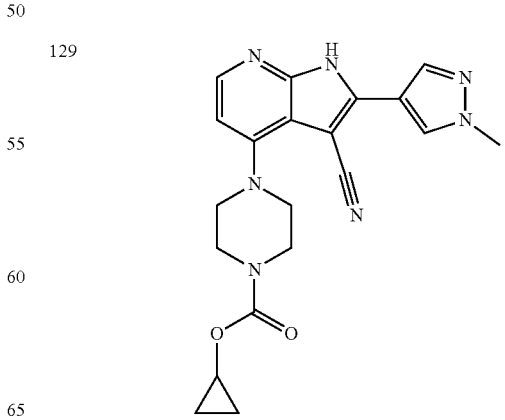 |

-continued
| # | Structure |
|---|---|
| 130 | 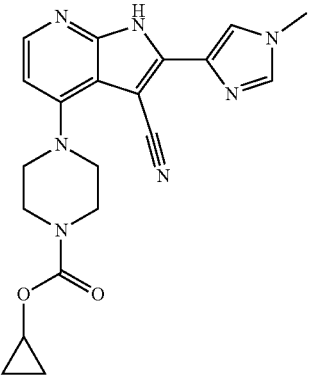 [SMILES: Cn1cnc(-c2[nH]c3nccc(N4CCN(C(=O)OC5CC5)CC4)c3c2C#N)c1] |
| 131 | 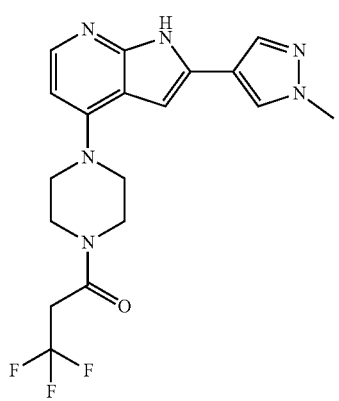 |
| 132 | 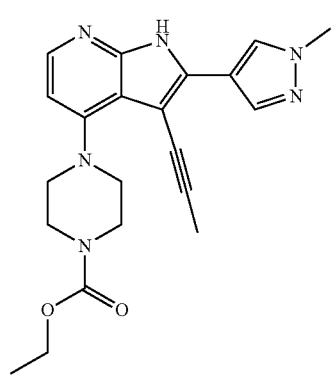 [SMILES: CC#Cc1c(-c2cnn(C)c2)[nH]c2nccc(N3CCN(C(=O)OCC)CC3)c12] |
| 133 | 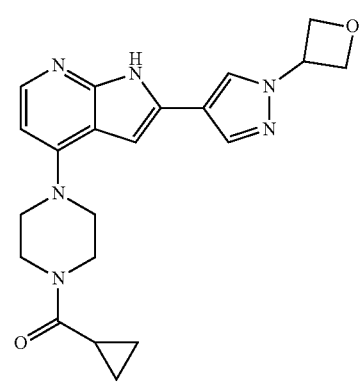 [SMILES: O=C(C1CC1)N1CCN(c2ccnc3[nH]c(-c4cnn(C5COC5)c4)cc23)CC1] |
-continued
| # | Structure |
|---|---|
| 134 | 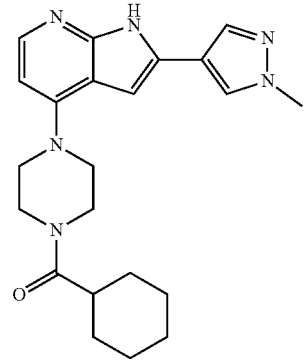 |
| 135 | 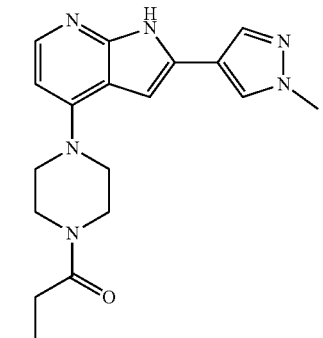 |
| 136 | 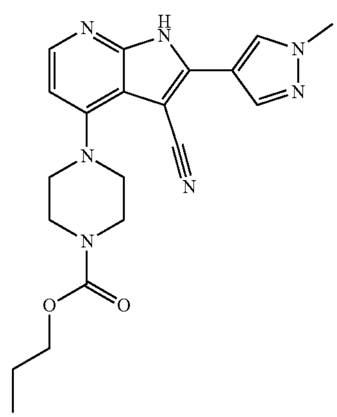 [SMILES: CCCOC(=O)N1CCN(c2ccnc3[nH]c(-c4cnn(C)c4)c(C#N)c23)CC1] |
| 137 | 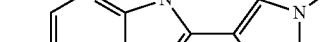 |

387
-continued
| # | Structure |
|---|---|
| 138 | 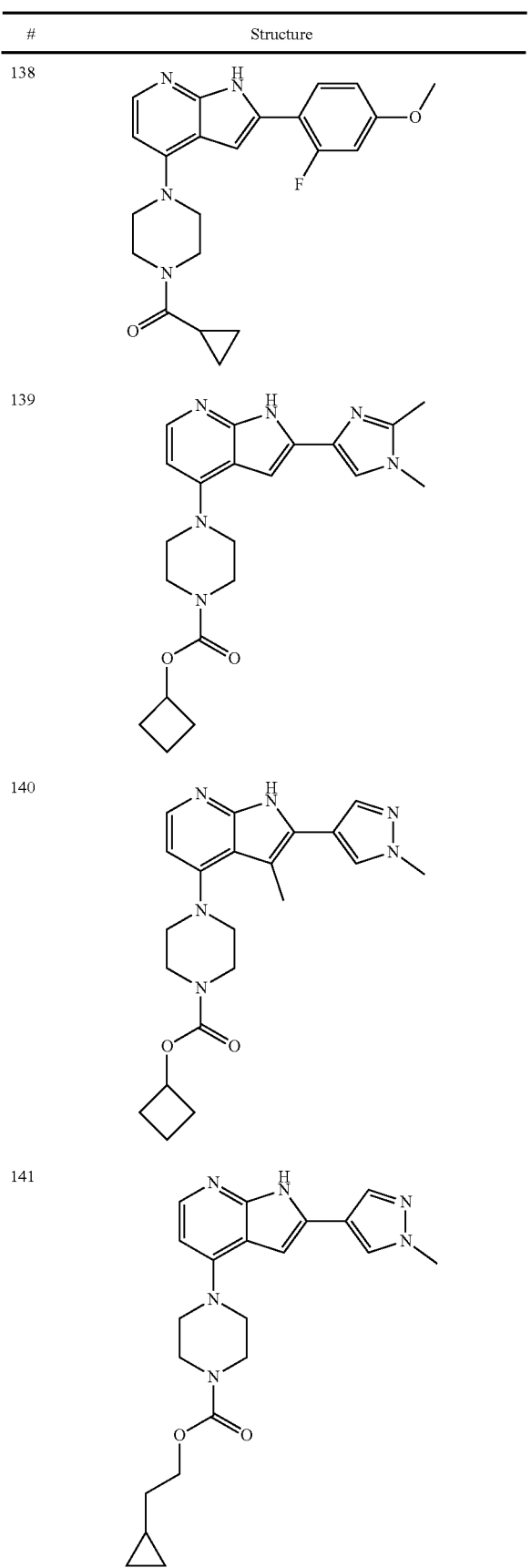 |
| 139 | 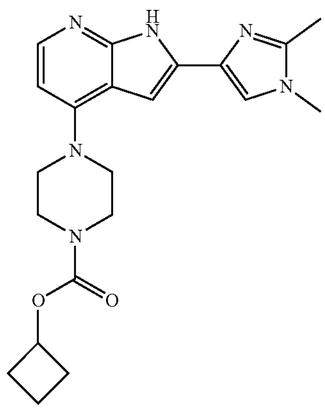 [SMILES: Cc1nc(-c2cc3c(N4CCN(C(=O)OC5CCC5)CC4)ccnc3[nH]2)cn1C] |
| 140 | 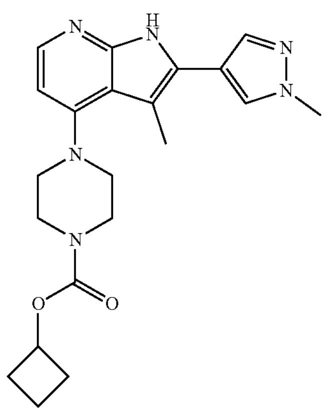 [SMILES: Cc1c(-c2cnn(C)c2)[nH]c2nccc(N3CCN(C(=O)OC4CCC4)CC3)c12] |
| 141 | 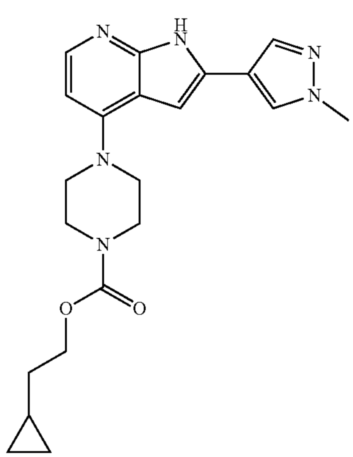 [SMILES: Cn1cc(-c2cc3c(N4CCN(C(=O)OCCC5CC5)CC4)ccnc3[nH]2)cn1] |
388
-continued
| # | Structure |
|---|---|
| 142 | 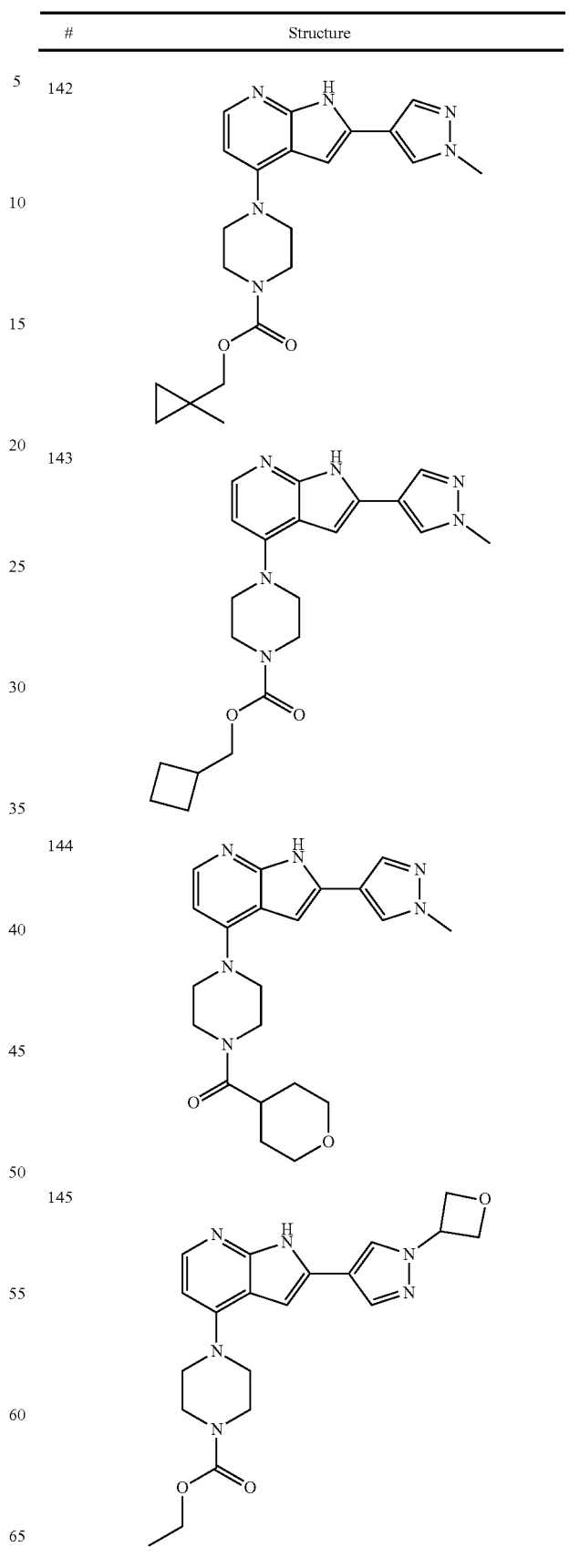 |
| 143 | 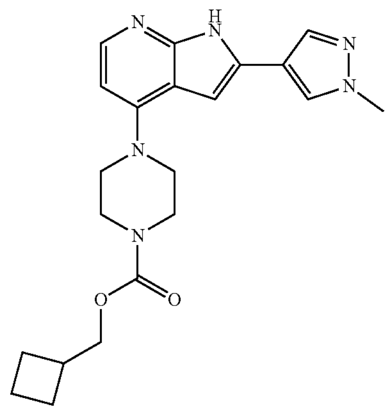 [SMILES: Cn1cc(-c2cc3c(N4CCN(C(=O)OCC5CCC5)CC4)ccnc3[nH]2)cn1] |
| 144 | 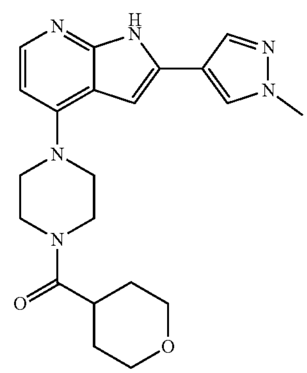 |
| 145 | 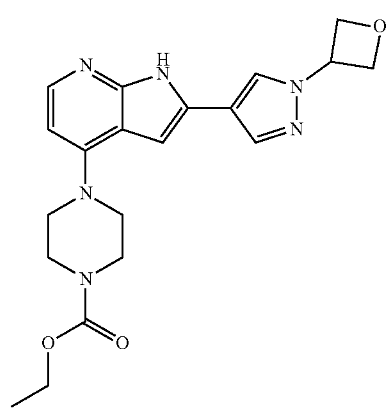 [SMILES: CCOC(=O)N1CCN(c2ccnc3[nH]c(-c4cnn(C5COC5)c4)cc23)CC1] |

| # | Structure |
|---|---|
| 146 | 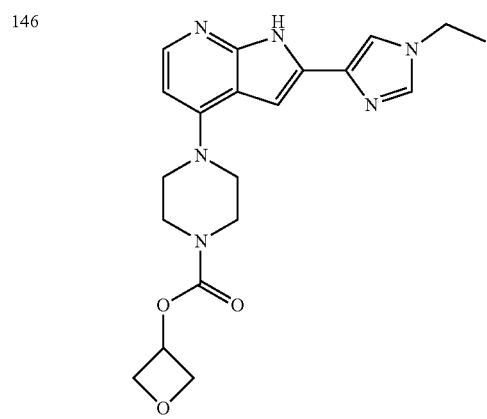 |
| 147 | 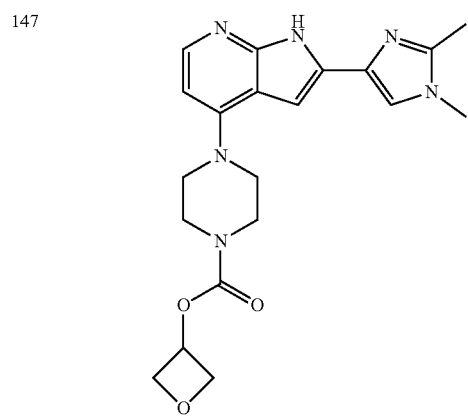 |
| 148 | 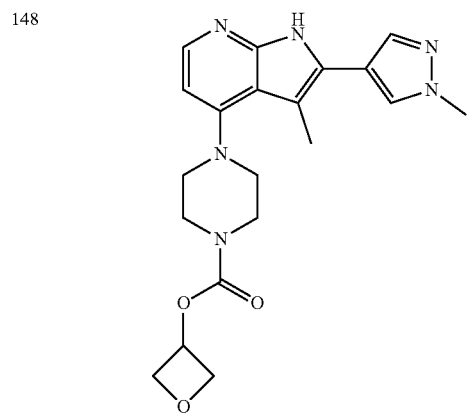 |
| # | Structure |
|---|---|
| 149 | 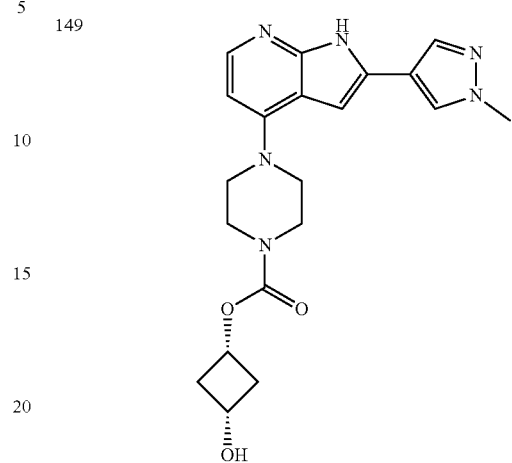 |
| 150 | 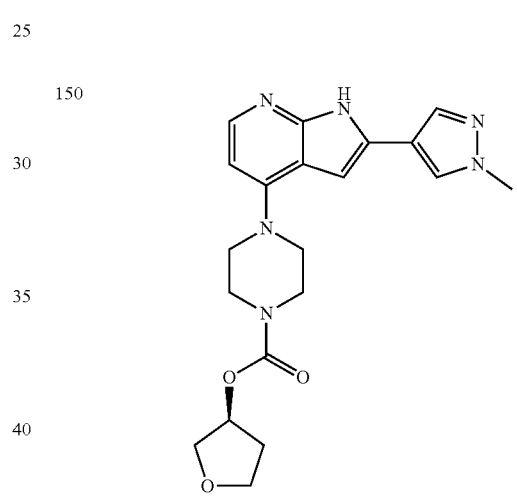 |
| 151 | 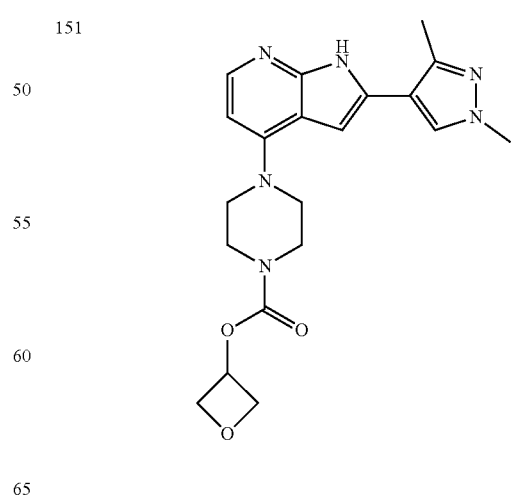 |

| # | Structure |
|---|---|
| 152 | 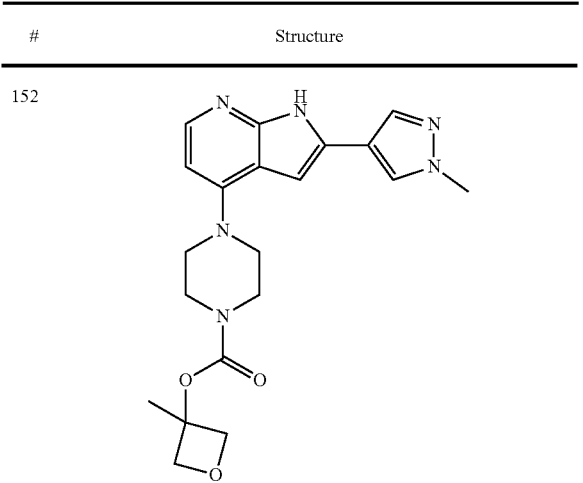 |
| 153 | 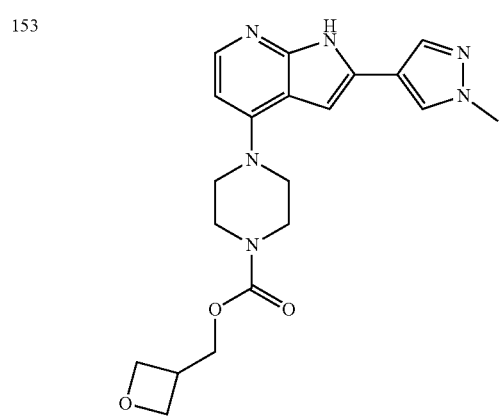 |
| 154 | 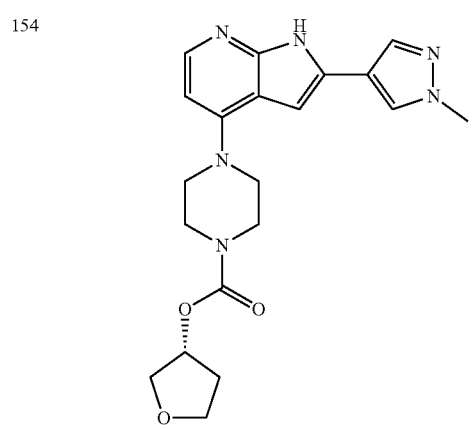 |
| # | Structure |
|---|---|
| 155 | 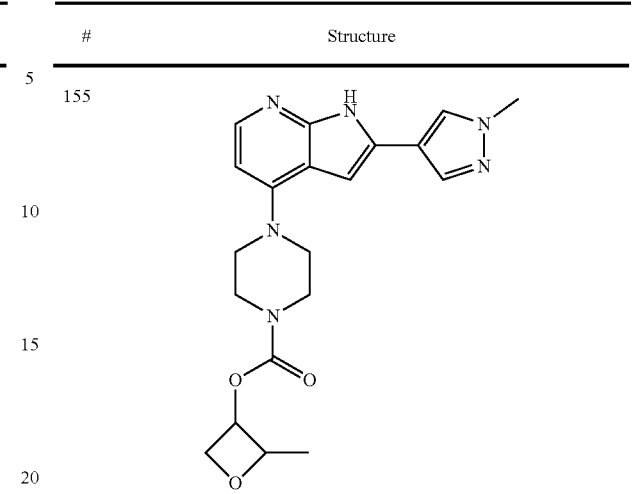 |
| 156 | 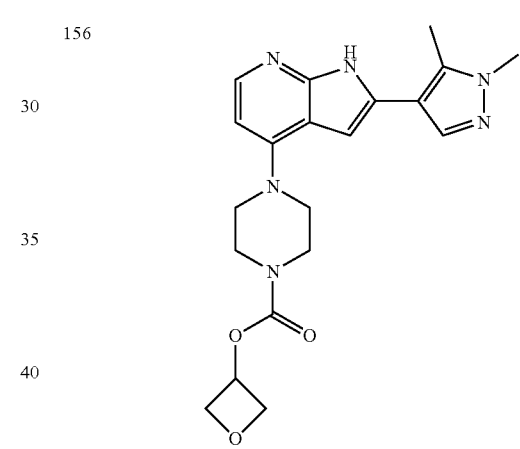 |
| 157 | 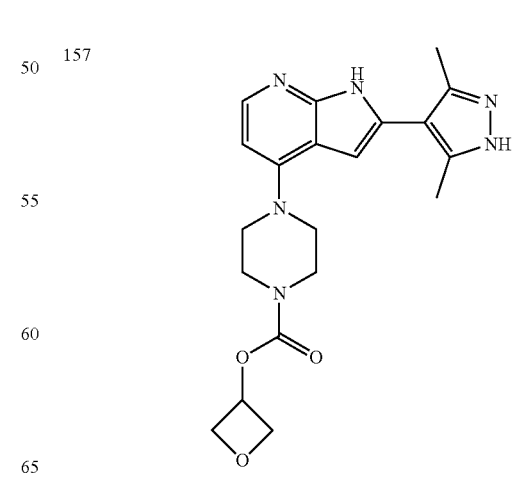 |

| # | Structure |
|---|---|
| 158 | 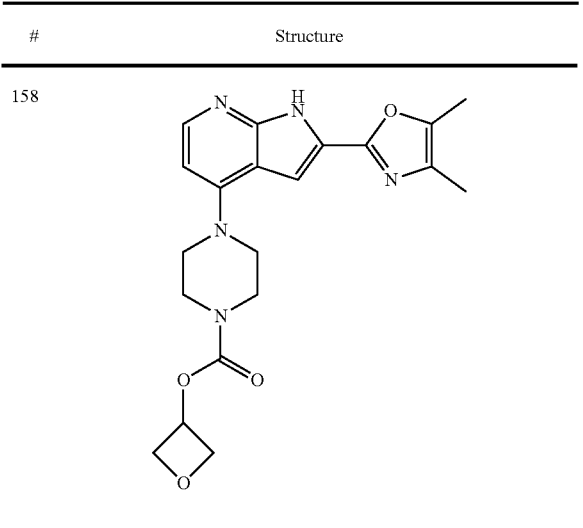 |
| 159 | 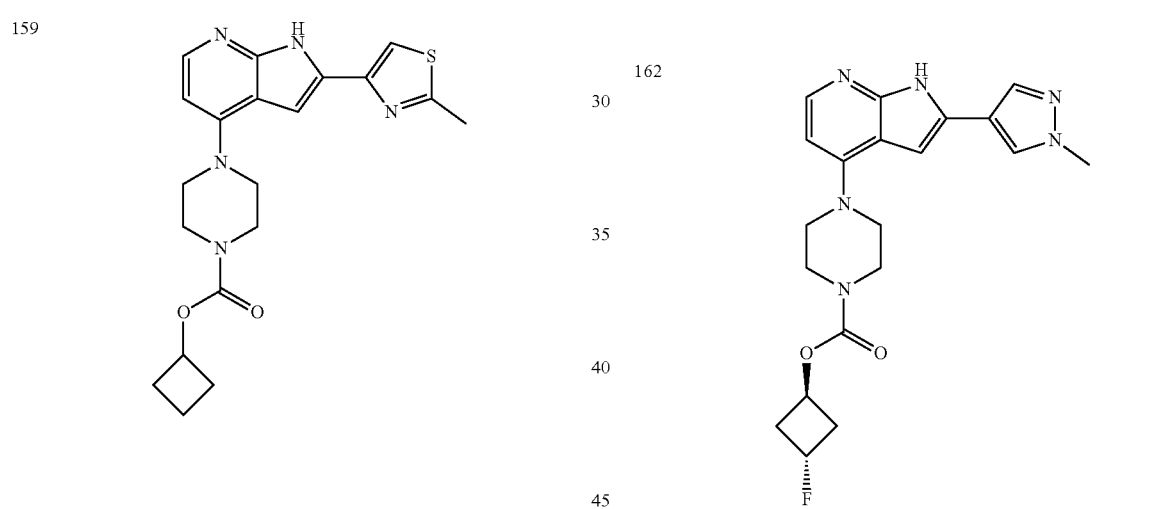 |
| 160 | |
| # | Structure |
|---|---|
| 161 | 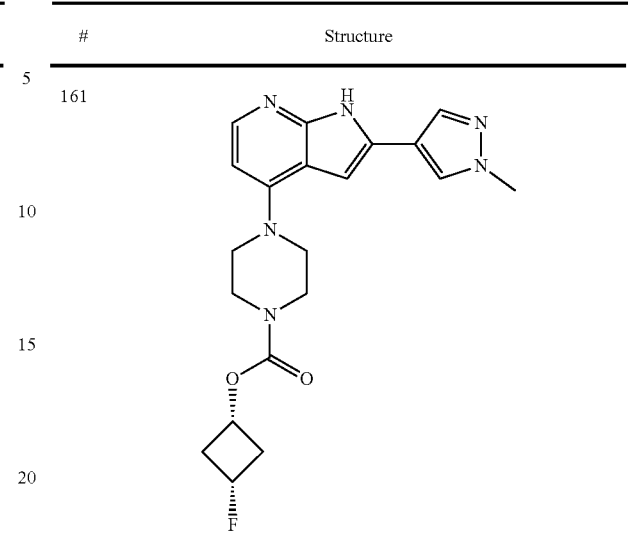 |
| 162 | |
| 163 | 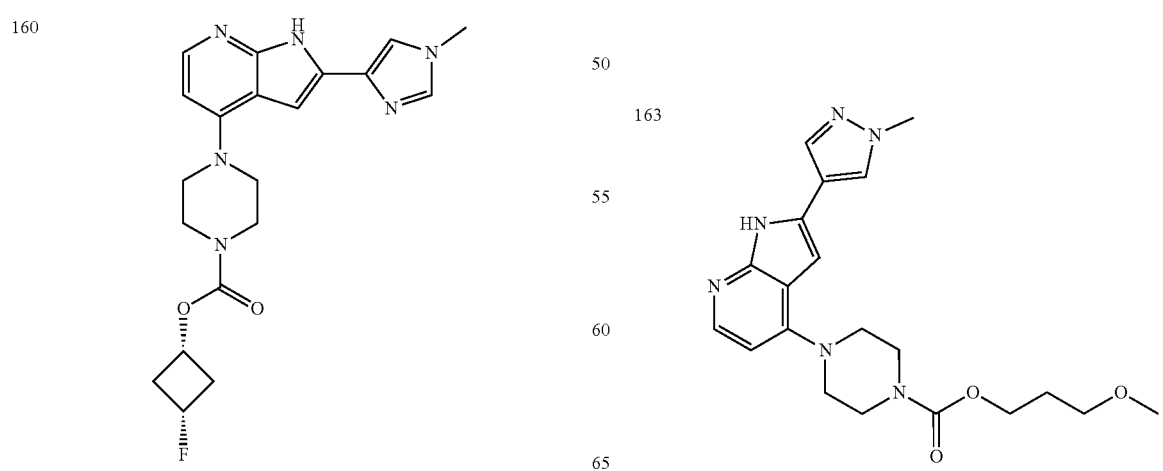 |

| # | Structure |
|---|---|
| 164 | 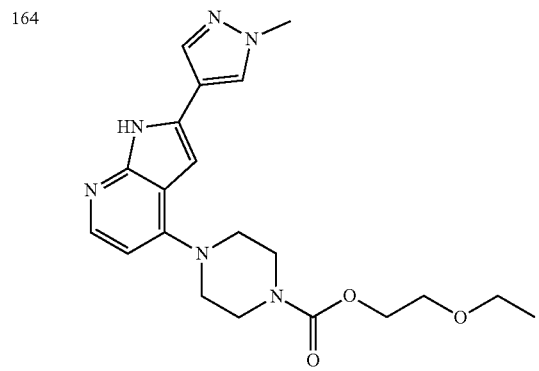 |
| 165 | 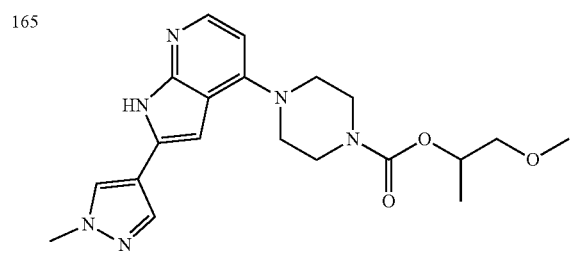 |
| 166 | 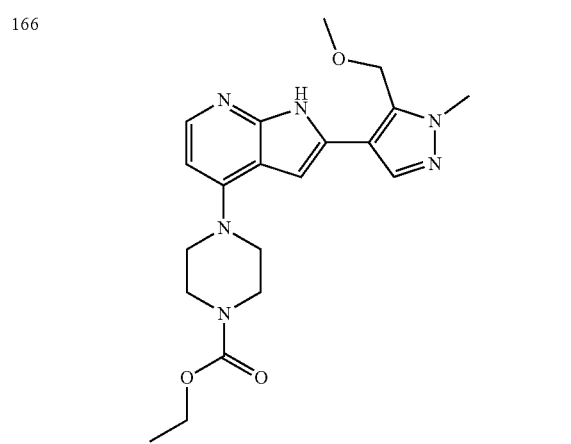 |
| 167 | 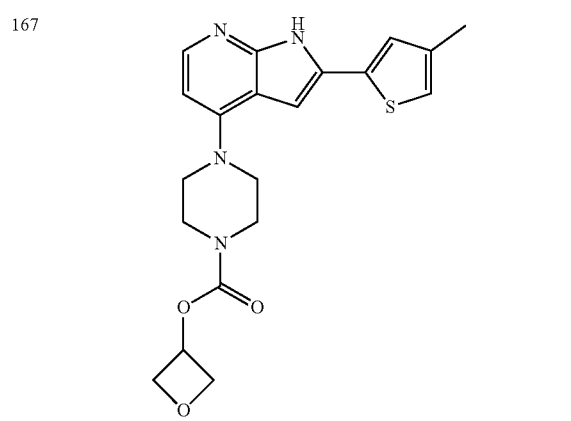 |
| # | Structure |
|---|---|
| 168 | 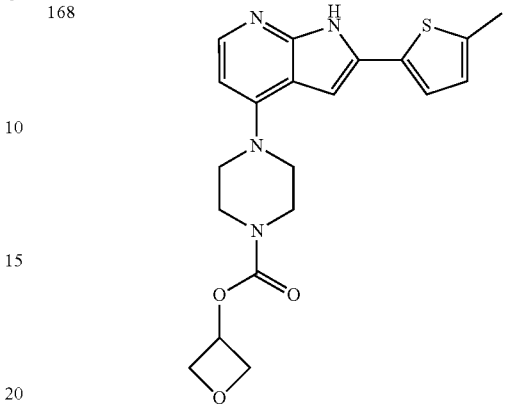 |
| 169 | 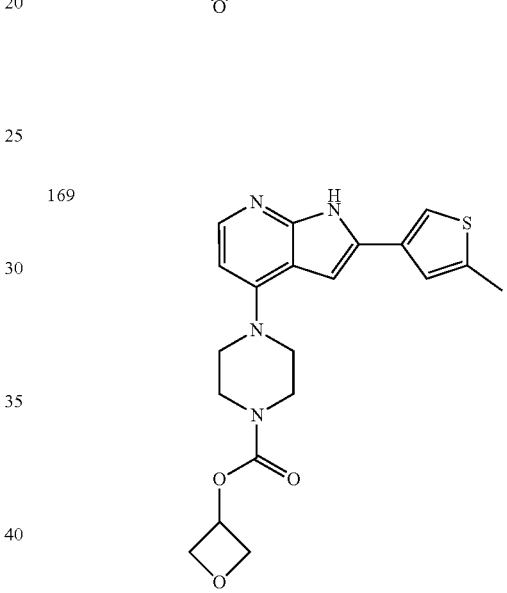 |
| 170 | 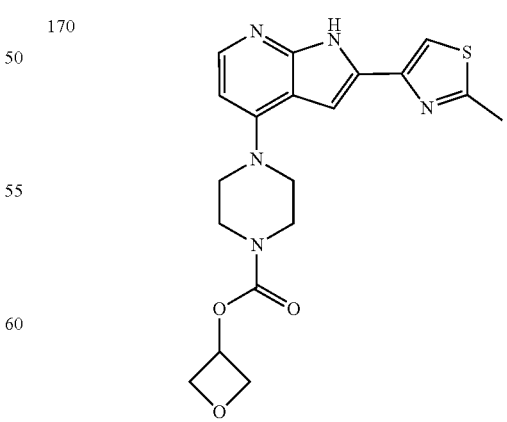 |

| # | Structure |
|---|---|
| 171 | (structure) |
| 172 | (structure) |
| 173 | (structure) |
| 174 | (structure) |
| 175 | (structure) |
| 177 | (structure) |
| 178 | (structure) |

| # | Structure |
|---|---|
| 179 | |
| 180 | |
| 181 | |
| 182 | 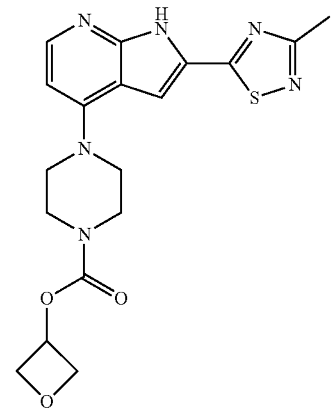 |
| 183 | 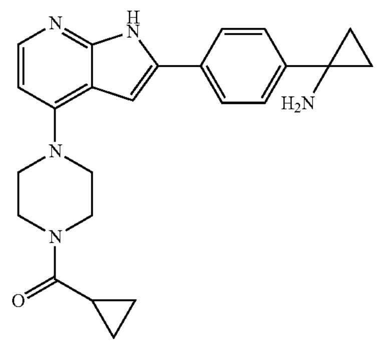 [SMILES: NC1(c2ccc(-c3cc4c(N5CCN(C(=O)C6CC6)CC5)ccnc4[nH]3)cc2)CC1] |
| 184 | 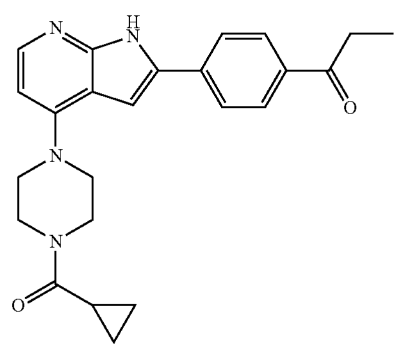 [SMILES: CCC(=O)c1ccc(-c2cc3c(N4CCN(C(=O)C5CC5)CC4)ccnc3[nH]2)cc1] |
| 185 | 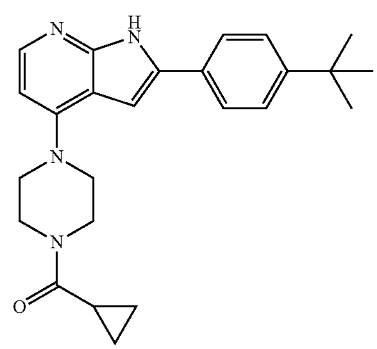 [SMILES: CC(C)(C)c1ccc(-c2cc3c(N4CCN(C(=O)C5CC5)CC4)ccnc3[nH]2)cc1] |

-continued

| # | Structure |
|---|---|
| 186 | 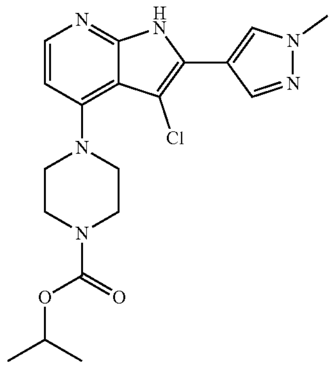 [SMILES: CC(C)OC(=O)N1CCN(c2ccnc3[nH]c(-c4cnn(C)c4)c(Cl)c23)CC1] |
| 187 | 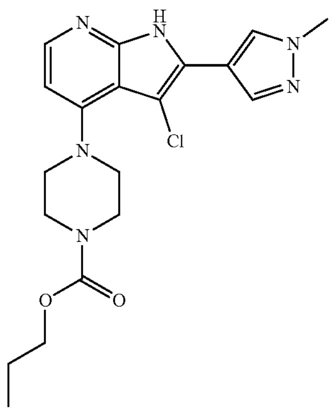 [SMILES: CCCOC(=O)N1CCN(c2ccnc3[nH]c(-c4cnn(C)c4)c(Cl)c23)CC1] |
| 188 | 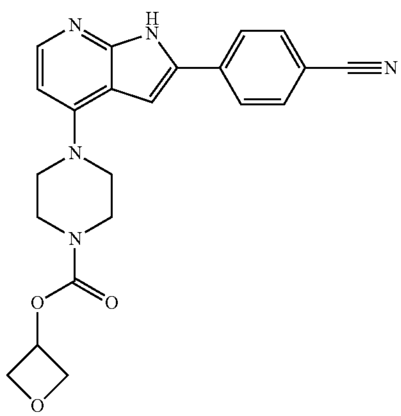 |
| 189 | 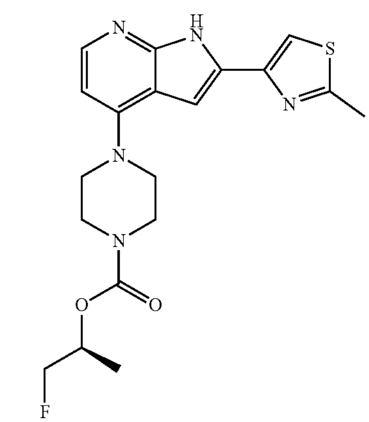 [SMILES: Cc1nc(-c2cc3c(N4CCN(C(=O)O[C@@H](C)CF)CC4)ccnc3[nH]2)cs1] |
| 190 | |
| 191 | |
| 192 | |
| 194 | |

| # | Structure |
|---|---|
| 195 | 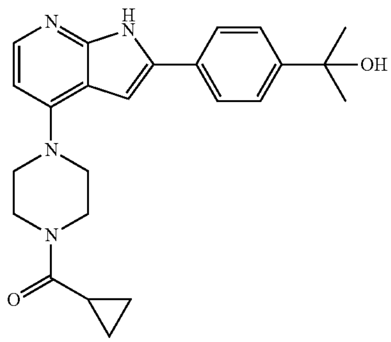 |
| 196 | 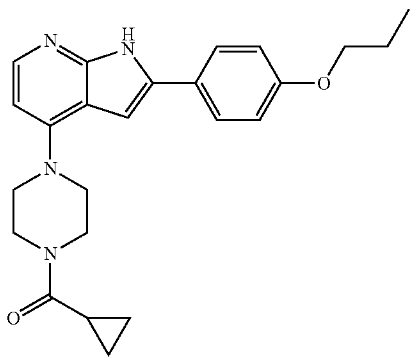 [SMILES: CCCOc1ccc(-c2cc3c(N4CCN(C(=O)C5CC5)CC4)ccnc3[nH]2)cc1] |
| 197 | 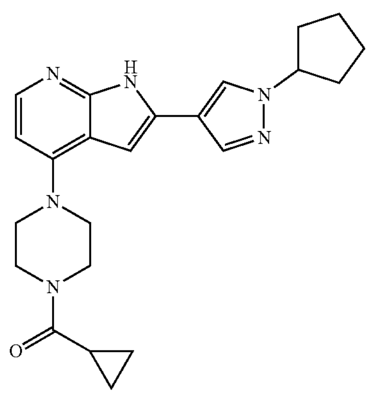 [SMILES: O=C(C1CC1)N1CCN(c2ccnc3[nH]c(-c4cnn(C5CCCC5)c4)cc23)CC1] |
| 198 | 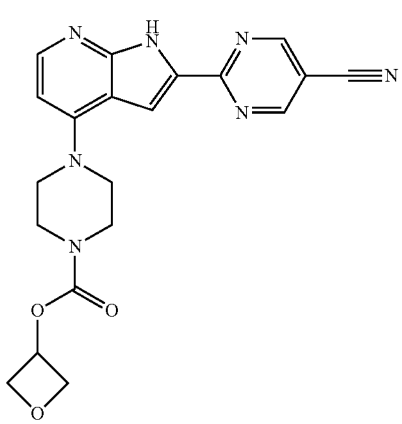 [SMILES: N#Cc1cnc(-c2cc3c(N4CCN(C(=O)OC5COC5)CC4)ccnc3[nH]2)nc1] |
| 199 | |
| 200 | |
| 201 | |

| # | Structure |
|---|---|
| 202 | 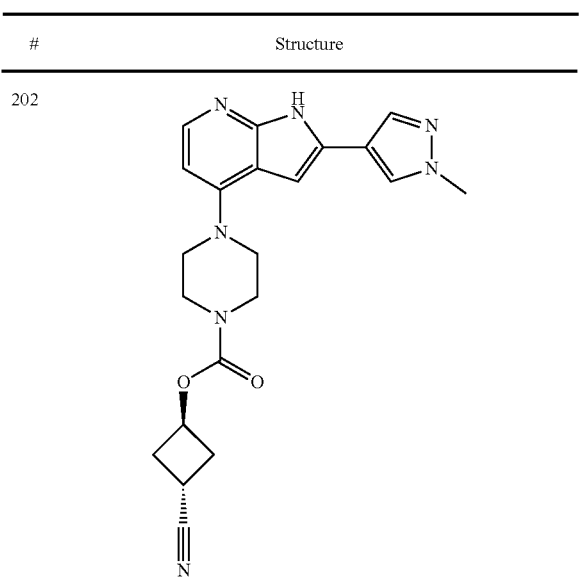 |
| 203 | 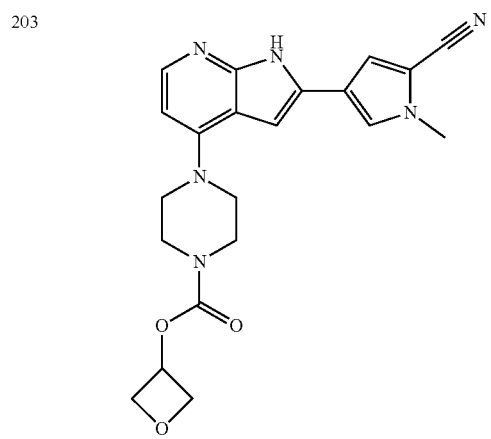 |
| 204 | 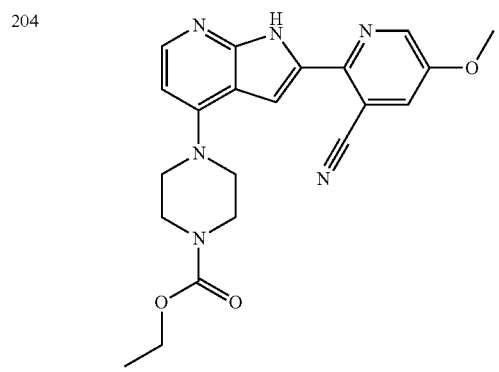 |
| # | Structure |
|---|---|
| 205 | 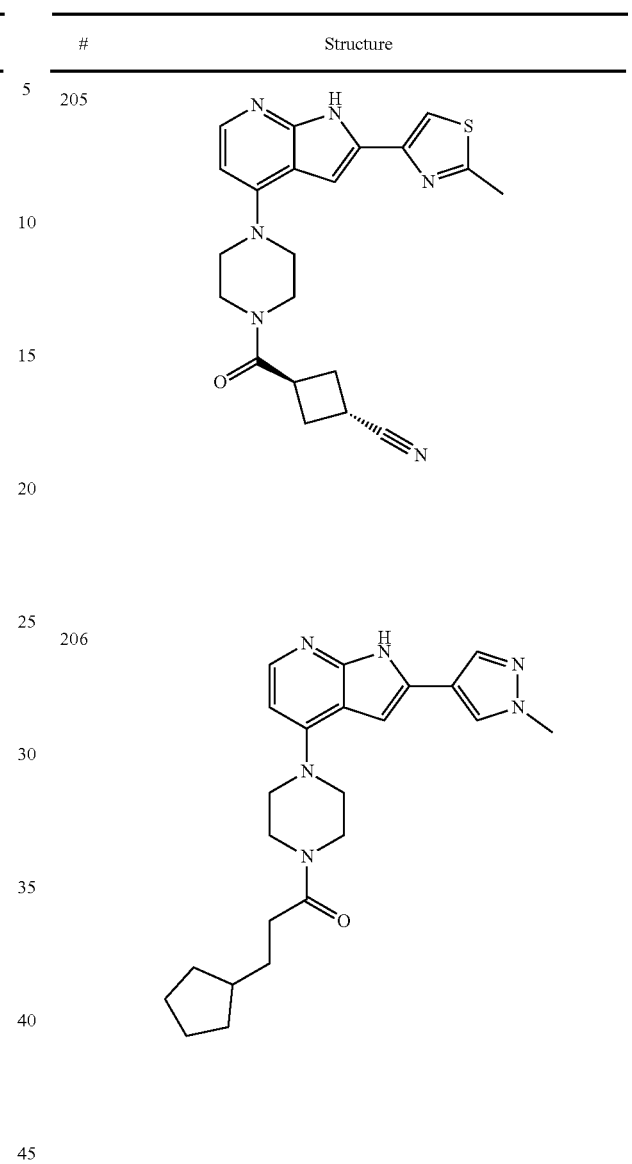 |
| 206 | |
| 207 | 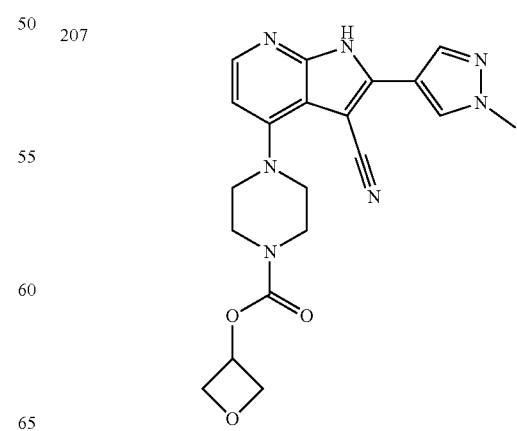 |

-continued
| # | Structure |
|---|---|
| 208 | 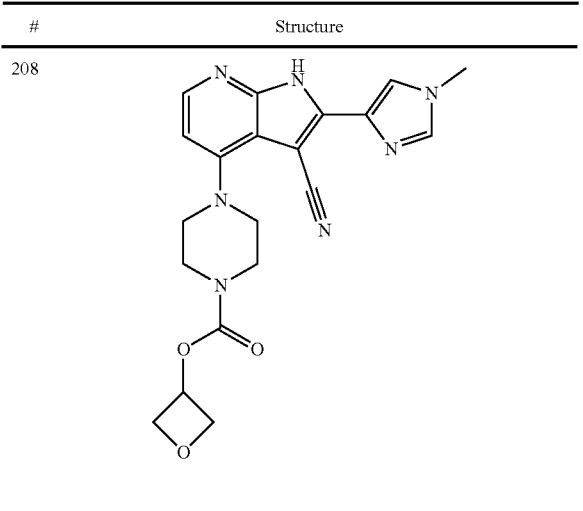 |
| 209 | 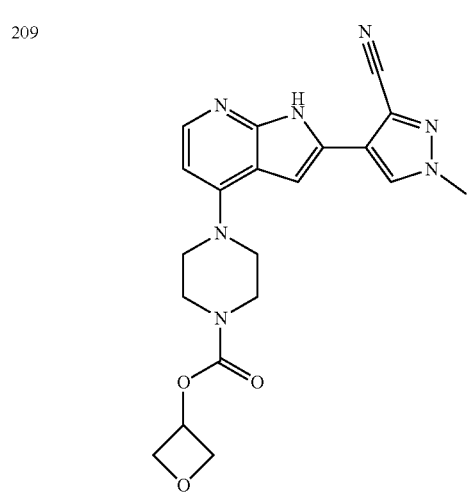 |
| 210 | 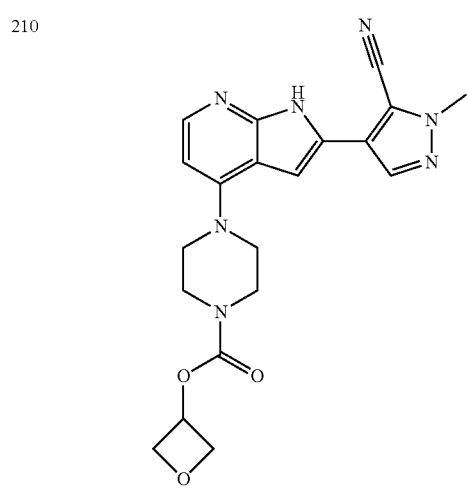 |
-continued
| # | Structure |
|---|---|
| 211 | 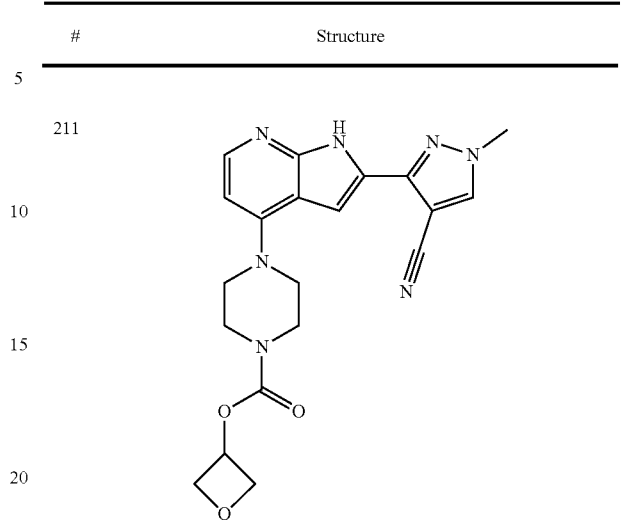 |
| 212 | 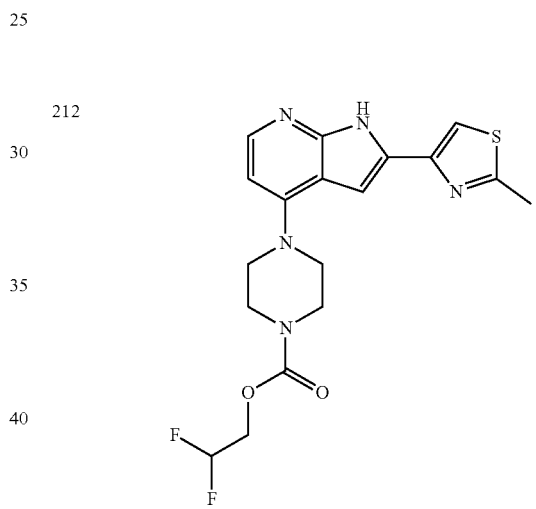 |
| 213 | 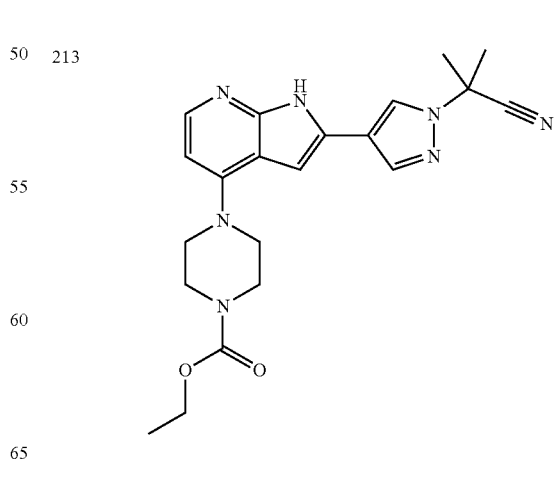 |

-continued
| # | Structure |
|---|---|
| 214 | 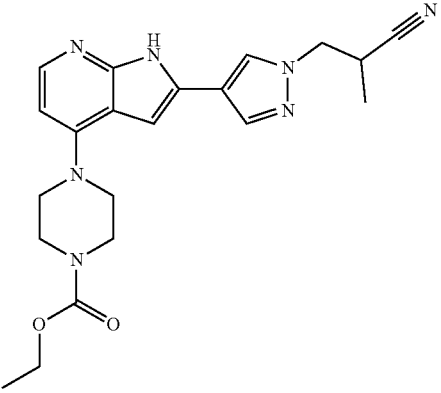 [SMILES: CCOC(=O)N1CCN(c2ccnc3[nH]c(-c4cnn(CC(C)C#N)c4)cc23)CC1] |
| 215 | 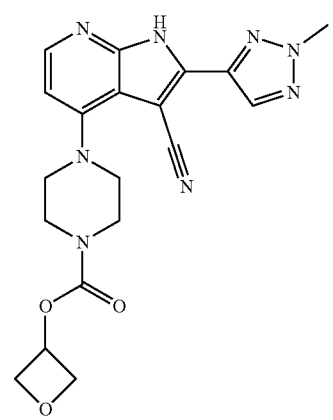 [SMILES: Cn1ncc(-c2[nH]c3nccc(N4CCN(C(=O)OC5COC5)CC4)c3c2C#N)n1] |
| 216 | 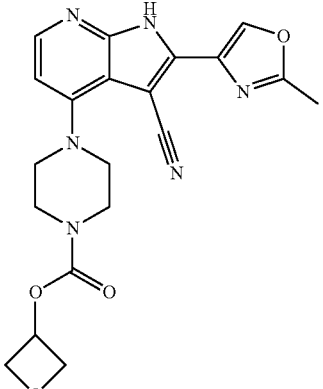 |
-continued
| # | Structure |
|---|---|
| 217 | 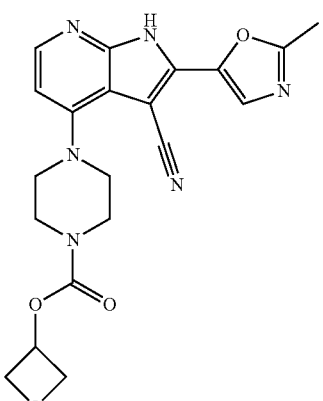 |
| 218 | 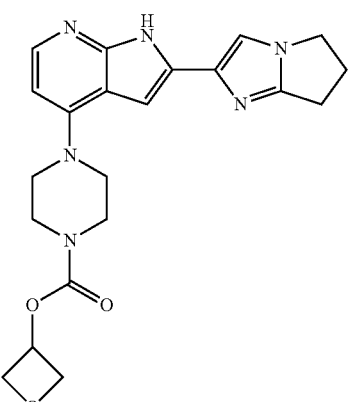 |
| 219 | 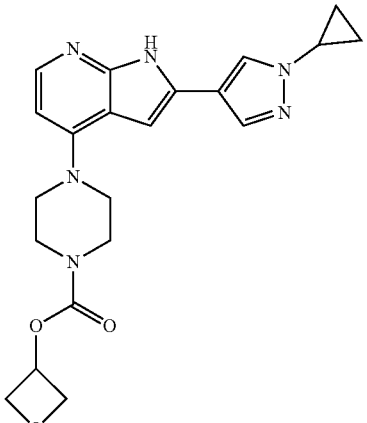 |

| # | Structure |
|---|---|
| 220 | 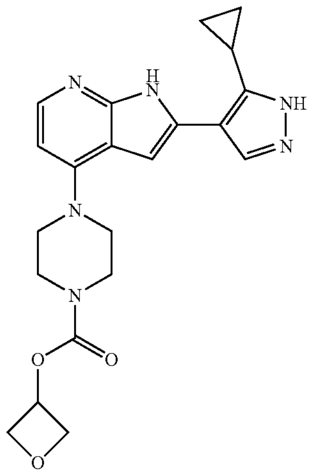 [SMILES: O=C(OC1COC1)N1CCN(c2ccnc3[nH]c(-c4cn[nH]c4C4CC4)cc23)CC1] |
| 221 | 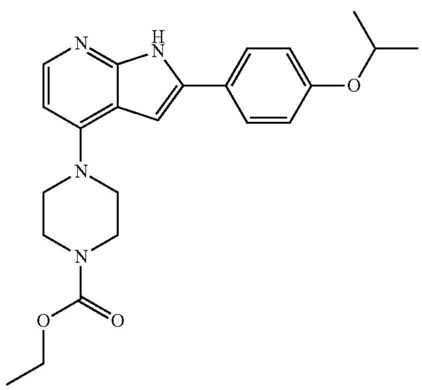 [SMILES: CCOC(=O)N1CCN(c2ccnc3[nH]c(-c4ccc(OC(C)C)cc4)cc23)CC1] |
| 222 | 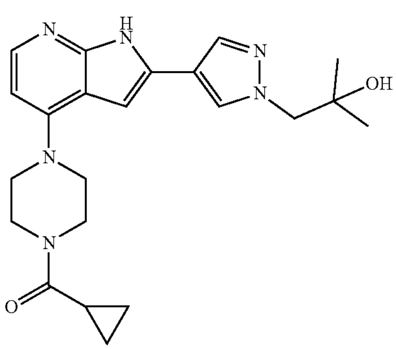 [SMILES: CC(C)(O)Cn1cc(-c2cc3c(N4CCN(C(=O)C5CC5)CC4)ccnc3[nH]2)cn1] |
| 223 | 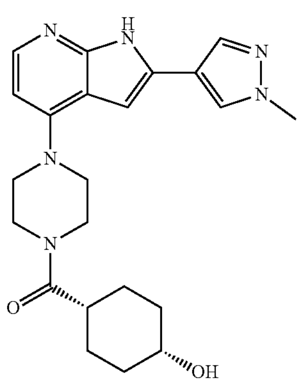 [SMILES: Cn1cc(-c2cc3c(N4CCN(C(=O)[C@H]5CC[C@@H](O)CC5)CC4)ccnc3[nH]2)cn1] |

| # | Structure |
|---|---|
| 224 | |
| 225 | |
| 226 | |
| 227 | |

413
-continued
| # | Structure |
|---|---|
| 228 | 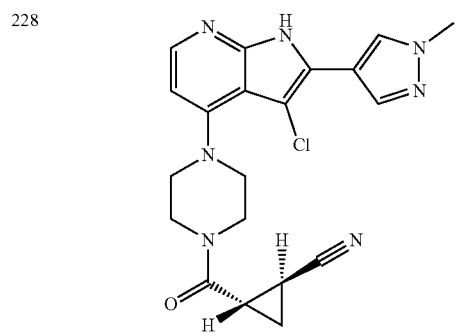 |
| 229 | 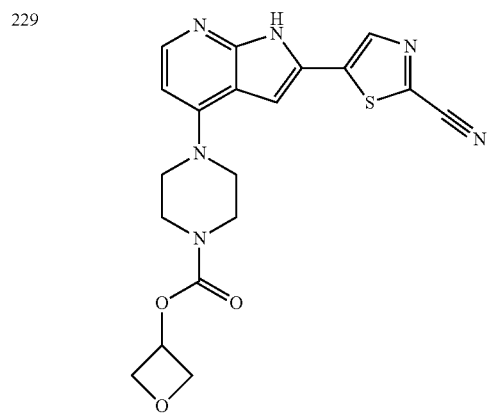 |
| 230 | 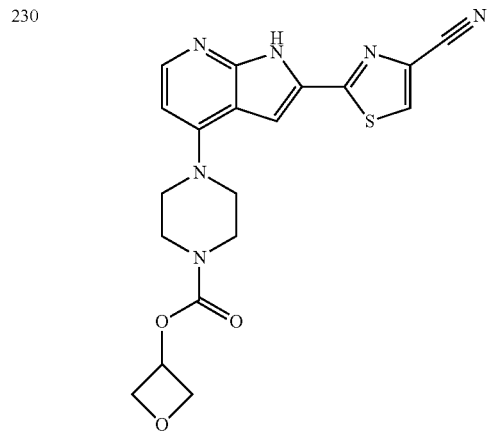 |
414
-continued
| # | Structure |
|---|---|
| 231 | 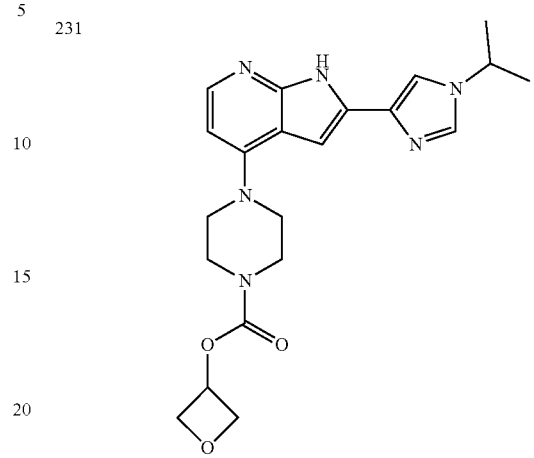 |
| 232 | 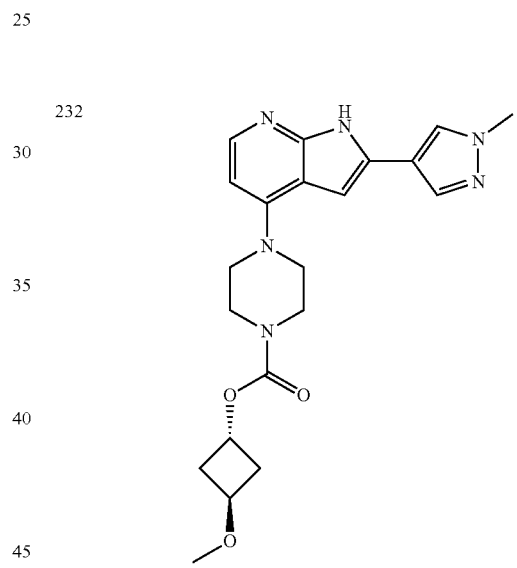 |
| 233 | 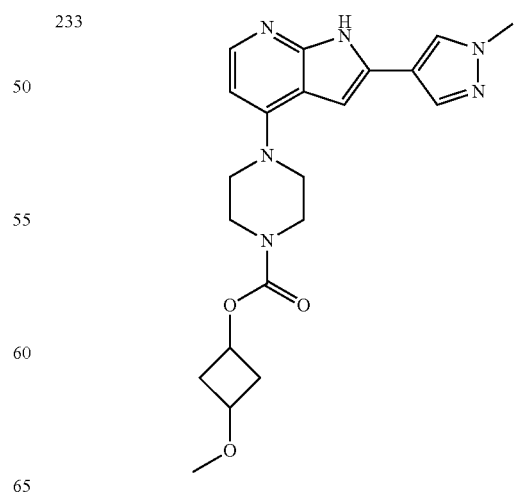 |

| # | Structure |
|---|---|
| 234 | 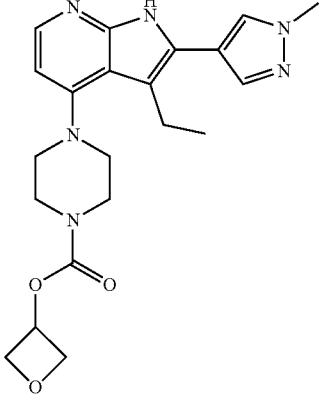 |
| 235 | |
| 236 | |
| # | Structure |
|---|---|
| 237 | 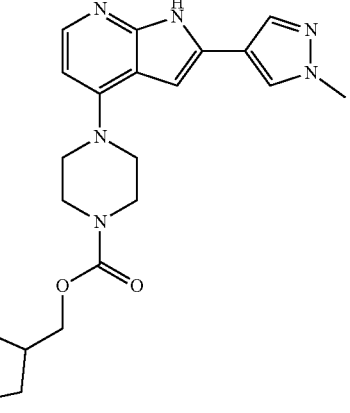 |
| 238 | |
| 239 | 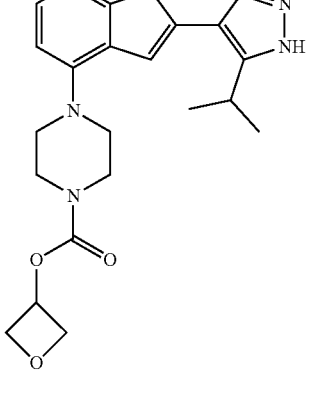 |
| 240 | 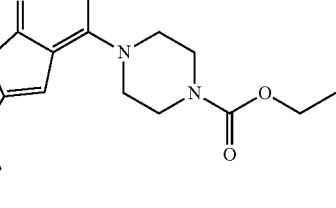 |

| # | Structure |
|---|---|
| 241 | 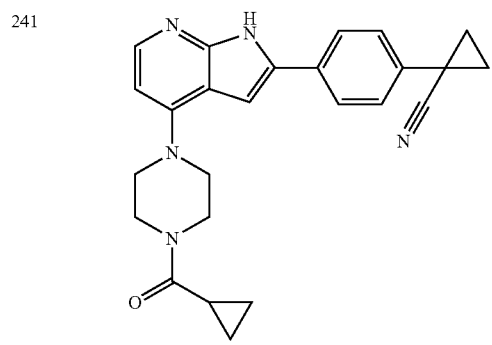 |
| 242 | 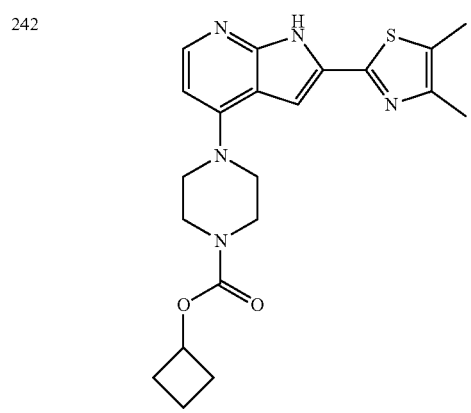 |
| 243 | 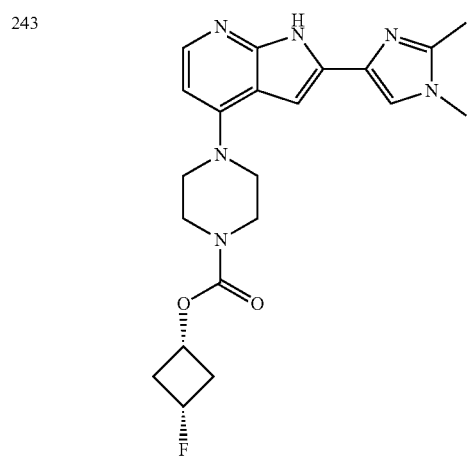 |
| # | Structure |
|---|---|
| 244 | 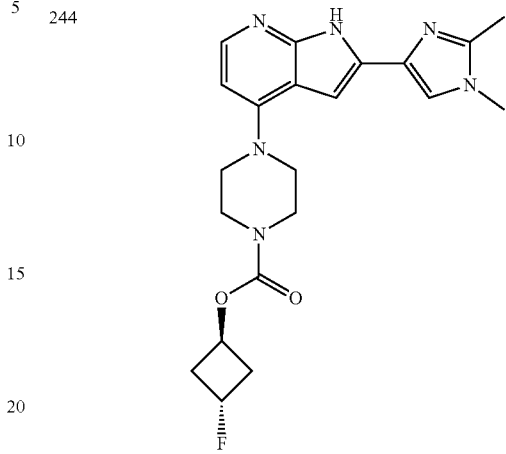 |
| 245 | 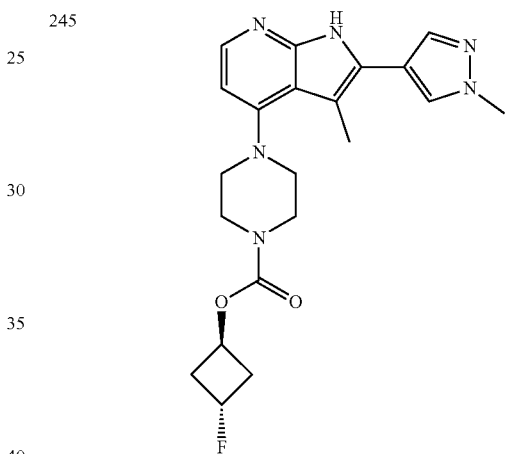 |
| 246 | 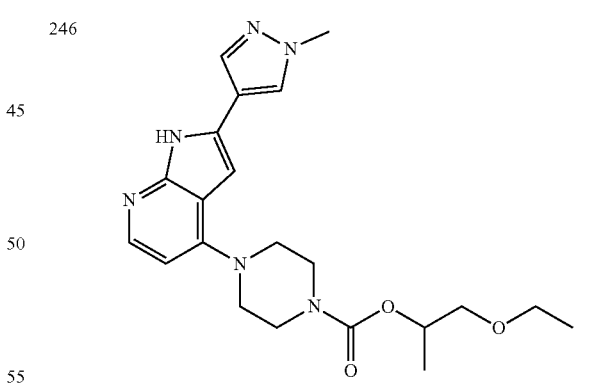 |
| 247 | 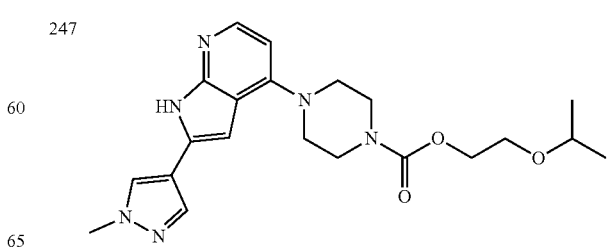 |

| # | Structure |
|---|---|
| 248 | 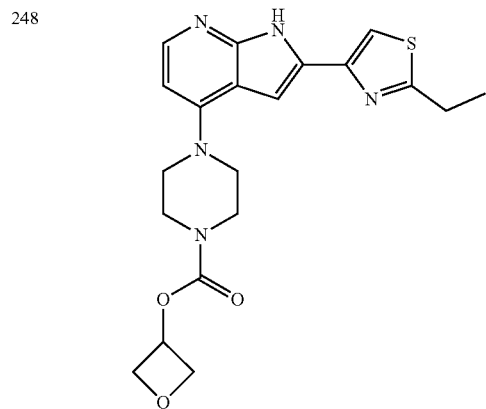 |
| 249 | 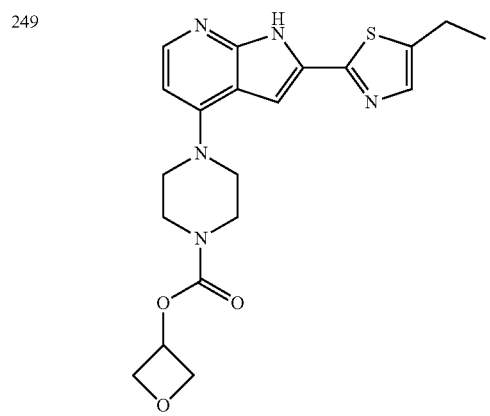 |
| 250 | 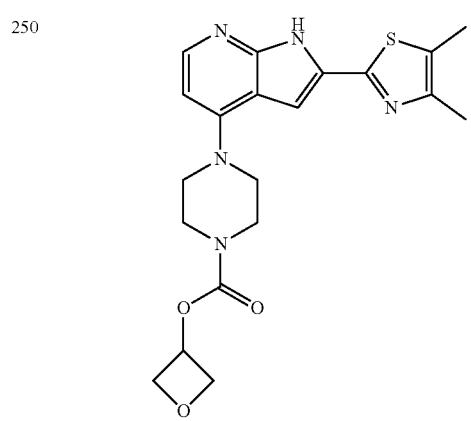 |
| # | Structure |
|---|---|
| 251 | 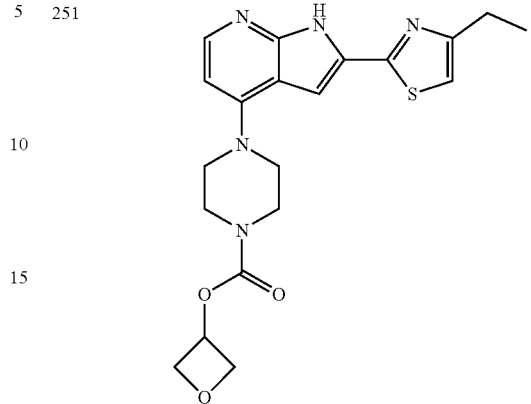 |
| 252 | 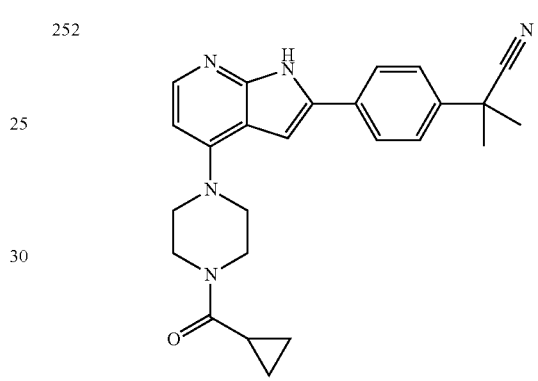 |
| 253 | 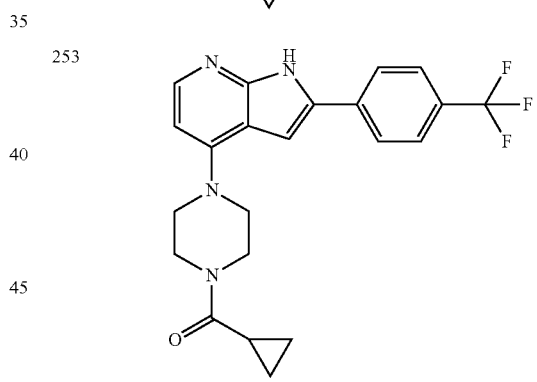 |
| 254 | 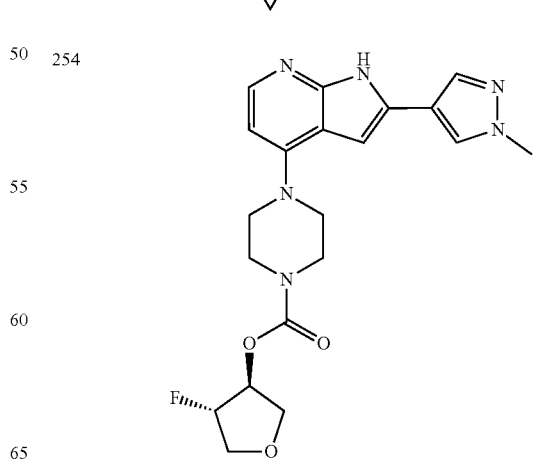 |

-continued
| # | Structure |
|---|---|
| 255 | 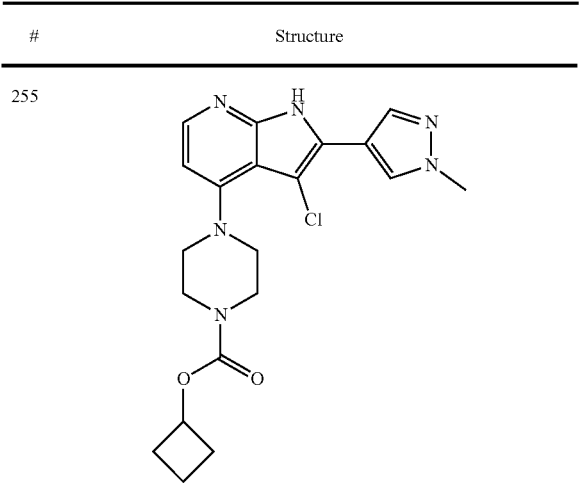 |
| 256 | 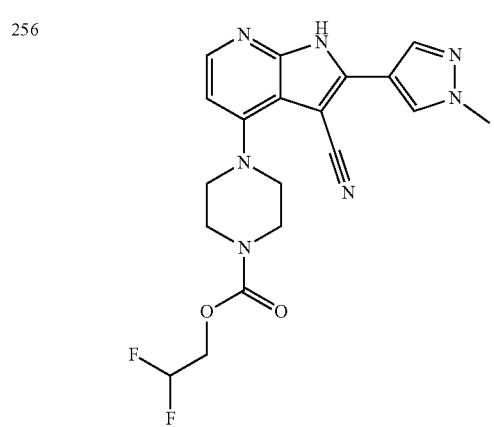 |
| 257 | 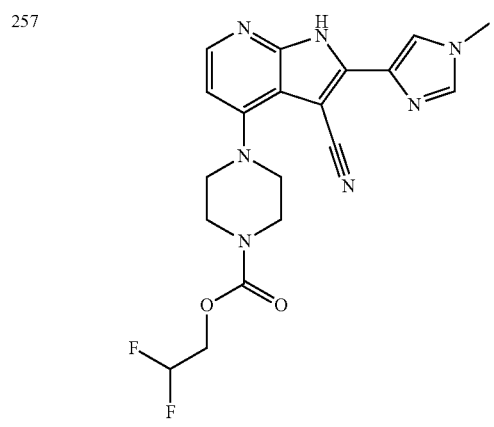 |
-continued
| # | Structure |
|---|---|
| 258 | 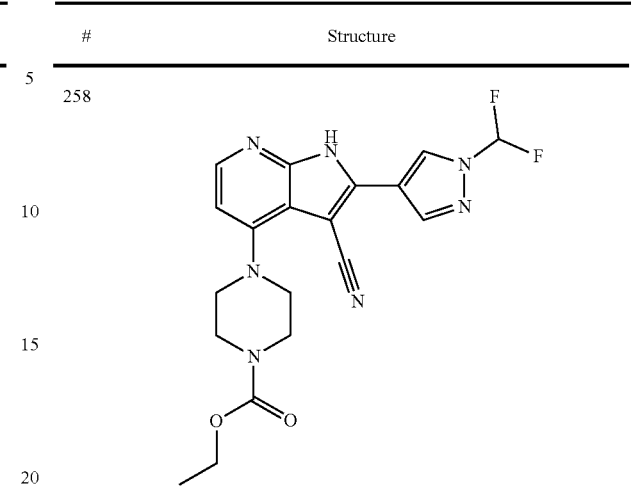 |
| 259 | 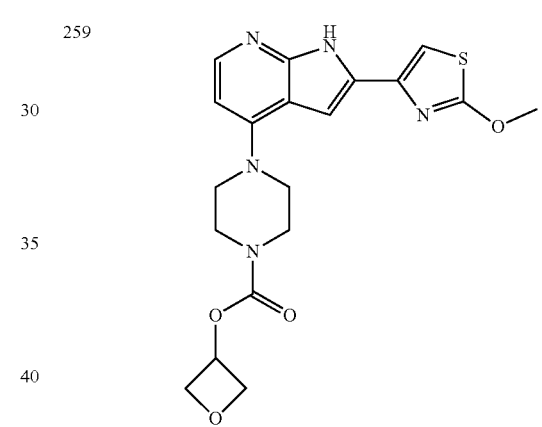 |
| 260 | 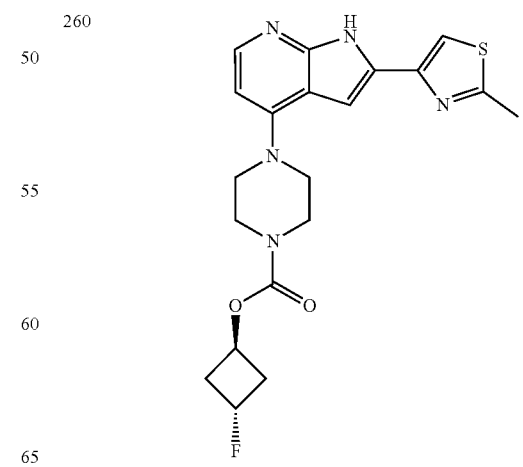 |

| # | Structure |
|---|---|
| 261 | 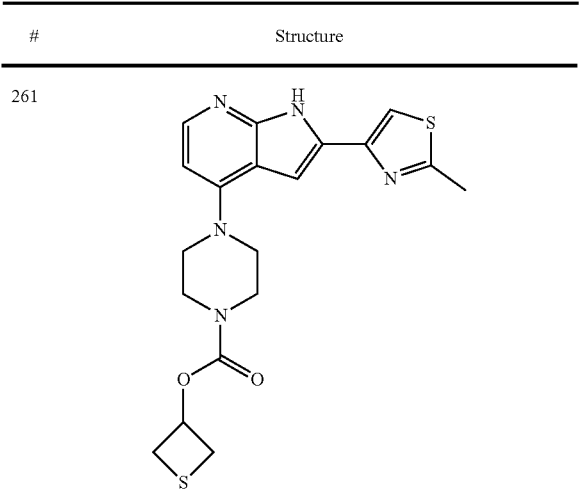 |
| 262 | 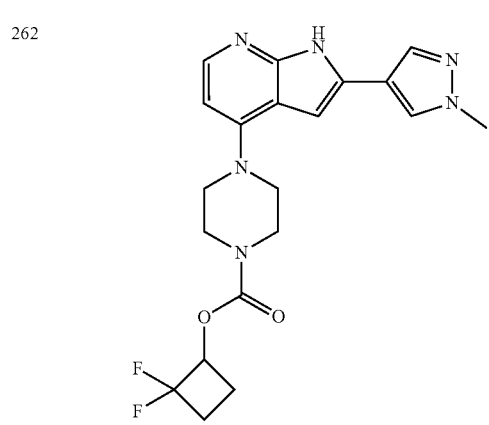 |
| 263 | 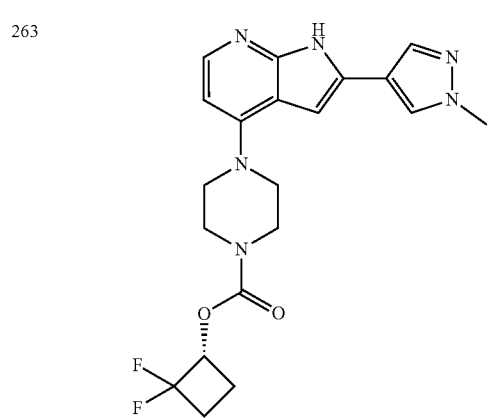 |
| # | Structure |
|---|---|
| 264 | 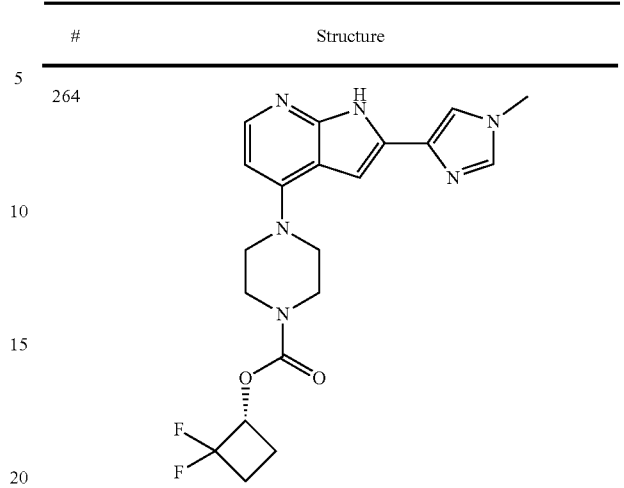 |
| 265 | 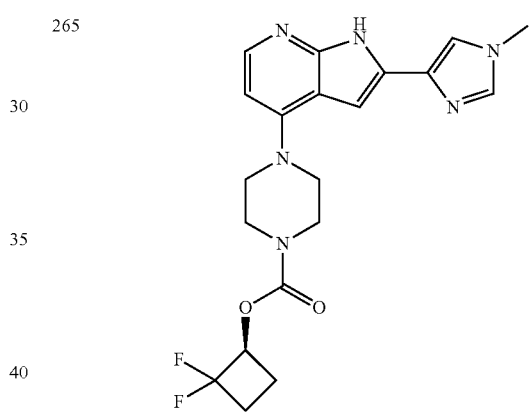 |
| 266 | 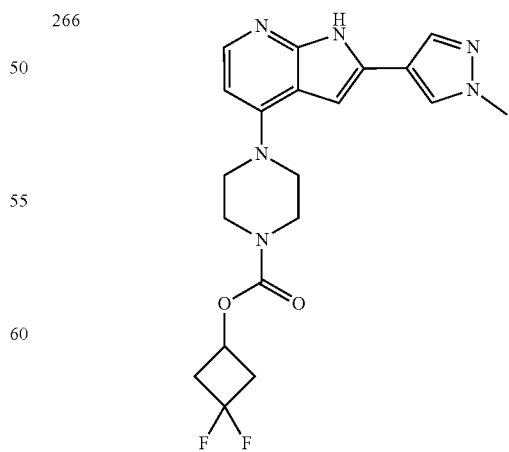 |

| # | Structure |
|---|---|
| 267 | 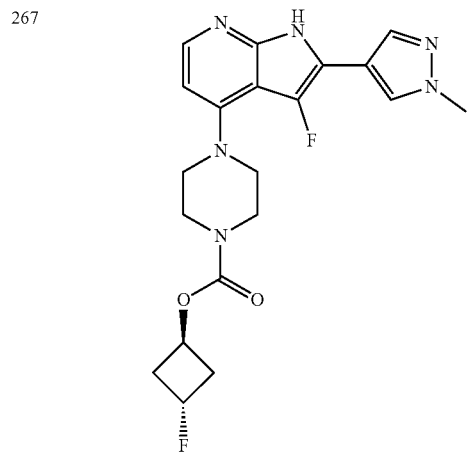 |
| 268 | 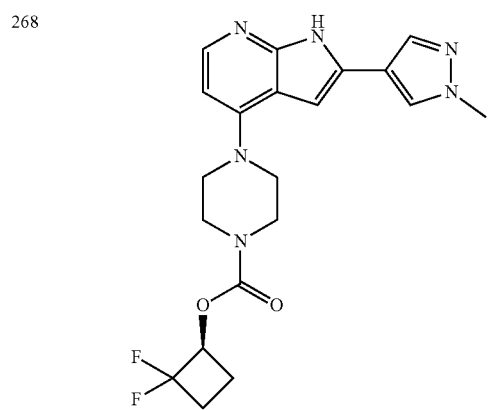 |
| 269 | 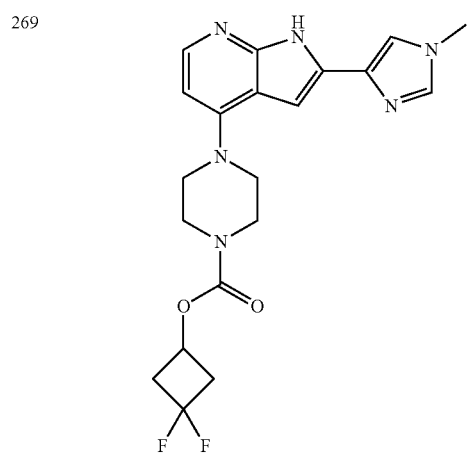 |
| # | Structure |
|---|---|
| 270 | 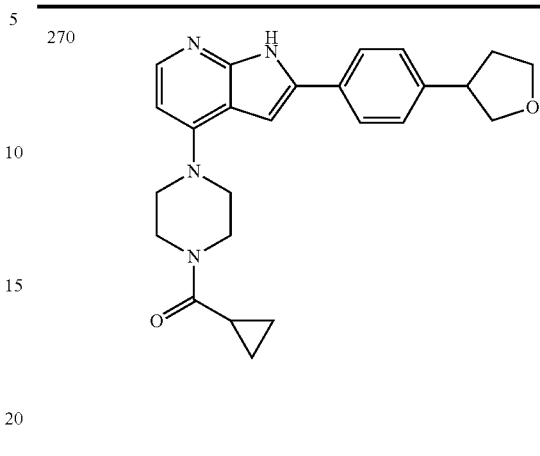 |
| 271 | 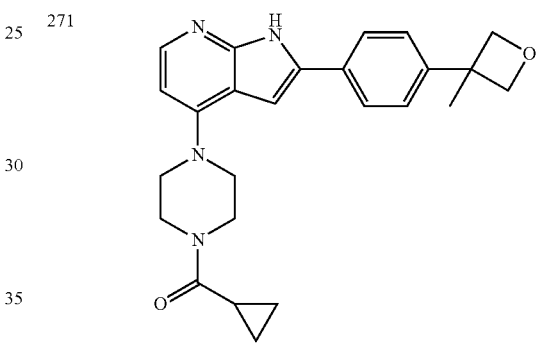 |
| 272 | 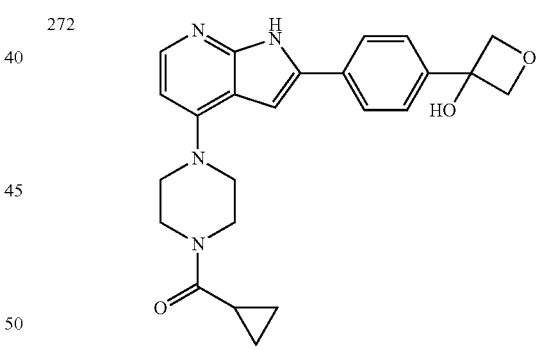 |
| 273 | 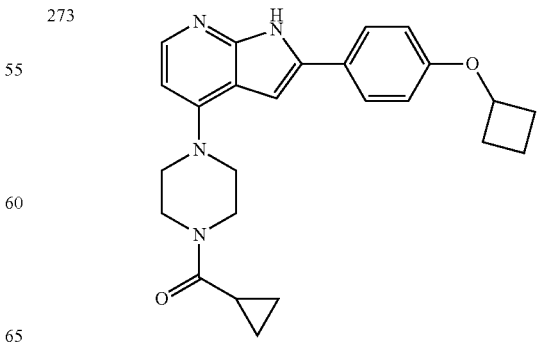 |

427
-continued
| # | Structure |
|---|---|
| 274 | 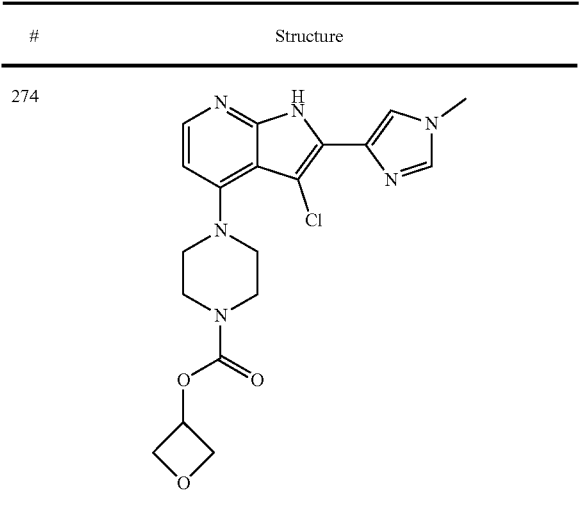 |
| 275 | 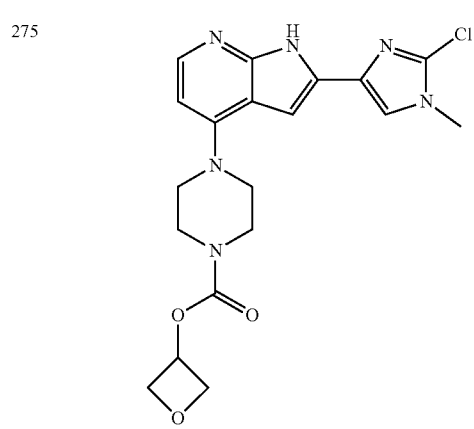 |
| 276 | 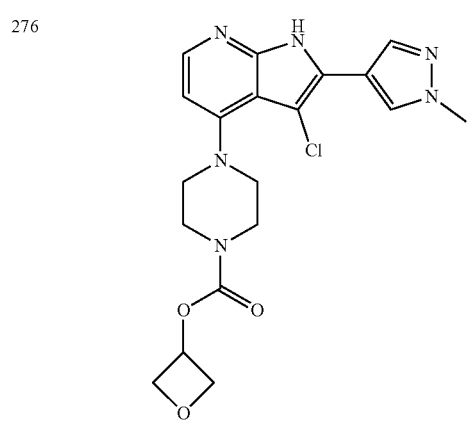 |
428
-continued
| # | Structure |
|---|---|
| 277 | 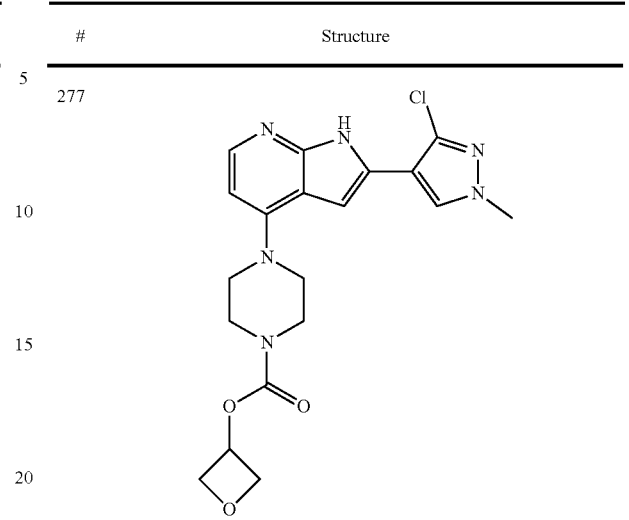 |
| 278 | 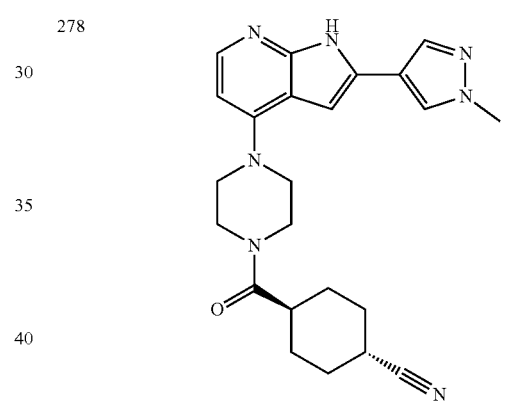 |
| 279 | 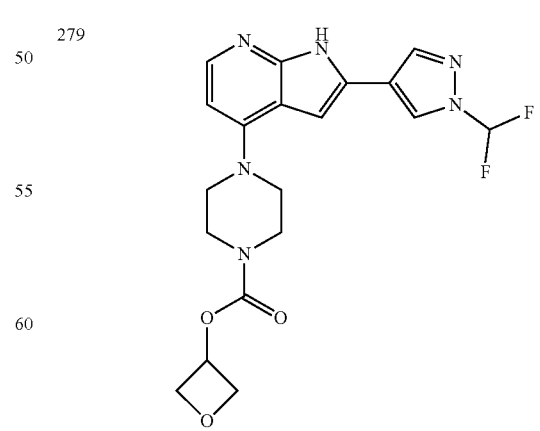 |

| # | Structure |
|---|---|
| 280 | 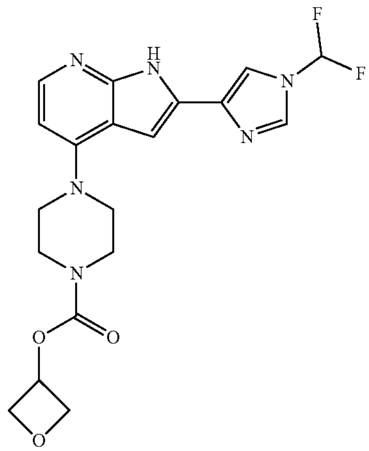 [SMILES: O=C(OC1COC1)N1CCN(c2ccnc3[nH]c(-c4cn(C(F)F)cn4)cc23)CC1] |
| 281 | 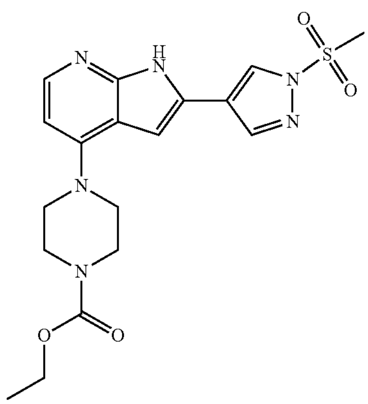 [SMILES: CCOC(=O)N1CCN(c2ccnc3[nH]c(-c4cnn(S(C)(=O)=O)c4)cc23)CC1] |
| 282 | 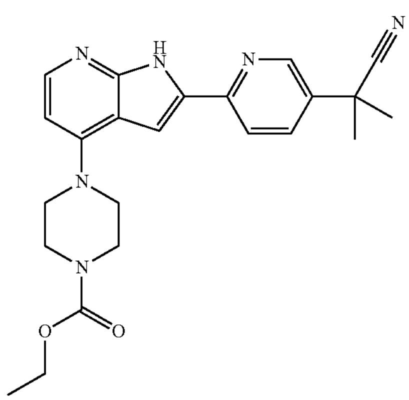 [SMILES: CCOC(=O)N1CCN(c2ccnc3[nH]c(-c4ccc(C(C)(C)C#N)cn4)cc23)CC1] |
| 283 | 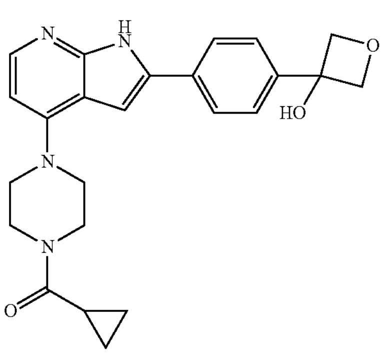 [SMILES: O=C(C1CC1)N1CCN(c2ccnc3[nH]c(-c4ccc(C5(O)COC5)cc4)cc23)CC1] |
| 284 | |
| 285 | |
| 286 | |
| 287 | |

| # | Structure |
|---|---|
| 288 | |
| 289 | |
| 290 | |
| 291 | 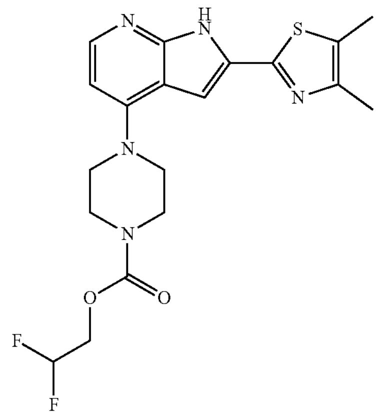 [SMILES: Cc1nc(-c2cc3c(N4CCN(C(=O)OCC(F)F)CC4)ccnc3[nH]2)sc1C] |
| 292 | 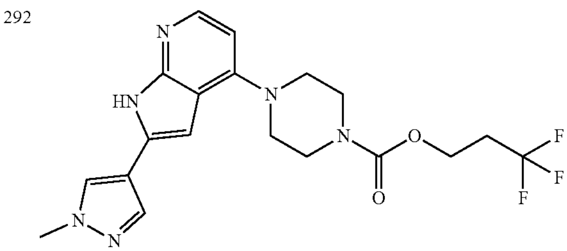 |
| 293 | 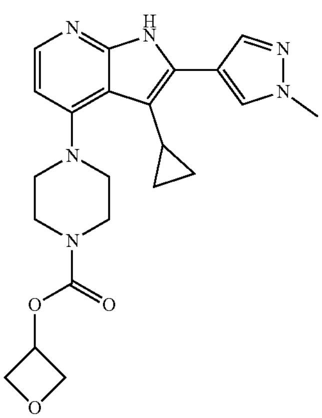 [SMILES: Cn1cc(-c2[nH]c3nccc(N4CCN(C(=O)OC5COC5)CC4)c3c2C2CC2)cn1] |
| 294 | 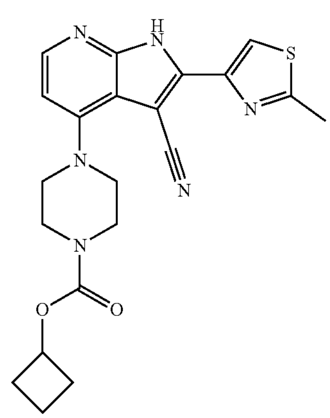 [SMILES: Cc1nc(-c2[nH]c3nccc(N4CCN(C(=O)OC5CCC5)CC4)c3c2C#N)cs1] |

TABLE-continued
| # | Structure |
|---|---|
| 295 | 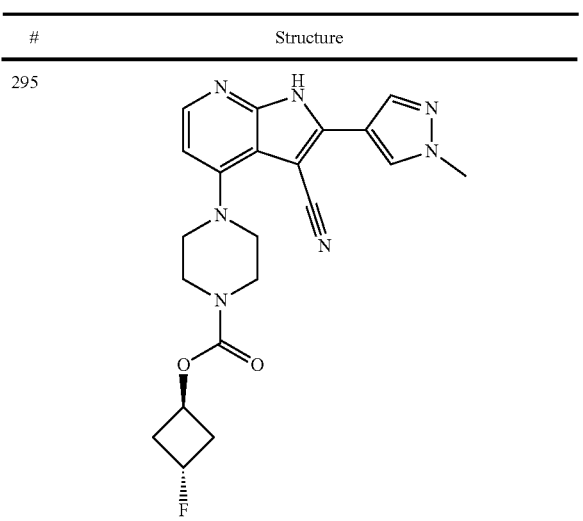 |
| 296 | 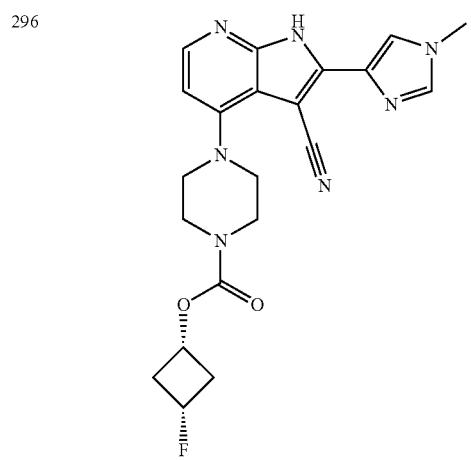 |
| 297 | 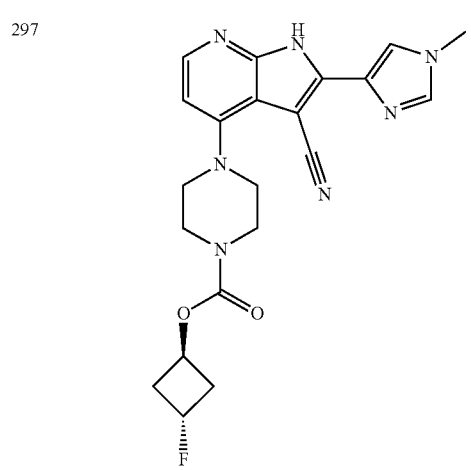 |
| # | Structure |
|---|---|
| 299 | 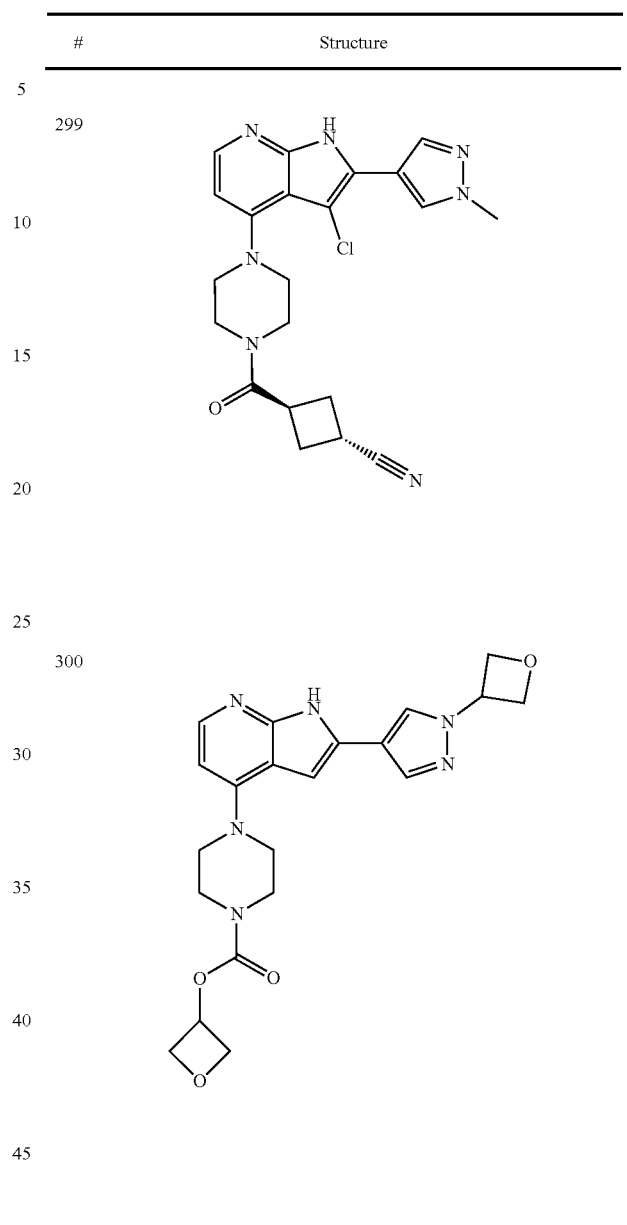 |
| 300 | |
| 301 | 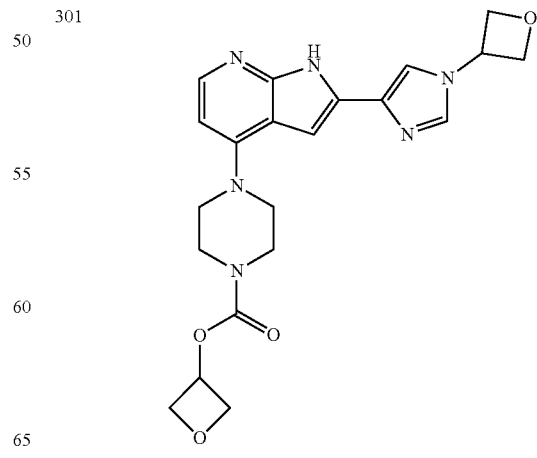 |

| # | Structure |
|---|---|
| 302 | 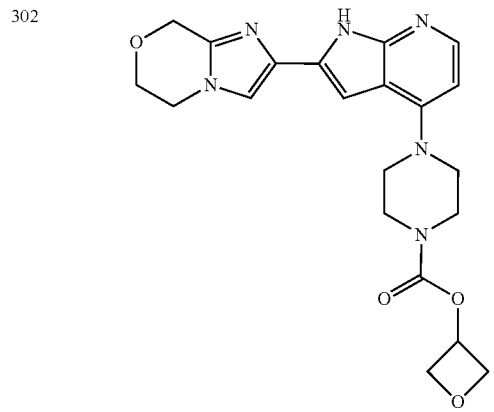 |
| 303 | 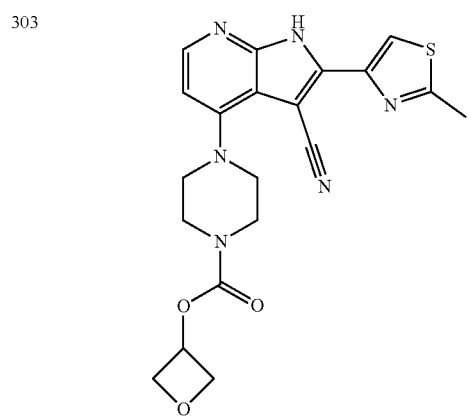 |
| 304 | 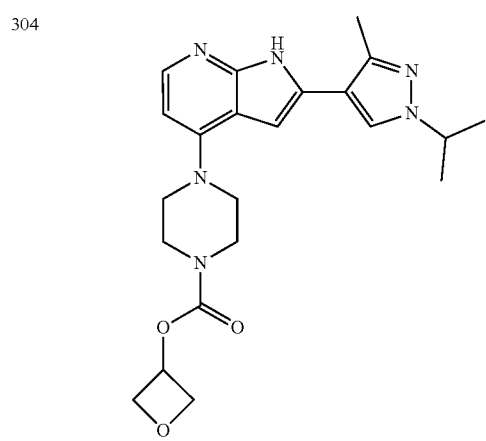 |
| # | Structure |
|---|---|
| 305 | 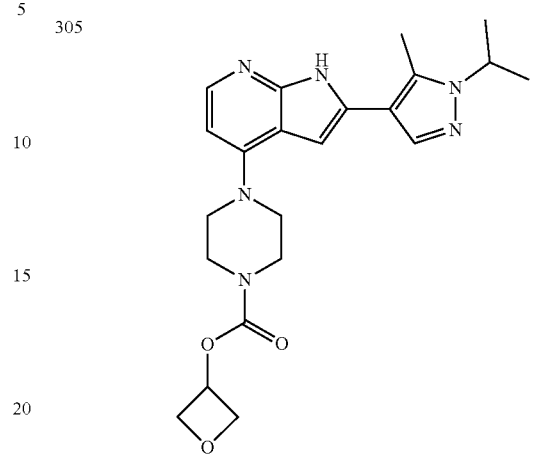 |
| 306 | 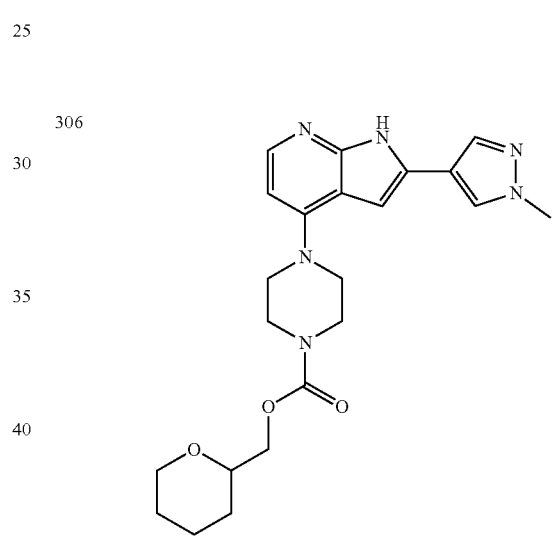 |
| 307 | 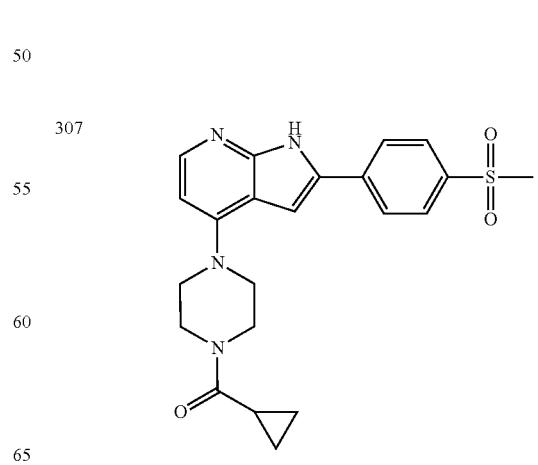 |

| # | Structure |
|---|---|
| 308 | 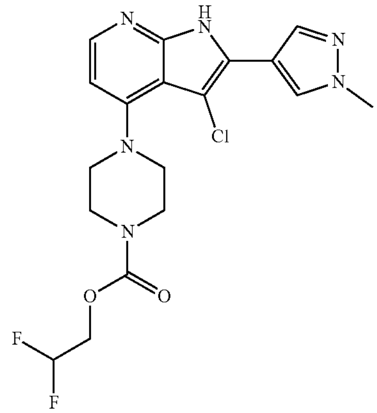 [SMILES: Cn1cc(-c2[nH]c3nccc(N4CCN(C(=O)OCC(F)F)CC4)c3c2Cl)cn1] |
| 309 | 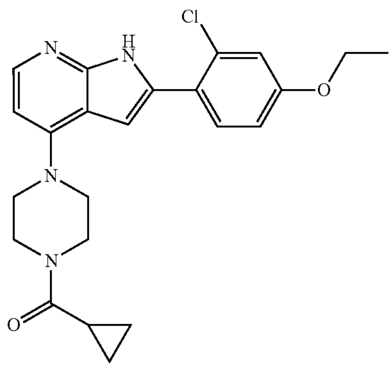 [SMILES: CCOc1ccc(-c2cc3c(N4CCN(C(=O)C5CC5)CC4)ccnc3[nH]2)c(Cl)c1] |
| 310 | 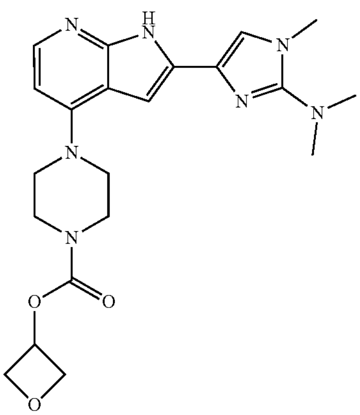 [SMILES: CN(C)c1nc(-c2cc3c(N4CCN(C(=O)OC5COC5)CC4)ccnc3[nH]2)cn1C] |
| 311 | 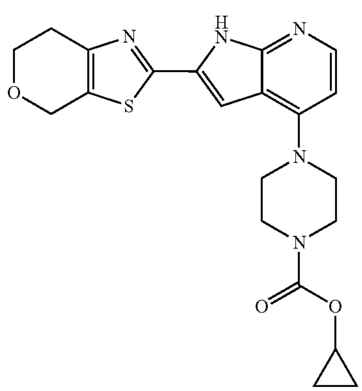 [SMILES: O=C(OC1CC1)N1CCN(c2ccnc3[nH]c(-c4nc5c(s4)COCC5)cc23)CC1] |
| 312 | |
| 313 | |
| 314 | |
| 315 | |

| # | Structure |
|---|---|
| 316 | 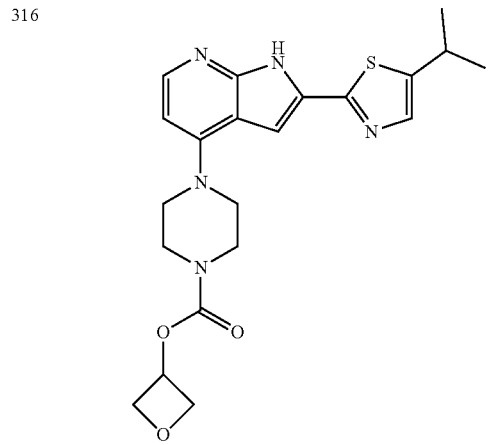 |
| 317 | 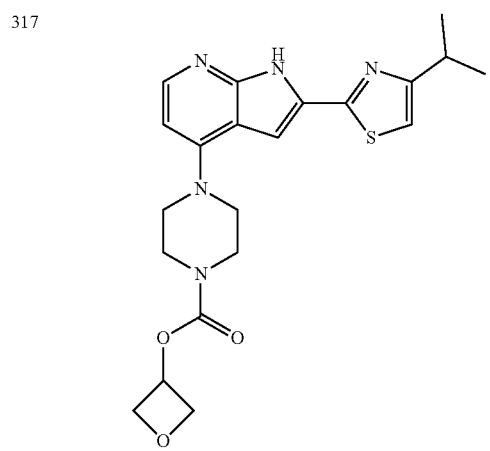 |
| 318 | 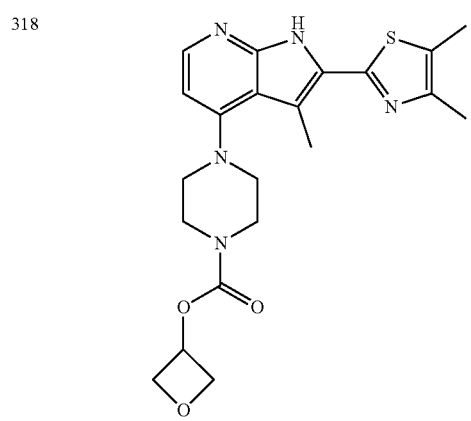 |
| # | Structure |
|---|---|
| 319 | 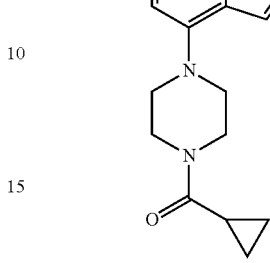 |
| 320 | 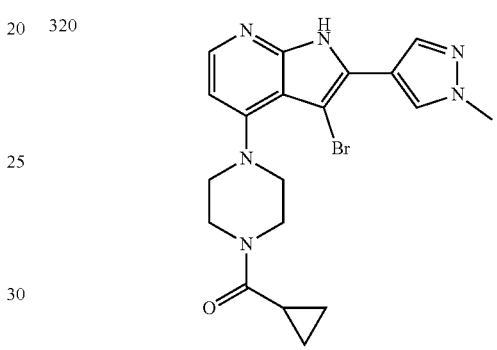 |
| 321 | 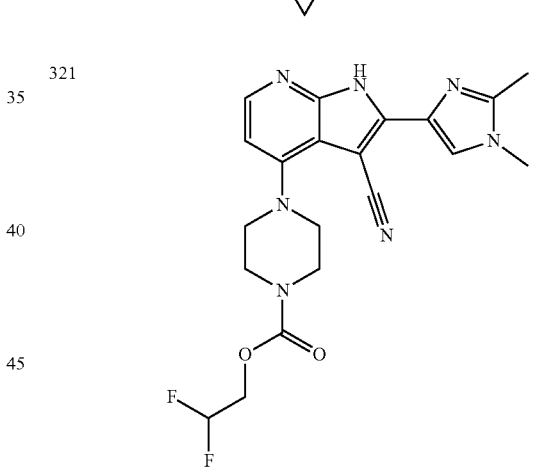 |
| 322 | 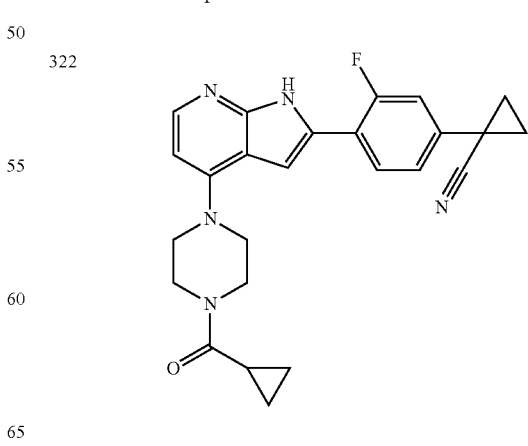 |

| # | Structure |
|---|---|
| 323 | 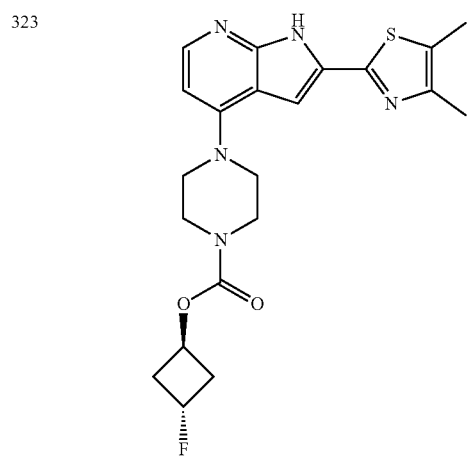 |
| 324 | 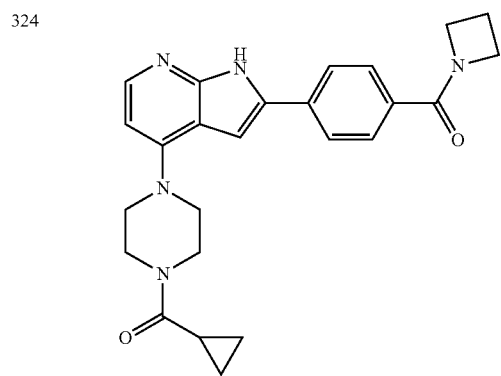 |
| 325 | 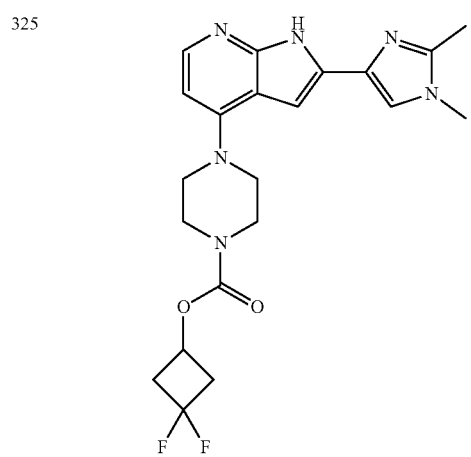 |
| # | Structure |
|---|---|
| 326 | 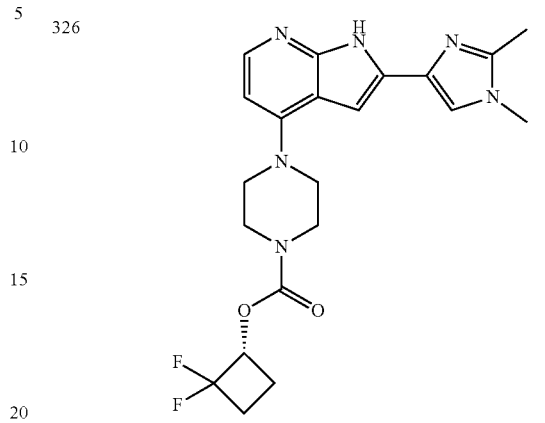 |
| 327 | 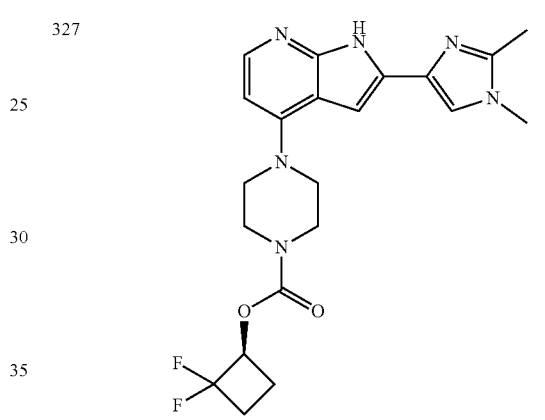 |
| 328 | 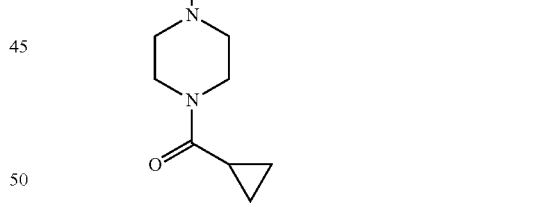 |
| 329 | 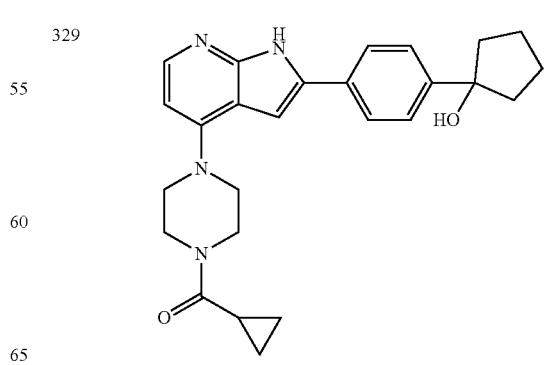 |

| # | Structure |
|---|---|
| 330 | 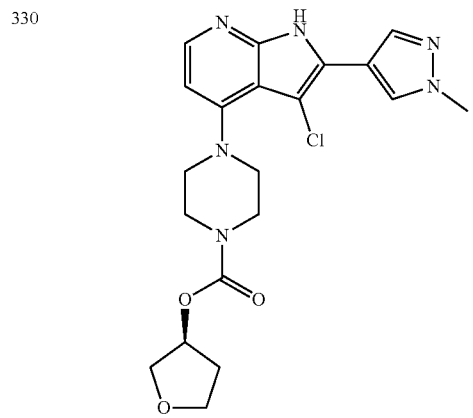 |
| 331 | 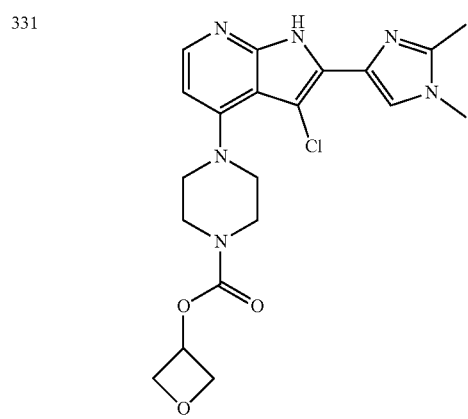 |
| 332 | 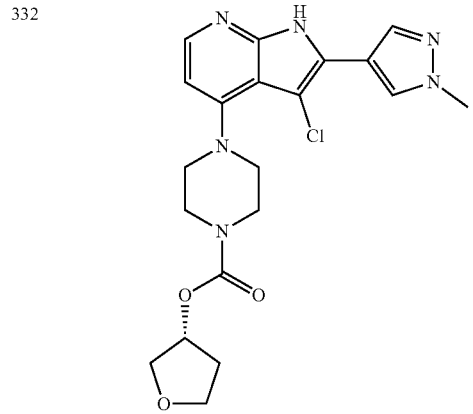 |
| # | Structure |
|---|---|
| 333 | 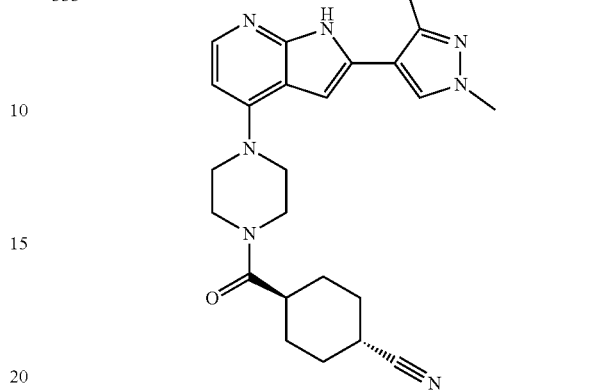 |
| 334 | 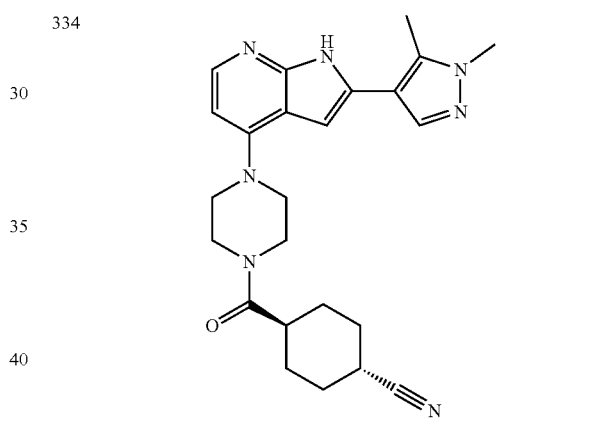 |
| 335 | 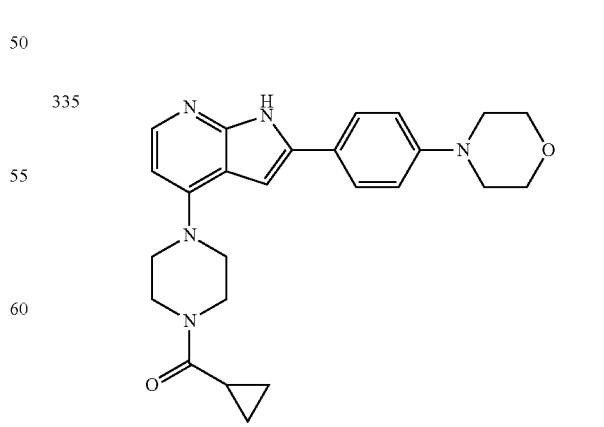 |

| # | Structure |
|---|---|
| 336 | 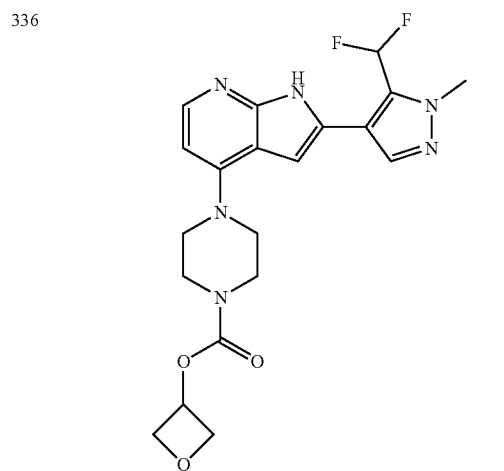 |
| 337 | 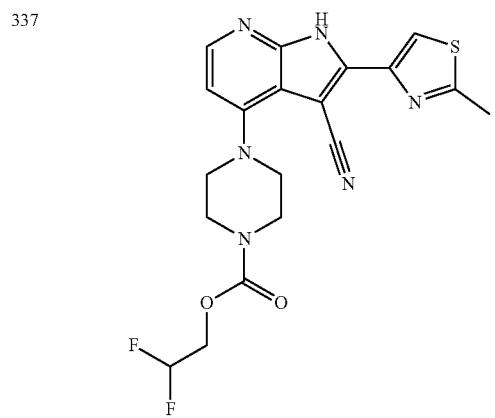 |
| 338 | 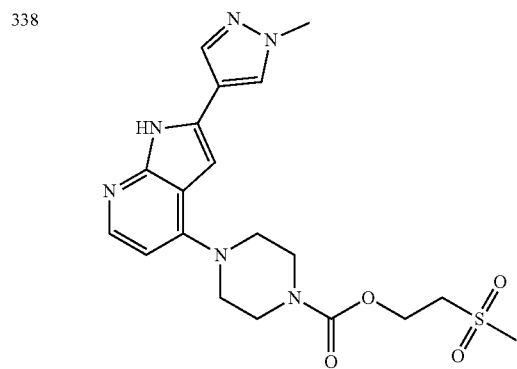 |
| # | Structure |
|---|---|
| 339 | 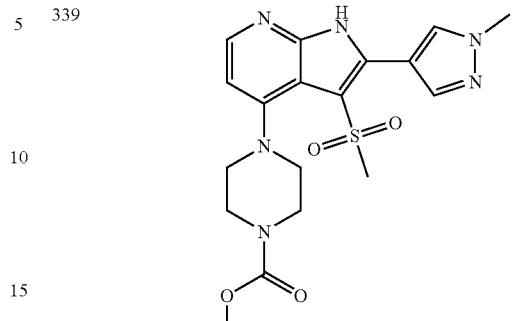 |
| 340 | 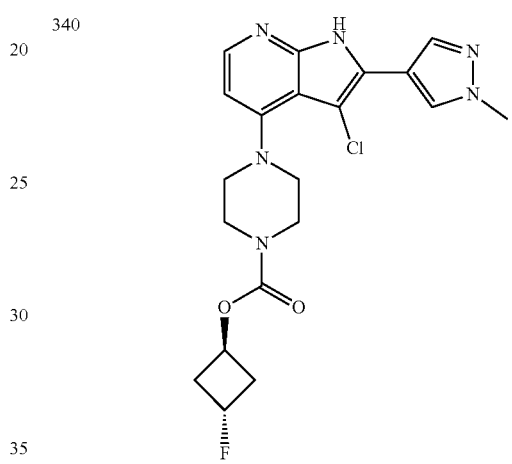 |
| 341 | 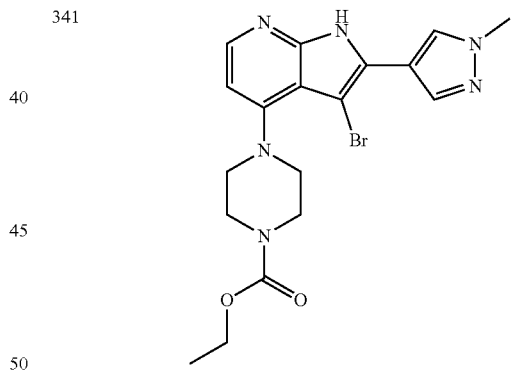 |
| 342 | 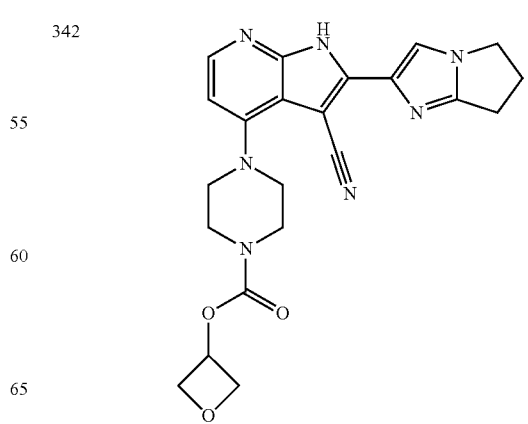 |

| # | Structure |
|---|---|
| 343 | 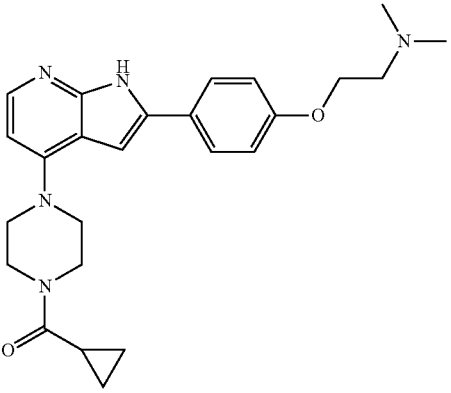 [SMILES: CN(C)CCOc1ccc(-c2cc3c(N4CCN(C(=O)C5CC5)CC4)ccnc3[nH]2)cc1] |
| 344 | 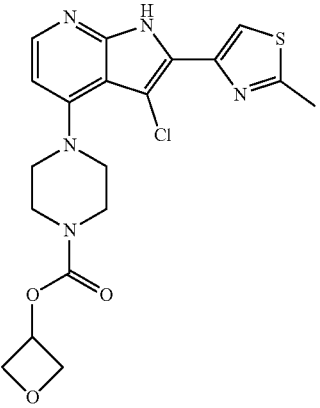 [SMILES: Cc1nc(-c2[nH]c3nccc(N4CCN(C(=O)OC5COC5)CC4)c3c2Cl)cs1] |
| 345 | 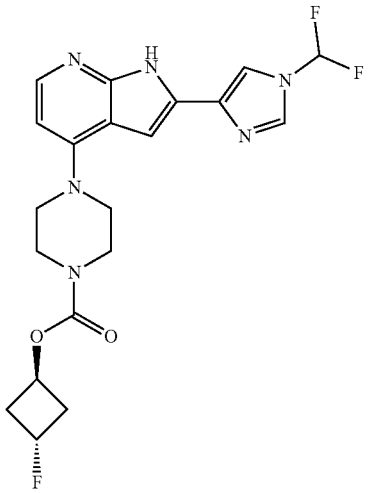 [SMILES: O=C(O[C@H]1C[C@H](F)C1)N1CCN(c2ccnc3[nH]c(-c4cn(C(F)F)cn4)cc23)CC1] |
| # | Structure |
|---|---|
| 346 | 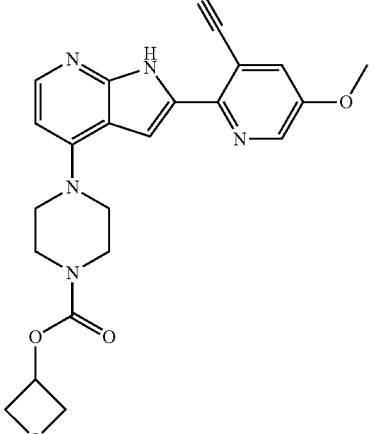 |
| 347 | 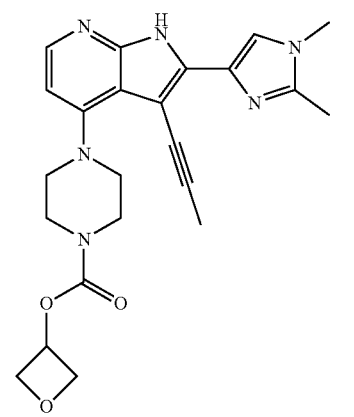 [SMILES: CC#Cc1c(-c2cn(C)c(C)n2)[nH]c2nccc(N3CCN(C(=O)OC4COC4)CC3)c12] |
| 348 | 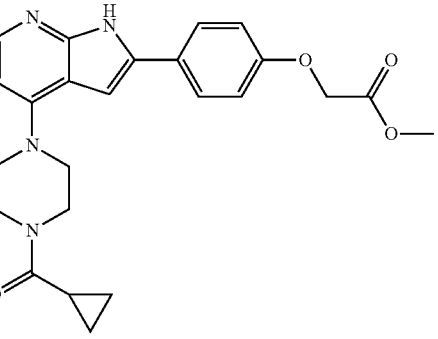 |
| 349 | 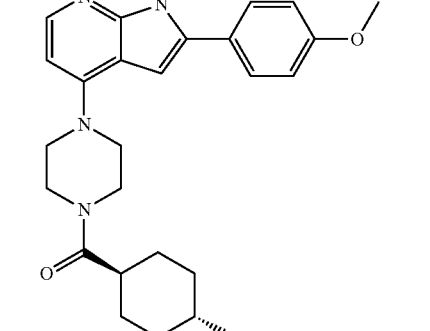 |

| # | Structure |
|---|---|
| 350 | 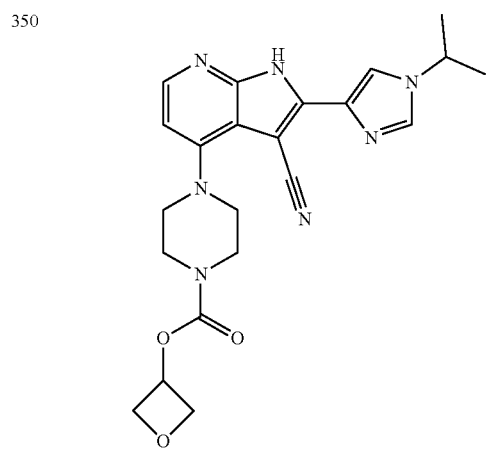 |
| 351 | 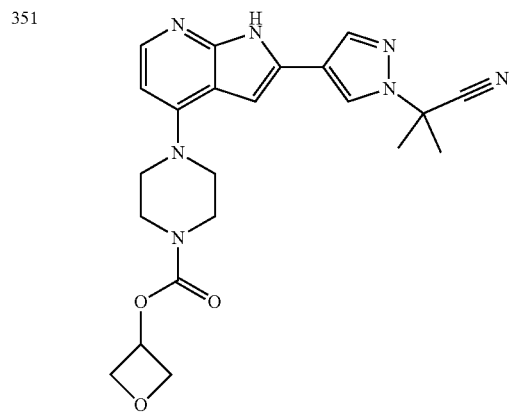 |
| 352 | 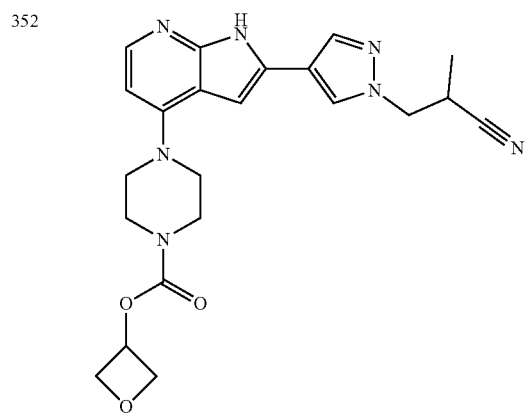 |
| # | Structure |
|---|---|
| 353 | 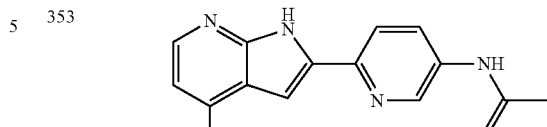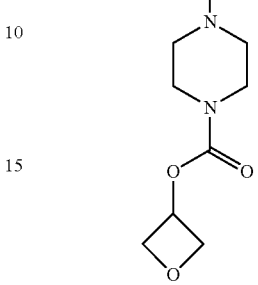 |
| 354 | 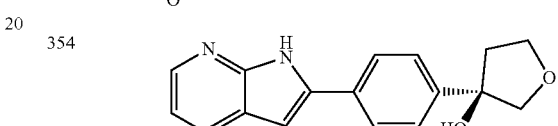 |
| 355 | 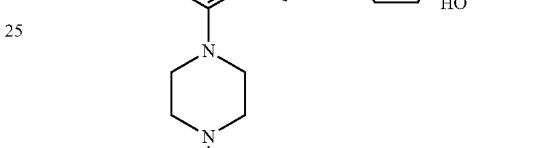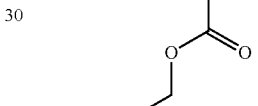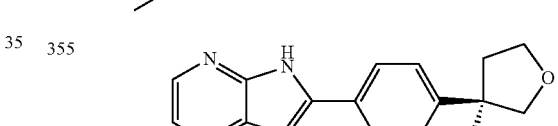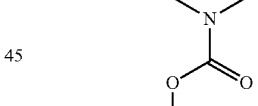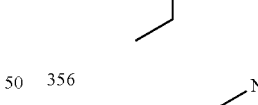 |
| 356 | 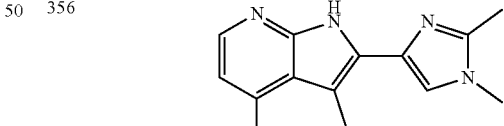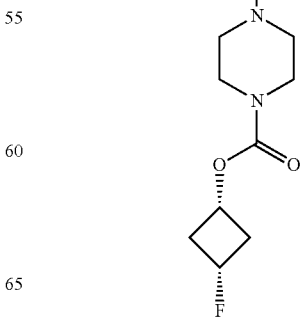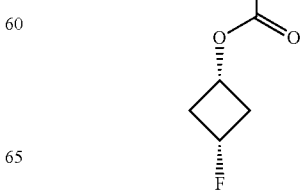 |

-continued

| # | Structure |
|---|---|
| 357 | 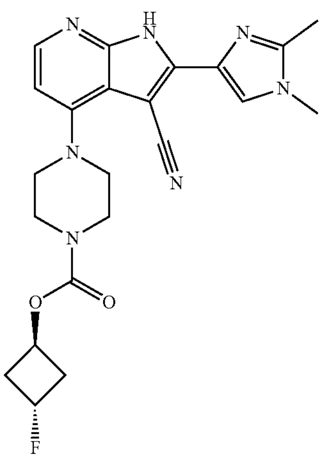 [SMILES: Cc1nc(-c2[nH]c3nccc(N4CCN(C(=O)O[C@H]5C[C@H](F)C5)CC4)c3c2C#N)cn1C] |
| 358 | 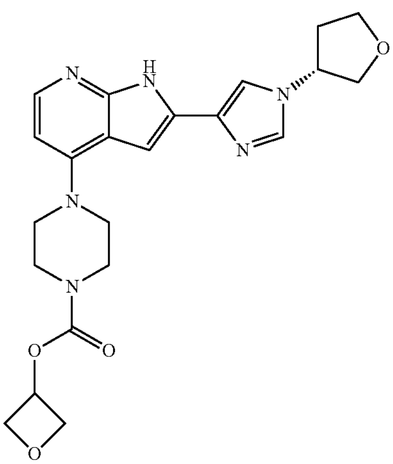 [SMILES: O=C(OC1COC1)N1CCN(c2ccnc3[nH]c(-c4cn([C@@H]5CCOC5)cn4)cc23)CC1] |
| 359 | 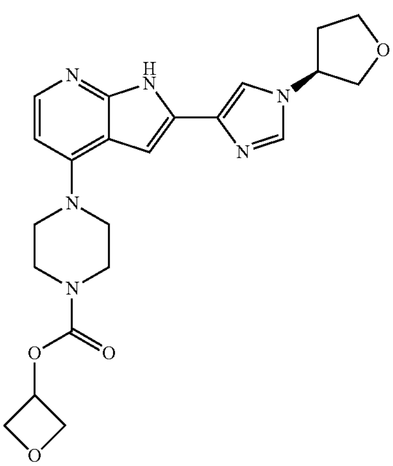 [SMILES: O=C(OC1COC1)N1CCN(c2ccnc3[nH]c(-c4cn([C@H]5CCOC5)cn4)cc23)CC1] |

-continued

| # | Structure |
|---|---|
| 360 | 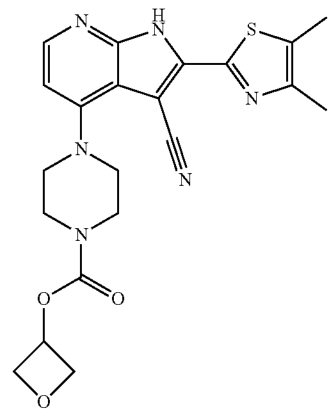 [SMILES: Cc1nc(-c2[nH]c3nccc(N4CCN(C(=O)OC5COC5)CC4)c3c2C#N)sc1C] |
| 361 | 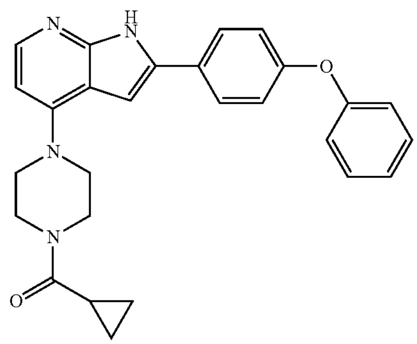 [SMILES: O=C(C1CC1)N1CCN(c2ccnc3[nH]c(-c4ccc(Oc5ccccc5)cc4)cc23)CC1] |
| 362 | 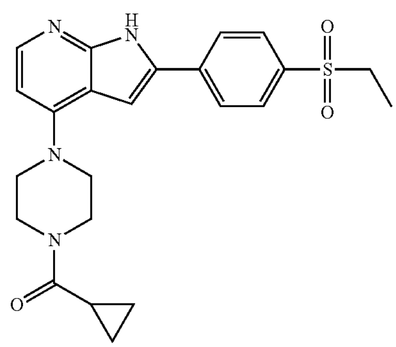 [SMILES: CCS(=O)(=O)c1ccc(-c2cc3c(N4CCN(C(=O)C5CC5)CC4)ccnc3[nH]2)cc1] |
| 363 | 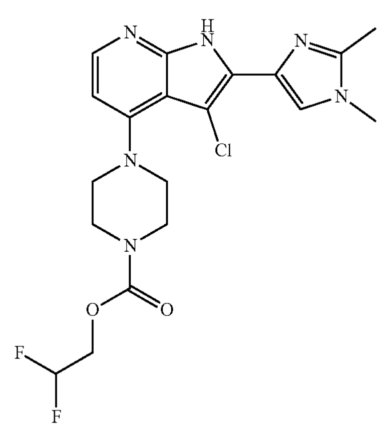 [SMILES: Cc1nc(-c2[nH]c3nccc(N4CCN(C(=O)OCC(F)F)CC4)c3c2Cl)cn1C] |

| # | Structure |
|---|---|
| 364 | 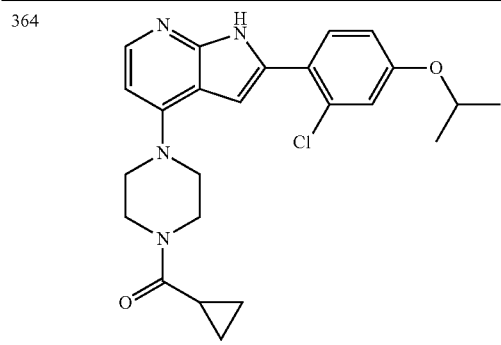 |
| 365 | 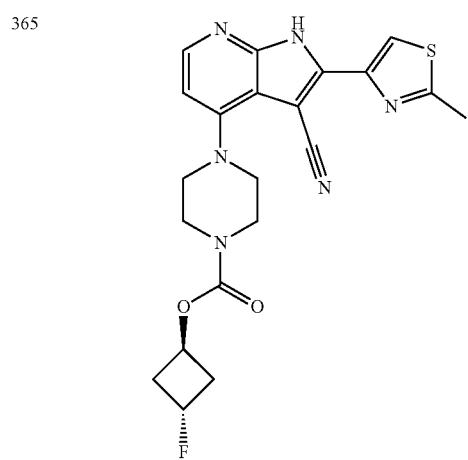 |
| 366 | 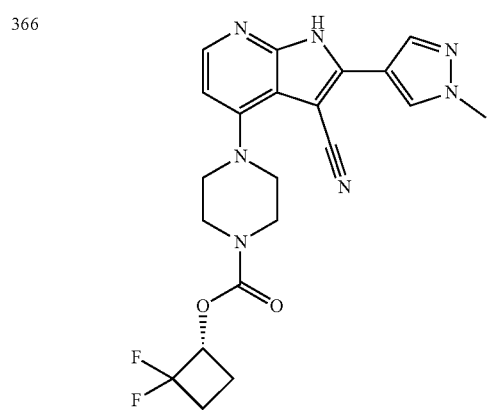 |
| 367 | 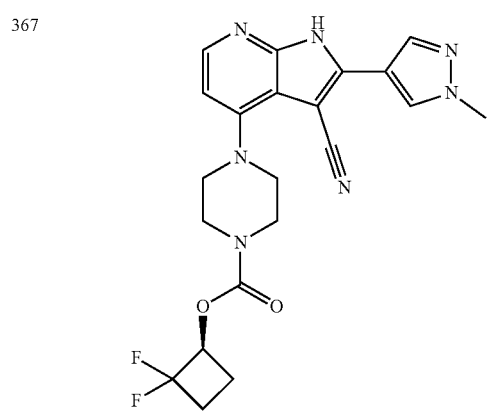 |
| # | Structure |
|---|---|
| 368 | 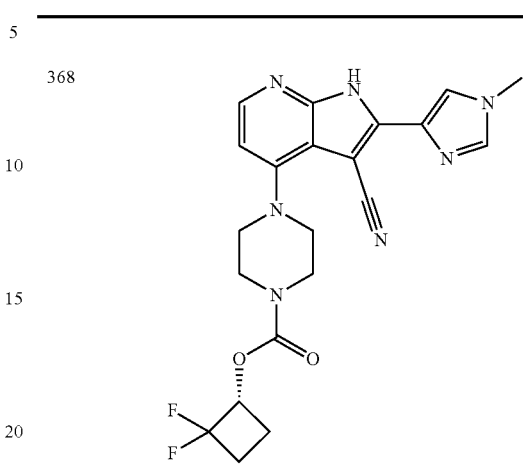 |
| 369 | 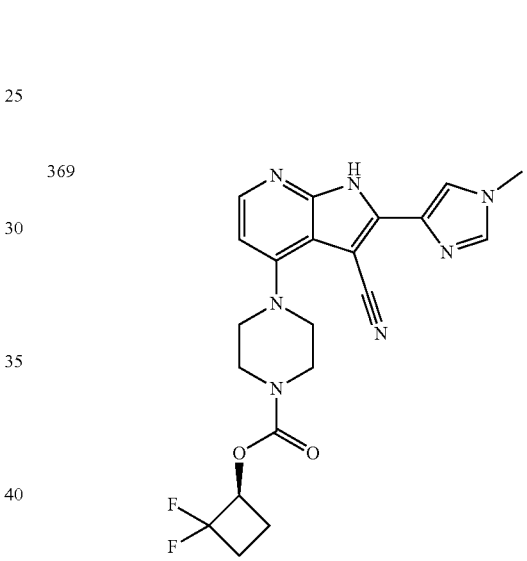 |
| 370 | 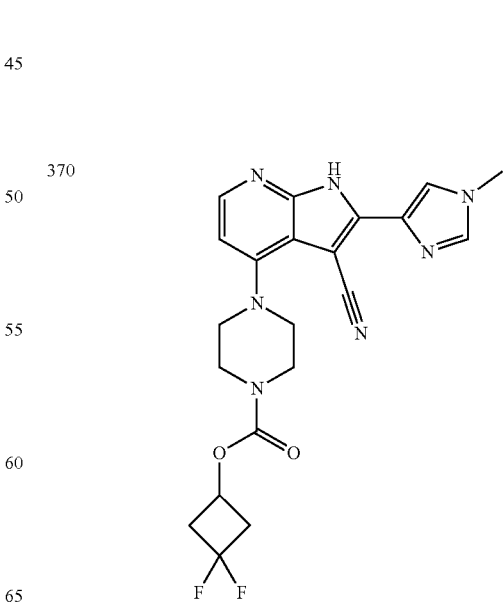 |

| # | Structure |
|---|---|
| 371 | 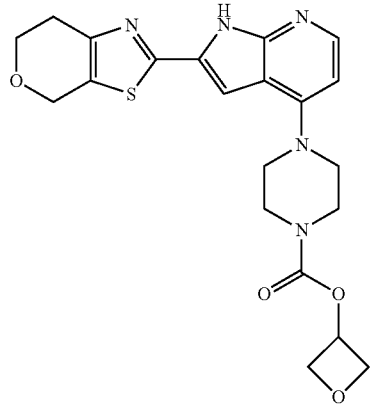 [SMILES: O=C(OC1COC1)N1CCN(c2ccnc3[nH]c(-c4nc5c(s4)COCC5)cc23)CC1] |
| 372 | 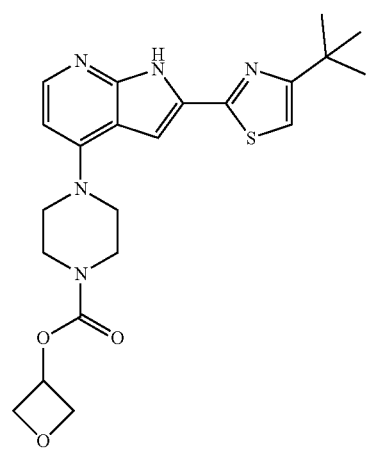 |
| 373 | 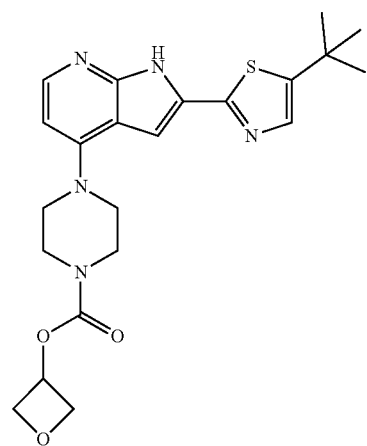 [SMILES: CC(C)(C)c1cnc(-c2cc3c(N4CCN(C(=O)OC5COC5)CC4)ccnc3[nH]2)s1] |
| # | Structure |
|---|---|
| 374 | 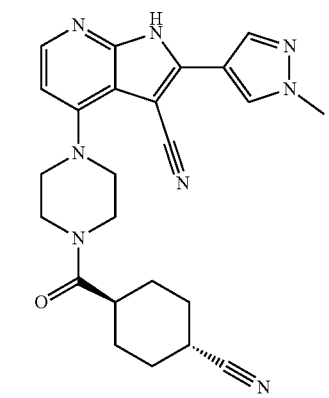 [SMILES: Cn1cc(-c2[nH]c3nccc(N4CCN(C(=O)[C@H]5CC[C@H](C#N)CC5)CC4)c3c2C#N)cn1] |
| 375 | 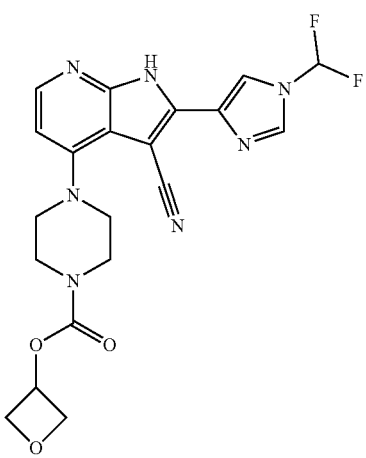 [SMILES: N#Cc1c(-c2cn(C(F)F)cn2)[nH]c2nccc(N3CCN(C(=O)OC4COC4)CC3)c12] |
| 376 | 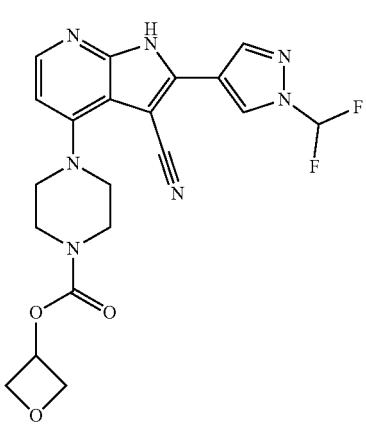 [SMILES: N#Cc1c(-c2cnn(C(F)F)c2)[nH]c2nccc(N3CCN(C(=O)OC4COC4)CC3)c12] |

| # | Structure |
|---|---|
| 377 | 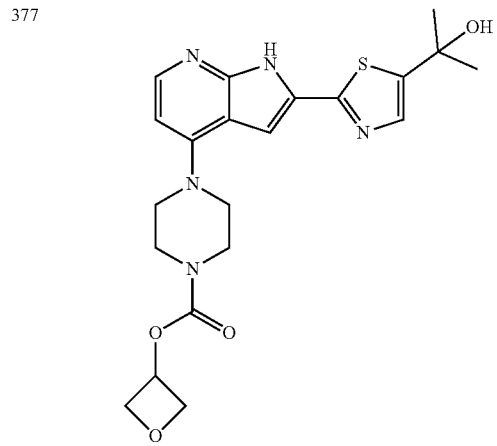 |
| 378 | 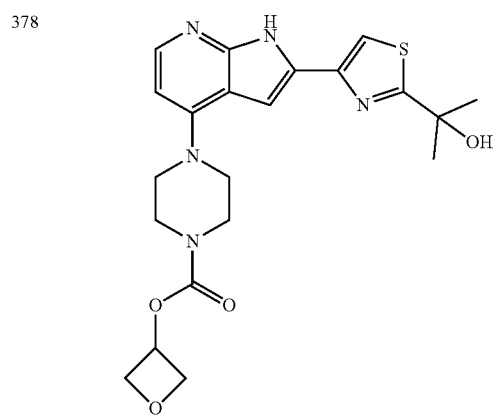 |
| 379 | 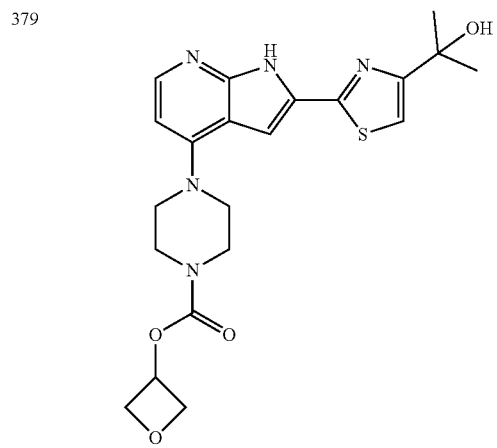 |
| # | Structure |
|---|---|
| 380 | 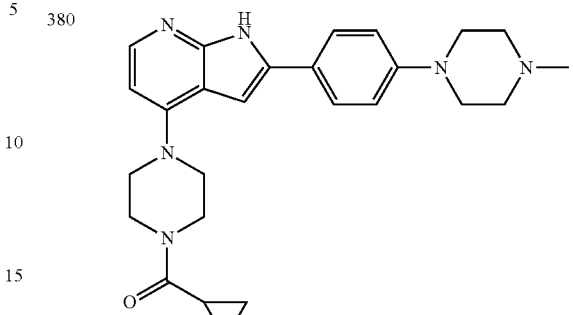 |
| 381 | 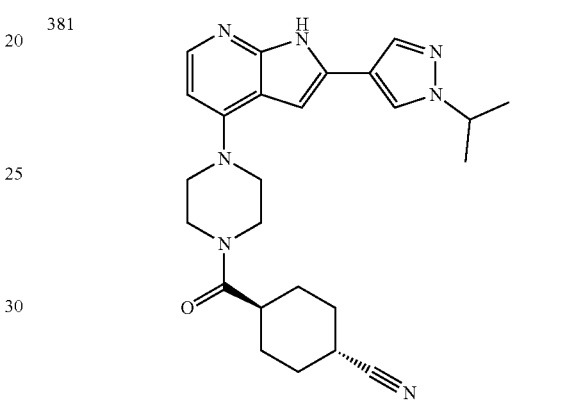 |
| 382 | 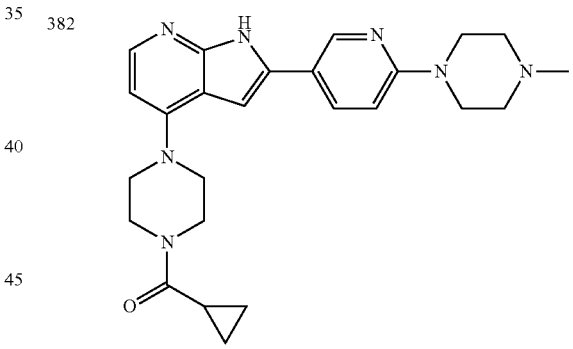 |
| 383 | 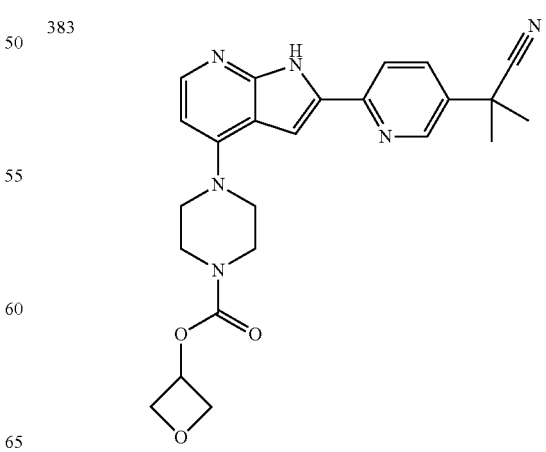 |

| # | Structure |
|---|---|
| 384 | 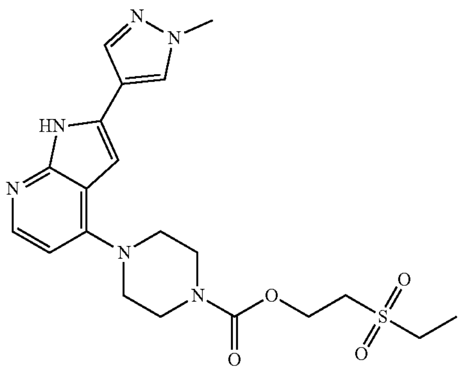 [SMILES: CCS(=O)(=O)CCOC(=O)N1CCN(c2ccnc3[nH]c(-c4cnn(C)c4)cc23)CC1] |
| 385 | 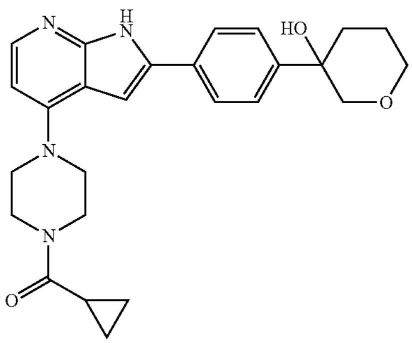 [SMILES: O=C(C1CC1)N1CCN(c2ccnc3[nH]c(-c4ccc(C5(O)CCCOC5)cc4)cc23)CC1] |
| 386 | 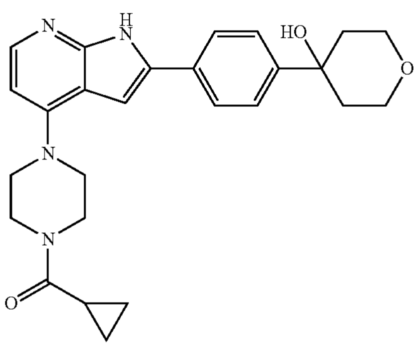 [SMILES: O=C(C1CC1)N1CCN(c2ccnc3[nH]c(-c4ccc(C5(O)CCOCC5)cc4)cc23)CC1] |
| 387 | 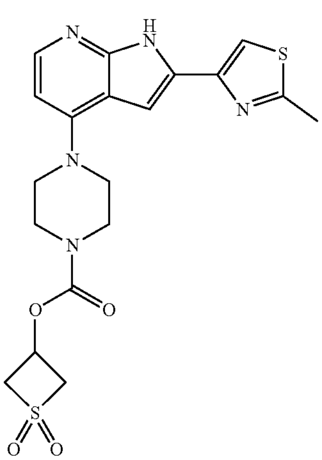 [SMILES: Cc1nc(-c2cc3c(N4CCN(C(=O)OC5CS(=O)(=O)C5)CC4)ccnc3[nH]2)cs1] |
| 388 | |
| 389 | |
| 390 | |
| 391 | |

| # | Structure |
|---|---|
| 392 | 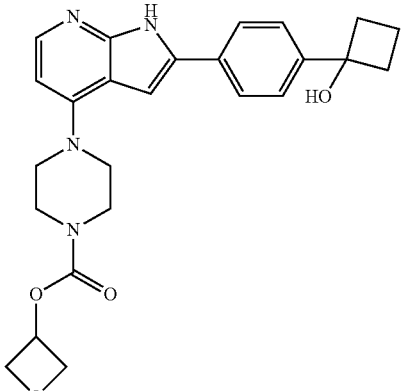 |
| 393 | 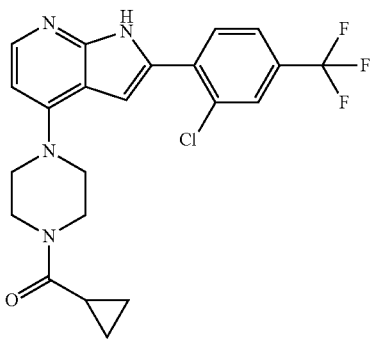 |
| 394 | 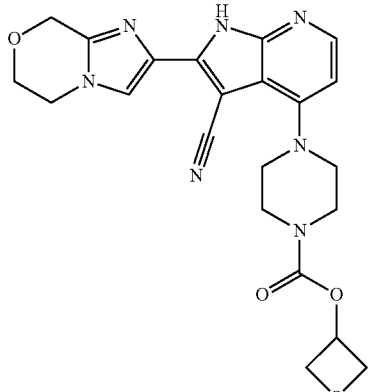 |
| 395 | 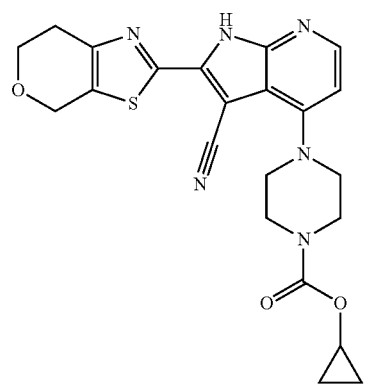 [SMILES: N#Cc1c(-c2nc3c(s2)COCC3)[nH]c2nccc(N3CCN(C(=O)OC4CC4)CC3)c12] |
| 396 | 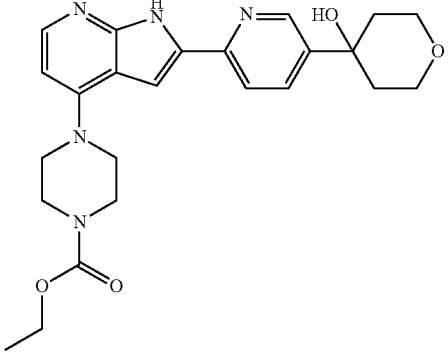 |
| 397 | 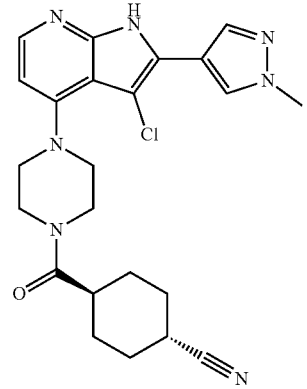 [SMILES: Cn1cc(-c2[nH]c3nccc(N4CCN(C(=O)[C@H]5CC[C@H](C#N)CC5)CC4)c3c2Cl)cn1] |
| 398 | 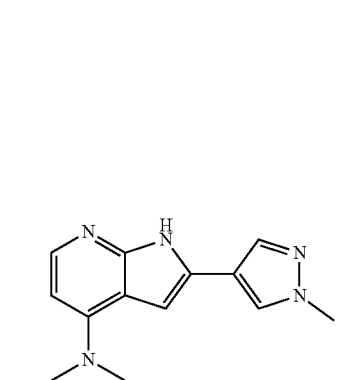 |

463
-continued

| # | Structure |
|---|---|
| 399 | |
| 400 | |
| 401 | |

464
-continued

| # | Structure |
|---|---|
| 402 | 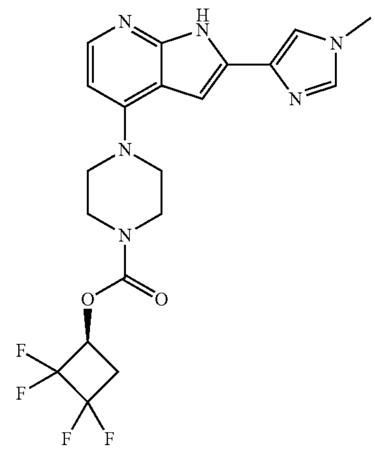 [SMILES: Cn1cnc(-c2cc3c(N4CCN(C(=O)O[C@H]5CC(F)(F)C5(F)F)CC4)ccnc3[nH]2)c1] |
| 403 | 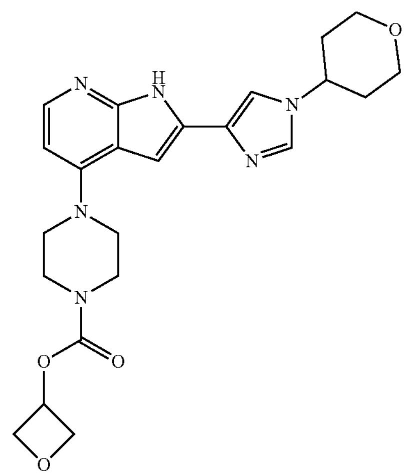 [SMILES: O=C(OC1COC1)N1CCN(c2ccnc3[nH]c(-c4cn(C5CCOCC5)cn4)cc23)CC1] |
| 404 | 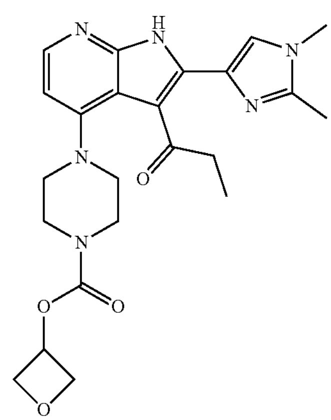 [SMILES: CCC(=O)c1c(-c2cn(C)c(C)n2)[nH]c2nccc(N3CCN(C(=O)OC4COC4)CC3)c12] |
| 405 | 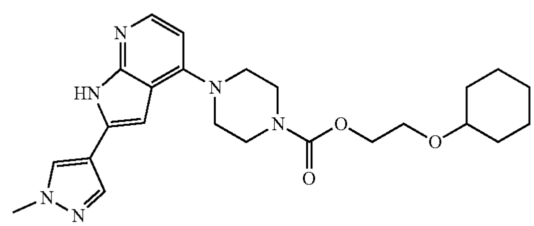 [SMILES: Cn1cc(-c2cc3c(N4CCN(C(=O)OCCOC5CCCCC5)CC4)ccnc3[nH]2)cn1] |

| # | Structure |
|---|---|
| 406 | 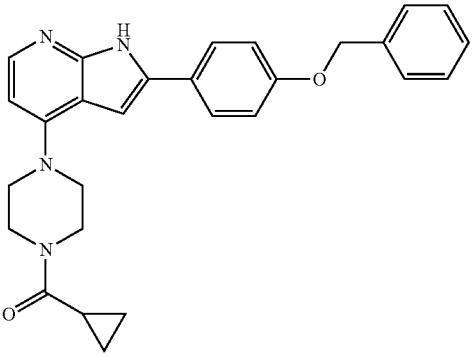 [SMILES: O=C(C1CC1)N1CCN(c2ccnc3[nH]c(-c4ccc(OCc5ccccc5)cc4)cc23)CC1] |
| 407 | 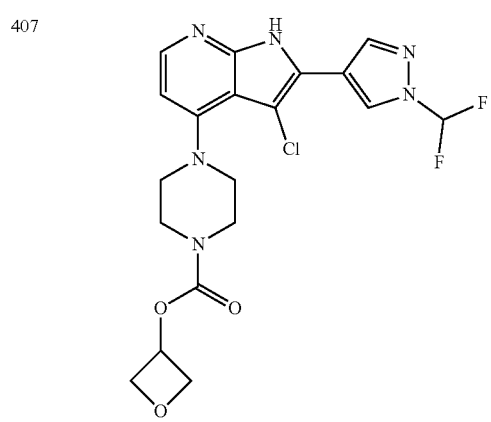 |
| 408 | 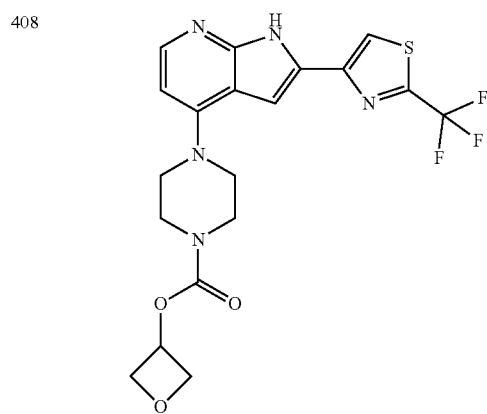 |
| # | Structure |
|---|---|
| 409 | 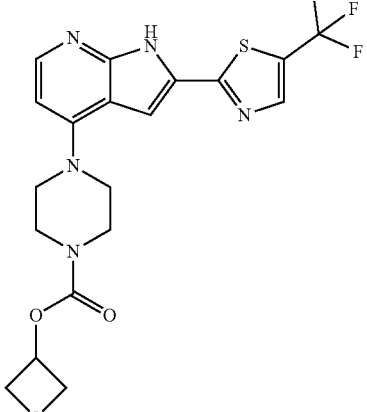 |
| 410 | 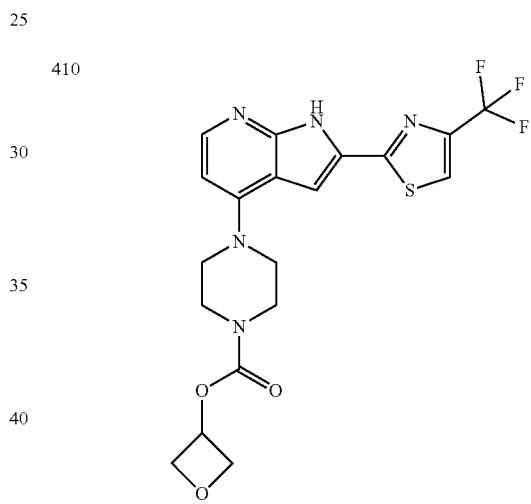 |
| 412 | 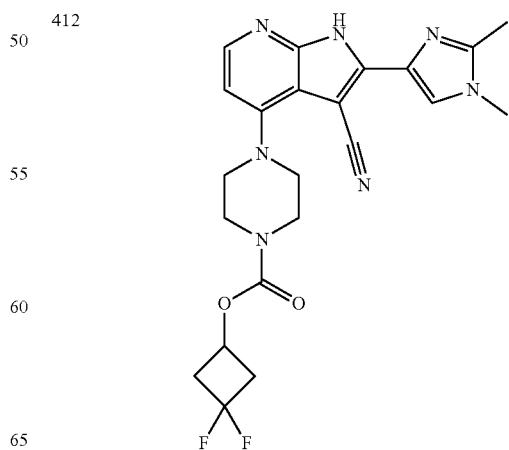 |

467
-continued
| # | Structure |
|---|---|
| 413 | 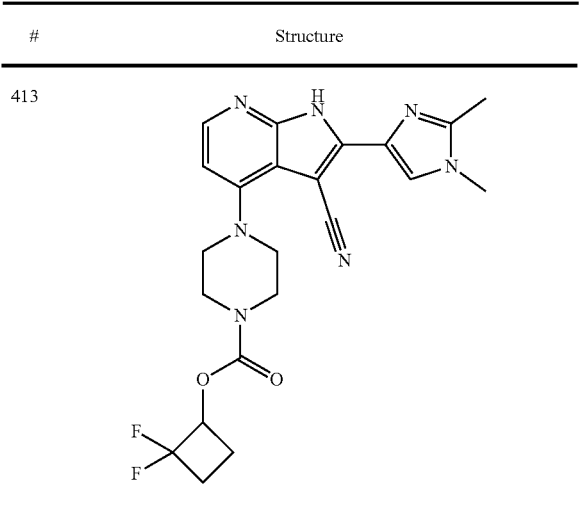 |
| 414 | 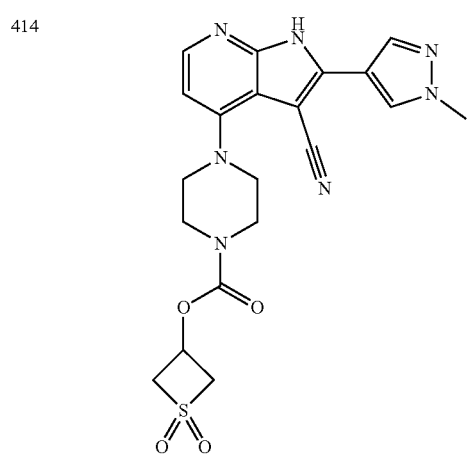 |
| 415 | 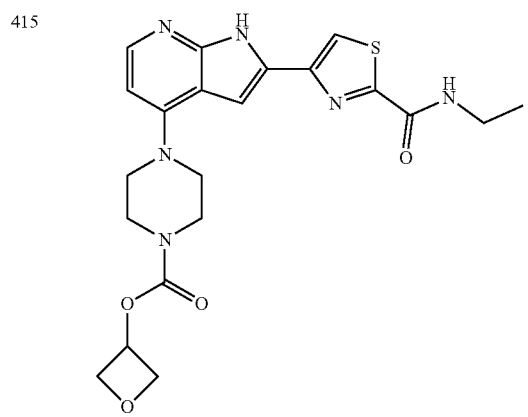 |
468
-continued
| # | Structure |
|---|---|
| 416 | 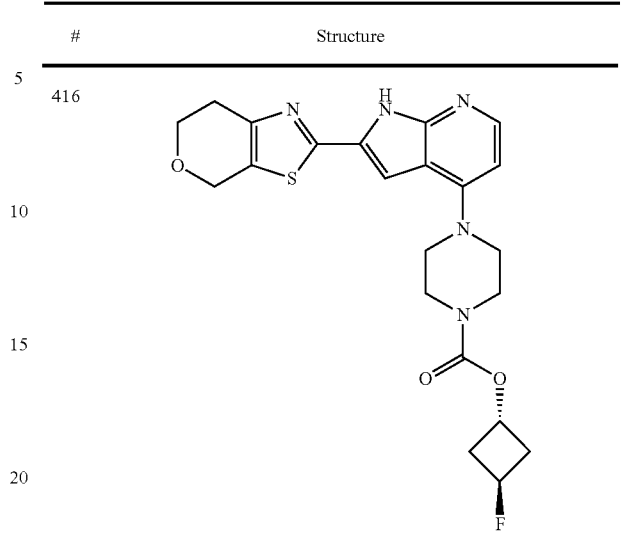 |
| 417 | 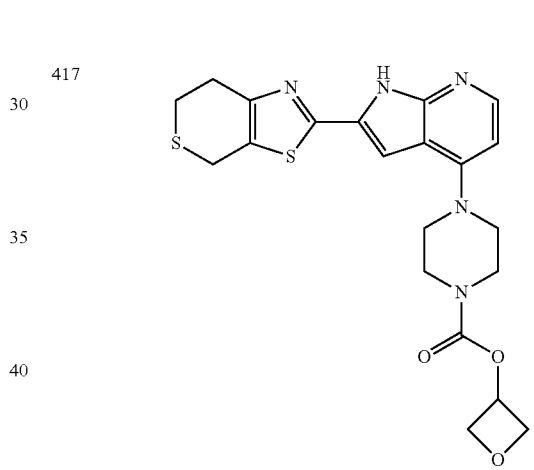 |
| 418 | 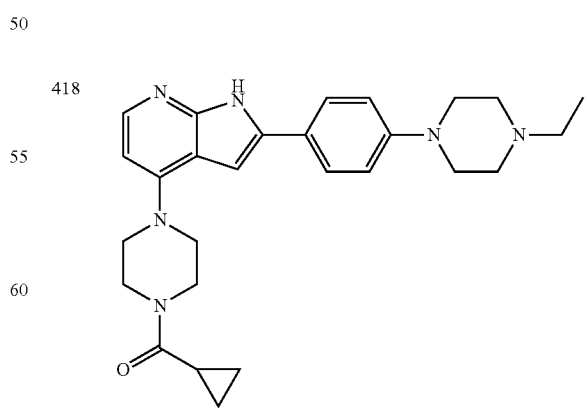 |

| # | Structure |
|---|---|
| 420 | 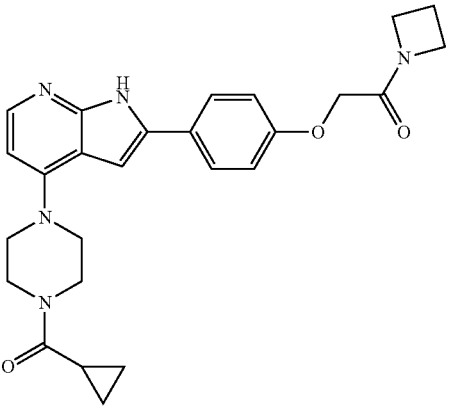 [SMILES: O=C(COc1ccc(-c2cc3c(N4CCN(C(=O)C5CC5)CC4)ccnc3[nH]2)cc1)N1CCC1] |
| 421 | 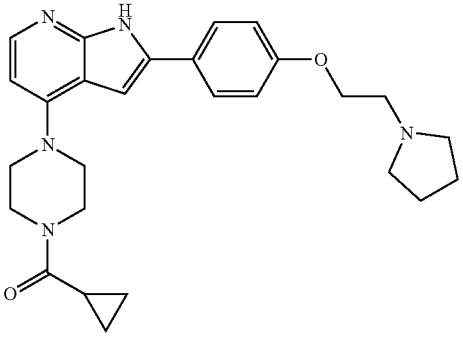 [SMILES: O=C(C1CC1)N1CCN(c2ccnc3[nH]c(-c4ccc(OCCN5CCCC5)cc4)cc23)CC1] |
| 422 | 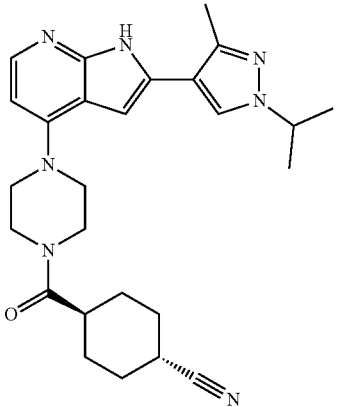 [SMILES: Cc1nn(C(C)C)cc1-c1cc2c(N3CCN(C(=O)[C@H]4CC[C@H](C#N)CC4)CC3)ccnc2[nH]1] |
| 423 | 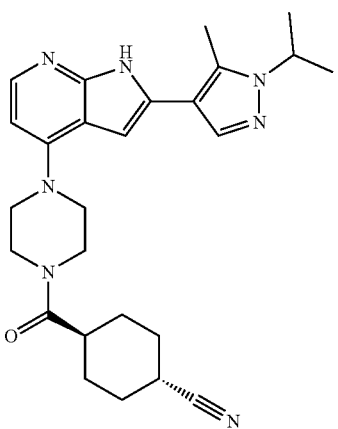 [SMILES: Cc1c(-c2cc3c(N4CCN(C(=O)[C@H]5CC[C@H](C#N)CC5)CC4)ccnc3[nH]2)cnn1C(C)C] |
| # | Structure |
|---|---|
| 424 | 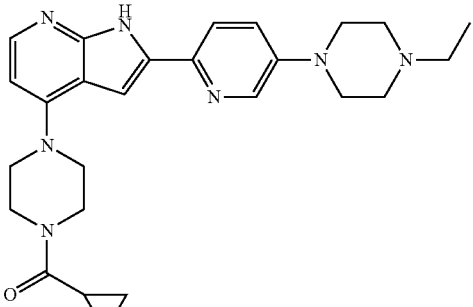 |
| 425 | 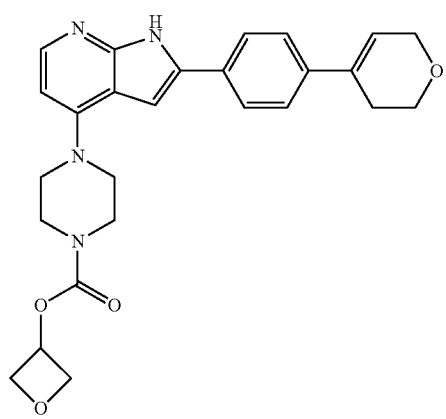 [SMILES: O=C(OC1COC1)N1CCN(c2ccnc3[nH]c(-c4ccc(C5=CCOCC5)cc4)cc23)CC1] |
| 426 | 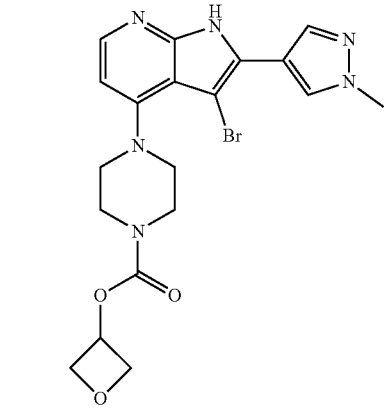 |
| 427 | 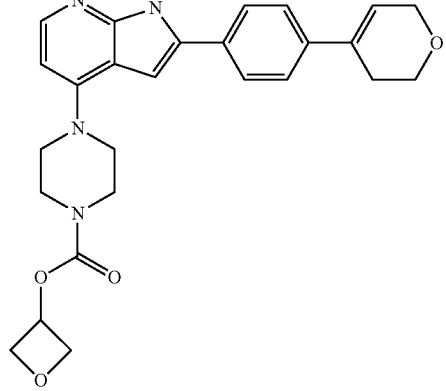 |

471
-continued
| # | Structure |
|---|---|
| 428 | 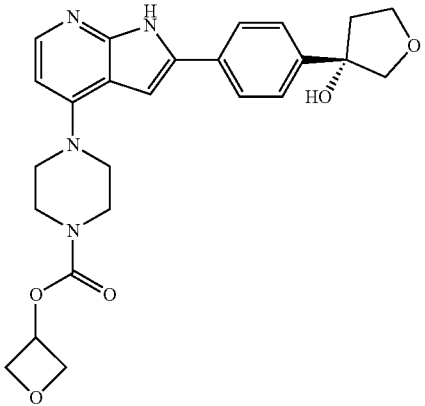 [SMILES: O=C(OC1COC1)N1CCN(c2ccnc3[nH]c(-c4ccc([C@@]5(O)CCOC5)cc4)cc23)CC1] |
| 429 | 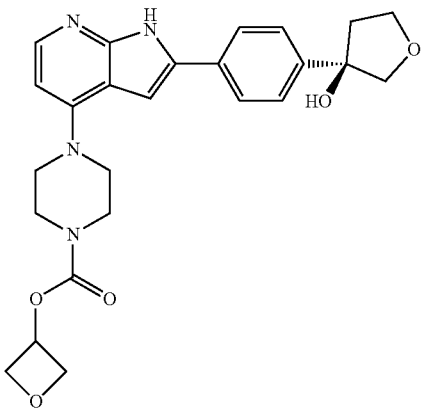 [SMILES: O=C(OC1COC1)N1CCN(c2ccnc3[nH]c(-c4ccc([C@]5(O)CCOC5)cc4)cc23)CC1] |
| 430 | 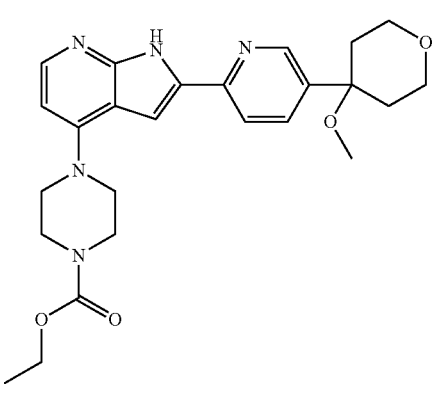 [SMILES: CCOC(=O)N1CCN(c2ccnc3[nH]c(-c4ccc(C5(OC)CCOCC5)cn4)cc23)CC1] |
| 431 | 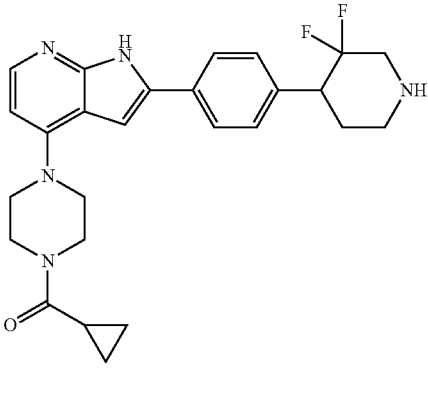 [SMILES: O=C(C1CC1)N1CCN(c2ccnc3[nH]c(-c4ccc(C5CCNCC5(F)F)cc4)cc23)CC1] |
472
-continued
| # | Structure |
|---|---|
| 432 | 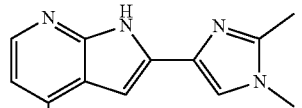 |
| 433 | 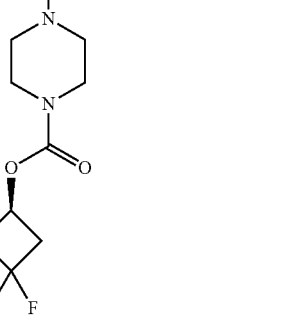 |
| 434 | 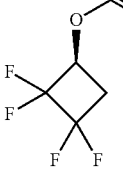 |

| # | Structure |
|---|---|
| 436 | 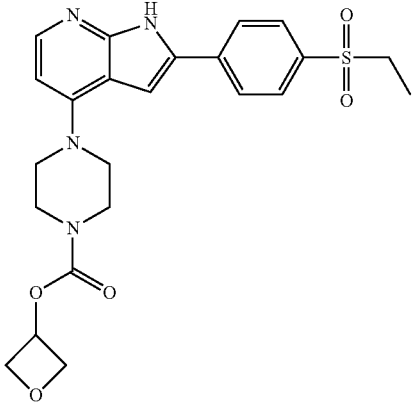 [SMILES: CCS(=O)(=O)c1ccc(-c2cc3c(N4CCN(C(=O)OC5COC5)CC4)ccnc3[nH]2)cc1] |
| 437 | 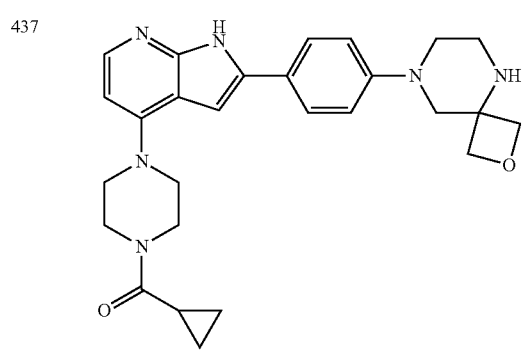 |
| 438 | 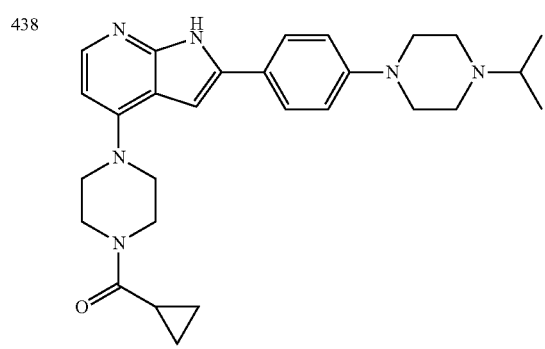 |
| 439 | 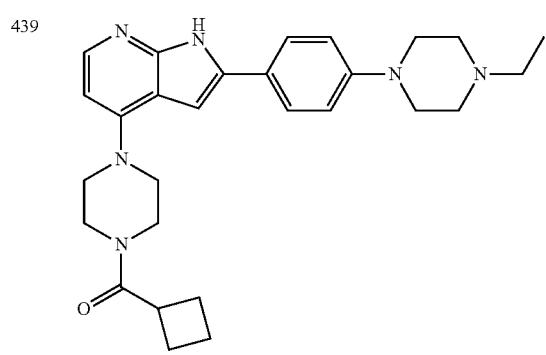 |
| # | Structure |
|---|---|
| 440 | 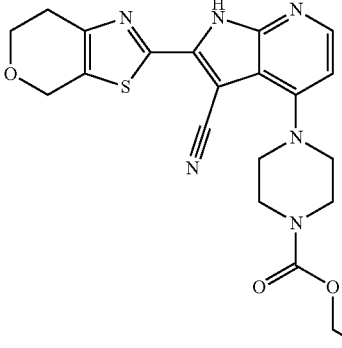 |
| 441 | 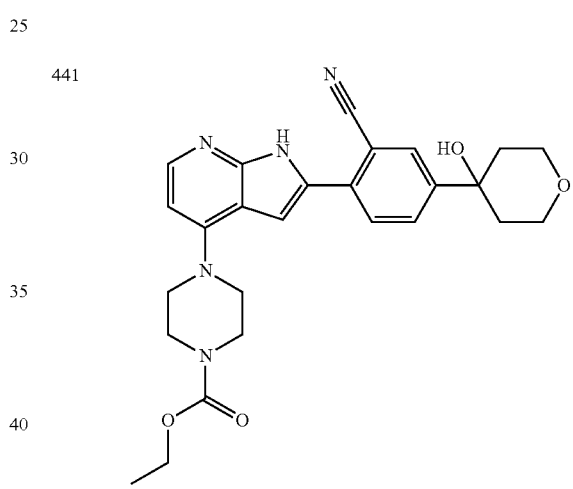 |
| 442 | 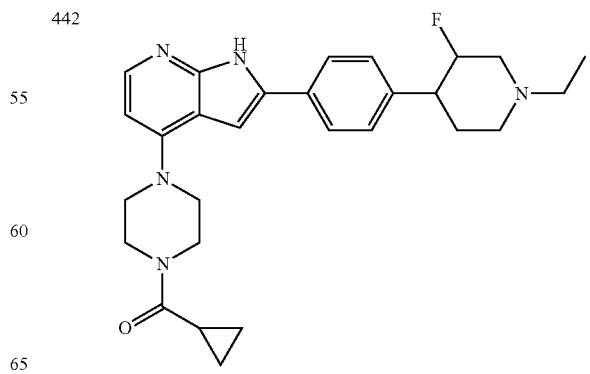 |

| # | Structure |
|---|---|
| 443 | 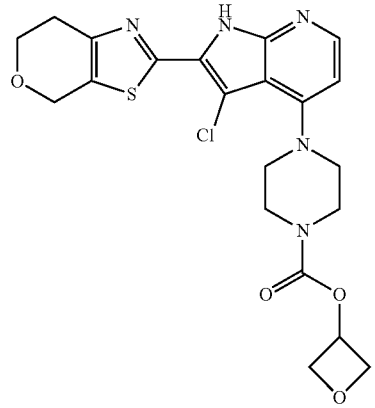 [SMILES: O=C(OC1COC1)N1CCN(c2ccnc3[nH]c(-c4nc5c(s4)COCC5)c(Cl)c23)CC1] |
| 444 | 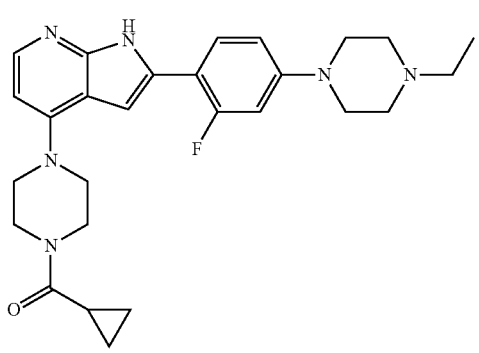 |
| 445 | 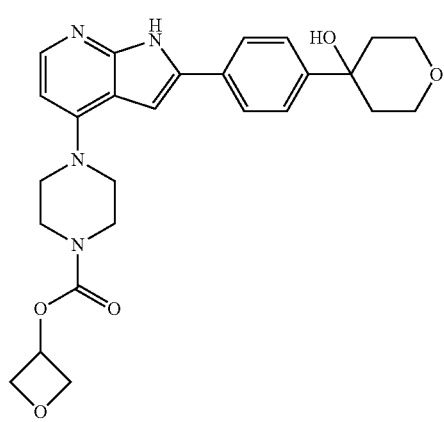 [SMILES: O=C(OC1COC1)N1CCN(c2ccnc3[nH]c(-c4ccc(C5(O)CCOCC5)cc4)cc23)CC1] |
| 446 | 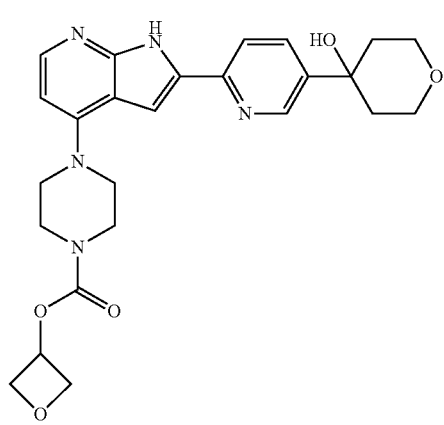 [SMILES: O=C(OC1COC1)N1CCN(c2ccnc3[nH]c(-c4ccc(C5(O)CCOCC5)cn4)cc23)CC1] |
| # | Structure |
|---|---|
| 447 | 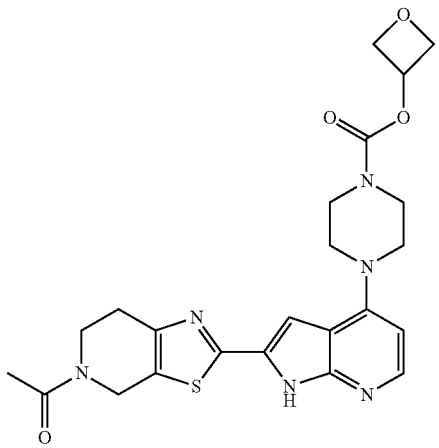 [SMILES: CC(=O)N1CCc2nc(-c3cc4c(N5CCN(C(=O)OC6COC6)CC5)ccnc4[nH]3)sc2C1] |
| 448 | 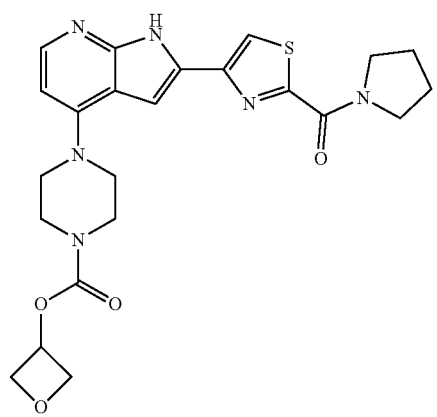 [SMILES: O=C(OC1COC1)N1CCN(c2ccnc3[nH]c(-c4csc(C(=O)N5CCCC5)n4)cc23)CC1] |
| 449 | 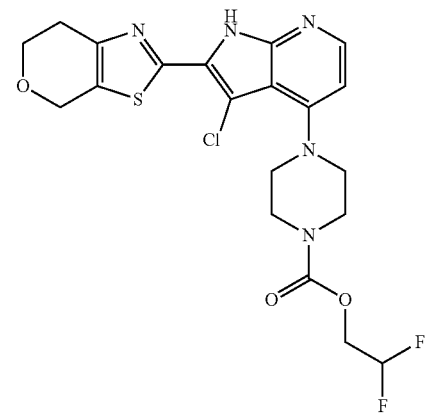 [SMILES: O=C(OCC(F)F)N1CCN(c2ccnc3[nH]c(-c4nc5c(s4)COCC5)c(Cl)c23)CC1] |

| # | Structure |
|---|---|
| 450 | 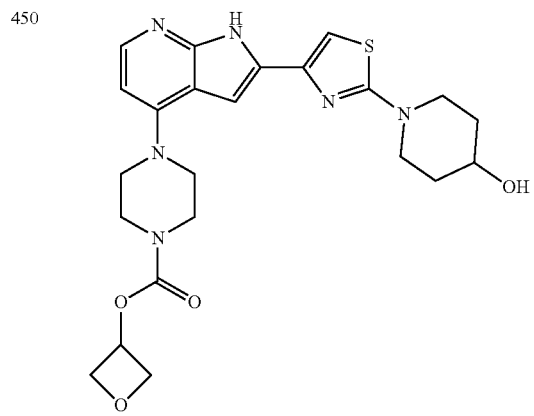 |
| 451 | 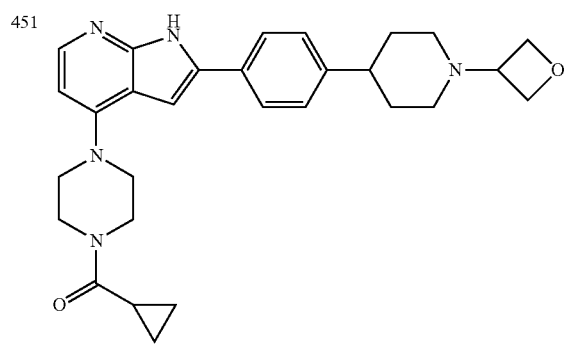 |
| 452 | 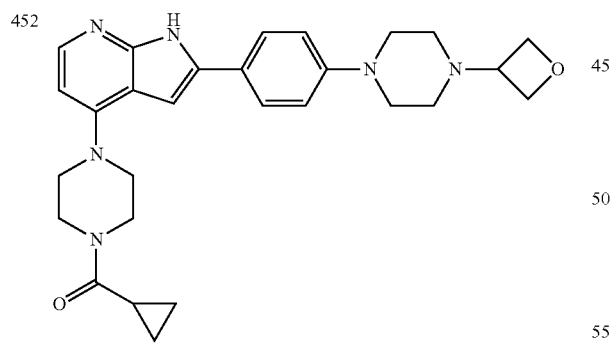 |
| 453 | 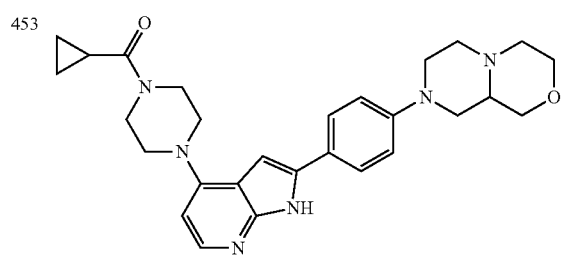 |
| # | Structure |
|---|---|
| 454 | 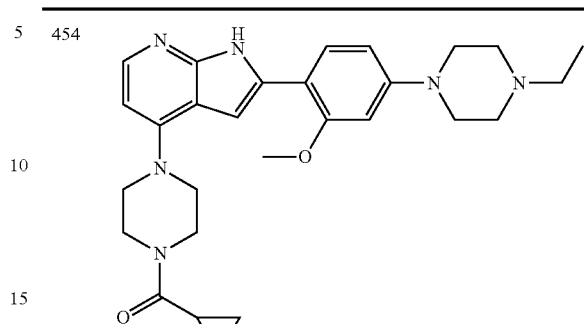 |
| 455 | 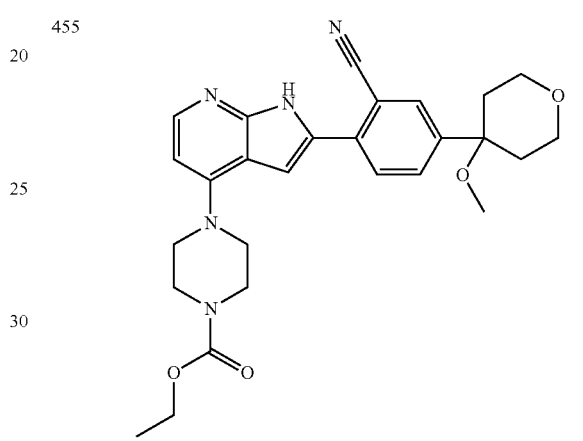 |
| 456 | 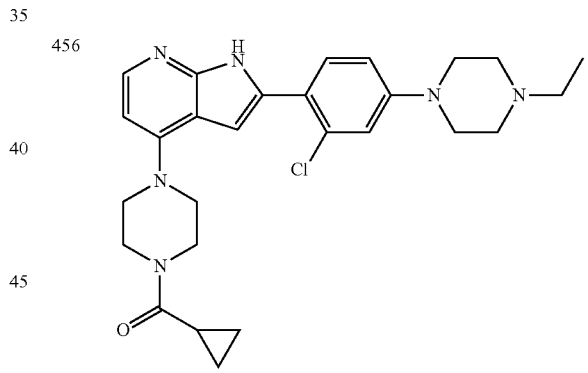 |
| 457 | 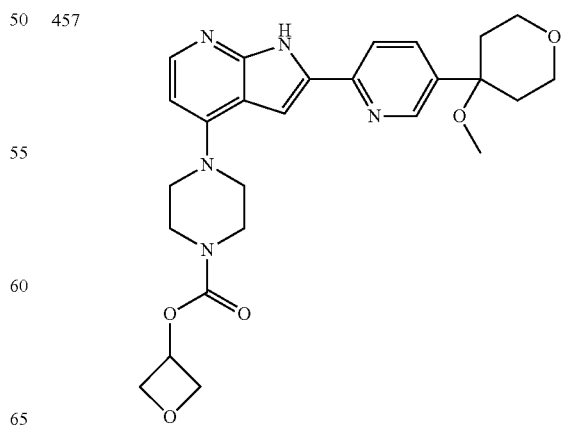 |

479
-continued
| # | Structure |
|---|---|
| 458 | 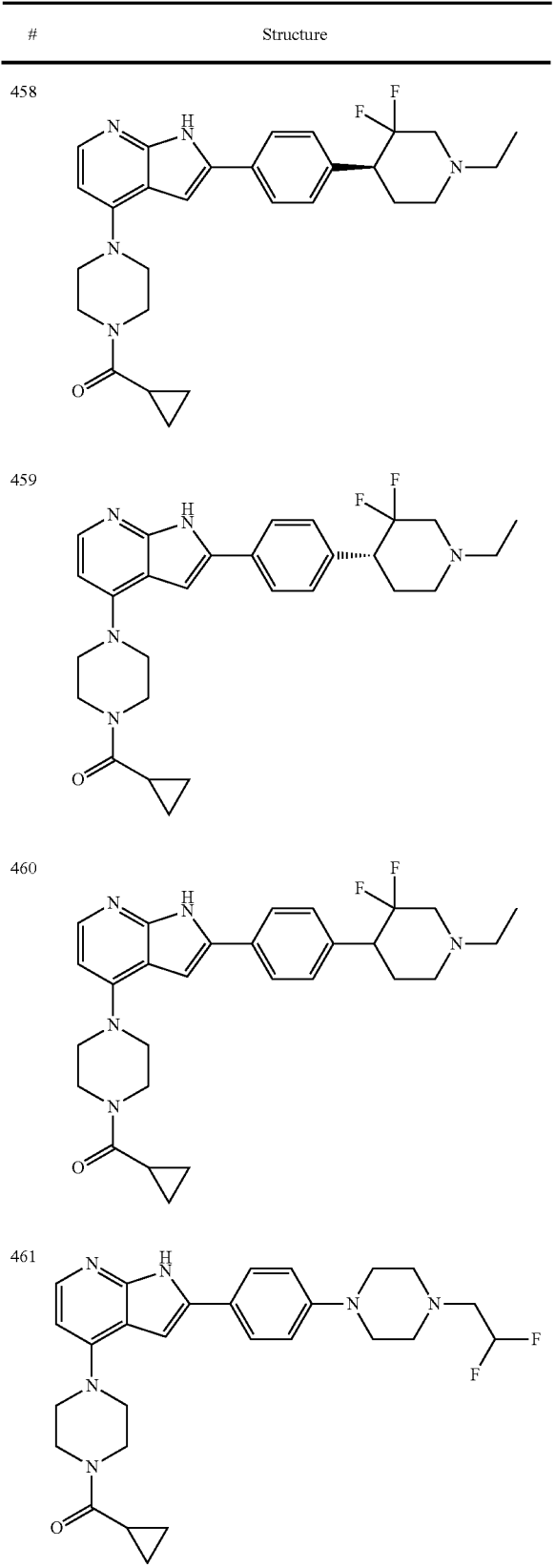 |
| 459 | 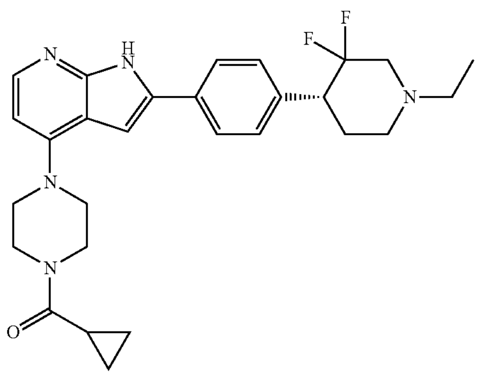 [SMILES: CCN1CC[C@H](c2ccc(-c3cc4c(N5CCN(C(=O)C6CC6)CC5)ccnc4[nH]3)cc2)C(F)(F)C1] |
| 460 | 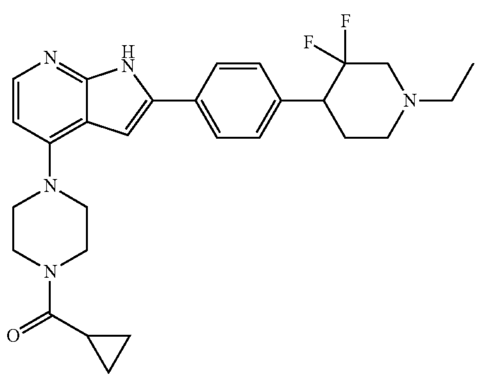 |
| 461 | 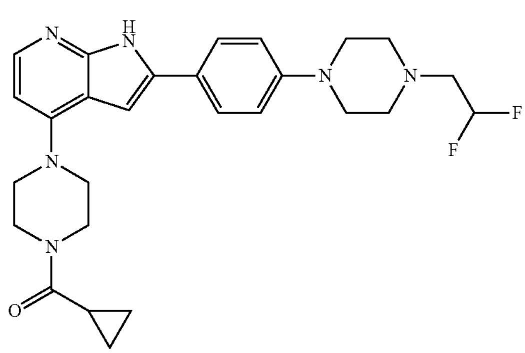 [SMILES: O=C(C1CC1)N1CCN(c2ccnc3[nH]c(-c4ccc(N5CCN(CC(F)F)CC5)cc4)cc23)CC1] |
480
-continued
| # | Structure |
|---|---|
| 462 | 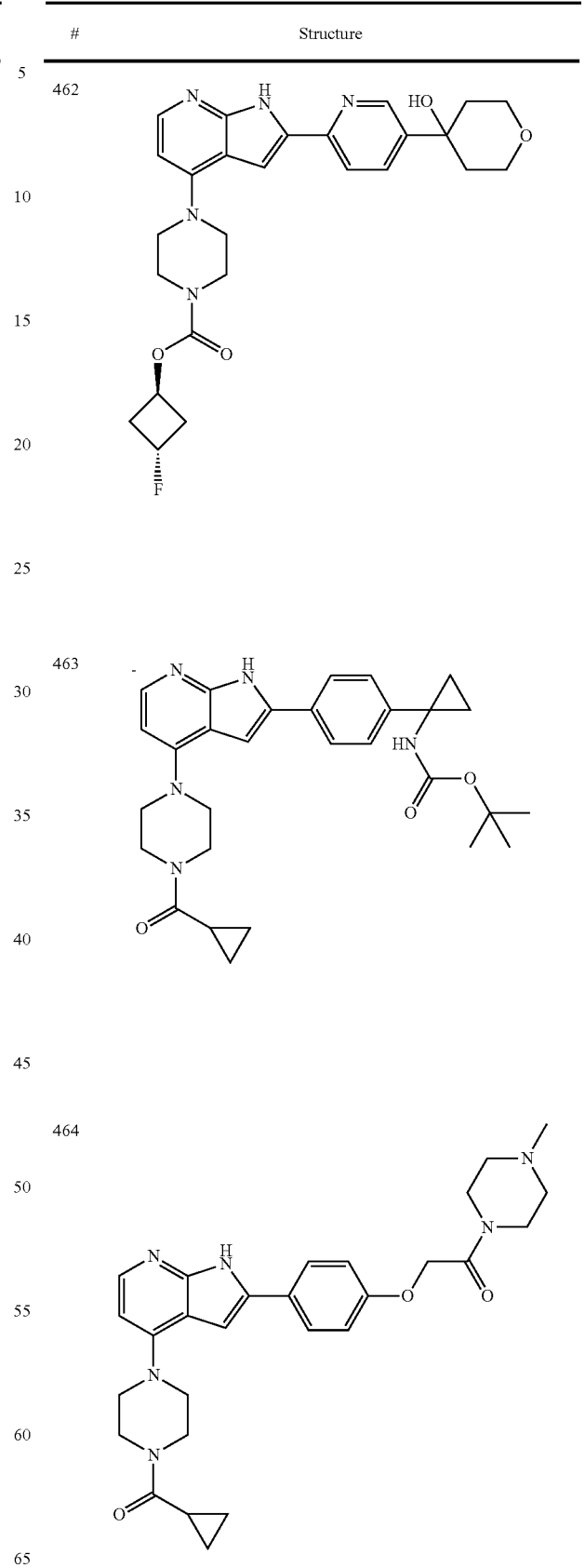 |
| 463 | 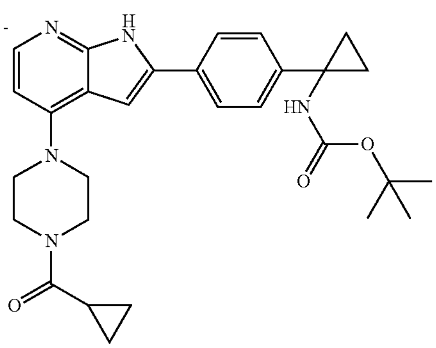 [SMILES: CC(C)(C)OC(=O)NC1(c2ccc(-c3cc4c(N5CCN(C(=O)C6CC6)CC5)c[c-]nc4[nH]3)cc2)CC1] |
| 464 | 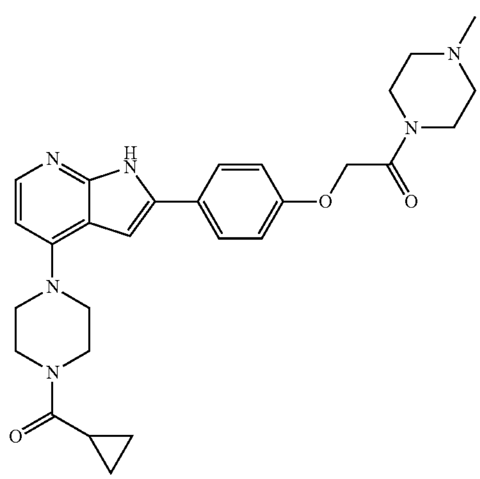 [SMILES: CN1CCN(C(=O)COc2ccc(-c3cc4c(N5CCN(C(=O)C6CC6)CC5)ccnc4[nH]3)cc2)CC1] |

481
-continued
| # | Structure |
|---|---|
| 465 | 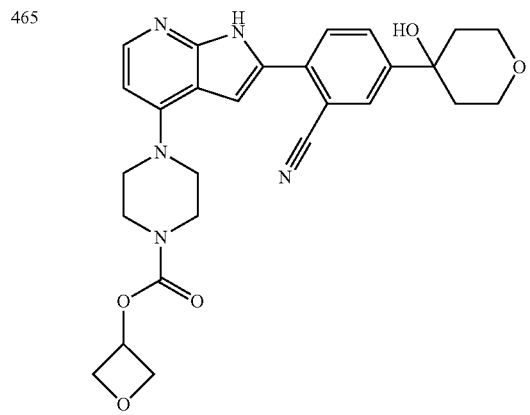 |
| 466 | 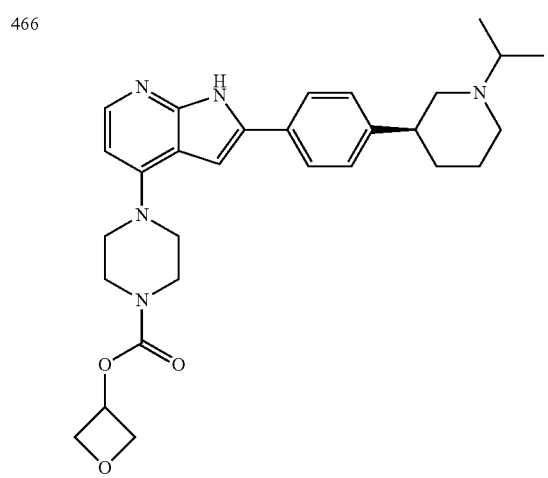 |
| 467 | 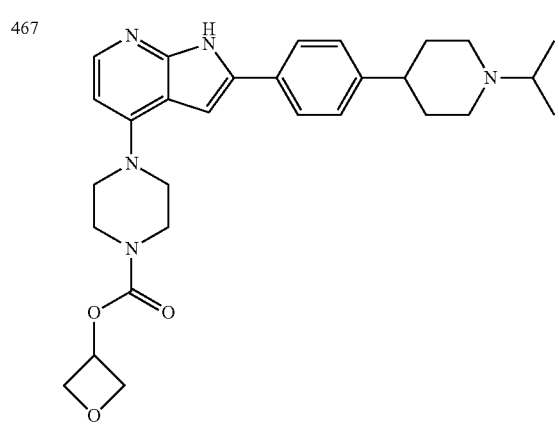 |
482
-continued
| # | Structure |
|---|---|
| 468 | 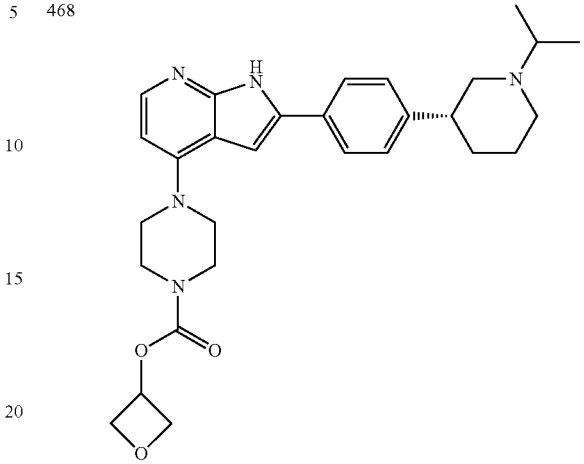 |
| 469 | 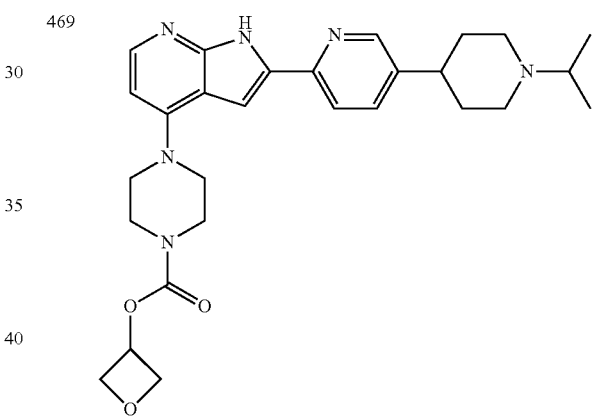 |
| 470 | 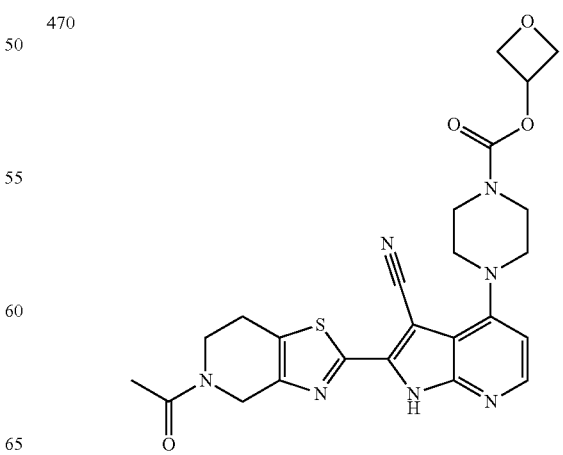 |

| # | Structure |
|---|---|
| 471 | 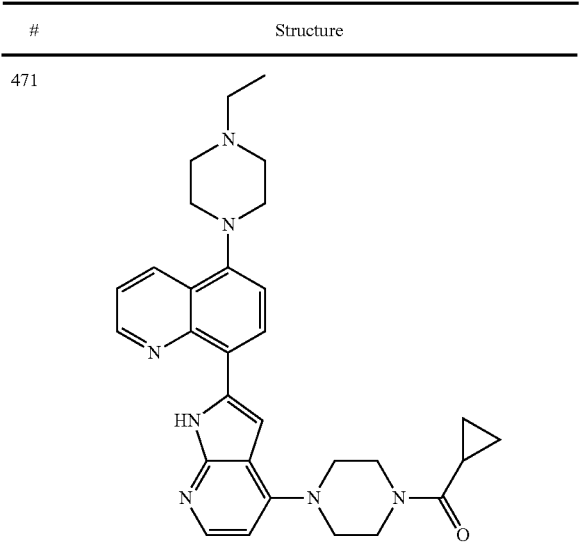 |
| 472 | 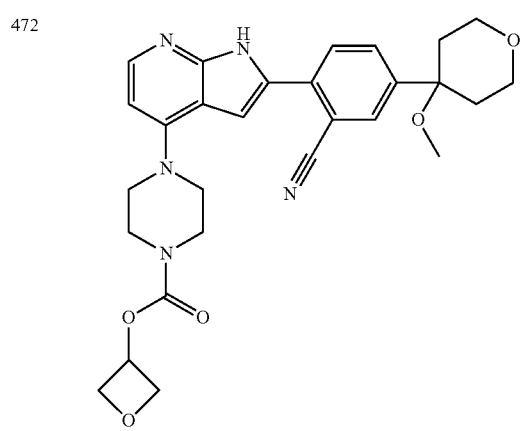 |
| 473 | 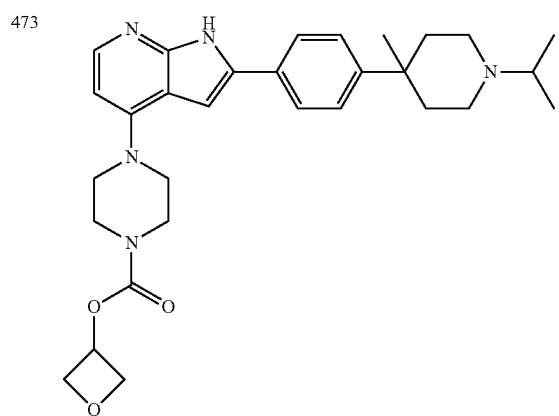 |
| # | Structure |
|---|---|
| 474 | 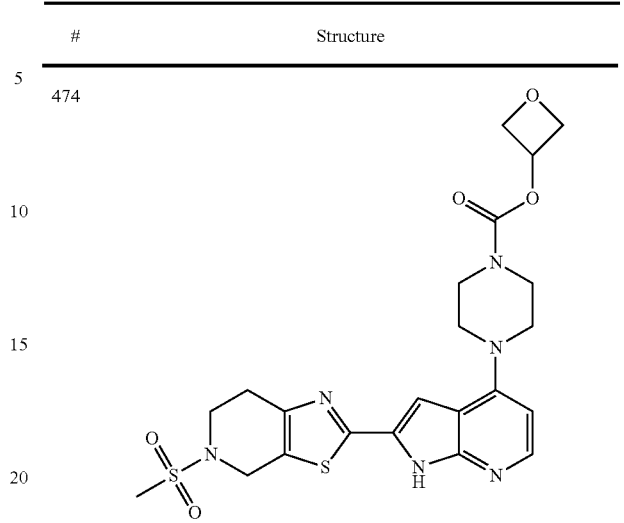 |
| 475 | 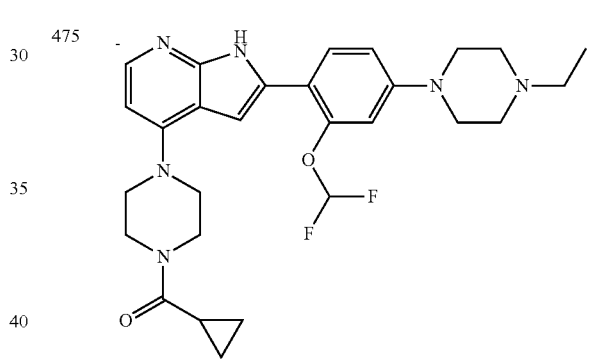 |
| 476 | 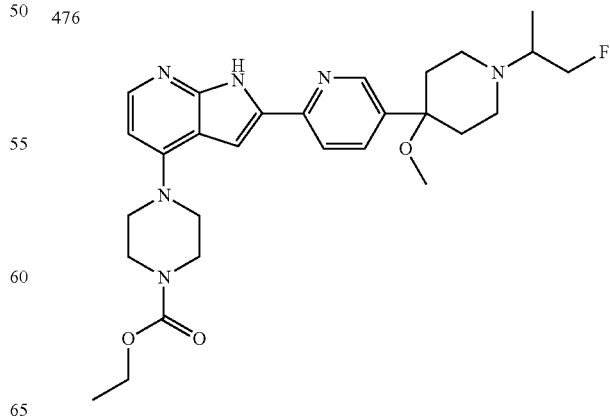 |

| # | Structure |
|---|---|
| 477 | 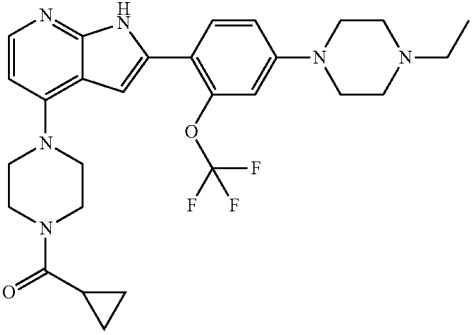 [SMILES: CCN1CCN(c2ccc(-c3cc4c(N5CCN(C(=O)C6CC6)CC5)ccnc4[nH]3)c(OC(F)(F)F)c2)CC1] |
| 478 | 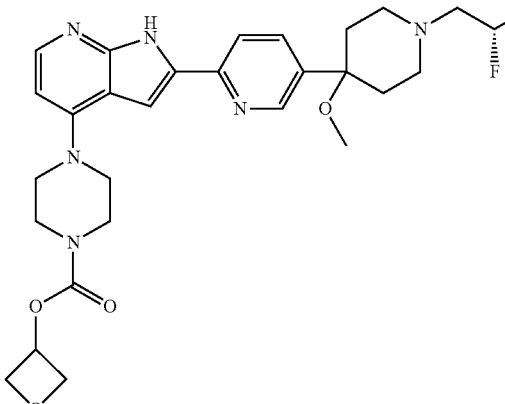 |
| # | Structure |
|---|---|
| 479 | 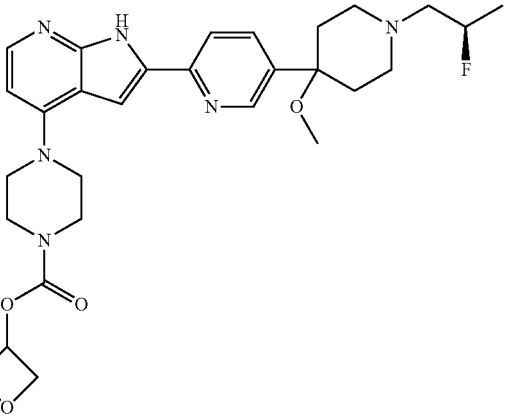 |
| 480 | 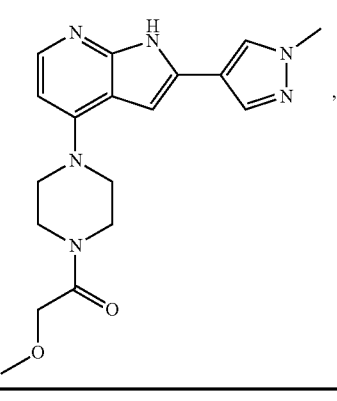 |
or a pharmaceutically acceptable salt thereof.
* * * * *

UNITED STATES PATENT AND TRADEMARK OFFICE
CERTIFICATE OF CORRECTION

PATENT NO. : 11,236,086 B2
APPLICATION NO. : 16/754184
DATED : February 1, 2022
INVENTOR(S) : Jason D. Brubaker Page 1 of 2

It is certified that error appears in the above-identified patent and that said Letters Patent is hereby corrected as shown below:

In the Claims

Column 346, Claim 1, Line 15, replace "-C(O)-($C_3$-$C_5$ carbocyclyl)," with -- -C(O)-($C_3$-$C_8$ carbocyclyl), --;

Column 346, Claim 1, Line 16-17, replace "-O-($C_0$-$C_4$ alkylene)-C(O)-($C_3$-$C_5$ carbocyclyl)," with -- -O-($C_0$-$C_4$ alkylene)-C(O)-($C_3$-$C_8$ carbocyclyl), --;

Column 346, Claim 1, Line 47, replace "-O-($C_1$-$C_4$-O-($C_1$-$C_4$ haloalkyl)," with -- -O-($C_1$-$C_4$ alkyl), -O-($C_1$-$C_4$ haloalkyl), --;

Column 346, Claim 1, Line 48-49, replace "-C(O)-O-($C_1$-$C_4$-S(O)$_p$-($C_1$-$C_4$ alkyl)," with -- -C(O)-O-($C_1$-$C_4$ alkyl), -S(O)$_p$-($C_1$-$C_4$ alkyl), --;

Column 347, Claim 4, Line 64, replace "Z is chosen from CH, NH, S, and 0;" with -- Z is chosen from CH, NH, S, and O; --;

Column 348, Claim 5, Line 10, replace "-O-($C_1$-$C_4$ alkyl-C(O)-($C_1$-$C_4$ alkyl)," with -- -O-($C_1$-$C_4$ alkyl), -C(O)-($C_1$-$C_4$ alkyl), --;

Column 348, Claim 5, Line 12, replace "-N($R^8$)-C(O)-($C_1$-$C_4$ alkyl-S(O)$_p$-($C_1$-$C_4$ alkyl)," with -- -N($R^8$)-C(O)-($C_1$-$C_4$ alkyl), -S(O)$_p$-($C_1$-$C_4$ alkyl), --;

Column 348, Claim 5, Line 22, replace "$R^{18}$" with -- $R^{1B}$ --;

Column 348, Claim 5, Line 23, replace "$R^{18}$" with -- $R^{1B}$ --;

Column 348, Claim 6, Line 40, replace "$R^{18}$" with -- $R^{1B}$ --;

Column 348, Claim 6, Line 52, replace "$R^{18}$" with -- $R^{1B}$ --;

Signed and Sealed this
Fifteenth Day of March, 2022

Drew Hirshfeld
*Performing the Functions and Duties of the
Under Secretary of Commerce for Intellectual Property and
Director of the United States Patent and Trademark Office*

CERTIFICATE OF CORRECTION (continued)
U.S. Pat. No. 11,236,086 B2

Column 348, Claim 6, Line 53, replace "$R^{18}$" with -- $R^{1B}$ --;

Column 350, Claim 11, Line 3-4, replace "-($C_0$-$C_3$ alkylene)-(monocyclic 0- or S-heterocyclyl)," with -- -($C_0$-$C_3$ alkylene)-(monocyclic O- or S-heterocyclyl), --; and Column 350, Claim 14, Line 33, replace "R2021," with -- R202I, --.